United States Patent [19]

Shapiro

[11] Patent Number: 4,684,393

[45] Date of Patent: Aug. 4, 1987

[54] HERBICIDAL THIOPHENESULFONAMIDES

[75] Inventor: Rafael Shapiro, Wilmington, Del.

[73] Assignee: E. I. DuPont de Nemours and Company, Wilmington, Del.

[21] Appl. No.: 724,835

[22] Filed: Apr. 23, 1985

Related U.S. Application Data

[63] Continuation-in-part of Ser. No. 686,834, Dec. 27, 1984, abandoned, which is a continuation-in-part of Ser. No. 619,277, Jun. 11, 1984, abandoned.

[51] Int. Cl.[4] .................. C07D 409/14; C07D 411/14; C07D 417/14; A01N 47/3

[52] U.S. Cl. ........................................ 71/90; 544/182; 544/215; 544/238; 544/253; 544/278; 544/295; 544/296; 544/320; 544/321; 544/323; 544/324; 544/331; 544/332; 548/266

[58] Field of Search .................... 71/90, 321; 544/332, 544/182, 215, 238, 253, 278, 295, 296, 320, 323, 324, 331

[56] References Cited

U.S. PATENT DOCUMENTS

| | | | |
|---|---|---|---|
| 4,398,939 | 8/1983 | Levitt | 71/90 |
| 4,443,244 | 4/1984 | Levitt | 71/93 |
| 4,465,505 | 8/1984 | Wolf | 71/92 |
| 4,511,392 | 4/1985 | Rorer | 71/90 |

FOREIGN PATENT DOCUMENTS

| | | | |
|---|---|---|---|
| 2112784 | 7/1983 | United Kingdom | 71/90 |

*Primary Examiner*—Robert Gerstl

[57] ABSTRACT

Thiophenesulfonamides such as N-[(4,6-dimethyl-pyrimidin-2-yl)aminocarbonyl]-3-(isoxazol-3-yl)-2-thiophenesulfonamide are useful as herbicides and plant growth regulants.

30 Claims, No Drawings

HERBICIDAL THIOPHENESULFONAMIDES

RELATED APPLICATION

This application is a continuation-in-part of copending application Ser. No. 686,834 filed Dec. 27, 1984 which in turn is a continuation-in-part of copending application Ser. No. 619,277 filed June 11, 1984 both now abandoned.

BACKGROUND OF THE INVENTION

U.S. Pat. No. 4,398,939, issued Aug. 16, 1983 to Levitt, discloses herbicidal thiophenesulfonylureas such as

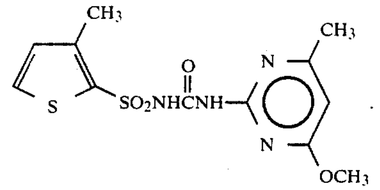

European Patent Application No. 30,142, published June 10, 1981, discloses herbicidal thiophene sulfonylureas such as

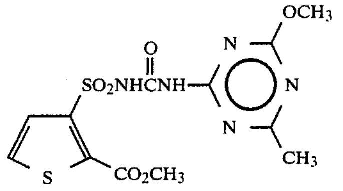

U.S. Pat. No. 4,378,991, issued Apr. 5, 1983 discloses o-phenyl sulfonylureas such as

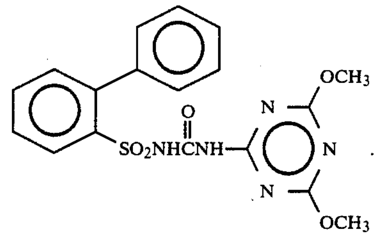

European Patent Application No. 83,975, published July 20, 1983, and European Patent Application No. 85,476, published Aug. 10, 1983, disclose herbicidal benzenesulfonamides of the formula

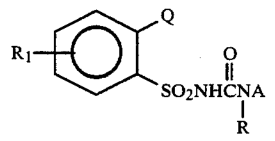

where Q is various 5- and 6-membered, saturated, unsaturated or partially unsaturated heterocyclic rings.

South African Patent Application No. 83/8416 (published May 12, 1984) discloses herbicidal sulfonamides of formula

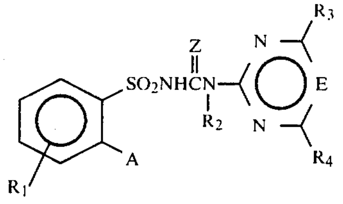

wherein A is an unsaturated or only partially saturated 5- or 6-membered heterocyclic ring system which is bonded through a carbon atom and contains 1, 2 or 3 heteroatoms and which may be substituted by $C_1$–$C_4$ alkyl, $C_1$–$C_4$ haloalkyl, $C_1$–$C_4$ alkoxy, $C_1$–$C_4$ alkylthio, $C_2$–$C_8$ alkoxyalkyl, di($C_1$–$C_4$ alkyl)amino, halogen, cyano or nitro.

SUMMARY OF THE INVENTION

This invention relates to novel compounds of Formulas Ia, Ib, and Ic, agriculturally suitable compositions containing them, and their method-of-use as general or selective pre-emergent and post-emergent herbicides or as plant growth regulants.

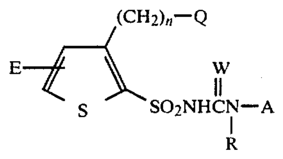

Ia

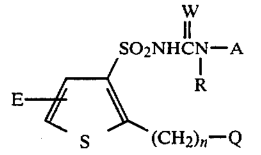

Ib

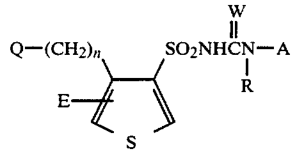

Ic wherein

R is H or $CH_3$;

n is 0, 1 or 2;

W is O or S;

Q is a phenyl ring or a saturated 5- or 6-membered ring containing 1 heteroatom selected from sulfur, nitrogen or oxygen or an unsaturated 5- or 6-membered ring containing 1–3 heteroatoms selected from 0–1 sulfur, 0–1 oxygen or 0–3 nitrogen and Q may optionally be substituted by one or more groups selected from SH, $C_1$–$C_4$ alkyl, $C_3$–$C_4$ alkenyl, $C_1$–$C_3$ haloalkyl, halogen, $C_1$–$C_3$ alkoxy, $C_1$–$C_4$ alkylthio, $C_3$–$C_4$ alkenylthio, $C_3$–$C_4$ alkenyloxy, $C_1$–$C_2$ haloalkoxy, $C_1$–$C_2$ haloalkylthio, $C_3$–$C_4$ alkynylthio, $C_1$–$C_4$ cyanoalkylthio, $C_1$–$C_2$ alkylcarbonylmethythio or $C_1$–$C_2$ alkoxycarbonylmethylthio;

E is H, $C_1$–$C_2$ alkyl, $C_1$–$C_2$ alkoxy, halogen, $NO_2$, $C_1$–$C_2$ haloalkyl, $C_1$–$C_2$ alkylthio, $C_1$–$C_2$ alkylsulfonyl, $C_1$–$C_2$ alkoxycarbonyl, $C_1$–$C_2$ dialkylaminosulfamoyl;

A is

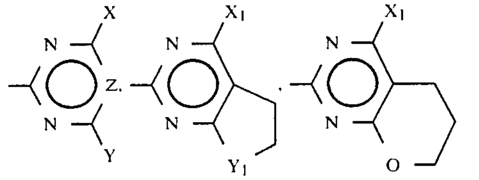

A-1 A-2 A-3

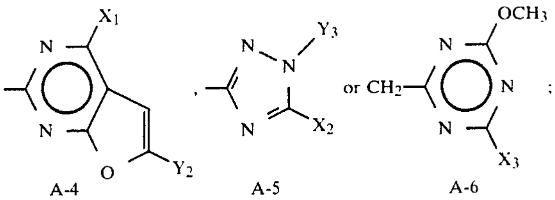

A-4 A-5 A-6

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_3$–$C_5$ cycloalkyl, $C_2$–$C_4$ alkynyl, C(O)$R_c$,

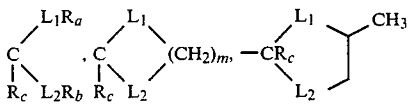

or $N(OCH_3)CH_3$;

m is 2 or 3;

$L_1$ and $L_2$ are independently O or S;

$R_a$ and $R_b$ are independently $C_1$–$C_2$ alkyl;

$R_c$ is H or $CH_3$;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $CH_2CH_3$ or $CH_2CF_3$; and $X_3$ is $CH_3$ or $OCH_3$;

and their agriculturally suitable salts; provided that (1) when X is F, Cl, Br or I, then Z is CH and Y is $OCF_2H$, $OCH_3$ $OC_2H_5$, $NH_2$, $N(OCH_3)CH_3$, $NHCH_3$, $N(CH_3)_2$;

(2) the total number of carbon atoms of Q must be less than or equal to 8;

(3) when X or Y is $OCF_2H$, then Z is CH;

(4) when Q is a saturated 5- or 6-membered ring containing one nitrogen atom, it is bonded to the thiophene ring through carbon; and (5) when W is S, then R is H, A is A-1 and Y is $CH_3$, $OCH_3$, $OC_2H_5$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

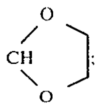

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy or the different butyl isomers.

Alkenyl denotes straight chain or branched alkenes, e.g. vinyl, 1-propenyl, 3-propenyl, isopropenyl or the different butenyl isomers.

Alkynyl denotes straight chain or branch alkynes, e.g., ethynyl, 1-propynyl, 2-propynyl or the different butynyl isomers.

Cycloalkyl denotes cyclopropyl, cyclobutyl or cyclopentyl.

The term "halogen", either alone or in compound words such as "haloalkyl", denotes fluorine, chlorine, bromine or iodine.

Alkylcarbonyl denotes acetyl or propionyl.

Alkoxycarbonyl denotes methoxycarbonyl or ethoxycarbonyl.

Alkylsulfonyl denotes methylsulfonyl or ethylsulfonyl.

Alkylthio, alkylamino, alkylsulfamoyl, etc. are defined in an analogous manner.

In terms such as $C_2$–$C_3$ alkylthioalkyl, the specified number of carbon atoms is meant to define the total number of carbon atoms in that substituent group. For example, $C_2$–$C_3$ alkylthioalkyl would designate $CH_2SCH_3$, $CH_2SC_2H_5$, $CH_2CH_2SCH_3$ or $CH(CH_3)SCH_3$, and $C_2$–$C_5$ alkoxyalkoxy would represent $OCH_2OCH_3$, through $O(CH_2)_4OCH_3$ or $OCH_2O(CH_2)_3CH_3$ and the various structural isomers embraced therein.

Preferred for their higher herbicidal activity, greater plant growth regulant activity and/or more favorable ease of synthesis are:

(1) Compounds of Formulas Ia–Ic where

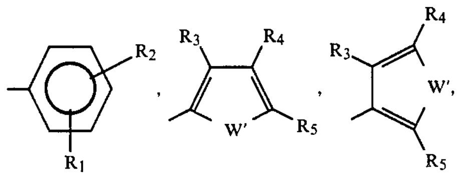

Q-1 Q-2 Q-3

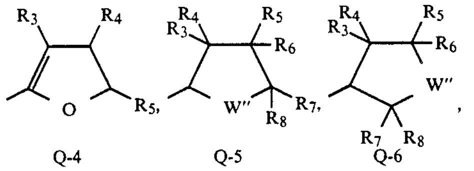

Q-4 Q-5 Q-6

-continued

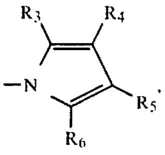

Q-7

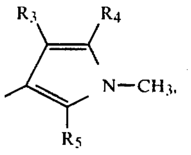

Q-9

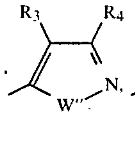

Q-10

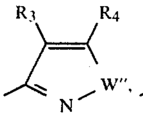

Q-11

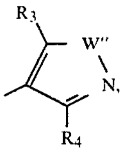

Q-12

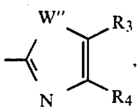

Q-13

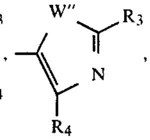

Q-14

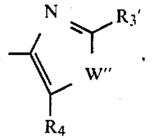

Q-15

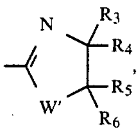

Q-16

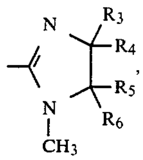

Q-17

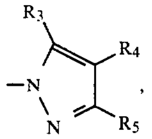

Q-18

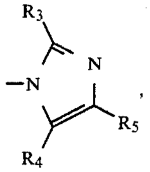

Q-19

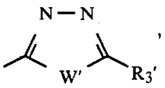

Q-20

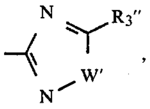

Q-21

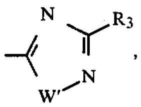

Q-22

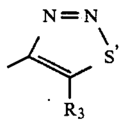

Q-23

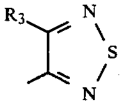

Q-24

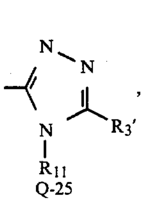

Q-25

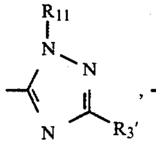

Q-26

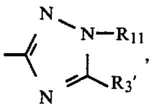

Q-27

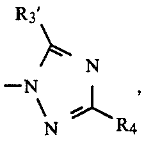

Q-28

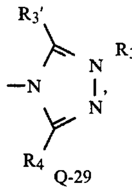

Q-29

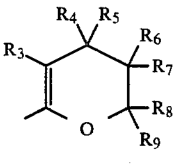

Q-30

-continued

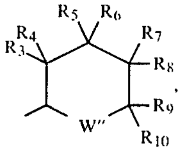

Q-31

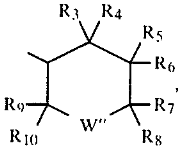

Q-32

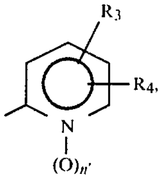

Q-33

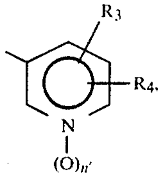

Q-34

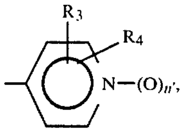

Q-35

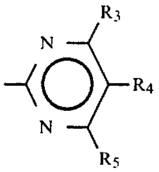

Q-36

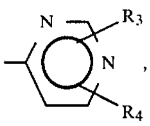

Q-37

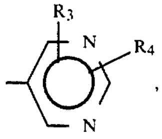

Q-38

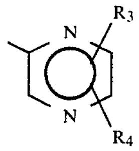

Q-39

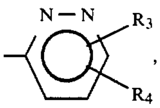

Q-40

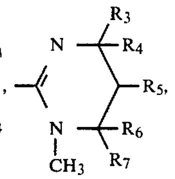

Q-41

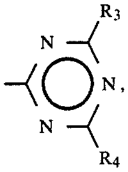

Q-43

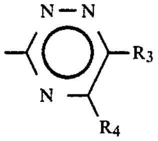

Q-44 or

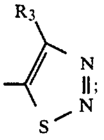

Q-45

$R_1$ is H, Cl, $CH_3$ or $OCH_3$;

$R_2$ is H, F, Cl, $CH_3$, $OCH_3$ or $CF_3$;

$R_3$, $R_4$, $R_5$, $R_6$, $R_7$, $R_8$, $R_9$ and $R_{10}$ are independently H or $CH_3$;

n' is 0 or 1;

$R_3'$ is H, SH, $C_1$–$C_3$ alkyl, $C_1$–$C_4$ alkylthio, $C_3$–$C_4$ alkenylthio, $C_3$–$C_4$ alkynylthio, $C_1$–$C_3$ cyanoalkylthio, $SCH_2CO_2CH_3$, $SCH_2CO_2C_2H_5$, $SCH_2C(O)CH_3$, halogen, $C_1$–$C_3$ alkoxy or $OCH_2CH{=}CH_2$;

$R_3''$ is H, $CH_3$, Cl or Br;

W' is O or S;

W'' is O or S or $NR_{11}$;

$R_{11}$ is H, $C_1$–$C_3$ alkyl or $CH_2CH{=}CH_2$;

(2) Compounds of Preferred 1 where E is H; A is A-1; X is $CH_3$, $OCH_3$, $OC_2H_5$, Cl or Br; Y is H, $CH_3$, $OCH_3$, $C_2H_5$, $OC_2H_5$, $CH_2OCH_3$, $CF_3$, $OCF_2H$, cyclopropyl, $OCH_2CF_3$, $NHCH_3$, $N(CH_3)_2$, $CH(OCH_3)_2$ or

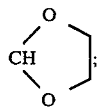

;

n' is 0; and $R_3'$ and $R_3''$ are independently H, $CH_3$ or Cl; R is H; and W is O; (3) Compounds of Preferred 2 where n is 0;

(4) Compounds of Preferred 3 where Y is $C_1$–$C_2$ alkyl, $OCH_3$, or $OCF_2H$;

(5) Compounds of Preferred 4 where $R_1$ is H, $R_2$ is H or Cl and Z is CH;

(6) Compounds of Preferred 5 of Formula Ia;

(7) Compounds of Preferred 5 of Formula Ib;

(8) Compounds of Preferred 5 of Formula Ic;

(9) Compounds of Preferred 6 where Q is Q-1;

(10) Compounds of Preferred 6 where Q is Q-2,

(11) Compounds of Preferred 6 where Q is Q-3;

(12) Compounds of Preferred 6 where Q is Q-5;

(13) Compounds of Preferred 6 where Q is Q-7;

(14) Compounds of Preferred 6 where Q is Q-10;

(15) Compounds of Preferred 6 where Q is Q-11;

(16) Compounds of Preferred 6 where Q is Q-15;

(17) Compounds of Preferred 6 where Q is Q-16;

(18) Compounds of Preferred 6 where Q is Q-20;

(19) Compounds of Preferred 6 where Q is Q-23;

(20) Compounds of Preferred 6 where Q is Q-28;

(21) Compounds of Preferred 6 where Q is Q-36;

(22) Compounds of Preferred 6 where Q is Q-39;

(23) Compounds of Preferred 7 where Q is Q-1;

(24) Compounds of Preferred 7 where Q is Q-2;

(25) Compounds of Preferred 7 where Q is Q-3;

(26) Compounds of Preferred 7 where Q is Q-5;

(27) Compounds of Preferred 7 where Q is Q-7;

(28) Compounds of Preferred 7 where Q is Q-10;

(29) Compounds of Preferred 7 where Q is Q-11;

(30) Compounds of Preferred 7 where Q is Q-15;

(31) Compounds of Preferred 7 where Q is Q-16;

(32) Compounds of Preferred 7 where Q is Q-20;

(33) Compounds of Preferred 7 where Q is Q-23;

(34) Compounds of Preferred 7 where Q is Q-28;

(35) Compounds of Preferred 7 where Q is Q-36;

(36) Compounds of Preferred 7 where Q is Q-39;

(37) Compounds of Preferred 8 where Q is Q-1;

(38) Compounds of Preferred 8 where Q is Q-2;

(39) Compounds of Preferred 8 where Q is Q-3;

(40) Compounds of Preferred 8 where Q is Q-5;

(41) Compounds of Preferred 8 where Q is Q-7;

(42) Compounds of Preferred 8 where Q is Q-10;

(43) Compounds of Preferred 8 where Q is Q-11;

(44) Compounds of Preferred 8 where Q is Q-15;

(45) Compounds of Preferred 8 where Q is Q-16;

(46) Compounds of Preferred 8 where Q is Q-20;

(47) Compounds of Preferred 8 where Q is Q-23;

(48) Compounds of Preferred 8 where Q is Q-28;

(49) Compounds of Preferred 8 where Q is Q-36;

(50) Compounds of Preferred 8 where Q is Q-39;

(51) Compounds of Preferred 16 where W'' is S;

(52) Compounds of Preferred 30 where W'' is S;

(53) Compounds of Preferred 44 where W'' is S;

Specifically Preferred for their highest herbicidal activity, greatest plant growth regulant activity and/or most favorable ease of synthesis are:

N-[(4,6-dimethylpyrimidin-2-yl)aminocarbonyl]-3-(isoxazol-3-yl)-2-thiophenesulfonamide, m.p. 172.5°–173° C.;

3-(isoxazol-3-yl)-N-[(4-methoxy-6-methylpyrimidin-2-yl)aminocarbonyl]-2-thiophenesulfonamide, m.p. 192° C.(d);

N-[(4,6-dimethoxypyrimidin-2-yl)aminocarbonyl]-3-(isoxazol-3-yl)-2-thiophenesulfonamide, m.p. 157°–158° C.;

3-(5-chloro-1H-1,2,4-triazol-1-yl)-N-[(4,6-dimethoxypyrimidin-2-yl)aminocarbonyl]-2-thiophenesulfonamide, m.p. 204°–205° C.(d);

N-[(4-methoxy-6-methylpyrimidin-2-yl)aminocarbonyl]-3-(1H-pyrrol-1-yl)-2-thiophenesulfonamide, m.p. 152°–155° C.;

N-[(4-methoxy-6-methyl-1,3,5-triazin-2-yl)aminocarbonyl]-3-(1H-pyrrol-1-yl)-2-thiophenesulfonamide, m.p. 144°–146° C.;

N-[(4,6-dimethoxypyrimidin-2-yl)aminocarbonyl]-3-(1H-pyrrol-1-yl)-2-thiophenesulfonamide, m.p. 142°–146° C.;

N-[(4,6-dimethylpyrimidin-2-yl)aminocarbonyl]-3-(1H-pyrrol-1-yl)-2-thiophenesulfonamide, m.p. 170°–173° C.;

N-[(4,6-dimethyl-1,3,5-triazin-2-yl)aminocarbonyl]-3-(1H-pyrrol-1-yl)-2-thiophenesulfonamide, m.p. 153°–156° C.;

N-[(4,6-dimethoxy-1,3,5-triazin-2-yl)aminocarbonyl]-3-(1H-pyrrol-1-yl)-2-thiophenesulfonamide, m.p. 156°–159° C.;

N-[(4-chloro-6-methoxypyridimin-2-yl)aminocarbonyl]-3-(2-methyl-4-thiazolyl)-2-thiophenesulfonamide, m.p. 146°–149° C.;

N-[(4-methoxy-6-methylpyrimidin-2-yl)aminocarbonyl]-3-(2-methyl-4-thiazolyl)-2-thiophenesulfonamide, m.p. 146°–149° C.;

N-[(4,6-dimethoxypyrimidin-2-yl)aminocarbonyl]-3-(2-methyl-4-thiazolyl)-2-thiophenesulfonamide, m.p. 164°–168° C.

Synthesis

The compounds of Formula I can be prepared by one or more of the methods described below in Equations 1 through 4.

Many of the compounds of Formula I can be prepared by reaction of a sulfonamide of Formula 2 with an appropriate methyl carbamate of Formula 3 in the presence of at least an equimolar amount of trimethylaluminum, according to Equation 1.

Equation 1

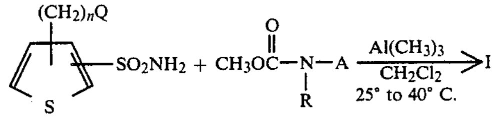

2 3

These reactions are carried out at 25° to 40° C. under an inert atmosphere and in an inert, dipolar aprotic solvent such as methylene chloride for 10 to 96 hours. Details of this reaction as well as the preparation of the carbamates of Formula 3 can be found in EPO Publication No. 13,480.

Many of the compounds of Formula I also can be prepared by reacting a sulfonylcarbamate of Formula 4 with an appropriate heterocyclic amine of Formula 5, according to Equation 1a.

Equation 1a

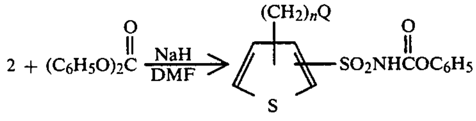

4

-continued

Equation 1a

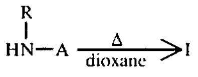

5

The reaction is carried out at 50° to 100° C. in a solvent such as 1,4-dioxane for 0.5 to 24 hours according to EPO Publication No. 44807. The required carbamates of Formula 4 are prepared by reacting the appropriate sulfonamide, 2, with diphenylcarbonate in the presence of equimolar quantities of a strong base, such as sodium or potassium hydride.

Some of the compounds of Formula I also can be prepared as shown in Equation 2.

Equation 2

(a)

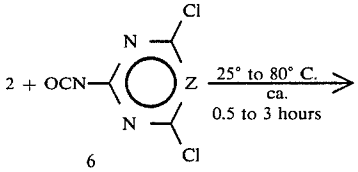

6

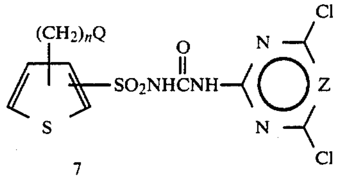

7

(b)

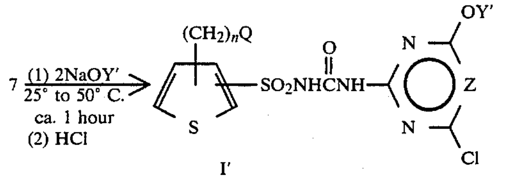

I'

(c)

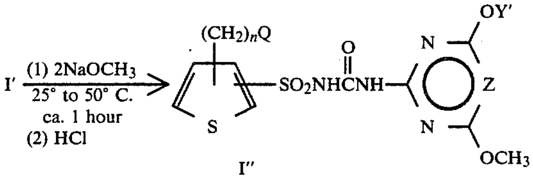

I'' wherein Y' is $CH_3$, $C_2H_5$ or $CH_2CF_3$.

This reaction series is performed according to the procedures disclosed by EPO Publication No. 30,140 and the requisite heterocyclic isocyanates of Formula 6 can be prepared according to methods described in Swiss No. 579,062, U.S. Pat. No. 3,919,228, U.S. Pat. No. 3,732,223 and U. von Gizycki, *Angew Chem. Int. Ed. Engl.* 1976, 10, 402 and 403.

Compounds of Formula I also may be prepared by reaction of a thienylsulfonylisocyanate of Formula 8 with the appropriate heterocyclic amine, as shown in Equation 3.

Equation 3

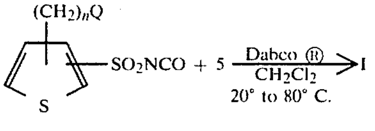

8

The reaction of Equation 3 is most successful when performed in an inert dipolar aprotic solvent such as methylene chloride, tetrahydrofuran or acetonitrile at temperatures between 20° and 80° C. A catalytic amount of 1,4-diazabicyclo[2.2.2]octane (Dabco ®) may be used to accelerate the reaction. In cases where the products are insoluble in the reaction solvent, isolation may be performed by simple filtration; when the products are soluble, isolation may be performed by evaporation of the solvent, trituration with a solvent such as 1-chlorobutane, diethyl ether or methanol and filtration.

Thienylsulfonylisocyanates of Formula 8, can be prepared from sulfonamides of Formula 2 by methods described in U.S. Pat. No. 4,238,621, as indicated in Equation 3a. Alternatively, these sulfonylisocyanates can be synthesized via a two-step procedure, consisting of (1) reacting sulfonamide 2 with n-butylisocyanate in the presence of one molar equivalent of a base such as potassium carbonate in a solvent such as 2-butanone or acetonitrile, to form n-butylsulfonylureas of Formula 9 and (2) reaction of 9 with phosgene using Dabco ® as a catalyst in refluxing xylene as solvent. This method is similar to the preparation found in "Newer Methods of Preparative Organic Chemistry," W. Forest, Ed., Vol. VI, Academic Press, NY, 1967, pp. 223-241. Equation 3b illustrates the procedure.

Equation 3a

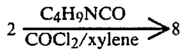

Equation 3b (1)

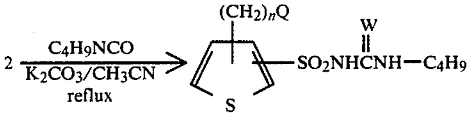

9

(2)

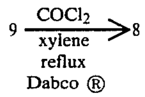

wherein W is O.

Sulfonyl isothiocyanates of Formula 8, wherein W is S, can be prepared by treatment of sulfonamides of Formula 2 with carbon disulfide and potassium hydroxide followed by reaction of the dipotassium salt with phosgene according to K. Hartke, *Arch. Pharm.*, 299, 174.

The compounds of Formula I also are available by the methodology described in South African Application No. 830441 and illustrated by Equation 4. Thienylsulfonamides of Formula 2 react with heterocyclic carbamates of Formula 10 in 1,4-dioxane at 20° to 80° C. for periods of 1 to 24 hours when 1 equivalent of 1,8-diazabicyclo[5.4.0]undec-7-ene (DBU) is added to the reaction mixture. The resultant products are isolated by dilution of the reaction mixture with water, acidification and subsequent filtration. Heterocyclic carbamates of Formula 10 in turn are synthesized by reaction of heterocyclic amines of Formula 5 with diphenyl carbonate or phenyl chloroformate in pyridine at temperatures ranging from 20° to 80° C., as indicated in Equation 4a.

Equation 4

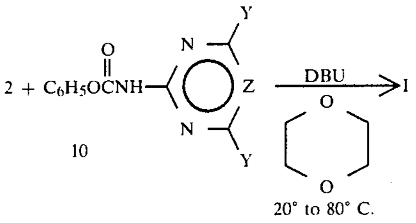

Equation 4a

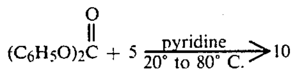

The synthesis of thienylsulfonylureas of Formula I rely upon the requisite intermediate thiophenesulfonamides of Formula 2.

Some of the intermediate sulfonamides of Formula 2 described above can be prepared from amines of Formula 11 by a two-step procedure, as shown in Equation 5. This consists of (5a) diazotizing 11 and coupling the diazonium salt with sulfur dioxide to form a sulfonyl chloride of Formula 12; and (5b) aminating 12 with ammonium hydroxide or anhydrous ammonia to form 2.

Equation 5

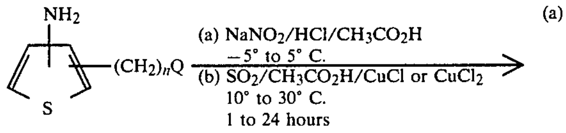

11

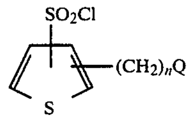

12

12 $\xrightarrow[-20° \text{ to } 40° \text{ C.}]{NH_4OH \text{ or } NH_3}$ 2 (b)

0.5 to 10 hours

The reaction of Equation 5a is accomplished by treating a solution of amine 11 in a mixture of concentrated hydrochloric acid and glacial acetic acid with a solution of sodium nitrite in water at −5° to 5° C. After stirring for 10–30 minutes at about 0° C. to insure complete diazotization, the solution is added to a mixture of an excess of sulfur dioxide and a catalytic amount of copper(I) chloride or copper(II) chloride in glacial acetic acid at about 10° C. The temperature is kept at about 10° C. for ¼ to 1 hour, then raised to 20° to 30° C. and held at that temperature for 2 to about 24 hours. This solution is then poured into a large excess of ice water. The sulfonyl chloride 12 can be isolated by filtration or by extraction into a solvent such as ethyl ether, methylene chloride or, preferably, 1-chlorobutane followed by evaporation of the solvent.

The amination described in the reaction of Equation 5b above is carried out conveniently by treating a solution of the sulfonyl chloride 12 with at least two mole equivalents of anhydrous ammonia in a solvent such as ethyl ether or methylene chloride as −20° to 30° C. If the sulfonamide product 2 is insoluble, it may be isolated by filtration followed by washing out the salts with water. If product 2 is soluble in the reaction solvent, it may be isolated by filtering off the precipitated ammonium chloride and evaporation of the solvent. Additionally, many sulfonamides 2 can be prepared by reaction of corresponding sulfonyl chlorides 12 with excess aqueous ammonium hydroxide in tetrahydrofuran at 0° to about 40° C. for 0.5 to 10 hours. The sulfonamide product 2 is isolated by evaporation of the tetrahydrofuran solvent, addition of water to the residue and filtration.

Alternatively, the intermediate sulfonyl chloride 12 can be prepared as shown below in Equation 6.

Equation 6

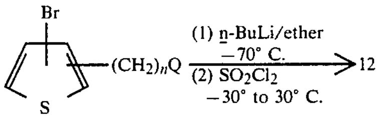

13

According to Equation 6, a lithium salt, prepared by reaction of 13 with n-butyllithium in ether at about −70° C., is added to sulfuryl choride in hexane at about −30° to −20° C. and stirred for 0.5 to 10 hours at −30° to 30° C. to yield sulfonyl chloride 12, according to teachings of S. N. Bhattacharya, C. Earborn and D. R. M. Walsh, *J. Chem Soc.* (*C*) 1968, 1265 and H. Quast and F. Kee, *Synthesis* 1974, 489. Subsequent reaction of 12 with ammonia or ammonium hydroxide as described above provides the corresponding sulfonamide.

Starting with an appropriate bromothiophene, and carrying out the procedures described in Equation 6, or simple modification thereof, one skilled in the art may prepare some of the other sulfonyl chlorides of Formula 12 described above. Of necessity, the reactions are limited to those cases in which the substituent $(CH_2)_nQ$ is inert to lithium reagents under the conditions of the reactions, which will be obvious to one skilled in the art. For a general review of metallation with lithium reagents, see H. W. Gschwend and H. R. Rodriguez, *Org. Reactions* 1979, 26, 1.

Some sulfonamides 2 are best prepared by the procedure of Equation 7 below.

Equation 7

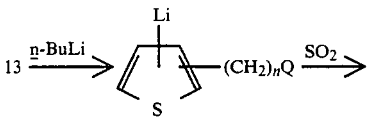

-continued

Equation 7

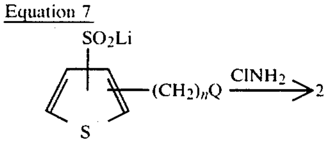

14

The preparation of sulfinic acid salts 14 by the procedure of Equation 7 is well known in the art; see U.S. Pat. No. 4,127,405 and H. W. Gschwend et al., loc. cit.. Sulfonamides 2 are best prepared by treatment of sulfinic acid salts with chloramine. In this procedure an ethereal solution or suspension of the salt 14 is treated at low temperature (25° to −30° C.) with a dry ethereal solution of chloramine. The reaction is stirred for a period of several minutes to several hours. After filtration, the reaction mixture is washed with aqueous bisulfite, dried and the solvent removed on a rotary evaporator. The crude product is further purified by usual methods such as crystallization or chromatography.

In the reaction shown in Equation 8, a thienylcopper compound of Formula 15 is reacted with an iodo- or bromoheterocycle ($X(CH_2)_nQ$ where X is I or Br and n is 0, 1 or 2) in a solvent such as pyridine or quinoline. The copper compounds of Formula 15 are prepared by reacting the corresponding lithium compounds with cuprous iodide or cuprous bromide in a solvent such as a diethyl ether. The detailed procedures for this type of reactions are described in the following references: M. Nilsson and C. Ullenius, *Acta Chem. Scand.* 1970, 24, 2379–2388; C. Ullenius, *Acta Chem. Scand.* 1972, 26, 3383–3386.

Equation 8

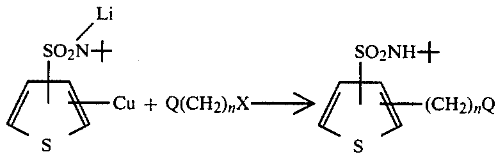

15 16

Treatment of the compounds of Formula 16 with an acid catalyst in an alcohol solvent or in trifluoroacetic acid removes the t-butyl group to yield compounds of Formula 2 as shown in Equation 9.

Equation 9

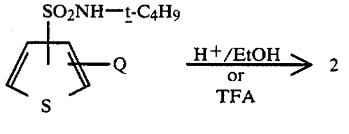

16

In the syntheses outlined above, the generalized designation of compounds of Formula I is meant to imply the $(CH_2)_nQ$ substituents and the sulfonylurea functional group are bonded to the thiophene ring in adjacent positions corresponding to one of the three possible combinations designated as Formula Ia, Ib, or Ic in the summary of the invention. It will be convenient for purposes of expediency and clarity of this teaching to use this generalized formula further in this disclosure. All values of Q, n, n', R, $R_1$, $R_2$, $R_3$, $R_3'$, $R_3''$, $R_4$, $R_5$, $R_6$, $R_7$, $R_8$, $R_9$, $R_{10}$, $R_{11}$, n', W, W', W'', A, X, Y, and Z are those described in the summary of the invention unless otherwise noted.

The heterocyclic thiophenesulfonamides of Formula 2 are important starting materials for the preparation of compounds of Formula I of this invention and specific examples are prepared by the following methods.

In the specific case where Q is Q-1 and n is 0, compound 17 can be prepared by the reaction sequence shown in Equation 10.

Equation 10

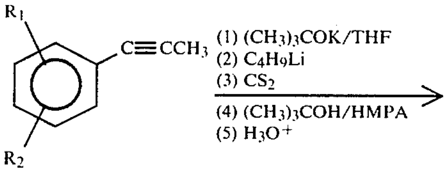

18

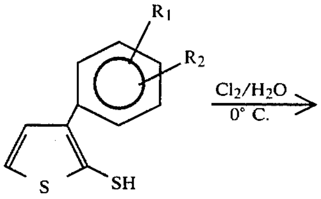

19

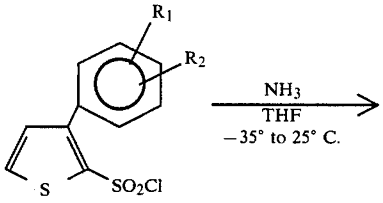

20

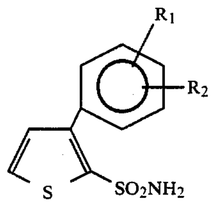

17

In this synthetic sequence, a 1-phenylpropyne of Formula 18 is metallated with excess base. Addition of carbon disulfide leads to a phenyl-substituted ketene dithiolate, which undergoes intramolecular cyclization to give 19 after proton quenching. The conditions necessary for this transformation are described by R. L. P. DeJong and L. Brandsma, *J. Organometal. Chem.* 1982, 238, C17. Mild oxidative chlorination of 19 leads to a sulfonyl chloride of Formula 20, which is converted to the sulfonamide 17 by treatment with ammonia in THF solution at temperatures of −35° to 25° C.

Alternatively, 17 can be prepared by route of Equation 11. 3-Phenylthiophene 21 reacts with n-butyllithium in diethyl ether at 25° C. for 0.5 hour to form lithiated intermediates which may be quenched using sulfuryl chloride. The resultant sulfonyl chlorides 20 and 20a then are treated with ammonia in THF solution as before to give 17 and isomeric 17a. The desired 17 can be isolated by chromatographic techniques known by one skilled in the art. Metallation of 21 has been described by R. Teardini, G. Martelli, P. Spagnolo, and M. Tiecco *J. Chem. Soc.*, C. 1970, 1464. For further details, cf. Equation 13.

Equation 11

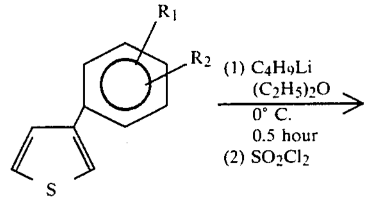

21

20 +

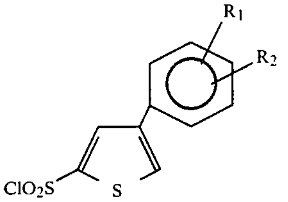

20a

20 + 20a

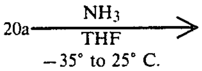

17 +

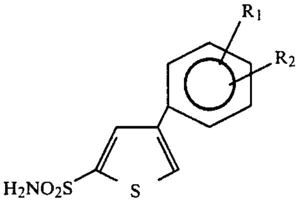

17a

Other useful intermediates are known in the art. 2-Phenyl-3-bromothiophene (Q-1, n is 0) may be prepared by the procedure of N. Gjoca and S. Gronowitz *Acta Chem. Scand.* 1972, 26, 1851; 3-bromo-2,2′-bithiophene (Q-2, W′ is S, n is 0) and 3-bromo-2,3′-bithiophene (Q-3, W′ is S, n is 0) by the procedure of, for instance, S. Gronowitz, J. Skramstad and B. Eriksson, *Ark. Kemi* 1967, 28, 99.

When n is 1 or 2, application of organocopper methodologies known to one in the art yield substituted thiophenes of Formula 21a, as shown in Equation 11a. Thus, a dithienylcopperlithium of Formula 21b can be reacted with alkylhalides of Formula H to yield 21a; conversion to sulfonamide 17b can be accomplished by means of Equation 11.

Equation 11a

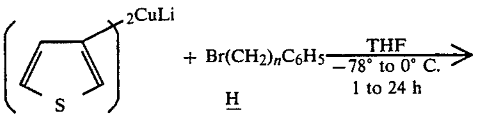

21b

-continued

Equation 11a

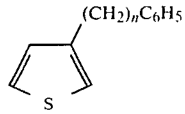

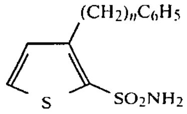

21a 17b

For the isomeric compounds of Formula 17b with generic structures of Formulae 2b and 2c, similar chemistry as in Equation 11a beginning with 2,3-dibromo- or 3,4-dibromothiophene will provide the requisite intermediates.

Equation 12 describes the synthesis of 3-(2-furanyl)- and 3-(2-thienyl)thiophenes of structure 24 (Q-2, n is 0).

Equation 12

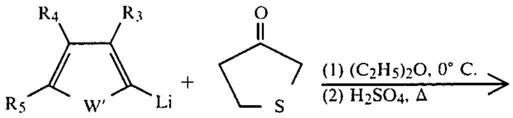

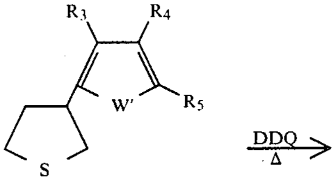

22

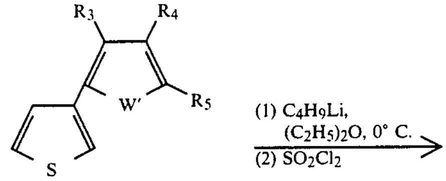

23

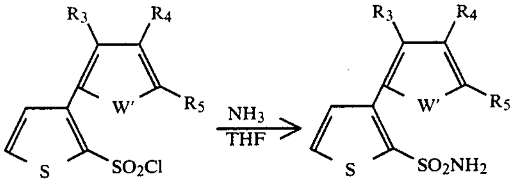

24a 24

According to the work described by H. Wynberg, A. Logothetis, and D. Verploeg *J. Am. Chem. Soc.* 1957, 79, 1972, 2-lithiofuran or 2-lithiothiophene is added to 3-ketotetrahydrothiophene in diethyl ether at a temperature of 0° C. The reaction is quenched with and distilled from sulfuric acid to afford 3-substituted dihydrothiophenes of Formula 22, which are dehydrogenated using 2,3-dichloro-5,6-dicyano 1,4-benzoquinone (DDQ), giving thiophenes of Formula 23. These thiophenes can be metallated in the 2-position selectively and can be added to sulfuryl chloride in hexane solution, resulting in sulfonylchlorides of Formula 24a which are converted into the desired sulfonamides 24 by treatment with ammonia in THF solution.

For those cases in which n is 1 or 2, a procedure entirely analogous to that of Equation 12 may be used, beginning with Q-2 synthons of Formula 200 (available commercially or obtained by methods obvious to one skilled in the art);

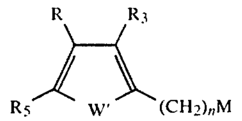

200 compounds of Formula 24b ultimately will be produced

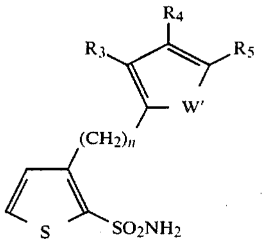

24b

Starting with the appropriate 3-substituted thiophene and following the metallation procedure indicated in Equation 12 or simple modification thereof, one skilled in the art may prepare many of the sulfonamides of Formula 2a. Only those 3-substituents which are inert to metallating reagents relative to the desired 2-metallation of the thiophene nucleus are compatible with this synthetic strategy; such substituents will be obvious to one skilled in the art.

In complement to the metallation-sulfonation sequence illustrated by Equation 12, equivalent metallation-sulfination may be performed to obtain the sulfonamides of Formula 2a. The latter sequence is described by Equation 13 and is entirely analogous to that of Equation 7.

Equation 13

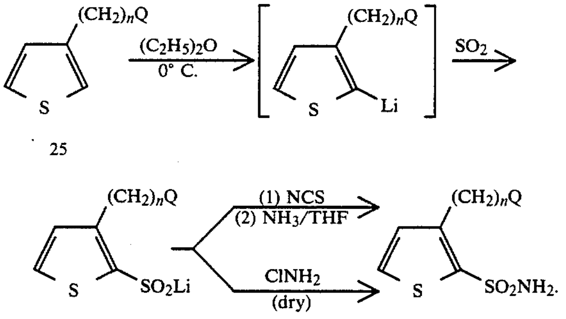

25 26 2a

Once sulfinate salts of Formula 26 have been made, they may be transformed into sulfonamides 2a directly by reaction with chloramine as described by G. H. Coleman and C. R. Hauser *J. Am. Chem. Soc.* 1928, 50, 1193. Sulfinate salts of Formula 26 also may be converted to 2a in a two-step process: chlorination to afford a sulfonyl chloride, as practiced by J. F. Sculley and E. V. Brown *J. Org. Chem.* 1954, 19, 894; W. E. Trull and E. Wellisch *J. Am. Chem. Soc.* 1952, 74, 5177 and Y. K. Yuriev and N. K. Sadavaya *J. Gen. Chem. USSR* 1964, 34, 1814 and treatment of the sulfonyl chloride with ammonia in an ethereal solvent such as THF. Any of these procedures also are compatible with those sulfinate salts of Formula 14 generated via Equation 7.

The use of the strategy of Equation 7 is especially appealing in those cases where metallation of the 3-substituted thiophene of Formula 25 in the 2-position is not possible due to the reactivity of the $(CH_2)_nQ$ substituent under the conditions of metallation. Formation of the 2-brominated thiophene 27 allows for exceedingly facile, mild halogen-metal exchange conditions to be used, as shown in Equation 14.

Equation 14

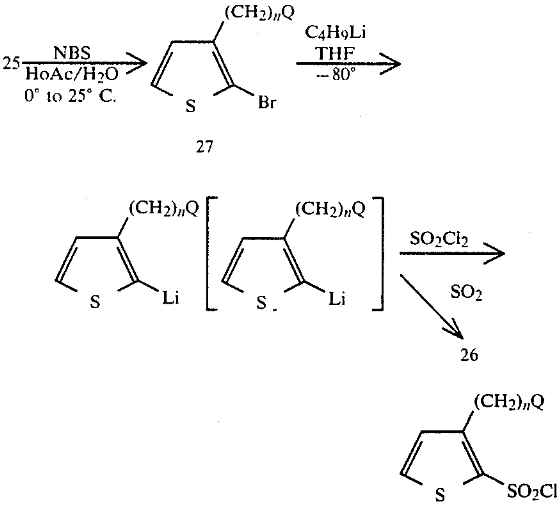

27 26 28

Electrophilic aromatic bromination of 3-substituted thiophenes of Formula 25 leads to the 2-brominated compound of Formula 27 selectively, as shown in the teachings of S. Gronowitz, P. Moses and A. B. Hornfeldt *Ark. Kem.* 1962, 17, 165. Subsequent halogen-metal exchange and sulfination with sulfur dioxide gives the sulfinate salt 26 or sulfination with sulfuryl chloride leads to the sulfonyl chloride 28.

In still other cases where $(CH_2)_nQ$ will suffer addition of most nucleophiles, $(CH_2)_nQ$ can be placed at the 3-position of the thiophene nucleus after the sulfonamide moiety or its synthetic equivalent has been incorporated at the 2-position. This strategy is shown in Equation 15.

Equation 15

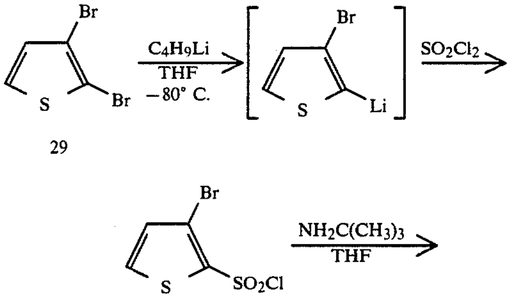

29 30

-continued

Equation 15

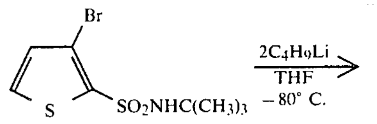

31

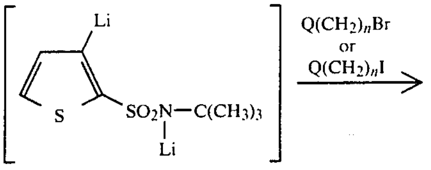

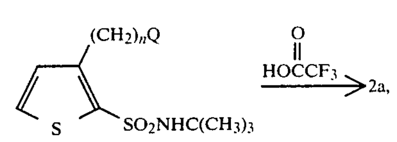

32

2,3-Dibromothiophene, 29 can be lithiated preferentially at the 2-position and treated with sulfuryl chloride to give the sulfonyl halide 30. Treatment with tert-butylamine results in the tert-butyl-protected sulfonamide of Formula 31. A second lithiumhalogen exchange reaction allows for an addition of the substituent $(CH_2)_nQ$, which may be added as an intact entity or as a synthetically equivalent substructure.

Given the general techniques of Equations 12 through 15, sulfonamides of Formula 2a may be prepared by the methods described below.

Compounds of Formula 35 can be prepared by use of the reaction sequence illustrated in Equation 16.

Equation 16

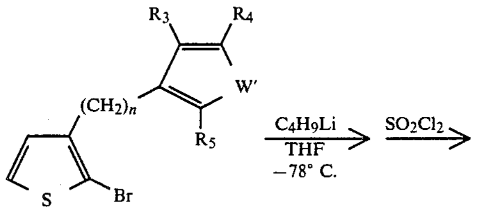

33

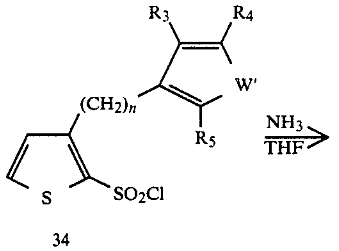

34

-continued

Equation 16

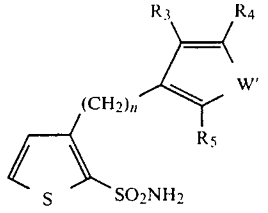

35

3-(3-Furanyl)- and 3(3-thienyl)-2-bromothiophenes of Formula 33 may be prepared from the methods of Y. Tamaru, Y. Yoshimi and Z. Yoshida, *Tetrahedron* 1979, 35, 329 or straightforward modifications thereof. By route of Equation 14 sulfonyl chlorides of Formula 34, and consequently sulfonamides 35, are obtained.

Using the procedure of C. Ullenius, *Acta. Chem. Scand.* 1972, 26, 3383 and M. Nilsson and C. Ullenius, *Acta. Chem. Scand.* 1970, 24, 2379 compounds of Formula 36 (Q-2, W=O, n=0) and 37 (Q-3, W'=0, n=O) can be prepared as shown in Equation 17. For those cases in which n is 1 or 2, straightforward modification of Equation 17 using the appropriate furanylcopper species will result in the desired thienylbromide of Formula 37a.

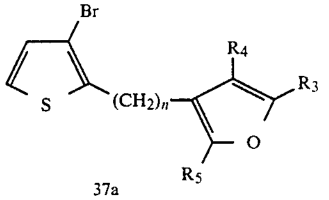

37a

Equation 17

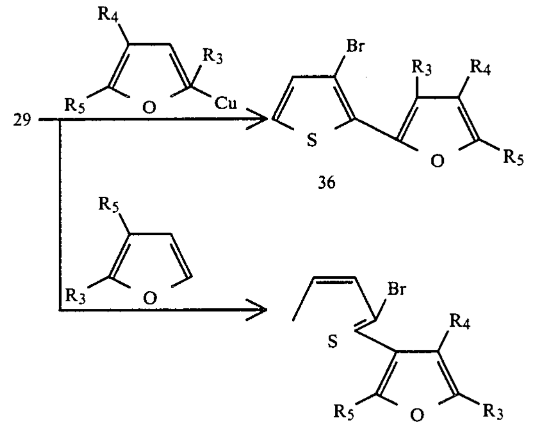

Sulfonamides containing a tetrahydrofuran or tetrahyrothiophene group (Q-4, Q-5, Q-6, W'=O, S) can be prepared by catalytic reduction of the corresponding furan or thiophene compounds as shown in Equation 18.

Equation 18

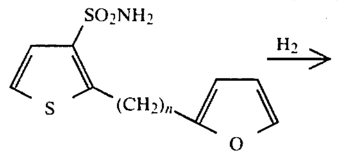

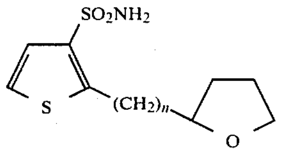

38

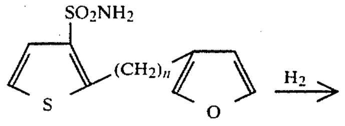

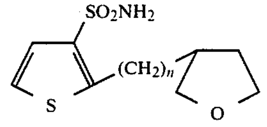

39

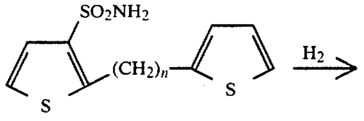

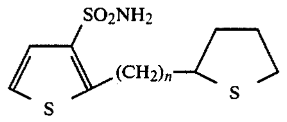

40

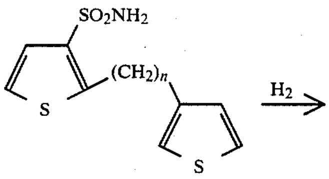

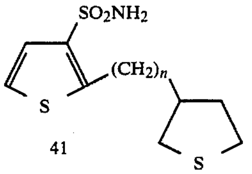

41

Selective reductions of the type shown in Equation 18 are well known in the literature. The choice of catalyst, solvent, pressure and temperature for reduction of furans has been reviewed by Samuel Sevadesh in "The Furans" by A. P. Dunlop and F. N. Peters, Reinhold Publishing Corporation, New York, N.Y. 1953, pp. 674–713; and by P. N. Rylander in "Catalytic Hydrogenation in Organic Synthesis"; Academic Press, 1979, pp. 227–234. The reduction of thiophenes is reviewed by H. D. Hartough in "Thiophene and Its Derivatives"; The Chemistry of Heterocyclic Compounds Series, Interscience Publishers, Inc., New York, N.Y. 1952, pp. 167–169.

Compounds of Formula 42 can be prepared as shown in Equation 19.

Equation 19

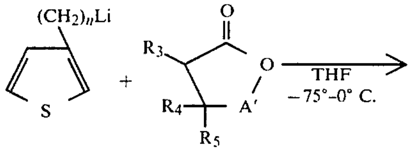

L

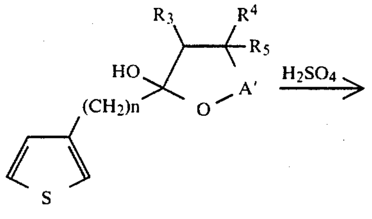

43

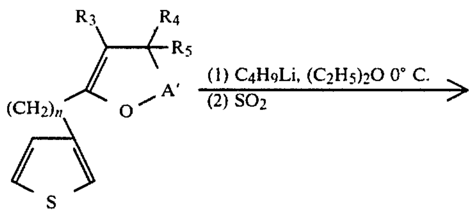

44

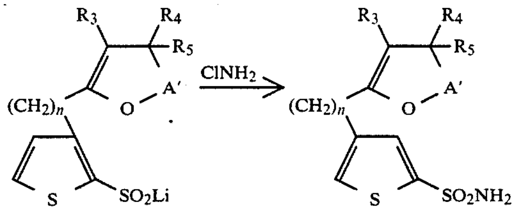

45 42 wherein A'=

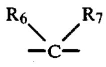

or

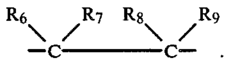

According to Equation 19, a lithiothiophene is reacted with lactone L at −78° to 0° C. in an ethereal solvent such as THF to form lactol 43. The lactol may be dehydrated using a strong acid such as sulfuric acid to form the thiophene of Formula 44. 44 may be lithiated by the route of Equation 13, using n-butyllithium as lithiating agent and diethyl ether as solvent at a temperature of about 0° C. Quenching of the reaction gives lithium sulfinates of Formula 45, which are isolated by evaporation of the reaction solvent. The sulfinate is treated with chloramine to yield 42. If desired, selective hydrogenation will yield compounds of Formula 46 ($R_4$=H).

3-(2-Tetrahydrofuranyl)- and 3-(2-tetrahydrapyranyl)thiophenes of Formula 46 also can be prepared as illustrated in Equation 20.

Equation 20

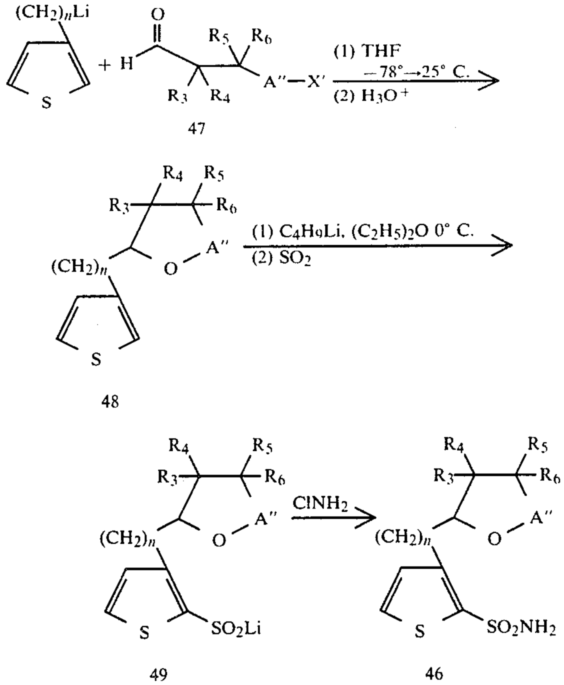

47

48

49

46 wherein A″=

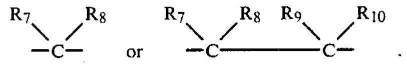
or

Reaction of a lithiothiophene with haloaldehydes of Formula 47 in inert solvents such as THF at temperatures of −78° to 25° C. affords thienylalkoxides which undergo intramolecular cyclization yielding cyclic ethers 48. These in turn are converted to sulfonamides 46 via the methods of Equation 13: metallation in diethyl ether with n-butyllithium at a temperature of ca. 0° C., followed by sulfination using sulfur dioxide gives lithium sulfinate 49. 49 in turn is treated with chloramine to give the target compound 46.

Sulfonamides of Formula 50 are prepared in a manner analogous to that of Equation 12, as shown by Equation 21.

Equation 21

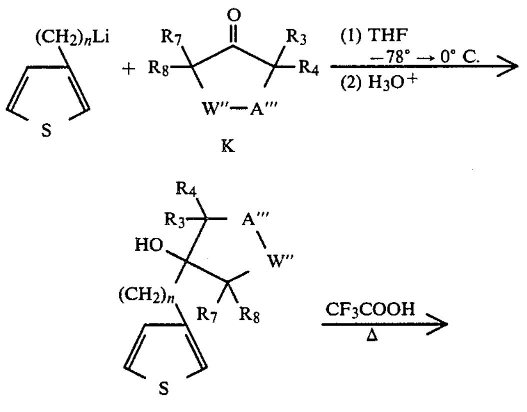

K

51

-continued

Equation 21

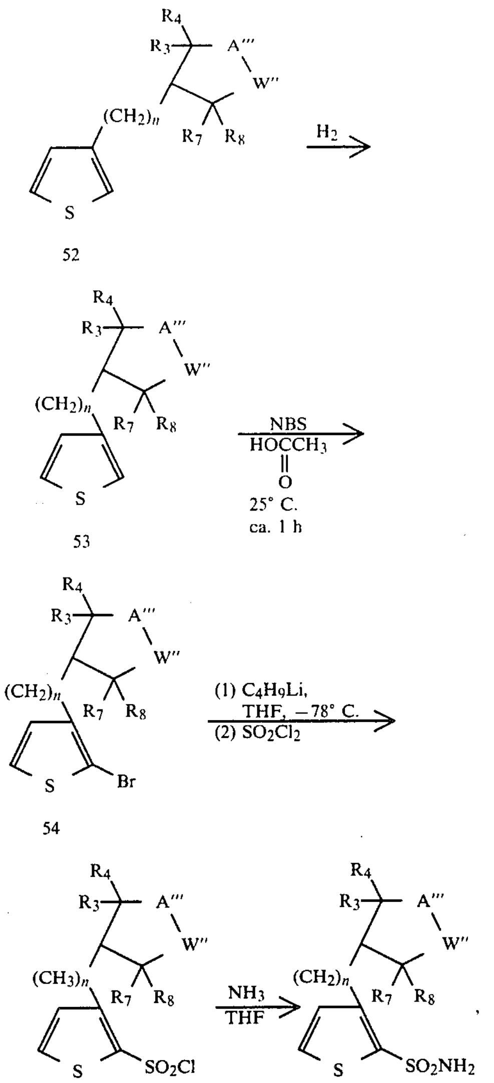

52

53

54

55

50 wherein A‴=

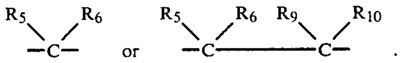
or

A lithiothiophene reacts with ketones of Formula K to give, after proton quench, tertiary alcohols of Formula 51. 51 is dehydrated, using a strong acid such as trifluoroacetic acid, resulting in compounds of Formula 52 as mixtures of double bond isomers that are selectively hydrogenated to give 53. Bromination using N-bromosuccinimide in acetic acid for ca. 1 hour at ambient temperatures results in bromides of Formula 54; these bromides undergo halogen-metal exchange as described in Equation 14 to lead to sulfonamides of Formula 50.

Compounds of Formula 56 (Q-7, n is 0) can be prepared as shown in Equation 22 by the reaction of the sodium salt of pyrrole with the bromothiophenesulfonamide in DMF with copper oxide catalyst.

Equation 22

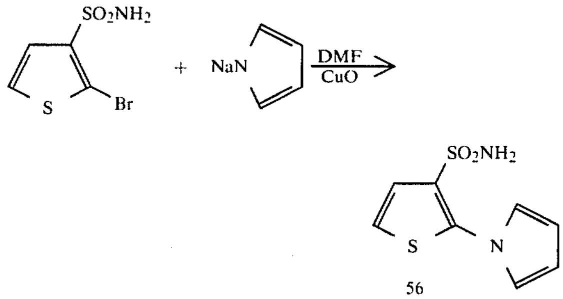

56

Alternatively, a 2-aminothiophene-3-sulfonamide can be prepared and reacted with 1,4-dicarbonyl compounds to give substituted compounds of Formula 60 as shown in Equation 23.

Equation 23

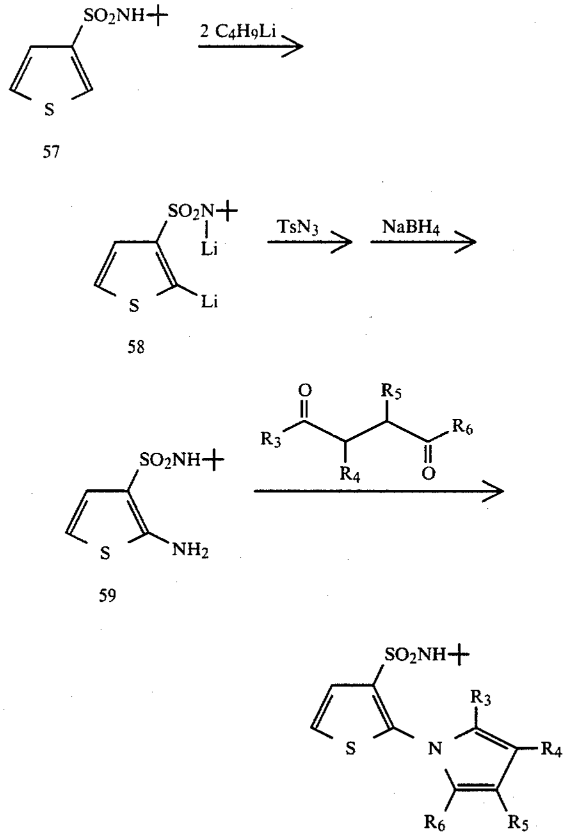

57

58

59

60

The tert-butyl sulfonamide of Formula 57 is treated with two equivalents of n-butyllithium at −50° to 80° C. in tetrahydrofuran to give the dilithio salt 58 by analogy with the teaching of J. G. Lombardion, *J. Org. Chem,* 1971, 36 1843. Treatment of 58 with tosylazide followed by reduction with sodium borohydride gives the aminothiophenesulfonamide 59 by the procedure of J. N. Reedy and V. Smeckus *Tetrahedron Lett.* 1983, 3795. Condensation with a 1,4-dicarbonyl compound gives the compound of Formula 60. Removal of the t-butyl group affords the free sulfonamide.

3-(1-Pyrrolyl)thiophene 61 can be synthesized by the methods of V. Effi, M. Cugnonde Sevricourt, S. Rault and M. Robba, *Heterocycles* 1981, 16, 1519. Its conversion to the sulfonamide 62 is described in Equation 24.

Equation 24

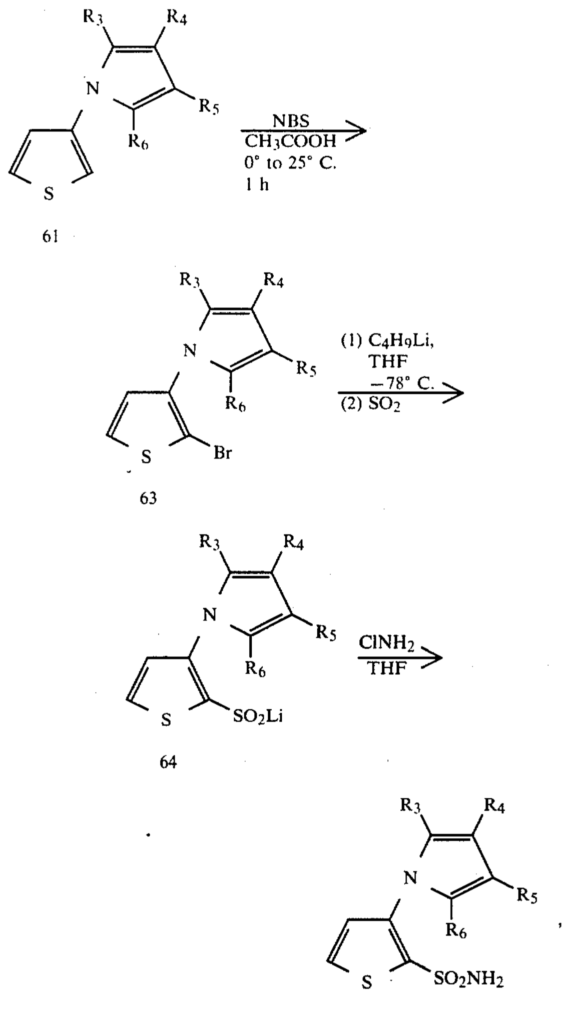

61

63

64

62

Selective 2-bromination of 61 may be performed by the use of NBS in acetic acid at temperatures of around 0° to 25° C. for 1 hour, resulting in compound of Formula 63. Using the process described in Equation 14, halogen-metal exchange in THF at −78° C. and quenching with sulfur dioxide gives lithium sulfinate 64. Amination using chloramine subsequently yields the sulfonamides of Formula 62.

Compounds of Formula 61a can be prepared using the route of Equation 24a.

Equation 24a

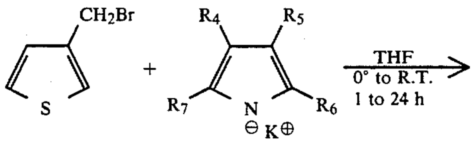

-continued

Equation 24a

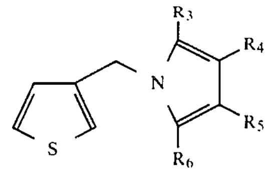

61a

Compounds of Formula 61b are prepared according to Equation 24b.

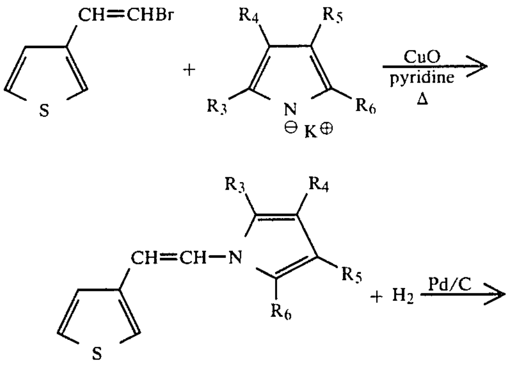

61c

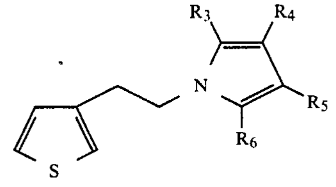

61b

Both 61b and 61a may be converted to sulfonamides of Formula 62a by means of Equation 24.

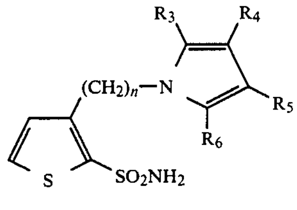

62a

The thiophene of Formula 70 (Q-9, n is 0) can be prepared as shown in Equation 26.

Equation 26

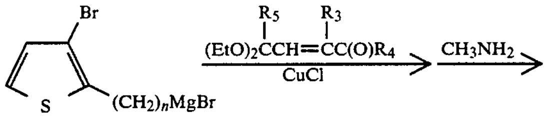

-continued

Equation 26

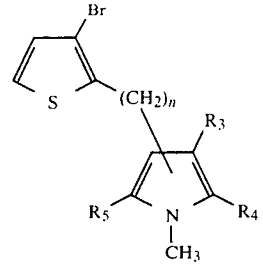

70

The condensation reaction of Equation 26 is well known in the art and has been reviewed by A. R. Jones and G. P. Bean in "The Chemistry of Pyrroles"; Academic Press, New York, N.Y. 1977. 3-(1-Methylpyrrol-3-yl)-thiophenes of Formula 71 may be synthesized according to Equation 27.

Equation 27

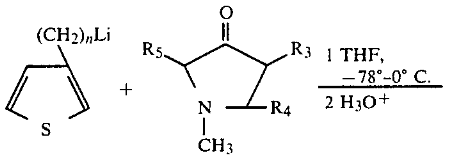

72

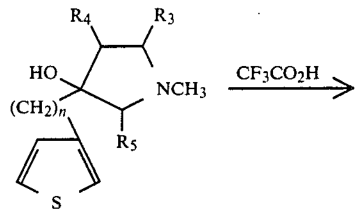

73

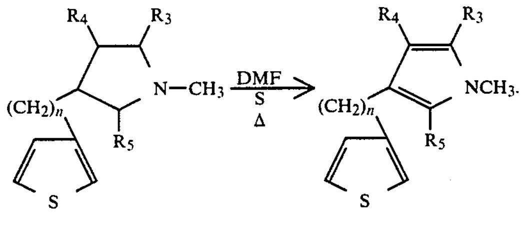

74 71

In a reaction similar to Equation 12, a lithiothiophene attacks the 1-methyl-3-pyrrolidinone, 72, in THF solution at temperatures of −78° to 0° C., resulting in tertiary alcohol 73. Dehydration of 73 by a strong acid such as trifluoroacetic acid results in dehydration products of Formula 74 as a mixture of regioisomers. Dehydrogenation of 74 in hot DMF with sulfur yields 71. Compounds of Formula 71 are converted to the respective sulfonamides of Formula 75 by route of the methods of Equation 14.

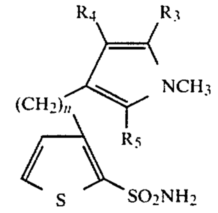

75

Certain methods of synthesis leading to the intemediate sulfonamides of this invention are similar for many values of Q in each of the three possible isomeric arrangements.

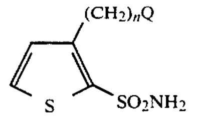

2a

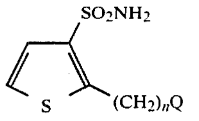

2b

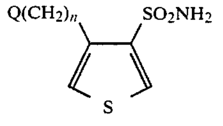

2c

It will be convenient to use the following generalized formulas in this disclosure when certain synthetic methods are applicable to all the necessary isomers.

In the outlined synthesis below, the use of $X^1$ and another substituent on the thiophene ring in undesignated positions is meant to imply that the values indicated are in adjacent positions and that when $X^1$ is in the 2-position, it is hydrogen and when in the 3-position it is bromine.

An example showing the preparation of certain (5-isoxazolyl)thiophenes of Formula 76 (Q-10, W″=O, n is 0) is shown in Equation 28.

Equation 28

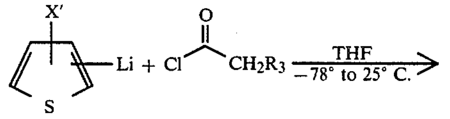

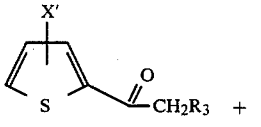

77

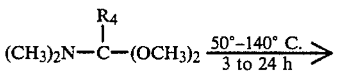

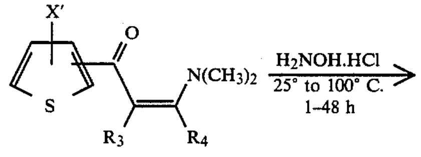

78

-continued

Equation 28

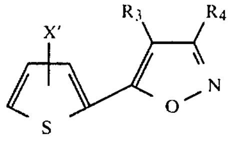

76 wherein X′ is 2-H or 3-Br

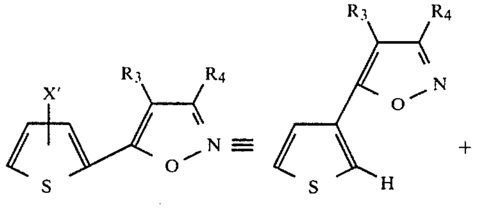

76a

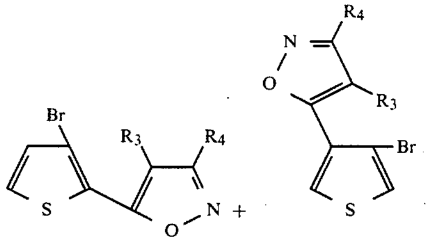

76b 76c

The lithiothiophene is reacted with an acylchloride in THF solution at temperatures of −78° to 25° C., yielding ketones of Formula 77. Treatment of these ketones with dimethyl alkanamide dimethylacetals in solvents such as toluene or DMF at temperatures of 50° to 140° C. for a period of 3 to 24 hours results in β-amino α,β-unsaturated ketones of Formula 78. Details of this class of reactions may be found in *Technical Information Bulletin*, "DMF Acetals"; Aldrich Chemical Co., December 1973 and Y. Lin and S. A. Lang, *J. Org. Chem.* 1980, 45, 4857. 78 is treated with hydroxylamine hydrochloride in solvents such as ethanol or aqueous 1,4-dioxane at temperatures of 25° to 100° C. for 1 to 48 hours and the product 76 is isolated by addition of water to the reaction medium and extraction into methylene chloride. Similar procedures are described by Y. Lin and S. A. Land, *J. Heterocycl. Chem.* 1977, 14, 345. Compounds of Formula 76 can be converted to the appropriate sulfonamides of Formula 79, by the procedures of Equation 13.

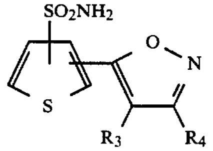

79

For those cases where n is 1 or 2, a modification of Equation 28 may be employed to yield sulfonamides of Formula 79a. Equation 28a illustrates this modification.

Equation 28a

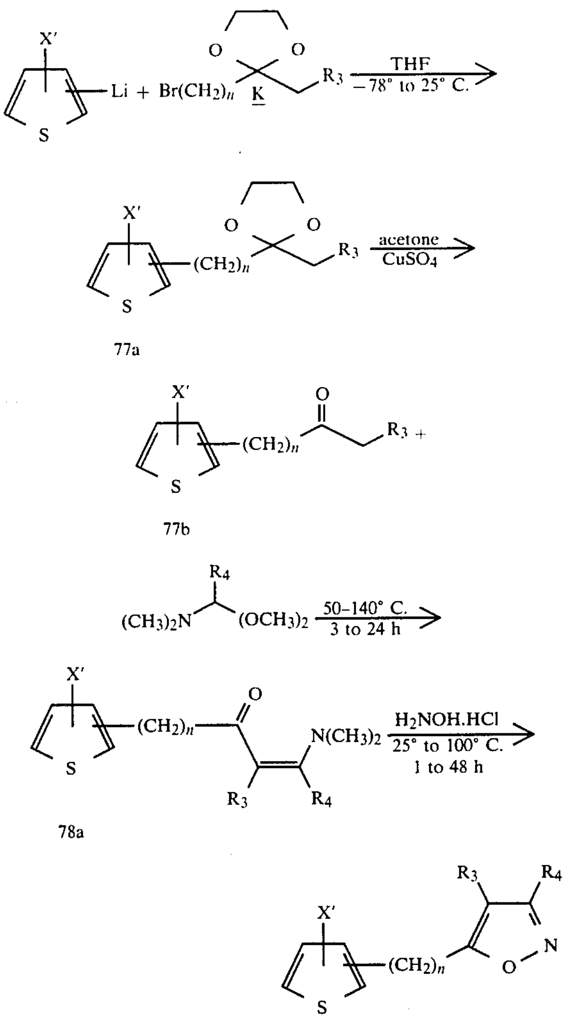

77a

77b

78a

76d

The appropriate lithiothiophene is reacted with an alkyl bromide of Formula K to give the thienylketals of Formula 77a. Transketalization using acetone and anhydrous copper (II) sulfate yield ketones of Formula 77b, which are converted to isoxazoles of Formula 76d in a manner entirely analogous to that described for Equation 28. The compounds of Formula 76d are converted to the appropriate sulfonamides of Formula 79a by the procedures of Equation 13.

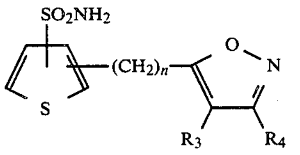

79a

Similarly, 5-isothiazolylthiophenes (Q-10, W'=S, n is 0) of Formula 80 can be synthesized from the thioanalogues of 78, as shown by Equation 29; those isothiazolylthiophenes (Q-10, W'=S, n is 1 or 2) of Formula 80a can be prepared in a similar fashion, as illustrated in Equation 29a.

Equation 29

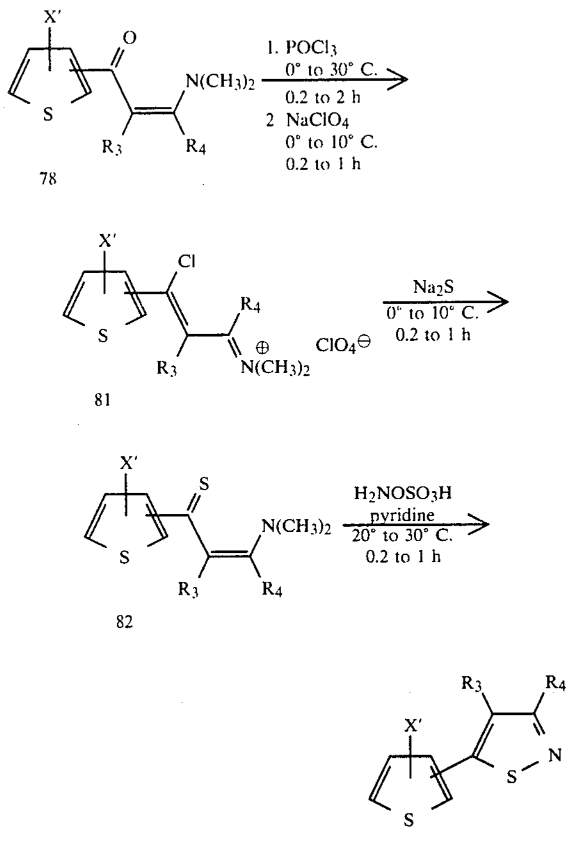

78

81

82

80 wherein X' is 2-H or 3-Br.

Equation 29a

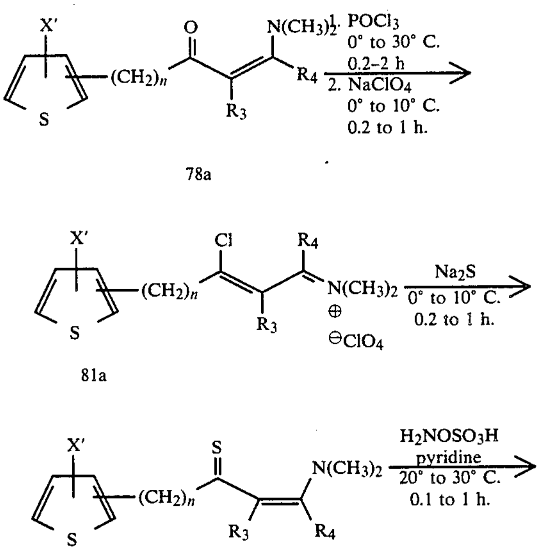

78a

81a

82a

-continued

Equation 29a

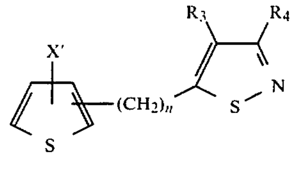

80a

Compounds of Formula 78 can be treated with phosphorous oxychloride in methylene chloride at 0° to 30° C. for 0.2 to 2 hours and followed by addition of sodium perchlorate in water at 0° to 10° C. for 0.2 to 1 hour to form perchlorate salts of Formula 81. Subsequently, 81 can be reacted with sodium sulfide monohydrate in DMF and water at 0° to 10° C. for periods of 0.2 to 1 hour to form thiones of Formula 82. Finally, these thiones will react with hydroxylamine-O-sulfonic acid and 2 equivalents of pyridine in methanol at temperatures of 20° to 30° C. for 0.2 to 1 hour to give 80. Thiophenes 80 and 80a may be converted to sulfonamides of Formula 83 and 83a by route of Equation 13.

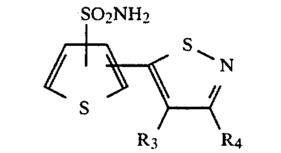

83

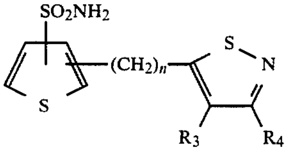

83a

The preparation of thiophenes of Formula 84 (Q=Q-11, W'' is $NR_{11}$) and 85 (Q=Q-10, W'' is $NR_{11}$) is illustrated in Equation 30.

Equation 30

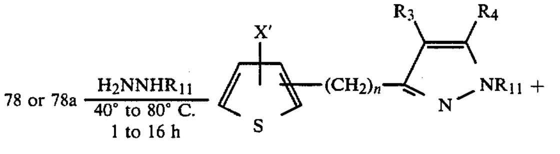

84

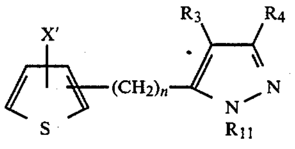

85

The α,β-unsaturated ketones of Formulae 78 and 78a from Equation 28 and 28a can be reacted with hydrazines in refluxing ethanol for periods of 1 to 16 hours. The product mixture of thiophenes of Formulae 84 and 85 are isolated by chromatographic methods which are well known to those skilled in the art. Conversion of either 84 or 85 to the corresponding sulfonamides of Formulae 86 and 87 proceeds by way of the processes described in Equation 14.

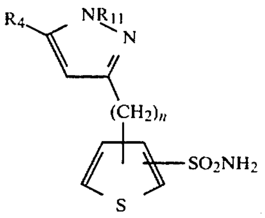

86

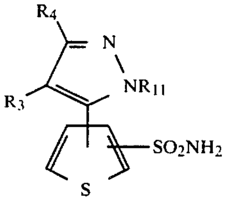

87

Equation 31 depicts the synthesis of 3-(3-isoxazolyl)-thiophenes of Formula 91.

Equation 31

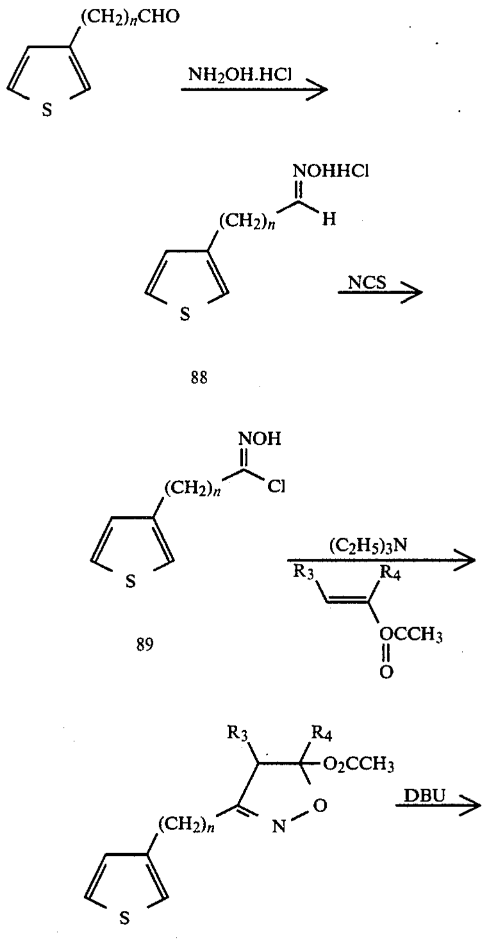

88

89

90

-continued

Equation 31

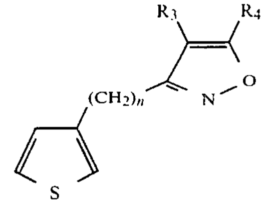

91

The 3-thienylaldehyde is reacted with hydroxylamine hydrochloride in ethanol to form oximes of Formula 88. These oximes are chlorinated by means of N-chlorosuccinimide (NCS), yielding chlorides of Formula 89 which, when reacted with vinyl acetates in the presence of one molar equivalent of triethylamine, undergo addition-cyclization to form acetates of Formula 90. Oxidative extrusion of acetic acid in hot DBU transforms 90 into thiophenes of Formula 91. Conversion to sulfonamides of Formula 92 can be accomplished by application of the chemistry described by Equation 13.

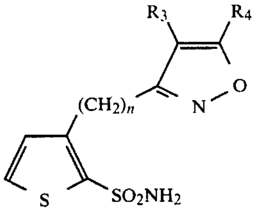

92

Equation 32 below illustrates a method for preparing 3-(3-bromothienyl)isoxazoles of Formula 93.

Equation 32

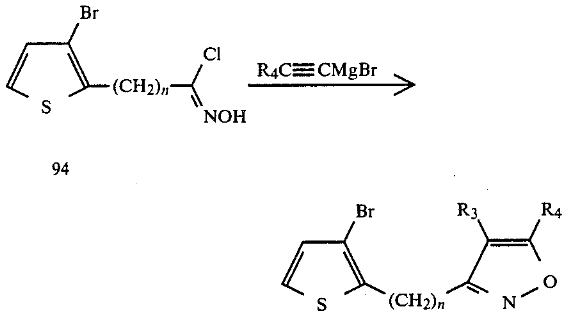

94

93 where $R_3$=H.

The reaction of Equation 32 is run by procedures similar to those taught by M. Lanella et al., *Chim. Ind.* (Milan) 1965, 47, 996 and by G. Gaudiano et al., *Gazz. Chim. Ital.* 1959, 89, 2466. Thus, a 3-bromo-2-thiophenehydroxamic acid chloride of Formula 94 is reacted with an appropriate acetylenic Grignard reagent in tetrahydrofuran at 0° to 30° C. for 1 to about 16 hours. The product is isolated by addition of water and ammonium chloride and extraction with methylene chloride. The acetylenic Grignard reagents are prepared from substituted acetylenes by procedures described in the cited references.

Another method of preparation of compounds of Formula 93 is shown in Equation 33.

Equation 33

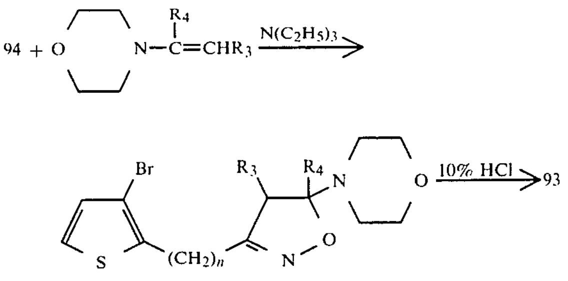

95

The reactions of Equation 33 above can be run by procedures similar to those described in G. Bianchetti et al., *Gazz. Chim. Ital.* 1963, 93, 1714. Thus, in Equation 33, 94 is reacted with an equimolar amount of triethylamine and a N-alkenylmorpholine in chloroform at reflux for 0.2 to about 1 hour to form a 5-(N-morpholino)-3-substituted-isoxazoline of Formula 95, which then is reacted with 10% hydrochloric acid at reflux for about 0.2 to 0.5 hour to from 93. The product 93 is isolated by extraction with methylene chloride.

Similarly, a reaction of the hydroxamic acid chloride with a vinyl acetate rather than an enamine can yield compounds of Formula 93 by the procedure of R. Micetich, *Can. J. Chem.* 1970, 48, 467.

(3-Isothiazolyl)thiophenes of Formula 96 can be prepared according to Equation 34.

Equation 34

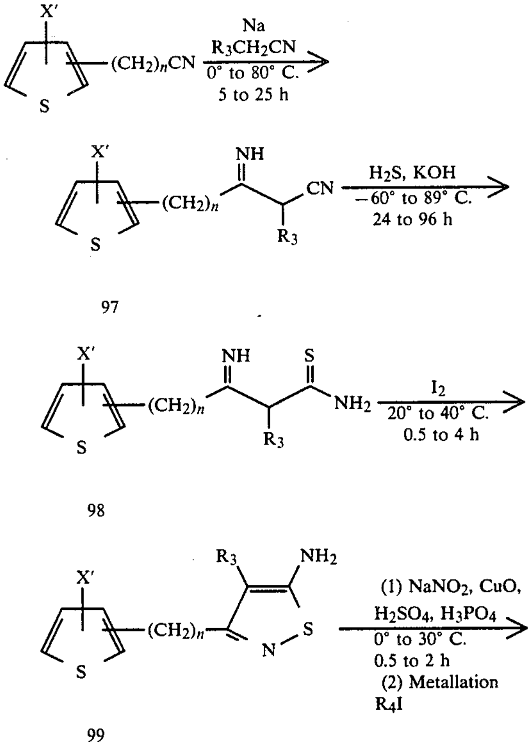

97

98

99

-continued

Equation 34

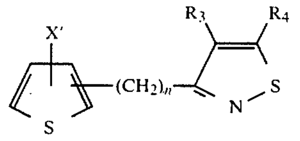

96

In Equation 34, the cyanothiophene can be reacted with an appropriate alkyl nitrile and sodium in a solvent such as ether or toluene at 0° to 80° C. for approximately 5 to 25 hours, forming mononitriles of Formula 97. Similar transformations may be found in U.S. Pat. No. 3,479,365, Netherlands No. 6,608,094 and T. Naito, S. Nakagawa, J. Okumura, K. Takahashi, K. Masuka and Y. Narita, *Bull. Chem. Soc. Japan* 1968, 41, 965. 97 can be reacted with hydrogen sulfide in the presence of a catalytic amount of potassium hydroxide in methylene chloride at −60° to 80° C. in a sealed vessel for 24 to 96 hours to give iminothioamides of Formula 98. Such a reaction parallels the work of T. Naito, S. Nakagawa and K. Takahashi, *Chem. Pharm. Bull.* 1968, 16, 148 and J. Goerdeles and H. Pohland, *Chem. Ber.* 1961, 94, 2950. Compounds of Formula 98 are cyclized by treatment with iodine in ether, chloroform or ethanol solution with potassium carbonate used as base at temperatures of 20° to 40° C. for 0.5 to 4 h, giving amines of Formula 99 in a manner similar to ibid., Netherlands No. 6,608,094 and J. Goerdeler and H. Pohland, *Angew. Chem.* 1962, 72, 77. Diazotization of 99 by nitrous acid generated in situ and reaction of the resultant diazonium salt with copper(II) oxide in 50% phosphoric acid at 0° C. for 2 hours followed by optional selective metallation and alkylation forms 96, in analogy to M. Beringer, B. Prijs and H. Erlenmeyer, *Helv. Chim. Acta* 1966, 49, 2466. Conversion to the corresponding sulfonamide 100 is accomplished using the synthetic scheme described in Equation 13.

100

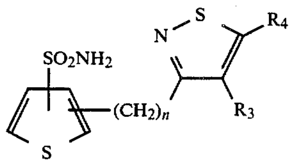

As shown in Equation 35 below, (3-bromothienyl-)isoxazoles of Formula 101 (Q-12, W'' is O) can be prepared by reacting compounds of Formula 102 with hydroxylamine hydrochloride.

Equation 35

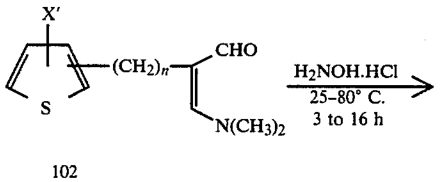

102

-continued

Equation 35

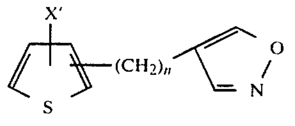

101

The reaction of Equation 35 is run in ethanol at 25° to 80° C. for 3 to 16 hours. The product is isolated by addition of water and extraction with methylene chloride. The product is purified by recrystallization or column chromatography. The starting materials are prepared by known methods, e.g., V. Hengartner et al., *J. Org. Chem.*, 1979, 44, 3748. For compounds of Formula 101a with substituents on the isoxazole ring, the reactions of Equation 36 illustrate a procedure similar to those described by H. Yasuda, *Yakugaku Zuschi*, 1959, 79, 623 and Bobranski and Wojtowski, *Roczniki Chem.*, 1964, 38, 1327.

Equation 36

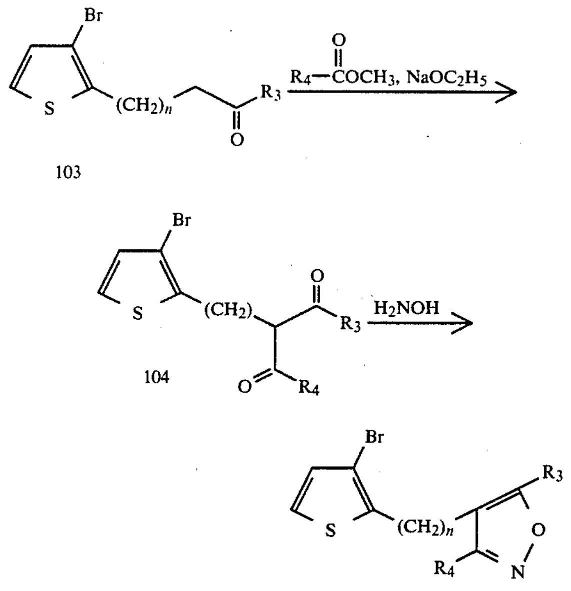

103

104

101a

4-Substituted isothiazoles of Formula 105 can be prepared in a manner analagous to that of Equation 29, beginning with those compounds of Formula 102. Subsequent conversion to sulfonamides of Formula 106 can be achieved by means of Equation 8.

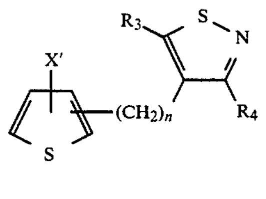

105

-continued

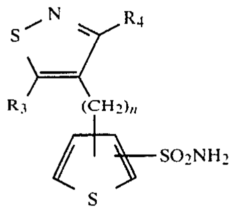

106

(1-Methylpyrazol-4-yl)thiophenes of Formula 107 (n=0) are prepared by the teachings of S. Liljefors and S. Gronowitz, *Chem. Scr.* 1979, 15, 102. The respective sulfonamides of Formula 108 may be synthesized by the methods described in Equation 8. When n is 1 or 2, the thiophenes of Formula 107, and their respective sulfonamides 108 are prepared in an analogous manner.

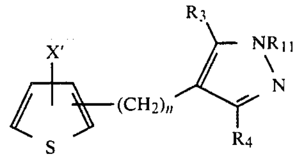

107

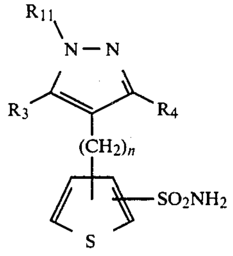

108

Equations 37 and 38 illustrate the preparation of (2-oxazolyl)thiophenes of Formula 109. Details of these preparations may be found in W. E. Cass, *J. Am. Chem. Soc.* 1942, 64, 785 and "Heterocyclic Compounds"; Vol. 5, R. C. Elderfield, Ed, J. Wiley and Sons, NY, 1957, Ch. 5.

Equation 37

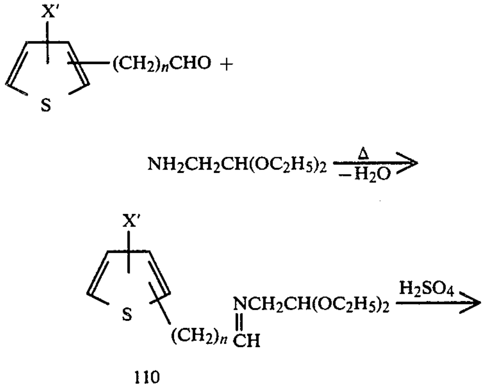

110

-continued

Equation 37

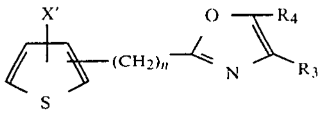

109 wherein $R_3$ and $R_4$ are H.

Equation 38

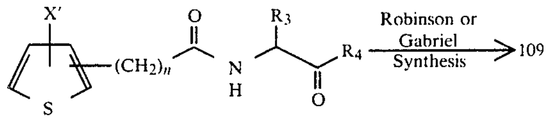

111

Thiophenes of Formula 109 can be converted to the corresponding sulfonamides of Formula 112 by the methods described in Equation 13.

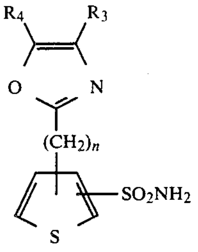

112

(2-Thiazolyl)thiophenes of Formula 113 can be prepared by the procedure of Equation 39.

Equation 39

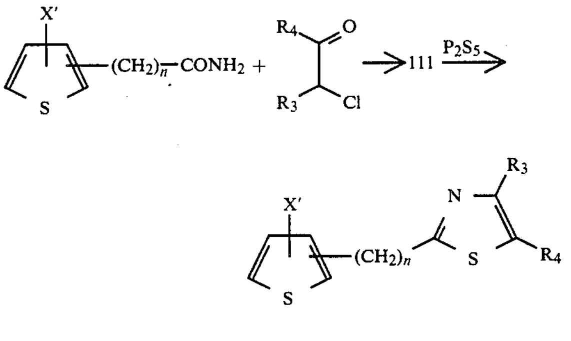

113

For details concerning the synthetic methods involved, see ibid. Conversion to sulfonamides of Formula 114 is accomplished using the techniques illustrated in Equation 13.

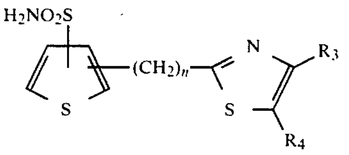

114

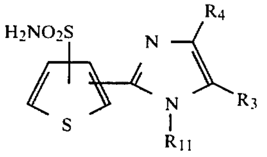

116

(1-Methylimidazol-2-yl)thiophenes of Formula 115 can be prepared by the method shown in Equation 40.

Equation 40

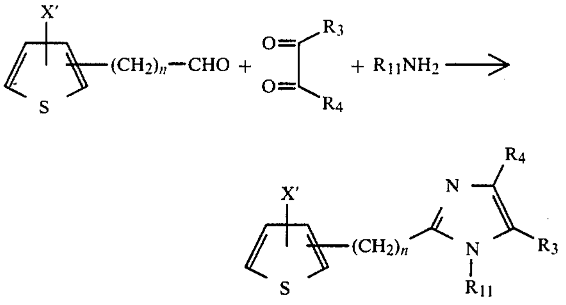

115

A condensation reaction between the thienylaldehyde, an α-diketone and an excess of an amine leads to imidazoles of Formula 115. For detailed discussion of such reactions, cf. ibid., Ch. 4, 5 and 8. Sulfonamides of Formula 116 can be prepared from 115 by means of Equation 13.

Equations 41, 42 and 43 show the synthetic approaches that can be taken to generate (5-oxazolyl)thiophenes of Formula 117.

Equation 41

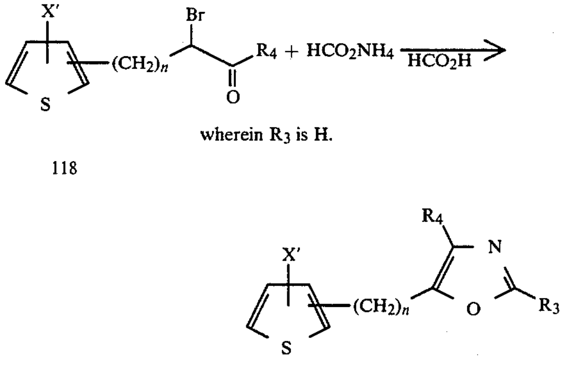

118

117

Equation 42

-continued

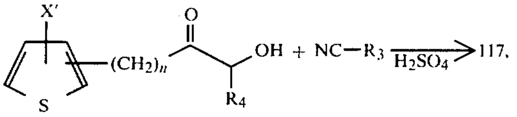

119

Equation 43

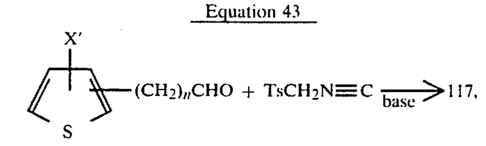

wherein $R_3$ and $R_4$ are H and Ts=

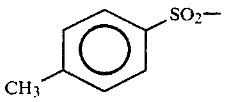

Details of the reactions depicted in Equations 39 and 40 are found in ibid., Ch. 5. The procedural details for Equation 41 are described by A. M. Van Leusen, B. E. Hogenboom and H. Serderius, *Tetrahedron Lett.* 1972, 2369. Compounds of Formula 118 are available by a route identical to or closely resembling the preparation of compounds of Formula 103 and subsequent bromination of the appropriate methylene moeity: details of such brominations have been recorded by S. Gronowitz. *Ark. Kem.* 1958, 13, 295. α-Hydroxyketones of Formula 119 in Equation 42 may be prepared from the appropriate thienylcarboxylic acid chlorides and appropriate 1,1,2,-tris[(trimethylsilyl)oxy]alkenes: cf. A. Wissner, J. E. Birnbaum and D. E. Wilson, *J. Med. Chem.* 1980, 23, 715. In all cases, transformation to sulfonamides of Formula 120 can be accomplished via Equation 13.

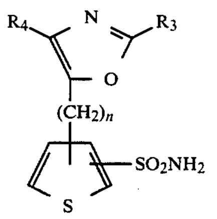

120

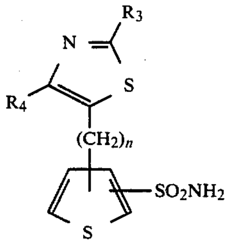

122

The analagous (5-thiazolyl)thiophenes of Formula 121 are prepared according to the process indicated in Equation 44, which is a straight-forward modification of Equation 41, above. Like synthons of Formula 117, those Formula 121 are converted to sulfonamides of Formula 122 by means of Equation 13.

Equation 44

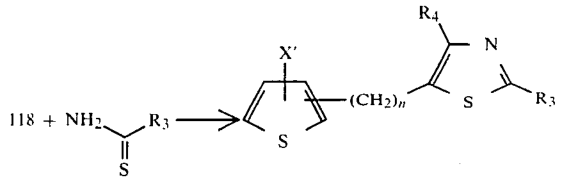

121

(5-Imidazolyl)thiophenes of Formula 123 are prepared according to Equation 45.

Equation 45

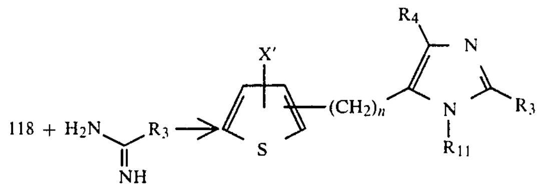

123

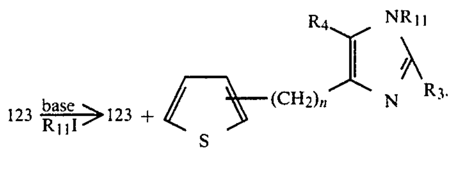

124

Reaction of the appropriate α-haloketone of Formula 119 with an amidine yields imidazoles of Formula 123 with $R_{11}=H$. N-alkylation may be achieved using common procedures, evident to those skilled in the art, to give compounds of Formula 123 and 124. Sulfonamides of Formula 125 and 126 are prepared via Equation 14.

125

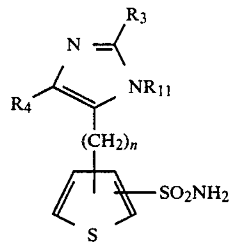

126

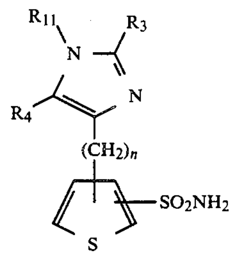

(4-Oxazolyl)thiophenes of Formula 127 can be prepared by procedures analogous to those described in Equations 41 or 42; substituent limitations and sulfonamide preparation to give compounds of Formula 128 via Equation 13 remain the same.

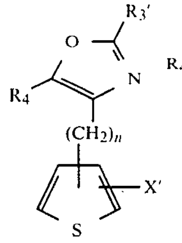

127

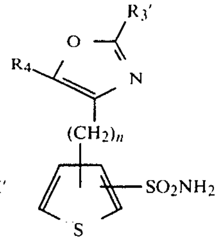

128

An alternative synthesis of the oxazoles of Formula 127 is shown in Equation 45a. It is analogous to that shown in Equation 41.

Equation 45a

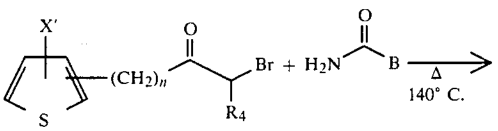

127a

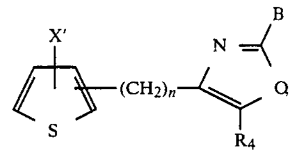

127b wherein $B=C_1-C_3$ alkyl, amino.

In the case where B=amino for compounds of Formula 127b, Sandmeyer-type reaction conditions afford new 2-substituted oxazoles, as shown in Equation 45b.

Equation 45b

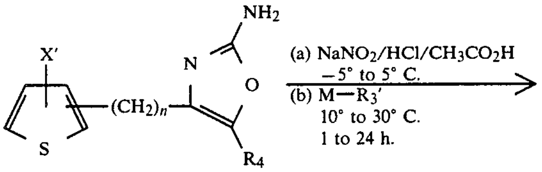

127b

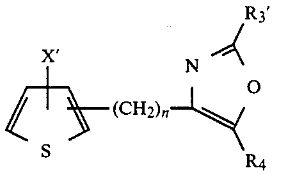

127

The (4-thiazolyl)thiophenes of Formula 129 are prepared in a manner analogous to that shown in Equation 45 using the thioamide of Equation 44. These thiazoles are transformed into sulfonamides of Formula 130 using the method of Equation 7. Analogously, the procedures using Equations 45a and 45b also will give thaizoles of Formula 129.

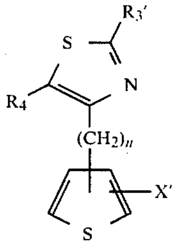

129

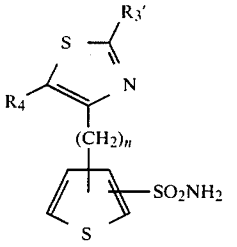

130

Compounds of Formula 131 or 132 (Q-16, W'=O) can be prepared by the procedures of the example shown in Equation 46.

Equation 46

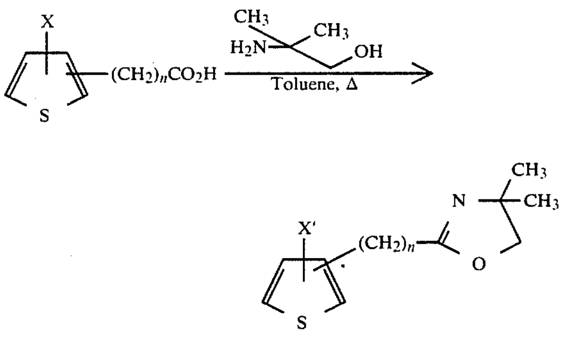

131

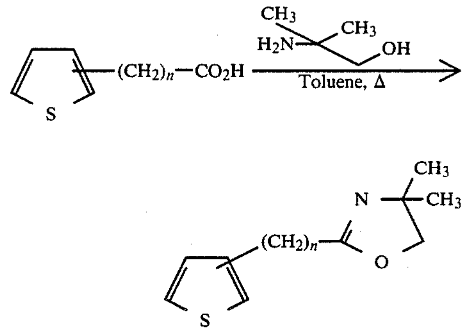

133

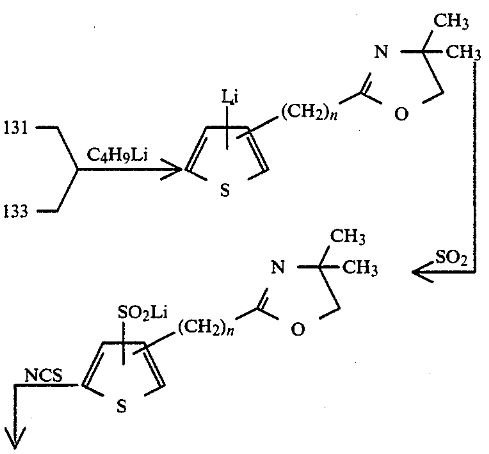

-continued

Equation 46

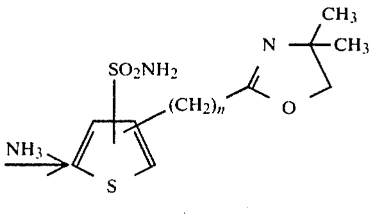

132

The formation of the 1,3-oxazolines of Equation 46 are prepared by heating the carboxylic acid and the appropriate amino alcohol in toluene to remove water by the procedure of H. L. Wehrmeister, *J. Org. Chem.*, 1961, 26, 3821. The product oxazoline 133 or 131 can be lithiated with n-butyllithium in ether solvent. Treatment with $SO_2$ and conversion to compounds of Formula 132 is carried out by the procedures outlined in Equation 13 or as shown in Equation 46 by oxidation of the sulfinate salt with NCS (N-chlorosuccinimide) followed by amination using $NH_3$.

Synthesis of intermediate oxazolines, thiazolines and imdiazolines where Q is Q-16 (W is S), Q-17 and Q-41 can be prepared by procedures similar to Equation 46 or by methods known in the art.

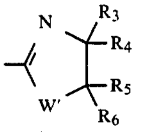

Q-16

W' = S

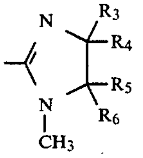

Q-17

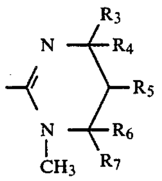

Q-41.

For supplementary methods see:

R. C. Elderfield, op. cit.

R. J. Fern and J. C. Riebsomer, *Chem. Rev.* 1954, 54, 543.

R. H. Wiley and L. L. Bennett, Jr., *Chem. Rev.* 1944, 44, 447.

Compounds of Formula 134 (Q-18, n is 0) can be prepared by the procedure of S. Gronowitz and S. Liljefors, *Chem. Scr.* 1979, 13, 157 as shown in Equation 47.

Equation 47

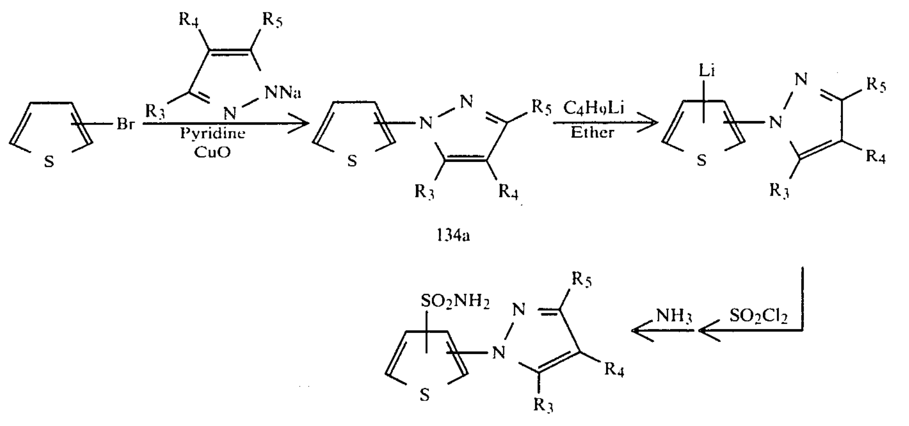

134a

134

According to Equation 47, a bromothiophene is reacted with the sodium salt of a pyrazole in pyridine containing a copper catalyst. The thienylpyrazole is lithiated and can be reacted with sulfuryl chloride by the procedures of S. N. Bhattacharya et al., *J. Chem. Soc., C,* 1968, 1265 to give compounds of Formula 134.

In those cases for Q-18 where n=1 or 2, the appropriate thiophenes of Formula 134c are prepared according to Equation 47a.

Equation 47a

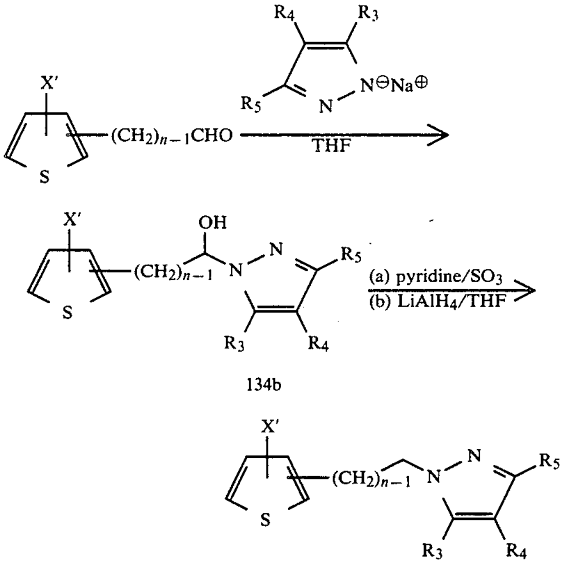

134b

134c

Conversion to the sulfonamides of Formula 134d is accomplished in a way identical to that shown in Equation 13.

In an analogous manner, compounds of Formula 135 or 136b (Q-19) can be prepared by the procedures shown in Equations 48 and 49.

Equation 48

-continued

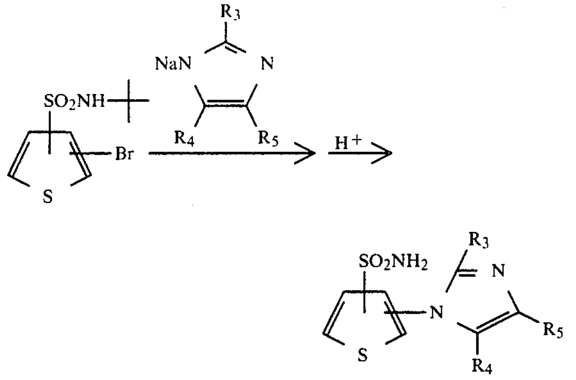

135

Equation 49

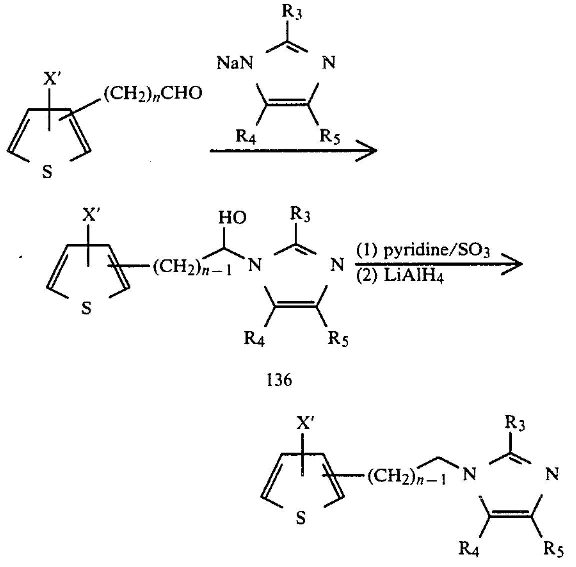

136

136b

The reactions are conducted in the presence of the appropriate solvent such a dimethylformamide, N-methylpyrolidone, THF or pyridine at temperatures from ambient to reflux for a period of one to twenty-four hours.

Equation 50 indicates the synthesis of thiophenes of Formula 137, bearing a Q-20 substituent.

Equation 50

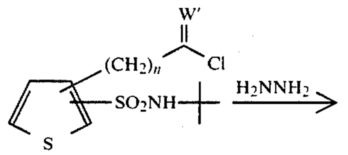

138

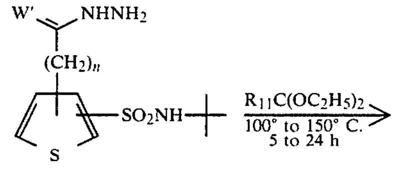

139

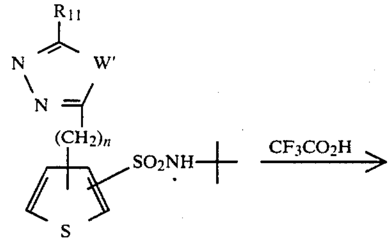

140

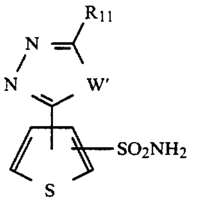

137

A chloride of Formula 138, when reacted with hydrazine, will result in a hydrazide of Formula 139. According to U.S. Pat. No. 3,808,223, reaction of 139 with an orthoester at 100° to 150° C. for 5 to 24 hours will yield oxadiazoles of Formula 140. Deprotection of the sulfonamide moiety using a strong acid such as trifluoroacetic acid results in the desired sulfonamides of Formula 137. Synthesis of the starting thiophenes of Formula 138 can be accomplished by the methods taught in European Patent Application No. 30,142.

Equation 50a illustrates the preparation of thiophenes of Formula 137a where $R_3$ is $SR_{12}$.

Equation 50a

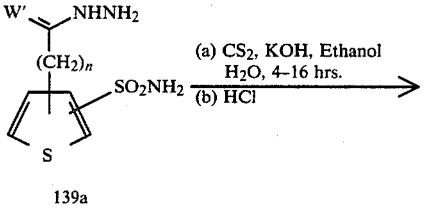

139a

-continued

Equation 50a

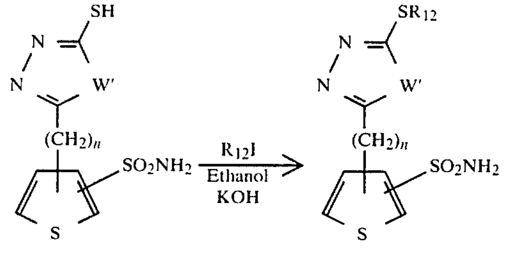

140a 137a wherein $R_{12}$=$C_1$-$C_4$ alkyl, $C_3$-$C_4$ alkenyl, $C_3$-$C_4$ alkynyl, $C_1$-$C_3$ cyanoalkyl, methoxycarbonylmethyl, ethoxycarbonylmethyl, methylcarbonylmethyl, or halogen.

The reactions of Equation 50a are run according to similar procedures described in E. Hoggarth, *J. Chem. Soc.* 4811 (1952). Thus, the hydrazide is reacted with carbon disulfide in ethanol in the presence of a base, such as potassium hydroxide at reflux for 4-16 hours, followed by addition of water and acidification with hydrochloric acid to form compound 140a. Further reaction of compound 140a with $R_{12}I$ in ethanol in the presence of base gives compound 137a.

Compounds of Formula 141 (Q-21, W'=O) are prepared by the procedure of P. DuBus, B. Decroix, J. Moreland and P. Pastour, *Ann. Chim.* (*Paris*) 1975, S14 t10, p 331 as shown in Equation 51.

Equation 51

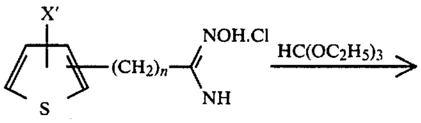

142

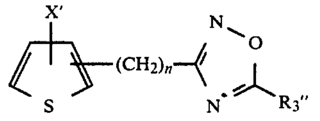

141

Compound 142 is reacted with excess triethylorthoformate at 100° to 150° C. for 1 to 24 hours to afford 141 ($R_3''$=H). $R_3''$ may be optionally substituted with Cl or Br by selective deprotonation and quenching with NCS or NBS, respectively.

For $R_3''$=$CH_3$, Compound 142 is reacted with acetylchloride and $BF_3.Et_2O$ according to U.S. Pat. No. 3,270,029.

Analogously, 1,3,4-thiadiazol-5-ylthiohenes of Formula 143 may be prepared following the techniques described by C. Ainsworth and R. G. Jones, *J. Am. Chem. Soc.* 1955, 77, 621 and H. Weidinger and J. Kranz, Ber. 1963, 96 1059.

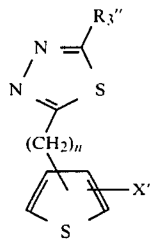

143

Equation 52 illustrates the preparation of 1,2,4-thiadiazol-3-ylthiophenes of Formula 144.

Equation 52

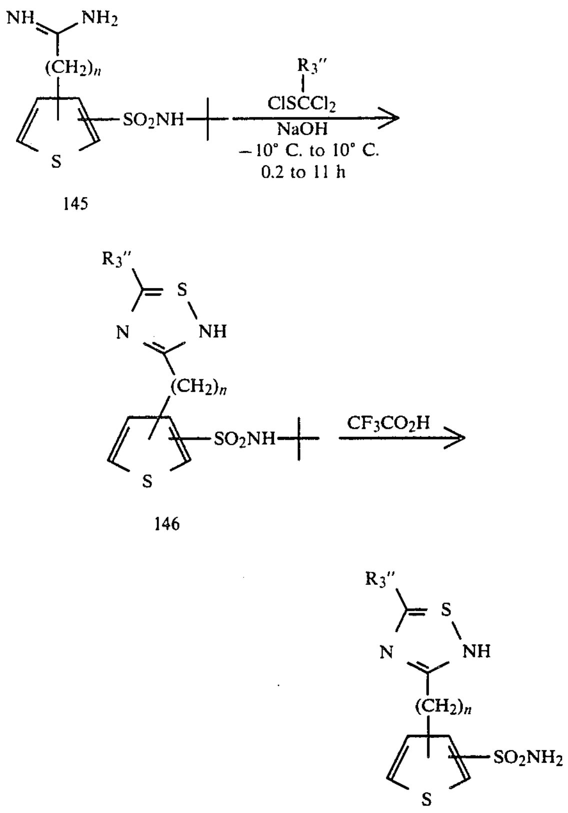

145

146

144

The reactions of Equation 52 may be run following similar methods found in J. Goerdeler and M. Budnowski, M. *Chem. Ber.* 1961, 94, 1682. Thus, an amidine of Formula 145, obtained via the corresponding carboxylate is treated with dichloromethylsulfenyl chloride and sodium hydroxide in a solvent such as aqueous 1,4-dioxane at temperatures of about 0° C. for 0.2 to 11 hours to form thiophene of Formula 146. Deprotection with a strong acid affords sulfonamide of Formula 144.

Y. Lin, S. A. Land, M. F. Lovell and N. A. Perkinson, *J. Org. Chem.*, 1979, 44, 4160 indicate methods of the formation of 1,2,4-oxadiazol-5-ylthiophenes of Formula 148, as shown in Equation 53.

Equation 53

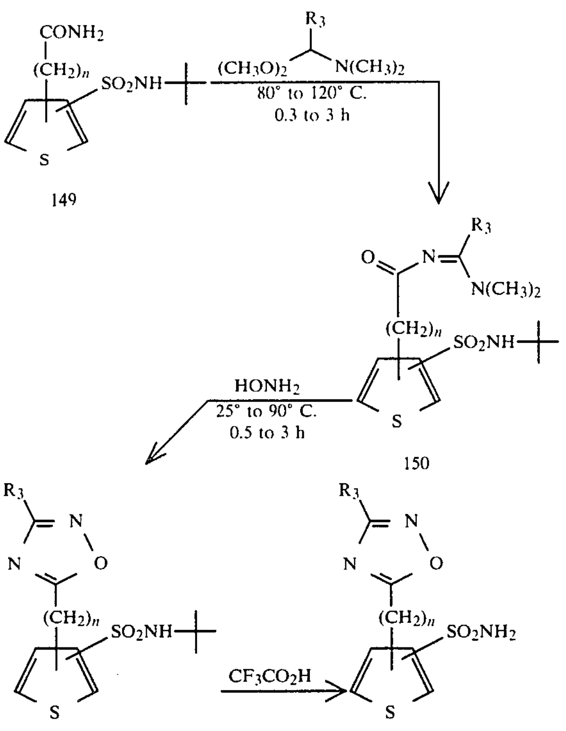

149

150

151

148

An amide of Formula 149, available by amination of the corresponding carboxylate is reacted with an excess of an alkanamide dimethylacetal at 80° to 120° C. for 0.3 to 3 hours, forming compounds of Formula 150. These compounds can be dissolved in aqueous 1,4-dioxane-acetic acid and reacted with hydroxylamine at temperatures ranging between 25° to 90° C. over 0.5 to 3 hours to form oxadiazoles of Formula 151, which are subsequently (or perhaps concomitantly) deprotected using a strong acid to give sulfonamides of Formula 148.

In a strictly analogous manner, using conditions similar to those described by Equation 53, 1,2,4-thiadiazol-5-ylthiophenes of Formula 152 can be prepared; cf. Y. Lin and S. A. Lang, *J. Org. Chem.* 1980, 45, 3750.

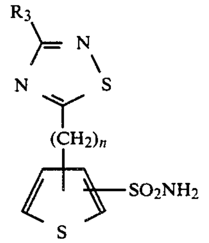

152

The 1,2,4-thiadiazol-4-ylthiophenes of Formula 153 can be prepared by the teachings of U.S. Pat. No. 3,940,407 and C. D. Hund and R. I. Mori, *J. Am. Chem. Soc.* 1955, 77, 5359. Equation 54 illustrates this process.

Equation 54

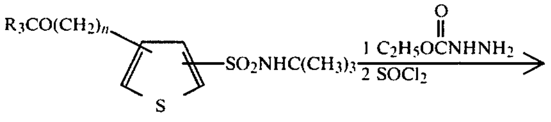

154

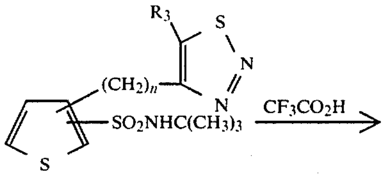

153

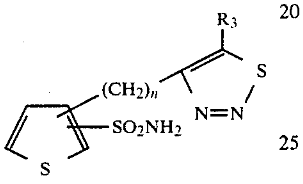

155

Ketones of Formula 154 react with ethyl carbazate to form the corresponding hydrazide; subsequent reaction with thionyl chloride results in compounds of Formula 155. Deprotection of these compounds using standard conditions leads to sulfonamides of Formula 153.

1,2,5-Thiadiazol-3-ylthiophenes of Formula 156 can be prepared from thiophenes of Formula 31 by several known methods, such as those of L. M. Weinstock, P. Davis, B. Handelsman and R. Tull, *J. Org. Chem.* 1967, 32, 2823; V. Bertini and P. Pino, *Angew Chem. Int. Ed. Engl.* 1966, 5, 514 and S. Mataka, A. Hosoki, K. Takahashi and M. Tashino, *Synthesis* 1979, 524.

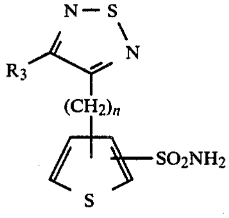

156

The methyl-1,3,4-triazol-2-ylthiophenes of Formula 157 can be prepared by the method shown in Equation 55.

Equation 55

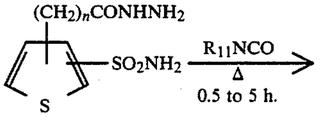

158

-continued

Equation 55

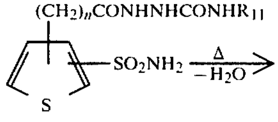

158a

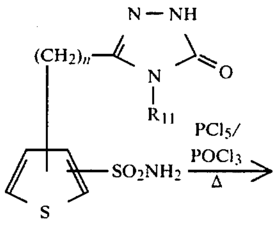

159

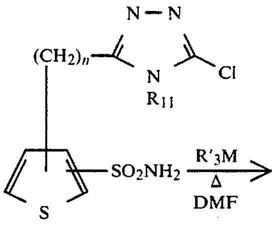

160

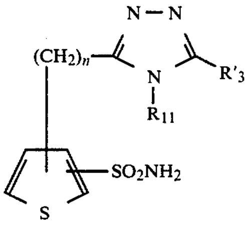

157

N-aminoamides of Formula 158 will react with isocyanates in solvents such as acetone or 2-butanone at reflux to afford adducts of Formula 158a. These in turn upon heating will cyclize with concomittant extrusion of water, yielding triazolones of Formula 159. Treatment with phosphorous pentachloride and phosphorous oxychloride at reflux gives 2-chlorotriazoles of Formula 160, which, upon treatment with a nucleophile $R_3'M$ in a polar, aprotic solvent such as DMF, yields the substituted sulfonamide of Formula 157. Compounds of Formula 158 in turn are synthesized from the treatment of esters of Formula 161 with hydrazines.

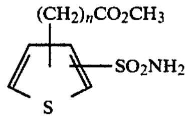

161

Methyl-1,2,4-triazol-5-ylthiophenes of Formula 162 can be synthesized by the route shown in Equation 56.

Equation 56

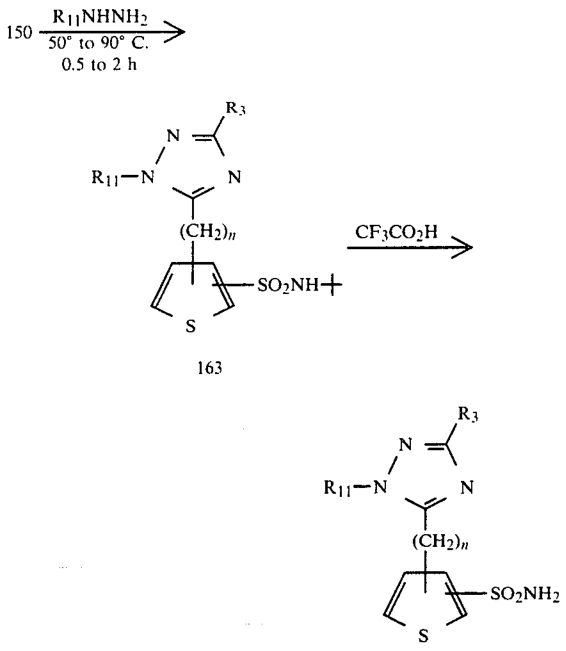

150

163

162

Y. Lin, S. A. Lang, M. F. Lovell and N. A. Perkinson, *J. Org. Chem.* 1979, 44, 460 have shown that reaction of a compound of Formula 150 with alkylhydrazines in acetic acid at temperatures of 50° to 90° C. for 0.5 to 2 hours will give triazoles of Formula 163. Deprotection to form sulfonamides of Formula 162 may be accomplished during cyclization, or may be removed afterwards by use of a strong acid.

Additionally, compounds of Formula 162 may be prepared in a manner analogous to that of Equation 55, using the appropriate cyanate or thiocyanate to give the required intermediate compounds of Formula 158b.

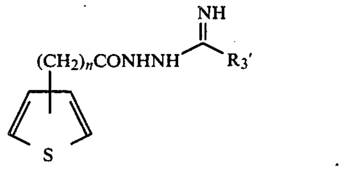

162

Methyl-1,2,4-triazol-3-ylthiophenes of Formula 164 where $R_3'=R_3$ are produced by the techniques described by M. Atkinson and J. Polya, *J. Chem. Soc.* 1954, 3319.

Equation 57

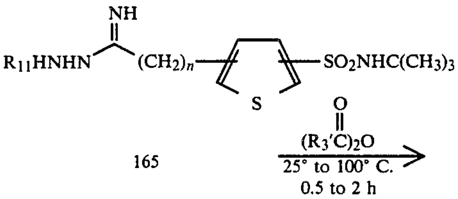

165

-continued

Equation 57

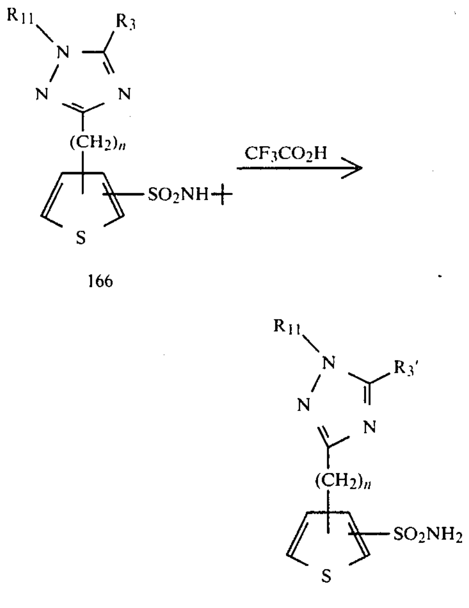

166

164

The hydrazine of Formula 165 reacts with an anhydride at temperatures ranging from 25° to 100° C. for approximately 0.5 to 2 hours, forming triazoles of Formula 166. Standard deprotection affords sulfonamides of Formula 164. Hydrazine 165 may be prepared by reaction of nitrile 161 with alkylhydrazines.

Similar treatment of hydrazine of Formula 165 with diphenylcarbonate or phosgene will result in triazolones of Formula 166a, as indicated in Equation 57a. Conversion to sulfonamides of Formula 164b is performed in a manner analogous to that of Equation 57.

Equation 57a

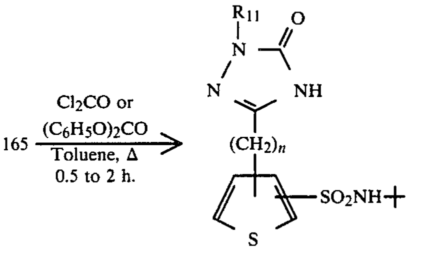

165

166a 1,2,4-Triazolylthiophenes of Formula 167 can be synthesized by the reaction sequence of Equation 58.

Equation 58

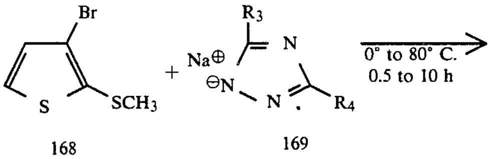

168

169

-continued

Equation 58

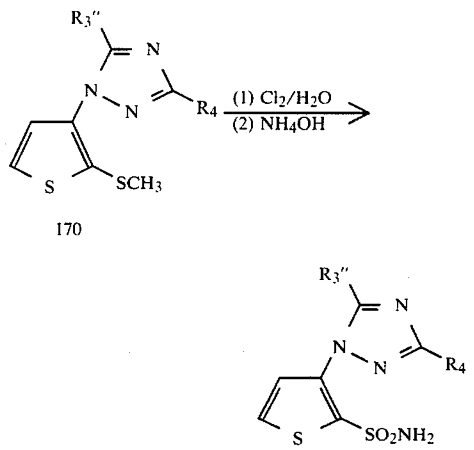

170

167

Similar to the preparation of thiophenes of Formula 134a, triazoles of Formula 170 can be formed by reaction of the bromothiophene of Formula 168 with a sodium 1,2,4-triazole salt of Formula 169. 170 then can be subjected to oxidative chlorination: amination of the intermediary sulfonyl chloride will result in sulfonamides of Formula 167.

Alternatively, sulfonamides of Formula 167 where $R_4$=H can be prepared by the route illustrated in Equation 58a.

Equation 58a

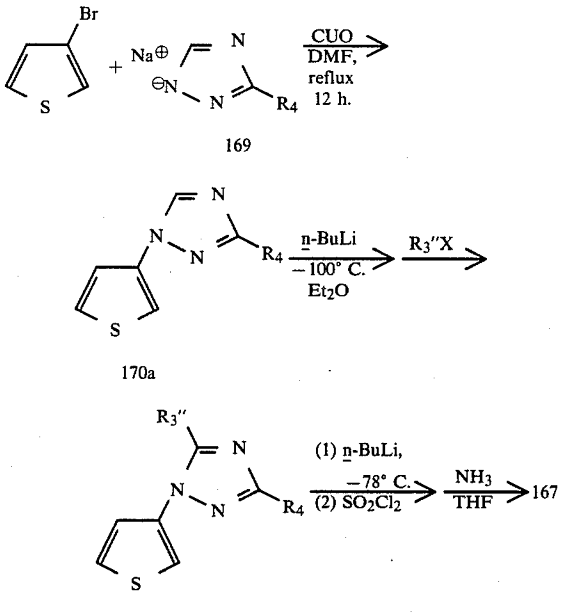

169

170a

170b

3-Bromothiophene is coupled with the sodium salt of a 1,2,4-triazole of Formula 169 in refluxing DMF using copper(II) catalysis. The resultant biaryl of Formula 170a then is regioselectively lithiated at −100° C. using n-butyllithium in diethyl ether; quenching with an electrophile, $R_3''X$, results in biaryls of Formula 170b. Sulfonamidation of 170b in a manner analogous to that described in Equation 12 gives the desired 167.

Those cases where n is 1 or 2, the sodio salt of the appropriate triazole may be added to aldehydes of Formula 170c, which can be converted by means of Equation 58b to sulfonamides of Formula 167a.

Equation 58b

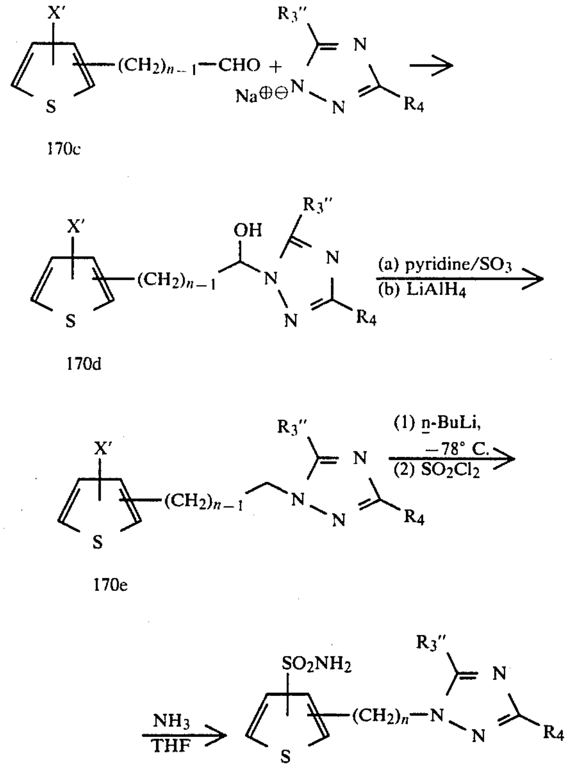

170c

170d

170e

167a

Compounds of Formula 171 can be prepared by reacting a 1-formyl-2-(3'-bromothienyl)hydrazine of Formula 172 with excess formamide at reflux for about 1 to 6 hours, according to the procedures described by C. Ainsworth et al., *J. Med. Pharm. Chem.* 1962, 5, 353 as shown in Equation 59 below.

Equation 59

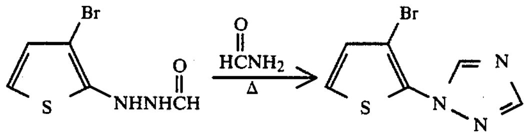

171

Alternatively, compounds of Formula 171 can be prepared from 2,3-dibromothiophene by reaction with the sodium salt of a 1,2,4-triazole of Formula 169 as shown in Equation 60.

Equation 60

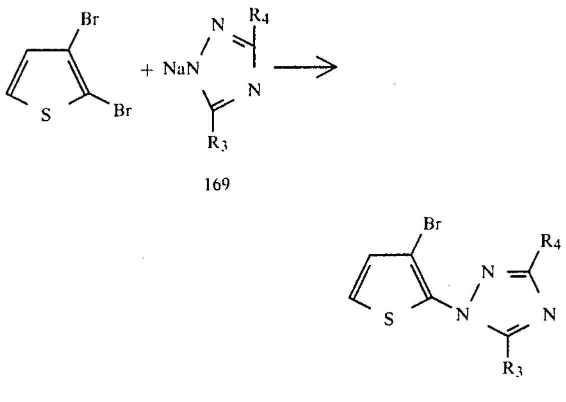

169

171a the reaction can be run by the procedures described in Equations 47, 48, and 49.

Compounds of Formula 171 may also be prepared by a modified Ullmann reaction, according to the teachings of M. Kahn and J. Polya, *J. Chem. Soc.*, C. 1970, 85.

Compounds of Formula 167a (Q-29) can be prepared by the procedures shown in Equation 61.

Equation 61

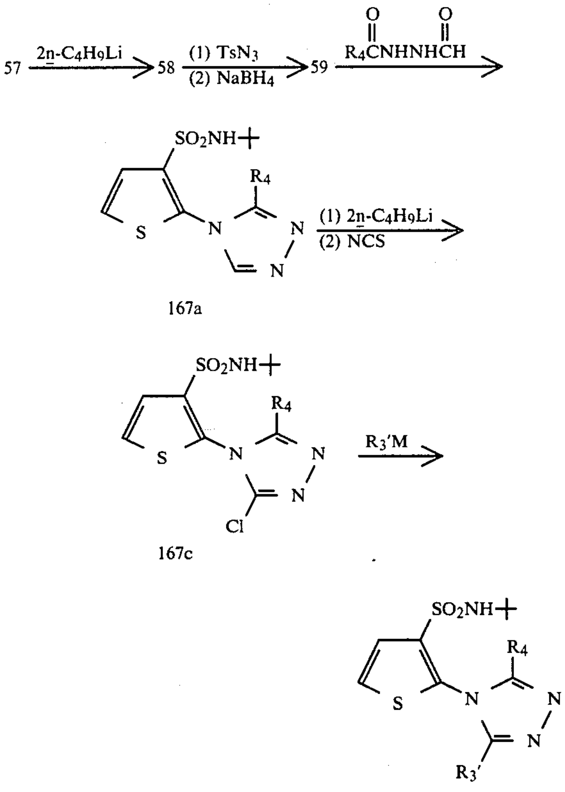

167a

167c

167d

The 2-amino-3-thiophene-t-butylsulfonamide 59, prepared by the procedures of Equation 23, is treated with N,N'-diacylhydrazine at 150° to 200° C. for 0.5 to 2 hours, according to methods known in the art, e.g., C. Ainsworth et al., op. cit. 1,3,4-Triazol-3-ylthiophenes of Formula 167b are formed as shown in Equation 62. An aminothiophene of Formula 172 will react with diacylhydrazines at high temperatures (150° to 200° C.) over a period of ca. 0.5 to 2 hours to result in triazoles of Formula 173. Conversion of these triazoles to sulfonamides of Formula 167b can be accomplished as shown in Equations 58 and 61.

Equation 62

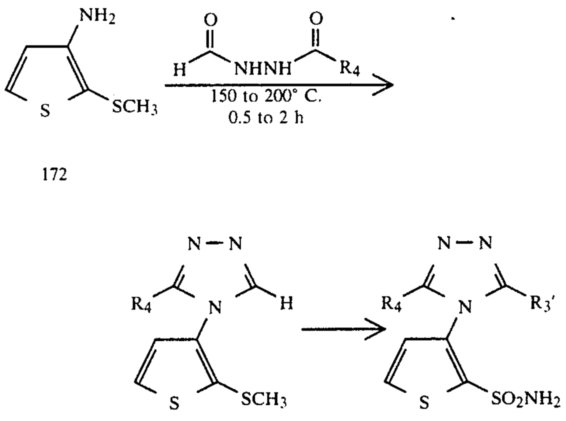

172

173

167b

In those cases where n is 1 or 2, a procedure entirely analogous to that of Equation 58b may be used to prepare sulfonamides of Formula 167e.

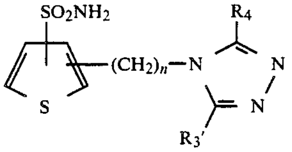

167c

3-Pyridinylthiophenes of Formulae 174, 175 and 176 are available by the methods of H. Wynberg, T. J. Van Bergen and R. M. Kellogg, *J. Org. Chem.* 1969, 34, 3175. In the case of 177, sulfonamides of this Formula can be prepared by route of Equation 7; for sulfonamides of Formulas 178 and 179, preparation will be better achieved by way of Equation 14.

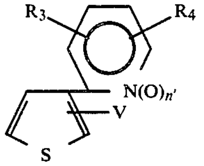

174, V = H

177, V = $SO_2NH_2$

-continued

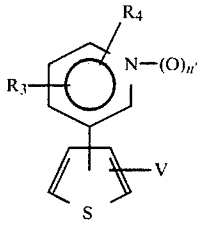

175, V = H
178, V = $SO_2NH_2$

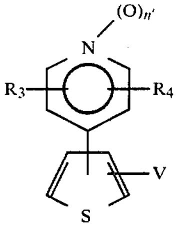

176, V = H
179, V = $SO_2NH_2$

Pyridinylthiophenesulfonamides where n′=1 (pyridine N-oxides) can be prepared by treatment of the corresponding pyridinylthiophenesulfonamides with m-chloroperbenzoic acid in chloroform. The resulting N-oxide readily precipitates from solution.

In those cases where n is 1 or 2, a synthetic sequence similar to that depicted in Equation 58b will lead to the desired sulfonamides of Formulae 177–179.

3-Pyrimidin-2-ylthiophenes of Formula 180 are prepared according to the techniques described by S. Gronowitz and S. Liljefors, *Acta Chem. Scand.* 1977, B 31, 771 and straightforward modifications thereof. Sulfonamides of Formula 181 are formed by means of Equation 14.

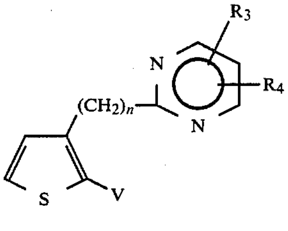

180, V = H
181, V = $SO_2NH_2$

3-Pyrimidin-4-ylthiophenes of Formula 182 are synthesized according to R. E. van der Stoel and H. C. van der Plas, *J. Chem. Soc., Perkin I* 1979, 2393. Conversion to sulfonamides of Formula 183 can be made by the synthetic sequence of Equation 14.

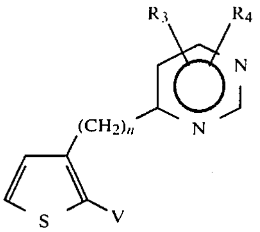

182, V = H
183, V = $SO_2NH_2$

3-Pyrimidin-5-ylthiophenes of Formula 184 are available by use of the synthesis described by S. Gronowitz and S. Liljefors, *Chem. Scr.* 1978, 13, 39 and *J. Org. Chem.* 1982, 47, 3177 and modifications thereof. Again, the preparation of the corresponding sulfonamides of Formula 185 can be accomplished by means of Equation 14.

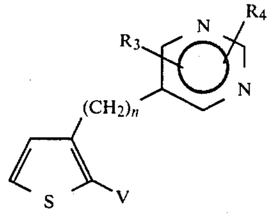

184, V = H
185, V = $SO_2NH_2$

3-Pyrazinylthiophenes of Formula 186 are prepared by the method of J. Bourguignon, J. -M. Bouchy, J. -C. Clinet and G. Queguiner, *C. R. Acad. Sci. Paris* C 1975, 281, 1019. The synthesis of the sulfonamides of Formula 187 can be achieved by use of the route described in Equation 14.

3-Pyridazin-3-ylthiophenes of Formula 188 are available by the method described by J. Bourguignon, C. Becue and G. Queguiner, *J. Chem. Res., Synop.* 1981, 4, 104. Conversion to the sulfonamides of Formula 189 is accomplished by means of Equation 14.

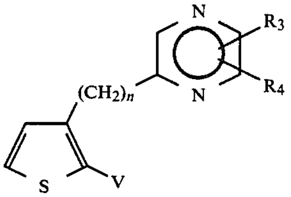

186, V = H
187, V = $SO_2NH_2$

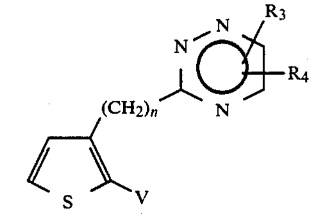

188, V = H
189, V = $SO_2NH_2$ 3-(1,3,5-triazin-2-yl)thiophenes of Formula 190 can be prepared by the methods of J. K. Chakrabarti, R. W. Goulding and A. Todd, *J. Chem. Soc., Perkin I* 1973, 2499. The appropriate 1,3,5-triazines needed for the synthesis are described by Smolin, E. M. and Rapoport, L. "The Chemistry of Heterocyclic Compounds," Vol 13, Wily-Interscience, NY. The corresponding sulfonamides of Formula 191 are formed by application of the chemistry described in Equation 14.

3-(1,2,4-triazin-3-yl)thiophenes of Formula 192 are available by a route essentially similar to the preparation of thiophenes of Formula 190, using the appropriate 1,2,4-triazines as made by the methods of A. Rybowski and H. C. van der Plas, *J. Org. Chem.* 1980, 45, 881. Again, the sulfonamides of Formula 193 are available by use of the synthetic procedure described in Equation 14.

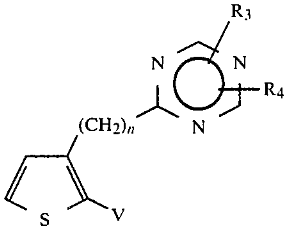

190, V = H
191, V = $SO_2NH_2$

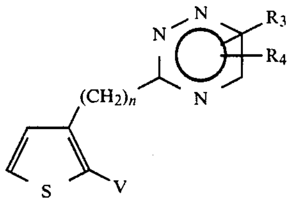

192, V = H
193, V = $SO_2NH_2$ 3-(1,2,3-Thiadiazol-5-yl)thiophenes of Formula 195 can be prepared by a straightforward modification of the synthesis of 153 described by Equation 54, beginning with thiophenes of Formula 196. These thiophenes in turn are available from the corresponding ketones.

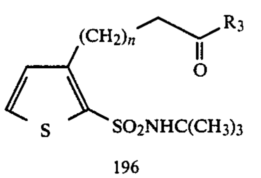

196

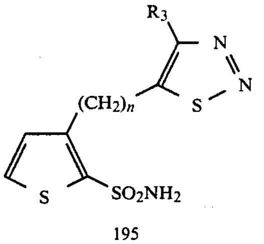

195

Compounds of Formula 2 where Q is Q-33, Q-34, Q-35, Q-37, Q-38, Q-39, Q-40, Q-43 and Q-44 can be prepared by the sequence of reactions outlined in Equations 8 and 9.

Pyrimidines and triazines of Formula 5 are necessary intermediates for the preparation of compounds of Formulas Ia, Ib and Ic of this invention. Such pyrimidines and triazines are either known compositions or may be prepared by methods obvious to those skilled in the art.

Agriculturally suitable salts of compounds of Formulas Ia, Ib and Ic can be prepared by a number of ways known in the art. For example, some such ways include (1) metal and quaternary ammonium salts made by treatment of compounds of Formulas Ia, Ib and Ic with solutions of metal or ammonium hydroxides, alkoxides or carbinates that are suffiently basic with respect to the substrates Ia, Ib and Ic; (2) cation exchange of those salts formed e.g. by (1) with an aqueous solution of a second cation; in particular, one whose resultant salt preferentially is sparingly soluble in aqueous solution and therefore precipitates from the solution; (3) cation exchange via passage through various cation exchange resins loaded with the cation to be exchanged; in particular, the exchange with cations whose resultant salts with Ia, Ib and Ic are water-soluble and (4) acid addition salts made by treatment of compounds of Formulas Ia, Ib and Ic with suitably strong acids such as trichloroacetic acid.or p-toluenesulfonic acid.

The compounds described in this invention are further illustrated by the following Examples 1 through 6.

EXAMPLE 1

3-(3-Thienyl)-4,5-dihydro-5-acetoxyisoxazole

To an ice-cooled mixture of 100 g thiophene-3-carboxaldehyde, 100 mL methanol, 100 mL water, and 80 g hydroxylamine hydrochloride was added 50% aqueous NaOH to neutrality (ca. 40 mL). Methanol was removed by rotary evaporation and the mixture was extracted with ether. The ether extracts were washed with brine, dried ($MgSO_4$), and concentrated to afford 117 g of crude oxime. This was dissolved in 100 mL of DMF and 110 g of N-chlorosuccinimide was added in portions at 15° C. After the addition, the mixture was allowed to stir at 15° C. for 1 h, and then the cooling bath was removed. A rapid exotherm caused the temperature to rise to 50° C. and ice was immediately added to the reaction mixture, which then was partitioned between ether and water. The ether layer was washed several times with water, then washed with brine, dried ($MgSO_4$), and filtered.

Vinyl acetate (100 mL) then was added, and the solution was heated at reflux while adding a solution of 80 mL of triethylamine in 250 mL of ether over a 4 hour period. The mixture was cooled and filtered and the filter cake was washed several times with water and was air-dried. This material was combined with more product obtained by separating the filtrate, washing the $Et_2O$ layer with brine, drying ($MgSO_4$), and concentration and trituration with ether (total yield 88.6 g, mp 98°-99° C.).

EXAMPLE 2

3-(3-Thienyl)isoxazole

To a solution of 88.6 g of the dihydroisoxazole in 300 mL of methylene chloride was added 88 g of 1,8-diazabicyclo[5.4.0]undec-7-ene (DBU) whereupon an exotherm caused the solvent to reflux. The solution was washed with aqueous HCl and with brine then was dried ($Na_2SO_4$), concentrated, and distilled to afford 52 g of the isoxazole, bp 75°-80° C./1 mm.

EXAMPLE 3

3-(3-Isoxazolyl)-2-thiophenesulfonyl chloride

To a solution of the thienylisoxazole in 300 mL of ether was added 60 mL of n-butyllithium as a 1.6M solution in hexane at −78° C. under nitrogen. After stirring for 10 min at −78° C., liquid $SO_2$ (10 mL) was added and the mixture was allowed to stand overnight at room temperature. Filtration afforded the sulfinate salt which was hygroscopic. This was stirred in 100 mL of 50% aqueous acetic acid while adding 13 g of N-chlorosuccinimide in portions at 0° C. After stirring for 30 minutes at room temperature, the mixture was diluted with 200 mL of ice water, filtered, washed with ice water, and air dried to afford 20 g of sulfonyl chloride, mp 92°–92.5° C.

EXAMPLE 4

3-(3-Isoxazolyl)-2-thiophenesulfonamide

A solution of 19.5 g of the sulfonyl chloride in 150 mL of methylene chloride was saturated with gaseous ammonia and was stirred for 16 h at 25°. The precipitate was filtered and washed with $CH_2Cl_2$, then with water and air-dried to afford 11.7 g of the title sulfonamide, mp 163°–164° C. Another 1.5 g of product was obtained by washing the $CH_2Cl_2$-soluble fraction with brine, drying ($Na_2SO_4$), concentration, and trituration with ether.

EXAMPLE 5

3-(3-Isoxazolyl)-2-thiophenesulfonylisocyanate

A mixture of 10 g of the sulfonamide, 100 mL of 2-butanone, 6 mL of n-butyl isocyanate, and 5 g of potassium carbonate was heated at refulx for 1 h, then was concentrated, acidified with cold, aqueous HCl, and filtered. The solid was dissolved in $CH_2Cl_2$, dried ($MgSO_4$) and concentrated to afford 12 g of the n-butyl urea. The butyl urea (11 g) was heated in 50 mL of xylene containing 0.2 g of 1,4-diazabicyclo[2.2.2.]octane at 135° C. while adding a solution of 4 mL of phosgene in 6 mL of xylene over a 1 h period. The mixture was cooled, filtered, and concentrated to an orange oil which had a strong IR absorption at 2250 $cm^{-1}$ indicative of a sulfonylisocyanate. This oil (11 g) was dissolved in 40 mL of methylene chloride and was used for the next reaction.

EXAMPLE 6

N-[(4,6-Dimethyl-pyrimidin-2-yl)aminocarbonyl]-3-(3-isoxazolyl)-2-thiophenesulfonamide To 6 mL of the isocyanate/$CH_2Cl_2$ solution (1.1 g of contained isocyanate) was added 0.4 g of 2-amino-4,6-dimethylpyrimidine in 5 mL of methylene chloride. The solvent was removed and the crude product was triturated with ether and filtered. Recrystallization from $CH_3CN$/n-BuCl afforded 250 mg of product, mp 172.5°–173°. NMR($CDCl_3$) δ2.4 (s, 6H9, 6.76 (s, 1H), 7.0 (d, 1H), 7.5 (d, 1H), 8.2 (d, 1H) 9.0 (d, 1H) 8.1 (br s, 1H), 10.6 (br s, 1H).

Using techniques described in Equations 1 to 62 and Examples 1 to 6 or simple modifications thereof, the compounds in Tables 1–6 may be synthesized by one skilled in the art.

General Structures for Tables

General Structure 1

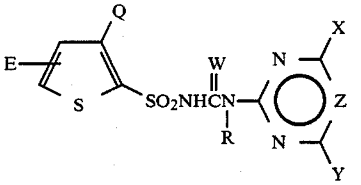

-continued

General Structures for Tables

General Structure 2

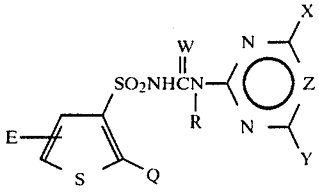

General Structure 3

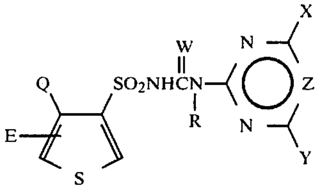

General Structure 4

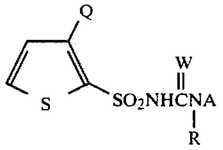

General Structure 5

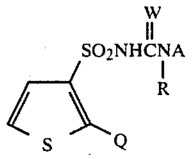

General Structure 6

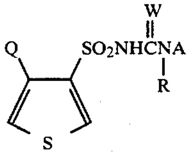

General Structure 7

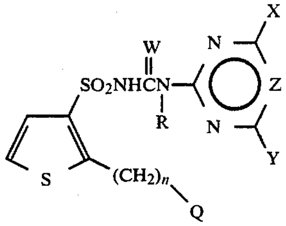

General Structure 8

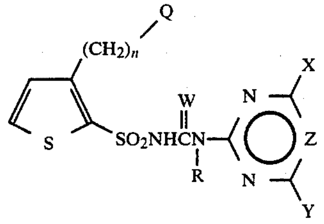

General Structure 9

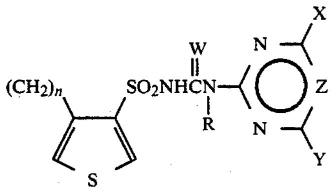

TABLE 1a

General Structure 1 wherein Q is Q-1.

| R | $R_1$ | $R_2$ | X | Y | Z | | m.p. °C. |
|---|---|---|---|---|---|---|---|
| H | H | H | $CH_3$ | $CH_3$ | CH | | |
| H | H | H | $CH_3$ | $CH_3$ | N | | |
| H | H | H | $CH_3$ | $OCH_3$ | CH | | 208-210 |
| H | H | H | $CH_3$ | $OCH_3$ | N | | 179-181 |
| H | H | H | $OCH_3$ | $OCH_3$ | CH | | 210-212 |
| H | H | H | Cl | $OCH_3$ | CH | | |
| H | H | H | $OCH_3$ | $OCH_3$ | N | | 182-185 |
| H | 4-Cl | H | $CH_3$ | $OCH_3$ | CH | | |
| H | H | 4-F | $CH_3$ | $CH_3$ | N | | |
| H | 4-$CH_3$ | H | $OCH_3$ | $OCH_3$ | CH | | |
| H | H | 4-$OCH_3$ | $CH_3$ | $OCH_3$ | N | | |
| H | H | 4-$CF_3$ | $CH_3$ | $OCH_3$ | CH | | |
| $CH_3$ | 3-$CH_3$ | 5-$CH_3$ | $CH_3$ | $CH_3$ | N | | |
| H | H | H | $OCH_3$ | $OCF_2H$ | CH | | |
| H | H | H | $OCH_3$ | cyclopropyl | N | | |
| H | H | H | $OC_2H_5$ | $OCH_3$ | N | | |
| H | H | H | O-n-$C_4H_9$ | $CH_3$ | CH | | |
| H | H | H | $OCH_2CF_3$ | $OCH_3$ | N | | |
| H | H | H | $OCH_2CH_2CH_2F$ | $CH_3$ | CH | | |
| H | H | H | $SCH_3$ | $OCH_3$ | CH | | |
| H | H | H | $SCH(CH_3)_2$ | $CH_3$ | N | | |
| H | H | H | $CH_2CH_2OCH_3$ | $CH_3$ | CH | | |
| H | H | H | $CH_2OCH_2CH_3$ | $OCH_3$ | N | | |
| H | H | H | $N(CH_2CH_3)_2$ | $CH_3$ | CH | | |
| H | H | H | $N(CH_2CH_2CH_3)$ | $OCH_3$ | N | | |
| H | H | H | $CH_3$ | $OCH_2CH{=}CH_2$ | CH | | |
| H | H | H | $OCH_3$ | $OCH_2C{\equiv}CCH_3$ | N | | |
| H | H | H | $CH_3$ | cyclopentyl | CH | | |
| H | H | H | $OCH_3$ | $CH_2SCH_3$ | N | | |
| H | H | H | $CH_3$ | $C(O)CH_3$ | CH | | |
| H | H | H | $CH_3$ | 1,3-dioxan-2-yl | N | | |
| H | H | H | $OCH_3$ | $N(OCH_3)CH_3$ | CH | | |
| H | H | H | $OCH_3$ | $OCH_3$ | CH | * | |
| H | H | H | $OCH_3$ | $CH_3$ | N | * | |
| H | 4-Cl | H | $OCH_3$ | $OCH_3$ | CH | * | |

W is O, unless indicated by * where W is S in all Tables.

TABLE 1b

General Structure 1

| Q | R | $R_3$ | $R_4$ | $R_5$ | X | Y | Z | W' | m.p. °C. |
|---|---|---|---|---|---|---|---|---|---|
| Q-2 | H | H | H | H | $CH_3$ | $OCH_3$ | CH | O | |
| Q-2 | H | H | H | H | $CH_3$ | $OCH_3$ | N | O | |
| Q-2 | H | H | H | H | $OCH_3$ | $OCH_3$ | CH | O | |
| Q-2 | H | H | H | H | $OCH_3$ | $OCH_3$ | N | O | |
| Q-2 | H | $CH_3$ | H | H | $CH_3$ | $CH_3$ | CH | O | |
| Q-2 | H | H | $CH_3$ | H | $CH_3$ | $OCH_3$ | N | O | |
| Q-2 | H | H | H | $CH_3$ | $CH_3$ | $OCH_3$ | CH | O | |
| Q-2 | $CH_3$ | H | H | H | CH | $CH_3$ | CH | O | |
| Q-2 | H | $CH_3$ | $CH_3$ | H | $OCH_3$ | $OCH_3$ | N | O | |
| Q-2 | H | H | H | H | Cl | $OCH_3$ | CH | S | |
| Q-2 | H | H | H | H | $CH_3$ | $OCH_3$ | CH | S | |
| Q-2 | H | H | H | H | $CH_3$ | $OCH_3$ | N | S | |
| Q-2 | H | H | H | H | $OCH_3$ | $OCH_3$ | CH | S | |
| Q-2 | H | H | H | H | $OCH_3$ | $OCH_3$ | N | S | |
| Q-2 | H | H | H | H | $CH_3$ | $CH_3$ | CH | S | |
| Q-2 | H | $CH_3$ | H | H | $CH_3$ | $CH_3$ | CH | S | |
| Q-2 | H | H | $CH_3$ | H | $CH_3$ | $CH_3$ | N | S | |
| Q-2 | H | H | H | $CH_3$ | $CH_3$ | $OCH_3$ | CH | S | |
| Q-2 | H | $CH_3$ | $CH_3$ | H | $CH_3$ | $OCH_3$ | N | S | |
| Q-2 | H | H | $CH_3$ | $CH_3$ | $OCH_3$ | $OCH_3$ | CH | S | |
| Q-2 | H | $CH_3$ | H | $CH_3$ | $OCH_3$ | $OCH_3$ | N | S | |
| Q-2 | H | $CH_3$ | $CH_3$ | $CH_3$ | $CH_3$ | $OCH_3$ | CH | S | |
| Q-2 | $CH_3$ | H | H | H | $CH_3$ | $CH_3$ | CH | S | |
| Q-2 | H | H | H | H | Cl | $OC_2H_5$ | CH | S | |
| Q-3 | H | H | H | H | $CH_3$ | $CH_3$ | CH | O | |
| Q-3 | H | H | H | H | $CH_3$ | $CH_3$ | N | O | |
| Q-3 | H | H | H | H | $CH_3$ | $OCH_3$ | CH | O | |
| Q-3 | H | H | H | H | $CH_3$ | $OCH_3$ | N | O | |
| Q-3 | H | H | H | H | $OCH_3$ | $OCH_3$ | CH | O | |
| Q-3 | H | H | H | H | $OCH_3$ | $OCH_3$ | N | O | |
| Q-3 | H | $CH_3$ | H | H | $CH_3$ | $CH_3$ | CH | O | |
| Q-3 | H | H | $CH_3$ | H | $CH_3$ | $CH_3$ | N | O | |
| Q-3 | H | H | H | $CH_3$ | $CH_3$ | $OCH_3$ | CH | O | |
| Q-3 | H | $CH_3$ | $CH_3$ | H | $CH_3$ | $OCH_3$ | N | O | |
| Q-3 | H | H | $CH_3$ | $CH_3$ | $OCH_3$ | $OCH_3$ | CH | O | |

TABLE 1b-continued

General Structure 1

| Q | R | $R_3$ | $R_4$ | $R_5$ | X | Y | Z | W' | m.p. °C. |
|---|---|---|---|---|---|---|---|---|---|
| Q-3 | H | $CH_3$ | H | $CH_3$ | $OCH_3$ | $OCH_3$ | N | O | |
| Q-3 | H | H | H | H | $OCH_3$ | $OCH_2CF_3$ | CH | O | |
| Q-3 | H | H | H | H | $OCH_3$ | $OCH_2CF_3$ | CH | O | |
| Q-3 | $CH_3$ | H | H | H | Cl | $OCH_3$ | CH | O | |
| Q-3 | H | H | H | H | $CH_3$ | $OCH_3$ | CH | S | |
| Q-3 | H | H | H | H | $OCH_3$ | $OCH_3$ | CH | S | |
| Q-3 | H | H | H | H | $OCH_3$ | $OCH_3$ | N | S | |
| Q-3 | H | $CH_3$ | H | H | $CH_3$ | $CH_3$ | CH | S | |
| Q-3 | H | H | $CH_3$ | H | $CH_3$ | $OCH_3$ | N | S | |
| Q-3 | H | H | H | $CH_3$ | $CH_3$ | $OCH_3$ | CH | S | |
| Q-3 | $CH_3$ | H | H | H | $CH_3$ | $CH_3$ | CH | S | |
| Q-3 | H | H | $CH_3$ | $CH_3$ | $OCH_3$ | $OCH_3$ | N | S | |
| Q-3 | H | H | H | H | $OCH_3$ | $CF_3$ | N | S | |
| Q-4 | H | H | H | H | $CH_3$ | $OCH_3$ | CH | — | |
| Q-4 | H | H | H | H | $OCH_3$ | Cl | CH | — | |
| Q-4 | H | H | H | H | $CH_3$ | $OCH_3$ | N | — | |
| Q-4 | H | H | H | H | $CH_3$ | $CH_3$ | CH | — | |
| Q-4 | H | H | H | H | $OCH_3$ | $OCH_3$ | CH | — | |
| Q-4 | H | H | H | H | $OCH_3$ | $OCH_3$ | N | — | |
| Q-4 | H | $CH_3$ | H | H | $CH_3$ | $CH_3$ | CH | — | |
| Q-4 | H | H | $CH_3$ | H | $CH_3$ | $OCH_3$ | N | — | |
| Q-4 | H | H | H | $CH_3$ | $CH_3$ | $OCH_3$ | CH | — | |
| Q-4 | $CH_3$ | H | H | H | $OCH_3$ | $OCH_3$ | CH | — | |
| Q-4 | $CH_3$ | $CH_3$ | $CH_3$ | $CH_3$ | $CH_3$ | $OCH_3$ | N | — | |
| Q-4 | H | $CH_3$ | H | $CH_3$ | $CH_3$ | $OCH_3$ | CH | — | |
| Q-4 | H | H | H | H | $OCH_3$ | $OCH_2CF_3$ | N | — | |
| Q-4 | H | H | H | H | $CH_3$ | $NHCH_3$ | CH | — | |
| Q-4 | H | H | H | H | $CH_3$ | $CH_3$ | CH | — | |
| Q-4 | H | H | H | H | $CH_3$ | $CH_3$ | N | — | |
| Q-9 | H | H | H | H | $CH_3$ | $OCH_3$ | CH | — | |
| Q-9 | H | H | H | H | $CH_3$ | $OCH_3$ | N | — | |
| Q-9 | H | H | H | H | $OCH_3$ | $OCH_3$ | CH | — | |
| Q-9 | H | H | H | H | $OCH_3$ | $OCH_3$ | N | — | |
| Q-9 | $CH_3$ | $CH_3$ | H | H | $CH_3$ | $CH_3$ | CH | — | |
| Q-9 | H | H | $CH_3$ | H | $CH_3$ | $OCH_3$ | N | — | |
| Q-9 | H | H | H | $CH_3$ | $OCH_3$ | $OCH_3$ | CH | — | |
| Q-9 | H | H | $CH_3$ | $CH_3$ | $CH_3$ | $OCH_3$ | CH | — | |
| Q-9 | H | H | H | H | Cl | $OCH_2CH_3$ | CH | — | |
| Q-9 | H | H | H | H | $OCH_3$ | $CH(OCH_3)_2$ | CH | — | |
| Q-9 | H | H | H | H | NHhd 2 | $CH_3$ | CH | — | |
| Q-9 | H | H | H | H | $NHCH(CH_3)_2$ | $CH_3$ | CH | — | |
| Q-9 | H | H | H | H | $CH_2O$-n-$C_4H_9$ | $CH_3$ | CH | — | |
| Q-9 | H | H | H | H | S-n-$C_4H_9$ | $CH_3$ | CH | — | |
| Q-9 | H | H | H | H | S-n-$CH_2CH_2F$ | $CH_3$ | CH | — | |

TABLE 1c

General Structure 1

| Q | R | $R_{3,}'$ | $R_4$ | X | Y | Z | W'' | m.p. °C. |
|---|---|---|---|---|---|---|---|---|
| Q-10 | H | H | H | $CH_3$ | $OCH_3$ | CH | O | |
| Q-10 | H | H | H | $CH_3$ | $CH_3$ | CH | O | |
| Q-10 | H | H | H | $OCH_3$ | $OCH_3$ | N | O | |
| Q-10 | H | H | H | $OCH_3$ | Cl | CH | O | |
| Q-10 | H | H | H | $OCH_3$ | $OCH_3$ | CH | O | |
| Q-10 | H | H | H | $OCH_3$ | $OCH_3$ | N | O | |
| Q-10 | H | H | H | $CH_3$ | $OCH_3$ | CH | S | |
| Q-10 | H | H | H | $CH_3$ | $OCH_3$ | N | S | |
| Q-10 | H | H | H | $OCH_3$ | $OCH_3$ | CH | S | |
| Q-10 | H | H | H | $OCH_3$ | $OCH_3$ | N | S | |
| Q-10 | H | H | H | $OCH_3$ | Cl | CH | $NCH_3$ | |
| Q-10 | H | H | H | $CH_3$ | $CH_3$ | CH | $NCH_3$ | |
| Q-10 | H | H | H | $CH_3$ | $OCH_3$ | N | $NCH_3$ | |
| Q-10 | H | H | H | $CH_3$ | $CH_3$ | N | $NCH_3$ | |
| Q-10 | H | H | H | $OCH_3$ | $OCH_3$ | CH | $NCH_3$ | |
| Q-10 | H | H | H | $OCH_3$ | $OCH_3$ | N | $NCH_3$ | |
| Q-10 | H | $CH_3$ | H | $CH_3$ | $CH_3$ | CH | O | |
| Q-10 | H | H | $CH_3$ | $CH_3$ | $OCH_3$ | N | O | |
| Q-10 | H | $CH_3$ | $CH_3$ | $CH_3$ | $OCH_3$ | CH | O | |
| Q-10 | $CH_3$ | H | H | $OCH_3$ | $OCH_3$ | N | O | |
| Q-10 | H | H | H | $CH_3$ | 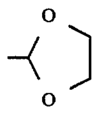 | CH | O | |

TABLE 1c-continued

General Structure 1

| Q | R | R3.' | R4 | X | Y | Z | W'' | m.p. °C. |
|---|---|---|---|---|---|---|---|---|
| Q-10 | H | CH3 | H | CH3 | CH3 | CH | S | |
| Q-10 | H | H | CH3 | CH3 | OCH3 | N | S | |
| Q-10 | H | CH3 | CH3 | CH3 | OCH3 | CH | S | |
| Q-10 | CH3 | CH3 | CH3 | CH3 | OCH3 | CH | S | |
| Q-10 | CH3 | H | H | OCH3 | OCH3 | N | S | |
| Q-10 | H | H | H | CH3 | OC2H5 | CH | S | |
| Q-10 | H | H | CH3 | CH3 | CH3 | N | NCH3 | |
| Q-10 | H | H | CH3 | CH3 | OCH3 | CH | NCH3 | |
| Q-10 | H | CH3 | CH3 | OCH3 | OCH3 | N | NCH3 | |
| Q-10 | CH3 | H | H | OCH3 | OCH3 | N | NCH3 | |
| Q-11 | H | H | H | CH3 | CH3 | N | O | |
| Q-11 | H | H | H | CH3 | CH3 | CH | O | 172.5-173 |
| Q-11 | H | H | H | CH3 | OCH3 | N | O | |
| Q-11 | H | H | H | CH3 | OCH3 | CH | O | 192(d) |
| Q-11 | H | H | H | OCH3 | OCH3 | CH | O | 157-158 |
| Q-11 | H | H | H | OCH3 | OCH3 | N | O | |
| Q-11 | H | H | H | CH3 | CH3 | CH | S | |
| Q-11 | H | H | H | CH3 | OCH3 | CH | S | |
| Q-11 | H | H | H | CH3 | OCH3 | CH | S | |
| Q-11 | H | H | H | OCH3 | OCH3 | CH | S | |
| Q-11 | H | H | H | CH3 | CH3 | CH | NCH3 | |
| Q-11 | H | H | H | CH3 | OCH3 | CH | NCH3 | |
| Q-11 | H | H | H | OCH3 | OCH3 | CH | NCH3 | |
| Q-11 | H | H | H | CH3 | OCH3 | N | NCH3 | |
| Q-11 | H | CH3 | H | CH3 | OCH3 | N | O | |
| Q-11 | H | H | CH3 | OCH3 | OCH3 | N | O | |
| Q-11 | H | CH3 | CH3 | CH3 | OCH3 | CH | O | |
| Q-11 | CH3 | H | H | CH3 | OCH3 | CH | O | |
| Q-11 | H | H | H | CH3 | C2H5 | N | O | |
| Q-11 | H | H | H | CH3 | CH2OCH3 | CH | O | |
| Q-11 | H | CH3 | H | CH3 | OCH3 | N | S | |
| Q-11 | H | H | CH3 | OCH3 | OCH3 | N | S | |
| Q-11 | H | CH3 | CH3 | CH3 | OCH3 | CH | S | |
| Q-11 | CH3 | H | H | CH3 | OCH3 | CH | S | |
| Q-11 | H | H | H | CH3 | C2H5 | N | S | |
| Q-11 | CH3 | CH3 | CH3 | CH3 | OCH3 | N | S | |
| Q-11 | H | H | H | Cl | OCH3 | CH | S | |
| Q-11 | H | CH3 | H | CH3 | CH3 | CH | NCH3 | |
| Q-11 | H | H | CH3 | CH3 | OCH3 | N | NCH3 | |
| Q-11 | H | CH3 | CH3 | CH3 | OCH3 | CH | NCH3 | |
| Q-11 | CH3 | H | H | OCH3 | OCH3 | N | NH | |
| Q-11 | H | H | H | CH3 | OCH3 | CH | NH | |
| Q-11 | H | H | H | OCH3 | OCH3 | CH | O* | |
| Q-11 | H | H | H | OCH3 | CH | N | O* | |
| Q-11 | H | H | H | CH3 | OCH3 | N | NCH3 | |
| Q-11 | H | H | H | CH3 | OCF2H | CH | NCH3 | |
| Q-11 | H | CH3 | H | OCH3 | OCH2CF3 | N | NCH3 | |
| Q-12 | H | H | H | CH3 | OCH3 | CH | O | |
| Q-12 | H | H | H | CH3 | OCH3 | N | O | |
| Q-12 | H | H | H | OCH3 | OCH3 | CH | O | |
| Q-12 | H | H | H | OCH3 | OCH3 | N | O | |
| Q-12 | H | H | H | CH3 | OCH3 | CH | S | |
| Q-12 | H | H | H | CH3 | OCH3 | N | S | |
| Q-12 | H | H | H | OCH3 | OCH3 | CH | S | |
| Q-12 | H | H | H | OCH3 | OCH3 | N | S | |
| Q-12 | H | H | H | CH3 | CH3 | N | NCH3 | |
| Q-12 | H | H | H | CH3 | OCH3 | CH | NCH3 | |
| Q-12 | H | H | H | CH3 | OCH3 | N | NCH3 | |
| Q-12 | H | H | H | OCH3 | OCH3 | CH | NCH3 | |
| Q-12 | H | H | H | OCH3 | OCH3 | N | NCH3 | |
| Q-12 | H | H | H | OCH3 | OCH3 | N | NH | |
| Q-12 | H | CH3 | H | CH3 | CH3 | CH | O | |
| Q-12 | H | H | CH3 | CH3 | OCH3 | N | O | |
| Q-12 | H | CH3 | CH3 | CH3 | OCH3 | CH | O | |
| Q-12 | CH3 | H | H | OCH3 | OCH3 | N | O | |
| Q-12 | CH3 | H | H | CH3 | CF3 | CH | O | |
| Q-12 | H | H | H | OCH3 | OCH2CF3 | N | | |
| Q-12 | H | CH3 | H | CH3 | OCH3 | CH | S | |
| Q-12 | H | H | CH3 | CH3 | OCH3 | N | S | |
| Q-12 | H | CH3 | CH3 | OCH3 | OCH3 | CH | S | |
| Q-12 | CH3 | H | H | OCH3 | OCH3 | N | S | |
| Q-12 | CH3 | CH3 | H | CH3 | NHCH3 | CH | S | |
| Q-12 | H | H | H | Br | OC2H5 | CH | S | |
| Q-12 | H | CH3 | H | CH3 | CH3 | CH | NH | |
| Q-12 | H | CH3 | H | CH3 | CH3 | CH | NCH3 | |
| Q-12 | H | H | CH3 | CH3 | OCH3 | N | NCH3 | |
| Q-12 | H | CH3 | CH3 | CH3 | CH3 | CH3 | NCH3 | |
| Q-12 | CH3 | CH3 | CH3 | CH3 | OCH3 | N | NCH3 | |
| Q-12 | CH3 | CH3 | CH3 | CH3 | OCH3 | CH | NCH3 | |

TABLE 1c-continued

General Structure 1

| Q | R | $R_3'$ | $R_4$ | X | Y | Z | W" | m.p. °C. |
|---|---|---|---|---|---|---|---|---|
| Q-12 | H | H | H | Br | $OCH_3$ | CH | $NCH_3$ | |
| Q-12 | H | H | H | $OCH_3$ | $N(CH_3)_2$ | CH | $NCH_3$ | |
| Q-13 | H | H | H | $CH_3$ | $OCH_3$ | CH | O | |
| Q-13 | H | H | H | $CH_3$ | $OCH_3$ | CH | O | |
| Q-13 | H | H | H | $CH_3$ | $CH_3$ | CH | O | |
| Q-13 | H | H | H | $CH_3$ | $OCH_3$ | N | O | |
| Q-13 | H | H | H | $OCH_3$ | $OCH_3$ | CH | O | |
| Q-13 | H | H | H | $CH_3$ | $CH_3$ | N | O | |
| Q-13 | H | H | H | $OCH_3$ | $OCH_3$ | N | O | |
| Q-13 | H | H | H | $CH_3$ | $OCH_3$ | CH | S | |
| Q-13 | H | H | H | $CH_3$ | $OCH_3$ | N | S | |
| Q-13 | H | H | H | $OCH_3$ | $OCH_3$ | CH | S | |
| Q-13 | H | H | H | $OCH_3$ | $OCH_3$ | N | S | |
| Q-13 | H | H | H | $CH_3$ | $OCH_3$ | CH | NH | |
| Q-13 | H | H | H | $CH_3$ | $OCH_3$ | N | NH | |
| Q-13 | H | H | H | $OCH_3$ | $OCH_3$ | CH | $NCH_3$ | 150-152 |
| Q-13 | H | H | H | $OCH_3$ | $OCH_3$ | N | NH | |
| Q-13 | H | $CH_3$ | H | $CH_3$ | $CH_3$ | CH | O | |
| Q-13 | H | H | $CH_3$ | $CH_3$ | $CH_3$ | N | O | |
| Q-13 | H | $CH_3$ | $CH_3$ | $CH_3$ | $OCH_3$ | CH | O | |
| Q-13 | $CH_3$ | H | H | $CH_3$ | $OCH_3$ | N | O | |
| Q-13 | H | H | H | $CH_3$ | $CH(OCH_3)_2$ | CH | O | |
| Q-13 | H | $CH_3$ | H | $CH_3$ | $OCH_3$ | CH | S | |
| Q-13 | H | H | $CH_3$ | $CH_3$ | $OCH_3$ | CH | S | |
| Q-13 | H | $CH_3$ | $CH_3$ | $CH_3$ | $OCH_3$ | N | S | |
| Q-13 | $CH_3$ | H | $CH_3$ | $OCH_3$ | $OCH_3$ | N | S | |
| Q-13 | $CH_3$ | $CH_3$ | $CH_3$ | $CH_3$ | $CH_3$ | N | S | |
| Q-13 | H | H | H | $OCH_3$ | 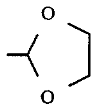 | CH | S | |
| Q-13 | H | $CH_3$ | H | $CH_3$ | $OCH_3$ | N | $NCH_3$ | |
| Q-13 | H | H | $CH_3$ | $CH_3$ | $OCH_3$ | N | $NCH_3$ | |
| Q-13 | H | $CH_3$ | $CH_3$ | $CH_3$ | $OCH_3$ | CH | $NCH_3$ | |
| Q-13 | $CH_3$ | H | H | $OCH_3$ | $OCH_3$ | CH | $NCH_3$ | |
| Q-13 | H | H | H | $CH_3$ | $OCH_3$ | N | NH | |
| Q-13 | H | H | H | Br | $OC_2H_5$ | CH | NH | |
| Q-13 | H | H | H | $OCH_3$ | $C_2H_5$ | N | NH | |
| Q-13 | H | H | H | $CH_3$ | $CH_3$ | CH | $NCH_3$ | |
| Q-13 | H | H | H | $CH_3$ | $CH_3$ | N | $NCH_3$ | |
| Q-13 | H | H | H | Cl | $OCH_3$ | CH | $NCH_3$ | |
| Q-14 | H | H | H | $CH_3$ | $CH_3$ | N | O | |
| Q-14 | H | H | H | $CH_3$ | $CH_3$ | CH | O | |
| Q-14 | H | H | H | $CH_3$ | $OCH_3$ | CH | O | |
| Q-14 | H | H | H | $CH_3$ | $OCH_3$ | CH | O | |
| Q-14 | H | H | H | $CH_3$ | $OCH_3$ | N | O | |
| Q-14 | H | H | H | $OCH_3$ | $OCH_3$ | CH | O | |
| Q-14 | H | H | H | $CH_3$ | $OCH_3$ | CH | S | |
| Q-14 | H | H | H | $CH_3$ | $OCH_3$ | N | S | |
| Q-14 | H | H | H | $OCH_3$ | $OCH_3$ | CH | S | |
| Q-14 | H | H | H | $OCH_3$ | $OCH_3$ | CH | S | |
| Q-14 | H | H | H | $OCH_3$ | $OCH_3$ | N | S | |
| Q-14 | H | H | H | $CH_3$ | $OCH_3$ | CH | $NCH_3$ | |
| Q-14 | H | H | H | $CH_3$ | $OCH_3$ | N | $NCH_3$ | |
| Q-14 | H | H | H | $OCH_3$ | $OCH_3$ | CH | NH | |
| Q-14 | H | H | H | $OCH_3$ | $OCH_3$ | N | $NCH_3$ | |
| Q-14 | H | $CH_3$ | H | $CH_3$ | $CH_3$ | CH | O | |
| Q-14 | H | H | $CH_3$ | $CH_3$ | $CH_3$ | N | O | |
| Q-14 | H | $CH_3$ | $CH_3$ | $CH_3$ | $OCH_3$ | CH | O | |
| Q-14 | $CH_3$ | $CH_3$ | $CH_3$ | $CH_3$ | $OCH_3$ | N | O | |
| Q-14 | H | H | H | $CH_3$ | $C_2H_5$ | N | O | |
| Q-14 | H | H | H | $CH_3$ | $OC_2H_5$ | N | O | |
| Q-14 | H | $CH_3$ | H | $CH_3$ | $OCH_3$ | CH | S | |
| Q-14 | H | H | $CH_3$ | $CH_3$ | $OCH_3$ | N | S | |
| Q-14 | H | $CH_3$ | $CH_3$ | $OCH_3$ | $OCH_3$ | CH | S | |
| Q-14 | $CH_3$ | $CH_3$ | $CH_3$ | $OCH_3$ | $OCH_3$ | CH | S | |
| Q-14 | H | H | H | $OCH_3$ | $C_2H_5$ | N | S | |
| Q-14 | H | H | H | $OCH_3$ | $OC_2H_5$ | N | S | |
| Q-14 | H | $CH_3$ | H | $CH_3$ | $OCH_3$ | CH | $NCH_3$ | |
| Q-14 | H | H | $CH_3$ | $CH_3$ | $OCH_3$ | N | $NCH_3$ | |
| Q-14 | H | $CH_3$ | $CH_3$ | $OCH_3$ | $OCH_3$ | CH | $NCH_3$ | |
| Q-14 | $CH_3$ | $CH_3$ | H | $OCH_3$ | $OCH_3$ | N | $NCH_3$ | |
| Q-14 | H | $CH_3$ | $CH_3$ | $CH_3$ | $OCH_3$ | CH | NH | |
| Q-14 | H | H | H | $CH_3$ | $OCH_3$ | N | NH | |
| Q-14 | H | H | H | $CH_3$ | $CH_2OCH_3$ | CH | $NCH_3$ | |

TABLE 1c-continued

General Structure 1

| Q | R | $R_3'$ | $R_4$ | X | Y | Z | W'' | m.p. °C. |
|---|---|---|---|---|---|---|---|---|
| Q-15 | H | H | H | $CH_3$ | $OCH_3$ | CH | O | |
| Q-15 | H | H | H | $CH_3$ | $OCH_3$ | N | O | |
| Q-15 | H | H | H | $OCH_3$ | $OCH_3$ | CH | O | |
| Q-15 | H | H | H | $OCH_3$ | $OCH_3$ | N | O | |
| Q-15 | H | $C_2H_5$ | H | $OCH_3$ | $OCH_3$ | CH | O | 134–136 |
| Q-15 | H | $CH_3$ | H | $CH_3$ | $OCH_3$ | CH | O | 150–152 |
| Q-15 | H | $CH_3$ | H | $CH_3$ | $CH_3$ | CH | O | 177–179 |
| Q-15 | H | $CH_3$ | H | $OCH_3$ | $OCH_3$ | CH | O | 133–134 |
| Q-15 | H | H | $CH_3$ | $CH_3$ | $CH_3$ | N | O | |
| Q-15 | H | $CH_3$ | H | $CH_3$ | $OCH_3$ | N | O | 158–160 |
| Q-15 | H | $CH_3$ | $CH_3$ | $CH_3$ | $OCH_3$ | CH | O | |
| Q-15 | H | $CH_3$ | H | $OCH_3$ | $OCH_3$ | N | O | 164–165 |
| Q-15 | $CH_3$ | H | H | $CH_3$ | $OCH_3$ | N | O | |
| Q-15 | H | $CH_3$ | H | $OCH_3$ | Cl | CH | O | 154–156 |
| Q-15 | $CH_3$ | $CH_3$ | $CH_3$ | $OCH_3$ | $OCH_3$ | CH | O | |
| Q-15 | H | H | H | $CH_3$ | $CF_3$ | CH | O | |
| Q-15 | H | H | H | $CH_3$ | $CF_3$ | N | O | |
| Q-15 | H | H | H | $OCH_3$ | $OCF_2H$ | CH | O | |
| Q-15 | $CH_3$ | H | H | $OCH_3$ | $OCF_2H$ | CH | O | |
| Q-15 | H | H | H | $CH_3$ | $CH_3$ | CH | O | |
| Q-15 | H | H | H | $CH_3$ | $CH_3$ | N | O | |
| Q-15 | H | H | H | $OCH_3$ | $OCH_3$ | CH | O* | |
| Q-15 | H | H | H | $OCH_3$ | $CH_3$ | N | O* | |
| Q-15 | H | H | H | $CH_3$ | $CH_3$ | N | S | |
| Q-15 | H | $CH_3$ | H | $CH_3$ | $OCH_3$ | CH | S | 146–149 |
| Q-15 | H | $CH_3$ | H | $CH_3$ | $OCH_3$ | N | S | 148–151 |
| Q-15 | H | $CH_3$ | H | $OCH_3$ | $OCH_3$ | CH | S | 164–168 |
| Q-15 | H | $CH_3$ | H | $OCH_3$ | $OCH_3$ | N | S | 170–173 |
| Q-15 | H | $CH_3$ | H | Cl | $OCH_3$ | CH | S | 141–149 |
| Q-15 | H | H | H | $CH_3$ | $OCH_3$ | CH | $NCH_3$ | |
| Q-15 | H | H | H | $CH_3$ | $OCH_3$ | N | $NCH_3$ | |
| Q-15 | H | H | H | $OCH_3$ | $OCH_3$ | CH | $NCH_3$ | |
| Q-15 | H | H | H | $OCH_3$ | $OCH_3$ | N | $NCH_3$ | |
| Q-15 | H | $CH_3$ | H | $CH_3$ | $CH_3$ | CH | S | 172–175 |
| Q-15 | H | H | $CH_3$ | $CH_3$ | $CH_3$ | N | S | |
| Q-15 | H | $CH_3$ | $CH_3$ | $CH_3$ | $OCH_3$ | CH | S | |
| Q-15 | $CH_3$ | H | H | $CH_3$ | $OCH_3$ | N | S | |
| Q-15 | $CH_3$ | H | $CH_3$ | $OCH_3$ | $OCH_3$ | CH | S | |
| Q-15 | H | H | H | Cl | $OC_2H_5$ | CH | S | |
| Q-15 | H | H | H | $OCH_3$ | $OCH_2CF_3$ | CH | S | |
| Q-15 | H | $CH_3$ | H | $CH_3$ | $CH_3$ | CH | $NCH_3$ | |
| Q-15 | H | H | $CH_3$ | $CH_3$ | $OCH_3$ | CH | $NCH_3$ | |
| Q-15 | H | $CH_3$ | $CH_3$ | $CH_3$ | $OCH_3$ | N | $NCH_3$ | |
| Q-15 | $CH_3$ | $CH_3$ | $CH_3$ | $CH_3$ | $OCH_3$ | N | $NCH_3$ | |
| Q-15 | $CH_3$ | H | H | $CH_3$ | $OCH_3$ | CH | NH | |
| Q-15 | H | H | H | $OCH_3$ | $OCH_3$ | N | NH | |
| Q-15 | H | H | H | $CH_3$ | $NHCH_3$ | CH | $NCH_3$ | |
| Q-15 | H | H | H | $OCH_3$ | $N(CH_3)_2$ | CH | $NCH_3$ | |
| Q-15 | H | H | H | $CH_3$ | $OCH_2C\equiv CH$ | N | S | |
| Q-15 | H | H | H | $CH_3$ | $CH_2C\equiv CH_3$ | CH | S | |
| Q-15 | H | H | H | $CH_3$ | $C\equiv CH$ | N | S | |
| Q-15 | H | $C_2H_5$ | H | $OCH_3$ | $OCH_3$ | CH | S | 127–129 |
| Q-15 | H | H | H | $OCH_3$ | $(CH_2)_3CH_2F$ | CH | S | |
| Q-15 | H | H | H | $OCH_3$ | 2-methyl-1,3-dioxolan-2-yl | N | S | |
| Q-15 | H | H | H | $OCH_3$ | 2-methyl-1,3-dithiolan-2-yl | CH | S | |
| Q-15 | H | H | H | $OCH_3$ | 2-methyl-1,3-dithian-2-yl | N | S | |
| Q-15 | H | H | H | $OCH_3$ | $OCH_3$ | CH | S* | |
| Q-15 | H | H | H | $OCH_3$ | $CH_3$ | N | S* | |

TABLE 1d

General Structure 1

| Q | R | $R_3$ | $R_4$ | $R_5$ | X | Y | Z | m.p. °C. |
|---|---|---|---|---|---|---|---|---|
| Q-18 | H | H | H | H | $CH_3$ | $CH_3$ | CH | 188–190 |
| Q-18 | H | H | H | H | $CH_3$ | $OCH_3$ | CH | 159–163 |
| Q-18 | H | H | H | H | $CH_3$ | $OCH_3$ | N | 133–136 |
| Q-18 | $CH_3$ | H | H | H | $CH_3$ | $OCH_3$ | N | |
| Q-18 | H | H | H | H | $OCH_3$ | $OCH_3$ | CH | 192–194 |
| Q-18 | H | H | H | H | $CH_3$ | $CH_3$ | CH | 165– |

TABLE 1d-continued

General Structure 1

| Q | R | $R_3$ | $R_4$ | $R_5$ | X | Y | Z | m.p. °C. |
|---|---|---|---|---|---|---|---|---|
| | | | | | | | | 167 |
| Q-18 | H | H | H | H | $OCH_3$ | $OCH_3$ | N | 163–166 |
| Q-18 | H | H | H | H | Cl | $OCH_3$ | CH | |
| Q-18 | H | $CH_3$ | H | H | $CH_3$ | $OCH_3$ | CH | |
| Q-18 | H | H | $CH_3$ | H | $CH_3$ | $OCH_3$ | N | |
| Q-18 | H | H | H | $CH_3$ | $CH_3$ | $CH_3$ | CH | |
| Q-18 | H | $CH_3$ | $CH_3$ | H | $CH_3$ | $CH_3$ | N | |
| Q-18 | H | H | $CH_3$ | $CH_3$ | $OCH_3$ | $OCH_3$ | CH | |
| Q-18 | H | $CH_3$ | H | $CH_3$ | $OCH_3$ | $OCH_3$ | N | |

TABLE 1d-continued

General Structure 1

| Q | R | $R_3$ | $R_4$ | $R_5$ | X | Y | Z | m.p. °C. |
|---|---|---|---|---|---|---|---|---|
| Q-18 | H | $CH_3$ | $CH_3$ | $CH_3$ | $CH_3$ | $OCH_3$ | CH | |
| Q-18 | H | H | H | H | $OCH_3$ | $CH(OCH_3)_2$ | CH | |
| Q-19 | $CH_3$ | H | H | H | Cl | $OCH_3$ | CH | |
| Q-19 | H | H | H | H | $CH_3$ | $OCH_3$ | CH | |
| Q-19 | H | H | H | H | $CH_3$ | $OCH_3$ | N | |
| Q-19 | H | H | H | H | $OCH_3$ | $OCH_3$ | CH | |
| Q-19 | H | H | H | H | $OCH_3$ | $OCH_3$ | N | |
| Q-19 | H | $CH_3$ | H | H | $CH_3$ | $CH_3$ | CH | |
| Q-19 | H | H | $CH_3$ | H | $CH_3$ | $CH_3$ | N | |
| Q-19 | H | H | H | $CH_3$ | $CH_3$ | $OCH_3$ | CH | |
| Q-19 | H | $CH_3$ | $CH_3$ | H | $CH_3$ | $OCH_3$ | N | |
| Q-19 | H | H | $CH_3$ | $CH_3$ | $OCH_3$ | $OCH_3$ | CH | |
| Q-19 | H | $CH_3$ | H | $CH_3$ | $OCH_3$ | $OCH_3$ | N | |
| Q-19 | H | H | H | H | $CH_3$ | $CH_3$ | CH | |
| Q-19 | H | $CH_3$ | $CH_3$ | $CH_3$ | $CH_3$ | $OCH_3$ | CH | |
| Q-19 | $CH_3$ | H | H | H | $CH_3$ | $OCH_3$ | N | |
| Q-19 | H | H | H | H | $OCH_3$ | 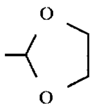 | CH | |

TABLE 1e

General Structure 1

| Q | R | R'3," | X | Y | Z | W' | m.p. °C. |
|---|---|---|---|---|---|---|---|
| Q-21 | H | H | $CH_3$ | $OCH_3$ | CH | O | |
| Q-21 | H | H | $CH_3$ | $OCH_3$ | N | O | |
| Q-21 | H | H | $OCH_3$ | $OCH_3$ | CH | O | |
| Q-21 | $CH_3$ | H | $OCH_3$ | $OCH_3$ | CH | O | |
| Q-21 | H | H | $OCH_3$ | $NHCH_3$ | CH | O | |
| Q-21 | H | H | $OCH_3$ | $OCH_3$ | N | O | |
| Q-21 | H | $CH_3$ | $CH_3$ | $OCH_3$ | CH | O | |
| Q-21 | $CH_3$ | $CH_3$ | $CH_3$ | $OCH_3$ | CH | O | |
| Q-21 | H | H | $CH_3$ | $CH_3$ | CH | O | |
| Q-21 | H | H | $CH_3$ | $CH_3$ | N | O | |
| Q-21 | H | H | $CH_3$ | $OCH_3$ | CH | S | |
| Q-21 | H | H | $CH_3$ | $OCH_3$ | N | S | |
| Q-21 | H | H | $OCH_3$ | $OCH_3$ | CH | S | |
| Q-21 | H | H | $OCH_3$ | $OCH_3$ | N | S | |
| Q-21 | H | $CH_3$ | $CH_3$ | $OCH_3$ | CH | S | |
| Q-21 | $CH_3$ | H | $CH_3$ | $OCH_3$ | CH | S | |
| Q-21 | H | H | $OCH_3$ | $N(CH_3)_2$ | N | S | |
| Q-22 | H | H | $CH_3$ | $OCH_3$ | CH | O | |
| Q-22 | H | H | $CH_3$ | $OCH_3$ | N | O | |
| Q-22 | H | H | $OCH_3$ | $OCH_3$ | CH | O | |
| Q-22 | H | H | $OCH_3$ | $OCH_3$ | N | O | |
| Q-22 | H | $CH_3$ | $CH_3$ | $OCH_3$ | CH | O | |
| Q-22 | H | $CH_3$ | $CH_3$ | $OCH_3$ | N | O | |
| Q-22 | $CH_3$ | $CH_3$ | $CH_3$ | $CH_3$ | CH | O | |
| Q-22 | H | H | $CH_3$ | $CH(OCH_3)_2$ | CH | O | |
| Q-22 | H | H | $CH_3$ | $C_2H_5$ | N | O | |
| Q-22 | H | H | $CH_3$ | $CH_3$ | CH | S | |
| Q-22 | H | H | $CH_3$ | $CH_3$ | N | S | |
| Q-22 | H | H | $CH_3$ | $OCH_3$ | CH | S | |
| Q-22 | H | H | $CH_3$ | $OCH_3$ | N | S | |
| Q-22 | H | H | $OCH_3$ | $OCH_3$ | CH | S | |
| Q-22 | H | H | $OCH_3$ | $OCH_3$ | N | S | |
| Q-22 | H | $CH_3$ | $CH_3$ | $OCH_3$ | CH | S | |
| Q-22 | $CH_3$ | $CH_3$ | $CH_3$ | $OCH_3$ | CH | S | |
| Q-22 | $CH_3$ | H | $CH_3$ | $OCH_3$ | N | S | |
| Q-22 | H | H | $CH_3$ | 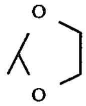 | CH | S | |
| Q-22 | H | H | $OCH_3$ | $C_2H_5$ | N | S | |
| Q-23 | H | H | $CH_3$ | $OCH_3$ | CH | — | |
| Q-23 | H | H | $CH_3$ | $OCH_3$ | N | — | |
| Q-23 | H | H | $OCH_3$ | $OCH_3$ | CH | — | |
| Q-23 | H | H | $OCH_3$ | $OCH_3$ | N | — | |
| Q-23 | H | $CH_3$ | $CH_3$ | $CH_3$ | CH | — | |
| Q-23 | H | $CH_3$ | $CH_3$ | $OCH_3$ | N | — | |
| Q-23 | $CH_3$ | H | $CH_3$ | $OCH_3$ | N | — | |
| Q-23 | $CH_3$ | $CH_3$ | $CH_3$ | $OCH_3$ | CH | — | |
| Q-23 | H | H | $CH_3$ | $OC_2H_5$ | N | — | |
| Q-23 | H | H | $CH_3$ | $CH_2OCH_3$ | CH | — | |
| Q-24 | H | H | $CH_3$ | $OCH_3$ | CH | — | |
| Q-24 | H | H | $CH_3$ | $OCH_3$ | N | — | |
| Q-24 | H | H | $OCH_3$ | $OCH_3$ | CH | — | |
| Q-24 | H | H | $OCH_3$ | $OCH_3$ | N | — | |
| Q-24 | H | $CH_3$ | $CH_3$ | $OCH_3$ | CH | — | |
| Q-24 | H | $CH_3$ | $CH_3$ | $CH_3$ | CH | — | |
| Q-24 | $CH_3$ | H | $CH_3$ | $CH_3$ | N | — | |

TABLE 1e-continued

General Structure 1

| Q | R | $R'_3$,'' | X | Y | Z | W' | m.p. °C. |
|---|---|---|---|---|---|---|---|
| Q-24 | H | H | $CH_3$ | $CF_3$ | CH | — | |
| Q-24 | H | H | $OCH_3$ | $OCF_2H$ | N | — | |
| Q-25 | H | H | $CH_3$ | $OCH_3$ | CH | —** | |
| Q-25 | H | H | $CH_3$ | $OCH_3$ | N | —** | |
| Q-25 | H | H | $OCH_3$ | $OCH_3$ | CH | —** | |
| Q-25 | H | H | $OCH_3$ | $OCH_3$ | N | —** | |
| Q-25 | $CH_3$ | H | $OCH_3$ | $OCH_3$ | N | —** | |
| Q-25 | H | H | $CH_3$ | $CH_3$ | CH | —** | |
| Q-25 | H | H | $CH_3$ | $CH_3$ | N | —** | |
| Q-25 | H | $CH_3$ | $CH_3$ | $OCH_3$ | CH | —** | |
| Q-25 | H | $CH_3$ | $CH_3$ | $OCH_3$ | N | —** | |
| Q-25 | $CH_3$ | $CH_3$ | $OCH_3$ | $OCH_3$ | N | —** | |
| Q-25 | H | H | $CH_3$ | $OCH_2CF_3$ | CH | —** | |
| Q-25 | H | H | $CH_3$ | $NHCH_3$ | N | —** | |
| Q-26 | H | H | $CH_3$ | $OCH_3$ | CH | —** | |
| Q-26 | H | H | $CH_3$ | $OCH_3$ | N | —** | |
| Q-26 | H | H | $OCH_3$ | $OCH_3$ | CH | —** | |
| Q-26 | H | $CH_3$ | $CH_3$ | $CH_3$ | N | —** | |
| Q-26 | H | $CH_3$ | $CH_3$ | $CH_3$ | CH | —** | |
| Q-26 | H | $CH_3$ | $CH_3$ | $OCH_3$ | N | —** | |
| Q-26 | H | $CH_3$ | $CH_3$ | $OCH_3$ | CH | —** | |
| Q-26 | H | $CH_3$ | $CH_3$ | $OCH_3$ | N | —** | |
| Q-26 | H | H | $CH_3$ | $CH_3$ | CH | —** | |
| Q-26 | H | H | $CH_3$ | $CH_3$ | N | —** | |
| Q-26 | H | $CH_3$ | $OCH_3$ | $OCH_3$ | CH | —** | |
| Q-26 | H | $CH_3$ | $OCH_3$ | $OCH_3$ | N | —** | |
| Q-26 | $CH_3$ | H | $CH_3$ | $OCH_3$ | CH | —** | |
| Q-26 | H | H | $CH_3$ | $N(CH_3)_2$ | CH | —** | |
| Q-26 | H | H | $CH_3$ | $N(CH_3)_2$ | N | —** | |
| Q-27 | H | H | $CH_3$ | $OCH_3$ | CH | —** | |
| Q-27 | H | H | $CH_3$ | $OCH_3$ | N | —** | |
| Q-27 | H | H | $OCH_3$ | $OCH_3$ | CH | —** | |
| Q-27 | H | H | $OCH_3$ | $OCH_3$ | N | —** | |
| Q-27 | H | H | $CH_3$ | $CH_3$ | CH | —** | |
| Q-27 | H | H | $CH_3$ | $CH_3$ | N | —** | |
| Q-27 | H | $CH_3$ | $CH_3$ | $CH_3$ | CH | —** | |
| Q-27 | H | H | Cl | $OC_2H_5$ | CH | —** | |
| Q-27 | H | $CH_3$ | $CH_3$ | $CH_3$ | N | —** | |
| Q-27 | H | $CH_3$ | $CH_3$ | $OCH_3$ | CH | —** | |
| Q-27 | H | $CH_3$ | $CH_3$ | $OCH_3$ | N | —** | |
| Q-27 | H | $CH_3$ | $OCH_3$ | $OCH_3$ | CH | —** | |
| Q-27 | H | $CH_3$ | $OCH_3$ | $OCH_3$ | N | —** | |
| Q-27 | $CH_3$ | $CH_3$ | $CH_3$ | $OCH_3$ | N | —** | |
| Q-27 | $CH_3$ | H | $CH_3$ | $OCH_3$ | N | —** | |
| Q-27 | H | H | $CH_3$ | $CH(OCH_3)_2$ | CH | —** | |
| Q-27 | H | H | $CH_3$ | $O(CH_2)_3CH_2Cl$ | CH | —** | |
| Q-25 | H | SH | $CH_3$ | $CH_3$ | CH | —** | |
| Q-25 | H | SH | $CH_3$ | $OCH_3$ | CH | —** | |
| Q-25 | H | SH | $OCH_3$ | $OCH_3$ | CH | —** | |
| Q-25 | H | SH | $OCH_3$ | Cl | CH | —** | |
| Q-25 | H | SH | $CH_3$ | $OCH_3$ | N | —** | |
| Q-25 | H | SH | $OCH_3$ | $OCH_3$ | N | —** | |
| Q-25 | H | $SCH_3$ | $CH_3$ | $CH_3$ | CH | —** | |
| Q-25 | H | $SCH_3$ | $CH_3$ | $OCH_3$ | CH | —** | |
| Q-25 | H | $SCH_3$ | $OCH_3$ | $OCH_3$ | CH | —** | |
| Q-25 | H | $SCH_3$ | $OCH_3$ | Cl | CH | —** | |
| Q-25 | H | $SCH_3$ | CH | $OCH_3$ | N | —** | |
| Q-25 | H | $SCH_3$ | $OCH_3$ | $OCH_3$ | N | —** | |
| Q-25 | H | $SCH_2CH{=}CH_2$ | $CH_3$ | $CH_3$ | CH | —** | |
| Q-25 | H | $SCH_2CH{=}CH_2$ | $CH_3$ | $OCH_3$ | CH | —** | |
| Q-25 | H | $SCH_2CH{=}CH_2$ | $OCH_3$ | $OCH_3$ | CH | —** | |
| Q-25 | H | $SCH_2CH{=}CH_2$ | $OCH_3$ | Cl | CH | —** | |
| Q-25 | H | $SCH_2CH{=}CH_2$ | $CH_3$ | $OCH_3$ | N | —** | |
| Q-25 | H | $SCH_2CH{=}CH_2$ | $OCH_3$ | $OCH_3$ | N | —** | |
| Q-25 | $CH_3$ | $SCH_3$ | $OCH_3$ | $OCH_3$ | CH | —** | |
| Q-25 | $CH_3$ | SH | $OCH_3$ | $OCH_3$ | CH | —** | |
| Q-25 | $CH_3$ | $SCH_2CH{=}CH_2$ | $OCH_3$ | $OCH_3$ | CH | —** | |

$R_{11}$ is —, unless indicated by ** where $R_{11}$ is $CH_3$ in all Tables.

TABLE 1f

General Structure 1

| Q | R | $R_3$ | $R_4$ | $R_5$ | X | Y | Z | m.p. °C. |
|---|---|---|---|---|---|---|---|---|
| Q-29 | H | H | H | — | $CH_3$ | $OCH_3$ | CH | |
| Q-29 | H | H | H | — | $CH_3$ | $OCH_3$ | N | |
| Q-29 | H | H | H | — | $OCH_3$ | $OCH_3$ | CH | |

TABLE 1f-continued

General Structure 1

| Q | R | $R_3$ | $R_4$ | $R_5$ | X | Y | Z | m.p. °C. |
|---|---|---|---|---|---|---|---|---|
| Q-29 | H | H | H | — | $OCH_3$ | $OCH_3$ | N | |
| Q-29 | H | H | H | — | $CH_3$ | $CH_3$ | CH | |
| Q-29 | H | H | H | — | $CH_3$ | $CH_3$ | N | |
| Q-29 | H | $CH_3$ | H | — | $CH_3$ | $OCH_3$ | CH | |
| Q-29 | H | $CH_3$ | H | — | $CH_3$ | $CH_3$ | CH | |
| Q-29 | H | $CH_3$ | $CH_3$ | — | $CH_3$ | $OCH_3$ | N | |
| Q-29 | $CH_3$ | $CH_3$ | $CH_3$ | — | $CH_3$ | $CH_3$ | N | |
| Q-29 | $CH_3$ | H | H | — | $OCH_3$ | $OCH_3$ | CH | |
| Q-29 | H | H | H | — | $CH_3$ | $OC_2H_5$ | N | |
| Q-29 | H | H | H | — | Cl | $OCH_3$ | CH | |
| Q-36 | H | H | H | H | $CH_3$ | $OCH_3$ | CH | |
| Q-36 | $CH_3$ | H | H | H | $CH_3$ | $OCH_3$ | CH | |
| Q-36 | H | H | H | H | $CH_3$ | $OCH_3$ | N | |
| Q-36 | H | H | H | H | $OCH_3$ | $OCH_3$ | CH | |
| Q-36 | H | H | H | H | $OCH_3$ | $OCH_3$ | N | |
| Q-36 | H | H | H | H | $OCH_3$ | $C_2H_5$ | CH | |
| Q-36 | H | H | H | H | $CH_3$ | $CH_3$ | CH | |
| Q-36 | H | H | H | H | $CH_3$ | $CH_3$ | N | |
| Q-36 | H | $CH_3$ | H | H | $CH_3$ | $CH_3$ | CH | |
| Q-36 | H | H | $CH_3$ | H | $CH_3$ | $CH_3$ | N | |
| Q-36 | H | $CH_3$ | H | $CH_3$ | $CH_3$ | $OCH_3$ | CH | |
| Q-36 | H | $CH_3$ | $CH_3$ | H | $CH_3$ | $OCH_3$ | N | |
| Q-36 | H | $CH_3$ | $CH_3$ | H | $CH_3$ | $OCH_3$ | N | |
| Q-36 | H | $CH_3$ | $CH_3$ | $CH_3$ | $OCH_3$ | $OCH_3$ | CH | |
| Q-36 | $CH_3$ | H | H | H | $OCH_3$ | $OCH_3$ | N | |
| Q-36 | H | H | H | H | $CH_3$ | $NHCH_3$ | CH | |
| Q-36 | H | H | H | H | $CH_3$ | $N(CH_3)_2$ | CH | |
| Q-37 | H | H | H | — | $CH_3$ | $OCH_3$ | CH | |
| Q-37 | H | H | H | — | $CH_3$ | $OCH_3$ | N | |
| Q-37 | H | H | H | — | $OCH_3$ | $OCH_3$ | CH | |
| Q-37 | H | H | H | — | $OCH_3$ | $OCH_3$ | N | |
| Q-37 | H | H | H | — | $CH_3$ | $CH_3$ | CH | |
| Q-37 | H | 2-$CH_3$ | H | — | $CH_3$ | $CH_3$ | CH | |
| Q-37 | H | 4-$CH_3$ | H | — | $CH_3$ | $CH_3$ | N | |
| Q-37 | H | 5-$CH_3$ | H | — | $CH_3$ | OCH | CH | |
| Q-37 | H | H | H | — | $CH_3$ | $CH_3$ | N | |
| Q-37 | H | 2-$CH_3$ | 4-$CH_3$ | — | $CH_3$ | $OCH_3$ | N | |
| Q-37 | H | 2-$CH_3$ | 5-$CH_3$ | — | $OCH_3$ | $OCH_3$ | CH | |
| Q-37 | H | 4-$CH_3$ | 5-$CH_3$ | — | $OCH_3$ | $OCH_3$ | N | |
| Q-37 | $CH_3$ | H | H | — | $CH_3$ | $OCH_3$ | CH | |
| Q-37 | H | H | H | — | $CH_3$ | $CH(OCH_3)_2$ | CH | |
| Q-37 | H | H | H | — | Cl | $OCH_3$ | CH | |
| Q-38 | H | H | H | — | $CH_3$ | $OCH_3$ | CH | |
| Q-38 | H | H | H | — | $CH_3$ | $OCH_3$ | N | |
| Q-38 | H | H | H | — | $OCH_3$ | $OCH_3$ | CH | |
| Q-38 | H | H | H | — | $OCH_3$ | $OCH_3$ | N | |
| Q-38 | H | 2-$CH_3$ | H | — | $CH_3$ | $CH_3$ | CH | |
| Q-38 | H | 4-$CH_3$ | H | — | $CH_3$ | $CH_3$ | N | |
| Q-38 | H | 2-$CH_3$ | 4-$CH_3$ | — | $CH_3$ | $OCH_3$ | CH | |
| Q-38 | H | 4-$CH_3$ | 4-$CH_3$ | — | $CH_3$ | $OCH_3$ | N | |
| Q-38 | H | H | H | — | $CH_3$ | $CH_3$ | N | |
| Q-38 | $CH_3$ | 4-$CH_3$ | 6-$CH_3$ | — | $OCH_3$ | $OCH_3$ | CH | |
| Q-38 | H | H | H | — | $CH_3$ | 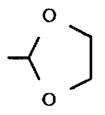 | CH | |
| Q-38 | H | H | H | — | $CH_3$ | $CH_3$ | CH | |
| Q-38 | H | H | H | — | $OCH_3$ | $C_2H_5$ | N | |
| Q-39 | H | H | H | — | $CH_3$ | $OCH_3$ | CH | |
| Q-39 | H | H | H | — | $CH_3$ | $OCH_3$ | N | |
| Q-39 | H | H | H | — | $CH_3$ | $CH_3$ | N | |
| Q-39 | H | H | H | — | $OCH_3$ | $OCH_3$ | CH | |
| Q-39 | H | H | H | — | $OCH_3$ | $OCH_3$ | N | |
| Q-39 | $CH_3$ | H | H | — | $OCH_3$ | $OCH_3$ | N | |
| Q-39 | H | 3-$CH_3$ | H | — | $CH_3$ | $CH_3$ | CH | |
| Q-39 | H | H | H | — | $CH_3$ | $CH_3$ | CH | |
| Q-39 | H | 5-$CH_3$ | H | — | $CH_3$ | $CH_3$ | N | |
| Q-39 | H | H | H | — | CL | $OC_2H_5$ | CH | |
| Q-39 | H | 6-$CH_3$ | H | — | $CH_3$ | $OCH_3$ | CH | |
| Q-39 | H | 3-$CH_3$ | 5-$CH_3$ | — | $CH_3$ | $OCH_3$ | N | |
| Q-39 | H | 3-$CH_3$ | 6-$CH_3$ | — | $OCH_3$ | $OCH_3$ | CH | |
| Q-39 | H | 5-$CH_3$ | 6-$CH_3$ | — | $OCH_3$ | $OCH_3$ | N | |
| Q-39 | H | H | H | — | $OCH_3$ | $OC_2H_5$ | N | |
| Q-39 | H | H | H | — | $OCH_3$ | $CH_2OCH_3$ | N | |
| Q-40 | H | H | H | — | $CH_3$ | $CH_3$ | CH | |

TABLE 1f-continued

| General Structure 1 | | | | | | | | |
|---|---|---|---|---|---|---|---|---|
| Q | R | $R_3$ | $R_4$ | $R_5$ | X | Y | Z | m.p. °C. |
| Q-40 | H | H | H | — | $CH_3$ | $OCH_3$ | CH | |
| Q-40 | H | H | H | — | $CH_3$ | $OCH_3$ | N | |
| Q-40 | H | H | H | — | $OCH_3$ | $OCH_3$ | CH | |
| Q-40 | H | H | H | — | $OCH_3$ | $OCH_3$ | N | |
| Q-40 | H | H | H | — | $CH_3$ | $CH_3$ | N | |
| Q-40 | H | 4-$CH_3$ | H | — | $CH_3$ | $CH_3$ | CH | |
| Q-40 | H | 5-$CH_3$ | H | — | $CH_3$ | $CH_3$ | N | |
| Q-40 | H | 6-$CH_3$ | H | — | $CH_3$ | $OCH_3$ | CH | |
| Q-40 | H | 4-$CH_3$ | 5-$CH_3$ | — | $CH_3$ | $OCH_3$ | N | |
| Q-40 | H | 4-$CH_3$ | 6-$CH_3$ | — | $OCH_3$ | $OCH_3$ | CH | |
| Q-40 | H | 5-$CH_3$ | 6-$CH_3$ | — | $OCH_3$ | $OCH_3$ | N | |
| Q-40 | $CH_3$ | H | H | — | $CH_3$ | $CH_3$ | CH | |
| Q-40 | H | H | H | — | $OCH_3$ | $CF_3$ | N | |
| Q-40 | H | H | H | — | $OCH_3$ | $OCF_2H$ | N | |
| Q-43 | H | H | H | — | $CH_3$ | $CH_3$ | CH | |
| Q-43 | H | H | H | — | $CH_3$ | $OCH_3$ | CH | |
| Q-43 | H | H | H | — | $CH_3$ | $OCH_3$ | N | |
| Q-43 | H | H | H | — | $OCH_3$ | $OCH_3$ | CH | |
| Q-43 | H | H | H | — | $OCH_3$ | $OCH_3$ | N | |
| Q-43 | $CH_3$ | H | H | — | $OCH_3$ | $OCH_3$ | CH | |
| Q-43 | H | $CH_3$ | $CH_3$ | — | $CH_3$ | $OCH_3$ | CH | |
| Q-43 | H | $CH_3$ | H | — | $CH_3$ | $CH_3$ | CH | |
| Q-43 | H | H | H | — | $CH_3$ | $CH_3$ | N | |
| Q-43 | H | H | H | — | $OCH_3$ | $OCH_2CF_3$ | N | |
| Q-43 | H | H | H | — | $OCH_3$ | $NHCH_3$ | N | |
| Q-44 | H | H | H | — | $CH_3$ | $OCH_3$ | CH | |
| Q-44 | H | H | H | — | $CH_3$ | $OCH_3$ | N | |
| Q-44 | H | H | H | — | $OCH_3$ | $OCH_3$ | CH | |
| Q-44 | H | H | H | — | $OCH_3$ | $OCH_3$ | N | |
| Q-44 | H | $CH_3$ | H | — | $CH_3$ | $CH_3$ | CH | |
| Q-44 | H | H | $CH_3$ | — | $CH_3$ | $CH_3$ | N | |
| Q-44 | H | $CH_3$ | $CH_3$ | — | $CH_3$ | $OCH_3$ | N | |
| Q-44 | $CH_3$ | H | H | — | $CH_3$ | $OCH_3$ | N | |
| Q-44 | H | H | H | — | $OCH_3$ | $N(CH_3)_2$ | N | |
| Q-44 | H | H | H | — | Br | $OCH_3$ | CH | |
| Q-44 | H | H | H | — | $CH_3$ | $CH_3$ | CH | |
| Q-44 | H | H | H | — | $CH_3$ | $CH_3$ | N | |
| Q-45 | H | H | — | — | $CH_3$ | $OCH_3$ | CH | |
| Q-45 | H | H | — | — | $CH_3$ | $OCH_3$ | N | |
| Q-45 | H | H | — | — | $OCH_3$ | $OCH_3$ | CH | |
| Q-45 | H | H | — | — | $OCH_3$ | $OCH_3$ | N | |
| Q-45 | H | $CH_3$ | — | — | $CH_3$ | $CH_3$ | CH | |
| Q-45 | $CH_3$ | H | — | — | $CH_3$ | $CH_3$ | N | |
| Q-45 | H | H | — | — | $OCH_3$ | $CH(OCH_3)_2$ | N | |
| Q-45 | H | H | — | — | $CH_3$ | $CH_3$ | CH | |
| Q-45 | H | H | — | — | $CH_3$ | $CH_3$ | N | |
| Q-45 | H | H | — | — | Cl | $OCH_3$ | CH | |

wherein W' is O.

TABLE 2a

| General Structure 1 wherein Q is Q-5. | | | | | | | | | | |
|---|---|---|---|---|---|---|---|---|---|---|
| R | $R_3$ | $R_4$ | $R_5$ | $R_6$ | $R_7$ | $R_8$ | X | Y | Z | m.p. °C. |
| H | H | H | H | H | H | H | $CH_3$ | $CH_3$ | N | |
| H | H | H | H | H | H | H | $CH_3$ | $OCH_3$ | CH | |
| H | H | H | H | H | H | H | $CH_3$ | $OCH_3$ | N | |
| H | H | H | H | H | H | H | $OCH_3$ | $OCH_3$ | CH | |
| H | H | H | H | H | H | H | $OCH_3$ | $OCH_3$ | N | |
| $CH_3$ | H | H | H | H | H | H | $OCH_3$ | $OCH_3$ | CH | |
| H | $CH_3$ | H | H | H | H | H | $CH_3$ | $CH_3$ | CH | |
| H | H | H | $CH_3$ | H | H | H | $CH_3$ | $CH_3$ | N | |
| H | H | H | H | H | $CH_3$ | H | $CH_3$ | $OCH_3$ | CH | |
| H | $CH_3$ | $CH_3$ | H | H | $CH_3$ | H | $CH_3$ | $OCH_3$ | N | |
| H | $CH_3$ | H | $CH_3$ | H | H | H | $OCH_3$ | $OCH_3$ | CH | |
| H | $CH_3$ | H | H | H | $CH_3$ | H | $OCH_3$ | $OCH_3$ | N | |
| H | H | H | $CH_3$ | H | $CH_3$ | H | $CH_3$ | $CH_3$ | CH | |
| H | $CH_3$ | H | $CH_3$ | H | $CH_3$ | H | $CH_3$ | $CH_3$ | N | |
| H | $CH_3$ | $CH_3$ | H | H | H | H | $CH_3$ | $OCH_3$ | CH | |
| H | H | H | H | $CH_3$ | H | H | $CH_3$ | $OCH_3$ | N | |
| H | H | H | H | H | $CH_3$ | $CH_3$ | $OCH_3$ | $OCH_3$ | CH | |
| H | $CH_3$ | $CH_3$ | $CH_3$ | H | H | H | $OCH_3$ | $OCH_3$ | N | |
| H | $CH_3$ | $CH_3$ | H | H | $CH_3$ | H | $CH_3$ | $CH_3$ | CH | |
| H | H | H | $CH_3$ | $CH_3$ | $CH_3$ | H | $CH_3$ | $CH_3$ | N | |
| H | $CH_3$ | H | $CH_3$ | $CH_3$ | $CH_3$ | H | $CH_3$ | $OCH_3$ | CH | |
| H | $CH_3$ | $CH_3$ | $CH_3$ | H | $CH_3$ | H | $CH_3$ | $OCH_3$ | N | |
| H | $CH_3$ | H | $CH_3$ | H | $CH_3$ | $CH_3$ | $OCH_3$ | $OCH_3$ | CH | |
| H | $CH_3$ | H | $CH_3$ | $CH_3$ | $CH_3$ | $CH_3$ | $CH_3$ | $CH_3$ | CH | |

TABLE 2a-continued

| General Structure 1 wherein Q is Q-5. | | | | | | | | | | |
|---|---|---|---|---|---|---|---|---|---|---|
| R | $R_3$ | $R_4$ | $R_5$ | $R_6$ | $R_7$ | $R_8$ | X | Y | Z | m.p. °C. |
| H | $CH_3$ | H | $CH_3$ | $CH_3$ | $CH_3$ | $CH_3$ | $CH_3$ | $CH_3$ | CH | |
| H | $CH_3$ | $CH_3$ | $CH_3$ | $CH_3$ | $CH_3$ | H | $CH_3$ | $CH_3$ | N | |
| H | $CH_3$ | $CH_3$ | $CH_3$ | $CH_3$ | $CH_3$ | $CH_3$ | $CH_3$ | $OCH_3$ | CH | |
| $CH_3$ | H | H | H | H | H | H | $CH_3$ | $OCH_3$ | N | |
| H | H | H | H | H | H | H | $OCH_3$ | $CH(OCH_3)_2$ | N | |
| H | H | H | H | H | H | H | $OCH_3$ | 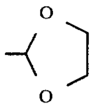 | N | |
| H | H | H | H | H | H | H | Cl | $OCH_3$ | CH | |
| H | H | H | H | H | H | H | $CH_3$ | $CH_3$ | CH | |

TABLE 2b

| General Structure 1 wherein Q is Q-6. | | | | | | | | | | | | |
|---|---|---|---|---|---|---|---|---|---|---|---|---|
| Q | R | $R_3$ | $R_4$ | $R_5$ | $R_6$ | $R_7$ | $R_8$ | X | Y | Z | W'' | m.p. °C. |
| Q-6 | H | H | H | H | H | H | H | $CH_3$ | $CH_3$ | CH | O | |
| Q-6 | H | H | H | H | H | H | H | $CH_3$ | $CH_3$ | N | O | |
| Q-6 | H | $CH_3$ | H | H | H | H | H | $CH_3$ | $OCH_3$ | CH | O | |
| Q-6 | H | H | H | $CH_3$ | H | H | H | $CH_3$ | $OCH_3$ | N | O | |
| Q-6 | H | H | H | H | H | $CH_3$ | H | $OCH_3$ | $OCH_3$ | CH | O | |
| Q-6 | H | $CH_3$ | H | $CH_3$ | H | H | H | $OCH_3$ | $OCH_3$ | N | O | |
| Q-6 | H | $CH_3$ | H | H | H | $CH_3$ | H | $CH_3$ | $CH_3$ | CH | O | |
| Q-6 | H | H | H | $CH_3$ | H | $CH_3$ | H | $CH_3$ | $CH_3$ | N | O | |
| Q-6 | H | $CH_3$ | $CH_3$ | H | H | H | H | $CH_3$ | $OCH_3$ | CH | O | |
| Q-6 | H | H | H | $CH_3$ | $CH_3$ | H | H | $CH_3$ | $OCH_3$ | N | O | |
| Q-6 | H | H | H | H | H | $CH_3$ | $CH_3$ | $OCH_3$ | $OCH_3$ | CH | O | |
| Q-6 | H | $CH_3$ | H | H | H | $CH_3$ | $CH_3$ | $OCH_3$ | $OCH_3$ | N | O | |
| Q-6 | H | $CH_3$ | $CH_3$ | H | H | $CH_3$ | H | $CH_3$ | $CH_3$ | CH | O | |
| Q-6 | H | $CH_3$ | H | $CH_3$ | $CH_3$ | H | H | $CH_3$ | $CH_3$ | N | O | |
| Q-6 | H | H | H | $CH_3$ | $CH_3$ | $CH_3$ | H | $CH_3$ | $OCH_3$ | CH | O | |
| Q-6 | H | $CH_3$ | $CH_3$ | $CH_3$ | H | H | H | $CH_3$ | $OCH_3$ | N | O | |
| Q-6 | H | H | H | $CH_3$ | $CH_3$ | $CH_3$ | H | $OCH_3$ | $OCH_3$ | CH | O | |
| Q-6 | H | $CH_3$ | H | $CH_3$ | $CH_3$ | $CH_3$ | H | $OCH_3$ | $OCH_3$ | N | O | |
| Q-6 | H | $CH_3$ | $CH_3$ | $CH_3$ | H | $CH_3$ | H | $CH_3$ | $CH_3$ | CH | O | |
| Q-6 | H | $CH_3$ | H | $CH_3$ | H | $CH_3$ | $CH_3$ | $CH_3$ | $CH_3$ | N | O | |
| Q-6 | H | $CH_3$ | $CH_3$ | $CH_3$ | $CH_3$ | H | H | $CH_3$ | $OCH_3$ | CH | O | |
| Q-6 | H | $CH_3$ | $CH_3$ | H | H | $CH_3$ | $CH_3$ | $CH_3$ | $OCH_3$ | N | O | |
| Q-6 | H | H | H | $CH_3$ | $CH_3$ | $CH_3$ | $CH_3$ | $OCH_3$ | $OCH_3$ | CH | O | |
| Q-6 | H | $CH_3$ | H | $CH_3$ | $CH_3$ | $CH_3$ | $CH_3$ | $OCH_3$ | $OCH_3$ | N | O | |
| Q-6 | H | $CH_3$ | $CH_3$ | $CH_3$ | H | $CH_3$ | $CH_3$ | $CH_3$ | $CH_3$ | CH | O | |
| Q-6 | H | $CH_3$ | $CH_3$ | $CH_3$ | $CH_3$ | $CH_3$ | H | $CH_3$ | $CH_3$ | N | O | |
| Q-6 | H | $CH_3$ | $CH_3$ | $CH_3$ | $CH_3$ | $CH_3$ | $CH_3$ | $CH_3$ | $OCH_3$ | CH | O | |
| Q-6 | $CH_3$ | H | H | H | H | H | H | $CH_3$ | $OCH_3$ | N | O | |
| Q-6 | H | H | H | H | H | H | H | Br | $OCH_3$ | CH | O | |
| Q-6 | H | H | H | H | H | H | H | Cl | $OC_2H_5$ | CH | O | |
| Q-6 | H | H | H | H | H | H | H | $OCH_3$ | $C_2H_5$ | CH | O | |
| Q-6 | H | H | H | H | H | H | H | $OCH_3$ | $OC_2H_5$ | CH | O | |
| Q-6 | H | H | H | H | H | H | H | $CH_3$ | $OCH_3$ | CH | O | |
| Q-6 | H | H | H | H | H | H | H | $CH_3$ | $OCH_3$ | N | O | |
| Q-6 | H | H | H | H | H | H | H | $OCH_3$ | $OCH_3$ | CH | O | |
| Q-6 | H | H | H | H | H | H | H | $OCH_3$ | $OCH_3$ | N | O | |
| Q-6 | $CH_3$ | H | H | H | H | H | H | $OCH_3$ | $OCH_3$ | CH | O | |
| Q-6 | H | H | H | H | H | H | H | $CH_3$ | $OCH_3$ | CH | S | |
| Q-6 | H | H | H | H | H | H | H | $CH_3$ | $OCH_3$ | N | S | |
| Q-6 | H | H | H | H | H | H | H | $OCH_3$ | $OCH_3$ | CH | S | |
| Q-6 | H | H | H | H | H | H | H | $OCH_3$ | $OCH_3$ | N | S | |
| Q-6 | H | H | H | H | H | H | H | $OCH_3$ | $C_2H_5$ | CH | S | |
| Q-6 | H | H | H | H | H | H | H | $CH_3$ | $CH_3$ | CH | S | |
| Q-6 | H | H | H | H | H | H | H | $CH_3$ | $CH_3$ | N | S | |
| Q-6 | H | $CH_3$ | H | H | H | H | H | $CH_3$ | $OCH_3$ | CH | S | |
| Q-6 | H | H | H | $CH_3$ | H | H | H | $CH_3$ | $OCH_3$ | N | S | |
| Q-6 | H | H | H | H | H | $CH_3$ | H | $OCH_3$ | $OCH_3$ | CH | S | |
| Q-6 | H | $CH_3$ | H | $CH_3$ | H | H | H | $OCH_3$ | $OCH_3$ | N | S | |
| Q-6 | H | $CH_3$ | H | H | H | $CH_3$ | H | $CH_3$ | $CH_3$ | CH | S | |
| Q-6 | H | H | H | $CH_3$ | H | $CH_3$ | H | $CH_3$ | $CH_3$ | N | S | |
| Q-6 | H | $CH_3$ | $CH_3$ | H | H | H | H | $CH_3$ | $OCH_3$ | CH | S | |
| Q-6 | H | H | H | $CH_3$ | $CH_3$ | H | H | $CH_3$ | $OCH_3$ | N | S | |
| Q-6 | H | H | H | H | H | H | H | $OCH_3$ | $CH_2OCH_3$ | CH | S | |
| Q-6 | H | H | H | H | H | H | H | $OCH_3$ | $CF_3$ | CH | S | |
| Q-6 | H | H | H | H | H | H | H | $OCH_3$ | $OCF_2H$ | CH | S | |
| Q-6 | H | H | H | H | H | $CH_3$ | $CH_3$ | $OCH_3$ | $OCH_3$ | CH | S | |
| Q-6 | H | $CH_3$ | H | H | H | $CH_3$ | $CH_3$ | $OCH_3$ | $OCH_3$ | N | S | |
| Q-6 | H | $CH_3$ | $CH_3$ | H | H | $CH_3$ | H | $CH_3$ | $CH_3$ | CH | S | |

TABLE 2b-continued

General Structure 1 wherein Q is Q-6.

| Q | R | $R_3$ | $R_4$ | $R_5$ | $R_6$ | $R_7$ | $R_8$ | X | Y | Z | W'' | m.p. °C. |
|---|---|---|---|---|---|---|---|---|---|---|---|---|
| Q-6 | H | $CH_3$ | H | $CH_3$ | $CH_3$ | H | H | $CH_3$ | $CH_3$ | N | S | |
| Q-6 | H | H | H | $CH_3$ | $CH_3$ | $CH_3$ | H | $CH_3$ | $OCH_3$ | CH | S | |
| Q-6 | H | $CH_3$ | $CH_3$ | $CH_3$ | H | H | H | $CH_3$ | $OCH_3$ | N | S | |
| Q-6 | H | H | H | $CH_3$ | $CH_3$ | $CH_3$ | H | $OCH_3$ | $OCH_3$ | CH | S | |
| Q-6 | H | $CH_3$ | H | $CH_3$ | $CH_3$ | $CH_3$ | H | $OCH_3$ | $OCH_3$ | N | S | |
| Q-6 | H | $CH_3$ | $CH_3$ | $CH_3$ | H | $CH_3$ | H | $CH_3$ | $CH_3$ | CH | S | |
| Q-6 | H | $CH_3$ | H | $CH_3$ | H | $CH_3$ | $CH_3$ | $CH_3$ | $CH_3$ | N | S | |
| Q-6 | H | $CH_3$ | $CH_3$ | $CH_3$ | $CH_3$ | H | H | $CH_3$ | $OCH_3$ | CH | S | |
| Q-6 | H | $CH_3$ | $CH_3$ | H | H | $CH_3$ | $CH_3$ | $CH_3$ | $OCH_3$ | N | S | |
| Q-6 | H | H | H | $CH_3$ | $CH_3$ | $CH_3$ | $CH_3$ | $OCH_3$ | $OCH_3$ | CH | S | |
| Q-6 | H | $CH_3$ | H | $CH_3$ | $CH_3$ | $CH_3$ | $CH_3$ | $OCH_3$ | $OCH_3$ | N | S | |
| Q-6 | H | $CH_3$ | $CH_3$ | $CH_3$ | H | $CH_3$ | $CH_3$ | $CH_3$ | $CH_3$ | CH | S | |
| Q-6 | H | $CH_3$ | $CH_3$ | $CH_3$ | $CH_3$ | $CH_3$ | H | $CH_3$ | $CH_3$ | N | S | |
| Q-6 | H | $CH_3$ | $CH_3$ | $CH_3$ | $CH_3$ | $CH_3$ | $CH_3$ | $CH_3$ | $OCH_3$ | CH | S | |
| Q-6 | $CH_3$ | H | H | H | H | H | H | $CH_3$ | $OCH_3$ | N | S | |

TABLE 2c

General Structure 1

| Q | R | $R_3$ | $R_4$ | $R_5$ | $R_6$ | X | Y | Z | W' | m.p. °C. |
|---|---|---|---|---|---|---|---|---|---|---|
| Q-7 | H | H | H | H | H | $CH_3$ | $OCH_3$ | CH | — | 152-155 |
| Q-7 | H | H | H | H | H | $CH_3$ | $OCH_3$ | N | — | 144-146 |
| Q-7 | H | H | H | H | H | $OCH_3$ | $OCH_3$ | CH | — | 167-170 |
| Q-7 | H | H | H | H | H | $OCH_3$ | $OCH_3$ | N | — | 156-159 |
| Q-7 | H | H | H | H | H | $CH_3$ | $CH_3$ | CH | — | 170-173 |
| Q-7 | H | H | H | H | H | $CH_3$ | $CH_3$ | N | — | 153-156 |
| Q-7 | H | $CH_3$ | H | H | H | $CH_3$ | $OCH_3$ | CH | — | |
| Q-7 | H | H | $CH_3$ | H | H | $CH_3$ | $OCH_3$ | N | — | |
| Q-7 | H | $CH_3$ | H | H | $CH_3$ | $OCH_3$ | $OCH_3$ | CH | — | |
| Q-7 | H | H | $CH_3$ | $CH_3$ | H | $OCH_3$ | $OCH_3$ | N | — | |
| Q-7 | H | $CH_3$ | $CH_3$ | H | H | $CH_3$ | $CH_3$ | CH | — | |
| Q-7 | H | $CH_3$ | $CH_3$ | $CH_3$ | H | $CH_3$ | $CH_3$ | N | — | |
| Q-7 | H | $CH_3$ | H | $CH_3$ | $CH_3$ | $CH_3$ | $OCH_3$ | CH | — | |
| Q-7 | H | $CH_3$ | $CH_3$ | $CH_3$ | $CH_3$ | $CH_3$ | $OCH_3$ | N | — | |
| Q-7 | $CH_3$ | H | H | H | H | $OCH_3$ | $OCH_3$ | CH | — | |
| Q-7 | $CH_3$ | $CH_3$ | $CH_3$ | $CH_3$ | $CH_3$ | $OCH_3$ | $OCH_3$ | CH | — | |
| Q-7 | H | H | H | H | H | $OCH_3$ | $OCH_2CF_3$ | CH | — | |
| Q-7 | H | H | H | H | H | $OCH_3$ | $NHCH_3$ | CH | — | |
| Q-7 | H | H | H | H | H | Cl | $OCH_3$ | CH | — | 157-159 |
| Q-7 | H | H | H | H | H | $OCH_3$ | $OCH_3$ | CH | — | * |
| Q-7 | H | H | H | H | H | $OCH_3$ | $CH_3$ | N | — | * |
| Q-7 | H | H | H | H | H | $OCH_3$ | CH | CH | — | * |
| Q-16 | H | $CH_3$ | $CH_3$ | H | H | $CH_3$ | $OCH_3$ | CH | O | 157-160 |
| Q-16 | H | $CH_3$ | $CH_3$ | H | H | $CH_3$ | $OCH_3$ | N | O | 137-140 |
| Q-16 | H | $CH_3$ | $CH_3$ | H | H | $OCH_3$ | $OCH_3$ | CH | O | |
| Q-16 | H | $CH_3$ | $CH_3$ | H | H | $OCH_3$ | $OCH_3$ | N | O | 138-141 |
| Q-16 | $CH_3$ | $CH_3$ | $CH_3$ | H | H | $CH_3$ | $OCH_3$ | N | O | |
| Q-16 | $CH_3$ | $CH_3$ | $CH_3$ | H | H | Cl | $OCH_3$ | CH | O | |
| Q-16 | H | $CH_3$ | $CH_3$ | H | H | $CH_3$ | $CH_3$ | CH | O | 185-188 |
| Q-16 | H | $CH_3$ | $CH_3$ | H | H | $CH_3$ | $CH_3$ | N | O | 163-167 |
| Q-16 | H | H | H | H | H | $CH_3$ | $OCH_3$ | CH | O | |
| Q-16 | H | H | H | H | H | $CH_3$ | $OCH_3$ | N | O | |
| Q-16 | H | H | H | H | H | $OCH_3$ | $OCH_3$ | CH | O | |
| Q-16 | H | H | H | H | H | $OCH_3$ | $OCH_3$ | N | O | |
| Q-16 | H | $CH_3$ | $CH_3$ | H | H | $OCH_3$ | $N(CH_3)_2$ | CH | O | |
| Q-16 | H | $CH_3$ | $CH_3$ | H | H | $OCH_3$ | $CH(OCH_3)_2$ | CH | O | |
| Q-16 | H | $CH_3$ | $CH_3$ | H | H | Cl | $OCH_3$ | CH | O | 158-161 |
| Q-16 | H | $CH_3$ | $CH_3$ | H | H | $CH_3$ | $CH_2OCH_3$ | N | O | |
| Q-16 | H | $CH_3$ | H | H | H | $CH_3$ | $CH_3$ | CH | O | |
| Q-16 | H | H | H | $CH_3$ | H | $CH_3$ | $CH_3$ | N | O | |
| Q-16 | H | $CH_3$ | H | $CH_3$ | H | $CH_3$ | $OCH_3$ | N | O | |
| Q-16 | H | H | H | $CH_3$ | $CH_3$ | $CH_3$ | $OCH_3$ | CH | O | |
| Q-16 | H | $CH_3$ | H | $CH_3$ | $CH_3$ | $OCH_3$ | $OCH_3$ | CH | O | |
| Q-16 | H | $CH_3$ | $CH_3$ | $CH_3$ | H | $OCH_3$ | $OCH_3$ | N | O | |
| Q-16 | H | $CH_3$ | $CH_3$ | $CH_3$ | H | $CH_3$ | $CH_3$ | CH | O | |
| Q-16 | H | $CH_3$ | $CH_3$ | $CH_3$ | $CH_3$ | $CH_3$ | $CH_3$ | N | O | |
| Q-16 | H | $CH_3$ | $CH_3$ | H | H | $CH_3$ | $CH_3$ | CH | S | |
| Q-16 | H | $CH_3$ | $CH_3$ | H | H | $CH_3$ | $CH_3$ | N | S | |
| Q-16 | H | $CH_3$ | $CH_3$ | H | H | $CH_3$ | $OCH_3$ | CH | S | |
| Q-16 | H | $CH_3$ | $CH_3$ | H | H | $CH_3$ | $OCH_3$ | N | S | |
| Q-16 | H | $CH_3$ | $CH_3$ | H | H | $OCH_3$ | $OCH_3$ | CH | S | |
| Q-16 | H | $CH_3$ | $CH_3$ | H | H | $OCH_3$ | $OCH_3$ | N | S | |
| Q-16 | H | $CH_3$ | $CH_3$ | H | H | Cl | $OCH_3$ | CH | S | |
| Q-16 | H | $CH_3$ | $CH_3$ | H | H | $CH_3$ | $NHCH_3$ | N | S | |
| Q-16 | H | $CH_3$ | $CH_3$ | H | H | $CH_3$ | $N(CH_3)_2$ | N | S | |
| Q-16 | H | H | H | H | H | $CH_3$ | $OCH_3$ | CH | S | |
| Q-16 | H | H | H | H | H | $CH_3$ | $OCH_3$ | N | S | |

TABLE 2c-continued

| Q | R | $R_3$ | $R_4$ | $R_5$ | $R_6$ | X | Y | Z | W' | m.p. °C. |
|---|---|---|---|---|---|---|---|---|---|---|
| | | | | | General Structure 1 | | | | | |
| Q-16 | H | H | H | H | H | $OCH_3$ | $OCH_3$ | CH | S | |
| Q-16 | H | H | H | H | H | $OCH_3$ | $OCH_3$ | N | S | |
| Q-16 | $CH_3$ | H | H | H | H | $CH_3$ | $CH_3$ | CH | S | |
| Q-16 | H | $CH_3$ | H | H | H | $CH_3$ | $CH_3$ | N | S | |
| Q-16 | H | H | H | $CH_3$ | H | $CH_3$ | $OCH_3$ | N | S | |
| Q-16 | H | $CH_3$ | H | $CH_3$ | H | $CH_3$ | $OCH_3$ | CH | S | |
| Q-16 | H | H | H | $CH_3$ | $CH_3$ | $OCH_3$ | $OCH_3$ | CH | S | |
| Q-16 | H | $CH_3$ | $CH_3$ | $CH_3$ | H | $OCH_3$ | $OCH_3$ | N | S | |
| Q-16 | H | $CH_3$ | $CH_3$ | $CH_3$ | H | $CH_3$ | $CH_3$ | CH | S | |
| Q-16 | H | $CH_3$ | H | $CH_3$ | $CH_3$ | $CH_3$ | $CH_3$ | N | S | |
| Q-16 | H | $CH_3$ | $CH_3$ | $CH_3$ | $CH_3$ | $CH_3$ | $OCH_3$ | CH | S | |
| Q-17 | H | H | H | H | H | Cl | $OCH_3$ | CH | — | |
| Q-17 | H | H | H | H | H | $CH_3$ | $CH_3$ | CH | — | |
| Q-17 | H | H | H | H | H | Cl | $OC_2H_5$ | CH | — | |
| Q-17 | H | H | H | H | H | $CH_3$ | $CH_3$ | N | — | |
| Q-17 | H | H | H | H | H | $OCH_3$ | $OCH_3$ | CH | — | |
| Q-17 | H | H | H | H | H | $OCH_3$ | $OCH_3$ | N | — | |
| Q-17 | H | H | H | H | H | $OCH_3$ | $OC_2H_5$ | CH | — | |
| Q-17 | H | H | H | H | H | $OCH_3$ | $OC_2H_5$ | N | — | |
| Q-17 | H | $CH_3$ | H | H | H | $CH_3$ | $CH_3$ | CH | — | |
| Q-17 | H | H | H | H | H | $CH_3$ | $CH(OCH_3)_2$ | N | — | |
| Q-17 | H | H | H | H | H | $CH_3$ | 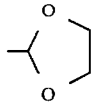 | N | — | |
| Q-17 | H | H | H | $CH_3$ | H | $CH_3$ | $CH_3$ | N | — | |
| Q-17 | H | $CH_3$ | $CH_3$ | H | H | $CH_3$ | $OCH_3$ | CH | — | |
| Q-17 | H | $CH_3$ | $CH_3$ | H | H | $CH_3$ | $OCH_3$ | N | — | |
| Q-17 | H | H | H | $CH_3$ | $CH_3$ | $OCH_3$ | $OCH_3$ | CH | — | |
| Q-17 | H | $CH_3$ | H | $CH_3$ | $CH_3$ | $OCH_3$ | $OCH_3$ | N | — | |
| Q-17 | H | $CH_3$ | $CH_3$ | $CH_3$ | H | $CH_3$ | $CH_3$ | CH | — | |
| Q-17 | H | $CH_3$ | $CH_3$ | $CH_3$ | H | $CH_3$ | $CH_3$ | N | — | |
| Q-17 | H | $CH_3$ | $CH_3$ | $CH_3$ | $CH_3$ | $CH_3$ | $OCH_3$ | CH | — | |
| Q-17 | $CH_3$ | H | H | H | H | $CH_3$ | $OCH_3$ | N | — | |

TABLE 2d

General Structure 1 wherein Q is Q-30

| R | $R_3$ | $R_4$ | $R_5$ | $R_6$ | $R_7$ | $R_8$ | $R_9$ | X | Y | Z | m.p. °C. |
|---|---|---|---|---|---|---|---|---|---|---|---|
| H | H | H | H | H | H | H | H | $CH_3$ | $OCH_3$ | CH | |
| H | H | H | H | H | H | H | H | $CH_3$ | $OCH_3$ | N | |
| H | H | H | H | H | H | H | H | $OCH_3$ | $OCH_3$ | CH | |
| H | H | H | H | H | H | H | H | $OCH_3$ | $OCH_3$ | N | |
| H | H | H | H | H | H | H | H | $CH_3$ | $CH_3$ | N | |
| H | H | H | H | H | H | H | H | $CH_3$ | $CH_3$ | CH | |
| $CH_3$ | H | H | H | H | H | H | H | $CH_3$ | $OCH_3$ | CH | |
| H | $CH_3$ | H | H | H | H | H | H | $CH_3$ | $OCH_3$ | N | |
| H | H | H | H | H | H | H | H | Cl | $OCH_3$ | CH | |
| H | H | $CH_3$ | H | H | H | H | H | $OCH_3$ | $OCH_3$ | CH | |
| H | H | H | H | $CH_3$ | H | H | H | $OCH_3$ | $OCH_3$ | N | |
| H | H | H | H | H | H | $CH_3$ | H | $CH_3$ | $CH_3$ | CH | |
| H | $CH_3$ | $CH_3$ | H | H | H | H | H | $CH_3$ | $CH_3$ | N | |
| H | $CH_3$ | H | H | $CH_3$ | H | H | H | $CH_3$ | $OCH_3$ | CH | |
| H | $CH_3$ | H | H | H | H | $CH_3$ | H | $CH_3$ | $OCH_3$ | N | |
| H | H | $CH_3$ | $CH_3$ | H | H | H | H | $OCH_3$ | $OCH_3$ | CH | |
| H | H | $CH_3$ | H | $CH_3$ | H | H | H | $OCH_3$ | $OCH_3$ | N | |
| H | H | $CH_3$ | H | H | H | $CH_3$ | H | $CH_3$ | $CH_3$ | CH | |
| H | H | H | H | $CH_3$ | $CH_3$ | H | H | $CH_3$ | $CH_3$ | N | |
| H | H | H | H | $CH_3$ | H | $CH_3$ | H | $CH_3$ | $OCH_3$ | CH | |
| H | H | H | H | H | H | $CH_3$ | $CH_3$ | $CH_3$ | $OCH_3$ | N | |
| H | $CH_3$ | $CH_3$ | $CH_3$ | H | H | H | H | $OCH_3$ | $OCH_3$ | CH | |
| H | $CH_3$ | $CH_3$ | H | $CH_3$ | H | H | H | $OCH_3$ | $OCH_3$ | N | |
| H | $CH_3$ | $CH_3$ | H | H | H | $CH_3$ | H | $CH_3$ | $CH_3$ | CH | |
| H | $CH_3$ | H | H | H | $CH_3$ | H | H | $CH_3$ | $CH_3$ | N | |
| H | $CH_3$ | H | H | $CH_3$ | H | $CH_3$ | H | $CH_3$ | $OCH_3$ | CH | |
| H | $CH_3$ | H | H | H | H | $CH_3$ | $CH_3$ | $CH_3$ | $OCH_3$ | N | |
| H | H | $CH_3$ | $CH_3$ | $CH_3$ | H | H | H | $OCH_3$ | $OCH_3$ | CH | |
| H | H | $CH_3$ | $CH_3$ | H | H | $CH_3$ | H | $OCH_3$ | $OCH_3$ | N | |
| H | H | $CH_3$ | H | $CH_3$ | $CH_3$ | H | H | $CH_3$ | $CH_3$ | CH | |
| H | H | $CH_3$ | H | $CH_3$ | H | $CH_3$ | H | $CH_3$ | $CH_3$ | N | |
| H | H | $CH_3$ | H | H | H | $CH_3$ | $CH_3$ | $CH_3$ | $OCH_3$ | CH | |
| H | H | H | H | $CH_3$ | $CH_3$ | $CH_3$ | H | $CH_3$ | $OCH_3$ | N | |
| H | H | H | H | $CH_3$ | H | $CH_3$ | $CH_3$ | $OCH_3$ | $OCH_3$ | CH | |
| H | $CH_3$ | $CH_3$ | $CH_3$ | $CH_3$ | H | H | H | $OCH_3$ | $OCH_3$ | N | |

TABLE 2d-continued

| General Structure 1 wherein Q is Q-30 | | | | | | | | | | | |
|---|---|---|---|---|---|---|---|---|---|---|---|
| R | $R_3$ | $R_4$ | $R_5$ | $R_6$ | $R_7$ | $R_8$ | $R_9$ | X | Y | Z | m.p. °C. |
| H | $CH_3$ | $CH_3$ | H | $CH_3$ | H | $CH_3$ | H | $CH_3$ | $CH_3$ | CH | |
| H | $CH_3$ | H | H | $CH_3$ | $CH_3$ | $CH_3$ | H | $CH_3$ | $OCH_3$ | N | |
| H | $CH_3$ | $CH_3$ | $CH_3$ | H | H | $CH_3$ | H | $CH_3$ | $OCH_3$ | CH | |
| H | $CH_3$ | H | H | $CH_3$ | H | $CH_3$ | $CH_3$ | $CH_3$ | $OCH_3$ | N | |
| H | $CH_3$ | $CH_3$ | H | $CH_3$ | $CH_3$ | H | H | $OCH_3$ | $OCH_3$ | CH | |
| H | $CH_3$ | $CH_3$ | H | H | H | $CH_3$ | $CH_3$ | $OCH_3$ | $OCH_3$ | N | |
| H | H | $CH_3$ | $CH_3$ | $CH_3$ | $CH_3$ | H | H | $CH_3$ | $CH_3$ | CH | |
| H | H | $CH_3$ | $CH_3$ | $CH_3$ | H | $CH_3$ | H | $CH_3$ | $CH_3$ | N | |
| H | H | $CH_3$ | H | $CH_3$ | $CH_3$ | $CH_3$ | H | $CH_3$ | $OCH_3$ | CH | |
| H | H | $CH_3$ | H | $CH_3$ | H | $CH_3$ | $CH_3$ | $CH_3$ | $OCH_3$ | N | |
| H | H | H | H | $CH_3$ | $CH_3$ | $CH_3$ | $CH_3$ | $OCH_3$ | $OCH_3$ | CH | |
| H | $CH_3$ | $CH_3$ | $CH_3$ | $CH_3$ | $CH_3$ | H | H | $OCH_3$ | $OCH_3$ | N | |
| H | $CH_3$ | $CH_3$ | H | $CH_3$ | $CH_3$ | $CH_3$ | H | $CH_3$ | $CH_3$ | CH | |
| H | $CH_3$ | $CH_3$ | H | $CH_3$ | H | $CH_3$ | $CH_3$ | $CH_3$ | $CH_3$ | N | |
| H | $CH_3$ | H | H | $CH_3$ | $CH_3$ | $CH_3$ | $CH_3$ | $CH_3$ | $OCH_3$ | CH | |
| H | $CH_3$ | $CH_3$ | $CH_3$ | H | H | $CH_3$ | $CH_3$ | $CH_3$ | $OCH_3$ | N | |
| H | H | $CH_3$ | $CH_3$ | $CH_3$ | H | $CH_3$ | $CH_3$ | $OCH_3$ | $OCH_3$ | CH | |
| H | H | $CH_3$ | H | $CH_3$ | $CH_3$ | $CH_3$ | $CH_3$ | $OCH_3$ | $OCH_3$ | N | |
| H | H | $CH_3$ | $CH_3$ | $CH_3$ | $CH_3$ | $CH_3$ | H | $CH_3$ | $CH_3$ | CH | |
| H | $CH_3$ | $CH_3$ | H | $CH_3$ | $CH_3$ | $CH_3$ | $CH_3$ | $CH_3$ | $CH_3$ | N | |
| H | $CH_3$ | $CH_3$ | $CH_3$ | $CH_3$ | H | $CH_3$ | $CH_3$ | $CH_3$ | $OCH_3$ | CH | |
| H | $CH_3$ | $CH_3$ | $CH_3$ | $CH_3$ | $CH_3$ | $CH_3$ | H | $CH_3$ | $OCH_3$ | N | |
| H | H | $CH_3$ | $CH_3$ | $CH_3$ | $CH_3$ | $CH_3$ | $CH_3$ | $OCH_3$ | $OCH_3$ | CH | |
| H | $CH_3$ | $CH_3$ | $CH_3$ | $CH_3$ | $CH_3$ | $CH_3$ | $CH_3$ | $OCH_3$ | $OCH_3$ | N | |
| $CH_3$ | $CH_3$ | $CH_3$ | $CH_3$ | $CH_3$ | $CH_3$ | $CH_3$ | $CH_3$ | $CH_3$ | $CH_3$ | CH | |
| H | H | H | H | H | H | H | H | $CH_3$ | $OC_2H_5$ | CH | |
| H | H | H | H | H | H | H | H | $CH_3$ | $CH_2OCH_3$ | CH | |

TABLE 2e

| General Structure 1 wherein Q is Q-31. | | | | | | | | | | | | |
|---|---|---|---|---|---|---|---|---|---|---|---|---|
| R | $R_3$ | $R_4$ | $R_5$ | $R_6$ | $R_7$ | $R_8$ | $R_9$ | $R_{10}$ | X | Y | Z | m.p. °C. |
| H | H | H | H | H | H | H | H | H | $CH_3$ | $OCH_3$ | CH | |
| H | H | H | H | H | H | H | H | H | $CH_3$ | $OCH_3$ | N | |
| H | H | H | H | H | H | H | H | H | $OCH_3$ | $OCH_3$ | CH | |
| H | H | H | H | H | H | H | H | H | $OCH_3$ | $OCH_3$ | N | |
| H | H | H | H | H | H | H | H | H | $CH_3$ | $CH_3$ | CH | |
| H | H | H | H | H | H | H | H | H | $CH_3$ | $CH_3$ | N | |
| H | H | H | H | H | H | H | H | H | Cl | $OCH_3$ | CH | |
| H | H | H | H | H | H | H | H | H | $CH_3$ | $C_2H_5$ | CH | |
| H | H | H | H | H | H | H | H | H | $CH_3$ | $CF_3$ | CH | |
| H | H | H | H | H | H | H | H | H | $CH_3$ | $OCF_2H$ | CH | |
| H | H | H | H | H | H | H | H | H | $CH_3$ | $OCH_2CF_3$ | CH | |
| H | $CH_3$ | H | H | H | H | H | H | H | $CH_3$ | $CH_3$ | CH | |
| H | H | H | $CH_3$ | H | H | H | H | H | $CH_3$ | $CH_3$ | N | |
| H | H | H | H | H | $CH_3$ | H | H | H | $CH_3$ | $OCH_3$ | CH | |
| H | H | H | H | H | H | H | $CH_3$ | H | $CH_3$ | $OCH_3$ | N | |
| H | $CH_3$ | $CH_3$ | H | H | H | H | H | H | $OCH_3$ | $OCH_3$ | CH | |
| H | H | H | $CH_3$ | $CH_3$ | H | H | H | H | $OCH_3$ | $OCH_3$ | N | |
| H | H | H | H | H | $CH_3$ | $CH_3$ | H | H | $CH_3$ | $CH_3$ | CH | |
| H | H | H | H | H | H | H | $CH_3$ | $CH_3$ | $CH_3$ | $CH_3$ | N | |
| H | H | H | $CH_3$ | H | H | H | $CH_3$ | H | $CH_3$ | $OCH_3$ | CH | |
| H | $CH_3$ | H | H | H | $CH_3$ | H | H | H | $CH_3$ | $OCH_3$ | N | |
| H | $CH_3$ | H | $CH_3$ | H | H | H | H | H | $OCH_3$ | $OCH_3$ | CH | |
| H | H | H | H | H | $CH_3$ | H | $CH_3$ | H | $OCH_3$ | $OCH_3$ | N | |
| H | $CH_3$ | $CH_3$ | $CH_3$ | H | H | H | H | H | $CH_3$ | $CH_3$ | CH | |
| H | $CH_3$ | H | H | H | $CH_3$ | $CH_3$ | H | H | $CH_3$ | $CH_3$ | N | |
| H | H | H | $CH_3$ | $CH_3$ | H | H | $CH_3$ | H | $CH_3$ | $OCH_3$ | CH | |
| H | H | H | $CH_3$ | $CH_3$ | $CH_3$ | H | H | H | $CH_3$ | $OCH_3$ | N | |
| H | $CH_3$ | H | H | H | $CH_3$ | H | $CH_3$ | H | $OCH_3$ | $OCH_3$ | CH | |
| H | $CH_3$ | $CH_3$ | H | H | H | H | $CH_3$ | $CH_3$ | $OCH_3$ | $OCH_3$ | N | |
| H | $CH_3$ | H | H | H | $CH_3$ | $CH_3$ | $CH_3$ | H | $CH_3$ | $CH_3$ | CH | |
| H | $CH_3$ | H | $CH_3$ | H | $CH_3$ | H | $CH_3$ | H | $CH_3$ | $CH_3$ | N | |
| H | H | H | $CH_3$ | $CH_3$ | $CH_3$ | $CH_3$ | H | H | $CH_3$ | $OCH_3$ | CH | |
| H | $CH_3$ | $CH_3$ | $CH_3$ | H | H | H | $CH_3$ | $CH_3$ | $CH_3$ | $OCH_3$ | N | |
| H | $CH_3$ | H | $CH_3$ | $CH_3$ | $CH_3$ | H | $CH_3$ | H | $OCH_3$ | $OCH_3$ | CH | |
| H | $CH_3$ | H | $CH_3$ | H | $CH_3$ | $CH_3$ | $CH_3$ | H | $OCH_3$ | $OCH_3$ | N | |
| H | $CH_3$ | $CH_3$ | $CH_3$ | H | $CH_3$ | H | $CH_3$ | H | $CH_3$ | $CH_3$ | CH | |
| H | $CH_3$ | H | $CH_3$ | $CH_3$ | $CH_3$ | $CH_3$ | $CH_3$ | H | $CH_3$ | $CH_3$ | N | |
| H | $CH_3$ | H | $CH_3$ | $CH_3$ | $CH_3$ | H | $CH_3$ | $CH_3$ | $CH_3$ | $OCH_3$ | CH | |
| H | $CH_3$ | H | $CH_3$ | $CH_3$ | $CH_3$ | $CH_3$ | $CH_3$ | $CH_3$ | $CH_3$ | $OCH_3$ | N | |
| H | $CH_3$ | $CH_3$ | $CH_3$ | $CH_3$ | $CH_3$ | $CH_3$ | $CH_3$ | H | $OCH_3$ | $OCH_3$ | CH | |
| $CH_3$ | H | H | H | H | H | H | H | H | $OCH_3$ | $OCH_3$ | N | |
| H | H | H | H | H | H | H | H | H | $CH_3$ | $OCH_3$ | CH | * |
| H | H | H | H | H | H | H | H | H | $CH_3$ | $OCH_3$ | N | * |
| H | H | H | H | H | H | H | H | H | $OCH_3$ | $OCH_3$ | CH | * |

TABLE 2e-continued

| General Structure 1 wherein Q is Q-31. | | | | | | | | | | | | |
|---|---|---|---|---|---|---|---|---|---|---|---|---|
| R | $R_3$ | $R_4$ | $R_5$ | $R_6$ | $R_7$ | $R_8$ | $R_9$ | $R_{10}$ | X | Y | Z | m.p. °C. |
| H | H | H | H | H | H | H | H | H | $OCH_3$ | $OCH_3$ | N | * |
| H | H | H | H | H | H | H | H | H | $CH_3$ | $CH_3$ | CH | * |
| H | H | H | H | H | H | H | H | H | $CH_3$ | $CH_3$ | N | * |
| H | H | H | H | H | H | H | H | H | Cl | $OCH_3$ | CH | * |

*Wherein W'' is O, unless indicated by ** where W'' is S in all Tables.

TABLE 2f

| General Structure 1 wherein Q is Q-32. | | | | | | | | | | | | |
|---|---|---|---|---|---|---|---|---|---|---|---|---|
| R | $R_3$ | $R_4$ | $R_5$ | $R_6$ | $R_7$ | $R_8$ | $R_9$ | $R_{10}$ | X | Y | Z | W'' |
| H | H | H | H | H | H | H | H | H | $CH_3$ | $CH_3$ | CH | O |
| H | H | H | H | H | H | H | H | H | $CH_3$ | $CH_3$ | N | O |
| H | H | H | H | H | H | H | H | H | Cl | $OCH_3$ | CH | O |
| H | H | H | H | H | H | H | H | H | $CH_3$ | $NHCH_3$ | CH | O |
| H | H | H | H | H | H | H | H | H | $CH_3$ | $N(CH_3)_2$ | CH | O |
| H | H | H | H | H | H | H | H | H | $CH_3$ | $CH(OCH_3)_2$ | CH | O |
| H | H | H | H | H | H | H | H | H | Br | $OCH_3$ | CH | O |
| H | $CH_3$ | H | H | H | H | H | H | H | $CH_3$ | $CH_3$ | CH | O |
| H | H | H | $CH_3$ | H | H | H | H | H | $CH_3$ | $CH_3$ | N | O |
| H | H | H | H | H | $CH_3$ | H | H | H | $CH_3$ | $OCH_3$ | CH | O |
| H | H | H | H | H | H | H | $CH_3$ | H | $CH_3$ | $OCH_3$ | N | O |
| H | $CH_3$ | $CH_3$ | H | H | H | H | H | H | $OCH_3$ | $OCH_3$ | CH | O |
| H | H | H | $CH_3$ | $CH_3$ | H | H | H | H | $OCH_3$ | $OCH_3$ | N | O |
| H | H | H | H | H | $CH_3$ | $CH_3$ | H | H | $CH_3$ | $CH_3$ | CH | O |
| H | H | H | H | H | H | H | $CH_3$ | $CH_3$ | $CH_3$ | $CH_3$ | N | O |
| H | H | H | $CH_2$ | H | H | H | $CH_3$ | H | $CH_3$ | $OCH_3$ | CH | O |
| H | $CH_3$ | H | H | H | $CH_3$ | H | H | H | $CH_3$ | $OCH_3$ | N | O |
| H | $CH_3$ | H | $CH_3$ | H | H | H | H | H | $OCH_3$ | $OCH_3$ | CH | O |
| H | H | H | H | H | $CH_3$ | H | $CH_3$ | H | $OCH_3$ | $OCH_3$ | N | O |
| H | $CH_3$ | $CH_3$ | $CH_3$ | H | H | H | H | H | $CH_3$ | $CH_3$ | CH | O |
| H | $CH_3$ | H | H | H | $CH_3$ | $CH_3$ | H | H | $CH_3$ | $CH_3$ | N | O |
| H | H | H | $CH_3$ | $CH_3$ | H | H | $CH_3$ | H | $CH_3$ | $OCH_3$ | CH | O |
| H | H | H | $CH_3$ | $CH_3$ | $CH_3$ | H | H | H | $CH_3$ | $OCH_3$ | N | O |
| H | $CH_3$ | H | H | H | $CH_3$ | H | $CH_3$ | H | $OCH_3$ | $OCH_3$ | CH | O |
| H | $CH_3$ | $CH_3$ | H | H | H | H | $CH_3$ | $CH_3$ | $OCH_3$ | $OCH_3$ | N | O |
| H | $CH_3$ | H | H | H | $CH_3$ | $CH_3$ | $CH_3$ | H | $CH_3$ | $CH_3$ | CH | O |
| H | $CH_3$ | H | $CH_3$ | H | $CH_3$ | H | $CH_3$ | H | $CH_3$ | $CH_3$ | N | O |
| H | H | H | $CH_3$ | $CH_3$ | $CH_3$ | $CH_3$ | H | H | $CH_3$ | $OCH_3$ | CH | O |
| H | $CH_3$ | $CH_3$ | $CH_3$ | H | H | H | $CH_3$ | $CH_3$ | $CH_3$ | $OCH_3$ | N | O |
| H | $CH_3$ | H | $CH_3$ | $CH_3$ | $CH_3$ | H | $CH_3$ | H | $OCH_3$ | $OCH_3$ | CH | O |
| H | $CH_3$ | H | $CH_3$ | H | $CH_3$ | $CH_3$ | $CH_3$ | H | $OCH_3$ | $OCH_3$ | N | O |
| H | $CH_3$ | $CH_3$ | $CH_3$ | H | $CH_3$ | H | $CH_3$ | H | $CH_3$ | $CH_3$ | CH | O |
| H | $CH_3$ | H | $CH_3$ | $CH_3$ | $CH_3$ | $CH_3$ | $CH_3$ | H | $CH_3$ | $CH_3$ | N | O |
| H | $CH_3$ | H | $CH_3$ | $CH_3$ | $CH_3$ | H | $CH_3$ | $CH_3$ | $CH_3$ | $OCH_3$ | CH | O |
| H | $CH_3$ | H | $CH_3$ | $CH_3$ | $CH_3$ | $CH_3$ | $CH_3$ | $CH_3$ | $CH_3$ | $OCH_3$ | N | O |
| H | $CH_3$ | $CH_3$ | $CH_3$ | $CH_3$ | $CH_3$ | $CH_3$ | $CH_3$ | H | $OCH_3$ | $OCH_3$ | CH | O |
| $CH_3$ | H | H | H | H | H | H | H | H | $OCH_3$ | $OCH_3$ | N | O |
| H | $CH_3$ | H | H | H | H | H | $CH_3$ | H | $CH_3$ | $OCH_3$ | CH | O |
| H | H | H | H | H | H | H | H | H | $CH_3$ | $OCH_3$ | CH | O |
| H | H | H | H | H | H | H | H | H | $CH_3$ | $OCH_3$ | N | O |
| H | H | H | H | H | H | H | H | H | $OCH_3$ | $OCH_3$ | CH | O |
| H | H | H | H | H | H | H | H | H | $OCH_3$ | $OCH_3$ | N | O |
| H | H | H | H | H | H | H | H | H | $CH_3$ | $OCH_3$ | CH | S |
| H | H | H | H | H | H | H | H | H | $CH_3$ | $OCH_3$ | N | S |
| H | H | H | H | H | H | H | H | H | $OCH_3$ | $OCH_3$ | CH | S |
| H | H | H | H | H | H | H | H | H | $OCH_3$ | $OCH_3$ | N | S |
| H | H | H | H | H | H | H | H | H | $CH_3$ | $CH_3$ | CH | S |
| H | H | H | H | H | H | H | H | H | $CH_3$ | $CH_3$ | N | S |
| H | H | H | H | H | H | H | H | H | Cl | $OCH_3$ | CH | S |
| H | H | H | H | H | H | H | H | H | $CH_3$ | 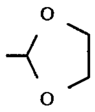 | CH | S |
| H | H | H | H | H | H | H | H | H | Cl | $OC_2H_5$ | CH | S |
| H | H | H | H | H | H | H | H | H | $CH_3$ | $C_2H_5$ | N | S |
| H | H | H | H | H | H | H | H | H | $CH_3$ | $OC_2H_5$ | N | S |
| H | $CH_3$ | H | H | H | H | H | H | H | $CH_3$ | $CH_3$ | CH | S |
| H | H | H | $CH_3$ | H | H | H | H | H | $CH_3$ | $CH_3$ | N | S |
| H | H | H | H | H | $CH_3$ | H | H | H | $CH_3$ | $OCH_3$ | CH | S |
| H | H | H | H | H | H | H | $CH_3$ | H | $CH_3$ | $OCH_3$ | N | S |
| H | $CH_3$ | $CH_3$ | H | H | H | H | H | H | $OCH_3$ | $OCH_3$ | CH | S |
| H | H | H | $CH_3$ | $CH_3$ | H | H | H | H | $OCH_3$ | $OCH_3$ | N | S |
| H | H | H | H | H | $CH_3$ | $CH_3$ | H | H | $CH_3$ | $CH_3$ | CH | S |
| H | H | H | H | H | H | H | $CH_3$ | $CH_3$ | $CH_3$ | $CH_3$ | N | S |

TABLE 2f-continued

General Structure 1 wherein Q is Q-32.

| R | $R_3$ | $R_4$ | $R_5$ | $R_6$ | $R_7$ | $R_8$ | $R_9$ | $R_{10}$ | X | Y | Z | W'' |
|---|---|---|---|---|---|---|---|---|---|---|---|---|
| H | H | H | $CH_3$ | H | H | H | $CH_3$ | H | $CH_3$ | $OCH_3$ | CH | S |
| H | $CH_3$ | H | H | H | $CH_3$ | H | H | H | $CH_3$ | $OCH_3$ | N | S |
| H | $CH_3$ | H | $CH_3$ | H | H | H | H | H | $OCH_3$ | $OCH_3$ | CH | S |
| H | H | H | H | H | $CH_3$ | H | $CH_3$ | H | $OCH_3$ | $OCH_3$ | N | S |
| H | $CH_3$ | $CH_3$ | $CH_3$ | H | H | H | H | H | $CH_3$ | $CH_3$ | CH | S |
| H | $CH_3$ | H | H | H | $CH_3$ | $CH_3$ | H | H | $CH_3$ | $CH_3$ | N | S |
| H | H | H | $CH_3$ | $CH_3$ | H | H | $CH_3$ | H | $CH_3$ | $OCH_3$ | CH | S |
| H | H | H | $CH_3$ | $CH_3$ | $CH_3$ | H | H | H | $CH_3$ | $OCH_3$ | N | S |
| H | $CH_3$ | H | H | H | $CH_3$ | H | $CH_3$ | H | $OCH_3$ | $OCH_3$ | CH | S |
| H | $CH_3$ | $CH_3$ | H | H | H | H | $CH_3$ | $CH_3$ | $OCH_3$ | $OCH_3$ | N | S |
| H | $CH_3$ | H | H | H | $CH_3$ | $CH_3$ | $CH_3$ | H | $CH_3$ | $CH_3$ | CH | S |
| H | $CH_3$ | H | $CH_3$ | H | $CH_3$ | H | $CH_3$ | H | $CH_3$ | $CH_3$ | N | S |
| H | H | H | $CH_3$ | $CH_3$ | $CH_3$ | $CH_3$ | H | H | $CH_3$ | $OCH_3$ | N | S |
| H | $CH_3$ | $CH_3$ | $CH_3$ | H | H | H | $CH_3$ | $CH_3$ | $CH_3$ | $OCH_3$ | N | S |
| H | $CH_3$ | H | $CH_3$ | $CH_3$ | $CH_3$ | H | $CH_3$ | H | $OCH_3$ | $OCH_3$ | CH | S |
| H | $CH_3$ | H | $CH_3$ | H | $CH_3$ | $CH_3$ | $CH_3$ | H | $OCH_3$ | $OCH_3$ | N | S |
| H | $CH_3$ | $CH_3$ | $CH_3$ | H | $CH_3$ | H | $CH_3$ | H | $CH_3$ | $CH_3$ | CH | S |
| H | $CH_3$ | H | $CH_3$ | $CH_3$ | $CH_3$ | $CH_3$ | $CH_3$ | H | $CH_3$ | $CH_3$ | N | S |
| H | $CH_3$ | H | $CH_3$ | $CH_3$ | $CH_3$ | H | $CH_3$ | $CH_3$ | $CH_3$ | $OCH_3$ | CH | S |
| H | $CH_3$ | H | $CH_3$ | $CH_3$ | $CH_3$ | $CH_3$ | $CH_3$ | $CH_3$ | $CH_3$ | $OCH_3$ | N | S |
| H | $CH_3$ | $CH_3$ | $CH_3$ | $CH_3$ | $CH_3$ | $CH_3$ | $CH_3$ | H | $OCH_3$ | $OCH_3$ | CH | S |
| $CH_3$ | H | H | H | H | H | H | H | H | $OCH_3$ | $OCH_3$ | N | S |
| H | $CH_3$ | H | H | H | H | H | $CH_3$ | H | $CH_3$ | $OCH_3$ | CH | S |

TABLE 2g

General Structure 1

| Q | R | $R_3$ | $R_4$ | $R_5$ | $R_6$ | $R_7$ | X | Y | Z | m.p. °C. |
|---|---|---|---|---|---|---|---|---|---|---|
| Q-41 | H | H | H | H | H | H | Cl | $OCH_3$ | CH | |
| Q-41 | H | H | H | H | H | H | Br | $OCH_3$ | CH | |
| Q-41 | H | H | H | H | H | H | Cl | $OC_2H_5$ | CH | |
| Q-41 | H | H | H | H | H | H | $CH_3$ | $CH_3$ | N | |
| Q-41 | H | H | H | H | H | H | $OCH_3$ | $OCH_3$ | CH | |
| Q-41 | H | H | H | H | H | H | $OCH_3$ | $OCH_3$ | N | |
| Q-41 | H | H | H | H | H | H | $OCH_3$ | $OC_2H_5$ | CH | |
| Q-41 | H | H | H | H | H | H | $OCH_3$ | $OC_2H_5$ | N | |
| Q-41 | H | H | H | H | H | H | $CH_3$ | $CH_3$ | CH | |
| Q-41 | H | H | H | H | H | H | $CH_3$ | $OCH_3$ | N | |
| Q-41 | H | H | H | H | H | H | $CH_3$ | $OCH_3$ | CH | |
| Q-41 | H | H | H | H | H | H | $CH_3$ | $CH_2OCH_3$ | CH | |
| Q-41 | H | H | H | H | H | H | $CH_3$ | $CF_3$ | N | |
| Q-41 | H | H | H | H | H | H | $CH_3$ | $OCF_2H$ | N | |
| Q-41 | H | $CH_3$ | H | H | H | H | $CH_3$ | $CH_3$ | CH | |
| Q-41 | H | H | H | $CH_3$ | H | H | $CH_3$ | $CH_3$ | N | |
| Q-41 | H | H | H | H | $CH_3$ | H | $CH_3$ | $OCH_3$ | CH | |
| Q-41 | H | $CH_3$ | $CH_3$ | H | H | H | $CH_3$ | $OCH_3$ | N | |
| Q-41 | H | $CH_3$ | $CH_3$ | H | H | H | $OCH_3$ | $OCH_3$ | CH | |
| Q-41 | H | $CH_3$ | $CH_3$ | H | H | H | $OCH_3$ | $OCH_3$ | N | |
| Q-41 | H | $CH_3$ | H | $CH_3$ | H | H | $CH_3$ | $CH_3$ | CH | |
| Q-41 | H | $CH_3$ | H | H | $CH_3$ | H | $CH_3$ | $CH_3$ | N | |
| Q-41 | H | H | H | $CH_3$ | $CH_3$ | H | $CH_3$ | $OCH_3$ | CH | |
| Q-41 | H | H | H | H | $CH_3$ | $CH_3$ | $CH_3$ | $OCH_3$ | N | |
| Q-41 | H | $CH_3$ | $CH_3$ | $CH_3$ | H | H | $OCH_3$ | $OCH_3$ | CH | |
| Q-41 | H | $CH_3$ | $CH_3$ | H | $CH_3$ | H | $OCH_3$ | $OCH_3$ | N | |
| Q-41 | H | $CH_3$ | H | $CH_3$ | $CH_3$ | H | $CH_3$ | $CH_3$ | CH | |
| Q-41 | H | $CH_3$ | H | H | $CH_3$ | $CH_3$ | $CH_3$ | $CH_3$ | N | |
| Q-41 | H | $CH_3$ | $CH_3$ | $CH_3$ | $CH_3$ | H | $CH_3$ | $OCH_3$ | CH | |
| Q-41 | H | $CH_3$ | $CH_3$ | H | $CH_3$ | $CH_3$ | $CH_3$ | $OCH_3$ | N | |
| Q-41 | H | $CH_3$ | H | $CH_3$ | $CH_3$ | $CH_3$ | $OCH_3$ | $OCH_3$ | CH | |
| Q-41 | H | $CH_3$ | $CH_3$ | $CH_3$ | $CH_3$ | $CH_3$ | $OCH_3$ | $OCH_3$ | N | |
| Q-41 | $CH_3$ | H | H | H | H | H | $CH_3$ | $CH_3$ | CH | |
| Q-41 | $CH_3$ | H | H | H | H | H | $CH_3$ | $OCH_3$ | CH | |

TABLE 3a

General Structure 1 wherein Q is Q-20

| R | $R'_3$ | X | Y | Z | W' | m.p. °C. |
|---|---|---|---|---|---|---|
| H | H | $CH_3$ | $OCH_3$ | CH | O | |
| H | H | $CH_3$ | $OCH_3$ | N | O | |
| H | H | $OCH_3$ | $OCH_3$ | CH | O | |
| H | H | $OCH_3$ | Cl | CH | O | |
| H | H | $OCH_3$ | $OCH_3$ | N | O | |
| H | H | $CH_3$ | $CH_3$ | CH | O | |
| H | $CH_3$ | $CH_3$ | $OCH_3$ | CH | O | |

TABLE 3a-continued

| General Structure 1 wherein Q is Q-20 | | | | | | |
|---|---|---|---|---|---|---|
| R | R'3 | X | Y | Z | W' | m.p. °C. |
| $CH_3$ | H | $CH_3$ | $OCH_3$ | N | O | |
| $CH_3$ | $CH_3$ | $OCH_3$ | $OCH_3$ | CH | O | |
| H | H | $CH_3$ | $OC_2H_5$ | N | O | |
| H | H | $CH_3$ | $CH_3$ | CH | S | |
| H | H | $CH_3$ | $CH_3$ | N | S | |
| H | H | $CH_3$ | $OCH_3$ | CH | S | |
| H | H | $CH_3$ | $OCH_3$ | N | S | |
| H | H | $OCH_3$ | $OCH_3$ | CH | S | |
| H | H | $OCH_3$ | $OCH_3$ | N | S | |
| $CH_3$ | H | $CH_3$ | $OCH_3$ | CH | S | |
| H | $CH_3$ | $CH_3$ | $OCH_3$ | N | S | |
| H | $CH_3$ | $CH_3$ | $CH_2OCH_3$ | N | S | |
| H | $C_2H_5$ | $CH_3$ | $CH_3$ | CH | O | |
| H | $C_2H_5$ | $CH_3$ | $CH_3$ | N | O | |
| H | $C_2H_5$ | $CH_3$ | $OCH_3$ | CH | O | |
| H | $C_2H_5$ | $CH_3$ | $OCH_3$ | N | O | |
| H | $C_2H_5$ | $OCH_3$ | $OCH_3$ | CH | O | |
| H | $C_2H_5$ | $OCH_3$ | $OCH_3$ | N | O | |
| H | $C_2H_5$ | $OCH_3$ | Cl | CH | O | |
| H | $C_2H_5$ | $CH_3$ | $CH_3$ | CH | S | |
| H | $C_2H_5$ | $CH_3$ | $CH_3$ | N | S | |
| H | $C_2H_5$ | $CH_3$ | $OCH_3$ | CH | S | |
| H | $C_2H_5$ | $CH_3$ | $OCH_3$ | N | S | |
| H | $C_2H_5$ | $OCH_3$ | $OCH_3$ | CH | S | |
| H | $C_2H_5$ | $OCH_3$ | $OCH_3$ | N | S | |
| H | $C_2H_5$ | $OCH_3$ | Cl | CH | S | |
| H | $C_2H_5$ | $OCH_3$ | $N(CH_3)_2$ | N | S | |
| $CH_3$ | n-$C_3H_7$ | $OCH_3$ | $OCH_3$ | CH | O | |
| $CH_3$ | n-$C_3H_7$ | $CH_3$ | $CH_3$ | CH | O | |
| $CH_3$ | n-$C_3H_7$ | $CH_3$ | $OCH_3$ | CH | O | |
| $CH_3$ | n-$C_3H_7$ | $OCH_3$ | $OCH_3$ | CH | O | |
| $CH_3$ | n-$C_3H_7$ | $OCH_3$ | $OCH_3$ | N | O | |
| $CH_3$ | n-$C_3H_7$ | $OCH_3$ | Cl | CH | O | |
| $CH_3$ | n-$C_3H_7$ | $CH_3$ | $OCH_2CF_3$ | CH | O | |
| H | n-$C_3H_7$ | $CH_3$ | $CH_3$ | CH | S | |
| H | n-$C_3H_7$ | $CH_3$ | $OCH_3$ | CH | S | |
| H | n-$C_3H_7$ | $CH_3$ | $OCH_3$ | N | S | |
| H | n-$C_3H_7$ | $OCH_3$ | $OCH_3$ | CH | S | |
| H | n-$C_3H_7$ | $OCH_3$ | $OCH_3$ | N | S | |
| H | n-$C_3H_7$ | $OCH_3$ | Cl | CH | S | |
| H | n-$C_3H_7$ | $CH_3$ | $CH(OCH_3)_2$ | CH | S | |
| H | i-$C_3H_7$ | $CH_3$ | $CH_3$ | CH | O | |
| H | i-$C_3H_7$ | $CH_3$ | $OCH_3$ | CH | O | |
| H | i-$C_3H_7$ | $CH_3$ | $OCH_3$ | N | O | |
| H | i-$C_3H_7$ | $OCH_3$ | $OCH_3$ | CH | O | |
| H | i-$C_3H_7$ | $OCH_3$ | $OCH_3$ | N | O | |
| H | i-$C_3H_7$ | $OCH_3$ | Cl | CH | O | |
| H | i-$C_3H_7$ | $CH_3$ | $CH_3$ | N | O | |
| H | i-$C_3H_7$ | $OCH_3$ | 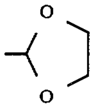 | CH | O | |
| $CH_3$ | i-$C_3H_7$ | $OCH_3$ | $OCH_3$ | CH | S | |
| H | i-$C_3H_7$ | $CH_3$ | $CH_3$ | CH | S | |
| H | i-$C_3H_7$ | $CH_3$ | $OCH_3$ | CH | S | |
| H | i-$C_3H_7$ | $CH_3$ | $OCH_3$ | N | S | |
| H | i-$C_3H_7$ | $OCH_3$ | $OCH_3$ | CH | S | |
| H | i-$C_3H_7$ | $OCH_3$ | $OCH_3$ | N | S | |
| H | i-$C_3H_7$ | $OCH_3$ | Cl | CH | S | |
| H | i-$C_3H_7$ | $CH_3$ | $OC_2H_5$ | N | S | |
| H | $SCH_3$ | $CH_3$ | $CH_3$ | CH | O | |
| H | $SCH_3$ | $CH_3$ | $OCH_3$ | CH | O | |
| H | $SCH_3$ | $CH_3$ | $OCH_3$ | N | O | |
| H | $SCH_3$ | $OCH_3$ | $OCH_3$ | CH | O | |
| H | $SCH_3$ | $OCH_3$ | $OCH_3$ | N | O | |
| H | $SCH_3$ | $OCH_3$ | Cl | CH | O | |
| H | $SCH_3$ | $OCH_3$ | $NHCH_3$ | CH | O | |
| $CH_3$ | $SCH_3$ | $OCH_3$ | $OCH_3$ | CH | O | |
| H | $SCH_3$ | $CH_3$ | $CH_3$ | CH | S | |
| H | $SCH_3$ | $CH_3$ | $CH_3$ | N | S | |
| H | $SCH_3$ | $CH_3$ | $OCH_3$ | CH | S | |
| H | $SCH_3$ | $CH_3$ | $OCH_3$ | N | S | |
| H | $SCH_3$ | $OCH_3$ | $OCH_3$ | CH | S | |
| H | $SCH_3$ | $OCH_3$ | $OCH_3$ | N | S | |
| H | $SCH_3$ | $OCH_3$ | Cl | CH | S | |

TABLE 3a-continued

General Structure 1 wherein Q is Q-20

| R | $R'_3$ | X | Y | Z | W' | m.p. °C. |
|---|---|---|---|---|---|---|
| $CH_3$ | $SC_2H_5$ | $OCH_3$ | $OCH_3$ | CH | O | |
| H | $SC_2H_5$ | $CH_3$ | $CH_3$ | CH | O | |
| H | $SC_2H_5$ | $CH_3$ | $CH_3$ | N | O | |
| H | $SC_2H_5$ | $CH_3$ | $OCH_3$ | CH | O | |
| H | $SC_2H_5$ | $CH_3$ | $OCH_3$ | N | O | |
| H | $SC_2H_5$ | $OCH_3$ | $OCH_3$ | CH | O | |
| H | $SC_2H_5$ | $OCH_3$ | $OCH_3$ | N | O | |
| H | $SC_2H_5$ | $OCH_3$ | Cl | CH | O | |
| H | $SC_2H_5$ | $CH_3$ | $CH_3$ | CH | S | |
| H | $SC_2H_5$ | $CH_3$ | $OCH_3$ | CH | S | |
| H | $SC_2H_5$ | $CH_3$ | $OCH_3$ | N | S | |
| H | $SC_2H_5$ | $OCH_3$ | $OCH_3$ | CH | S | |
| H | $SC_2H_5$ | $CH_3$ | $OCH_3$ | N | S | |
| H | $SC_2H_5$ | $OCH_3$ | Cl | CH | S | |
| H | $SC_2H_5$ | $CH_3$ | $OC_2H_5$ | N | S | |
| H | $S-\underline{n}-C_3H_7$ | $CH_3$ | $CH_3$ | CH | O | |
| H | $S-\underline{n}-C_3H_7$ | $CH_3$ | $CH_2OCH_3$ | CH | O | |
| H | $S-\underline{n}-C_3H_7$ | $CH_3$ | $OCH_3$ | CH | O | |
| H | $S-\underline{n}-C_3H_7$ | $CH_3$ | $OCH_3$ | N | O | |
| H | $S-\underline{n}-C_3H_7$ | $OCH_3$ | $OCH_3$ | CH | O | |
| H | $S-\underline{n}-C_3H_7$ | $OCH_3$ | $OCH_3$ | N | O | |
| H | $S-\underline{n}-C_3H_7$ | $OCH_3$ | Cl | CH | O | |
| $CH_3$ | $S-\underline{n}-C_3H_7$ | $OCH_3$ | $OCH_3$ | CH | S | |
| H | $S-\underline{n}-C_3H_7$ | $CH_3$ | $CH_3$ | CH | S | |
| H | $S-\underline{n}-C_3H_7$ | $CH_3$ | $CH_3$ | N | S | |
| H | $S-\underline{n}-C_3H_7$ | $CH_3$ | $OCH_3$ | CH | S | |
| H | $S-\underline{n}-C_3H_7$ | $OCH_3$ | $OCH_3$ | CH | S | |
| H | $S-\underline{n}-C_3H_7$ | $OCH_3$ | $OCH_3$ | N | S | |
| H | $S-\underline{n}-C_3H_7$ | $CH_3$ | Cl | CH | S | |
| H | $S-\underline{n}-C_3H_7$ | $CH_3$ | $OCH_3$ | CH | O | |
| H | $S-\underline{n}-C_3H_7$ | $OCH_3$ | $OCH_3$ | CH | S | |
| H | $S-\underline{n}-C_3H_7$ | $CH_3$ | $OCH_3$ | N | S | |
| $CH_3$ | $S-\underline{n}-C_4H_9$ | $OCH_3$ | $OCH_3$ | CH | O | |
| H | $S-\underline{n}-C_4H_9$ | $CH_3$ | $CH_3$ | CH | O | |
| H | $S-\underline{n}-C_4H_9$ | $CH_3$ | $CH_3$ | N | O | |
| H | $S-\underline{n}-C_4H_9$ | $CH_3$ | $OCH_3$ | CH | O | |
| H | $S-\underline{n}-C_4H_9$ | $CH_3$ | $OCH_3$ | N | O | |
| H | $S-\underline{n}-C_4H_9$ | $OCH_3$ | $OCH_3$ | CH | O | |
| H | $S-\underline{n}-C_4H_9$ | $OCH_3$ | $OCH_3$ | N | O | |
| H | $S-\underline{n}-C_4H_9$ | $OCH_3$ | Cl | CH | O | |
| H | $S-\underline{n}-C_4H_9$ | $CH_3$ | $CH_3$ | CH | S | |
| H | $S-\underline{n}-C_4H_9$ | $CH_3$ | $OCH_3$ | N | S | |
| H | $S-\underline{n}-C_4H_9$ | $CH_3$ | $OCH_3$ | CH | S | |
| H | $S-\underline{n}-C_4H_9$ | $OCH_3$ | $OCH_3$ | N | S | |
| H | $S-\underline{n}-C_4H_9$ | $OCH_3$ | $OCH_3$ | CH | S | |
| H | $S-\underline{n}-C_4H_9$ | $OCH_3$ | $OCH_3$ | N | S | |
| H | $S-\underline{n}-C_4H_9$ | $OCH_3$ | $OCF_2H$ | N | S | |
| H | $S-\underline{n}-C_4H_9$ | $OCH_3$ | $OCH_3$ | CH | O | |
| H | $S-\underline{n}-C_4H_9$ | $CH_3$ | $OCH_3$ | N | O | |
| H | $S-\underline{n}-C_4H_9$ | $OCH_3$ | $OCH_3$ | CH | S | |
| H | $S-\underline{n}-C_4H_9$ | $CH_3$ | $OCH_3$ | CH | S | |
| H | $S-\underline{n}-C_4H_9$ | $CH_3$ | $OCH_3$ | N | O | |
| H | $S-\underline{n}-C_4H_9$ | $CH_3$ | $OCH_3$ | CH | O | |
| H | $S-\underline{n}-C_4H_9$ | $OCH_3$ | $OCH_3$ | CH | S | |
| H | $S-\underline{n}-C_4H_9$ | $OCH_3$ | $OCH_3$ | N | S | |
| H | $S-\underline{n}-C_4H_9$ | $CH_3$ | $OCH_3$ | CH | O | |
| H | $S-\underline{n}-C_4H_9$ | $OCH_3$ | $OCH_3$ | N | O | |
| H | $S-\underline{n}-C_4H_9$ | $OCH_3$ | $OCH_3$ | CH | S | |
| H | $S-\underline{n}-C_4H_9$ | $CH_3$ | $OCH_3$ | N | S | |
| H | $SCH_2CH=CH_2$ | $CH_3$ | $CH_3$ | CH | O | |
| H | $SCH_2CH=CH_2$ | $CH_3$ | $OCH_3$ | N | O | |
| H | $SCH_2CH=CH_2$ | $CH_3$ | $OCH_3$ | CH | O | |
| H | $SCH_2CH=CH_2$ | $OCH_3$ | $OCH_3$ | N | O | |
| H | $SCH_2CH=CH_2$ | $OCH_3$ | $OCH_3$ | CH | O | |
| H | $SCH_2CH=CH_2$ | $OCH_3$ | $OCH_3$ | N | O | |
| H | $SCH_2CH=CH_2$ | $OCH_3$ | Cl | CH | O | |
| H | $SCH_2CH=CH_2$ | $CH_3$ | $OCH_2CF_3$ | CH | O | |
| $CH_3$ | $SCH_2CH=CH_2$ | $OCH_3$ | $OCH_3$ | CH | S | |
| H | $SCH_2CH=CH_2$ | $CH_3$ | $CH_3$ | CH | S | |
| H | $SCH_2CH=CH_2$ | $CH_3$ | $CH_3$ | N | S | |
| H | $SCH_2CH=CH_2$ | $CH_3$ | $OCH_3$ | CH | S | |
| H | $SCH_2CH=CH_2$ | $CH_3$ | $OCH_3$ | N | S | |
| H | $SCH_2CH=CH_2$ | $OCH_3$ | $OCH_3$ | CH | S | |
| H | $SCH_2CH=CH_2$ | $OCH_3$ | $OCH_3$ | N | S | |
| H | $SCH_2CH=CH_2$ | $OCH_3$ | Cl | CH | S | |
| H | $\underline{E}-SCH=CHCH_3$ | $CH_3$ | $OCH_3$ | CH | O | |
| H | $\underline{E}-SCH=CHCH_3$ | $CH_3$ | $OCH_3$ | N | O | |
| H | $\underline{E}-SCH=CHCH_3$ | $OCH_3$ | $OCH_3$ | CH | O | |
| H | $\underline{E}-SCH=CHCH_3$ | $OCH_3$ | $OCH_3$ | N | O | |

TABLE 3a-continued

General Structure 1 wherein Q is Q-20

| R | $R'_3$ | X | Y | Z | W' | m.p. °C. |
|---|---|---|---|---|---|---|
| H | E—$SCH=CHCH_3$ | $CH_3$ | $OCH_3$ | N | S | |
| H | E—$SCH=CHCH_3$ | $CH_3$ | $OCH_3$ | CH | S | |
| H | E—$SCH=CHCH_3$ | $OCH_3$ | $OCH_3$ | CH | S | |
| H | E—$SCH=CHCH_3$ | $OCH_3$ | Cl | CH | S | |
| H | Z—$SCH=CHCH_3$ | $CH_3$ | $OCH_3$ | N | O | |
| H | Z—$SCH=CHCH_3$ | $OCH_3$ | $OCH_3$ | CH | O | |
| H | Z—$SCH=CHCH_3$ | $OCH_3$ | $OCH_3$ | N | O | |
| H | Z—$SCH=CHCH_3$ | $OCH_3$ | Cl | CH | O | |
| H | Z—$SCH=CHCH_3$ | $CH_3$ | $CH_3$ | CH | S | |
| H | Z—$SCH=CHCH_3$ | $OCH_3$ | $OCH_3$ | CH | S | |
| H | Z—$SCH=CHCH_3$ | $CH_3$ | $OCH_3$ | N | S | |
| H | Z—$SCH=CHCH_3$ | $OCH_3$ | $OCH_3$ | N | S | |
| H | $S(CH_2)_2CH=CH_2$ | $OCH_3$ | $OCH_3$ | CH | O | |
| H | $S(CH_2)_2CH=CH_2$ | $OCH_3$ | $OCH_3$ | N | O | |
| H | $S(CH_2)_2CH=CH_2$ | $CH_3$ | $OCH_3$ | CH | O | |
| H | $S(CH_2)_2CH=CH_2$ | $OCH_3$ | Cl | CH | O | |
| H | $S(CH_2)_2CH=CH_2$ | $OCH_3$ | $OCH_3$ | CH | S | |
| H | $S(CH_2)_2CH=CH_2$ | $CH_3$ | $OCH_3$ | N | S | |
| H | $S(CH_2)_2CH=CH_2$ | $OCH_3$ | $OCH_3$ | N | S | |
| H | $S(CH_2)_2CH=CH_2$ | $CH_3$ | $CH_3$ | CH | S | |
| H | E—$SCH_2CH=CHCH_3$ | $OCH_3$ | $OCH_3$ | CH | O | |
| H | E—$SCH_2CH=CHCH_3$ | $OCH_3$ | $OCH_3$ | N | O | |
| H | E—$SCH_2CH=CHCH_3$ | $CH_3$ | $OCH_3$ | CH | O | |
| H | E—$SCH_2CH=CHCH_3$ | $OCH_3$ | Cl | CH | O | |
| H | E—$SCH_2CH=CHCH_3$ | $OCH_3$ | $OCH_3$ | CH | S | |
| H | E—$SCH_2CH=CHCH_3$ | $CH_3$ | $OCH_3$ | N | S | |
| H | E—$SCH_2CH=CHCH_3$ | $CH_3$ | $OCH_3$ | CH | S | |
| H | E—$SCH_2CH=CHCH_3$ | $CH_3$ | $CH_3$ | CH | S | |
| H | Z—$SCH_2CH=CHCH_3$ | $CH_3$ | $OCH_3$ | CH | O | |
| H | Z—$SCH_2CH=CHCH_3$ | $CH_3$ | $OCH_3$ | N | O | |
| H | Z—$SCH_2CH=CHCH_3$ | $OCH_3$ | $OCH_3$ | CH | O | |
| H | Z—$SCH_2CH=CHCH_3$ | $OCH_3$ | Cl | CH | O | |
| H | Z—$SCH_2CH=CHCH_3$ | $CH_3$ | $OCH_3$ | CH | S | |
| H | Z—$SCH_2CH=CHCH_3$ | $CH_3$ | $OCH_3$ | N | S | |
| H | Z—$SCH_2CH=CHCH_3$ | $OCH_3$ | $OCH_3$ | CH | S | |
| H | Z—$SCH_2CH=CHCH_3$ | $OCH_3$ | $OCH_3$ | N | S | |
| H | E—$SCH=CHC_2H_5$ | $OCH_3$ | $OCH_3$ | CH | O | |
| H | E—$SCH=CHC_2H_5$ | $OCH_3$ | $OCH_3$ | N | O | |
| H | E—$SCH=CHC_2H_5$ | $CH_3$ | $OCH_3$ | CH | O | |
| H | E—$SCH=CHC_2H_5$ | $OCH_3$ | Cl | CH | O | |
| H | E—$SCH=CHC_2H_5$ | $OCH_3$ | $OCH_3$ | CH | S | |
| H | E—$SCH=CHC_2H_5$ | $CH_3$ | $CH_3$ | CH | S | |
| H | E—$SCH=CHC_2H_5$ | $CH_3$ | $OCH_3$ | N | S | |
| H | E—$SCH=CHC_2H_5$ | $CH_3$ | $OCH_3$ | CH | S | |
| H | Z—$SCH=CHC_2H_5$ | $OCH_3$ | $OCH_3$ | CH | O | |
| H | Z—$SCH=CHC_2H_5$ | $OCH_3$ | $OCH_3$ | N | O | |
| H | Z—$SCH=CHC_2H_5$ | $CH_3$ | $CH_3$ | CH | O | |
| H | Z—$SCH=CHC_2H_5$ | $CH_3$ | $OCH_3$ | N | O | |
| H | Z—$SCH=CHC_2H_5$ | $OCH_3$ | $OCH_3$ | CH | S | |
| H | Z—$SCH=CHC_2H_5$ | $CH_3$ | $OCH_3$ | CH | S | |
| H | Z—$SCH=CHC_2H_5$ | $CH_3$ | $OCH_3$ | N | S | |
| H | Z—$SCH=CHC_2H_5$ | $OCH_3$ | Cl | CH | S | |
| H | $SCH_2C{\equiv}CH$ | $CH_3$ | $OCH_3$ | CH | O | |
| H | $SCH_2C{\equiv}CH$ | $CH_3$ | $OCH_3$ | N | O | |
| H | $SCH_2C{\equiv}CH$ | $OCH_3$ | $OCH_3$ | CH | O | |
| H | $SCH_2C{\equiv}CH$ | $OCH_3$ | $OCH_3$ | N | O | |
| H | $SCH_2C{\equiv}CH$ | $CH_3$ | $OCH_3$ | CH | S | |
| H | $SCH_2C{\equiv}CH$ | $OCH_3$ | $OCH_3$ | N | S | |
| H | $SCH_2C{\equiv}CH$ | $OCH_3$ | $OCH_3$ | CH | S | |
| H | $SCH_2C{\equiv}CH$ | $OCH_3$ | Cl | CH | S | |
| $CH_3$ | $SCH_2C{\equiv}CH$ | $OCH_3$ | $OCH_3$ | CH | S | |
| H | $SC{\equiv}CCH_3$ | $CH_3$ | $CH_3$ | CH | O | |
| H | $SC{\equiv}CCH_3$ | $CH_3$ | $OCH_3$ | N | O | |
| H | $SC{\equiv}CCH_3$ | $CH_3$ | $OCH_3$ | CH | O | |
| H | $SC{\equiv}CCH_3$ | $OCH_3$ | $OCH_3$ | N | O | |
| H | $SC{\equiv}CCH_3$ | $OCH_3$ | $OCH_3$ | CH | S | |
| H | $SC{\equiv}CCH_3$ | $CH_3$ | $OCH_3$ | N | S | |
| H | $SC{\equiv}CCH_3$ | $CH_3$ | $OCH_3$ | CH | S | |
| H | $SC{\equiv}CCH_3$ | $OCH_3$ | $OCH_3$ | N | S | |
| H | $S(CH_2)_2C{\equiv}CH$ | $CH_3$ | $OCH_3$ | CH | O | |
| H | $S(CH_2)_2C{\equiv}CH$ | $CH_3$ | $OCH_3$ | N | O | |
| H | $S(CH_2)_2C{\equiv}CH$ | $OCH_3$ | $OCH_3$ | CH | O | |
| H | $S(CH_2)_2C{\equiv}CH$ | $OCH_3$ | $OCH_3$ | N | O | |
| H | $S(CH_2)_2C{\equiv}CH$ | $CH_3$ | $OCH_3$ | CH | S | |
| H | $S(CH_2)_2C{\equiv}CH$ | $CH_3$ | $OCH_3$ | N | S | |
| H | $S(CH_2)_2C{\equiv}CH$ | $OCH_3$ | $OCH_3$ | CH | S | |
| H | $S(CH_2)_2C{\equiv}CH$ | $OCH_3$ | $OCH_3$ | N | S | |
| H | $SCH_2C{\equiv}CCH_3$ | $CH_3$ | $CH_3$ | CH | O | |
| H | $SCH_2C{\equiv}CCH_3$ | $CH_3$ | $OCH_3$ | N | O | |

TABLE 3a-continued

General Structure 1 wherein Q is Q-20

| R | $R'_3$ | X | Y | Z | W' | m.p. °C. |
|---|---|---|---|---|---|---|
| H | $SCH_2C\equiv CCH_3$ | $CH_3$ | $OCH_3$ | CH | O | |
| H | $SCH_2C\equiv CCH_3$ | $OCH_3$ | $OCH_3$ | CH | O | |
| H | $SCH_2C\equiv CCH_3$ | $OCH_3$ | $OCH_3$ | CH | S | |
| H | $SCH_2C\equiv CCH_3$ | $OCH_3$ | $OCH_3$ | N | S | |
| H | $SCH_2C\equiv CCH_3$ | $CH_3$ | $OCH_3$ | CH | S | |
| H | $SCH_2C\equiv CCH_3$ | $OCH_3$ | Cl | CH | S | |
| H | $SC\equiv CC_2H_5$ | $CH_3$ | $OCH_3$ | N | O | |
| H | $SC\equiv CC_2H_5$ | $OCH_3$ | $OCH_3$ | CH | O | |
| H | $SC\equiv CC_2H_5$ | $OCH_3$ | $OCH_3$ | CH | S | |
| H | $SC\equiv CC_2H_5$ | $CH_3$ | $CH_3$ | CH | S | |
| $CH_3$ | $SC\equiv CC_2H_5$ | $CH_3$ | $OCH_3$ | CH | O | |
| H | $CH_2CN$ | $CH_3$ | $CH_3$ | CH | O | |
| H | $CH_2CN$ | $CH_3$ | $OCH_3$ | N | O | |
| H | $CH_2CN$ | $CH_3$ | $OCH_3$ | CH | O | |
| H | $CH_2CN$ | $OCH_3$ | $OCH_3$ | N | O | |
| H | $CH_2CN$ | $OCH_3$ | $OCH_3$ | CH | O | |
| H | $CH_2CN$ | $OCH_3$ | Cl | CH | O | |
| H | $CH_2CN$ | $CH_3$ | $NHCH_3$ | N | O | |
| $CH_3$ | $CH_2CN$ | $OCH_3$ | $OCH_3$ | CH | S | |
| H | $CH_2CN$ | $CH_3$ | $CH_3$ | CH | S | |
| H | $CH_2CN$ | $CH_3$ | $CH_3$ | N | S | |
| H | $CH_2CN$ | $CH_3$ | $OCH_3$ | CH | S | |
| H | $CH_2CN$ | $CH_3$ | $OCH_3$ | N | S | |
| H | $CH_2CN$ | $OCH_3$ | $OCH_3$ | CH | S | |
| H | $CH_2CN$ | $OCH_3$ | $OCH_3$ | N | S | |
| H | $CH_2CN$ | $OCH_3$ | Cl | CH | S | |
| $CH_3$ | $CH_2CO_2CH_3$ | $CH_3$ | $OCH_3$ | CH | O | |
| H | $CH_2CO_2CH_3$ | $CH_3$ | $CH_3$ | CH | O | |
| H | $CH_2CO_2CH_3$ | $CH_3$ | $OCH_3$ | CH | O | |
| H | $CH_2CO_2CH_3$ | $CH_3$ | $OCH_3$ | N | O | |
| H | $CH_2CO_2CH_3$ | $OCH_3$ | $OCH_3$ | CH | O | |
| H | $CH_2CO_2CH_3$ | $OCH_3$ | $OCH_3$ | N | O | |
| H | $CH_2CO_2CH_3$ | $OCH_3$ | Cl | CH | O | |
| H | $CH_2CO_2CH_3$ | $CH_3$ | $CH_3$ | CH | S | |
| H | $CH_2CO_2CH_3$ | $CH_3$ | $OCH_3$ | N | S | |
| H | $CH_2CO_2CH_3$ | $CH_3$ | $OCH_3$ | CH | S | |
| H | $CH_2CO_2CH_3$ | $OCH_3$ | $OCH_3$ | N | S | |
| H | $CH_2CO_2CH_3$ | $OCH_3$ | $OCH_3$ | CH | S | |
| H | $CH_2CO_2CH_3$ | $OCH_3$ | Cl | CH | S | |
| H | $CH_2CO_2CH_3$ | $CH_3$ | $N(CH_3)_2$ | N | S | |
| H | $CH_2CO_2C_2H_5$ | $CH_3$ | $CH_3$ | CH | O | |
| H | $CH_2CO_2C_2H_5$ | $CH_3$ | $OCH_3$ | N | O | |
| H | $CH_2CO_2C_2H_5$ | $CH_3$ | $OCH_3$ | CH | O | |
| H | $CH_2CO_2C_2H_5$ | $OCH_3$ | $OCH_3$ | N | O | |
| H | $CH_2CO_2C_2H_5$ | $OCH_3$ | $OCH_3$ | CH | O | |
| H | $CH_2CO_2C_2H_5$ | $OCH_3$ | Cl | CH | O | |
| H | $CH_2CO_2C_2H_5$ | $OC_2H_5$ | Cl | CH | O | |
| $CH_3$ | $CH_2CO_2C_2H_5$ | $OCH_3$ | $OCH_3$ | CH | S | |
| H | $CH_2CO_2C_2H_5$ | $CH_3$ | $CH_3$ | CH | S | |
| H | $CH_2CO_2C_2H_5$ | $CH_3$ | $CH_3$ | N | S | |
| H | $CH_2CO_2C_2H_5$ | $CH_3$ | $OCH_3$ | CH | S | |
| H | $CH_2CO_2C_2H_5$ | $CH_3$ | $OCH_3$ | N | S | |
| H | $CH_2CO_2C_2H_5$ | $OCH_3$ | $OCH_3$ | CH | S | |
| H | $CH_2CO_2C_2H_5$ | $OCH_3$ | $OCH_3$ | N | S | |
| H | $CH_2CO_2C_2H_5$ | $OCH_3$ | Cl | CH | S | |
| $CH_3$ | $CH_2OCH_3$ | $OCH_3$ | $OCH_3$ | CH | O | |
| H | $CH_2OCH_3$ | $CH_3$ | $CH_3$ | CH | O | |
| H | $CH_2OCH_3$ | $CH_3$ | $CH_3$ | N | O | |
| H | $CH_2OCH_3$ | $CH_3$ | $OCH_3$ | CH | O | |
| H | $CH_2OCH_3$ | $CH_3$ | $OCH_3$ | N | O | |
| H | $CH_2OCH_3$ | $OCH_3$ | $OCH_3$ | CH | O | |
| H | $CH_2OCH_3$ | $OCH_3$ | $OCH_3$ | N | O | |
| H | $CH_2OCH_3$ | $OCH_3$ | Cl | CH | O | |
| H | $CH_2OCH_3$ | $CH_3$ | $CH_3$ | CH | S | |
| H | $CH_2OCH_3$ | $CH_3$ | $OCH_3$ | N | S | |
| H | $CH_2OCH_3$ | $CH_3$ | $OCH_3$ | CH | S | |
| H | $CH_2OCH_3$ | $OCH_3$ | $OCH_3$ | N | S | |
| H | $CH_2OCH_3$ | $OCH_3$ | $OCH_3$ | CH | S | |
| H | $CH_2OCH_3$ | $OCH_3$ | Cl | CH | S | |
| H | $CH_2OCH_3$ | $CH_3$ | $CH(OCH_3)_2$ | CH | S | |
| H | $CH_2OC_2H_5$ | $CH_3$ | $CH_3$ | CH | O | |
| H | $CH_2OC_2H_5$ | $CH_3$ | $OCH_3$ | N | O | |
| H | $CH_2OC_2H_5$ | $CH_3$ | $OCH_3$ | CH | O | |
| H | $CH_2OC_2H_5$ | $OCH_3$ | $OCH_3$ | N | O | |
| H | $CH_2OC_2H_5$ | $OCH_3$ | $OCH_3$ | CH | O | |
| H | $CH_2OC_2H_5$ | $OCH_3$ | Cl | CH | O | |
| H | $CH_2OC_2H_5$ | $OCH_3$ | Br | CH | O | |
| $CH_3$ | $CH_2OC_2H_5$ | $CH_3$ | $OCH_3$ | CH | S | |
| H | $CH_2OC_2H_5$ | $CH_3$ | $CH_3$ | CH | S | |

TABLE 3a-continued

General Structure 1 wherein Q is Q-20

| R | R'$_3$ | X | Y | Z | W' | m.p. °C. |
|---|---|---|---|---|---|---|
| H | $CH_2OC_2H_5$ | $CH_3$ | $CH_3$ | N | S | |
| H | $CH_2OC_2H_5$ | $CH_3$ | $OCH_3$ | CH | S | |
| H | $CH_2OC_2H_5$ | $CH_3$ | $OCH_3$ | N | S | |
| H | $CH_2OC_2H_5$ | $OCH_3$ | $OCH_3$ | CH | S | |
| H | $CH_2OC_2H_5$ | $OCH_3$ | $OCH_3$ | N | S | |
| H | $CH_2OC_2H_5$ | $OCH_3$ | Cl | CH | S | |
| $CH_3$ | $(CH_2)_2COCH_3$ | $OCH_3$ | $OCH_3$ | CH | O | |
| H | $(CH_2)_2COCH_3$ | $CH_3$ | $CH_3$ | CH | O | |
| H | $(CH_2)_2COCH_3$ | $CH_3$ | $CH_3$ | N | O | |
| H | $(CH_2)_2COCH_3$ | $CH_3$ | $OCH_3$ | CH | O | |
| H | $(CH_2)_2COCH_3$ | $CH_3$ | $OCH_3$ | N | O | |
| H | $(CH_2)_2COCH_3$ | $OCH_3$ | $OCH_3$ | CH | O | |
| H | $(CH_2)_2COCH_3$ | $OCH_3$ | $OCH_3$ | N | O | |
| H | $(CH_2)_2COCH_3$ | $OCH_3$ | Cl | CH | O | |
| H | $(CH_2)_2COCH_3$ | $CH_3$ | $CH_3$ | CH | S | |
| H | $(CH_2)_2COCH_3$ | $CH_3$ | $OCH_3$ | N | S | |
| H | $(CH_2)_2COCH_3$ | $CH_3$ | $OCH_3$ | CH | S | |
| H | $(CH_2)_2COCH_3$ | $OCH_3$ | $OCH_3$ | N | S | |
| H | $(CH_2)_2COCH_3$ | $OCH_3$ | $OCH_3$ | CH | S | |
| H | $(CH_2)_2COCH_3$ | $OCH_3$ | Cl | CH | S | |
| H | $(CH_2)_2COCH_3$ | $CH_3$ | 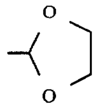 | CH | S | |
| H | $(CH_2)_2CN$ | $CH_3$ | $OCH_3$ | CH | O | |
| H | $(CH_2)_2CN$ | $CH_3$ | $OCH_3$ | N | O | |
| H | $(CH_2)_2CN$ | $OCH_3$ | $OCH_3$ | CH | O | |
| H | $(CH_2)_2CN$ | $OCH_3$ | $OCH_3$ | N | O | |
| H | $(CH_2)_2CN$ | $CH_3$ | $CH_3$ | CH | S | |
| H | $(CH_2)_2CN$ | $CH_3$ | $OCH_3$ | N | S | |
| H | $(CH_2)_2CN$ | $OCH_3$ | $OCH_3$ | CH | S | |
| H | $(CH_2)_2CN$ | $OCH_3$ | Cl | CH | S | |
| H | $CH(CH_3)CN$ | $OCH_3$ | $OCH_3$ | CH | O | |
| H | $CH(CH_3)CN$ | $OCH_3$ | $OCH_3$ | N | O | |
| H | $CH(CH_3)CN$ | $CH_3$ | $OCH_3$ | CH | S | |
| H | $CH(CH_3)CN$ | $CH_3$ | $OCH_3$ | N | S | |
| H | $(CH_2)_3CN$ | $CH_3$ | $OCH_3$ | CH | O | |
| H | $(CH_2)_3CN$ | $CH_3$ | $OCH_3$ | N | O | |
| H | $(CH_2)_3CN$ | $OCH_3$ | $OCH_3$ | CH | O | |
| H | $(CH_2)_3CN$ | $OCH_3$ | $OCH_3$ | N | O | |
| H | $(CH_2)_3CN$ | $CH_3$ | $CH_3$ | CH | S | |
| H | $(CH_2)_3CN$ | $CH_3$ | $OCH_3$ | N | S | |
| H | $(CH_2)_3CN$ | $OCH_3$ | $OCH_3$ | $CH_3$ | S | |
| H | $(CH_2)_3CN$ | $OCH_3$ | $OCH_3$ | N | S | |
| H | $CH_2CH(CH_3)CN$ | $CH_3$ | $OCH_3$ | CH | O | |
| H | $CH_2CH(CH_3)CN$ | $CH_3$ | $OCH_3$ | N | O | |
| H | $CH_2CH(CH_3)CN$ | $OCH_3$ | $OCH_3$ | CH | S | |
| H | $CH_2CH(CH_3)CN$ | $OCH_3$ | Cl | CH | S | |
| H | $CH_2CH(CH_3)CN$ | $CH_3$ | $CH_3$ | CH | O | |
| H | $CH_2CH(CH_3)CN$ | $CH_3$ | $OCH_3$ | N | O | |
| H | $CH_2CH(CH_3)CN$ | $OCH_3$ | $OCH_3$ | CH | S | |
| H | $CH_2CH(CH_3)CN$ | $OCH_3$ | $CH_3$ | CH | S | |
| $CH_3$ | $CH_2CH(CH_3)CN$ | $OCH_3$ | $OCH_3$ | CH | S | |
| H | $CH(CN)C_2H_5$ | $CH_3$ | $OCH_3$ | N | O | |
| H | $CH(CN)C_2H_5$ | $OCH_3$ | $OCH_3$ | CH | O | |
| H | $CH(CN)C_2H_5$ | $OCH_3$ | $OCH_3$ | N | S | |
| H | $CH(CN)C_2H_5$ | $OCH_3$ | Cl | CH | S | |
| H | $C(CH_3)_2CN$ | $CH_3$ | $CH_3$ | CH | O | |
| H | $C(CH_3)_2CN$ | $OCH_3$ | $OCH_3$ | CH | O | |
| H | $C(CH_3)_2CN$ | $OCH_3$ | $OCH_3$ | N | S | |
| H | $C(CH_3)_2CN$ | $OCH_3$ | $OCH_3$ | CH | S | |
| H | $CH(CH_3)CO_2CH_3$ | $OCH_3$ | $OCH_3$ | CH | O | |
| H | $CH(CH_3)CO_2CH_3$ | $OCH_3$ | $OCH_3$ | N | O | |
| H | $CH(CH_3)CO_2CH_3$ | $CH_3$ | $OCH_3$ | CH | S | |
| H | $CH(CH_3)CO_2CH_3$ | $CH_3$ | $OCH_3$ | N | S | |
| H | $(CH_2)_3CO_2CH_3$ | $CH_3$ | $OCH_3$ | CH | O | |
| H | $(CH_2)_3CO_2CH_3$ | $CH_3$ | $OCH_3$ | N | O | |
| H | $(CH_2)_3CO_2CH_3$ | $OCH_3$ | $OCH_3$ | CH | O | |
| H | $(CH_2)_3CO_2CH_3$ | $OCH_3$ | $OCH_3$ | N | O | |
| H | $(CH_2)_3CO_2CH_3$ | $CH_3$ | $OCH_3$ | CH | S | |
| H | $(CH_2)_3CO_2CH_3$ | $CH_3$ | $OCH_3$ | N | S | |
| H | $(CH_2)_3CO_2CH_3$ | $OCH_3$ | $OCH_3$ | CH | S | |
| H | $(CH_2)_3CO_2CH_3$ | $OCH_3$ | $OCH_3$ | N | S | |
| H | $CH_2CH(CH_3)CO_2CH_3$ | $CH_3$ | $OCH_3$ | CH | O | |
| H | $CH_2CH(CH_3)CO_2CH_3$ | $CH_3$ | $OCH_3$ | N | O | |

TABLE 3a-continued

General Structure 1 wherein Q is Q-20

| R | R'3 | X | Y | Z | W' | m.p. °C. |
|---|---|---|---|---|---|---|
| H | $CH_2CH(CH_3)CO_2CH_3$ | $OCH_3$ | $OCH_3$ | CH | S | |
| H | $CH_2CH(CH_3)CO_2CH_3$ | $OCH_3$ | $OCH_3$ | N | S | |
| H | $CH_2CH(CH_3)CO_2CH_3$ | $CH_3$ | $OCH_3$ | CH | O | |
| H | $CH_2CH(CH_3)CO_2CH_3$ | $CH_3$ | $OCH_3$ | N | O | |
| H | $CH_2CH(CH_3)CO_2CH_3$ | $OCH_3$ | $OCH_3$ | CH | S | |
| H | $CH_2CH(CH_3)CO_2CH_3$ | $OCH_3$ | $OCH_3$ | N | S | |
| H | $CH(CO_2CH_3)C_2H_5$ | $CH_3$ | $OCH_3$ | N | O | |
| H | $CH(CO_2CH_3)C_2H_5$ | $OCH_3$ | $OCH_3$ | CH | O | |
| H | $CH(CO_2CH_3)C_2H_5$ | $OCH_3$ | $OCH_3$ | N | S | |
| H | $CH(CO_2CH_3)C_2H_5$ | $OCH_3$ | $OCH_3$ | CH | S | |
| H | $C(CH_3)_2CO_3CH_3$ | $CH_3$ | $OCH_3$ | N | O | |
| H | $C(CH_3)_2CO_3CH_3$ | $OCH_3$ | $OCH_3$ | CH | O | |
| H | $C(CH_3)_2CO_3CH_3$ | $CH_3$ | $OCH_3$ | N | S | |
| H | $C(CH_3)_2CO_3CH_3$ | $OCH_3$ | $OCH_3$ | CH | S | |
| H | $(CH_2)_2CO_2C_2H_5$ | $CH_3$ | $CH_3$ | CH | O | |
| H | $(CH_2)_2CO_2C_2H_5$ | $CH_3$ | $OCH_3$ | N | O | |
| H | $(CH_2)_2CO_2C_2H_5$ | $OCH_3$ | $OCH_3$ | CH | O | |
| H | $(CH_2)_2CO_2C_2H_5$ | $OCH_3$ | $OCH_3$ | N | O | |
| H | $(CH_2)_2CO_2C_2H_5$ | $OCH_3$ | $OCH_3$ | CH | S | |
| H | $(CH_2)_2CO_2C_2H_5$ | $CH_3$ | $OCH_3$ | N | S | |
| H | $(CH_2)_2CO_2C_2H_5$ | $OCH_3$ | $OCH_3$ | CH | S | |
| H | $(CH_2)_2CO_2C_2H_5$ | $OCH_3$ | $OCH_3$ | N | S | |
| H | $CH(CH_3)CO_2C_2H_5$ | $OCH_3$ | $OCH_3$ | CH | O | |
| H | $CH(CH_3)CO_2C_2H_5$ | $OCH_3$ | $OCH_3$ | N | O | |
| H | $CH(CH_3)CO_2C_2H_5$ | $CH_3$ | $OCH_3$ | CH | S | |
| H | $CH(CH_3)CO_2C_2H_5$ | $CH_3$ | $OCH_3$ | N | S | |
| H | $(CH_2)_3CO_2C_2H_5$ | $CH_3$ | $OCH_3$ | CH | O | |
| H | $(CH_2)_3CO_2C_2H_5$ | $CH_3$ | $OCH_3$ | N | O | |
| H | $(CH_2)_3CO_2C_2H_5$ | $OCH_3$ | $OCH_3$ | CH | O | |
| H | $(CH_2)_3CO_2C_2H_5$ | $OCH_3$ | $OCH_3$ | N | O | |
| H | $(CH_2)_3CO_2C_2H_5$ | $CH_3$ | $OCH_3$ | CH | S | |
| H | $(CH_2)_3CO_2C_2H_5$ | $CH_3$ | $OCH_3$ | N | S | |
| H | $(CH_2)_3CO_2C_2H_5$ | $OCH_3$ | $OCH_3$ | CH | S | |
| H | $(CH_2)_3CO_2C_2H_5$ | $OCH_3$ | $OCH_3$ | N | S | |
| H | $CH_2CH(CH_3)CO_2C_2H_5$ | $CH_3$ | $OCH_3$ | CH | O | |
| H | $CH_2CH(CH_3)CO_2C_2H_5$ | $CH_3$ | $OCH_3$ | N | O | |
| H | $CH_2CH(CH_3)CO_2C_2H_5$ | $OCH_3$ | $OCH_3$ | CH | S | |
| H | $CH_2CH(CH_3)CO_2C_2H_5$ | $OCH_3$ | $OCH_3$ | N | S | |
| H | $CH_2CH(CH_3)CO_2C_2H_5$ | $CH_3$ | $OCH_3$ | CH | O | |
| H | $CH_2CH(CH_3)CO_2C_2H_5$ | $CH_3$ | $OCH_3$ | N | O | |
| H | $CH_2CH(CH_3)CO_2C_2H_5$ | $CH_3$ | $OCH_3$ | CH | S | |
| H | $CH_2CH(CH_3)CO_2C_2H_5$ | $OCH_3$ | $OCH_3$ | N | S | |
| H | $CH(CO_2C_2H_5)C_2H_5$ | $CH_3$ | $OCH_3$ | N | O | |
| H | $CH(CO_2C_2H_5)C_2H_5$ | $OCH_3$ | $OCH_3$ | CH | O | |
| H | $CH(CO_2C_2H_5)C_2H_5$ | $OCH_3$ | $OCH_3$ | N | S | |
| H | $CH(CO_2C_2H_5)C_2H_5$ | $OCH_3$ | $OCH_3$ | CH | S | |
| H | $C(CH_3)_2CO_2C_2H_5$ | $CH_3$ | $OCH_3$ | N | O | |
| H | $C(CH_3)_2CO_2C_2H_5$ | $OCH_3$ | $OCH_3$ | CH | O | |
| H | $C(CH_3)_2CO_2C_2H_5$ | $CH_3$ | $OCH_3$ | N | O | |
| H | $C(CH_3)_2CO_2C_2H_5$ | $OCH_3$ | $OCH_3$ | CH | S | |
| H | $(CH_2)_2OCH_3$ | $CH_3$ | $CH_3$ | CH | O | |
| H | $(CH_2)_2OCH_3$ | $CH_3$ | $OCH_3$ | N | O | |
| H | $(CH_2)_2OCH_3$ | $OCH_3$ | $OCH_3$ | CH | O | |
| H | $(CH_2)_2OCH_3$ | $OCH_3$ | $OCH_3$ | N | O | |
| H | $(CH_2)_2OCH_3$ | $OCH_3$ | $OCH_3$ | CH | S | |
| H | $(CH_2)_2OCH_3$ | $CH_3$ | $OCH_3$ | N | S | |
| H | $(CH_2)_2OCH_3$ | $OCH_3$ | $OCH_3$ | CH | S | |
| H | $(CH_2)_2OCH_3$ | $OCH_3$ | $OCH_3$ | N | S | |
| H | $CH(CH_3)OCH_3$ | $OCH_3$ | $OCH_3$ | CH | O | |
| H | $CH(CH_3)OCH_3$ | $OCH_3$ | $OCH_3$ | N | O | |
| H | $CH(CH_3)OCH_3$ | $CH_3$ | $OCH_3$ | CH | S | |
| H | $CH(CH_3)OCH_3$ | $CH_3$ | $OCH_3$ | N | S | |
| H | $(CH_2)_3OCH_3$ | $CH_3$ | $OCH_3$ | CH | O | |
| H | $(CH_2)_3OCH_3$ | $CH_3$ | $OCH_3$ | N | O | |
| H | $(CH_2)_3OCH_3$ | $OCH_3$ | $OCH_3$ | CH | O | |
| H | $(CH_2)_3OCH_3$ | $OCH_3$ | $OCH_3$ | N | O | |
| H | $(CH_2)_3OCH_3$ | $CH_3$ | $OCH_3$ | CH | S | |
| H | $(CH_2)_3OCH_3$ | $CH_3$ | $OCH_3$ | N | S | |
| H | $(CH_2)_3OCH_3$ | $OCH_3$ | $OCH_3$ | CH | S | |
| H | $(CH_2)_3OCH_3$ | $OCH_3$ | $OCH_3$ | N | S | |
| H | $CH_2CH(CH_3)OCH_3$ | $CH_3$ | $OCH_3$ | CH | O | |
| H | $CH_2CH(CH_3)OCH_3$ | $CH_3$ | $OCH_3$ | N | O | |
| H | $CH_2CH(CH_3)OCH_3$ | $OCH_3$ | $OCH_3$ | CH | S | |
| H | $CH_2CH(CH_3)OCH_3$ | $OCH_3$ | $OCH_3$ | N | S | |
| H | $CH_2CH(CH_3)OCH_3$ | $CH_3$ | $OCH_3$ | CH | O | |
| H | $CH_2CH(CH_3)OCH_3$ | $CH_3$ | $OCH_3$ | N | O | |
| H | $CH_2CH(CH_3)OCH_3$ | $CH_3$ | $OCH_3$ | CH | S | |
| H | $CH_2CH(CH_3)OCH_3$ | $OCH_3$ | $OCH_3$ | N | S | |
| H | $CH(OCH_3)C_2H_5$ | $CH_3$ | $OCH_3$ | N | O | |

TABLE 3a-continued

General Structure 1 wherein Q is Q-20

| R | R'$_3$ | X | Y | Z | W' | m.p. °C. |
|---|---|---|---|---|---|---|
| H | $CH(OCH_3)C_2H_5$ | $OCH_3$ | $OCH_3$ | CH | O | |
| H | $CH(OCH_3)C_2H_5$ | $OCH_3$ | $OCH_3$ | N | S | |
| H | $CH(OCH_3)C_2H_5$ | $OCH_3$ | $OCH_3$ | CH | S | |
| H | $C(CH_3)_2OCH_3$ | $CH_3$ | $OCH_3$ | N | O | |
| H | $C(CH_3)_2OCH_3$ | $OCH_3$ | $OCH_3$ | CH | O | |
| H | $C(CH_3)_2OCH_3$ | $CH_3$ | $OCH_3$ | N | O | |
| H | $C(CH_3)_2OCH_3$ | $OCH_3$ | $OCH_3$ | CH | S | |
| H | $(CH_2)_2OC_2H_5$ | $CH_3$ | $CH_3$ | CH | O | |
| H | $(CH_2)_2OC_2H_5$ | $CH_3$ | $OCH_3$ | N | O | |
| H | $(CH_2)_2OC_2H_5$ | $OCH_3$ | $OCH_3$ | CH | O | |
| H | $(CH_2)_2OC_2H_5$ | $OCH_3$ | $OCH_3$ | N | O | |
| H | $(CH_2)_2OC_2H_5$ | $OCH_3$ | $OCH_3$ | CH | S | |
| H | $(CH_2)_2OC_2H_5$ | $CH_3$ | $OCH_3$ | N | S | |
| H | $(CH_2)_2OC_2H_5$ | $OCH_3$ | $OCH_3$ | CH | S | |
| H | $(CH_2)_2OC_2H_5$ | $OCH_3$ | $OCH_3$ | N | S | |
| H | $CH(CH_3)OC_2H_5$ | $OCH_3$ | $OCH_3$ | CH | O | |
| H | $CH(CH_3)OC_2H_5$ | $OCH_3$ | $OCH_3$ | N | O | |
| H | $CH(CH_3)OC_2H_5$ | $CH_3$ | $OCH_3$ | CH | S | |
| H | $CH(CH_3)OC_2H_5$ | $CH_3$ | $OCH_3$ | N | S | |
| H | $(CH_2)_3OC_2H_5$ | $CH_3$ | $OCH_3$ | CH | O | |
| H | $(CH_2)_3OC_2H_5$ | $CH_3$ | $OCH_3$ | N | O | |
| H | $(CH_2)_3OC_2H_5$ | $OCH_3$ | $OCH_3$ | CH | O | |
| H | $(CH_2)_3OC_2H_5$ | $OCH_3$ | $OCH_3$ | N | O | |
| H | $(CH_2)_3OC_2H_5$ | $CH_3$ | $OCH_3$ | CH | S | |
| H | $(CH_2)_3OC_2H_5$ | $CH_3$ | $OCH_3$ | N | S | |
| H | $(CH_2)_3OC_2H_5$ | $OCH_3$ | $OCH_3$ | CH | S | |
| H | $(CH_2)_3OC_2H_5$ | $OCH_3$ | $OCH_3$ | N | S | |
| H | $CH_2CH(CH_3)OC_2H_5$ | $CH_3$ | $OCH_3$ | CH | O | |
| H | $CH_2CH(CH_3)OC_2H_5$ | $CH_3$ | $OCH_3$ | N | O | |
| H | $CH_2CH(CH_3)OC_2H_5$ | $OCH_3$ | $OCH_3$ | CH | S | |
| H | $CH_2CH(CH_3)OC_2H_5$ | $OCH_3$ | $OCH_3$ | N | S | |
| H | $CH(CH_3)CH_2OC_2H_5$ | $CH_3$ | $OCH_3$ | CH | O | |
| H | $CH(CH_3)CH_2OC_2H_5$ | $CH_3$ | $OCH_3$ | N | O | |
| H | $CH(CH_3)CH_2OC_2H_5$ | $CH_3$ | $OCH_3$ | CH | S | |
| H | $CH(CH_3)CH_2OC_2H_5$ | $OCH_3$ | $OCH_3$ | N | S | |
| H | $CH(OC_2H_5)C_2H_5$ | $CH_3$ | $OCH_3$ | N | O | |
| H | $CH(OC_2H_5)C_2H_5$ | $OCH_3$ | $OCH_3$ | CH | O | |
| H | $CH(OC_2H_5)C_2H_5$ | $OCH_3$ | $OCH_3$ | N | S | |
| H | $CH(OC_2H_5)C_2H_5$ | $OCH_3$ | $OCH_3$ | CH | S | |
| H | $CH(CH_3)_2OC_2H_5$ | $CH_3$ | $OCH_3$ | N | O | |
| H | $CH(CH_3)_2OC_2H_5$ | $OCH_3$ | $OCH_3$ | CH | O | |
| H | $CH(CH_3)_2OC_2H_5$ | $CH_3$ | $OCH_3$ | N | O | |
| H | $C(CH_3)_2OC_2H_5$ | $OCH_3$ | $OCH_3$ | CH | S | |
| H | $(CH_2)CH_2COCH_3$ | $CH_3$ | $CH_3$ | CH | O | |
| H | $(CH_2)CH_2COCH_3$ | $CH_3$ | $OCH_3$ | N | O | |
| H | $(CH_2)CH_2COCH_3$ | $OCH_3$ | $OCH_3$ | CH | O | |
| H | $(CH_2)CH_2COCH_3$ | $OCH_3$ | $OCH_3$ | N | O | |
| H | $(CH_2)CH_2COCH_3$ | $OCH_3$ | $OCH_3$ | CH | S | |
| H | $(CH_2)CH_2COCH_3$ | $CH_3$ | $OCH_3$ | N | S | |
| H | $(CH_2)CH_2COCH_3$ | $OCH_3$ | $OCH_3$ | CH | S | |
| H | $(CH_2)CH_2COCH_3$ | $OCH_3$ | $OCH_3$ | N | S | |
| H | $CH(CH_3)CH_2COCH_3$ | $OCH_3$ | $OCH_3$ | CH | O | |
| H | $CH(CH_3)CH_2COCH_3$ | $OCH_3$ | $OCH_3$ | N | O | |
| H | $CH(CH_3)CH_2COCH_3$ | $CH_3$ | $OCH_3$ | CH | S | |
| H | $CH(CH_3)CH_2COCH_3$ | $CH_3$ | $OCH_3$ | N | S | |
| H | $(CH_2)_3CH_2COCH_3$ | $CH_3$ | $OCH_3$ | CH | O | |
| H | $(CH_2)_3CH_2COCH_3$ | $CH_3$ | $OCH_3$ | N | O | |
| H | $(CH_2)_3CH_2COCH_3$ | $OCH_3$ | $OCH_3$ | CH | O | |
| H | $(CH_2)_3CH_2COCH_3$ | $OCH_3$ | $OCH_3$ | N | O | |
| H | $(CH_2)_3CH_2COCH_3$ | $CH_3$ | $OCH_3$ | CH | S | |
| H | $(CH_2)_3CH_2COCH_3$ | $CH_3$ | $OCH_3$ | N | S | |
| H | $(CH_2)_3CH_2COCH_3$ | $OCH_3$ | $OCH_3$ | CH | S | |
| H | $(CH_2)_3CH_2COCH_3$ | $OCH_3$ | $OCH_3$ | N | S | |
| H | $CH_2CH(CH_3)CH_2COCH_3$ | $CH_3$ | $OCH_3$ | CH | O | |
| H | $CH_2CH(CH_3)CH_2COCH_3$ | $CH_3$ | $OCH_3$ | N | O | |
| H | $CH_2CH(CH_3)CH_2COCH_3$ | $OCH_3$ | $OCH_3$ | CH | S | |
| H | $CH_2CH(CH_3)CH_2COCH_3$ | $OCH_3$ | $OCH_3$ | N | S | |
| H | $CH(CH_3)CH_2CH_2COCH_3$ | $CH_3$ | $OCH_3$ | CH | O | |
| H | $CH(CH_3)CH_2CH_2COCH_3$ | $CH_3$ | $OCH_3$ | N | O | |
| H | $CH(CH_3)CH_2CH_2COCH_3$ | $CH_3$ | $OCH_3$ | CH | S | |
| H | $CH(CH_3)CH_2CH_2COCH_3$ | $OCH_3$ | $OCH_3$ | N | S | |
| H | $CH(C_2H_5)CH_2COCH_3$ | $CH_3$ | $OCH_3$ | N | O | |
| H | $CH(C_2H_5)CH_2OCH_3$ | $OCH_3$ | $OCH_3$ | CH | O | |
| H | $CH(C_2H_5)CH_2OCH_3$ | $OCH_3$ | $OCH_3$ | N | S | |
| H | $CH(C_2H_5)CH_2OCH_3$ | $OCH_3$ | $OCH_3$ | CH | S | |
| H | $CH(CH_3)_2CH_2COCH_3$ | $CH_3$ | $OCH_3$ | N | O | |
| H | $CH(CH_3)_2CH_2COCH_3$ | $OCH_3$ | $OCH_3$ | CH | O | |
| H | $CH(CH_3)_2CH_2COCH_3$ | $CH_3$ | $OCH_3$ | N | O | |
| H | $C(CH_3)_2CH_2COCH_3$ | $OCH_3$ | $OCH_3$ | CH | S | |

TABLE 3a-continued

| General Structure 1 wherein Q is Q-20 | | | | | | |
|---|---|---|---|---|---|---|
| R | R'3 | X | Y | Z | W' | m.p. °C. |
| H | H | $OCH_3$ | $OCH_3$ | CH | O* | |
| H | H | $OCH_3$ | $OCH_3$ | CH | S* | |
| H | $CH_3$ | $OCH_3$ | $OCH_3$ | CH | O* | |
| H | $CH_3$ | $OCH_3$ | $OCH_3$ | CH | S* | |
| H | $SCH_3$ | $OCH_3$ | $OCH_3$ | CH | O* | |
| H | $SCH_3$ | $OCH_3$ | $OCH_3$ | CH | S* | |
| H | $SCH_2CH{=}CH_2$ | $OCH_3$ | $OCH_3$ | CH | O* | |
| H | $SCH_3CH{=}CH_2$ | $OCH_3$ | $OCH_3$ | CH | S* | |
| H | SH | $OCH_3$ | $OCH_3$ | CH | O* | |
| H | SH | $OCH_3$ | $OCH_3$ | CH | S* | |

W is O, unless indicated by * where W is S in all Tables.

TABLE 3b

| General Structure 1 wherein Q is Q-28. | | | | | | |
|---|---|---|---|---|---|---|
| R | $R_3'$ | $R_4$ | X | Y | Z | m.p. °C. |
| H | H | H | $CH_3$ | $OCH_3$ | CH | |
| H | H | H | $CH_3$ | $OCH_3$ | N | |
| H | H | H | $OCH_3$ | $OCH_3$ | CH | |
| H | H | H | $OCH_3$ | $OCH_3$ | N | |
| H | H | H | $CH_3$ | $CH_3$ | CH | |
| H | H | H | $CH_3$ | $CH_3$ | N | |
| H | $CH_3$ | H | $CH_3$ | $OCH_3$ | CH | |
| H | H | H | Br | $OCH_3$ | CH | |
| H | H | $CH_3$ | $CH_3$ | $OCH_3$ | N | |
| H | $CH_3$ | $CH_3$ | $OCH_3$ | $OCH_3$ | CH | |
| $CH_3$ | $CH_3$ | $CH_3$ | $OCH_3$ | $OCH_3$ | N | |
| H | H | H | $CH_3$ | 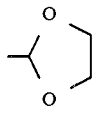 | CH | |
| H | H | H | $CH_3$ | $C_2H_5$ | CH | |
| H | $CH_3$ | H | $CH_3$ | $CH_3$ | CH | 220-222 |
| H | $CH_3$ | H | $CH_3$ | $OCH_3$ | N | 189-192 |
| H | $CH_3$ | H | $OCH_3$ | $OCH_3$ | CH | 198-207 |
| H | $CH_3$ | H | $OCH_3$ | $OCH_3$ | N | |
| H | $CH_3$ | H | $OCH_3$ | Cl | CH | 217-218 |
| H | $CH_3$ | H | $CH_3$ | $CH_3$ | N | |
| H | Cl | H | $CH_3$ | $CH_3$ | CH | 211-213 |

TABLE 3b-continued

| General Structure 1 wherein Q is Q-28. | | | | | | |
|---|---|---|---|---|---|---|
| R | $R_3'$ | $R_4$ | X | Y | Z | m.p. °C. |
| H | Cl | H | $CH_3$ | $CH_3$ | N | 195-197 |
| H | Cl | H | $CH_3$ | $OCH_3$ | CH | |
| H | Cl | H | $CH_3$ | $OCH_3$ | N | 175-177 |
| H | Cl | H | $OCH_3$ | $OCH_3$ | CH | 204-205 |
| H | Cl | H | $OCH_3$ | $OCH_3$ | N | 187-188 |
| H | Cl | H | $OCH_3$ | Cl | CH | 205-206 |
| H | Cl | $CH_3$ | $CH_3$ | $OCH_3$ | CH | |
| H | Cl | $CH_3$ | $CH_3$ | $OCH_3$ | N | |
| H | Cl | $CH_3$ | $OCH_3$ | $OCH_3$ | CH | |
| H | Cl | $CH_3$ | $OCH_3$ | $OCH_3$ | N | |
| H | Br | H | $OCH_3$ | $OCH_3$ | CH | |
| H | Br | H | $CH_3$ | $CH_3$ | CH | |
| H | Br | H | $CH_3$ | $OCH_3$ | N | |
| H | Br | H | $CH_3$ | $OCH_3$ | CH | |
| H | Br | H | $OCH_3$ | $OCH_3$ | N | |
| H | Br | H | $OCH_3$ | $OCH_3$ | CH | |
| H | Br | H | $OCH_3$ | Cl | CH | |
| H | H | H | $OCH_3$ | $OCH_3$ | CH* | |
| H | $CH_3$ | H | $OCH_3$ | $OCH_3$ | CH* | |
| H | H | $CH_3$ | $OCH_3$ | $OCH_3$ | CH* | |
| H | $CH_3$ | $CH_3$ | $OCH_3$ | $OCH_3$ | CH* | |
| H | Cl | H | $OCH_3$ | $OCH_3$ | CH* | |
| H | Cl | $CH_3$ | $OCH_3$ | $OCH_3$ | CH* | |
| H | Br | H | $OCH_3$ | $OCH_3$ | CH* | |
| H | Br | $CH_3$ | $OCH_3$ | $OCH_3$ | CH* | |

*Wherein W is O, unless indicated by * where W is S in all Tables.

TABLE 3c

| General Structure 1 | | | | | | | | |
|---|---|---|---|---|---|---|---|---|
| Q | R | $R_3$ | $R_4$ | X | Y | Z | n' | m.p. °C. |
| Q-33 | H | H | H | $CH_3$ | $OCH_3$ | CH | 0 | |
| Q-33 | H | H | H | $CH_3$ | $OCH_3$ | N | 0 | 173-176(d) |
| Q-33 | H | H | H | $OCH_3$ | $OCH_3$ | CH | 0 | 198-203(d) |
| Q-33 | H | H | H | $OCH_3$ | $OCH_3$ | N | 0 | 172-174 |
| Q-33 | H | H | H | $CH_3$ | $CH_3$ | CH | 0 | 130-133 |
| Q-33 | H | 3-$CH_3$ | H | $CH_3$ | $OCH_3$ | CH | 0 | |
| Q-33 | H | 4-$CH_3$ | H | $CH_3$ | $OCH_3$ | CH | 0 | |
| Q-33 | H | 5-$CH_3$ | H | $CH_3$ | $OCH_3$ | CH | 0 | |
| Q-33 | H | H | H | $CH_3$ | $CH_3$ | N | 0 | |
| Q-33 | H | 6-$CH_3$ | H | $CH_3$ | $OCH_3$ | CH | 0 | |
| Q-33 | H | 3-$CH_3$ | 5-$CH_3$ | $CH_3$ | $OCH_3$ | N | 0 | |
| Q-33 | H | 4-$CH_3$ | 6-$CH_3$ | $CH_3$ | $OCH_3$ | N | 0 | |
| Q-33 | $CH_3$ | H | H | $OCH_3$ | $OCH_3$ | CH | 0 | |
| Q-33 | H | H | H | $CH_3$ | $CH_2OCH_3$ | CH | 0 | |
| Q-33 | H | H | H | Cl | $OC_2H_5$ | CH | 0 | |
| Q-33 | H | H | H | $CH_3$ | $CF_3$ | CH | 0 | |
| Q-33 | H | H | H | Cl | $OCH_3$ | CH | 1 | 180 |
| Q-33 | H | H | H | $CH_3$ | $OCH_3$ | CH | 1 | 160-162 |
| Q-33 | H | H | H | $CH_3$ | $OCH_3$ | N | 1 | 223-226 |
| Q-33 | H | H | H | $OCH_3$ | $OCH_3$ | CH | 1 | 182-185 |
| Q-33 | H | H | H | $OCH_3$ | $OCH_3$ | N | 1 | 218-220 |
| Q-33 | H | H | H | $CH_3$ | $CH_3$ | CH | 1 | 159-161 |
| Q-33 | H | 3-$CH_3$ | H | $CH_3$ | $OCH_3$ | CH | 1 | |
| Q-33 | H | 4-$CH_3$ | H | $CH_3$ | $OCH_3$ | CH | 1 | |
| Q-33 | H | 5-$CH_3$ | H | $CH_3$ | $OCH_3$ | CH | 1 | |
| Q-33 | H | H | H | $CH_3$ | $CH_3$ | N | 1 | |
| Q-33 | H | 6-$CH_3$ | H | $CH_3$ | $OCH_3$ | CH | 1 | |

TABLE 3c-continued

General Structure 1

| Q | R | $R_3$ | $R_4$ | X | Y | Z | n' | m.p. °C. |
|---|---|---|---|---|---|---|---|---|
| Q-33 | H | 3-$CH_3$ | 5-$CH_3$ | $CH_3$ | $OCH_3$ | N | 1 | |
| Q-33 | H | 4-$CH_3$ | 6-$CH_3$ | $CH_3$ | $OCH_3$ | N | 1 | |
| Q-33 | $CH_3$ | H | H | $OCH_3$ | $OCH_3$ | CH | 1 | |
| Q-33 | H | H | H | $CH_3$ | $CH_2OCH_3$ | CH | 1 | |
| Q-33 | H | H | H | Cl | $OC_2H_5$ | CH | 1 | |
| Q-33 | H | H | H | $CH_3$ | $CF_3$ | CH | 1 | |
| Q-34 | H | H | H | $CH_3$ | $OCH_3$ | CH | 0 | |
| Q-34 | H | H | H | $CH_3$ | $OCH_3$ | N | 0 | |
| Q-34 | H | H | H | $OCH_3$ | $OCH_3$ | CH | 0 | |
| Q-34 | H | H | H | $OCH_3$ | $OCH_3$ | N | 0 | |
| Q-34 | H | 2-$CH_3$ | H | $CH_3$ | $CH_3$ | CH | 0 | |
| Q-34 | H | 4-$CH_3$ | H | $CH_3$ | $CH_3$ | N | 0 | |
| Q-34 | H | 5-$CH_3$ | H | $CH_3$ | $OCH_3$ | CH | 0 | |
| Q-34 | H | 6-$CH_3$ | H | $CH_3$ | $OCH_3$ | N | 0 | |
| Q-34 | H | 2-$CH_3$ | 6-$CH_3$ | $OCH_3$ | $OCH_3$ | CH | 0 | |
| Q-34 | H | 4-$CH_3$ | 6-$CH_3$ | $OCH_3$ | $OCH_3$ | N | 0 | |
| Q-34 | H | H | H | $CH_3$ | $CH_3$ | N | 0 | |
| Q-34 | $CH_3$ | H | H | $CH_3$ | $CH_3$ | CH | 0 | |
| Q-34 | H | H | H | $CH_3$ | $CH_3$ | CH | 0 | |
| Q-34 | H | H | H | $CH_3$ | $OCF_2H$ | CH | 0 | |
| Q-34 | H | H | H | $CH_3$ | $OCH_3$ | CH | 1 | |
| Q-34 | H | H | H | $CH_3$ | $OCH_3$ | N | 1 | |
| Q-34 | H | H | H | $OCH_3$ | $OCH_3$ | CH | 1 | |
| Q-34 | H | H | H | $OCH_3$ | $OCH_3$ | N | 1 | |
| Q-34 | H | 2-$CH_3$ | H | $CH_3$ | $CH_3$ | CH | 1 | |
| Q-34 | H | 4-$CH_3$ | H | $CH_3$ | $CH_3$ | N | 1 | |
| Q-34 | H | 5-$CH_3$ | H | $CH_3$ | $OCH_3$ | CH | 1 | |
| Q-34 | H | 6-$CH_3$ | H | $CH_3$ | $CH_3$ | N | 1 | |
| Q-34 | H | 2-$CH_3$ | 6-$CH_3$ | $OCH_3$ | $OCH_3$ | CH | 1 | |
| Q-34 | H | 4-$CH_3$ | 6-$CH_3$ | $OCH_3$ | $OCH_3$ | N | 1 | |
| Q-34 | H | H | H | $CH_3$ | $CH_3$ | N | 1 | |
| Q-34 | $CH_3$ | H | H | $CH_3$ | $CH_3$ | CH | 1 | |
| Q-34 | H | H | H | $CH_3$ | $CH_3$ | CH | 1 | |
| Q-34 | H | H | H | $CH_3$ | $OCF_2H$ | CH | 1 | |
| Q-35 | H | H | H | $CH_3$ | $OCH_3$ | CH | 0 | |
| Q-35 | H | H | H | $CH_3$ | $OCH_3$ | N | 0 | |
| Q-35 | H | H | H | $OCH_3$ | $OCH_3$ | CH | 0 | |
| Q-35 | H | H | H | $OCH_3$ | $OCH_3$ | N | 0 | |
| Q-35 | H | 2-$CH_3$ | H | $CH_3$ | $CH_3$ | CH | 0 | |
| Q-35 | H | H | H | Cl | $OCH_3$ | CH | 0 | |
| Q-35 | H | 3-$CH_3$ | H | $CH_3$ | $CH_3$ | N | 0 | |
| Q-35 | H | 2-$CH_3$ | 6-$CH_3$ | $CH_3$ | $OCH_3$ | CH | 0 | |
| Q-35 | H | 2-$CH_3$ | 3-$CH_3$ | $CH_3$ | $OCH_3$ | N | 0 | |
| Q-35 | H | 3-$CH_3$ | 5-$CH_3$ | $CH_3$ | $OCH_3$ | N | 0 | |
| Q-35 | H | H | H | $CH_3$ | $CH_3$ | N | 0 | |
| Q-35 | $CH_3$ | H | H | $OCH_3$ | $OCH_3$ | CH | 0 | |
| Q-35 | H | H | H | $CH_3$ | $OCH_2CF_3$ | CH | 0 | |
| Q-35 | H | H | H | $CH_3$ | $CH_3$ | CH | 0 | |
| Q-35 | H | H | H | $CH_3$ | $OCH_3$ | CH | 1 | |
| Q-35 | H | H | H | $CH_3$ | $OCH_3$ | N | 1 | |
| Q-35 | H | H | H | $OCH_3$ | $OCH_3$ | CH | 1 | |
| Q-35 | H | H | H | $OCH_3$ | $OCH_3$ | N | 1 | |
| Q-35 | H | 2-$CH_3$ | H | $CH_3$ | $CH_3$ | CH | 1 | |
| Q-35 | H | H | H | Cl | $OCH_3$ | CH | 1 | |
| Q-35 | H | 3-$CH_3$ | H | $CH_3$ | $CH_3$ | N | 1 | |
| Q-35 | H | 2-$CH_3$ | 6-$CH_3$ | $CH_3$ | $OCH_3$ | CH | 1 | |
| Q-35 | H | 2-$CH_3$ | 3-$CH_3$ | $CH_3$ | $OCH_3$ | N | 1 | |
| Q-35 | H | 3-$CH_3$ | 5-$CH_3$ | $CH_3$ | $OCH_3$ | N | 1 | |
| Q-35 | H | H | H | $CH_3$ | $CH_3$ | N | 1 | |
| Q-35 | $CH_3$ | H | H | $OCH_3$ | $OCH_3$ | CH | 1 | |
| Q-35 | H | H | H | $CH_3$ | $OCH_2CF_3$ | CH | 1 | |
| Q-35 | H | H | H | $CH_3$ | $CH_3$ | CH | 1 | |

TABLE 4a

General Structure 2 wherein Q is Q-1.

| R | $R_1$ | $R_2$ | X | Y | Z | m.p. °C. |
|---|---|---|---|---|---|---|
| H | H | H | $CH_3$ | $CH_3$ | CH | 165-170 |
| H | H | H | $CH_3$ | $CH_3$ | N | |
| H | H | H | $CH_3$ | $OCH_3$ | CH | 175-180 |
| H | H | H | $CH_3$ | $OCH_3$ | N | 179-182 |
| H | H | H | $OCH_3$ | $OCH_3$ | CH | 179-183 |
| H | H | H | Cl | $OCH_3$ | CH | 171-173 |
| H | H | H | $OCH_3$ | $OCH_3$ | N | 163-166 |
| H | 4-Cl | H | $CH_3$ | $OCH_3$ | CH | |
| H | H | 4-F | $CH_3$ | $CH_3$ | N | |

TABLE 4a-continued

General Structure 2 wherein Q is Q-1.

| R | $R_1$ | $R_2$ | X | Y | Z | m.p. °C. |
|---|---|---|---|---|---|---|
| H | 4-$CH_3$ | H | $OCH_3$ | $OCH_3$ | CH | |
| H | H | 4-$OCH_3$ | $CH_3$ | $OCH_3$ | N | |
| H | H | 4-$CF_3$ | $CH_3$ | $OCH_3$ | CH | |
| $CH_3$ | 3-$CH_3$ | 5-$CH_3$ | $CH_3$ | $CH_3$ | N | |
| H | H | H | $OCH_3$ | $OCF_2H$ | CH | |
| H | H | H | $OCH_3$ | cyclopropyl | N | |
| H | H | H | $OC_2H_5$ | $OCH_3$ | N | |
| H | H | H | O—n-$C_4H_9$ | $CH_3$ | CH | |
| H | H | H | $OCH_2CF_3$ | $OCH_3$ | N | |
| H | H | H | $OCH_2CH_2CH_2F$ | $CH_3$ | CH | |
| H | H | H | $SCH_3$ | $OCH_3$ | CH | |
| H | H | H | $SCH(CH_3)_2$ | $CH_3$ | N | |
| H | H | H | $CH_2CH_2OCH_3$ | $CH_3$ | CH | |
| H | H | H | $CH_2OCH_2CH_3$ | $OCH_3$ | N | |
| H | H | H | $N(CH_2CH_3)_2$ | $CH_3$ | CH | |
| H | H | H | $N(CH_2CH_2CH_3)$ | $OCH_3$ | N | |
| H | H | H | $CH_3$ | $OCH_2CH{=}CH_2$ | CH | |
| H | H | H | $OCH_3$ | $OCH_2C{\equiv}CCH_3$ | N | |
| H | H | H | $CH_3$ | cyclopentyl | CH | |
| H | H | H | $OCH_3$ | $CH_2SCH_3$ | N | |
| H | H | H | $CH_3$ | $C(O)CH_3$ | CH | |
| H | H | H | $CH_3$ | 1,3-dioxan-2-yl | N | |
| H | H | H | $OCH_3$ | $N(OCH_3)CH_3$ | CH | |
| H | H | H | $OCH_3$ | $OCH_3$ | CH * | |
| H | H | H | $OCH_3$ | $CH_3$ | N * | |
| H | 4-Cl | H | $OCH_3$ | $OCH_3$ | CH * | |
| H | H | H | $OCH_3$ | $OCH_3$ | CH ** | 155-158 |
| H | H | H | $OCH_3$ | $CH_3$ | N ** | 100-104 |

W is O, unless indicated by * where W is S in all Tables.
E is H, unless indicated by ** where E is 4-Br in all Tables.

TABLE 4b

General Structure 2

| Q | R | $R_3$ | $R_4$ | $R_5$ | X | Y | Z | W' | m.p. °C. |
|---|---|---|---|---|---|---|---|---|---|
| Q-2 | H | H | H | H | $CH_3$ | $OCH_3$ | CH | O | |
| Q-2 | H | H | H | H | $CH_3$ | $OCH_3$ | N | O | |
| Q-2 | H | H | H | H | $OCH_3$ | $OCH_3$ | CH | O | |
| Q-2 | H | H | H | H | $OCH_3$ | $OCH_3$ | N | O | |
| Q-2 | H | $CH_3$ | H | H | $CH_3$ | $CH_3$ | CH | O | |
| Q-2 | H | H | $CH_3$ | H | $CH_3$ | $OCH_3$ | N | O | |
| Q-2 | H | H | H | $CH_3$ | $CH_3$ | $OCH_3$ | CH | O | |
| Q-2 | $CH_3$ | H | H | H | CH | $CH_3$ | CH | O | |
| Q-2 | H | $CH_3$ | $CH_3$ | H | $OCH_3$ | $OCH_3$ | N | O | |
| Q-2 | H | H | H | H | Cl | $OCH_3$ | CH | S | |
| Q-2 | H | H | H | H | $CH_3$ | $OCH_3$ | CH | S | |
| Q-2 | H | H | H | H | $CH_3$ | $OCH_3$ | N | S | |
| Q-2 | H | H | H | H | $OCH_3$ | $OCH_3$ | CH | S | |
| Q-2 | H | H | H | H | $OCH_3$ | $OCH_3$ | N | S | |
| Q-2 | H | H | H | H | $CH_3$ | $CH_3$ | CH | S | |
| Q-2 | H | $CH_3$ | H | H | $CH_3$ | $CH_3$ | CH | S | |
| Q-2 | H | H | $CH_3$ | H | $CH_3$ | $CH_3$ | N | S | |
| Q-2 | H | H | H | $CH_3$ | $CH_3$ | $OCH_3$ | CH | S | |
| Q-2 | H | $CH_3$ | $CH_3$ | H | $CH_3$ | $OCH_3$ | N | S | |
| Q-2 | H | H | $CH_3$ | $CH_3$ | $OCH_3$ | $OCH_3$ | CH | S | |
| Q-2 | H | $CH_3$ | H | $CH_3$ | $OCH_3$ | $OCH_3$ | N | S | |
| Q-2 | H | $CH_3$ | $CH_3$ | $CH_3$ | $CH_3$ | $OCH_3$ | CH | S | |
| Q-2 | $CH_3$ | H | H | H | $CH_3$ | $CH_3$ | CH | S | |
| Q-2 | H | H | H | H | Cl | $OC_2H_5$ | CH | S | |
| Q-3 | H | H | H | H | $CH_3$ | $CH_3$ | CH | O | |
| Q-3 | H | H | H | H | $CH_3$ | $CH_3$ | N | O | |
| Q-3 | H | H | H | H | $CH_3$ | $OCH_3$ | CH | O | |
| Q-3 | H | H | H | H | $CH_3$ | $OCH_3$ | N | O | |
| Q-3 | H | H | H | H | $OCH_3$ | $OCH_3$ | CH | O | |
| Q-3 | H | H | H | H | $OCH_3$ | $OCH_3$ | N | O | |
| Q-3 | H | $CH_3$ | H | H | $CH_3$ | $CH_3$ | CH | O | |
| Q-3 | H | H | $CH_3$ | H | $CH_3$ | $CH_3$ | N | O | |
| Q-3 | H | H | H | $CH_3$ | $CH_3$ | $OCH_3$ | CH | O | |
| Q-3 | H | $CH_3$ | $CH_3$ | H | $CH_3$ | $OCH_3$ | N | O | |
| Q-3 | H | H | $CH_3$ | $CH_3$ | $OCH_3$ | $OCH_3$ | CH | O | |
| Q-3 | H | $CH_3$ | H | $CH_3$ | $OCH_3$ | $OCH_3$ | N | O | |
| Q-3 | H | H | H | H | $OCH_3$ | $OCH_2CF_3$ | CH | O | |
| Q-3 | H | H | H | H | $OCH_3$ | $OCH_2CF_3$ | CH | O | |
| Q-3 | $CH_3$ | H | H | H | Cl | $OCH_3$ | CH | O | |
| Q-3 | H | H | H | H | $CH_3$ | $OCH_3$ | CH | S | |
| Q-3 | H | H | H | H | $OCH_3$ | $OCH_3$ | CH | S | 133-135 |

TABLE 4b-continued

General Structure 2

| Q | R | $R_3$ | $R_4$ | $R_5$ | X | Y | Z | W' | m.p. °C. |
|---|---|---|---|---|---|---|---|---|---|
| Q-3 | H | H | H | H | $OCH_3$ | $OCH_3$ | N | S | |
| Q-3 | H | $CH_3$ | H | H | $CH_3$ | $CH_3$ | CH | S | |
| Q-3 | H | H | $CH_3$ | H | $CH_3$ | $OCH_3$ | N | S | |
| Q-3 | H | H | H | $CH_3$ | $CH_3$ | $OCH_3$ | CH | S | |
| Q-3 | $CH_3$ | H | H | H | $CH_3$ | $CH_3$ | CH | S | |
| Q-3 | H | H | $CH_3$ | $CH_3$ | $OCH_3$ | $OCH_3$ | N | S | |
| Q-3 | H | H | H | H | $OCH_3$ | $CF_3$ | N | S | |
| Q-4 | H | H | H | H | $CH_3$ | $OCH_3$ | CH | — | |
| Q-4 | H | H | H | H | $OCH_3$ | Cl | CH | — | |
| Q-4 | H | H | H | H | $CH_3$ | $OCH_3$ | N | — | 192-199 |
| Q-4 | H | H | H | H | $CH_3$ | $CH_3$ | CH | — | |
| Q-4 | H | H | H | H | $OCH_3$ | $OCH_3$ | CH | — | 140-144 |
| Q-4 | H | H | H | H | $OCH_3$ | $OCH_3$ | N | — | |
| Q-4 | H | $CH_3$ | H | H | $CH_3$ | $CH_3$ | CH | — | |
| Q-4 | H | H | $CH_3$ | H | $CH_3$ | $OCH_3$ | N | — | |
| Q-4 | H | H | H | $CH_3$ | $CH_3$ | $OCH_3$ | CH | — | |
| Q-4 | $CH_3$ | H | H | H | $OCH_3$ | $OCH_3$ | CH | — | |
| Q-4 | $CH_3$ | $CH_3$ | $CH_3$ | $CH_3$ | $CH_3$ | $OCH_3$ | N | — | |
| Q-4 | H | $CH_3$ | H | $CH_3$ | $CH_3$ | $OCH_3$ | CH | — | |
| Q-4 | H | H | H | H | $OCH_3$ | $OCH_2CF_3$ | N | — | |
| Q-4 | H | H | H | H | $CH_3$ | $NHCH_3$ | CH | — | |
| Q-4 | H | H | H | H | $CH_3$ | $CH_3$ | CH | — | |
| Q-4 | H | H | H | H | $CH_3$ | $CH_3$ | N | — | |
| Q-9 | H | H | H | H | $CH_3$ | $OCH_3$ | CH | — | |
| Q-9 | H | H | H | H | $CH_3$ | $OCH_3$ | N | — | |
| Q-9 | H | H | H | H | $OCH_3$ | $OCH_3$ | CH | — | |
| Q-9 | H | H | H | H | $OCH_3$ | $OCH_3$ | N | — | |
| Q-9 | $CH_3$ | $CH_3$ | H | H | $CH_3$ | $CH_3$ | CH | — | |
| Q-9 | H | H | $CH_3$ | H | $CH_3$ | $OCH_3$ | N | — | |
| Q-9 | H | H | H | $CH_3$ | $OCH_3$ | $OCH_3$ | CH | — | |
| Q-9 | H | H | $CH_3$ | $CH_3$ | $CH_3$ | $OCH_3$ | CH | — | |
| Q-9 | H | H | H | H | Cl | $OCH_2CH_3$ | CH | — | |
| Q-9 | H | H | H | H | $OCH_3$ | $CH(OCH_3)_2$ | CH | — | |
| Q-9 | H | H | H | H | $NH_2$ | $CH_3$ | CH | — | |
| Q-9 | H | H | H | H | $NHCH(CH_3)_2$ | $CH_3$ | CH | — | |
| Q-9 | H | H | H | H | $CH_2O$—n-$C_4H_9$ | $CH_3$ | CH | — | |
| Q-9 | H | H | H | H | S—n-$C_4H_9$ | $CH_3$ | CH | — | |
| Q-9 | H | H | H | H | S—n-$CH_2CH_2F$ | $CH_3$ | CH | — | |

TABLE 4c

General Structure 2

| Q | R | $R_3'$ | $R_4$ | X | Y | Z | W'' | m.p. °C. |
|---|---|---|---|---|---|---|---|---|
| Q-10 | H | H | H | $CH_3$ | $OCH_3$ | CH | O | |
| Q-10 | H | H | H | $CH_3$ | $CH_3$ | CH | O | |
| Q-10 | H | H | H | $OCH_3$ | $OCH_3$ | N | O | |
| Q-10 | H | H | H | $OCH_3$ | Cl | CH | O | |
| Q-10 | H | H | H | $OCH_3$ | $OCH_3$ | CH | O | 157-161 |
| Q-10 | H | H | H | $OCH_3$ | $OCH_3$ | N | O | |
| Q-10 | H | H | H | $CH_3$ | $OCH_3$ | CH | S | |
| Q-10 | H | H | H | $CH_3$ | $OCH_3$ | N | S | |
| Q-10 | H | H | H | $OCH_3$ | $OCH_3$ | CH | S | |
| Q-10 | H | H | H | $OCH_3$ | $OCH_3$ | N | S | |
| Q-10 | H | H | H | $OCH_3$ | Cl | CH | $NCH_3$ | 193-195 |
| Q-10 | H | H | H | $CH_3$ | $CH_3$ | CH | $NCH_3$ | 112-115 |
| Q-10 | H | H | H | $CH_3$ | $OCH_3$ | N | $NCH_3$ | 190-192 |
| Q-10 | H | H | H | $CH_3$ | $CH_3$ | N | $NCH_3$ | 185-189 |
| Q-10 | H | H | H | $OCH_3$ | $OCH_3$ | CH | $NCH_3$ | 202-204 |
| Q-10 | H | H | H | $OCH_3$ | $CH_3$ | CH | $NCH_3$ | 171-174 |
| Q-10 | H | $CH_3$ | H | $CH_3$ | $CH_3$ | CH | O | |
| Q-10 | H | H | $CH_3$ | $CH_3$ | $OCH_3$ | N | O | |
| Q-10 | H | $CH_3$ | $CH_3$ | $CH_3$ | $OCH_3$ | CH | O | |
| Q-10 | $CH_3$ | H | H | $OCH_3$ | $OCH_3$ | N | O | |
| Q-10 | H | H | H | $CH_3$ | 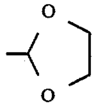 | CH | O | |
| Q-10 | H | $CH_3$ | H | $CH_3$ | $CH_3$ | CH | S | |
| Q-10 | H | H | $CH_3$ | $CH_3$ | $OCH_3$ | N | S | |
| Q-10 | H | $CH_3$ | $CH_3$ | $CH_3$ | $OCH_3$ | CH | S | |
| Q-10 | $CH_3$ | $CH_3$ | $CH_3$ | $CH_3$ | $OCH_3$ | CH | S | |
| Q-10 | $CH_3$ | H | H | $OCH_3$ | $OCH_3$ | N | S | |
| Q-10 | H | H | H | $CH_3$ | $OC_2H_5$ | CH | S | |
| Q-10 | H | H | $CH_3$ | $CH_3$ | $CH_3$ | N | $NCH_3$ | |

TABLE 4c-continued

| | | | | General Structure 2 | | | | |
|---|---|---|---|---|---|---|---|---|
| Q | R | $R_3'$ | $R_4$ | X | Y | Z | W'' | m.p. °C. |
| Q-10 | H | H | $CH_3$ | $CH_3$ | $OCH_3$ | CH | $NCH_3$ | |
| Q-10 | H | $CH_3$ | $CH_3$ | $OCH_3$ | $OCH_3$ | N | $NCH_3$ | |
| Q-10 | $CH_3$ | H | H | $OCH_3$ | $OCH_3$ | N | $NCH_3$ | |
| Q-11 | H | H | H | $CH_3$ | $CH_3$ | N | O | |
| Q-11 | H | H | H | $CH_3$ | $CH_3$ | CH | O | |
| Q-11 | H | H | H | $CH_3$ | $OCH_3$ | N | O | |
| Q-11 | H | H | H | $CH_3$ | $OCH_3$ | CH | O | |
| Q-11 | H | H | H | $OCH_3$ | $OCH_3$ | CH | O | |
| Q-11 | H | H | H | $OCH_3$ | $OCH_3$ | N | O | |
| Q-11 | H | H | H | $CH_3$ | $CH_3$ | CH | S | |
| Q-11 | H | H | H | $CH_3$ | $OCH_3$ | CH | S | |
| Q-11 | H | H | H | $CH_3$ | $OCH_3$ | CH | S | |
| Q-11 | H | H | H | $OCH_3$ | $OCH_3$ | CH | S | |
| Q-11 | H | H | H | $CH_3$ | $CH_3$ | CH | $NCH_3$ | |
| Q-11 | H | H | H | $CH_3$ | $OCH_3$ | CH | $NCH_3$ | |
| Q-11 | H | H | H | $OCH_3$ | $OCH_3$ | CH | $NCH_3$ | |
| Q-11 | H | H | H | $CH_3$ | $OCH_3$ | N | $NCH_3$ | |
| Q-11 | H | $CH_3$ | H | $CH_3$ | $OCH_3$ | N | O | |
| Q-11 | H | H | $CH_3$ | $OCH_3$ | $OCH_3$ | N | O | |
| Q-11 | H | $CH_3$ | $CH_3$ | $CH_3$ | $OCH_3$ | CH | O | |
| Q-11 | $CH_3$ | H | H | $CH_3$ | $OCH_3$ | CH | O | |
| Q-11 | H | H | H | $CH_3$ | $C_2H_5$ | N | O | |
| Q-11 | H | H | H | $CH_3$ | $CH_2OCH_3$ | CH | O | |
| Q-11 | H | $CH_3$ | H | $CH_3$ | $OCH_3$ | N | S | |
| Q-11 | H | H | $CH_3$ | $OCH_3$ | $OCH_3$ | N | S | |
| Q-11 | H | $CH_3$ | $CH_3$ | $CH_3$ | $OCH_3$ | CH | S | |
| Q-11 | $CH_3$ | H | H | $CH_3$ | $OCH_3$ | CH | S | |
| Q-11 | H | H | H | $CH_3$ | $C_2H_5$ | N | S | |
| Q-11 | $CH_3$ | $CH_3$ | $CH_3$ | $CH_3$ | $OCH_3$ | N | S | |
| Q-11 | H | H | H | Cl | $OCH_3$ | CH | $NCH_3$ | |
| Q-11 | H | $CH_3$ | H | $CH_3$ | $CH_3$ | CH | $NCH_3$ | |
| Q-11 | H | H | $CH_3$ | $CH_3$ | $OCH_3$ | N | $NCH_3$ | |
| Q-11 | H | $CH_3$ | $CH_3$ | $CH_3$ | $OCH_3$ | CH | $NCH_3$ | |
| Q-11 | $CH_3$ | H | H | $OCH_3$ | $OCH_3$ | N | NH | |
| Q-11 | H | H | H | $CH_3$ | $OCH_3$ | CH | NH | |
| Q-11 | H | H | H | $OCH_3$ | $OCH_3$ | CH | O* | |
| Q-11 | H | H | H | $OCH_3$ | CH | N | O* | |
| Q-11 | H | H | H | $CH_3$ | $OCH_3$ | N | $NCH_3$ | |
| Q-11 | H | H | H | $CH_3$ | $OCF_2H$ | CH | $NCH_3$ | |
| Q-11 | H | $CH_3$ | H | $OCH_3$ | $OCH_2CF_3$ | N | $NCH_3$ | |
| Q-12 | H | H | H | $CH_3$ | $OCH_3$ | CH | O | |
| Q-12 | H | H | H | $CH_3$ | $OCH_3$ | N | O | |
| Q-12 | H | H | H | $OCH_3$ | $OCH_3$ | CH | O | |
| Q-12 | H | H | H | $OCH_3$ | $OCH_3$ | N | O | |
| Q-12 | H | H | H | $CH_3$ | $OCH_3$ | CH | S | |
| Q-12 | H | H | H | $CH_3$ | $OCH_3$ | N | S | |
| Q-12 | H | H | H | $OCH_3$ | $OCH_3$ | CH | S | |
| Q-12 | H | H | H | $OCH_3$ | $OCH_3$ | N | S | |
| Q-12 | H | H | H | $CH_3$ | $CH_3$ | N | $NCH_3$ | |
| Q-12 | H | H | H | $CH_3$ | $OCH_3$ | CH | $NCH_3$ | |
| Q-12 | H | H | H | $CH_3$ | $OCH_3$ | N | $NCH_3$ | |
| Q-12 | H | H | H | $OCH_3$ | $OCH_3$ | CH | $NCH_3$ | |
| Q-12 | H | H | H | $OCH_3$ | $OCH_3$ | N | $NCH_3$ | |
| Q-12 | H | H | H | $OCH_3$ | $OCH_3$ | N | NH | |
| Q-12 | H | $CH_3$ | H | $CH_3$ | $CH_3$ | CH | O | |
| Q-12 | H | H | $CH_3$ | $CH_3$ | $OCH_3$ | N | O | |
| Q-12 | H | $CH_3$ | $CH_3$ | $CH_3$ | $OCH_3$ | CH | O | |
| Q-12 | $CH_3$ | H | H | $OCH_3$ | $OCH_3$ | N | O | |
| Q-12 | $CH_3$ | H | H | $CH_3$ | $CF_3$ | CH | O | |
| Q-12 | H | H | H | $OCH_3$ | $OCH_2CF_3$ | N | | |
| Q-12 | H | $CH_3$ | H | $CH_3$ | $OCH_3$ | CH | S | |
| Q-12 | H | H | $CH_3$ | $CH_3$ | $OCH_3$ | N | S | |
| Q-12 | H | $CH_3$ | $CH_3$ | $OCH_3$ | $OCH_3$ | CH | S | |
| Q-12 | $CH_3$ | H | H | $OCH_3$ | $OCH_3$ | N | S | |
| Q-12 | $CH_3$ | $CH_3$ | H | $CH_3$ | $NHCH_3$ | CH | S | |
| Q-12 | H | H | H | Br | $OC_2H_5$ | CH | S | |
| Q-12 | H | $CH_3$ | H | $CH_3$ | $CH_3$ | CH | NH | |
| Q-12 | H | $CH_3$ | H | $CH_3$ | $CH_3$ | CH | $NCH_3$ | |
| Q-12 | H | H | $CH_3$ | $CH_3$ | $OCH_3$ | N | $NCH_3$ | |
| Q-12 | H | $CH_3$ | $CH_3$ | $CH_3$ | $CH_3$ | $CH_3$ | $NCH_3$ | |
| Q-12 | $CH_3$ | $CH_3$ | $CH_3$ | $CH_3$ | $OCH_3$ | N | $NCH_3$ | |
| Q-12 | $CH_3$ | $CH_3$ | $CH_3$ | $CH_3$ | $OCH_3$ | CH | $NCH_3$ | |
| Q-12 | H | H | H | Br | $OCH_3$ | CH | $NCH_3$ | |
| Q-12 | H | H | H | $OCH_3$ | $N(CH_3)_2$ | CH | $NCH_3$ | |
| Q-13 | H | H | H | $CH_3$ | $OCH_3$ | CH | O | |
| Q-13 | H | H | H | $CH_3$ | $OCH_3$ | CH | O | |
| Q-13 | H | H | H | $CH_3$ | $CH_3$ | CH | O | |
| Q-13 | H | H | H | $CH_3$ | $OCH_3$ | N | O | |
| Q-13 | H | H | H | $OCH_3$ | $OCH_3$ | CH | O | |
| Q-13 | H | H | H | $CH_3$ | $CH_3$ | N | O | |

TABLE 4c-continued

| General Structure 2 | | | | | | | | |
|---|---|---|---|---|---|---|---|---|
| Q | R | $R_3'$ | $R_4$ | X | Y | Z | W'' | m.p. °C. |
| Q-13 | H | H | H | $OCH_3$ | $OCH_3$ | N | O | |
| Q-13 | H | H | H | $CH_3$ | $OCH_3$ | CH | S | |
| Q-13 | H | H | H | $CH_3$ | $OCH_3$ | N | S | |
| Q-13 | H | H | H | $OCH_3$ | $OCH_3$ | CH | S | |
| Q-13 | H | H | H | $OCH_3$ | $OCH_3$ | N | S | |
| Q-13 | H | H | H | $CH_3$ | $OCH_3$ | CH | NH | |
| Q-13 | H | H | H | $CH_3$ | $OCH_3$ | N | NH | |
| Q-13 | H | H | H | $OCH_3$ | $OCH_3$ | CH | $NCH_3$ | |
| Q-13 | H | H | H | $OCH_3$ | $OCH_3$ | N | NH | |
| Q-13 | H | $CH_3$ | H | $CH_3$ | $CH_3$ | CH | O | |
| Q-13 | H | H | $CH_3$ | $CH_3$ | $CH_3$ | N | O | |
| Q-13 | H | $CH_3$ | $CH_3$ | $CH_3$ | $OCH_3$ | CH | O | |
| Q-13 | $CH_3$ | H | H | $CH_3$ | $OCH_3$ | N | O | |
| Q-13 | H | H | H | $CH_3$ | $CH(OCH_3)_2$ | CH | O | |
| Q-13 | H | $CH_3$ | H | $CH_3$ | $OCH_3$ | CH | S | |
| Q-13 | H | H | $CH_3$ | $CH_3$ | $OCH_3$ | CH | S | |
| Q-13 | H | $CH_3$ | $CH_3$ | $CH_3$ | $OCH_3$ | N | S | |
| Q-13 | $CH_3$ | H | $CH_3$ | $OCH_3$ | $OCH_3$ | N | S | |
| Q-13 | $CH_3$ | $CH_3$ | $CH_3$ | $CH_3$ | $CH_3$ | N | S | |
| Q-13 | H | H | H | $OCH_3$ | 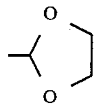 | CH | S | |
| Q-13 | H | $CH_3$ | H | $CH_3$ | $OCH_3$ | N | $NCH_3$ | |
| Q-13 | H | H | $CH_3$ | $CH_3$ | $OCH_3$ | N | $NCH_3$ | |
| Q-13 | H | $CH_3$ | $CH_3$ | $CH_3$ | $OCH_3$ | CH | $NCH_3$ | |
| Q-13 | $CH_3$ | H | H | $OCH_3$ | $OCH_3$ | CH | $NCH_3$ | |
| Q-13 | H | H | H | $CH_3$ | $OCH_3$ | N | NH | |
| Q-13 | H | H | H | Br | $OC_2H_5$ | CH | NH | |
| Q-13 | H | H | H | $OCH_3$ | $C_2H_5$ | N | NH | |
| Q-13 | H | H | H | $CH_3$ | $CH_3$ | CH | $NCH_3$ | |
| Q-13 | H | H | H | $CH_3$ | $CH_3$ | N | $NCH_3$ | |
| Q-13 | H | H | H | Cl | $OCH_3$ | CH | $NCH_3$ | |
| Q-14 | H | H | H | $CH_3$ | $CH_3$ | N | O | |
| Q-14 | H | H | H | $CH_3$ | $CH_3$ | CH | O | |
| Q-14 | H | H | H | $CH_3$ | $OCH_3$ | CH | O | |
| Q-14 | H | H | H | $CH_3$ | $OCH_3$ | CH | O | |
| Q-14 | H | H | H | $CH_3$ | $OCH_3$ | N | O | |
| Q-14 | H | H | H | $OCH_3$ | $OCH_3$ | CH | O | |
| Q-14 | H | H | H | $CH_3$ | $OCH_3$ | CH | S | |
| Q-14 | H | H | H | $CH_3$ | $OCH_3$ | N | S | |
| Q-14 | H | H | H | $OCH_3$ | $OCH_3$ | CH | S | |
| Q-14 | H | H | H | $OCH_3$ | $OCH_3$ | CH | S | |
| Q-14 | H | H | H | $OCH_3$ | $OCH_3$ | N | S | |
| Q-14 | H | H | H | $CH_3$ | $OCH_3$ | CH | $NCH_3$ | |
| Q-14 | H | H | H | $CH_3$ | $OCH_3$ | N | $NCH_3$ | |
| Q-14 | H | H | H | $OCH_3$ | $OCH_3$ | CH | NH | |
| Q-14 | H | H | H | $OCH_3$ | $OCH_3$ | N | $NCH_3$ | |
| Q-14 | H | $CH_3$ | H | $CH_3$ | $CH_3$ | CH | O | |
| Q-14 | H | H | $CH_3$ | $CH_3$ | $CH_3$ | N | O | |
| Q-14 | H | $CH_3$ | $CH_3$ | $CH_3$ | $OCH_3$ | CH | O | |
| Q-14 | $CH_3$ | $CH_3$ | $CH_3$ | $CH_3$ | $OCH_3$ | N | O | |
| Q-14 | H | H | H | $CH_3$ | $C_2H_5$ | N | O | |
| Q-14 | H | H | H | $CH_3$ | $OC_2H_5$ | N | O | |
| Q-14 | H | $CH_3$ | H | $CH_3$ | $OCH_3$ | CH | S | |
| Q-14 | H | H | $CH_3$ | $CH_3$ | $OCH_3$ | N | S | |
| Q-14 | H | $CH_3$ | $CH_3$ | $OCH_3$ | $OCH_3$ | CH | S | |
| Q-14 | $CH_3$ | $CH_3$ | $CH_3$ | $OCH_3$ | $OCH_3$ | CH | S | |
| Q-14 | H | H | H | $OCH_3$ | $C_2H_5$ | N | S | |
| Q-14 | H | H | H | $OCH_3$ | $OC_2H_5$ | N | S | |
| Q-14 | H | $CH_3$ | H | $CH_3$ | $OCH_3$ | CH | $NCH_3$ | |
| Q-14 | H | H | $CH_3$ | $CH_3$ | $OCH_3$ | N | $NCH_3$ | |
| Q-14 | H | $CH_3$ | $CH_3$ | $OCH_3$ | $OCH_3$ | CH | $NCH_3$ | |
| Q-14 | $CH_3$ | $CH_3$ | H | $OCH_3$ | $OCH_3$ | N | $NCH_3$ | |
| Q-14 | H | $CH_3$ | $CH_3$ | $CH_3$ | $OCH_3$ | CH | NH | |
| Q-14 | H | H | H | $CH_3$ | $OCH_3$ | N | NH | |
| Q-14 | H | H | H | $CH_3$ | $CH_2OCH_3$ | CH | $NCH_3$ | |
| Q-15 | H | H | H | $CH_3$ | $OCH_3$ | CH | O | |
| Q-15 | H | H | H | $CH_3$ | $OCH_3$ | N | O | |
| Q-15 | H | H | H | $OCH_3$ | $OCH_3$ | CH | O | |
| Q-15 | H | H | H | $OCH_3$ | $OCH_3$ | N | O | |
| Q-15 | H | $C_2H_5$ | H | $OCH_3$ | $OCH_3$ | CH | O | |
| Q-15 | H | $CH_3$ | H | $CH_3$ | $OCH_3$ | CH | O | |
| Q-15 | H | $CH_3$ | H | $CH_3$ | $CH_3$ | CH | O | |
| Q-15 | H | $CH_3$ | H | $OCH_3$ | $OCH_3$ | CH | O | |
| Q-15 | H | H | $CH_3$ | $CH_3$ | $CH_3$ | N | O | |

TABLE 4c-continued

General Structure 2

| Q | R | $R_3'$ | $R_4$ | X | Y | Z | W'' | m.p. °C. |
|---|---|---|---|---|---|---|---|---|
| Q-15 | H | $CH_3$ | H | $CH_3$ | $OCH_3$ | N | O | |
| Q-15 | H | $CH_3$ | $CH_3$ | $CH_3$ | $OCH_3$ | CH | O | |
| Q-15 | H | $CH_3$ | H | $OCH_3$ | $OCH_3$ | N | O | |
| Q-15 | $CH_3$ | H | H | $CH_3$ | $OCH_3$ | N | O | |
| Q-15 | H | $CH_3$ | H | $OCH_3$ | Cl | CH | O | |
| Q-15 | $CH_3$ | $CH_3$ | $CH_3$ | $OCH_3$ | $OCH_3$ | CH | O | |
| Q-15 | H | H | H | $CH_3$ | $CF_3$ | CH | O | |
| Q-15 | H | H | H | $CH_3$ | $CF_3$ | N | O | |
| Q-15 | H | H | H | $OCH_3$ | $OCF_2H$ | CH | O | |
| Q-15 | $CH_3$ | H | H | $OCH_3$ | $OCF_2H$ | CH | O | |
| Q-15 | H | H | H | $CH_3$ | $CH_3$ | CH | O | |
| Q-15 | H | H | H | $CH_3$ | $CH_3$ | N | O | |
| Q-15 | H | H | H | $OCH_3$ | $OCH_3$ | CH | O* | |
| Q-15 | H | H | H | $OCH_3$ | $CH_3$ | N | O* | |
| Q-15 | H | H | H | $CH_3$ | $CH_3$ | N | S | |
| Q-15 | H | $CH_3$ | H | $CH_3$ | $OCH_3$ | CH | S | |
| Q-15 | H | $CH_3$ | H | $CH_3$ | $OCH_3$ | N | S | |
| Q-15 | H | $CH_3$ | H | $OCH_3$ | $OCH_3$ | CH | S | |
| Q-15 | H | $CH_3$ | H | $OCH_3$ | $OCH_3$ | N | S | |
| Q-15 | H | $CH_3$ | H | Cl | $OCH_3$ | CH | S | |
| Q-15 | H | H | H | $CH_3$ | $OCH_3$ | CH | $NCH_3$ | |
| Q-15 | H | H | H | $CH_3$ | $OCH_3$ | N | $NCH_3$ | |
| Q-15 | H | H | H | $OCH_3$ | $OCH_3$ | CH | $NCH_3$ | |
| Q-15 | H | H | H | $OCH_3$ | $OCH_3$ | N | $NCH_3$ | |
| Q-15 | H | $CH_3$ | H | $CH_3$ | $CH_3$ | CH | S | |
| Q-15 | H | H | $CH_3$ | $CH_3$ | $CH_3$ | N | S | |
| Q-15 | H | $CH_3$ | $CH_3$ | $CH_3$ | $OCH_3$ | CH | S | |
| Q-15 | $CH_3$ | H | H | $CH_3$ | $OCH_3$ | N | S | |
| Q-15 | $CH_3$ | H | $CH_3$ | $OCH_3$ | $OCH_3$ | CH | S | |
| Q-15 | H | H | H | Cl | $OC_2H_5$ | CH | S | |
| Q-15 | H | H | H | $OCH_3$ | $OCH_2CF_3$ | CH | S | |
| Q-15 | H | $CH_3$ | H | $CH_3$ | $CH_3$ | CH | $NCH_3$ | |
| Q-15 | H | H | $CH_3$ | $CH_3$ | $OCH_3$ | CH | $NCH_3$ | |
| Q-15 | H | $CH_3$ | $CH_3$ | $CH_3$ | $OCH_3$ | N | $NCH_3$ | |
| Q-15 | $CH_3$ | $CH_3$ | $CH_3$ | $CH_3$ | $OCH_3$ | N | $NCH_3$ | |
| Q-15 | $CH_3$ | H | H | $CH_3$ | $OCH_3$ | CH | NH | |
| Q-15 | H | H | H | $OCH_3$ | $OCH_3$ | N | NH | |
| Q-15 | H | H | H | $CH_3$ | $NHCH_3$ | CH | $NCH_3$ | |
| Q-15 | H | H | H | $OCH_3$ | $N(CH_3)_2$ | CH | $NCH_3$ | |
| Q-15 | H | H | H | $CH_3$ | $OCH_2C\equiv CH$ | N | S | |
| Q-15 | H | H | H | $CH_3$ | $CH_2C\equiv CH_3$ | CH | S | |
| Q-15 | H | H | H | $CH_3$ | $C\equiv CH$ | N | S | |
| Q-15 | H | $C_2H_5$ | H | $OCH_3$ | $OCH_3$ | CH | S | |
| Q-15 | H | H | H | $OCH_3$ | $(CH_2)_3CH_2F$ | CH | S | |
| Q-15 | H | H | H | $OCH_3$ | 2-methyl-1,3-dioxolan-2-yl | N | S | |
| Q-15 | H | H | H | $OCH_3$ | 2-methyl-1,3-dithiolan-2-yl | CH | S | |
| Q-15 | H | H | H | $OCH_3$ | 2-methyl-1,3-dithian-2-yl | N | S | |
| Q-15 | H | H | H | $OCH_3$ | $OCH_3$ | CH | S* | |
| Q-15 | H | H | H | $OCH_3$ | $CH_3$ | N | S* | |

TABLE 4d

General Structure 2

| Q | R | $R_3$ | $R_4$ | $R_5$ | X | Y | Z | m.p. °C. |
|---|---|---|---|---|---|---|---|---|
| Q-18 | H | H | H | H | $CH_3$ | $CH_3$ | CH | 198–200 |
| Q-18 | H | H | H | H | $CH_3$ | $OCH_3$ | CH | |
| Q-18 | H | H | H | H | $CH_3$ | $OCH_3$ | N | 177–179 |
| Q-18 | $CH_3$ | H | H | H | $CH_3$ | $OCH_3$ | N | |
| Q-18 | H | H | H | H | $OCH_3$ | $OCH_3$ | CH | 178–182 |
| Q-18 | H | H | H | H | $CH_3$ | $CH_3$ | CH | |
| Q-18 | H | H | H | H | $OCH_3$ | $OCH_3$ | N | 185–188 |
| Q-18 | H | H | H | H | Cl | $OCH_3$ | CH | |
| Q-18 | H | $CH_3$ | H | H | $CH_3$ | $OCH_3$ | CH | |
| Q-18 | H | H | $CH_3$ | H | $CH_3$ | $OCH_3$ | N | |
| Q-18 | H | H | H | $CH_3$ | $CH_3$ | $CH_3$ | CH | |
| Q-18 | H | $CH_3$ | $CH_3$ | H | $CH_3$ | $CH_3$ | N | |
| Q-18 | H | H | $CH_3$ | $CH_3$ | $OCH_3$ | $OCH_3$ | CH | |
| Q-18 | H | $CH_3$ | H | $CH_3$ | $OCH_3$ | $OCH_3$ | N | |
| Q-18 | H | $CH_3$ | $CH_3$ | $CH_3$ | $CH_3$ | $OCH_3$ | CH | |
| Q-18 | H | H | H | H | $OCH_3$ | $CH(OCH_3)_2$ | CH | |
| Q-19 | $CH_3$ | H | H | H | Cl | $OCH_3$ | CH | |
| Q-19 | H | H | H | H | $CH_3$ | $OCH_3$ | CH | |
| Q-19 | H | H | H | H | $CH_3$ | $OCH_3$ | N | |
| Q-19 | H | H | H | H | $OCH_3$ | $OCH_3$ | CH | |

TABLE 4d-continued

| | | | | | General Structure 2 | | | |
|---|---|---|---|---|---|---|---|---|
| Q | R | $R_3$ | $R_4$ | $R_5$ | X | Y | Z | m.p. °C. |
| Q-19 | H | H | H | H | $OCH_3$ | $OCH_3$ | N | |
| Q-19 | H | $CH_3$ | H | H | $CH_3$ | $CH_3$ | CH | |
| Q-19 | H | H | $CH_3$ | H | $CH_3$ | $CH_3$ | N | |
| Q-19 | H | H | H | $CH_3$ | $CH_3$ | $OCH_3$ | CH | |
| Q-19 | H | $CH_3$ | $CH_3$ | H | $CH_3$ | $OCH_3$ | N | |
| Q-19 | H | H | $CH_3$ | $CH_3$ | $OCH_3$ | $OCH_3$ | CH | |
| Q-19 | H | $CH_3$ | H | $CH_3$ | $OCH_3$ | $OCH_3$ | N | |
| Q-19 | H | H | H | H | $CH_3$ | $CH_3$ | CH | |
| Q-19 | H | $CH_3$ | $CH_3$ | $CH_3$ | $CH_3$ | $OCH_3$ | CH | |
| Q-19 | $CH_3$ | H | H | H | $CH_3$ | $OCH_3$ | N | |
| Q-19 | H | H | H | H | $OCH_3$ | 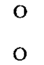 | CH | |

TABLE 4e

| | | | General Structure 2 | | | | |
|---|---|---|---|---|---|---|---|
| Q | R | R'3'' | X | Y | Z | W' | m.p. °C. |
| Q-21 | H | H | $CH_3$ | $OCH_3$ | CH | O | |
| Q-21 | H | H | $CH_3$ | $OCH_3$ | N | O | |
| Q-21 | H | H | $OCH_3$ | $OCH_3$ | CH | O | |
| Q-21 | $CH_3$ | H | $OCH_3$ | $OCH_3$ | CH | O | |
| Q-21 | H | H | $OCH_3$ | $NHCH_3$ | CH | O | |
| Q-21 | H | H | $OCH_3$ | $OCH_3$ | N | O | |
| Q-21 | H | $CH_3$ | $CH_3$ | $OCH_3$ | CH | O | |
| Q-21 | $CH_3$ | $CH_3$ | $CH_3$ | $OCH_3$ | CH | O | |
| Q-21 | H | H | $CH_3$ | $CH_3$ | CH | O | |
| Q-21 | H | H | $CH_3$ | $CH_3$ | N | O | |
| Q-21 | H | H | $CH_3$ | $OCH_3$ | CH | S | |
| Q-21 | H | H | $CH_3$ | $OCH_3$ | N | S | |
| Q-21 | H | H | $OCH_3$ | $OCH_3$ | CH | S | |
| Q-21 | H | H | $OCH_3$ | $OCH_3$ | N | S | |
| Q-21 | H | $CH_3$ | $CH_3$ | $OCH_3$ | CH | S | |
| Q-21 | $CH_3$ | H | $CH_3$ | $OCH_3$ | CH | S | |
| Q-21 | H | H | $OCH_3$ | $N(CH_3)_2$ | N | S | |
| Q-22 | H | H | $CH_3$ | $OCH_3$ | CH | O | |
| Q-22 | H | H | $CH_3$ | $OCH_3$ | N | O | |
| Q-22 | H | H | $OCH_3$ | $OCH_3$ | CH | O | |
| Q-22 | H | H | $OCH_3$ | $OCH_3$ | N | O | |
| Q-22 | H | $CH_3$ | $CH_3$ | $OCH_3$ | CH | O | |
| Q-22 | H | $CH_3$ | $CH_3$ | $OCH_3$ | N | O | |
| Q-22 | $CH_3$ | $CH_3$ | $CH_3$ | $CH_3$ | CH | O | |
| Q-22 | H | H | $CH_3$ | $CH(OCH_3)_2$ | CH | O | |
| Q-22 | H | H | $CH_3$ | $C_2H_5$ | N | O | |
| Q-22 | H | H | $CH_3$ | $CH_3$ | CH | S | |
| Q-22 | H | H | $CH_3$ | $CH_3$ | N | S | |
| Q-22 | H | H | $CH_3$ | $OCH_3$ | CH | S | |
| Q-22 | H | H | $CH_3$ | $OCH_3$ | N | S | |
| Q-22 | H | H | $OCH_3$ | $OCH_3$ | CH | S | |
| Q-22 | H | H | $OCH_3$ | $OCH_3$ | N | S | |
| Q-22 | H | $CH_3$ | $CH_3$ | $OCH_3$ | CH | S | |
| Q-22 | $CH_3$ | $CH_3$ | $CH_3$ | $OCH_3$ | CH | S | |
| Q-22 | $CH_3$ | H | $CH_3$ | $OCH_3$ | N | S | |
| Q-22 | H | H | $CH_3$ | 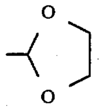 | CH | S | |
| Q-22 | H | H | $OCH_3$ | $C_2H_5$ | N | S | |
| Q-23 | H | H | $CH_3$ | $OCH_3$ | CH | — | |
| Q-23 | H | H | $CH_3$ | $OCH_3$ | N | — | |
| Q-23 | H | H | $OCH_3$ | $OCH_3$ | CH | — | |
| Q-23 | H | H | $OCH_3$ | $OCH_3$ | N | — | |
| Q-23 | H | $CH_3$ | $CH_3$ | $CH_3$ | CH | — | |
| Q-23 | H | $CH_3$ | $CH_3$ | $OCH_3$ | N | — | |
| Q-23 | $CH_3$ | H | $CH_3$ | $OCH_3$ | N | — | |
| Q-23 | $CH_3$ | $CH_3$ | $CH_3$ | $OCH_3$ | CH | — | |
| Q-23 | H | H | $CH_3$ | $OC_2H_5$ | N | — | |
| Q-23 | H | H | $CH_3$ | $CH_2OCH_3$ | CH | — | |
| Q-24 | H | H | $CH_3$ | $OCH_3$ | CH | — | |
| Q-24 | H | H | $CH_3$ | $OCH_3$ | N | — | |
| Q-24 | H | H | $OCH_3$ | $OCH_3$ | CH | — | |
| Q-24 | H | H | $OCH_3$ | $OCH_3$ | N | — | |
| Q-24 | H | $CH_3$ | $CH_3$ | $OCH_3$ | CH | — | |
| Q-24 | H | $CH_3$ | $CH_3$ | $CH_3$ | CH | — | |

TABLE 4e-continued

| | | | General Structure 2 | | | | |
|---|---|---|---|---|---|---|---|
| Q | R | $R'_3''$ | X | Y | Z | W' | m.p. °C. |
| Q-24 | $CH_3$ | H | $CH_3$ | $CH_3$ | N | — | |
| Q-24 | H | H | $CH_3$ | $CF_3$ | CH | — | |
| Q-24 | H | H | $OCH_3$ | $OCF_2H$ | N | — | |
| Q-25 | H | H | $CH_3$ | $OCH_3$ | CH | —** | |
| Q-25 | H | H | $CH_3$ | $OCH_3$ | N | —** | |
| Q-25 | H | H | $OCH_3$ | $OCH_3$ | CH | —** | |
| Q-25 | H | H | $OCH_3$ | $OCH_3$ | N | —** | |
| Q-25 | $CH_3$ | H | $OCH_3$ | $OCH_3$ | N | —** | |
| Q-25 | H | H | $CH_3$ | $CH_3$ | CH | —** | |
| Q-25 | H | H | $CH_3$ | $CH_3$ | N | —** | |
| Q-25 | H | $CH_3$ | $CH_3$ | $OCH_3$ | CH | —** | |
| Q-25 | H | $CH_3$ | $CH_3$ | $OCH_3$ | N | —** | |
| Q-25 | $CH_3$ | $CH_3$ | $OCH_3$ | $OCH_3$ | N | —** | |
| Q-25 | H | H | $CH_3$ | $OCH_2CF_3$ | CH | —** | |
| Q-25 | H | H | $CH_3$ | $NHCH_3$ | N | —** | |
| Q-26 | H | H | $CH_3$ | $OCH_3$ | CH | —** | |
| Q-26 | H | H | $CH_3$ | $OCH_3$ | N | —** | |
| Q-26 | H | H | $OCH_3$ | $OCH_3$ | CH | —** | |
| Q-26 | H | $CH_3$ | $CH_3$ | $CH_3$ | N | —** | |
| Q-26 | H | $CH_3$ | $CH_3$ | $CH_3$ | CH | —** | |
| Q-26 | H | $CH_3$ | $CH_3$ | $OCH_3$ | N | —** | |
| Q-26 | H | $CH_3$ | $CH_3$ | $OCH_3$ | CH | —** | |
| Q-26 | H | $CH_3$ | $CH_3$ | $OCH_3$ | N | —** | |
| Q-26 | H | H | $CH_3$ | $CH_3$ | CH | —** | |
| Q-26 | H | H | $CH_3$ | $CH_3$ | N | —** | |
| Q-26 | H | $CH_3$ | $OCH_3$ | $OCH_3$ | CH | —** | |
| Q-26 | H | $CH_3$ | $OCH_3$ | $OCH_3$ | N | —** | |
| Q-26 | $CH_3$ | H | $CH_3$ | $OCH_3$ | CH | —** | |
| Q-26 | H | H | $CH_3$ | $N(CH_3)_2$ | CH | —** | |
| Q-26 | H | H | $CH_3$ | $N(CH_3)_2$ | N | —** | |
| Q-27 | H | H | $CH_3$ | $OCH_3$ | CH | —** | |
| Q-27 | H | H | $CH_3$ | $OCH_3$ | N | —** | |
| Q-27 | H | H | $OCH_3$ | $OCH_3$ | CH | —** | |
| Q-27 | H | H | $OCH_3$ | $OCH_3$ | N | —** | |
| Q-27 | H | H | $CH_3$ | $CH_3$ | CH | —** | |
| Q-27 | H | H | $CH_3$ | $CH_3$ | N | —** | |
| Q-27 | H | $CH_3$ | $CH_3$ | $CH_3$ | CH | —** | |
| Q-27 | H | H | Cl | $OC_2H_5$ | CH | —** | |
| Q-27 | H | $CH_3$ | $CH_3$ | $CH_3$ | N | —** | |
| Q-27 | H | $CH_3$ | $CH_3$ | $OCH_3$ | CH | —** | |
| Q-27 | H | $CH_3$ | $CH_3$ | $OCH_3$ | N | —** | |
| Q-27 | H | $CH_3$ | $OCH_3$ | $OCH_3$ | CH | —** | |
| Q-27 | H | $CH_3$ | $OCH_3$ | $OCH_3$ | N | —** | |
| Q-27 | $CH_3$ | $CH_3$ | $CH_3$ | $OCH_3$ | N | —** | |
| Q-27 | $CH_3$ | H | $CH_3$ | $OCH_3$ | N | —** | |
| Q-27 | H | H | $CH_3$ | $CH(OCH_3)_2$ | CH | —** | |
| Q-27 | H | H | $CH_3$ | $O(CH_2)_3CH_2Cl$ | CH | —** | |
| Q-25 | H | SH | $CH_3$ | $CH_3$ | CH | —** | 210-219 |
| Q-25 | H | SH | $CH_3$ | $OCH_3$ | CH | —** | 220-222 |
| Q-25 | H | SH | $OCH_3$ | $OCH_3$ | CH | —** | 171-173 |
| Q-25 | H | SH | $OCH_3$ | Cl | CH | —** | 180-182 |
| Q-25 | H | SH | $CH_3$ | $OCH_3$ | N | —** | 169-171 |
| Q-25 | H | SH | $OCH_3$ | $OCH_3$ | N | —** | 209-213 |
| Q-25 | H | $SCH_3$ | $CH_3$ | $CH_3$ | CH | —** | 154-160 |
| Q-25 | H | $SCH_3$ | $CH_3$ | $OCH_3$ | CH | —** | 142-145 |
| Q-25 | H | $SCH_3$ | $OCH_3$ | $OCH_3$ | CH | —** | 178-180 |
| Q-25 | H | $SCH_3$ | $OCH_3$ | Cl | CH | —** | 192-195 |
| Q-25 | H | $SCH_3$ | CH | $OCH_3$ | N | —** | 198-200 |
| Q-25 | H | $SCH_3$ | $OCH_3$ | $OCH_3$ | N | —** | 152-153 |
| Q-25 | H | $SCH_2CH{=}CH_2$ | $CH_3$ | $CH_3$ | CH | —** | 173-175 |
| Q-25 | H | $SCH_2CH{=}CH_2$ | $CH_3$ | $OCH_3$ | CH | —** | 154-159 |
| Q-25 | H | $SCH_2CH{=}CH_2$ | $OCH_3$ | $OCH_3$ | CH | —** | 115-117 |
| Q-25 | H | $SCH_2CH{=}CH_2$ | $OCH_3$ | Cl | CH | —** | 114-116 |
| Q-25 | H | $SCH_2CH{=}CH_2$ | $CH_3$ | $OCH_3$ | N | —** | 142-145 |
| Q-25 | H | $SCH_2CH{=}CH_2$ | $OCH_3$ | $OCH_3$ | N | —** | 91-93 |
| Q-25 | $CH_3$ | $SCH_3$ | $OCH_3$ | $OCH_3$ | CH | —** | |
| Q-25 | $CH_3$ | SH | $OCH_3$ | $OCH_3$ | CH | —** | |
| Q-25 | $CH_3$ | $SCH_2CH{=}CH_2$ | $OCH_3$ | $OCH_3$ | CH | —** | |

$R_{11}$ is —, unless indicated by ** where $R_{11}$ is $CH_3$ in all Tables.

TABLE 4f

| | | | General Structure 2 | | | | | |
|---|---|---|---|---|---|---|---|---|
| Q | R | $R_3$ | $R_4$ | $R_5$ | X | Y | Z | m.p. °C. |
| Q-29 | H | H | H | — | $CH_3$ | $OCH_3$ | CH | |
| Q-29 | H | H | H | — | $CH_3$ | $OCH_3$ | N | |
| Q-29 | H | H | H | — | $OCH_3$ | $OCH_3$ | CH | |

TABLE 4f-continued

| | | | General Structure 2 | | | | | |
|---|---|---|---|---|---|---|---|---|
| Q | R | $R_3$ | $R_4$ | $R_5$ | X | Y | Z | m.p. °C. |
| Q-29 | H | H | H | — | $OCH_3$ | $OCH_3$ | N | |
| Q-29 | H | H | H | — | $CH_3$ | $CH_3$ | CH | |
| Q-29 | H | H | H | — | $CH_3$ | $CH_3$ | N | |

TABLE 4f-continued

General Structure 2

| Q | R | $R_3$ | $R_4$ | $R_5$ | X | Y | Z | m.p. °C. |
|---|---|---|---|---|---|---|---|---|
| Q-29 | H | $CH_3$ | H | — | $CH_3$ | $OCH_3$ | CH | |
| Q-29 | H | $CH_3$ | H | — | $CH_3$ | $CH_3$ | CH | |
| Q-29 | H | $CH_3$ | $CH_3$ | — | $CH_3$ | $OCH_3$ | N | |
| Q-29 | $CH_3$ | $CH_3$ | $CH_3$ | — | $CH_3$ | $CH_3$ | N | |
| Q-29 | $CH_3$ | H | H | — | $OCH_3$ | $OCH_3$ | CH | |
| Q-29 | H | H | H | — | $CH_3$ | $OC_2H_5$ | N | |
| Q-29 | H | H | H | — | Cl | $OCH_3$ | CH | |
| Q-36 | H | H | H | H | $CH_3$ | $OCH_3$ | CH | |
| Q-36 | $CH_3$ | H | H | H | $CH_3$ | $OCH_3$ | CH | |
| Q-36 | H | H | H | H | $CH_3$ | $OCH_3$ | N | |
| Q-36 | H | H | H | H | $OCH_3$ | $OCH_3$ | CH | |
| Q-36 | H | H | H | H | $OCH_3$ | $OCH_3$ | N | |
| Q-36 | H | H | H | H | $OCH_3$ | $C_2H_5$ | CH | |
| Q-36 | H | H | H | H | $CH_3$ | $CH_3$ | CH | |
| Q-36 | H | H | H | H | $CH_3$ | $CH_3$ | N | |
| Q-36 | H | $CH_3$ | H | H | $CH_3$ | $CH_3$ | CH | |
| Q-36 | H | H | $CH_3$ | H | $CH_3$ | $CH_3$ | N | |
| Q-36 | H | $CH_3$ | H | $CH_3$ | $CH_3$ | $OCH_3$ | CH | |
| Q-36 | H | $CH_3$ | $CH_3$ | H | $CH_3$ | $OCH_3$ | N | |
| Q-36 | H | $CH_3$ | $CH_3$ | $CH_3$ | $OCH_3$ | $OCH_3$ | CH | |
| Q-36 | $CH_3$ | H | H | H | $OCH_3$ | $OCH_3$ | N | |
| Q-36 | H | H | H | H | $CH_3$ | $NHCH_3$ | CH | |
| Q-36 | H | H | H | H | $CH_3$ | $N(CH_3)_2$ | CH | |
| Q-37 | H | H | H | — | $CH_3$ | $OCH_3$ | CH | |
| Q-37 | H | H | H | — | $CH_3$ | $OCH_3$ | N | |
| Q-37 | H | H | H | — | $OCH_3$ | $OCH_3$ | CH | |
| Q-37 | H | H | H | — | $OCH_3$ | $OCH_3$ | N | |
| Q-37 | H | H | H | — | $CH_3$ | $CH_3$ | CH | |
| Q-37 | H | 2-$CH_3$ | H | — | $CH_3$ | $CH_3$ | CH | |
| Q-37 | H | 4-$CH_3$ | H | — | $CH_3$ | $CH_3$ | N | |
| Q-37 | H | 5-$CH_3$ | H | — | $CH_3$ | OCH | CH | |
| Q-37 | H | H | H | — | $CH_3$ | $CH_3$ | N | |
| Q-37 | H | 2-$CH_3$ | 4-$CH_3$ | — | $CH_3$ | $OCH_3$ | N | |
| Q-37 | H | 2-$CH_3$ | 5-$CH_3$ | — | $OCH_3$ | $OCH_3$ | CH | |
| Q-37 | H | 4-$CH_3$ | 5-$CH_3$ | — | $OCH_3$ | $OCH_3$ | N | |
| Q-37 | $CH_3$ | H | H | — | $CH_3$ | $OCH_3$ | CH | |
| Q-37 | H | H | H | — | $CH_3$ | $CH(OCH_3)_2$ | CH | |
| Q-37 | H | H | H | — | Cl | $OCH_3$ | CH | |
| Q-38 | H | H | H | — | $CH_3$ | $OCH_3$ | CH | |
| Q-38 | H | H | H | — | $CH_3$ | $OCH_3$ | N | |
| Q-38 | H | H | H | — | $OCH_3$ | $OCH_3$ | CH | |
| Q-38 | H | H | H | — | $OCH_3$ | $OCH_3$ | N | |
| Q-38 | H | 2-$CH_3$ | H | — | $CH_3$ | $CH_3$ | CH | |
| Q-38 | H | 4-$CH_3$ | H | — | $CH_3$ | $CH_3$ | N | |
| Q-38 | H | 2-$CH_3$ | 4-$CH_3$ | — | $CH_3$ | $OCH_3$ | CH | |
| Q-38 | H | 4-$CH_3$ | 4-$CH_3$ | — | $CH_3$ | $OCH_3$ | N | |
| Q-38 | H | H | H | — | $CH_3$ | $CH_3$ | N | |
| Q-38 | $CH_3$ | 4-$CH_3$ | 6-$CH_3$ | — | $OCH_3$ | $OCH_3$ | CH | |
| Q-38 | H | H | H | — | $CH_3$ | 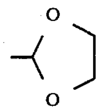 | CH | |
| Q-38 | H | H | H | — | $CH_3$ | $CH_3$ | CH | |
| Q-38 | H | H | H | — | $OCH_3$ | $C_2H_5$ | N | |
| Q-39 | H | H | H | — | $CH_3$ | $OCH_3$ | CH | |
| Q-39 | H | H | H | — | $CH_3$ | $OCH_3$ | N | |
| Q-39 | H | H | H | — | $CH_3$ | $CH_3$ | N | |
| Q-39 | H | H | H | — | $OCH_3$ | $OCH_3$ | CH | |

TABLE 4f-continued

General Structure 2

| Q | R | $R_3$ | $R_4$ | $R_5$ | X | Y | Z | m.p. °C. |
|---|---|---|---|---|---|---|---|---|
| Q-39 | H | H | H | — | $OCH_3$ | $OCH_3$ | N | |
| Q-39 | $CH_3$ | H | H | — | $OCH_3$ | $OCH_3$ | N | |
| Q-39 | H | 3-$CH_3$ | H | — | $CH_3$ | $CH_3$ | CH | |
| Q-39 | H | H | H | — | $CH_3$ | $CH_3$ | CH | |
| Q-39 | H | 5-$CH_3$ | H | — | $CH_3$ | $CH_3$ | N | |
| Q-39 | H | H | H | — | Cl | $OC_2H_5$ | CH | |
| Q-39 | H | 6-$CH_3$ | H | — | $CH_3$ | $OCH_3$ | CH | |
| Q-39 | H | 3-$CH_3$ | 5-$CH_3$ | — | $CH_3$ | $OCH_3$ | N | |
| Q-39 | H | 3-$CH_3$ | 6-$CH_3$ | — | $OCH_3$ | $OCH_3$ | CH | |
| Q-39 | H | 5-$CH_3$ | 6-$CH_3$ | — | $OCH_3$ | $OCH_3$ | N | |
| Q-39 | H | H | H | — | $OCH_3$ | $OC_2H_5$ | N | |
| Q-39 | H | H | H | — | $OCH_3$ | $CH_2OCH_3$ | N | |
| Q-40 | H | H | H | — | $CH_3$ | $CH_3$ | CH | |
| Q-40 | H | H | H | — | $CH_3$ | $OCH_3$ | CH | |
| Q-40 | H | H | H | — | $CH_3$ | $OCH_3$ | N | |
| Q-40 | H | H | H | — | $OCH_3$ | $OCH_3$ | CH | |
| Q-40 | H | H | H | — | $OCH_3$ | $OCH_3$ | N | |
| Q-40 | H | H | H | — | $CH_3$ | $CH_3$ | N | |
| Q-40 | H | 4-$CH_3$ | H | — | $CH_3$ | $CH_3$ | CH | |
| Q-40 | H | 5-$CH_3$ | H | — | $CH_3$ | $CH_3$ | N | |
| Q-40 | H | 6-$CH_3$ | H | — | $CH_3$ | $OCH_3$ | CH | |
| Q-40 | H | 4-$CH_3$ | 5-$CH_3$ | — | $CH_3$ | $OCH_3$ | N | |
| Q-40 | H | 4-$CH_3$ | 6-$CH_3$ | — | $OCH_3$ | $OCH_3$ | CH | |
| Q-40 | H | 5-$CH_3$ | 6-$CH_3$ | — | $OCH_3$ | $OCH_3$ | N | |
| Q-40 | $CH_3$ | H | H | — | $CH_3$ | $CH_3$ | CH | |
| Q-40 | H | H | H | — | $OCH_3$ | $CF_3$ | N | |
| Q-40 | H | H | H | — | $OCH_3$ | $OCF_2H$ | N | |
| Q-43 | H | H | H | — | $CH_3$ | $CH_3$ | CH | |
| Q-43 | H | H | H | — | $CH_3$ | $OCH_3$ | CH | |
| Q-43 | H | H | H | — | $CH_3$ | $OCH_3$ | N | |
| Q-43 | H | H | H | — | $OCH_3$ | $OCH_3$ | CH | |
| Q-43 | H | H | H | — | $OCH_3$ | $OCH_3$ | N | |
| Q-43 | $CH_3$ | H | H | — | $OCH_3$ | $OCH_3$ | CH | |
| Q-43 | H | $CH_3$ | $CH_3$ | — | $CH_3$ | $OCH_3$ | CH | |
| Q-43 | H | $CH_3$ | H | — | $CH_3$ | $CH_3$ | CH | |
| Q-43 | H | H | H | — | $CH_3$ | $CH_3$ | N | |
| Q-43 | H | H | H | — | $OCH_3$ | $OCH_2CF_3$ | N | |
| Q-43 | H | H | H | — | $OCH_3$ | $NHCH_3$ | N | |
| Q-44 | H | H | H | — | $CH_3$ | $OCH_3$ | CH | |
| Q-44 | H | H | H | — | $CH_3$ | $OCH_3$ | N | |
| Q-44 | H | H | H | — | $OCH_3$ | $OCH_3$ | CH | |
| Q-44 | H | H | H | — | $OCH_3$ | $OCH_3$ | N | |
| Q-44 | H | $CH_3$ | H | — | $CH_3$ | $CH_3$ | CH | |
| Q-44 | H | H | $CH_3$ | — | $CH_3$ | $CH_3$ | N | |
| Q-44 | H | $CH_3$ | $CH_3$ | — | $CH_3$ | $OCH_3$ | N | |
| Q-44 | $CH_3$ | H | H | — | $CH_3$ | $OCH_3$ | N | |
| Q-44 | H | H | H | — | $OCH_3$ | $N(CH_3)_2$ | N | |
| Q-44 | H | H | H | — | Br | $OCH_3$ | CH | |
| Q-44 | H | H | H | — | $CH_3$ | $CH_3$ | CH | |
| Q-44 | H | H | H | — | $CH_3$ | $CH_3$ | N | |
| Q-45 | H | H | — | — | $CH_3$ | $OCH_3$ | CH | |
| Q-45 | H | H | — | — | $CH_3$ | $OCH_3$ | N | |
| Q-45 | H | H | — | — | $OCH_3$ | $OCH_3$ | CH | |
| Q-45 | H | H | — | — | $OCH_3$ | $OCH_3$ | N | |
| Q-45 | H | $CH_3$ | — | — | $CH_3$ | $CH_3$ | CH | |
| Q-45 | $CH_3$ | H | — | — | $CH_3$ | $CH_3$ | N | |
| Q-45 | H | H | — | — | $OCH_3$ | $CH(OCH_3)_2$ | N | |
| Q-45 | H | H | — | — | $CH_3$ | $CH_3$ | CH | |
| Q-45 | H | H | — | — | $CH_3$ | $CH_3$ | N | |
| Q-45 | H | H | — | — | Cl | $OCH_3$ | CH | |

Wherein W' is O.

TABLE 5a

| R | $R_3$ | $R_4$ | $R_5$ | $R_6$ | $R_7$ | $R_8$ | X | Y | Z | m.p. °C. |
|---|---|---|---|---|---|---|---|---|---|---|
| General Structure 2 wherein Q is Q-5. | | | | | | | | | | |
| H | H | H | H | H | H | H | $CH_3$ | $CH_3$ | N | |
| H | H | H | H | H | H | H | $CH_3$ | $OCH_3$ | CH | |
| H | H | H | H | H | H | H | $CH_3$ | $OCH_3$ | N | |
| H | H | H | H | H | H | H | $OCH_3$ | $OCH_3$ | CH | |
| H | H | H | H | H | H | H | $OCH_3$ | $OCH_3$ | N | |
| $CH_3$ | H | H | H | H | H | H | $OCH_3$ | $OCH_3$ | CH | |
| H | $CH_3$ | H | H | H | H | H | $CH_3$ | $CH_3$ | CH | |
| H | H | H | $CH_3$ | H | H | H | $CH_3$ | $CH_3$ | N | |
| H | H | H | H | H | $CH_3$ | H | $CH_3$ | $OCH_3$ | CH | |
| H | $CH_3$ | $CH_3$ | H | H | $CH_3$ | H | $CH_3$ | $OCH_3$ | N | |

TABLE 5a-continued

| R | $R_3$ | $R_4$ | $R_5$ | $R_6$ | $R_7$ | $R_8$ | X | Y | Z | m.p. °C. |
|---|---|---|---|---|---|---|---|---|---|---|
| H | $CH_3$ | H | $CH_3$ | H | H | H | $OCH_3$ | $OCH_3$ | CH | |
| H | $CH_3$ | H | H | H | $CH_3$ | H | $OCH_3$ | $OCH_3$ | N | |
| H | H | H | $CH_3$ | H | $CH_3$ | H | $CH_3$ | $CH_3$ | CH | |
| H | $CH_3$ | H | $CH_3$ | H | $CH_3$ | H | $CH_3$ | $CH_3$ | N | |
| H | $CH_3$ | $CH_3$ | H | H | H | H | $CH_3$ | $OCH_3$ | CH | |
| H | H | H | H | $CH_3$ | H | H | $CH_3$ | $OCH_3$ | N | |
| H | H | H | H | H | $CH_3$ | $CH_3$ | $OCH_3$ | $OCH_3$ | CH | |
| H | $CH_3$ | $CH_3$ | $CH_3$ | H | H | H | $OCH_3$ | $OCH_3$ | N | |
| H | $CH_3$ | $CH_3$ | H | H | $CH_3$ | H | $CH_3$ | $CH_3$ | CH | |
| H | H | H | $CH_3$ | $CH_3$ | $CH_3$ | H | $CH_3$ | $CH_3$ | N | |
| H | $CH_3$ | H | $CH_3$ | $CH_3$ | $CH_3$ | H | $CH_3$ | $OCH_3$ | CH | |
| H | $CH_3$ | $CH_3$ | $CH_3$ | H | $CH_3$ | H | $CH_3$ | $OCH_3$ | N | |
| H | $CH_3$ | H | $CH_3$ | H | $CH_3$ | $CH_3$ | $OCH_3$ | $OCH_3$ | CH | |
| H | $CH_3$ | H | $CH_3$ | $CH_3$ | $CH_3$ | $CH_3$ | $CH_3$ | $CH_3$ | CH | |
| H | $CH_3$ | H | $CH_3$ | $CH_3$ | $CH_3$ | $CH_3$ | $CH_3$ | $CH_3$ | CH | |
| H | $CH_3$ | $CH_3$ | $CH_3$ | $CH_3$ | $CH_3$ | H | $CH_3$ | $CH_3$ | N | |
| H | $CH_3$ | $CH_3$ | $CH_3$ | $CH_3$ | $CH_3$ | $CH_3$ | $CH_3$ | $OCH_3$ | CH | |
| $CH_3$ | H | H | H | H | H | H | $CH_3$ | $OCH_3$ | N | |
| | | | | | Wherein W″ is 0. | | | | | |
| H | H | H | H | H | H | H | $OCH_3$ | $CH(OCH_3)_2$ | N | |
| H | H | H | H | H | H | H | $OCH_3$ | 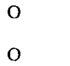 | N | |
| H | H | H | H | H | H | H | Cl | $OCH_3$ | CH | |
| H | H | H | H | H | H | H | $CH_3$ | $CH_3$ | CH | |

TABLE 5b

General Structure 2 wherein Q is Q-6.

| Q | R | $R_3$ | $R_4$ | $R_5$ | $R_6$ | $R_7$ | $R_8$ | X | Y | Z | W″ | m.p. °C. |
|---|---|---|---|---|---|---|---|---|---|---|---|---|
| Q-6 | H | H | H | H | H | H | H | $CH_3$ | $CH_3$ | CH | O | |
| Q-6 | H | H | H | H | H | H | H | $CH_3$ | $CH_3$ | N | O | |
| Q-6 | H | $CH_3$ | H | H | H | H | H | $CH_3$ | $OCH_3$ | CH | O | |
| Q-6 | H | H | H | $CH_3$ | H | H | H | $CH_3$ | $OCH_3$ | N | O | |
| Q-6 | H | H | H | H | H | $CH_3$ | H | $OCH_3$ | $OCH_3$ | CH | O | |
| Q-6 | H | $CH_3$ | H | $CH_3$ | H | H | H | $OCH_3$ | $OCH_3$ | N | O | |
| Q-6 | H | $CH_3$ | H | H | H | $CH_3$ | H | $CH_3$ | $CH_3$ | CH | O | |
| Q-6 | H | H | H | $CH_3$ | H | $CH_3$ | H | $CH_3$ | $CH_3$ | N | O | |
| Q-6 | H | $CH_3$ | $CH_3$ | H | H | H | H | $CH_3$ | $OCH_3$ | CH | O | |
| Q-6 | H | H | H | $CH_3$ | $CH_3$ | H | H | $CH_3$ | $OCH_3$ | N | O | |
| Q-6 | H | H | H | H | H | $CH_3$ | $CH_3$ | $OCH_3$ | $OCH_3$ | CH | O | |
| Q-6 | H | $CH_3$ | H | H | H | $CH_3$ | $CH_3$ | $OCH_3$ | $OCH_3$ | N | O | |
| Q-6 | H | $CH_3$ | $CH_3$ | H | H | $CH_3$ | H | $CH_3$ | $CH_3$ | CH | O | |
| Q-6 | H | $CH_3$ | H | $CH_3$ | $CH_3$ | H | H | $CH_3$ | $CH_3$ | N | O | |
| Q-6 | H | H | H | $CH_3$ | $CH_3$ | $CH_3$ | H | $CH_3$ | $OCH_3$ | CH | O | |
| Q-6 | H | $CH_3$ | $CH_3$ | $CH_3$ | H | H | H | $CH_3$ | $OCH_3$ | N | O | |
| Q-6 | H | H | H | $CH_3$ | $CH_3$ | $CH_3$ | H | $OCH_3$ | $OCH_3$ | CH | O | |
| Q-6 | H | $CH_3$ | H | $CH_3$ | $CH_3$ | $CH_3$ | H | $OCH_3$ | $OCH_3$ | N | O | |
| Q-6 | H | $CH_3$ | $CH_3$ | $CH_3$ | H | $CH_3$ | H | $CH_3$ | $CH_3$ | CH | O | |
| Q-6 | H | $CH_3$ | H | $CH_3$ | H | $CH_3$ | $CH_3$ | $CH_3$ | $CH_3$ | N | O | |
| Q-6 | H | $CH_3$ | $CH_3$ | $CH_3$ | $CH_3$ | H | H | $CH_3$ | $OCH_3$ | CH | O | |
| Q-6 | H | $CH_3$ | $CH_3$ | H | H | $CH_3$ | $CH_3$ | $CH_3$ | $OCH_3$ | N | O | |
| Q-6 | H | H | H | $CH_3$ | $CH_3$ | $CH_3$ | $CH_3$ | $OCH_3$ | $OCH_3$ | CH | O | |
| Q-6 | H | $CH_3$ | H | $CH_3$ | $CH_3$ | $CH_3$ | $CH_3$ | $OCH_3$ | $OCH_3$ | N | O | |
| Q-6 | H | $CH_3$ | $CH_3$ | $CH_3$ | H | $CH_3$ | $CH_3$ | $CH_3$ | $CH_3$ | CH | O | |
| Q-6 | H | $CH_3$ | $CH_3$ | $CH_3$ | $CH_3$ | $CH_3$ | H | $CH_3$ | $CH_3$ | N | O | |
| Q-6 | H | $CH_3$ | $CH_3$ | $CH_3$ | $CH_3$ | $CH_3$ | $CH_3$ | $CH_3$ | $OCH_3$ | CH | O | |
| Q-6 | $CH_3$ | H | H | H | H | H | H | $CH_3$ | $OCH_3$ | N | O | |
| Q-6 | H | H | H | H | H | H | H | Br | $OCH_3$ | CH | O | |
| Q-6 | H | H | H | H | H | H | H | Cl | $OC_2H_5$ | CH | O | |
| Q-6 | H | H | H | H | H | H | H | $OCH_3$ | $C_2H_5$ | CH | O | |
| Q-6 | H | H | H | H | H | H | H | $OCH_3$ | $OC_2H_5$ | CH | O | |
| Q-6 | H | H | H | H | H | H | H | $CH_3$ | $OCH_3$ | CH | O | |
| Q-6 | H | H | H | H | H | H | H | $CH_3$ | $OCH_3$ | N | O | |
| Q-6 | H | H | H | H | H | H | H | $OCH_3$ | $OCH_3$ | CH | O | |
| Q-6 | H | H | H | H | H | H | H | $OCH_3$ | $OCH_3$ | N | O | |
| Q-6 | $CH_3$ | H | H | H | H | H | H | $OCH_3$ | $OCH_3$ | CH | O | |
| Q-6 | H | H | H | H | H | H | H | $CH_3$ | $OCH_3$ | CH | S | |
| Q-6 | H | H | H | H | H | H | H | $CH_3$ | $OCH_3$ | N | S | |
| Q-6 | H | H | H | H | H | H | H | $OCH_3$ | $OCH_3$ | CH | S | |
| Q-6 | H | H | H | H | H | H | H | $OCH_3$ | $OCH_3$ | N | S | |
| Q-6 | H | H | H | H | H | H | H | $OCH_3$ | $C_2H_5$ | CH | S | |
| Q-6 | H | H | H | H | H | H | H | $CH_3$ | $CH_3$ | CH | S | |
| Q-6 | H | H | H | H | H | H | H | $CH_3$ | $CH_3$ | N | S | |
| Q-6 | H | $CH_3$ | H | H | H | H | H | $CH_3$ | $OCH_3$ | CH | S | |
| Q-6 | H | H | H | $CH_3$ | H | H | H | $CH_3$ | $OCH_3$ | N | S | |
| Q-6 | H | H | H | H | H | $CH_3$ | H | $OCH_3$ | $OCH_3$ | CH | S | |

TABLE 5b-continued

General Structure 2 wherein Q is Q-6.

| Q | R | $R_3$ | $R_4$ | $R_5$ | $R_6$ | $R_7$ | $R_8$ | X | Y | Z | W'' | m.p. °C. |
|---|---|---|---|---|---|---|---|---|---|---|---|---|
| Q-6 | H | $CH_3$ | H | $CH_3$ | H | H | H | $OCH_3$ | $OCH_3$ | N | S | |
| Q-6 | H | $CH_3$ | H | H | H | $CH_3$ | H | $CH_3$ | $CH_3$ | CH | S | |
| Q-6 | H | H | H | $CH_3$ | H | $CH_3$ | H | $CH_3$ | $CH_3$ | N | S | |
| Q-6 | H | $CH_3$ | $CH_3$ | H | H | H | H | $CH_3$ | $OCH_3$ | CH | S | |
| Q-6 | H | H | H | $CH_3$ | $CH_3$ | H | H | $CH_3$ | $OCH_3$ | N | S | |
| Q-6 | H | H | H | H | H | H | H | $OCH_3$ | $CH_2OCH_3$ | CH | S | |
| Q-6 | H | H | H | H | H | H | H | $OCH_3$ | $CF_3$ | CH | S | |
| Q-6 | H | H | H | H | H | H | H | $OCH_3$ | $OCF_2H$ | CH | S | |
| Q-6 | H | H | H | H | H | $CH_3$ | $CH_3$ | $OCH_3$ | $OCH_3$ | CH | S | |
| Q-6 | H | $CH_3$ | H | H | H | $CH_3$ | $CH_3$ | $OCH_3$ | $OCH_3$ | N | S | |
| Q-6 | H | $CH_3$ | $CH_3$ | H | H | $CH_3$ | H | $CH_3$ | $CH_3$ | CH | S | |
| Q-6 | H | $CH_3$ | H | $CH_3$ | $CH_3$ | H | H | $CH_3$ | $CH_3$ | N | S | |
| Q-6 | H | H | H | $CH_3$ | $CH_3$ | $CH_3$ | H | $CH_3$ | $OCH_3$ | CH | S | |
| Q-6 | H | $CH_3$ | $CH_3$ | $CH_3$ | H | H | H | $CH_3$ | $OCH_3$ | N | S | |
| Q-6 | H | H | H | $CH_3$ | $CH_3$ | $CH_3$ | H | $OCH_3$ | $OCH_3$ | CH | S | |
| Q-6 | H | $CH_3$ | H | $CH_3$ | $CH_3$ | $CH_3$ | H | $OCH_3$ | $OCH_3$ | N | S | |
| Q-6 | H | $CH_3$ | $CH_3$ | $CH_3$ | H | $CH_3$ | H | $CH_3$ | $CH_3$ | CH | S | |
| Q-6 | H | $CH_3$ | H | $CH_3$ | H | $CH_3$ | $CH_3$ | $CH_3$ | $CH_3$ | N | S | |
| Q-6 | H | $CH_3$ | $CH_3$ | $CH_3$ | $CH_3$ | H | H | $CH_3$ | $OCH_3$ | CH | S | |
| Q-6 | H | $CH_3$ | $CH_3$ | H | H | $CH_3$ | $CH_3$ | $CH_3$ | $OCH_3$ | N | S | |
| Q-6 | H | H | H | $CH_3$ | $CH_3$ | $CH_3$ | $CH_3$ | $OCH_3$ | $OCH_3$ | CH | S | |
| Q-6 | H | $CH_3$ | H | $CH_3$ | $CH_3$ | $CH_3$ | $CH_3$ | $OCH_3$ | $OCH_3$ | N | S | |
| Q-6 | H | $CH_3$ | $CH_3$ | $CH_3$ | H | $CH_3$ | $CH_3$ | $CH_3$ | $CH_3$ | CH | S | |
| Q-6 | H | $CH_3$ | $CH_3$ | $CH_3$ | $CH_3$ | $CH_3$ | H | $CH_3$ | $CH_3$ | N | S | |
| Q-6 | H | $CH_3$ | $CH_3$ | $CH_3$ | $CH_3$ | $CH_3$ | $CH_3$ | $CH_3$ | $OCH_3$ | CH | S | |
| Q-6 | $CH_3$ | H | H | H | H | H | H | $CH_3$ | $OCH_3$ | N | S | |

TABLE 5c

General Structure 2

| Q | R | $R_3$ | $R_4$ | $R_5$ | $R_6$ | X | Y | Z | W' | m.p. °C. |
|---|---|---|---|---|---|---|---|---|---|---|
| Q-7 | H | H | H | H | H | $CH_3$ | $OCH_3$ | CH | — | |
| Q-7 | H | H | H | H | H | $CH_3$ | $OCH_3$ | N | — | |
| Q-7 | H | H | H | H | H | $OCH_3$ | $OCH_3$ | CH | — | |
| Q-7 | H | H | H | H | H | $OCH_3$ | $OCH_3$ | N | — | |
| Q-7 | H | H | H | H | H | $CH_3$ | $CH_3$ | CH | — | |
| Q-7 | H | H | H | H | H | $CH_3$ | $CH_3$ | N | — | |
| Q-7 | H | $CH_3$ | H | H | H | $CH_3$ | $OCH_3$ | CH | — | |
| Q-7 | H | H | $CH_3$ | H | H | $CH_3$ | $OCH_3$ | N | — | |
| Q-7 | H | $CH_3$ | H | H | $CH_3$ | $OCH_3$ | $OCH_3$ | CH | — | |
| Q-7 | H | H | $CH_3$ | $CH_3$ | H | $OCH_3$ | $OCH_3$ | N | — | |
| Q-7 | H | $CH_3$ | $CH_3$ | H | H | $CH_3$ | $CH_3$ | CH | — | |
| Q-7 | H | $CH_3$ | $CH_3$ | $CH_3$ | H | $CH_3$ | $CH_3$ | N | — | |
| Q-7 | H | $CH_3$ | H | $CH_3$ | $CH_3$ | $CH_3$ | $OCH_3$ | CH | — | |
| Q-7 | H | $CH_3$ | $CH_3$ | $CH_3$ | $CH_3$ | $CH_3$ | $OCH_3$ | N | — | |
| Q-7 | $CH_3$ | H | H | H | H | $OCH_3$ | $OCH_3$ | CH | — | |
| Q-7 | $CH_3$ | $CH_3$ | $CH_3$ | $CH_3$ | $CH_3$ | $OCH_3$ | $OCH_3$ | CH | — | |
| Q-7 | H | H | H | H | H | $OCH_3$ | $OCH_3CF_3$ | CH | — | |
| Q-7 | H | H | H | H | H | $OCH_3$ | $NHCH_3$ | CH | — | |
| Q-7 | H | H | H | H | H | Cl | $OCH_3$ | CH | — | |
| Q-7 | H | H | H | H | H | $OCH_3$ | $OCH_3$ | CH | —* | |
| Q-7 | H | H | H | H | H | $OCH_3$ | $CH_3$ | N | —* | |
| Q-7 | H | H | H | H | H | $OCH_3$ | $CH_3$ | CH | —* | |
| Q-16 | H | $CH_3$ | $CH_3$ | H | H | $CH_3$ | $OCH_3$ | CH | O | 181–183 |
| Q-16 | H | $CH_3$ | $CH_3$ | H | H | $CH_3$ | $OCH_3$ | N | O | 175–176.5 |
| Q-16 | H | $CH_3$ | $CH_3$ | H | H | $OCH_3$ | $OCH_3$ | CH | O | 176–178 |
| Q-16 | H | $CH_3$ | $CH_3$ | H | H | $OCH_3$ | $OCH_3$ | N | O | 174–176 |
| Q-16 | $CH_3$ | $CH_3$ | $CH_3$ | H | H | $CH_3$ | $OCH_3$ | N | O | |
| Q-16 | $CH_3$ | $CH_3$ | $CH_3$ | H | H | Cl | $OCH_3$ | CH | O | |
| Q-16 | H | $CH_3$ | $CH_3$ | H | H | $CH_3$ | $CH_3$ | CH | O | 175–182 |
| Q-16 | H | $CH_3$ | $CH_3$ | H | H | $CH_3$ | $CH_3$ | N | O | |
| Q-16 | H | H | H | H | H | $CH_3$ | $OCH_3$ | CH | O | |
| Q-16 | H | H | H | H | H | $CH_3$ | $OCH_3$ | N | O | |
| Q-16 | H | H | H | H | H | $OCH_3$ | $OCH_3$ | CH | O | |
| Q-16 | H | H | H | H | H | $OCH_3$ | $OCH_3$ | N | O | |
| Q-16 | H | $CH_3$ | $CH_3$ | H | H | $OCH_3$ | $N(CH_3)_2$ | CH | O | |
| Q-16 | H | $CH_3$ | $CH_3$ | H | H | $OCH_3$ | $CH(OCH_3)_2$ | CH | O | |
| Q-16 | H | $CH_3$ | $CH_3$ | H | H | Cl | $OCH_3$ | CH | O | 168–171 |
| Q-16 | H | $CH_3$ | $CH_3$ | H | H | $CH_3$ | $CH_2OCH_3$ | N | O | |
| Q-16 | H | $CH_3$ | H | H | H | $CH_3$ | $CH_3$ | CH | O | |
| Q-16 | H | H | H | $CH_3$ | H | $CH_3$ | $CH_3$ | N | O | |
| Q-16 | H | $CH_3$ | H | $CH_3$ | H | $CH_3$ | $OCH_3$ | N | O | |
| Q-16 | H | H | H | $CH_3$ | $CH_3$ | $CH_3$ | $OCH_3$ | CH | O | |
| Q-16 | H | $CH_3$ | H | $CH_3$ | $CH_3$ | $OCH_3$ | $OCH_3$ | CH | O | |
| Q-16 | H | $CH_3$ | $CH_3$ | $CH_3$ | H | $OCH_3$ | $OCH_3$ | N | O | |
| Q-16 | H | $CH_3$ | $CH_3$ | $CH_3$ | H | $CH_3$ | $CH_3$ | CH | O | |

TABLE 5c-continued

General Structure 2

| Q | R | $R_3$ | $R_4$ | $R_5$ | $R_6$ | X | Y | Z | W' | m.p. °C. |
|---|---|---|---|---|---|---|---|---|---|---|
| Q-16 | H | $CH_3$ | $CH_3$ | $CH_3$ | $CH_3$ | $CH_3$ | $CH_3$ | N | O | |
| Q-16 | H | $CH_3$ | $CH_3$ | H | H | $CH_3$ | $CH_3$ | CH | S | |
| Q-16 | H | $CH_3$ | $CH_3$ | H | H | $CH_3$ | $CH_3$ | N | S | |
| Q-16 | H | $CH_3$ | $CH_3$ | H | H | $CH_3$ | $OCH_3$ | CH | S | |
| Q-16 | H | $CH_3$ | $CH_3$ | H | H | $CH_3$ | $OCH_3$ | N | S | |
| Q-16 | H | $CH_3$ | $CH_3$ | H | H | $OCH_3$ | $OCH_3$ | CH | S | |
| Q-16 | H | $CH_3$ | $CH_3$ | H | H | $OCH_3$ | $OCH_3$ | N | S | |
| Q-16 | H | $CH_3$ | $CH_3$ | H | H | Cl | $OCH_3$ | CH | S | |
| Q-16 | H | $CH_3$ | $CH_3$ | H | H | $CH_3$ | $NHCH_3$ | N | S | |
| Q-16 | H | $CH_3$ | $CH_3$ | H | H | $CH_3$ | $N(CH_3)_2$ | N | S | |
| Q-16 | H | H | H | H | H | $CH_3$ | $OCH_3$ | CH | S | |
| Q-16 | H | H | H | H | H | $CH_3$ | $OCH_3$ | N | S | |
| Q-16 | H | H | H | H | H | $OCH_3$ | $OCH_3$ | CH | S | |
| Q-16 | H | H | H | H | H | $OCH_3$ | $OCH_3$ | N | S | |
| Q-16 | $CH_3$ | H | H | H | H | $CH_3$ | $CH_3$ | CH | S | |
| Q-16 | H | $CH_3$ | H | H | H | $CH_3$ | $CH_3$ | N | S | |
| Q-16 | H | H | H | $CH_3$ | H | $CH_3$ | $OCH_3$ | N | S | |
| Q-16 | H | $CH_3$ | H | $CH_3$ | H | $CH_3$ | $OCH_3$ | CH | S | |
| Q-16 | H | H | H | $CH_3$ | $CH_3$ | $OCH_3$ | $OCH_3$ | CH | S | |
| Q-16 | H | $CH_3$ | $CH_3$ | $CH_3$ | H | $OCH_3$ | $OCH_3$ | N | S | |
| Q-16 | H | $CH_3$ | $CH_3$ | $CH_3$ | H | $CH_3$ | $CH_3$ | CH | S | |
| Q-16 | H | $CH_3$ | H | $CH_3$ | $CH_3$ | $CH_3$ | $CH_3$ | N | S | |
| Q-16 | H | $CH_3$ | $CH_3$ | $CH_3$ | $CH_3$ | $CH_3$ | $OCH_3$ | CH | S | |
| Q-17 | H | H | H | H | H | Cl | $OCH_3$ | CH | — | |
| Q-17 | H | H | H | H | H | $CH_3$ | $CH_3$ | CH | — | |
| Q-17 | H | H | H | H | H | Cl | $OC_2H_5$ | CH | — | |
| Q-17 | H | H | H | H | H | $CH_3$ | $CH_3$ | N | — | |
| Q-17 | H | H | H | H | H | $OCH_3$ | $OCH_3$ | CH | — | |
| Q-17 | H | H | H | H | H | $OCH_3$ | $OCH_3$ | N | — | |
| Q-17 | H | H | H | H | H | $OCH_3$ | $OC_2H_5$ | CH | — | |
| Q-17 | H | H | H | H | H | $OCH_3$ | $OC_2H_5$ | N | — | |
| Q-17 | H | $CH_3$ | H | H | H | $CH_3$ | $CH_3$ | CH | — | |
| Q-17 | H | H | H | H | H | $CH_3$ | $CH(OCH_3)_2$ | N | — | |
| Q-17 | H | H | H | H | H | $CH_3$ | 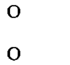 | N | — | |
| Q-17 | H | H | H | $CH_3$ | H | $CH_3$ | $CH_3$ | N | — | |
| Q-17 | H | $CH_3$ | $CH_3$ | H | H | $CH_3$ | $OCH_3$ | CH | — | |
| Q-17 | H | $CH_3$ | $CH_3$ | H | H | $CH_3$ | $OCH_3$ | N | — | |
| Q-17 | H | H | H | $CH_3$ | $CH_3$ | $OCH_3$ | $OCH_3$ | CH | — | |
| Q-17 | H | $CH_3$ | H | $CH_3$ | $CH_3$ | $OCH_3$ | $OCH_3$ | N | — | |
| Q-17 | H | $CH_3$ | $CH_3$ | $CH_3$ | H | $CH_3$ | $CH_3$ | CH | — | |
| Q-17 | H | $CH_3$ | $CH_3$ | $CH_3$ | H | $CH_3$ | $CH_3$ | N | — | |
| Q-17 | H | $CH_3$ | $CH_3$ | $CH_3$ | $CH_3$ | $CH_3$ | $OCH_3$ | CH | — | |
| Q-17 | $CH_3$ | H | H | H | H | $CH_3$ | $OCH_3$ | N | — | |

TABLE 5d

General Structure 2 wherein Q is Q-30

| R | $R_3$ | $R_4$ | $R_5$ | $R_6$ | $R_7$ | $R_8$ | $R_9$ | X | Y | Z | m.p. °C. |
|---|---|---|---|---|---|---|---|---|---|---|---|
| H | H | H | H | H | H | H | H | $CH_3$ | $OCH_3$ | CH | |
| H | H | H | H | H | H | H | H | $CH_3$ | $OCH_3$ | N | |
| H | H | H | H | H | H | H | H | $OCH_3$ | $OCH_3$ | CH | |
| H | H | H | H | H | H | H | H | $OCH_3$ | $OCH_3$ | N | |
| H | H | H | H | H | H | H | H | $CH_3$ | $CH_3$ | N | |
| H | H | H | H | H | H | H | H | $CH_3$ | $CH_3$ | CH | |
| $CH_3$ | H | H | H | H | H | H | H | $CH_3$ | $OCH_3$ | CH | |
| H | $CH_3$ | H | H | H | H | H | H | $CH_3$ | $OCH_3$ | N | |
| H | H | H | H | H | H | H | H | Cl | $OCH_3$ | CH | |
| H | H | $CH_3$ | H | H | H | H | H | $OCH_3$ | $OCH_3$ | CH | |
| H | H | H | H | $CH_3$ | H | H | H | $OCH_3$ | $OCH_3$ | N | |
| H | H | H | H | H | H | $CH_3$ | H | $CH_3$ | $CH_3$ | CH | |
| H | $CH_3$ | $CH_3$ | H | H | H | H | H | $CH_3$ | $CH_3$ | N | |
| H | $CH_3$ | H | H | $CH_3$ | H | H | H | $CH_3$ | $OCH_3$ | CH | |
| H | $CH_3$ | H | H | H | H | $CH_3$ | H | $CH_3$ | $OCH_3$ | N | |
| H | H | $CH_3$ | $CH_3$ | H | H | H | H | $OCH_3$ | $OCH_3$ | CH | |
| H | H | $CH_3$ | H | $CH_3$ | H | H | H | $OCH_3$ | $OCH_3$ | N | |
| H | H | $CH_3$ | H | H | H | $CH_3$ | H | $CH_3$ | $CH_3$ | CH | |
| H | H | H | H | $CH_3$ | $CH_3$ | H | H | $CH_3$ | $CH_3$ | N | |
| H | H | H | H | $CH_3$ | H | $CH_3$ | H | $CH_3$ | $OCH_3$ | CH | |
| H | H | H | H | H | H | $CH_3$ | $CH_3$ | $CH_3$ | $OCH_3$ | N | |
| H | $CH_3$ | $CH_3$ | $CH_3$ | H | H | H | H | $OCH_3$ | $OCH_3$ | CH | |
| H | $CH_3$ | $CH_3$ | H | $CH_3$ | H | H | H | $OCH_3$ | $OCH_3$ | N | |
| H | $CH_3$ | $CH_3$ | H | H | H | $CH_3$ | H | $CH_3$ | $CH_3$ | CH | |
| H | $CH_3$ | H | H | H | $CH_3$ | H | H | $CH_3$ | $CH_3$ | N | |
| H | $CH_3$ | H | H | $CH_3$ | H | $CH_3$ | H | $CH_3$ | $OCH_3$ | CH | |

TABLE 5d-continued

General Structure 2 wherein Q is Q-30

| R | $R_3$ | $R_4$ | $R_5$ | $R_6$ | $R_7$ | $R_8$ | $R_9$ | X | Y | Z | m.p. °C. |
|---|---|---|---|---|---|---|---|---|---|---|---|
| H | $CH_3$ | H | H | H | H | $CH_3$ | $CH_3$ | $CH_3$ | $OCH_3$ | N | |
| H | H | $CH_3$ | $CH_3$ | $CH_3$ | H | H | H | $OCH_3$ | $OCH_3$ | CH | |
| H | H | $CH_3$ | $CH_3$ | H | H | $CH_3$ | H | $OCH_3$ | $OCH_3$ | N | |
| H | H | $CH_3$ | H | $CH_3$ | $CH_3$ | H | H | $CH_3$ | $CH_3$ | CH | |
| H | H | $CH_3$ | H | $CH_3$ | H | $CH_3$ | H | $CH_3$ | $CH_3$ | N | |
| H | H | $CH_3$ | H | H | H | $CH_3$ | $CH_3$ | $CH_3$ | $OCH_3$ | CH | |
| H | H | H | H | $CH_3$ | $CH_3$ | $CH_3$ | H | $CH_3$ | $OCH_3$ | N | |
| H | H | H | H | $CH_3$ | H | $CH_3$ | $CH_3$ | $OCH_3$ | $OCH_3$ | CH | |
| H | $CH_3$ | $CH_3$ | $CH_3$ | $CH_3$ | H | H | H | $OCH_3$ | $OCH_3$ | N | |
| H | $CH_3$ | $CH_3$ | H | $CH_3$ | H | $CH_3$ | H | $CH_3$ | $CH_3$ | CH | |
| H | $CH_3$ | H | H | $CH_3$ | $CH_3$ | $CH_3$ | H | $CH_3$ | $OCH_3$ | N | |
| H | $CH_3$ | $CH_3$ | $CH_3$ | H | H | $CH_3$ | H | $CH_3$ | $OCH_3$ | CH | |
| H | $CH_3$ | H | H | $CH_3$ | H | $CH_3$ | $CH_3$ | $CH_3$ | $OCH_3$ | N | |
| H | $CH_3$ | $CH_3$ | H | $CH_3$ | $CH_3$ | H | H | $OCH_3$ | $OCH_3$ | CH | |
| H | $CH_3$ | $CH_3$ | H | H | H | $CH_3$ | $CH_3$ | $OCH_3$ | $OCH_3$ | N | |
| H | H | $CH_3$ | $CH_3$ | $CH_3$ | $CH_3$ | H | H | $CH_3$ | $CH_3$ | CH | |
| H | H | $CH_3$ | $CH_3$ | $CH_3$ | H | $CH_3$ | H | $CH_3$ | $CH_3$ | N | |
| H | H | $CH_3$ | H | $CH_3$ | $CH_3$ | $CH_3$ | H | $CH_3$ | $OCH_3$ | CH | |
| H | H | $CH_3$ | H | $CH_3$ | H | $CH_3$ | $CH_3$ | $CH_3$ | $OCH_3$ | N | |
| H | H | H | H | $CH_3$ | $CH_3$ | $CH_3$ | $CH_3$ | $OCH_3$ | $OCH_3$ | CH | |
| H | $CH_3$ | $CH_3$ | $CH_3$ | $CH_3$ | $CH_3$ | H | H | $OCH_3$ | $OCH_3$ | N | |
| H | $CH_3$ | $CH_3$ | H | $CH_3$ | $CH_3$ | $CH_3$ | H | $CH_3$ | $CH_3$ | CH | |
| H | $CH_3$ | $CH_3$ | H | $CH_3$ | H | $CH_3$ | $CH_3$ | $CH_3$ | $CH_3$ | N | |
| H | $CH_3$ | H | H | $CH_3$ | $CH_3$ | $CH_3$ | $CH_3$ | $CH_3$ | $OCH_3$ | CH | |
| H | $CH_3$ | $CH_3$ | $CH_3$ | H | H | $CH_3$ | $CH_3$ | $CH_3$ | $OCH_3$ | N | |
| H | H | $CH_3$ | $CH_3$ | $CH_3$ | H | $CH_3$ | $CH_3$ | $OCH_3$ | $OCH_3$ | CH | |
| H | H | $CH_3$ | H | $CH_3$ | $CH_3$ | $CH_3$ | $CH_3$ | $OCH_3$ | $OCH_3$ | N | |
| H | H | $CH_3$ | $CH_3$ | $CH_3$ | $CH_3$ | $CH_3$ | H | $CH_3$ | $CH_3$ | CH | |
| H | $CH_3$ | $CH_3$ | H | $CH_3$ | $CH_3$ | $CH_3$ | $CH_3$ | $CH_3$ | $CH_3$ | N | |
| H | $CH_3$ | $CH_3$ | $CH_3$ | $CH_3$ | H | $CH_3$ | $CH_3$ | $CH_3$ | $OCH_3$ | CH | |
| H | $CH_3$ | $CH_3$ | $CH_3$ | $CH_3$ | $CH_3$ | $CH_3$ | H | $CH_3$ | $OCH_3$ | N | |
| H | H | $CH_3$ | $CH_3$ | $CH_3$ | $CH_3$ | $CH_3$ | $CH_3$ | $OCH_3$ | $OCH_3$ | CH | |
| H | $CH_3$ | $CH_3$ | $CH_3$ | $CH_3$ | $CH_3$ | $CH_3$ | $CH_3$ | $OCH_3$ | $OCH_3$ | N | |
| $CH_3$ | $CH_3$ | $CH_3$ | $CH_3$ | $CH_3$ | $CH_3$ | $CH_3$ | $CH_3$ | $CH_3$ | $CH_3$ | CH | |
| H | H | H | H | H | H | H | H | $CH_3$ | $OC_2H_5$ | CH | |
| H | H | H | H | H | H | H | H | $CH_3$ | $CH_2OCH_3$ | CH | |

TABLE 5e

General Structure 2 wherein Q is Q-31.

| R | $R_3$ | $R_4$ | $R_5$ | $R_6$ | $R_7$ | $R_8$ | $R_9$ | $R_{10}$ | X | Y | Z | m.p. °C. |
|---|---|---|---|---|---|---|---|---|---|---|---|---|
| H | H | H | H | H | H | H | H | H | $CH_3$ | $OCH_3$ | CH | |
| H | H | H | H | H | H | H | H | H | $CH_3$ | $OCH_3$ | N | |
| H | H | H | H | H | H | H | H | H | $OCH_3$ | $OCH_3$ | CH | |
| H | H | H | H | H | H | H | H | H | $OCH_3$ | $OCH_3$ | N | |
| H | H | H | H | H | H | H | H | H | $CH_3$ | $CH_3$ | CH | |
| H | H | H | H | H | H | H | H | H | $CH_3$ | $CH_3$ | N | |
| H | H | H | H | H | H | H | H | H | Cl | $OCH_3$ | CH | |
| H | H | H | H | H | H | H | H | H | $CH_3$ | $C_2H_5$ | CH | |
| H | H | H | H | H | H | H | H | H | $CH_3$ | $CF_3$ | CH | |
| H | H | H | H | H | H | H | H | H | $CH_3$ | $OCF_2H$ | CH | |
| H | H | H | H | H | H | H | H | H | $CH_3$ | $OCH_2CF_3$ | CH | |
| H | $CH_3$ | H | H | H | H | H | H | H | $CH_3$ | $CH_3$ | CH | |
| H | H | H | $CH_3$ | H | H | H | H | H | $CH_3$ | $CH_3$ | N | |
| H | H | H | H | H | $CH_3$ | H | H | H | $CH_3$ | $OCH_3$ | CH | |
| H | H | H | H | H | H | H | $CH_3$ | H | $CH_3$ | $OCH_3$ | N | |
| H | $CH_3$ | $CH_3$ | H | H | H | H | H | H | $OCH_3$ | $OCH_3$ | CH | |
| H | H | H | $CH_3$ | $CH_3$ | H | H | H | H | $OCH_3$ | $OCH_3$ | N | |
| H | H | H | H | H | $CH_3$ | $CH_3$ | H | H | $CH_3$ | $CH_3$ | CH | |
| H | H | H | H | H | H | H | $CH_3$ | $CH_3$ | $CH_3$ | $CH_3$ | N | |
| H | H | H | $CH_3$ | H | H | H | $CH_3$ | H | $CH_3$ | $OCH_3$ | CH | |
| H | $CH_3$ | H | H | H | $CH_3$ | H | H | H | $CH_3$ | $OCH_3$ | N | |
| H | $CH_3$ | H | $CH_3$ | H | H | H | H | H | $OCH_3$ | $OCH_3$ | CH | |
| H | H | H | H | H | $CH_3$ | H | $CH_3$ | H | $OCH_3$ | $OCH_3$ | N | |
| H | $CH_3$ | $CH_3$ | $CH_3$ | H | H | H | H | H | $CH_3$ | $CH_3$ | CH | |
| H | $CH_3$ | H | H | H | $CH_3$ | $CH_3$ | H | H | $CH_3$ | $CH_3$ | N | |
| H | H | H | $CH_3$ | $CH_3$ | H | H | $CH_3$ | H | $CH_3$ | $OCH_3$ | CH | |
| H | H | H | $CH_3$ | $CH_3$ | $CH_3$ | H | H | H | $CH_3$ | $OCH_3$ | N | |
| H | $CH_3$ | H | H | H | $CH_3$ | H | $CH_3$ | H | $OCH_3$ | $OCH_3$ | CH | |
| H | $CH_3$ | $CH_3$ | H | H | H | H | $CH_3$ | $CH_3$ | $OCH_3$ | $OCH_3$ | N | |
| H | $CH_3$ | H | H | H | $CH_3$ | $CH_3$ | $CH_3$ | H | $CH_3$ | $CH_3$ | CH | |
| H | $CH_3$ | H | $CH_3$ | H | $CH_3$ | H | $CH_3$ | H | $CH_3$ | $CH_3$ | N | |
| H | H | H | $CH_3$ | $CH_3$ | $CH_3$ | $CH_3$ | H | H | $CH_3$ | $OCH_3$ | CH | |
| H | $CH_3$ | $CH_3$ | $CH_3$ | H | H | H | $CH_3$ | $CH_3$ | $CH_3$ | $OCH_3$ | N | |
| H | $CH_3$ | H | $CH_3$ | $CH_3$ | $CH_3$ | H | $CH_3$ | H | $OCH_3$ | $OCH_3$ | CH | |
| H | $CH_3$ | H | $CH_3$ | H | $CH_3$ | $CH_3$ | $CH_3$ | H | $OCH_3$ | $OCH_3$ | N | |

TABLE 5e-continued

General Structure 2 wherein Q is Q-31.

| R | $R_3$ | $R_4$ | $R_5$ | $R_6$ | $R_7$ | $R_8$ | $R_9$ | $R_{10}$ | X | Y | Z | m.p. °C. |
|---|---|---|---|---|---|---|---|---|---|---|---|---|
| H | $CH_3$ | $CH_3$ | $CH_3$ | H | $CH_3$ | H | $CH_3$ | H | $CH_3$ | $CH_3$ | CH | |
| H | $CH_3$ | H | $CH_3$ | $CH_3$ | $CH_3$ | $CH_3$ | $CH_3$ | H | $CH_3$ | $CH_3$ | N | |
| H | $CH_3$ | H | $CH_3$ | $CH_3$ | $CH_3$ | H | $CH_3$ | $CH_3$ | $CH_3$ | $OCH_3$ | CH | |
| H | $CH_3$ | H | $CH_3$ | $CH_3$ | $CH_3$ | $CH_3$ | $CH_3$ | $CH_3$ | $CH_3$ | $OCH_3$ | N | |
| H | $CH_3$ | $CH_3$ | $CH_3$ | $CH_3$ | $CH_3$ | $CH_3$ | $CH_3$ | H | $OCH_3$ | $OCH_3$ | CH | |
| $CH_3$ | H | H | H | H | H | H | H | H | $OCH_3$ | $OCH_3$ | N | |
| H | H | H | H | H | H | H | H | H | $CH_3$ | $OCH_3$ | CH | * |
| H | H | H | H | H | H | H | H | H | $CH_3$ | $OCH_3$ | N | * |
| H | H | H | H | H | H | H | H | H | $OCH_3$ | $OCH_3$ | CH | * |
| H | H | H | H | H | H | H | H | H | $OCH_3$ | $OCH_3$ | N | * |
| H | H | H | H | H | H | H | H | H | $CH_3$ | $CH_3$ | CH | * |
| H | H | H | H | H | H | H | H | H | $CH_3$ | $CH_3$ | N | * |
| H | H | H | H | H | H | H | H | H | Cl | $OCH_3$ | CH | * |

*Wherein W" is O, unless indicated by ** where W" is S in all Tables.

TABLE 5f

General Structure 2 wherein Q is Q-32.

| R | $R_3$ | $R_4$ | $R_5$ | $R_6$ | $R_7$ | $R_8$ | $R_9$ | $R_{10}$ | X | Y | Z | W" |
|---|---|---|---|---|---|---|---|---|---|---|---|---|
| H | H | H | H | H | H | H | H | H | $CH_3$ | $CH_3$ | CH | O |
| H | H | H | H | H | H | H | H | H | $CH_3$ | $CH_3$ | N | O |
| H | H | H | H | H | H | H | H | H | Cl | $OCH_3$ | CH | O |
| H | H | H | H | H | H | H | H | H | $CH_3$ | $NHCH_3$ | CH | O |
| H | H | H | H | H | H | H | H | H | $CH_3$ | $N(CH_3)_2$ | CH | O |
| H | H | H | H | H | H | H | H | H | $CH_3$ | $CH(OCH_3)_2$ | CH | O |
| H | H | H | H | H | H | H | H | H | Br | $OCH_3$ | CH | O |
| H | $CH_3$ | H | H | H | H | H | H | H | $CH_3$ | $CH_3$ | CH | O |
| H | H | H | $CH_3$ | H | H | H | H | H | $CH_3$ | $CH_3$ | N | O |
| H | H | H | H | H | $CH_3$ | H | H | H | $CH_3$ | $OCH_3$ | CH | O |
| H | H | H | H | H | H | H | $CH_3$ | H | $CH_3$ | $OCH_3$ | N | O |
| H | $CH_3$ | $CH_3$ | H | H | H | H | H | H | $OCH_3$ | $OCH_3$ | CH | O |
| H | H | H | $CH_3$ | $CH_3$ | H | H | H | H | $OCH_3$ | $OCH_3$ | N | O |
| H | H | H | H | H | $CH_3$ | $CH_3$ | H | H | $CH_3$ | $CH_3$ | CH | O |
| H | H | H | H | H | H | H | $CH_3$ | $CH_3$ | $CH_3$ | $CH_3$ | N | O |
| H | H | H | $CH_3$ | H | H | H | $CH_3$ | H | $CH_3$ | $OCH_3$ | CH | O |
| H | $CH_3$ | H | H | H | $CH_3$ | H | H | H | $CH_3$ | $OCH_3$ | N | O |
| H | $CH_3$ | H | $CH_3$ | H | H | H | H | H | $OCH_3$ | $OCH_3$ | CH | O |
| H | H | H | H | H | $CH_3$ | H | $CH_3$ | H | $OCH_3$ | $OCH_3$ | N | O |
| H | $CH_3$ | $CH_3$ | $CH_3$ | H | H | H | H | H | $CH_3$ | $CH_3$ | CH | O |
| H | $CH_3$ | H | H | H | $CH_3$ | $CH_3$ | H | H | $CH_3$ | $CH_3$ | N | O |
| H | H | H | $CH_3$ | $CH_3$ | H | H | $CH_3$ | H | $CH_3$ | $OCH_3$ | CH | O |
| H | H | H | $CH_3$ | $CH_3$ | $CH_3$ | H | H | H | $CH_3$ | $OCH_3$ | N | O |
| H | $CH_3$ | H | H | H | $CH_3$ | H | $CH_3$ | H | $OCH_3$ | $OCH_3$ | CH | O |
| H | $CH_3$ | $CH_3$ | H | H | H | H | $CH_3$ | $CH_3$ | $OCH_3$ | $OCH_3$ | N | O |
| H | $CH_3$ | H | H | H | $CH_3$ | $CH_3$ | $CH_3$ | H | $CH_3$ | $CH_3$ | CH | O |
| H | $CH_3$ | H | $CH_3$ | H | $CH_3$ | H | $CH_3$ | H | $CH_3$ | $CH_3$ | N | O |
| H | H | H | $CH_3$ | $CH_3$ | $CH_3$ | $CH_3$ | H | H | $CH_3$ | $OCH_3$ | CH | O |
| H | $CH_3$ | $CH_3$ | $CH_3$ | H | H | H | $CH_3$ | $CH_3$ | $CH_3$ | $OCH_3$ | N | O |
| H | $CH_3$ | H | $CH_3$ | $CH_3$ | $CH_3$ | H | $CH_3$ | H | $OCH_3$ | $OCH_3$ | CH | O |
| H | $CH_3$ | H | $CH_3$ | H | $CH_3$ | $CH_3$ | $CH_3$ | H | $OCH_3$ | $OCH_3$ | N | O |
| H | $CH_3$ | $CH_3$ | $CH_3$ | H | $CH_3$ | H | $CH_3$ | H | $CH_3$ | $CH_3$ | CH | O |
| H | $CH_3$ | H | $CH_3$ | $CH_3$ | $CH_3$ | $CH_3$ | $CH_3$ | H | $CH_3$ | $CH_3$ | N | O |
| H | $CH_3$ | H | $CH_3$ | $CH_3$ | $CH_3$ | H | $CH_3$ | $CH_3$ | $CH_3$ | $OCH_3$ | CH | O |
| H | $CH_3$ | H | $CH_3$ | $CH_3$ | $CH_3$ | $CH_3$ | $CH_3$ | $CH_3$ | $CH_3$ | $OCH_3$ | N | O |
| H | $CH_3$ | $CH_3$ | $CH_3$ | $CH_3$ | $CH_3$ | $CH_3$ | $CH_3$ | H | $OCH_3$ | $OCH_3$ | CH | O |
| $CH_3$ | H | H | H | H | H | H | H | H | $OCH_3$ | $OCH_3$ | N | O |
| H | $CH_3$ | H | H | H | H | H | $CH_3$ | H | $CH_3$ | $OCH_3$ | CH | O |
| H | H | H | H | H | H | H | H | H | $CH_3$ | $OCH_3$ | CH | O |
| H | H | H | H | H | H | H | H | H | $CH_3$ | $OCH_3$ | N | O |
| H | H | H | H | H | H | H | H | H | $OCH_3$ | $OCH_3$ | CH | O |
| H | H | H | H | H | H | H | H | H | $OCH_3$ | $OCH_3$ | N | O |
| H | H | H | H | H | H | H | H | H | $CH_3$ | $OCH_3$ | CH | S |
| H | H | H | H | H | H | H | H | H | $CH_3$ | $OCH_3$ | N | S |
| H | H | H | H | H | H | H | H | H | $OCH_3$ | $OCH_3$ | CH | S |
| H | H | H | H | H | H | H | H | H | $OCH_3$ | $OCH_3$ | N | S |
| H | H | H | H | H | H | H | H | H | $CH_3$ | $CH_3$ | CH | S |
| H | H | H | H | H | H | H | H | H | $CH_3$ | $CH_3$ | N | S |
| H | H | H | H | H | H | H | H | H | Cl | $OCH_3$ | CH | S |
| | | | | | | | | | | O | | |
| H | H | H | H | H | H | H | H | H | $CH_3$ | O | CH | S |
| H | H | H | H | H | H | H | H | H | Cl | $OC_2H_5$ | CH | S |
| H | H | H | H | H | H | H | H | H | $CH_3$ | $C_2H_5$ | N | S |
| H | H | H | H | H | H | H | H | H | $CH_3$ | $OC_2H_5$ | N | S |
| H | $CH_3$ | H | H | H | H | H | H | H | $CH_3$ | $CH_3$ | CH | S |
| H | H | H | $CH_3$ | H | H | H | H | H | $CH_3$ | $CH_3$ | N | S |
| H | H | H | H | H | $CH_3$ | H | H | H | $CH_3$ | $OCH_3$ | CH | S |

TABLE 5f-continued

| General Structure 2 wherein Q is Q-32. | | | | | | | | | | | | |
|---|---|---|---|---|---|---|---|---|---|---|---|---|
| R | $R_3$ | $R_4$ | $R_5$ | $R_6$ | $R_7$ | $R_8$ | $R_9$ | $R_{10}$ | X | Y | Z | W'' |
| H | H | H | H | H | H | H | $CH_3$ | H | $CH_3$ | $OCH_3$ | N | S |
| H | $CH_3$ | $CH_3$ | H | H | H | H | H | H | $OCH_3$ | $OCH_3$ | CH | S |
| H | H | H | $CH_3$ | $CH_3$ | H | H | H | H | $OCH_3$ | $OCH_3$ | N | S |
| H | H | H | H | H | $CH_3$ | $CH_3$ | H | H | $CH_3$ | $CH_3$ | CH | S |
| H | H | H | H | H | H | H | $CH_3$ | $CH_3$ | $CH_3$ | $CH_3$ | N | S |
| H | H | H | $CH_3$ | H | H | H | $CH_3$ | H | $CH_3$ | $OCH_3$ | CH | S |
| H | $CH_3$ | H | H | H | $CH_3$ | H | H | H | $CH_3$ | $OCH_3$ | N | S |
| H | $CH_3$ | H | $CH_3$ | H | H | H | H | H | $OCH_3$ | $OCH_3$ | CH | S |
| H | H | H | H | H | $CH_3$ | H | $CH_3$ | H | $OCH_3$ | $OCH_3$ | N | S |
| H | $CH_3$ | $CH_3$ | $CH_3$ | H | H | H | H | H | $CH_3$ | $CH_3$ | CH | S |
| H | $CH_3$ | H | H | H | $CH_3$ | $CH_3$ | H | H | $CH_3$ | $CH_3$ | N | S |
| H | H | H | $CH_3$ | $CH_3$ | H | H | $CH_3$ | H | $CH_3$ | $OCH_3$ | CH | S |
| H | H | H | $CH_3$ | $CH_3$ | $CH_3$ | H | H | H | $CH_3$ | $OCH_3$ | N | S |
| H | $CH_3$ | H | H | H | $CH_3$ | H | $CH_3$ | H | $OCH_3$ | $OCH_3$ | CH | S |
| H | $CH_3$ | $CH_3$ | H | H | H | H | $CH_3$ | $CH_3$ | $OCH_3$ | $OCH_3$ | N | S |
| H | $CH_3$ | H | H | H | $CH_3$ | $CH_3$ | $CH_3$ | H | $CH_3$ | $CH_3$ | CH | S |
| H | $CH_3$ | H | $CH_3$ | H | $CH_3$ | H | $CH_3$ | H | $CH_3$ | $CH_3$ | N | S |
| H | H | H | $CH_3$ | $CH_3$ | $CH_3$ | $CH_3$ | H | H | $CH_3$ | $OCH_3$ | N | S |
| H | $CH_3$ | $CH_3$ | $CH_3$ | H | H | H | $CH_3$ | $CH_3$ | $CH_3$ | $OCH_3$ | N | S |
| H | $CH_3$ | H | $CH_3$ | $CH_3$ | $CH_3$ | H | $CH_3$ | H | $OCH_3$ | $OCH_3$ | CH | S |
| H | $CH_3$ | H | $CH_3$ | H | $CH_3$ | $CH_3$ | $CH_3$ | H | $OCH_3$ | $OCH_3$ | N | S |
| H | $CH_3$ | $CH_3$ | $CH_3$ | H | $CH_3$ | H | $CH_3$ | H | $CH_3$ | $CH_3$ | CH | S |
| H | $CH_3$ | H | $CH_3$ | $CH_3$ | $CH_3$ | $CH_3$ | $CH_3$ | H | $CH_3$ | $CH_3$ | N | S |
| H | $CH_3$ | H | $CH_3$ | $CH_3$ | $CH_3$ | H | $CH_3$ | $CH_3$ | $CH_3$ | $OCH_3$ | CH | S |
| H | $CH_3$ | H | $CH_3$ | $CH_3$ | $CH_3$ | $CH_3$ | $CH_3$ | $CH_3$ | $CH_3$ | $OCH_3$ | N | S |
| H | $CH_3$ | $CH_3$ | $CH_3$ | $CH_3$ | $CH_3$ | $CH_3$ | $CH_3$ | H | $OCH_3$ | $OCH_3$ | CH | S |
| $CH_3$ | H | H | H | H | H | H | H | H | $OCH_3$ | $OCH_3$ | N | S |
| H | $CH_3$ | H | H | H | H | H | $CH_3$ | H | $CH_3$ | $OCH_3$ | CH | S |

TABLE 5g

| General Structure 2 | | | | | | | | | | | |
|---|---|---|---|---|---|---|---|---|---|---|---|
| Q | R | $R_3$ | $R_4$ | $R_5$ | $R_6$ | $R_7$ | X | Y | Z | W | m.p. °C. |
| Q-41 | H | H | H | H | H | H | Cl | $OCH_3$ | CH | | |
| Q-41 | H | H | H | H | H | H | Br | $OCH_3$ | CH | | |
| Q-41 | H | H | H | H | H | H | Cl | $OC_2H_5$ | CH | | |
| Q-41 | H | H | H | H | H | H | $CH_3$ | $CH_3$ | N | | |
| Q-41 | H | H | H | H | H | H | $OCH_3$ | $OCH_3$ | CH | | |
| Q-41 | H | H | H | H | H | H | $OCH_3$ | $OCH_3$ | N | | |
| Q-41 | H | H | H | H | H | H | $OCH_3$ | $OC_2H_5$ | CH | | |
| Q-41 | H | H | H | H | H | H | $OCH_3$ | $OC_2H_5$ | N | | |
| Q-41 | H | H | H | H | H | H | $CH_3$ | $CH_3$ | CH | | |
| Q-41 | H | H | H | H | H | H | $CH_3$ | $OCH_3$ | N | | |
| Q-41 | H | H | H | H | H | H | $CH_3$ | $OCH_3$ | CH | | |
| Q-41 | H | H | H | H | H | H | $CH_3$ | $CH_2OCH_3$ | CH | | |
| Q-41 | H | H | H | H | H | H | $CH_3$ | $CF_3$ | N | | |
| Q-41 | H | H | H | H | H | H | $CH_3$ | $OCF_2H$ | N | | |
| Q-41 | H | $CH_3$ | H | H | H | H | $CH_3$ | $CH_3$ | CH | | |
| Q-41 | H | H | H | $CH_3$ | H | H | $CH_3$ | $CH_3$ | N | | |
| Q-41 | H | H | H | H | $CH_3$ | H | $CH_3$ | $OCH_3$ | CH | | |
| Q-41 | H | $CH_3$ | $CH_3$ | H | H | H | $CH_3$ | $OCH_3$ | N | | |
| Q-41 | H | $CH_3$ | $CH_3$ | H | H | H | $OCH_3$ | $OCH_3$ | CH | | |
| Q-41 | H | $CH_3$ | $CH_3$ | H | H | H | $OCH_3$ | $OCH_3$ | N | | |
| Q-41 | H | $CH_3$ | H | $CH_3$ | H | H | $CH_3$ | $CH_3$ | CH | | |
| Q-41 | H | $CH_3$ | H | H | $CH_3$ | H | $CH_3$ | $CH_3$ | N | | |
| Q-41 | H | H | H | $CH_3$ | $CH_3$ | H | $CH_3$ | $OCH_3$ | CH | | |
| Q-41 | H | H | H | H | $CH_3$ | $CH_3$ | $CH_3$ | $OCH_3$ | N | | |
| Q-41 | H | $CH_3$ | $CH_3$ | $CH_3$ | H | H | $OCH_3$ | $OCH_3$ | CH | | |
| Q-41 | H | $CH_3$ | $CH_3$ | H | $CH_3$ | H | $OCH_3$ | $OCH_3$ | N | | |
| Q-41 | H | $CH_3$ | H | $CH_3$ | $CH_3$ | H | $CH_3$ | $CH_3$ | CH | | |
| Q-41 | H | $CH_3$ | H | H | $CH_3$ | $CH_3$ | $CH_3$ | $CH_3$ | N | | |
| Q-41 | H | $CH_3$ | $CH_3$ | $CH_3$ | $CH_3$ | H | $CH_3$ | $OCH_3$ | CH | | |
| Q-41 | H | $CH_3$ | $CH_3$ | H | $CH_3$ | $CH_3$ | $CH_3$ | $OCH_3$ | N | | |
| Q-41 | H | $CH_3$ | H | $CH_3$ | $CH_3$ | $CH_3$ | $OCH_3$ | $OCH_3$ | CH | — | |
| Q-41 | H | $CH_3$ | $CH_3$ | $CH_3$ | $CH_3$ | $CH_3$ | $OCH_3$ | $OCH_3$ | N | — | |
| Q-41 | $CH_3$ | H | H | H | H | H | $CH_3$ | $CH_3$ | CH | — | |
| Q-41 | $CH_3$ | H | H | H | H | H | $CH_3$ | $OCH_3$ | CH | — | |
| Q-42 | H | H | H | H | H | H | $CH_3$ | $CH_3$ | CH | — | |
| Q-42 | H | H | H | H | H | H | $CH_3$ | $CH_3$ | N | O | |
| Q-42 | H | H | H | H | H | H | $CH_3$ | $OCH_2CF_3$ | N | O | |
| Q-42 | H | H | H | H | H | H | $CH_3$ | $NHCH_3$ | N | O | |
| Q-42 | H | H | H | H | H | H | $CH_3$ | $N(CH_3)_2$ | N | O | |
| Q-42 | H | H | H | H | H | H | $CH_3$ | $CH(OCH_3)_2$ | N | O | |
| Q-42 | $CH_3$ | H | H | H | H | H | $CH_3$ | $OCH_3$ | CH | O | |
| Q-42 | $CH_3$ | H | H | H | H | H | $CH_3$ | $OCH_3$ | N | O | |
| Q-42 | H | $CH_3$ | H | H | H | H | $CH_3$ | $CH_3$ | CH | O | |
| Q-42 | H | H | H | $CH_3$ | H | H | $CH_3$ | $CH_3$ | N | O | |
| Q-42 | H | H | H | H | $CH_3$ | H | $CH_3$ | $OCH_3$ | CH | O | |

TABLE 5g-continued

| General Structure 2 | | | | | | | | | | | |
|---|---|---|---|---|---|---|---|---|---|---|---|
| Q | R | $R_3$ | $R_4$ | $R_5$ | $R_6$ | $R_7$ | X | Y | Z | W | m.p. °C. |
| Q-42 | H | $CH_3$ | $CH_3$ | H | H | H | $CH_3$ | $OCH_3$ | N | O | |
| Q-42 | H | $CH_3$ | $CH_3$ | H | H | H | $OCH_3$ | $OCH_3$ | CH | O | |
| Q-42 | H | $CH_3$ | H | $CH_3$ | H | H | $OCH_3$ | $OCH_3$ | N | O | |
| Q-42 | H | $CH_3$ | H | H | $CH_3$ | H | $CH_3$ | $CH_3$ | CH | O | |
| Q-42 | H | H | H | $CH_3$ | $CH_3$ | H | $CH_3$ | $CH_3$ | N | O | |
| Q-42 | H | H | H | H | $CH_3$ | $CH_3$ | $CH_3$ | $OCH_3$ | CH | O | |
| Q-42 | H | $CH_3$ | $CH_3$ | $CH_3$ | H | H | $CH_3$ | $OCH_3$ | N | O | |
| Q-42 | H | $CH_3$ | $CH_3$ | H | $CH_3$ | H | $OCH_3$ | $OCH_3$ | CH | O | |
| Q-42 | H | $CH_3$ | H | $CH_3$ | $CH_3$ | H | $OCH_3$ | $OCH_3$ | N | O | |
| Q-42 | H | H | H | $CH_3$ | $CH_3$ | $CH_3$ | $CH_3$ | $CH_3$ | CH | O | |
| Q-42 | H | $CH_3$ | H | H | $CH_3$ | $CH_3$ | $CH_3$ | $CH_3$ | N | O | |
| Q-42 | H | $CH_3$ | $CH_3$ | $CH_3$ | $CH_3$ | H | $CH_3$ | $OCH_3$ | CH | O | |
| Q-42 | H | $CH_3$ | $CH_3$ | H | $CH_3$ | $CH_3$ | $CH_3$ | $OCH_3$ | N | O | |
| Q-42 | H | $CH_3$ | H | $CH_3$ | $CH_3$ | $CH_3$ | $OCH_3$ | $OCH_3$ | CH | O | |
| Q-42 | H | $CH_3$ | $CH_3$ | $CH_3$ | $CH_3$ | $CH_3$ | $OCH_3$ | $OCH_3$ | N | O | |
| Q-42 | H | H | H | H | H | H | $CH_3$ | $OCH_3$ | CH | O | |
| Q-42 | H | H | H | H | H | H | $CH_3$ | $OCH_3$ | N | O | |
| Q-42 | H | H | H | H | H | H | $OCH_3$ | $OCH_3$ | CH | O | |
| Q-42 | H | H | H | H | H | H | $OCH_3$ | $OCH_3$ | N | O | |
| Q-42 | H | H | H | H | H | H | $CH_3$ | $OCH_3$ | CH | S | |
| Q-42 | H | H | H | H | H | H | $CH_3$ | $OCH_3$ | N | S | |
| Q-42 | H | H | H | H | H | H | $OCH_3$ | $OCH_3$ | CH | S | |
| Q-42 | H | H | H | H | H | H | $OCH_3$ | $OCH_3$ | N | S | |
| Q-42 | H | H | H | H | H | H | $CH_3$ | $CH_3$ | CH | S | |
| Q-42 | H | H | H | H | H | H | $CH_3$ | $CH_3$ | N | S | |
| Q-42 | H | H | H | H | H | H | $CH_3$ | 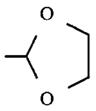 | N | S | |
| Q-42 | H | H | H | H | H | H | Br | $OC_2H_5$ | CH | S | |
| Q-42 | H | H | H | H | H | H | $OCH_3$ | $CH_2OCH_3$ | N | S | |
| Q-42 | $CH_3$ | H | H | H | H | H | $CH_3$ | $OCH_3$ | CH | S | |
| Q-42 | $CH_3$ | H | H | H | H | H | $CH_3$ | $OCH_3$ | N | S | |
| Q-42 | H | $CH_3$ | H | H | H | H | $CH_3$ | $CH_3$ | CH | S | |
| Q-42 | H | H | H | $CH_3$ | H | H | $CH_3$ | $CH_3$ | N | S | |
| Q-42 | H | H | H | H | $CH_3$ | H | $CH_3$ | $OCH_3$ | CH | S | |
| Q-42 | H | $CH_3$ | $CH_3$ | H | H | H | $CH_3$ | $OCH_3$ | N | S | |
| Q-42 | H | $CH_3$ | $CH_3$ | H | H | H | $OCH_3$ | $OCH_3$ | CH | S | |
| Q-42 | H | $CH_3$ | H | $CH_3$ | H | H | $OCH_3$ | $OCH_3$ | N | S | |
| Q-42 | H | $CH_3$ | H | H | $CH_3$ | H | $CH_3$ | $CH_3$ | CH | S | |
| Q-42 | H | H | H | $CH_3$ | $CH_3$ | H | $CH_3$ | $CH_3$ | N | S | |
| Q-42 | H | H | H | H | $CH_3$ | $CH_3$ | $CH_3$ | $OCH_3$ | CH | S | |
| Q-42 | H | $CH_3$ | $CH_3$ | $CH_3$ | H | H | $CH_3$ | $OCH_3$ | N | S | |
| Q-42 | H | $CH_3$ | $CH_3$ | H | $CH_3$ | H | $OCH_3$ | $OCH_3$ | CH | S | |
| Q-42 | H | $CH_3$ | H | $CH_3$ | $CH_3$ | H | $OCH_3$ | $OCH_3$ | N | S | |
| Q-42 | H | H | H | $CH_3$ | $CH_3$ | $CH_3$ | $CH_3$ | $CH_3$ | CH | S | |
| Q-42 | H | $CH_3$ | H | H | $CH_3$ | $CH_3$ | $CH_3$ | $CH_3$ | N | S | |
| Q-42 | H | $CH_3$ | $CH_3$ | $CH_3$ | $CH_3$ | H | $CH_3$ | $OCH_3$ | CH | S | |
| Q-42 | H | $CH_3$ | $CH_3$ | H | $CH_3$ | $CH_3$ | $CH_3$ | $OCH_3$ | N | S | |
| Q-42 | H | $CH_3$ | H | $CH_3$ | $CH_3$ | $CH_3$ | $OCH_3$ | $OCH_3$ | CH | S | |
| Q-42 | H | $CH_3$ | $CH_3$ | $CH_3$ | $CH_3$ | $CH_3$ | $OCH_3$ | $OCH_3$ | N | S | |

TABLE 6a

| General Structure 2 wherein Q is Q-20 | | | | | | |
|---|---|---|---|---|---|---|
| R | $R'_3$ | X | Y | Z | W' | m.p. °C. |
| H | H | $CH_3$ | $OCH_3$ | CH | O | |
| H | H | $CH_3$ | $OCH_3$ | N | O | 150–153 |
| H | H | $OCH_3$ | $OCH_3$ | CH | O | 186–188 |
| H | H | $OCH_3$ | Cl | CH | O | |
| H | H | $OCH_3$ | $OCH_3$ | N | O | |
| H | H | $CH_3$ | $CH_3$ | CH | O | |
| H | $CH_3$ | $CH_3$ | $OCH_3$ | CH | O | |
| $CH_3$ | H | $CH_3$ | $OCH_3$ | N | O | |
| $CH_3$ | $CH_3$ | $OCH_3$ | $OCH_3$ | CH | O | |
| H | H | $CH_3$ | $OC_2H_5$ | N | O | |
| H | H | $CH_3$ | $CH_3$ | CH | S | |
| H | H | $CH_3$ | $CH_3$ | N | S | |
| H | H | $CH_3$ | $OCH_3$ | CH | S | |
| H | H | $CH_3$ | $OCH_3$ | N | S | |
| H | H | $OCH_3$ | $OCH_3$ | CH | S | |
| H | H | $OCH_3$ | $OCH_3$ | N | S | |
| $CH_3$ | H | $CH_3$ | $OCH_3$ | CH | S | |
| H | $CH_3$ | $CH_3$ | $OCH_3$ | N | S | |
| H | $CH_3$ | $CH_3$ | $CH_2OCH_3$ | N | S | |

TABLE 6a-continued

| General Structure 2 wherein Q is Q-20 | | | | | | |
|---|---|---|---|---|---|---|
| R | R'₃ | X | Y | Z | W' | m.p. °C. |
| H | $C_2H_5$ | $CH_3$ | $CH_3$ | CH | O | |
| H | $C_2H_5$ | $CH_3$ | $CH_3$ | N | O | |
| H | $C_2H_5$ | $CH_3$ | $OCH_3$ | CH | O | |
| H | $C_2H_5$ | $CH_3$ | $OCH_3$ | N | O | |
| H | $C_2H_5$ | $OCH_3$ | $OCH_3$ | CH | O | |
| H | $C_2H_5$ | $OCH_3$ | $OCH_3$ | N | O | |
| H | $C_2H_5$ | $OCH_3$ | Cl | CH | O | |
| H | $C_2H_5$ | $CH_3$ | $CH_3$ | CH | S | |
| H | $C_2H_5$ | $CH_3$ | $CH_3$ | N | S | |
| H | $C_2H_5$ | $CH_3$ | $OCH_3$ | CH | S | |
| H | $C_2H_5$ | $CH_3$ | $OCH_3$ | N | S | |
| H | $C_2H_5$ | $OCH_3$ | $OCH_3$ | CH | S | |
| H | $C_2H_5$ | $OCH_3$ | $OCH_3$ | N | S | |
| H | $C_2H_5$ | $OCH_3$ | Cl | CH | S | |
| H | $C_2H_5$ | $OCH_3$ | $N(CH_3)_2$ | N | S | |
| $CH_3$ | n-$C_3H_7$ | $OCH_3$ | $OCH_3$ | CH | O | |
| $CH_3$ | n-$C_3H_7$ | $CH_3$ | $CH_3$ | CH | O | |
| $CH_3$ | n-$C_3H_7$ | $CH_3$ | $OCH_3$ | CH | O | |
| $CH_3$ | n-$C_3H_7$ | $OCH_3$ | $OCH_3$ | CH | O | |
| $CH_3$ | n-$C_3H_7$ | $OCH_3$ | $OCH_3$ | N | O | |
| $CH_3$ | n-$C_3H_7$ | $OCH_3$ | Cl | CH | O | |
| $CH_3$ | n-$C_3H_7$ | $CH_3$ | $OCH_2CF_3$ | CH | O | |
| H | n-$C_3H_7$ | $CH_3$ | $CH_3$ | CH | S | |
| H | n-$C_3H_7$ | $CH_3$ | $OCH_3$ | CH | S | |
| H | n-$C_3H_7$ | $CH_3$ | $OCH_3$ | N | S | |
| H | n-$C_3H_7$ | $OCH_3$ | $OCH_3$ | CH | S | |
| H | n-$C_3H_7$ | $OCH_3$ | $OCH_3$ | N | S | |
| H | n-$C_3H_7$ | $OCH_3$ | Cl | CH | S | |
| H | n-$C_3H_7$ | $CH_3$ | $CH(OCH_3)_2$ | CH | S | |
| H | i-$C_3H_7$ | $CH_3$ | $CH_3$ | CH | O | |
| H | i-$C_3H_7$ | $CH_3$ | $OCH_3$ | CH | O | |
| H | i-$C_3H_7$ | $CH_3$ | $OCH_3$ | N | O | |
| H | i-$C_3H_7$ | $OCH_3$ | $OCH_3$ | CH | O | |
| H | i-$C_3H_7$ | $OCH_3$ | $OCH_3$ | N | O | |
| H | i-$C_3H_7$ | $OCH_3$ | Cl | CH | O | |
| H | i-$C_3H_7$ | $CH_3$ | $CH_3$ | N | O | |
| H | i-$C_3H_7$ | $OCH_3$ | 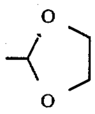 | CH | O | |
| $CH_3$ | i-$C_3H_7$ | $OCH_3$ | $OCH_3$ | CH | S | |
| H | i-$C_3H_7$ | $CH_3$ | $CH_3$ | CH | S | |
| H | i-$C_3H_7$ | $CH_3$ | $OCH_3$ | CH | S | |
| H | i-$C_3H_7$ | $CH_3$ | $OCH_3$ | N | S | |
| H | i-$C_3H_7$ | $OCH_3$ | $OCH_3$ | CH | S | |
| H | i-$C_3H_7$ | $OCH_3$ | $OCH_3$ | N | S | |
| H | i-$C_3H_7$ | $OCH_3$ | Cl | CH | S | |
| H | i-$C_3H_7$ | $CH_3$ | $OC_2H_5$ | N | S | |
| H | $SCH_3$ | $CH_3$ | $CH_3$ | CH | O | 175-177 |
| H | $SCH_3$ | $CH_3$ | $OCH_3$ | CH | O | 148-149 |
| H | $SCH_3$ | $CH_3$ | $OCH_3$ | N | O | 167-170 |
| H | $SCH_3$ | $OCH_3$ | $OCH_3$ | CH | O | 178-180 |
| H | $SCH_3$ | $OCH_3$ | $OCH_3$ | N | O | 146-151 |
| H | $SCH_3$ | $OCH_3$ | Cl | CH | O | 163-169 |
| H | $SCH_3$ | $OCH_3$ | $NHCH_3$ | CH | O | |
| $CH_3$ | $SCH_3$ | $OCH_3$ | $OCH_3$ | CH | S | |
| H | $SCH_3$ | $CH_3$ | $CH_3$ | CH | S | |
| H | $SCH_3$ | $CH_3$ | $CH_3$ | N | S | |
| H | $SCH_3$ | $CH_3$ | $OCH_3$ | CH | S | |
| H | $SCH_3$ | $CH_3$ | $OCH_3$ | N | S | |
| H | $SCH_3$ | $OCH_3$ | $OCH_3$ | CH | S | |
| H | $SCH_3$ | $OCH_3$ | $OCH_3$ | N | S | |
| H | $SCH_3$ | $OCH_3$ | Cl | CH | S | |
| $CH_3$ | $SC_2H_5$ | $OCH_3$ | $OCH_3$ | CH | O | |
| H | $SC_2H_5$ | $CH_3$ | $CH_3$ | CH | O | 168-177 |
| H | $SC_2H_5$ | $CH_3$ | $CH_3$ | N | O | |
| H | $SC_2H_5$ | $CH_3$ | $OCH_3$ | CH | O | |
| H | $SC_2H_5$ | $CH_3$ | $OCH_3$ | N | O | |
| H | $SC_2H_5$ | $OCH_3$ | $OCH_3$ | CH | O | |
| H | $SC_2H_5$ | $OCH_3$ | $OCH_3$ | N | O | |
| H | $SC_2H_5$ | $OCH_3$ | Cl | CH | O | |
| H | $SC_2H_5$ | $CH_3$ | $CH_3$ | CH | S | |
| H | $SC_2H_5$ | $CH_3$ | $OCH_3$ | CH | S | |
| H | $SC_2H_5$ | $CH_3$ | $OCH_3$ | N | S | |
| H | $SC_2H_5$ | $OCH_3$ | $OCH_3$ | CH | S | |
| H | $SC_2H_5$ | $CH_3$ | $OCH_3$ | N | S | |

TABLE 6a-continued

| General Structure 2 wherein Q is Q-20 | | | | | | |
|---|---|---|---|---|---|---|
| R | R'$_3$ | X | Y | Z | W' | m.p. °C. |
| H | $SC_2H_5$ | $OCH_3$ | Cl | CH | S | |
| H | $SC_2H_5$ | $CH_3$ | $OC_2H_5$ | N | S | |
| H | S—n-$C_3H_7$ | $CH_3$ | $CH_3$ | CH | O | |
| H | S—n-$C_3H_7$ | $CH_3$ | $CH_2OCH_3$ | CH | O | |
| H | S—n-$C_3H_7$ | $CH_3$ | $OCH_3$ | CH | O | |
| H | S—n-$C_3H_7$ | $CH_3$ | $OCH_3$ | N | O | |
| H | S—n-$C_3H_7$ | $OCH_3$ | $OCH_3$ | CH | O | |
| H | S—n-$C_3H_7$ | $OCH_3$ | $OCH_3$ | N | O | |
| H | S—n-$C_3H_7$ | $OCH_3$ | Cl | CH | O | |
| $CH_3$ | S—n-$C_3H_7$ | $OCH_3$ | $OCH_3$ | CH | S | |
| H | S—n-$C_3H_7$ | $CH_3$ | $CH_3$ | CH | S | |
| H | S—n-$C_3H_7$ | $CH_3$ | $CH_3$ | N | S | |
| H | S—n-$C_3H_7$ | $CH_3$ | $OCH_3$ | CH | S | |
| H | S—n-$C_3H_7$ | $OCH_3$ | $OCH_3$ | CH | S | |
| H | S—n-$C_3H_7$ | $OCH_3$ | $OCH_3$ | N | S | |
| H | S—n-$C_3H_7$ | $CH_3$ | Cl | CH | S | |
| H | S—n-$C_3H_7$ | $CH_3$ | $OCH_3$ | CH | O | |
| H | S—n-$C_3H_7$ | $OCH_3$ | $OCH_3$ | CH | S | |
| H | S—n-$C_3H_7$ | $CH_3$ | $OCH_3$ | N | S | |
| $CH_3$ | S—n-$C_4H_9$ | $OCH_3$ | $OCH_3$ | CH | O | |
| H | S—n-$C_4H_9$ | $CH_3$ | $CH_3$ | CH | O | |
| H | S—n-$C_4H_9$ | $CH_3$ | $CH_3$ | N | O | |
| H | S—n-$C_4H_9$ | $CH_3$ | $OCH_3$ | CH | O | |
| H | S—n-$C_4H_9$ | $CH_3$ | $OCH_3$ | N | O | |
| H | S—n-$C_4H_9$ | $OCH_3$ | $OCH_3$ | CH | O | |
| H | S—n-$C_4H_9$ | $OCH_3$ | $OCH_3$ | N | O | |
| H | S—n-$C_4H_9$ | $OCH_3$ | Cl | CH | O | |
| H | S—n-$C_4H_9$ | $CH_3$ | $CH_3$ | CH | S | |
| H | S—n-$C_4H_9$ | $CH_3$ | $OCH_3$ | N | S | |
| H | S—n-$C_4H_9$ | $CH_3$ | $OCH_3$ | CH | S | |
| H | S—n-$C_4H_9$ | $OCH_3$ | $OCH_3$ | N | S | |
| H | S—n-$C_4H_9$ | $OCH_3$ | $OCH_3$ | CH | S | |
| H | S—n-$C_4H_9$ | $OCH_3$ | $OCH_3$ | N | S | |
| H | S—n-$C_4H_9$ | $OCH_3$ | $OCF_2H$ | N | S | |
| H | S—n-$C_4H_9$ | $OCH_3$ | $OCH_3$ | CH | O | |
| H | S—n-$C_4H_9$ | $CH_3$ | $OCH_3$ | N | O | |
| H | S—n-$C_4H_9$ | $OCH_3$ | $OCH_3$ | CH | S | |
| H | S—n-$C_4H_9$ | $CH_3$ | $OCH_3$ | CH | S | |
| H | S—n-$C_4H_9$ | $CH_3$ | $OCH_3$ | N | O | |
| H | S—n-$C_4H_9$ | $CH_3$ | $OCH_3$ | CH | O | |
| H | S—n-$C_4H_9$ | $OCH_3$ | $OCH_3$ | CH | S | |
| H | S—n-$C_4H_9$ | $OCH_3$ | $OCH_3$ | N | S | |
| H | S—n-$C_4H_9$ | $CH_3$ | $OCH_3$ | CH | O | |
| H | S—n-$C_4H_9$ | $OCH_3$ | $OCH_3$ | N | O | |
| H | S—n-$C_4H_9$ | $OCH_3$ | $OCH_3$ | CH | S | |
| H | S—n-$C_4H_9$ | $CH_3$ | $OCH_3$ | N | S | |
| H | $SCH_2CH=CH_2$ | $CH_3$ | $CH_3$ | CH | O | 169–170 |
| H | $SCH_2CH=CH_2$ | $CH_3$ | $OCH_3$ | N | O | 148–151 |
| H | $SCH_2CH=CH_2$ | $CH_3$ | $OCH_3$ | CH | O | 134–138 |
| H | $SCH_2CH=CH_2$ | $OCH_3$ | $OCH_3$ | N | O | 149–152 |
| H | $SCH_2CH=CH_2$ | $OCH_3$ | $OCH_3$ | CH | O | 165–168 |
| H | $SCH_2CH=CH_2$ | $OCH_3$ | $OCH_3$ | N | O | |
| H | $SCH_2CH=CH_2$ | $OCH_3$ | Cl | CH | O | 144–146 |
| H | $SCH_2CH=CH_2$ | $CH_3$ | $OCH_2CF_3$ | CH | O | |
| $CH_3$ | $SCH_2CH=CH_2$ | $OCH_3$ | $OCH_3$ | CH | S | |
| H | $SCH_2CH=CH_2$ | $CH_3$ | $CH_3$ | CH | S | |
| H | $SCH_2CH=CH_2$ | $CH_3$ | $CH_3$ | N | S | |
| H | $SCH_2CH=CH_2$ | $CH_3$ | $OCH_3$ | CH | S | |
| H | $SCH_2CH=CH_2$ | $CH_3$ | $OCH_3$ | N | S | |
| H | $SCH_2CH=CH_2$ | $OCH_3$ | $OCH_3$ | CH | S | |
| H | $SCH_2CH=CH_2$ | $OCH_3$ | $OCH_3$ | N | S | |
| H | $SCH_2CH=CH_2$ | $OCH_3$ | Cl | CH | S | |
| H | E—$SCH=CHCH_3$ | $CH_3$ | $OCH_3$ | CH | O | |
| H | E—$SCH=CHCH_3$ | $CH_3$ | $OCH_3$ | N | O | |
| H | E—$SCH=CHCH_3$ | $OCH_3$ | $OCH_3$ | CH | O | |
| H | E—$SCH=CHCH_3$ | $OCH_3$ | $OCH_3$ | N | O | |
| H | E—$SCH=CHCH_3$ | $CH_3$ | $OCH_3$ | N | S | |
| H | E—$SCH=CHCH_3$ | $CH_3$ | $OCH_3$ | CH | S | |
| H | E—$SCH=CHCH_3$ | $OCH_3$ | $OCH_3$ | CH | S | |
| H | E—$SCH=CHCH_3$ | $OCH_3$ | Cl | CH | S | |
| H | Z—$SCH=CHCH_3$ | $CH_3$ | $OCH_3$ | N | O | |
| H | Z—$SCH=CHCH_3$ | $OCH_3$ | $OCH_4$ | CH | O | |
| H | Z—$SCH=CHCH_3$ | $OCH_3$ | $OCH_3$ | N | O | |
| H | Z—$SCH=CHCH_3$ | $OCH_3$ | Cl | CH | O | |
| H | Z—$SCH=CHCH_3$ | $CH_3$ | $CH_3$ | CH | S | |
| H | Z—$SCH=CHCH_3$ | $OCH_3$ | $OCH_3$ | CH | S | |
| H | Z—$SCH=CHCH_3$ | $CH_3$ | $OCH_3$ | N | S | |
| H | Z—$SCH=CHCH_3$ | $OCH_3$ | $OCH_3$ | N | S | |
| H | $S(CH_2)_2CH=CH_2$ | $OCH_3$ | $OCH_3$ | CH | O | |
| H | $S(CH_2)_2CH=CH_2$ | $OCH_3$ | $OCH_3$ | N | O | |

TABLE 6a-continued

| General Structure 2 wherein Q is Q-20 | | | | | | |
|---|---|---|---|---|---|---|
| R | $R'_3$ | X | Y | Z | W' | m.p. °C. |
| H | $S(CH_2)_2CH=CH_2$ | $CH_3$ | $OCH_3$ | CH | O | |
| H | $S(CH_2)_2CH=CH_2$ | $OCH_3$ | Cl | CH | O | |
| H | $S(CH_2)_2CH=CH_2$ | $OCH_3$ | $OCH_3$ | CH | S | |
| H | $S(CH_2)_2CH=CH_2$ | $CH_3$ | $OCH_3$ | N | S | |
| H | $S(CH_2)_2CH=CH_2$ | $OCH_3$ | $OCH_3$ | N | S | |
| H | $S(CH_2)_2CH=CH_2$ | $CH_3$ | $CH_3$ | CH | S | |
| H | $\underline{E}-SCH_2CH=CHCH_3$ | $OCH_3$ | $OCH_3$ | CH | O | |
| H | $\underline{E}-SCH_2CH=CHCH_3$ | $OCH_3$ | $OCH_3$ | N | O | |
| H | $\underline{E}-SCH_2CH=CHCH_3$ | $CH_3$ | $OCH_3$ | CH | O | |
| H | $\underline{E}-SCH_2CH=CHCH_3$ | $OCH_3$ | Cl | CH | O | |
| H | $\underline{E}-SCH_2CH=CHCH_3$ | $OCH_3$ | $OCH_3$ | CH | S | |
| H | $\underline{E}-SCH_2CH=CHCH_3$ | $CH_3$ | $OCH_3$ | N | S | |
| H | $\underline{E}-SCH_2CH=CHCH_3$ | $CH_3$ | $OCH_3$ | CH | S | |
| H | $\underline{E}-SCH_2CH=CHCH_3$ | $CH_3$ | $CH_3$ | CH | S | |
| H | $\underline{Z}-SCH_2CH=CHCH_3$ | $CH_3$ | $OCH_3$ | CH | O | |
| H | $\underline{Z}-SCH_2CH=CHCH_3$ | $CH_3$ | $OCH_3$ | N | O | |
| H | $\underline{Z}-SCH_2CH=CHCH_3$ | $OCH_3$ | $OCH_3$ | CH | O | |
| H | $\underline{Z}-SCH_2CH=CHCH_3$ | $OCH_3$ | Cl | CH | O | |
| H | $\underline{Z}-SCH_2CH=CHCH_3$ | $CH_3$ | $OCH_3$ | CH | S | |
| H | $\underline{Z}-SCH_2CH=CHCH_3$ | $CH_3$ | $OCH_3$ | N | S | |
| H | $\underline{Z}-SCH_2CH=CHCH_3$ | $OCH_3$ | $OCH_3$ | CH | S | |
| H | $\underline{Z}-SCH_2CH=CHCH_3$ | $OCH_3$ | $OCH_3$ | N | S | |
| H | $\underline{E}-SCH=CHC_2H_5$ | $OCH_3$ | $OCH_3$ | CH | O | |
| H | $\underline{E}-SCH=CHC_2H_5$ | $OCH_3$ | $OCH_3$ | N | O | |
| H | $\underline{E}-SCH=CHC_2H_5$ | $CH_3$ | $OCH_3$ | CH | O | |
| H | $\underline{E}-SCH=CHC_2H_5$ | $OCH_3$ | Cl | CH | O | |
| H | $\underline{E}-SCH=CHC_2H_5$ | $OCH_3$ | $OCH_3$ | CH | S | |
| H | $\underline{E}-SCH=CHC_2H_5$ | $CH_3$ | $CH_3$ | CH | S | |
| H | $\underline{E}-SCH=CHC_2H_5$ | $CH_3$ | $OCH_3$ | N | S | |
| H | $\underline{E}-SCH=CHC_2H_5$ | $CH_3$ | $OCH_3$ | CH | S | |
| H | $\underline{Z}-SCH=CHC_2H_5$ | $OCH_3$ | $OCH_3$ | CH | O | |
| H | $\underline{Z}-SCH=CHC_2H_5$ | $OCH_3$ | $OCH_3$ | N | O | |
| H | $\underline{Z}-SCH=CHC_2H_5$ | $CH_3$ | $CH_3$ | CH | O | |
| H | $\underline{Z}-SCH=CHC_2H_5$ | $CH_3$ | $OCH_3$ | N | O | |
| H | $\underline{Z}-SCH=CHC_2H_5$ | $OCH_3$ | $OCH_3$ | CH | S | |
| H | $\underline{Z}-SCH=CHC_2H_5$ | $CH_3$ | $OCH_3$ | CH | S | |
| H | $\underline{Z}-SCH=CHC_2H_5$ | $CH_3$ | $OCH_3$ | N | S | |
| H | $\underline{Z}-SCH=CHC_2H_5$ | $OCH_3$ | Cl | CH | S | |
| H | $SCH_2C\equiv CH$ | $CH_3$ | $OCH_3$ | CH | O | |
| H | $SCH_2C\equiv CH$ | $CH_3$ | $OCH_3$ | N | O | |
| H | $SCH_2C\equiv CH$ | $OCH_3$ | $OCH_3$ | CH | O | |
| H | $SCH_2C\equiv CH$ | $OCH_3$ | $OCH_3$ | N | O | |
| H | $SCH_2C\equiv CH$ | $CH_3$ | $OCH_3$ | CH | S | |
| H | $SCH_2C\equiv CH$ | $OCH_3$ | $OCH_3$ | N | S | |
| H | $SCH_2C\equiv CH$ | $OCH_3$ | $OCH_3$ | CH | S | |
| H | $SCH_2C\equiv CH$ | $OCH_3$ | Cl | CH | S | |
| $CH_3$ | $SCH_2C\equiv CH$ | $OCH_3$ | $OCH_3$ | CH | S | |
| H | $SC\equiv CCH_3$ | $CH_3$ | $CH_3$ | CH | O | |
| H | $SC\equiv CCH_3$ | $CH_3$ | $OCH_3$ | N | O | |
| H | $SC\equiv CCH_3$ | $CH_3$ | $OCH_3$ | CH | O | |
| H | $SC\equiv CCH_3$ | $OCH_3$ | $OCH_3$ | N | O | |
| H | $SC\equiv CCH_3$ | $OCH_3$ | $OCH_3$ | CH | S | |
| H | $SC\equiv CCH_3$ | $CH_3$ | $OCH_3$ | N | S | |
| H | $SC\equiv CCH_3$ | $CH_3$ | $OCH_3$ | CH | S | |
| H | $SC\equiv CCH_3$ | $OCH_3$ | $OCH_3$ | N | S | |
| H | $S(CH_2)_2C\equiv CH$ | $CH_3$ | $OCH_3$ | CH | O | |
| H | $S(CH_2)_2C\equiv CH$ | $CH_3$ | $OCH_3$ | N | O | |
| H | $S(CH_2)_2C\equiv CH$ | $OCH_3$ | $OCH_3$ | CH | O | |
| H | $S(CH_2)_2C\equiv CH$ | $OCH_3$ | $OCH_3$ | N | O | |
| H | $S(CH_2)_2C\equiv CH$ | $CH_3$ | $OCH_3$ | CH | S | |
| H | $S(CH_2)_2C\equiv CH$ | $CH_3$ | $OCH_3$ | N | S | |
| H | $S(CH_2)_2C\equiv CH$ | $OCH_3$ | $OCH_3$ | CH | S | |
| H | $S(CH_2)_2C\equiv CH$ | $OCH_3$ | $OCH_3$ | N | S | |
| H | $SCH_2C\equiv CCH_3$ | $CH_3$ | $CH_3$ | CH | O | |
| H | $SCH_2C\equiv CCH_3$ | $CH_3$ | $OCH_3$ | N | O | |
| H | $SCH_2C\equiv CCH_3$ | $CH_3$ | $OCH_3$ | CH | O | |
| H | $SCH_2C\equiv CCH_3$ | $OCH_3$ | $OCH_3$ | CH | O | |
| H | $SCH_2C\equiv CCH_3$ | $OCH_3$ | $OCH_3$ | CH | S | |
| H | $SCH_2C\equiv CCH_3$ | $OCH_3$ | $OCH_3$ | N | S | |
| H | $SCH_2C\equiv CCH_3$ | $CH_3$ | $OCH_3$ | CH | S | |
| H | $SCH_2C\equiv CCH_3$ | $OCH_3$ | Cl | CH | S | |
| H | $SC\equiv CC_2H_5$ | $CH_3$ | $OCH_3$ | N | O | |
| H | $SC\equiv CC_2H_5$ | $OCH_3$ | $OCH_3$ | CH | O | |
| H | $SC\equiv CC_2H_5$ | $OCH_3$ | $OCH_3$ | CH | S | |
| H | $SC\equiv CC_2H_5$ | $CH_3$ | $CH_3$ | CH | S | |
| $CH_3$ | $SC\equiv CC_2H_5$ | $CH_3$ | $OCH_3$ | CH | O | |
| H | $CH_2CN$ | $CH_3$ | $CH_3$ | CH | O | |
| H | $CH_2CN$ | $CH_3$ | $OCH_3$ | N | O | |
| H | $CH_2CN$ | $CH_3$ | $OCH_3$ | CH | O | |
| H | $CH_2CN$ | $OCH_3$ | $OCH_3$ | N | O | |

TABLE 6a-continued

| R | R'3 | X | Y | Z | W' | m.p. °C. |
|---|---|---|---|---|---|---|
| | General Structure 2 wherein Q is Q-20 | | | | | |
| H | $CH_2CN$ | $OCH_3$ | $OCH_3$ | CH | O | |
| H | $CH_2CN$ | $OCH_3$ | Cl | CH | O | |
| H | $CH_2CN$ | $CH_3$ | $NHCH_3$ | N | O | |
| $CH_3$ | $CH_2CN$ | $OCH_3$ | $OCH_3$ | CH | S | |
| H | $CH_2CN$ | $CH_3$ | $CH_3$ | CH | S | |
| H | $CH_2CN$ | $CH_3$ | $CH_3$ | N | S | |
| H | $CH_2CN$ | $CH_3$ | $OCH_3$ | CH | S | |
| H | $CH_2CN$ | $CH_3$ | $OCH_3$ | N | S | |
| H | $CH_2CN$ | $OCH_3$ | $OCH_3$ | CH | S | |
| H | $CH_2CN$ | $OCH_3$ | $OCH_3$ | N | S | |
| H | $CH_2CN$ | $OCH_3$ | Cl | CH | S | |
| $CH_3$ | $CH_2CO_2CH_3$ | $CH_3$ | $OCH_3$ | CH | O | |
| H | $CH_2CO_2CH_3$ | $CH_3$ | $CH_3$ | CH | O | |
| H | $CH_2CO_2CH_3$ | $CH_3$ | $OCH_3$ | CH | O | |
| H | $CH_2CO_2CH_3$ | $CH_3$ | $OCH_3$ | N | O | |
| H | $CH_2CO_2CH_3$ | $OCH_3$ | $OCH_3$ | CH | O | |
| H | $CH_2CO_2CH_3$ | $OCH_3$ | $OCH_3$ | N | O | |
| H | $CH_2CO_2CH_2$ | $OCH_3$ | Cl | CH | O | |
| H | $CH_2CO_2CH_3$ | $CH_3$ | $CH_3$ | CH | S | |
| H | $CH_2CO_2CH_3$ | $CH_3$ | $OCH_3$ | N | S | |
| H | $CH_2CO_2CH_3$ | $CH_3$ | $OCH_3$ | CH | S | |
| H | $CH_2CO_2CH_3$ | $OCH_3$ | $OCH_3$ | N | S | |
| H | $CH_2CO_2CH_3$ | $OCH_3$ | $OCH_3$ | CH | S | |
| H | $CH_2CO_2CH_3$ | $OCH_3$ | Cl | CH | S | |
| H | $CH_2CO_2CH_3$ | $CH_3$ | $N(CH_3)_2$ | N | S | |
| H | $CH_2CO_2C_2H_5$ | $CH_3$ | $CH_3$ | CH | O | |
| H | $CH_2CO_2C_2H_5$ | $CH_3$ | $OCH_3$ | N | O | |
| H | $CH_2CO_2C_2H_5$ | $CH_3$ | $OCH_3$ | CH | O | |
| H | $CH_2CO_2C_2H_5$ | $OCH_3$ | $OCH_3$ | N | O | |
| H | $CH_2CO_2C_2H_5$ | $OCH_3$ | $OCH_3$ | CH | O | |
| H | $CH_2CO_2C_2H_5$ | $OCH_3$ | Cl | CH | O | |
| H | $CH_2CO_2C_2H_5$ | $OC_2H_5$ | Cl | CH | O | |
| $CH_3$ | $CH_2CO_2C_2H_5$ | $OCH_3$ | $OCH_3$ | CH | S | |
| H | $CH_2CO_2C_2H_5$ | $CH_3$ | $CH_3$ | CH | S | |
| H | $CH_2CO_2C_2H_5$ | $CH_3$ | $CH_3$ | N | S | |
| H | $CH_2CO_2C_2H_5$ | $CH_3$ | $OCH_3$ | CH | S | |
| H | $CH_2CO_2C_2H_5$ | $CH_3$ | $OCH_3$ | N | S | |
| H | $CH_2CO_2C_2H_5$ | $OCH_3$ | $OCH_3$ | CH | S | |
| H | $CH_2CO_2C_2H_5$ | $OCH_3$ | $OCH_3$ | N | S | |
| H | $CH_2CO_2C_2H_5$ | $OCH_3$ | Cl | CH | S | |
| $CH_3$ | $CH_2OCH_3$ | $OCH_3$ | $OCH_3$ | CH | O | |
| H | $CH_2OCH_3$ | $CH_3$ | $CH_3$ | CH | O | |
| H | $CH_2OCH_3$ | $CH_3$ | $CH_3$ | N | O | |
| H | $CH_2OCH_3$ | $CH_3$ | $OCH_3$ | CH | O | |
| H | $CH_2OCH_3$ | $CH_3$ | $OCH_3$ | N | O | |
| H | $CH_2OCH_3$ | $OCH_3$ | $OCH_3$ | CH | O | |
| H | $CH_2OCH_3$ | $OCH_3$ | $OCH_3$ | N | O | |
| H | $CH_2OCH_3$ | $OCH_3$ | Cl | CH | O | |
| H | $CH_2OCH_3$ | $CH_3$ | $CH_3$ | CH | S | |
| H | $CH_2OCH_3$ | $CH_3$ | $OCH_3$ | N | S | |
| H | $CH_2OCH_3$ | $CH_3$ | $OCH_3$ | CH | S | |
| H | $CH_2OCH_3$ | $OCH_3$ | $OCH_3$ | N | S | |
| H | $CH_2OCH_3$ | $OCH_3$ | $OCH_3$ | CH | S | |
| H | $CH_2OCH_3$ | $OCH_3$ | Cl | CH | S | |
| H | $CH_2OCH_3$ | $CH_3$ | $CH(OCH_3)_2$ | CH | S | |
| H | $CH_2OC_2H_5$ | $CH_3$ | $CH_3$ | CH | O | |
| H | $CH_2OC_2H_5$ | $CH_3$ | $OCH_3$ | N | O | |
| H | $CH_2OC_2H_5$ | $CH_3$ | $OCH_3$ | CH | O | |
| H | $CH_2OC_2H_5$ | $OCH_3$ | $OCH_3$ | N | O | |
| H | $CH_2OC_2H_5$ | $OCH_3$ | $OCH_3$ | CH | O | |
| H | $CH_2OC_2H_5$ | $OCH_3$ | Cl | CH | O | |
| H | $CH_2OC_2H_5$ | $OCH_3$ | Br | CH | O | |
| $CH_3$ | $CH_2OC_2H_5$ | $CH_3$ | $OCH_3$ | CH | S | |
| H | $CH_2OC_2H_5$ | $CH_3$ | $CH_3$ | CH | S | |
| H | $CH_2OC_2H_5$ | $CH_3$ | $CH_3$ | N | S | |
| H | $CH_2OC_2H_5$ | $CH_3$ | $OCH_3$ | CH | S | |
| H | $CH_2OC_2H_5$ | $CH_3$ | $OCH_3$ | N | S | |
| H | $CH_2OC_2H_5$ | $OCH_3$ | $OCH_3$ | CH | S | |
| H | $CH_2OC_2H_5$ | $OCH_3$ | $OCH_3$ | N | S | |
| H | $CH_2OC_2H_5$ | $OCH_3$ | Cl | CH | S | |
| $CH_3$ | $(CH_2)_2COCH_3$ | $OCH_3$ | $OCH_3$ | CH | O | |
| H | $(CH_2)_2COCH_3$ | $CH_3$ | $CH_3$ | CH | O | |
| H | $(CH_2)_2COCH_3$ | $CH_3$ | $CH_3$ | N | O | |
| H | $(CH_2)_2COCH_3$ | $CH_3$ | $OCH_3$ | CH | O | |
| H | $(CH_2)_2COCH_3$ | $CH_3$ | $OCH_3$ | N | O | |
| H | $(CH_2)_2COCH_3$ | $OCH_3$ | $OCH_3$ | CH | O | |
| H | $(CH_2)_2COCH_3$ | $OCH_3$ | $OCH_3$ | N | O | |
| H | $(CH_2)_2COCH_3$ | $OCH_3$ | Cl | CH | O | |
| H | $(CH_2)_2COCH_3$ | $CH_3$ | $CH_3$ | CH | S | |
| H | $(CH_2)_2COCH_3$ | $CH_3$ | $OCH_3$ | N | S | |

TABLE 6a-continued

| | General Structure 2 wherein Q is Q-20 | | | | | |
|---|---|---|---|---|---|---|
| R | R'3 | X | Y | Z | W' | m.p. °C. |
| H | $(CH_2)_2COCH_3$ | $CH_3$ | $OCH_3$ | CH | S | |
| H | $(CH_2)_2COCH_3$ | $OCH_3$ | $OCH_3$ | N | S | |
| H | $(CH_2)_2COCH_3$ | $OCH_3$ | $OCH_3$ | CH | S | |
| H | $(CH_2)_2COCH_3$ | $OCH_3$ | Cl | CH | S | |
| H | $(CH_2)_2COCH_3$ | $CH_3$ | O | CH | S | |
| H | $(CH_2)_2CN$ | $CH_3$ | $OCH_3$ | CH | O | |
| H | $(CH_2)_2CN$ | $CH_3$ | $OCH_3$ | N | O | |
| H | $(CH_2)_2CN$ | $OCH_3$ | $OCH_3$ | CH | O | |
| H | $(CH_2)_2CN$ | $OCH_3$ | $OCH_3$ | N | O | |
| H | $(CH_2)_2CN$ | $CH_3$ | $CH_3$ | CH | S | |
| H | $(CH_2)_2CN$ | $CH_3$ | $OCH_3$ | N | S | |
| H | $(CH_2)_2CN$ | $OCH_3$ | $OCH_3$ | CH | S | |
| H | $(CH_2)_2CN$ | $OCH_3$ | Cl | CH | S | |
| H | $CH(CH_3)CN$ | $OCH_3$ | $OCH_3$ | CH | O | |
| H | $CH(CH_3)CN$ | $OCH_3$ | $OCH_3$ | N | O | |
| H | $CH(CH_3)CN$ | $CH_3$ | $OCH_3$ | CH | S | |
| H | $CH(CH_3)CN$ | $CH_3$ | $OCH_3$ | N | S | |
| H | $(CH_2)_3CN$ | $CH_3$ | $OCH_3$ | CH | O | |
| H | $(CH_2)_3CN$ | $CH_3$ | $OCH_3$ | N | O | |
| H | $(CH_2)_3CN$ | $OCH_3$ | $OCH_3$ | CH | O | |
| H | $(CH_2)_3CN$ | $OCH_3$ | $OCH_3$ | N | O | |
| H | $(CH_2)_3CN$ | $CH_3$ | $CH_3$ | CH | S | |
| H | $(CH_2)_3CN$ | $CH_3$ | $OCH_3$ | N | S | |
| H | $(CH_2)_3CN$ | $OCH_3$ | $OCH_3$ | $CH_3$ | S | |
| H | $(CH_2)_3CN$ | $OCH_3$ | $OCH_3$ | N | S | |
| H | $CH_2CH(CH_3)CN$ | $CH_3$ | $OCH_3$ | CH | O | |
| H | $CH_2CH(CH_3)CN$ | $CH_3$ | $OCH_3$ | N | O | |
| H | $CH_2CH(CH_3)CN$ | $OCH_3$ | $OCH_3$ | CH | S | |
| H | $CH_2CH(CH_3)CN$ | $OCH_3$ | Cl | CH | S | |
| H | $CH_2CH(CH_3)CN$ | $CH_3$ | $CH_3$ | CH | O | |
| H | $CH_2CH(CH_3)CN$ | $CH_3$ | $OCH_3$ | N | O | |
| H | $CH_2CH(CH_3)CN$ | $OCH_3$ | $OCH_3$ | CH | S | |
| H | $CH_2CH(CH_3)CN$ | $OCH_3$ | $CH_3$ | CH | S | |
| $CH_3$ | $CH_2CH(CH_3)CN$ | $OCH_3$ | $OCH_3$ | CH | S | |
| H | $CH(CN)C_2H_5$ | $CH_3$ | $OCH_3$ | N | O | |
| H | $CH(CN)C_2H_5$ | $OCH_3$ | $OCH_3$ | CH | O | |
| H | $CH(CN)C_2H_5$ | $OCH_3$ | $OCH_3$ | N | S | |
| H | $CH(CN)C_2H_5$ | $OCH_3$ | Cl | CH | S | |
| H | $C(CH_3)_2CN$ | $CH_3$ | $CH_3$ | CH | O | |
| H | $C(CH_3)_2CN$ | $OCH_3$ | $OCH_3$ | CH | O | |
| H | $C(CH_3)_2CN$ | $OCH_3$ | $OCH_3$ | N | S | |
| H | $C(CH_3)_2CN$ | $OCH_3$ | $OCH_3$ | CH | S | |
| H | $CH(CH_3)CO_2CH_3$ | $OCH_3$ | $OCH_3$ | CH | O | |
| H | $CH(CH_3)CO_2CH_3$ | $OCH_3$ | $OCH_3$ | N | O | |
| H | $CH(CH_3)CO_2CH_3$ | $CH_3$ | $OCH_3$ | CH | S | |
| H | $CH(CH_3)CO_2CH_3$ | $CH_3$ | $OCH_3$ | N | S | |
| H | $(CH_2)_3CO_2CH_3$ | $CH_3$ | $OCH_3$ | CH | O | |
| H | $(CH_2)_3CO_2CH_3$ | $CH_3$ | $OCH_3$ | N | O | |
| H | $(CH_2)_3CO_2CH_3$ | $OCH_3$ | $OCH_3$ | CH | O | |
| H | $(CH_2)_3CO_2CH_3$ | $OCH_3$ | $OCH_3$ | N | O | |
| H | $(CH_2)_3CO_2CH_3$ | $CH_3$ | $OCH_3$ | CH | S | |
| H | $(CH_2)_3CO_2CH_3$ | $CH_3$ | $OCH_3$ | N | S | |
| H | $(CH_2)_3CO_2CH_3$ | $OCH_3$ | $OCH_3$ | CH | S | |
| H | $(CH_2)_3CO_2CH_3$ | $OCH_3$ | $OCH_3$ | N | S | |
| H | $CH_2CH(CH_3)CO_2CH_3$ | $CH_3$ | $OCH_3$ | CH | O | |
| H | $CH_2CH(CH_3)CO_2CH_3$ | $CH_3$ | $OCH_3$ | N | O | |
| H | $CH_2CH(CH_3)CO_2CH_3$ | $OCH_3$ | $OCH_3$ | CH | S | |
| H | $CH_2CH(CH_3)CO_2CH_3$ | $OCH_3$ | $OCH_3$ | N | S | |
| H | $CH_2CH(CH_3)CO_2CH_3$ | $CH_3$ | $OCH_3$ | CH | O | |
| H | $CH_2CH(CH_3)CO_2CH_3$ | $CH_3$ | $OCH_3$ | N | O | |
| H | $CH_2CH(CH_3)CO_2CH_3$ | $OCH_3$ | $OCH_3$ | CH | S | |
| H | $CH_2CH(CH_3)CO_2CH_3$ | $OCH_3$ | $OCH_3$ | N | S | |
| H | $CH(CO_2CH_3)C_2H_5$ | $CH_3$ | $OCH_3$ | N | O | |
| H | $CH(CO_2CH_3)C_2H_5$ | $OCH_3$ | $OCH_3$ | CH | O | |
| H | $CH(CO_2CH_3)C_2H_5$ | $OCH_3$ | $OCH_3$ | N | S | |
| H | $CH(CO_2CH_3)C_2H_5$ | $OCH_3$ | $OCH_3$ | CH | S | |
| H | $C(CH_3)_2CO_3CH_3$ | $CH_3$ | $OCH_3$ | N | O | |
| H | $C(CH_3)_2CO_3CH_3$ | $OCH_3$ | $OCH_3$ | CH | O | |
| H | $C(CH_3)_2CO_3CH_3$ | $CH_3$ | $OCH_3$ | N | S | |
| H | $C(CH_3)_2CO_3CH_3$ | $OCH_3$ | $OCH_3$ | CH | S | |
| H | $(CH_2)_2CO_2C_2H_5$ | $CH_3$ | $CH_3$ | CH | O | |
| H | $(CH_2)_2CO_2C_2H_5$ | $CH_3$ | $OCH_3$ | N | O | |
| H | $(CH_2)_2CO_2C_2H_5$ | $OCH_3$ | $OCH_3$ | CH | O | |
| H | $(CH_2)_2CO_2C_2H_5$ | $OCH_3$ | $OCH_3$ | N | O | |
| H | $(CH_2)_2CO_2C_2H_5$ | $OCH_3$ | $OCH_3$ | CH | S | |
| H | $(CH_2)_2CO_2C_2H_5$ | $CH_3$ | $OCH_3$ | N | S | |
| H | $(CH_2)_2CO_2C_2H_5$ | $OCH_3$ | $OCH_3$ | CH | S | |
| H | $(CH_2)_2CO_2C_2H_5$ | $OCH_3$ | $OCH_3$ | N | S | |
| H | $CH(CH_3)CO_2C_2H_5$ | $OCH_3$ | $OCH_3$ | CH | O | |
| H | $CH(CH_3)CO_2C_2H_5$ | $OCH_3$ | $OCH_3$ | N | O | |

TABLE 6a-continued

| General Structure 2 wherein Q is Q-20 | | | | | | |
|---|---|---|---|---|---|---|
| R | R'3 | X | Y | Z | W' | m.p. °C. |
| H | $CH(CH_3)CO_2C_2H_5$ | $CH_3$ | $OCH_3$ | CH | S | |
| H | $CH(CH_3)CO_2C_2H_5$ | $CH_3$ | $OCH_3$ | N | S | |
| H | $(CH_2)_3CO_2C_2H_5$ | $CH_3$ | $OCH_3$ | CH | O | |
| H | $(CH_2)_3CO_2C_2H_5$ | $CH_3$ | $OCH_3$ | N | O | |
| H | $(CH_2)_3CO_2C_2H_5$ | $OCH_3$ | $OCH_3$ | CH | O | |
| H | $(CH_2)_3CO_2C_2H_5$ | $OCH_3$ | $OCH_3$ | N | O | |
| H | $(CH_2)_3CO_2C_2H_5$ | $CH_3$ | $OCH_3$ | CH | S | |
| H | $(CH_2)_3CO_2C_2H_5$ | $CH_3$ | $OCH_3$ | N | S | |
| H | $(CH_2)_3CO_2C_2H_5$ | $OCH_3$ | $OCH_3$ | CH | S | |
| H | $(CH_2)_3CO_2C_2H_5$ | $OCH_3$ | $OCH_3$ | N | S | |
| H | $CH_2CH(CH_3)CO_2C_2H_5$ | $CH_3$ | $OCH_3$ | CH | O | |
| H | $CH_2CH(CH_3)CO_2C_2H_5$ | $CH_3$ | $OCH_3$ | N | O | |
| H | $CH_2CH(CH_3)CO_2C_2H_5$ | $OCH_3$ | $OCH_3$ | CH | S | |
| H | $CH_2CH(CH_3)CO_2C_2H_5$ | $OCH_3$ | $OCH_3$ | N | S | |
| H | $CH_2CH(CH_3)CO_2C_2H_5$ | $CH_3$ | $OCH_3$ | CH | O | |
| H | $CH_2CH(CH_3)CO_2C_2H_5$ | $CH_3$ | $OCH_3$ | N | O | |
| H | $CH_2CH(CH_3)CO_2C_2H_5$ | $CH_3$ | $OCH_3$ | CH | S | |
| H | $CH_2CH(CH_3)CO_2C_2H_5$ | $OCH_3$ | $OCH_3$ | N | S | |
| H | $CH(CO_2C_2H_5)C_2H_5$ | $CH_3$ | $OCH_3$ | N | O | |
| H | $CH(CO_2C_2H_5)C_2H_5$ | $OCH_3$ | $OCH_3$ | CH | O | |
| H | $CH(CO_2C_2H_5)C_2H_5$ | $OCH_3$ | $OCH_3$ | N | S | |
| H | $CH(CO_2C_2H_5)C_2H_5$ | $OCH_3$ | $OCH_3$ | CH | S | |
| H | $C(CH_3)_2CO_2C_2H_5$ | $CH_3$ | $OCH_3$ | N | O | |
| H | $C(CH_3)_2CO_2C_2H_5$ | $OCH_3$ | $OCH_3$ | CH | O | |
| H | $C(CH_3)_2CO_2C_2H_5$ | $CH_3$ | $OCH_3$ | N | O | |
| H | $C(CH_3)_2CO_2C_2H_5$ | $OCH_3$ | $OCH_3$ | CH | S | |
| H | $(CH_2)_2OCH_3$ | $CH_3$ | $CH_3$ | CH | O | |
| H | $(CH_2)_2OCH_3$ | $CH_3$ | $OCH_3$ | N | O | |
| H | $(CH_2)_2OCH_3$ | $OCH_3$ | $OCH_3$ | CH | O | |
| H | $(CH_2)_2OCH_3$ | $OCH_3$ | $OCH_3$ | N | O | |
| H | $(CH_2)_2OCH_3$ | $OCH_3$ | $OCH_3$ | CH | S | |
| H | $(CH_2)_2OCH_3$ | $CH_3$ | $OCH_3$ | N | S | |
| H | $(CH_2)_2OCH_3$ | $OCH_3$ | $OCH_3$ | CH | S | |
| H | $(CH_2)_2OCH_3$ | $OCH_3$ | $OCH_3$ | N | S | |
| H | $CH(CH_3)OCH_3$ | $OCH_3$ | $OCH_3$ | CH | O | |
| H | $CH(CH_3)OCH_3$ | $OCH_3$ | $OCH_3$ | N | O | |
| H | $CH(CH_3)OCH_3$ | $CH_3$ | $OCH_3$ | CH | S | |
| H | $CH(CH_3)OCH_3$ | $CH_3$ | $OCH_3$ | N | S | |
| H | $(CH_2)_3OCH_3$ | $CH_3$ | $OCH_3$ | CH | O | |
| H | $(CH_2)_3OCH_3$ | $CH_3$ | $OCH_3$ | N | O | |
| H | $(CH_2)_3OCH_3$ | $OCH_3$ | $OCH_3$ | CH | O | |
| H | $(CH_2)_3OCH_3$ | $OCH_3$ | $OCH_3$ | N | O | |
| H | $(CH_2)_3OCH_3$ | $CH_3$ | $OCH_3$ | CH | S | |
| H | $(CH_2)_3OCH_3$ | $CH_3$ | $OCH_3$ | N | S | |
| H | $(CH_2)_3OCH_3$ | $OCH_3$ | $OCH_3$ | CH | S | |
| H | $(CH_2)_3OCH_3$ | $OCH_3$ | $OCH_3$ | N | S | |
| H | $CH_2CH(CH_3)OCH_3$ | $CH_3$ | $OCH_3$ | CH | O | |
| H | $CH_2CH(CH_3)OCH_3$ | $CH_3$ | $OCH_3$ | N | O | |
| H | $CH_2CH(CH_3)OCH_3$ | $OCH_3$ | $OCH_3$ | CH | S | |
| H | $CH_2CH(CH_3)OCH_3$ | $OCH_3$ | $OCH_3$ | N | S | |
| H | $CH_2CH(CH_3)OCH_3$ | $CH_3$ | $OCH_3$ | CH | O | |
| H | $CH_2CH(CH_3)OCH_3$ | $CH_3$ | $OCH_3$ | N | O | |
| H | $CH_2CH(CH_3)OCH_3$ | $CH_3$ | $OCH_3$ | CH | S | |
| H | $CH_2CH(CH_3)OCH_3$ | $OCH_3$ | $OCH_3$ | N | S | |
| H | $CH(OCH_3)C_2H_5$ | $CH_3$ | $OCH_3$ | N | O | |
| H | $CH(OCH_3)C_2H_5$ | $OCH_3$ | $OCH_3$ | CH | O | |
| H | $CH(OCH_3)C_2H_5$ | $OCH_3$ | $OCH_3$ | N | S | |
| H | $CH(OCH_3)C_2H_5$ | $OCH_3$ | $OCH_3$ | CH | S | |
| H | $C(CH_3)_2OCH_3$ | $CH_3$ | $OCH_3$ | N | O | |
| H | $C(CH_3)_2OCH_3$ | $OCH_3$ | $OCH_3$ | CH | O | |
| H | $C(CH_3)_2OCH_3$ | $CH_3$ | $OCH_3$ | N | O | |
| H | $C(CH_3)_2OCH_3$ | $OCH_3$ | $OCH_3$ | CH | S | |
| H | $(CH_2)_2OC_2H_5$ | $CH_3$ | $CH_3$ | CH | O | |
| H | $(CH_2)_2OC_2H_5$ | $CH_3$ | $OCH_3$ | N | O | |
| H | $(CH_2)_2OC_2H_5$ | $OCH_3$ | $OCH_3$ | CH | O | |
| H | $(CH_2)_2OC_2H_5$ | $OCH_3$ | $OCH_3$ | N | O | |
| H | $(CH_2)_2OC_2H_5$ | $OCH_3$ | $OCH_3$ | CH | S | |
| H | $(CH_2)_2OC_2H_5$ | $CH_3$ | $OCH_3$ | N | S | |
| H | $(CH_2)_2OC_2H_5$ | $OCH_3$ | $OCH_3$ | CH | S | |
| H | $(CH_2)_2OC_2H_5$ | $OCH_3$ | $OCH_3$ | N | S | |
| H | $CH(CH_3)OC_2H_5$ | $OCH_3$ | $OCH_3$ | CH | O | |
| H | $CH(CH_3)OC_2H_5$ | $OCH_3$ | $OCH_3$ | N | O | |
| H | $CH(CH_3)OC_2H_5$ | $CH_3$ | $OCH_3$ | CH | S | |
| H | $CH(CH_3)OC_2H_5$ | $CH_3$ | $OCH_3$ | N | S | |
| H | $(CH_2)_3OC_2H_5$ | $CH_3$ | $OCH_3$ | CH | O | |
| H | $(CH_2)_3OC_2H_5$ | $CH_3$ | $OCH_3$ | N | O | |
| H | $(CH_2)_3OC_2H_5$ | $OCH_3$ | $OCH_3$ | CH | O | |
| H | $(CH_2)_3OC_2H_5$ | $OCH_3$ | $OCH_3$ | N | O | |
| H | $(CH_2)_3OC_2H_5$ | $CH_3$ | $OCH_3$ | CH | S | |
| H | $(CH_2)_3OC_2H_5$ | $CH_3$ | $OCH_3$ | N | S | |

TABLE 6a-continued

| R | R'3 | X | Y | Z | W' | m.p. °C. |
|---|---|---|---|---|---|---|
| | General Structure 2 wherein Q is Q-20 | | | | | |
| H | $(CH_2)_3OC_2H_5$ | $OCH_3$ | $OCH_3$ | CH | S | |
| H | $(CH_2)_3OC_2H_5$ | $OCH_3$ | $OCH_3$ | N | S | |
| H | $CH_2CH(CH_3)OC_2H_5$ | $CH_3$ | $OCH_3$ | CH | O | |
| H | $CH_2CH(CH_3)OC_2H_5$ | $CH_3$ | $OCH_3$ | N | O | |
| H | $CH_2CH(CH_3)OC_2H_5$ | $OCH_3$ | $OCH_3$ | CH | S | |
| H | $CH_2CH(CH_3)OC_2H_5$ | $OCH_3$ | $OCH_3$ | N | S | |
| H | $CH(CH_3)CH_2OC_2H_5$ | $CH_3$ | $OCH_3$ | CH | O | |
| H | $CH(CH_3)CH_2OC_2H_5$ | $CH_3$ | $OCH_3$ | N | O | |
| H | $CH(CH_3)CH_2OC_2H_5$ | $CH_3$ | $OCH_3$ | CH | S | |
| H | $CH(CH_3)CH_2OC_2H_5$ | $OCH_3$ | $OCH_3$ | N | S | |
| H | $CH(OC_2H_5)C_2H_5$ | $CH_3$ | $OCH_3$ | N | O | |
| H | $CH(OC_2H_5)C_2H_5$ | $OCH_3$ | $OCH_3$ | CH | O | |
| H | $CH(OC_2H_5)C_2H_5$ | $OCH_3$ | $OCH_3$ | N | S | |
| H | $CH(OC_2H_5)C_2H_5$ | $OCH_3$ | $OCH_3$ | CH | S | |
| H | $CH(CH_3)_2OC_2H_5$ | $CH_3$ | $OCH_3$ | N | O | |
| H | $CH(CH_3)_2OC_2H_5$ | $OCH_3$ | $OCH_3$ | CH | O | |
| H | $CH(CH_3)_2OC_2H_5$ | $CH_3$ | $OCH_3$ | N | O | |
| H | $C(CH_3)_2OC_2H_5$ | $OCH_3$ | $OCH_3$ | CH | S | |
| H | $(CH_2)CH_2COCH_3$ | $CH_3$ | $CH_3$ | CH | O | |
| H | $(CH_2)CH_2COCH_3$ | $CH_3$ | $OCH_3$ | N | O | |
| H | $(CH_2)CH_2COCH_3$ | $OCH_3$ | $OCH_3$ | CH | O | |
| H | $(CH_2)CH_2COCH_3$ | $OCH_3$ | $OCH_3$ | N | O | |
| H | $(CH_2)CH_2COCH_3$ | $OCH_3$ | $OCH_3$ | CH | S | |
| H | $(CH_2)CH_2COCH_3$ | $CH_3$ | $OCH_3$ | N | S | |
| H | $(CH_2)CH_2COCH_3$ | $OCH_3$ | $OCH_3$ | CH | S | |
| H | $(CH_2)CH_2COCH_3$ | $OCH_3$ | $OCH_3$ | N | S | |
| H | $CH(CH_3)CH_2COCH_3$ | $OCH_3$ | $OCH_3$ | CH | O | |
| H | $CH(CH_3)CH_2COCH_3$ | $OCH_3$ | $OCH_3$ | N | O | |
| H | $CH(CH_3)CH_2COCH_3$ | $CH_3$ | $OCH_3$ | CH | S | |
| H | $CH(CH_3)CH_2COCH_3$ | $CH_3$ | $OCH_3$ | N | S | |
| H | $(CH_2)_3CH_2COCH_3$ | $CH_3$ | $OCH_3$ | CH | O | |
| H | $(CH_2)_3CH_2COCH_3$ | $CH_3$ | $OCH_3$ | N | O | |
| H | $(CH_2)_3CH_2COCH_3$ | $OCH_3$ | $OCH_3$ | CH | O | |
| H | $(CH_2)_3CH_2COCH_3$ | $OCH_3$ | $OCH_3$ | N | O | |
| H | $(CH_2)_3CH_2COCH_3$ | $CH_3$ | $OCH_3$ | CH | S | |
| H | $(CH_2)_3CH_2COCH_3$ | $CH_3$ | $OCH_3$ | N | S | |
| H | $(CH_2)_3CH_2COCH_3$ | $OCH_3$ | $OCH_3$ | CH | S | |
| H | $(CH_2)_3CH_2COCH_3$ | $OCH_3$ | $OCH_3$ | N | S | |
| H | $CH_2CH(CH_3)CH_2COCH_3$ | $CH_3$ | $OCH_3$ | CH | O | |
| H | $CH_2CH(CH_3)CH_2COCH_3$ | $CH_3$ | $OCH_3$ | N | O | |
| H | $CH_2CH(CH_3)CH_2COCH_3$ | $OCH_3$ | $OCH_3$ | CH | S | |
| H | $CH_2CH(CH_3)CH_2COCH_3$ | $OCH_3$ | $OCH_3$ | N | S | |
| H | $CH(CH_3)CH_2CH_2COCH_3$ | $CH_3$ | $OCH_3$ | CH | O | |
| H | $CH(CH_3)CH_2CH_2COCH_3$ | $CH_3$ | $OCH_3$ | N | O | |
| H | $CH(CH_3)CH_2CH_2COCH_3$ | $CH_3$ | $OCH_3$ | CH | S | |
| H | $CH(CH_3)CH_2CH_2COCH_3$ | $OCH_3$ | $OCH_3$ | N | S | |
| H | $CH(C_2H_5)CH_2COCH_3$ | $CH_3$ | $OCH_3$ | N | O | |
| H | $CH(C_2H_5)CH_2OCH_3$ | $OCH_3$ | $OCH_3$ | CH | O | |
| H | $CH(C_2H_5)CH_2OCH_3$ | $OCH_3$ | $OCH_3$ | N | S | |
| H | $CH(C_2H_5)CH_2OCH_3$ | $OCH_3$ | $OCH_3$ | CH | S | |
| H | $CH(CH_3)_2CH_2COCH_3$ | $CH_3$ | $OCH_3$ | N | O | |
| H | $CH(CH_3)_2CH_2COCH_3$ | $OCH_3$ | $OCH_3$ | CH | O | |
| H | $CH(CH_3)_2CH_2COCH_3$ | $CH_3$ | $OCH_3$ | N | O | |
| H | $C(CH_3)_2CH_2COCH_3$ | $OCH_3$ | $OCH_3$ | CH | S | |
| H | H | $OCH_3$ | $OCH_3$ | CH | O * | |
| H | H | $OCH_3$ | $OCH_3$ | CH | S * | |
| H | $CH_3$ | $OCH_3$ | $OCH_3$ | CH | O * | |
| H | $CH_3$ | $OCH_3$ | $OCH_3$ | CH | S * | |
| H | $SCH_3$ | $OCH_3$ | $OCH_3$ | CH | O * | |
| H | $SCH_3$ | $OCH_3$ | $OCH_3$ | CH | S * | |
| H | $SCH_2CH{=}CH_2$ | $OCH_3$ | $OCH_3$ | CH | O * | |
| H | $SCH_3CH{=}CH_2$ | $OCH_3$ | $OCH_3$ | CH | S * | |
| H | SH | $OCH_3$ | $OCH_3$ | CH | O * | |
| H | SH | $OCH_3$ | $OCH_3$ | CH | S * | |

W is O, unless indicated by * where W is S in all Tables.

TABLE 6b

| R | $R_3'$ | $R_4$ | X | Y | Z | m.p. °C. |
|---|---|---|---|---|---|---|
| | General Structure 2 wherein Q is Q-28. | | | | | |
| H | H | H | $CH_3$ | $OCH_3$ | CH | 216–218 |
| H | H | H | $CH_3$ | $OCH_3$ | N | 197–200 |
| H | H | H | $OCH_3$ | $OCH_3$ | CH | 180–186 |
| H | H | H | $OCH_3$ | $OCH_3$ | N | 196–198 |
| H | H | H | $CH_3$ | $CH_3$ | CH | 242–244 |
| H | H | H | $CH_3$ | $CH_3$ | N | |
| H | $CH_3$ | H | $CH_3$ | $OCH_3$ | CH | |
| H | H | H | Cl | $OCH_3$ | CH | 206–208 |

TABLE 6b-continued

| R | $R_3'$ | $R_4$ | X | Y | Z | m.p. °C. |
|---|---|---|---|---|---|---|
| | General Structure 2 wherein Q is Q-28. | | | | | |
| H | H | $CH_3$ | $CH_3$ | $OCH_3$ | N | |
| H | $CH_3$ | $CH_3$ | $OCH_3$ | $OCH_3$ | CH | |
| $CH_3$ | $CH_3$ | $CH_3$ | $OCH_3$ | $OCH_3$ | N | |

TABLE 6b-continued

| General Structure 2 wherein Q is Q-28. | | | | | | |
|---|---|---|---|---|---|---|
| R | R3' | R4 | X | Y | Z | m.p. °C. |
| H | H | H | $CH_3$ | 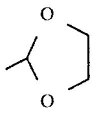 | CH | |
| H | H | H | $CH_3$ | $C_2H_5$ | CH | |
| H | $CH_3$ | H | $CH_3$ | $CH_3$ | CH | |
| H | $CH_3$ | H | $CH_3$ | $OCH_3$ | N | |
| H | $CH_3$ | H | $OCH_3$ | $OCH_3$ | CH | |
| H | $CH_3$ | H | $OCH_3$ | $OCH_3$ | N | |
| H | $CH_3$ | H | $OCH_3$ | Cl | CH | |
| H | $CH_3$ | H | $CH_3$ | $CH_3$ | N | |
| H | Cl | H | $CH_3$ | $CH_3$ | CH | |
| H | Cl | H | $CH_3$ | $CH_3$ | N | |
| H | Cl | H | $CH_3$ | $OCH_3$ | CH | |
| H | Cl | H | $CH_3$ | $OCH_3$ | N | |
| H | Cl | H | $OCH_3$ | $OCH_3$ | CH | |
| H | Cl | H | $OCH_3$ | $OCH_3$ | N | |
| H | Cl | H | $OCH_3$ | Cl | CH | |
| H | Cl | $CH_3$ | $CH_3$ | $OCH_3$ | CH | |
| H | Cl | $CH_3$ | $CH_3$ | $OCH_3$ | N | |
| H | Cl | $CH_3$ | $OCH_3$ | $OCH_3$ | CH | |
| H | Cl | $CH_3$ | $OCH_3$ | $OCH_3$ | N | |
| H | Br | H | $OCH_3$ | $OCH_3$ | CH | |
| H | Br | H | $CH_3$ | $CH_3$ | CH | |
| H | Br | H | $CH_3$ | $OCH_3$ | N | |
| H | Br | H | $CH_3$ | $OCH_3$ | CH | |
| H | Br | H | $OCH_3$ | $OCH_3$ | N | |
| H | Br | H | $OCH_3$ | $OCH_3$ | CH | |
| H | Br | H | $OCH_3$ | Cl | CH | |
| H | H | H | $OCH_3$ | $OCH_3$ | CH* | |
| H | $CH_3$ | H | $OCH_3$ | $OCH_3$ | CH* | |
| H | H | $CH_3$ | $OCH_3$ | $OCH_3$ | CH* | |
| H | $CH_3$ | $CH_3$ | $OCH_3$ | $OCH_3$ | CH* | |
| H | Cl | H | $OCH_3$ | $OCH_3$ | CH* | |
| H | Cl | $CH_3$ | $OCH_3$ | $OCH_3$ | CH* | |
| H | Br | H | $OCH_3$ | $OCH_3$ | CH* | |
| H | Br | $CH_3$ | $OCH_3$ | $OCH_3$ | CH* | |

*Wherein W is O, unless indicated by * where W is S in all Tables.

TABLE 6c

| General Structure 2 | | | | | | | | |
|---|---|---|---|---|---|---|---|---|
| Q | R | R3 | R4 | X | Y | Z | n' | m.p °C. |
| Q-33 | H | H | H | $CH_3$ | $OCH_3$ | CH | 0 | 168-173 |
| Q-33 | H | H | H | $CH_3$ | $OCH_3$ | N | 0 | 189-190 |
| Q-33 | H | H | H | $OCH_3$ | $OCH_3$ | CH | 0 | 195-196 |
| Q-33 | H | H | H | $OCH_3$ | $OCH_3$ | N | 0 | 183-185 |
| Q-33 | H | H | H | $CH_3$ | $CH_3$ | CH | 0 | 164-167 |
| Q-33 | H | 3-$CH_3$ | H | $CH_3$ | $OCH_3$ | CH | 0 | |
| Q-33 | H | 4-$CH_3$ | H | $CH_3$ | $OCH_3$ | CH | 0 | |
| Q-33 | H | 5-$CH_3$ | H | $CH_3$ | $OCH_3$ | CH | 0 | |
| Q-33 | H | H | H | $CH_3$ | $CH_3$ | N | 0 | |
| Q-33 | H | 6-$CH_3$ | H | $CH_3$ | $OCH_3$ | CH | 0 | |
| Q-33 | H | 3-$CH_3$ | 5-$CH_3$ | $CH_3$ | $OCH_3$ | N | 0 | |
| Q-33 | H | 4-$CH_3$ | 6-$CH_3$ | $CH_3$ | $OCH_3$ | N | 0 | |
| Q-33 | $CH_3$ | H | H | $OCH_3$ | $OCH_3$ | CH | 0 | |
| Q-33 | H | H | H | $CH_3$ | $CH_2OCH_3$ | CH | 0 | |
| Q-33 | H | H | H | Cl | $OCH_3$ | CH | 0 | 183-184 |
| Q-33 | H | H | H | $CH_3$ | $CF_3$ | CH | 0 | |
| Q-33 | H | H | H | Cl | $OCH_3$ | CH | 1 | 184-187 |
| Q-33 | H | H | H | $CH_3$ | $OCH_3$ | CH | 1 | 185-187 |
| Q-33 | H | H | H | $CH_3$ | $OCH_3$ | N | 1 | 200 |
| Q-33 | H | H | H | $OCH_3$ | $OCH_3$ | CH | 1 | 191-192 |
| Q-33 | H | H | H | $OCH_3$ | $OCH_3$ | N | 1 | 190 |
| Q-33 | H | H | H | $CH_3$ | $CH_3$ | CH | 1 | 171-174 |
| Q-33 | H | 3-$CH_3$ | H | $CH_3$ | $OCH_3$ | CH | 1 | |
| Q-33 | H | 4-$CH_3$ | H | $CH_3$ | $OCH_3$ | CH | 1 | |
| Q-33 | H | 5-$CH_3$ | H | $CH_3$ | $OCH_3$ | CH | 1 | |
| Q-33 | H | H | H | $CH_3$ | $CH_3$ | N | 1 | |
| Q-33 | H | 6-$CH_3$ | H | $CH_3$ | $OCH_3$ | CH | 1 | |
| Q-33 | H | 3-$CH_3$ | 5-$CH_3$ | $CH_3$ | $OCH_3$ | N | 1 | |
| Q-33 | H | 4-$CH_3$ | 6-$CH_3$ | $CH_3$ | $CH_3$ | N | 1 | |
| Q-33 | $CH_3$ | H | H | $OCH_3$ | $OCH_3$ | CH | 1 | |
| Q-33 | H | H | H | $CH_3$ | $CH_2OCH_3$ | CH | 1 | |
| Q-33 | H | H | H | Cl | $OC_2H_5$ | CH | 1 | |
| Q-33 | H | H | H | $CH_3$ | $CF_3$ | CH | 1 | |
| Q-34 | H | H | H | $CH_3$ | $OCH_3$ | CH | 0 | |
| Q-34 | H | H | H | $CH_3$ | $OCH_3$ | N | 0 | |
| Q-34 | H | H | H | $OCH_3$ | $OCH_3$ | CH | 0 | |
| Q-34 | H | H | H | $OCH_3$ | $OCH_3$ | N | 0 | |
| Q-34 | H | 2-$CH_3$ | H | $CH_3$ | $CH_3$ | CH | 0 | |
| Q-34 | H | 4-$CH_3$ | H | $CH_3$ | $CH_3$ | N | 0 | |
| Q-34 | H | 5-$CH_3$ | H | $CH_3$ | $OCH_3$ | CH | 0 | |
| Q-34 | H | 6-$CH_3$ | H | $CH_3$ | $OCH_3$ | N | 0 | |
| Q-34 | H | 2-$CH_3$ | 6-$CH_3$ | $OCH_3$ | $OCH_3$ | CH | 0 | |
| Q-34 | H | 4-$CH_3$ | 6-$CH_3$ | $OCH_3$ | $OCH_3$ | N | 0 | |
| Q-34 | H | H | H | $CH_3$ | $CH_3$ | N | 0 | |
| Q-34 | $CH_3$ | H | H | $CH_3$ | $CH_3$ | CH | 0 | |
| Q-34 | H | H | H | $CH_3$ | $CH_3$ | CH | 0 | |
| Q-34 | H | H | H | $CH_3$ | $OCF_2H$ | CH | 0 | |
| Q-34 | H | H | H | $CH_3$ | $OCH_3$ | CH | 1 | |
| Q-34 | H | H | H | $CH_3$ | $OCH_3$ | N | 1 | |
| Q-34 | H | H | H | $OCH_3$ | $OCH_3$ | CH | 1 | |
| Q-34 | H | H | H | $OCH_3$ | $OCH_3$ | N | 1 | |
| Q-34 | H | 2-$CH_3$ | H | $CH_3$ | $CH_3$ | CH | 1 | |

TABLE 6c-continued

General Structure 2

| Q | R | $R_3$ | $R_4$ | X | Y | Z | n' | m.p °C. |
|---|---|---|---|---|---|---|---|---|
| Q-34 | H | 4-$CH_3$ | H | $CH_3$ | $CH_3$ | N | 1 | |
| Q-34 | H | 5-$CH_3$ | H | $CH_3$ | $OCH_3$ | CH | 1 | |
| Q-34 | H | 6-$CH_3$ | H | $CH_3$ | $OCh_3$ | N | 1 | |
| Q-34 | H | 2-$CH_3$ | 6-$CH_3$ | $OCH_3$ | $OCH_3$ | CH | 1 | |
| Q-34 | H | 4-$CH_3$ | 6-$CH_3$ | $OCH_3$ | $OCH_3$ | N | 1 | |
| Q-34 | H | H | H | $CH_3$ | $CH_3$ | N | 1 | |
| Q-34 | $CH_3$ | H | H | $CH_3$ | $CH_3$ | CH | 1 | |
| Q-34 | H | H | H | $CH_3$ | $CH_3$ | CH | 1 | |
| Q-34 | H | H | H | $CH_3$ | $OCF_2H$ | CH | 1 | |
| Q-35 | H | H | H | $CH_3$ | $OCH_3$ | CH | 0 | |
| Q-35 | H | H | H | $CH_3$ | $OCH_3$ | N | 0 | |
| Q-35 | H | H | H | $OCH_3$ | $OCH_3$ | CH | 0 | |
| Q-35 | H | H | H | $OCH_3$ | $OCH_3$ | N | 0 | |
| Q-35 | H | 2-$CH_3$ | H | $CH_3$ | $CH_3$ | CH | 0 | |
| Q-35 | H | H | H | Cl | $OCH_3$ | CH | 0 | |
| Q-35 | H | 3-$CH_3$ | H | $CH_3$ | $CH_3$ | N | 0 | |
| Q-35 | H | 2-$CH_3$ | 6-$CH_3$ | $CH_3$ | $OCH_3$ | CH | 0 | |
| Q-35 | H | 2-$CH_3$ | 3-$CH_3$ | $CH_3$ | $OCH_3$ | N | 0 | |
| Q-35 | H | 3-$CH_3$ | 5-$CH_3$ | $CH_3$ | $OCH_3$ | N | 0 | |
| Q-35 | H | H | H | $CH_3$ | $CH_3$ | N | 0 | |
| Q-35 | $CH_3$ | H | H | $OCH_3$ | $OCH_3$ | CH | 0 | |
| Q-35 | H | H | H | $CH_3$ | $OCH_2CF_3$ | CH | 0 | |
| Q-35 | H | H | H | $CH_3$ | $CH_3$ | CH | 0 | |
| Q-35 | H | H | H | $CH_3$ | $OCH_3$ | CH | 1 | |
| Q-35 | H | H | H | $CH_3$ | $OCH_3$ | N | 1 | |
| Q-35 | H | H | H | $OCH_3$ | $OCH_3$ | CH | 1 | |
| Q-35 | H | H | H | $OCH_3$ | $OCH_3$ | N | 1 | |
| Q-35 | H | 2-$CH_3$ | H | $CH_3$ | $CH_3$ | CH | 1 | |
| Q-35 | H | H | H | Cl | $OCH_3$ | CH | 1 | |
| Q-35 | H | 3-$CH_3$ | H | $CH_3$ | $CH_3$ | N | 1 | |
| Q-35 | H | 2-$CH_3$ | 6-$CH_3$ | $CH_3$ | $OCH_3$ | CH | 1 | |
| Q-35 | H | 2-$CH_3$ | 3-$CH_3$ | $CH_3$ | $OCH_3$ | N | 1 | |
| Q-35 | H | 3-$CH_3$ | 5-$CH_3$ | $CH_3$ | $OCH_3$ | N | 1 | |
| Q-35 | H | H | H | $CH_3$ | $CH_3$ | N | 1 | |
| Q-35 | $CH_3$ | H | H | $OCH_3$ | $OCH_3$ | CH | 1 | |
| Q-35 | H | H | H | $CH_3$ | $OCH_2CF_3$ | CH | 1 | |
| Q-35 | H | H | H | $CH_3$ | $CH_3$ | CH | 1 | |

TABLE 7a

General Structure 3 wherein Q is Q-1.

| R | $R_1$ | $R_2$ | X | Y | Z | m.p. °C. |
|---|---|---|---|---|---|---|
| H | H | H | $CH_3$ | $CH_3$ | CH | |
| H | H | H | $CH_3$ | $CH_3$ | N | |
| H | H | H | $CH_3$ | $OCH_3$ | CH | |
| H | H | H | $CH_3$ | $OCH_3$ | N | |
| H | H | H | $OCH_3$ | $OCH_3$ | CH | |
| H | H | H | Cl | $OCH_3$ | CH | |
| H | H | H | $OCH_3$ | $OCH_3$ | N | |
| H | 4-Cl | H | $CH_3$ | $OCH_3$ | CH | |
| H | H | 4-F | $CH_3$ | $CH_3$ | N | |
| H | 4-$CH_3$ | H | $OCH_3$ | $OCH_3$ | CH | |
| H | H | 4-$OCH_3$ | $CH_3$ | $OCH_3$ | N | |
| H | H | 4-$CF_3$ | $CH_3$ | $OCH_3$ | CH | |
| $CH_3$ | 3-$CH_3$ | 5-$CH_3$ | $CH_3$ | $CH_3$ | N | |
| H | H | H | $OCH_3$ | $OCF_2H$ | CH | |
| H | H | H | $OCH_3$ | cyclopropyl | N | |
| H | H | H | $OC_2H_5$ | $OCH_3$ | N | |
| H | H | H | O—n-$C_4H_9$ | $CH_3$ | CH | |
| H | H | H | $OCH_2CF_3$ | $OCH_3$ | N | |
| H | H | H | $OCH_2CH_2CH_2F$ | $CH_3$ | CH | |
| H | H | H | $SCH_3$ | $OCH_3$ | CH | |
| H | H | H | $SCH(CH_3)_2$ | $CH_3$ | N | |
| H | H | H | $CH_2CH_2OCH_3$ | $CH_3$ | CH | |
| H | H | H | $CH_2OCH_2CH_3$ | $OCH_3$ | N | |
| H | H | H | $N(CH_2CH_3)_2$ | $CH_3$ | CH | |
| H | H | H | $N(CH_2CH_2CH_3)$ | $OCH_3$ | N | |
| H | H | H | $CH_3$ | $OCH_2CH{=}CH_2$ | CH | |
| H | H | H | $OCH_3$ | $OCH_2C{\equiv}CCH_3$ | N | |
| H | H | H | $CH_3$ | cyclopentyl | CH | |
| H | H | H | $OCH_3$ | $CH_2SCH_3$ | N | |
| H | H | H | $CH_3$ | $C(O)CH_3$ | CH | |
| H | H | H | $CH_3$ | 1,3-dioxan-2-yl | N | |
| H | H | H | $OCH_3$ | $N(OCH_3)CH_3$ | CH | |
| H | H | H | $OCH_3$ | $OCH_3$ | CH | * |
| H | H | H | $OCH_3$ | $CH_3$ | N | * |

TABLE 7a-continued

General Structure 3 wherein Q is Q-1.

| R | $R_1$ | $R_2$ | X | Y | Z | m.p. °C. |
|---|---|---|---|---|---|---|
| H | 4-Cl | H | $OCH_3$ | $OCH_3$ | CH | * |

W is O, unless indicated by * where W is S in all Tables.

TABLE 7b

General Structure 3

| Q | R | $R_3$ | $R_4$ | $R_5$ | X | Y | Z | W' | m.p. °C. |
|---|---|---|---|---|---|---|---|---|---|
| Q-2 | H | H | H | H | $CH_3$ | $OCH_3$ | CH | O | |
| Q-2 | H | H | H | H | $CH_3$ | $OCH_3$ | N | O | |
| Q-2 | H | H | H | H | $OCH_3$ | $OCH_3$ | CH | O | |
| Q-2 | H | H | H | H | $OCH_3$ | $OCH_3$ | N | O | |
| Q-2 | H | $CH_3$ | H | H | $CH_3$ | $CH_3$ | CH | O | |
| Q-2 | H | H | $CH_3$ | H | $CH_3$ | $OCH_3$ | N | O | |
| Q-2 | H | H | H | $CH_3$ | $CH_3$ | $OCH_3$ | CH | O | |
| Q-2 | $CH_3$ | H | H | H | CH | $CH_3$ | CH | O | |
| Q-2 | H | $CH_3$ | $CH_3$ | H | $OCH_3$ | $OCH_3$ | N | O | |
| Q-2 | H | H | H | H | Cl | $OCH_3$ | CH | S | |
| Q-2 | H | H | H | H | $CH_3$ | $OCH_3$ | CH | S | |
| Q-2 | H | H | H | H | $CH_3$ | $OCH_3$ | N | S | |
| Q-2 | H | H | H | H | $OCH_3$ | $OCH_3$ | CH | S | |
| Q-2 | H | H | H | H | $OCH_3$ | $OCH_3$ | N | S | |
| Q-2 | H | H | H | H | $CH_3$ | $CH_3$ | CH | S | |
| Q-2 | H | $CH_3$ | H | H | $CH_3$ | $CH_3$ | CH | S | |
| Q-2 | H | H | $CH_3$ | H | $CH_3$ | $CH_3$ | N | S | |
| Q-2 | H | H | H | $CH_3$ | $CH_3$ | $OCH_3$ | CH | S | |
| Q-2 | H | $CH_3$ | $CH_3$ | H | $CH_3$ | $OCH_3$ | N | S | |
| Q-2 | H | H | $CH_3$ | $CH_3$ | $OCH_3$ | $OCH_3$ | CH | S | |
| Q-2 | H | $CH_3$ | H | $CH_3$ | $OCH_3$ | $OCH_3$ | N | S | |
| Q-2 | H | $CH_3$ | $CH_3$ | $CH_3$ | $CH_3$ | $OCH_3$ | CH | S | |
| Q-2 | $CH_3$ | H | H | H | $CH_3$ | $CH_3$ | CH | S | |
| Q-2 | H | H | H | H | Cl | $OC_2H_5$ | CH | S | |
| Q-3 | H | H | H | H | $CH_3$ | $CH_3$ | CH | O | |
| Q-3 | H | H | H | H | $CH_3$ | $CH_3$ | N | O | |
| Q-3 | H | H | H | H | $CH_3$ | $OCH_3$ | CH | O | |
| Q-3 | H | H | H | H | $CH_3$ | $OCH_3$ | N | O | |
| Q-3 | H | H | H | H | $OCH_3$ | $OCH_3$ | CH | O | |
| Q-3 | H | H | H | H | $OCH_3$ | $OCH_3$ | N | O | |
| Q-3 | H | $CH_3$ | H | H | $CH_3$ | $CH_3$ | CH | O | |
| Q-3 | H | H | $CH_3$ | H | $CH_3$ | $CH_3$ | N | O | |
| Q-3 | H | H | H | $CH_3$ | $CH_3$ | $OCH_3$ | CH | O | |
| Q-3 | H | $CH_3$ | $CH_3$ | H | $CH_3$ | $OCH_3$ | N | O | |
| Q-3 | H | H | $CH_3$ | $CH_3$ | $OCH_3$ | $OCH_3$ | CH | O | |
| Q-3 | H | $CH_3$ | H | $CH_3$ | $OCH_3$ | $OCH_3$ | N | O | |
| Q-3 | H | H | H | H | $OCH_3$ | $OCH_2CF_3$ | CH | O | |
| Q-3 | H | H | H | H | $OCH_3$ | $OCH_2CF_3$ | CH | O | |
| Q-3 | $CH_3$ | H | H | H | Cl | $OCH_3$ | CH | O | |
| Q-3 | H | H | H | H | $CH_3$ | $OCH_3$ | CH | S | |
| Q-3 | H | H | H | H | $OCH_3$ | $OCH_3$ | CH | S | |
| Q-3 | H | H | H | H | $OCH_3$ | $OCH_3$ | N | S | |
| Q-3 | H | $CH_3$ | H | H | $CH_3$ | $CH_3$ | CH | S | |
| Q-3 | H | H | $CH_3$ | H | $CH_3$ | $OCH_3$ | N | S | |
| Q-3 | H | H | H | $CH_3$ | $CH_3$ | $OCH_3$ | CH | S | |
| Q-3 | $CH_3$ | H | H | H | $CH_3$ | $CH_3$ | CH | S | |
| Q-3 | H | H | $CH_3$ | $CH_3$ | $OCH_3$ | $OCH_3$ | N | S | |
| Q-3 | H | H | H | H | $OCH_3$ | $CF_3$ | N | S | |
| Q-4 | H | H | H | H | $CH_3$ | $OCH_3$ | CH | — | |
| Q-4 | H | H | H | H | $OCH_3$ | Cl | CH | — | |
| Q-4 | H | H | H | H | $CH_3$ | $OCH_3$ | N | — | |
| Q-4 | H | H | H | H | $CH_3$ | $CH_3$ | CH | — | |
| Q-4 | H | H | H | H | $OCH_3$ | $OCH_3$ | CH | — | |
| Q-4 | H | H | H | H | $OCH_3$ | $OCH_3$ | N | — | |
| Q-4 | H | $CH_3$ | H | H | $CH_3$ | $CH_3$ | CH | — | |
| Q-4 | H | H | $CH_3$ | H | $CH_3$ | $OCH_3$ | N | — | |
| Q-4 | H | H | H | $CH_3$ | $CH_3$ | $OCH_3$ | CH | — | |
| Q-4 | $CH_3$ | H | H | H | $OCH_3$ | $OCH_3$ | CH | — | |
| Q-4 | $CH_3$ | $CH_3$ | $CH_3$ | $CH_3$ | $CH_3$ | $OCH_3$ | N | — | |
| Q-4 | H | $CH_3$ | H | $CH_3$ | $CH_3$ | $OCH_3$ | CH | — | |
| Q-4 | H | H | H | H | $OCH_3$ | $OCH_2CF_3$ | N | — | |
| Q-4 | H | H | H | H | $CH_3$ | $NHCH_3$ | CH | — | |
| Q-4 | H | H | H | H | $CH_3$ | $CH_3$ | CH | — | |
| Q-4 | H | H | H | H | $CH_3$ | $CH_3$ | N | — | |
| Q-9 | H | H | H | H | $CH_3$ | $OCH_3$ | CH | — | |
| Q-9 | H | H | H | H | $CH_3$ | $OCH_3$ | N | — | |
| Q-9 | H | H | H | H | $OCH_3$ | $OCH_3$ | CH | — | |
| Q-9 | H | H | H | H | $OCH_3$ | $OCH_3$ | N | — | |
| Q-9 | $CH_3$ | $CH_3$ | H | H | $CH_3$ | $CH_3$ | CH | — | |

TABLE 7b-continued

General Structure 3

| Q | R | $R_3$ | $R_4$ | $R_5$ | X | Y | Z | W' | m.p. °C. |
|---|---|---|---|---|---|---|---|---|---|
| Q-9 | H | H | $CH_3$ | H | $CH_3$ | $OCH_3$ | N | — | |
| Q-9 | H | H | H | $CH_3$ | $OCH_3$ | $OCH_3$ | CH | — | |
| Q-9 | H | H | $CH_3$ | $CH_3$ | $CH_3$ | $OCH_3$ | CH | — | |
| Q-9 | H | H | H | H | Cl | $OCH_2CH_3$ | CH | — | |
| Q-9 | H | H | H | H | $OCH_3$ | $CH(OCH_3)_2$ | CH | — | |
| Q-9 | H | H | H | H | $NH_2$ | $CH_3$ *CH* | — | | |
| Q-9 | H | H | H | H | $NHCH(CH_3)_2$ | $CH_3$ | CH | — | |
| Q-9 | H | H | H | H | $CH_2O$—n-$C_4H_9$ | $CH_3$ | CH | — | |
| Q-9 | H | H | H | H | S—n-$C_4H_9$ | $CH_3$ | CH | — | |
| Q-9 | H | H | H | H | S—n-$CH_2CH_2F$ | $CH_3$ | CH | — | |

TABLE 7c

General Structure 3

| Q | R | $R_3$' | $R_4$ | X | Y | Z | W'' | m.p. °C. |
|---|---|---|---|---|---|---|---|---|
| Q-10 | H | H | H | $CH_3$ | $OCH_3$ | CH | O | |
| Q-10 | H | H | H | $CH_3$ | $CH_3$ | CH | O | |
| Q-10 | H | H | H | $OCH_3$ | $OCH_3$ | N | O | |
| Q-10 | H | H | H | $OCH_3$ | Cl | CH | O | |
| Q-10 | H | H | H | $OCH_3$ | $OCH_3$ | CH | O | |
| Q-10 | H | H | H | $OCH_3$ | $OCH_3$ | N | O | |
| Q-10 | H | H | H | $CH_3$ | $OCH_3$ | CH | S | |
| Q-10 | H | H | H | $CH_3$ | $OCH_3$ | N | S | |
| Q-10 | H | H | H | $OCH_3$ | $OCH_3$ | CH | S | |
| Q-10 | H | H | H | $OCH_3$ | $OCH_3$ | N | S | |
| Q-10 | H | H | H | $OCH_3$ | Cl | CH | $NCH_3$ | |
| Q-10 | H | H | H | $CH_3$ | $CH_3$ | CH | $NCH_3$ | |
| Q-10 | H | H | H | $CH_3$ | $OCH_3$ | N | $NCH_3$ | |
| Q-10 | H | H | H | $CH_3$ | $CH_3$ | N | $NCH_3$ | |
| Q-10 | H | H | H | $OCH_3$ | $OCH_3$ | CH | $NCH_3$ | |
| Q-10 | H | H | H | $OCH_3$ | $OCH_3$ | N | $NCH_3$ | |
| Q-10 | H | $CH_3$ | H | $CH_3$ | $CH_3$ | CH | O | |
| Q-10 | H | H | $CH_3$ | $CH_3$ | $OCH_3$ | N | O | |
| Q-10 | H | $CH_3$ | $CH_3$ | $CH_3$ | $OCH_3$ | CH | O | |
| Q-10 | $CH_3$ | H | H | $OCH_3$ | $OCH_3$ | N | O | |
| Q-10 | H | H | H | $CH_3$ | 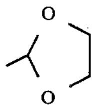 | CH | O | |
| Q-10 | H | $CH_3$ | H | $CH_3$ | $CH_3$ | CH | S | |
| Q-10 | H | H | $CH_3$ | $CH_3$ | $OCH_3$ | N | S | |
| Q-10 | H | $CH_3$ | $CH_3$ | $CH_3$ | $OCH_3$ | CH | S | |
| Q-10 | $CH_3$ | $CH_3$ | $CH_3$ | $CH_3$ | $OCH_3$ | CH | S | |
| Q-10 | $CH_3$ | H | H | $OCH_3$ | $OCH_3$ | N | S | |
| Q-10 | H | H | H | $CH_3$ | $OC_2H_5$ | CH | S | |
| Q-10 | H | H | $CH_3$ | $CH_3$ | $CH_3$ | N | $NCH_3$ | |
| Q-10 | H | H | $CH_3$ | $CH_3$ | $OCH_3$ | CH | $NCH_3$ | |
| Q-10 | H | $CH_3$ | $CH_3$ | $OCH_3$ | $OCH_3$ | N | $NCH_3$ | |
| Q-10 | $CH_3$ | H | H | $OCH_3$ | $OCH_3$ | N | $NCH_3$ | |
| Q-11 | H | H | H | $CH_3$ | $CH_3$ | N | O | |
| Q-11 | H | H | H | $CH_3$ | $CH_3$ | CH | O | |
| Q-11 | H | H | H | $CH_3$ | $OCH_3$ | N | O | |
| Q-11 | H | H | H | $CH_3$ | $OCH_3$ | CH | O | |
| Q-11 | H | H | H | $OCH_3$ | $OCH_3$ | CH | O | |
| Q-11 | H | H | H | $OCH_3$ | $OCH_3$ | N | O | |
| Q-11 | H | H | H | $CH_3$ | $CH_3$ | CH | S | |
| Q-11 | H | H | H | $CH_3$ | $OCH_3$ | CH | S | |
| Q-11 | H | H | H | $CH_3$ | $OCH_3$ | CH | S | |
| Q-11 | H | H | H | $OCH_3$ | $OCH_3$ | CH | S | |
| Q-11 | H | H | H | $CH_3$ | $CH_3$ | CH | $NCH_3$ | |
| Q-11 | H | H | H | $CH_3$ | $OCH_3$ | CH | $NCH_3$ | |
| Q-11 | H | H | H | $OCH_3$ | $OCH_3$ | CH | $NCH_3$ | |
| Q-11 | H | H | H | $CH_3$ | $OCH_3$ | N | $NCH_3$ | |
| Q-11 | H | $CH_3$ | H | $CH_3$ | $OCH_3$ | N | O | |
| Q-11 | H | H | $CH_3$ | $OCH_3$ | $OCH_3$ | N | O | |
| Q-11 | H | $CH_3$ | $CH_3$ | $CH_3$ | $OCH_3$ | CH | O | |
| Q-11 | $CH_3$ | H | H | $CH_3$ | $OCH_3$ | CH | O | |
| Q-11 | H | H | H | $CH_3$ | $C_2H_5$ | N | O | |
| Q-11 | H | H | H | $CH_3$ | $CH_2OCH_3$ | CH | O | |
| Q-11 | H | $CH_3$ | H | $CH_3$ | $OCH_3$ | N | S | |
| Q-11 | H | H | $CH_3$ | $OCH_3$ | $OCH_3$ | N | S | |
| Q-11 | H | $CH_3$ | $CH_3$ | $CH_3$ | $OCH_3$ | CH | S | |
| Q-11 | $CH_3$ | H | H | $CH_3$ | $OCH_3$ | CH | S | |
| Q-11 | H | H | H | $CH_3$ | $C_2H_5$ | N | S | |

TABLE 7c-continued

| Q | R | $R_3'$ | $R_4$ | X | Y | Z | W'' | m.p. °C. |
|---|---|---|---|---|---|---|---|---|
| | | | | | General Structure 3 | | | |
| Q-11 | $CH_3$ | $CH_3$ | $CH_3$ | $CH_3$ | $OCH_3$ | N | S | |
| Q-11 | H | H | H | Cl | $OCH_3$ | CH | S | |
| Q-11 | H | $CH_3$ | H | $CH_3$ | $CH_3$ | CH | $NCH_3$ | |
| Q-11 | H | H | $CH_3$ | $CH_3$ | $OCH_3$ | N | $NCH_3$ | |
| Q-11 | H | $CH_3$ | $CH_3$ | $CH_3$ | $OCH_3$ | CH | $NCH_3$ | |
| Q-11 | $CH_3$ | H | H | $OCH_3$ | $OCH_3$ | N | NH | |
| Q-11 | H | H | H | $CH_3$ | $OCH_3$ | CH | NH | |
| Q-11 | H | H | H | $OCH_3$ | $OCH_3$ | CH | O* | |
| Q-11 | H | H | H | $OCH_3$ | CH | N | O* | |
| Q-11 | H | H | H | $CH_3$ | $OCH_3$ | N | $NCH_3$ | |
| Q-11 | H | H | H | $CH_3$ | $OCF_2H$ | CH | $NCH_3$ | |
| Q-11 | H | $CH_3$ | H | $OCH_3$ | $OCH_2CF_3$ | N | $NCH_3$ | |
| Q-12 | H | H | H | $CH_3$ | $OCH_3$ | CH | O | |
| Q-12 | H | H | H | $CH_3$ | $OCH_3$ | N | O | |
| Q-12 | H | H | H | $OCH_3$ | $OCH_3$ | CH | O | |
| Q-12 | H | H | H | $OCH_3$ | $OCH_3$ | N | O | |
| Q-12 | H | H | H | $CH_3$ | $OCH_3$ | CH | S | |
| Q-12 | H | H | H | $CH_3$ | $OCH_3$ | N | S | |
| Q-12 | H | H | H | $OCH_3$ | $OCH_3$ | CH | S | |
| Q-12 | H | H | H | $OCH_3$ | $OCH_3$ | N | S | |
| Q-12 | H | H | H | $CH_3$ | $CH_3$ | N | $NCH_3$ | |
| Q-12 | H | H | H | $CH_3$ | $OCH_3$ | CH | $NCH_3$ | |
| Q-12 | H | H | H | $CH_3$ | $OCH_3$ | N | $NCH_3$ | |
| Q-12 | H | H | H | $OCH_3$ | $OCH_3$ | CH | $NCH_3$ | |
| Q-12 | H | H | H | $OCH_3$ | $OCH_3$ | N | $NCH_3$ | |
| Q-12 | H | H | H | $OCH_3$ | $OCH_3$ | N | NH | |
| Q-12 | H | $CH_3$ | H | $CH_3$ | $CH_3$ | CH | O | |
| Q-12 | H | H | $CH_3$ | $CH_3$ | $OCH_3$ | N | O | |
| Q-12 | H | $CH_3$ | $CH_3$ | $CH_3$ | $OCH_3$ | CH | O | |
| Q-12 | $CH_3$ | H | H | $OCH_3$ | $OCH_3$ | N | O | |
| Q-12 | $CH_3$ | H | H | $CH_3$ | $CF_3$ | CH | O | |
| Q-12 | H | H | H | $OCH_3$ | $OCH_2CF_3$ | N | | |
| Q-12 | H | $CH_3$ | H | $CH_3$ | $OCH_3$ | CH | S | |
| Q-12 | H | H | $CH_3$ | $CH_3$ | $OCH_3$ | N | S | |
| Q-12 | H | $CH_3$ | $CH_3$ | $OCH_3$ | $OCH_3$ | CH | S | |
| Q-12 | $CH_3$ | H | H | $OCH_3$ | $OCH_3$ | N | S | |
| Q-12 | $CH_3$ | $CH_3$ | H | $CH_3$ | $NHCH_3$ | CH | S | |
| Q-12 | H | H | H | Br | $OC_2H_5$ | CH | S | |
| Q-12 | H | $CH_3$ | H | $CH_3$ | $CH_3$ | CH | NH | |
| Q-12 | H | $CH_3$ | H | $CH_3$ | $CH_3$ | CH | $NCH_3$ | |
| Q-12 | H | H | $CH_3$ | $CH_3$ | $OCH_3$ | N | $NCH_3$ | |
| Q-12 | H | $CH_3$ | $CH_3$ | $CH_3$ | $CH_3$ | $CH_3$ | $NCH_3$ | |
| Q-12 | $CH_3$ | $CH_3$ | $CH_3$ | $CH_3$ | $OCH_3$ | N | $NCH_3$ | |
| Q-12 | $CH_3$ | $CH_3$ | $CH_3$ | $CH_3$ | $OCH_3$ | CH | $NCH_3$ | |
| Q-12 | H | H | H | Br | $OCH_3$ | CH | $NCH_3$ | |
| Q-12 | H | H | H | $OCH_3$ | $N(CH_3)_2$ | CH | $NCH_3$ | |
| Q-13 | H | H | H | $CH_3$ | $OCH_3$ | CH | O | |
| Q-13 | H | H | H | $CH_3$ | $OCH_3$ | CH | O | |
| Q-13 | H | H | H | $CH_3$ | $CH_3$ | CH | O | |
| Q-13 | H | H | H | $CH_3$ | $OCH_3$ | N | O | |
| Q-13 | H | H | H | $OCH_3$ | $OCH_3$ | CH | O | |
| Q-13 | H | H | H | $CH_3$ | $CH_3$ | N | O | |
| Q-13 | H | H | H | $OCH_3$ | $OCH_3$ | N | O | |
| Q-13 | H | H | H | $CH_3$ | $OCH_3$ | CH | S | |
| Q-13 | H | H | H | $CH_3$ | $OCH_3$ | N | S | |
| Q-13 | H | H | H | $OCH_3$ | $OCH_3$ | CH | S | |
| Q-13 | H | H | H | $OCH_3$ | $OCH_3$ | N | S | |
| Q-13 | H | H | H | $CH_3$ | $OCH_3$ | CH | NH | |
| Q-13 | H | H | H | $CH_3$ | $OCH_3$ | N | NH | |
| Q-13 | H | H | H | $OCH_3$ | $OCH_3$ | CH | $NCH_3$ | |
| Q-13 | H | H | H | $OCH_3$ | $OCH_3$ | N | NH | |
| Q-13 | H | $CH_3$ | H | $CH_3$ | $CH_3$ | CH | O | |
| Q-13 | H | H | $CH_3$ | $CH_3$ | $CH_3$ | N | O | |
| Q-13 | H | $CH_3$ | $CH_3$ | $CH_3$ | $OCH_3$ | CH | O | |
| Q-13 | $CH_3$ | H | H | $CH_3$ | $OCH_3$ | N | O | |
| Q-13 | H | H | H | $CH_3$ | $CH(OCH_3)_2$ | CH | O | |
| Q-13 | H | $CH_3$ | H | $CH_3$ | $OCH_3$ | CH | S | |
| Q-13 | H | H | $CH_3$ | $CH_3$ | $OCH_3$ | CH | S | |
| Q-13 | H | $CH_3$ | $CH_3$ | $CH_3$ | $OCH_3$ | N | S | |
| Q-13 | $CH_3$ | H | $CH_3$ | $OCH_3$ | $OCH_3$ | N | S | |
| Q-13 | $CH_3$ | $CH_3$ | $CH_3$ | $CH_3$ | $CH_3$ | N | S | |
| Q-13 | H | H | H | $OCH_3$ | O<br>O | CH | S | |
| Q-13 | H | $CH_3$ | H | $CH_3$ | $OCH_3$ | N | $NCH_3$ | |
| Q-13 | H | H | $CH_3$ | $CH_3$ | $OCH_3$ | N | $NCH_3$ | |
| Q-13 | H | $CH_3$ | $CH_3$ | $CH_3$ | $OCH_3$ | CH | $NCH_3$ | |
| Q-13 | $CH_3$ | H | H | $OCH_3$ | $OCH_3$ | CH | $NCH_3$ | |
| Q-13 | H | H | H | $CH_3$ | $OCH_3$ | N | NH | |
| Q-13 | H | H | H | Br | $OC_2H_5$ | CH | NH | |
| Q-13 | H | H | H | $OCH_3$ | $C_2H_5$ | N | NH | |

TABLE 7c-continued

| | | | | | General Structure 3 | | | |
|---|---|---|---|---|---|---|---|---|
| Q | R | $R_{3'}$ | $R_4$ | X | Y | Z | W'' | m.p. °C. |
| Q-13 | H | H | H | $CH_3$ | $CH_3$ | CH | $NCH_3$ | |
| Q-13 | H | H | H | $CH_3$ | $CH_3$ | N | $NCH_3$ | |
| Q-13 | H | H | H | Cl | $OCH_3$ | CH | $NCH_3$ | |
| Q-14 | H | H | H | $CH_3$ | $CH_3$ | N | O | |
| Q-14 | H | H | H | $CH_3$ | $CH_3$ | CH | O | |
| Q-14 | H | H | H | $CH_3$ | $OCH_3$ | CH | O | |
| Q-14 | H | H | H | $CH_3$ | $OCH_3$ | CH | O | |
| Q-14 | H | H | H | $CH_3$ | $OCH_3$ | N | O | |
| Q-14 | H | H | H | $OCH_3$ | $OCH_3$ | CH | O | |
| Q-14 | H | H | H | $CH_3$ | $OCH_3$ | CH | S | |
| Q-14 | H | H | H | $CH_3$ | $OCH_3$ | N | S | |
| Q-14 | H | H | H | $OCH_3$ | $OCH_3$ | CH | S | |
| Q-14 | H | H | H | $OCH_3$ | $OCH_3$ | CH | S | |
| Q-14 | H | H | H | $OCH_3$ | $OCH_3$ | N | S | |
| Q-14 | H | H | H | $CH_3$ | $OCH_3$ | CH | $NCH_3$ | |
| Q-14 | H | H | H | $CH_3$ | $OCH_3$ | N | $NCH_3$ | |
| Q-14 | H | H | H | $OCH_3$ | $OCH_3$ | CH | NH | |
| Q-14 | H | H | H | $OCH_3$ | $OCH_3$ | N | $NCH_3$ | |
| Q-14 | H | $CH_3$ | H | $CH_3$ | $CH_3$ | CH | O | |
| Q-14 | H | H | $CH_3$ | $CH_3$ | $CH_3$ | N | O | |
| Q-14 | H | $CH_3$ | $CH_3$ | $CH_3$ | $OCH_3$ | CH | O | |
| Q-14 | $CH_3$ | $CH_3$ | $CH_3$ | $CH_3$ | $OCH_3$ | N | O | |
| Q-14 | H | H | H | $CH_3$ | $C_2H_5$ | N | O | |
| Q-14 | H | H | H | $CH_3$ | $OC_2H_5$ | N | O | |
| Q-14 | H | $CH_3$ | H | $CH_3$ | $OCH_3$ | CH | S | |
| Q-14 | H | H | $CH_3$ | $CH_3$ | $OCH_3$ | N | S | |
| Q-14 | H | $CH_3$ | $CH_3$ | $OCH_3$ | $OCH_3$ | CH | S | |
| Q-14 | $CH_3$ | $CH_3$ | $CH_3$ | $OCH_3$ | $OCH_3$ | CH | S | |
| Q-14 | H | H | H | $OCH_3$ | $C_2H_5$ | N | S | |
| Q-14 | H | H | H | $OCH_3$ | $OC_2H_5$ | N | S | |
| Q-14 | H | $CH_3$ | H | $CH_3$ | $OCH_3$ | CH | $NCH_3$ | |
| Q-14 | H | H | $CH_3$ | $CH_3$ | $OCH_3$ | N | $NCH_3$ | |
| Q-14 | H | $CH_3$ | $CH_3$ | $OCH_3$ | $OCH_3$ | CH | $NCH_3$ | |
| Q-14 | $CH_3$ | $CH_3$ | H | $OCH_3$ | $OCH_3$ | N | $NCH_3$ | |
| Q-14 | H | $CH_3$ | $CH_3$ | $CH_3$ | $OCH_3$ | CH | NH | |
| Q-14 | H | H | H | $CH_3$ | $OCH_3$ | N | NH | |
| Q-14 | H | H | H | $CH_3$ | $CH_2OCH_3$ | CH | $NCH_3$ | |
| Q-15 | H | H | H | $CH_3$ | $OCH_3$ | CH | O | |
| Q-15 | H | H | H | $CH_3$ | $OCH_3$ | N | O | |
| Q-15 | H | H | H | $OCH_3$ | $OCH_3$ | CH | O | |
| Q-15 | H | H | H | $OCH_3$ | $OCH_3$ | N | O | |
| Q-15 | H | $C_2H_5$ | H | $OCH_3$ | $OCH_3$ | CH | O | |
| Q-15 | H | $CH_3$ | H | $CH_3$ | $OCH_3$ | CH | O | |
| Q-15 | H | $CH_3$ | H | $CH_3$ | $CH_3$ | CH | O | |
| Q-15 | H | $CH_3$ | H | $OCH_3$ | $OCH_3$ | CH | O | |
| Q-15 | H | H | $CH_3$ | $CH_3$ | $CH_3$ | N | O | |
| Q-15 | H | $CH_3$ | H | $CH_3$ | $OCH_3$ | N | O | |
| Q-15 | H | $CH_3$ | $CH_3$ | $CH_3$ | $OCH_3$ | CH | O | |
| Q-15 | H | $CH_3$ | H | $OCH_3$ | $OCH_3$ | N | O | |
| Q-15 | $CH_3$ | H | H | $CH_3$ | $OCH_3$ | N | O | |
| Q-15 | H | $CH_3$ | H | $OCH_3$ | Cl | CH | O | |
| Q-15 | $CH_3$ | $CH_3$ | $CH_3$ | $OCH_3$ | $OCH_3$ | CH | O | |
| Q-15 | H | H | H | $CH_3$ | $CF_3$ | CH | O | |
| Q-15 | H | H | H | $CH_3$ | $CF_3$ | N | O | |
| Q-15 | H | H | H | $OCH_3$ | $OCF_2H$ | CH | O | |
| Q-15 | $CH_3$ | H | H | $OCH_3$ | $OCF_2H$ | CH | O | |
| Q-15 | H | H | H | $CH_3$ | $CH_3$ | CH | O | |
| Q-15 | H | H | H | $CH_3$ | $CH_3$ | N | O | |
| Q-15 | H | H | H | $OCH_3$ | $OCH_3$ | CH | O* | |
| Q-15 | H | H | H | $OCH_3$ | $CH_3$ | N | O* | |
| Q-15 | H | H | H | $CH_3$ | $CH_3$ | N | S | |
| Q-15 | H | $CH_3$ | H | $CH_3$ | $OCH_3$ | CH | S | |
| Q-15 | H | $CH_3$ | H | $CH_3$ | $OCH_3$ | N | S | |
| Q-15 | H | $CH_3$ | H | $OCH_3$ | $OCH_3$ | CH | S | |
| Q-15 | H | $CH_3$ | H | $OCH_3$ | $OCH_3$ | N | S | |
| Q-15 | H | $CH_3$ | H | Cl | $OCH_3$ | CH | S | |
| Q-15 | H | H | H | $CH_3$ | $OCH_3$ | CH | $NCH_3$ | |
| Q-15 | H | H | H | $CH_3$ | $OCH_3$ | N | $NCH_3$ | |
| Q-15 | H | H | H | $OCH_3$ | $OCH_3$ | CH | $NCH_3$ | |
| Q-15 | H | H | H | $OCH_3$ | $OCH_3$ | N | $NCH_3$ | |
| Q-15 | H | $CH_3$ | H | $CH_3$ | $CH_3$ | CH | S | |
| Q-15 | H | H | $CH_3$ | $CH_3$ | $CH_3$ | N | S | |
| Q-15 | H | $CH_3$ | $CH_3$ | $CH_3$ | $OCH_3$ | CH | S | |
| Q-15 | $CH_3$ | H | H | $CH_3$ | $OCH_3$ | N | S | |
| Q-15 | $CH_3$ | H | $CH_3$ | $OCH_3$ | $OCH_3$ | CH | S | |
| Q-15 | H | H | H | Cl | $OC_2H_5$ | CH | S | |
| Q-15 | H | H | H | $OCH_3$ | $OCH_2CF_3$ | CH | S | |
| Q-15 | H | $CH_3$ | H | $CH_3$ | $CH_3$ | CH | $NCH_3$ | |
| Q-15 | H | H | $CH_3$ | $CH_3$ | $OCH_3$ | CH | $NCH_3$ | |
| Q-15 | H | $CH_3$ | $CH_3$ | $CH_3$ | $OCH_3$ | N | $NCH_3$ | |

TABLE 7c-continued

| General Structure 3 | | | | | | | | |
|---|---|---|---|---|---|---|---|---|
| Q | R | $R_{3}$,' | $R_4$ | X | Y | Z | W'' | m.p. °C. |
| Q-15 | $CH_3$ | $CH_3$ | $CH_3$ | $CH_3$ | $OCH_3$ | N | $NCH_3$ | |
| Q-15 | $CH_3$ | H | H | $CH_3$ | $OCH_3$ | CH | NH | |
| Q-15 | H | H | H | $OCH_3$ | $OCH_3$ | N | NH | |
| Q-15 | H | H | H | $CH_3$ | $NHCH_3$ | CH | $NCH_3$ | |
| Q-15 | H | H | H | $OCH_3$ | $N(CH_3)_2$ | CH | $NCH_3$ | |
| Q-15 | H | H | H | $CH_3$ | $OCH_2C{\equiv}CH$ | N | S | |
| Q-15 | H | H | H | $CH_3$ | $CH_2C{\equiv}CH_3$ | CH | S | |
| Q-15 | H | H | H | $CH_3$ | $C{\equiv}CH$ | N | S | |
| Q-15 | H | $C_2H_5$ | H | $OCH_3$ | $OCH_3$ | CH | S | |
| Q-15 | H | H | H | $OCH_3$ | $(CH_2)_3CH_2F$ | CH | S | |
| Q-15 | H | H | H | $OCH_3$ | 2-methyl-1,3-dioxolan-2-yl | N | S | |
| Q-15 | H | H | H | $OCH_3$ | 2-methyl-1,3-dithiolan-2-yl | CH | S | |
| Q-15 | H | H | H | $OCH_3$ | 2-methyl-1,3-dithian-2-yl | N | S | |
| Q-15 | H | H | H | $OCH_3$ | $OCH_3$ | CH | S* | |
| Q-15 | H | H | H | $OCH_3$ | $CH_3$ | N | S* | |

TABLE 7d

| General Structure 3 | | | | | | | | |
|---|---|---|---|---|---|---|---|---|
| Q | R | $R_3$ | $R_4$ | $R_5$ | X | Y | Z | m.p. °C. |
| Q-18 | H | H | H | H | $CH_3$ | $CH_3$ | CH | |
| Q-18 | H | H | H | H | $CH_3$ | $OCH_3$ | CH | |
| Q-18 | H | H | H | H | $CH_3$ | $OCH_3$ | N | |
| Q-18 | $CH_3$ | H | H | H | $CH_3$ | $OCH_3$ | N | |
| Q-18 | H | H | H | H | $OCH_3$ | $OCH_3$ | CH | |
| Q-18 | H | H | H | H | $CH_3$ | $CH_3$ | CH | |
| Q-18 | H | H | H | H | $OCH_3$ | $OCH_3$ | N | |
| Q-18 | H | H | H | H | Cl | $OCH_3$ | CH | |
| Q-18 | H | $CH_3$ | H | H | $CH_3$ | $OCH_3$ | CH | |
| Q-18 | H | H | $CH_3$ | H | $CH_3$ | $OCH_3$ | N | |
| Q-18 | H | H | H | $CH_3$ | $CH_3$ | $CH_3$ | CH | |
| Q-18 | H | $CH_3$ | $CH_3$ | H | $CH_3$ | $CH_3$ | N | |
| Q-18 | H | H | $CH_3$ | $CH_3$ | $OCH_3$ | $OCH_3$ | CH | |
| Q-18 | H | $CH_3$ | H | $CH_3$ | $OCH_3$ | $OCH_3$ | N | |
| Q-18 | H | $CH_3$ | $CH_3$ | $CH_3$ | $CH_3$ | $OCH_3$ | CH | |
| Q-18 | H | H | H | H | $OCH_3$ | $CH(OCH_3)_2$ | CH | |
| Q-19 | $CH_3$ | H | H | H | Cl | $OCH_3$ | CH | |

TABLE 7d-continued

| General Structure 3 | | | | | | | | |
|---|---|---|---|---|---|---|---|---|
| Q | R | $R_3$ | $R_4$ | $R_5$ | X | Y | Z | m.p. °C. |
| Q-19 | H | H | H | H | $CH_3$ | $OCH_3$ | CH | |
| Q-19 | H | H | H | H | $CH_3$ | $OCH_3$ | N | |
| Q-19 | H | H | H | H | $OCH_3$ | $OCH_3$ | CH | |
| Q-19 | H | H | H | H | $OCH_3$ | $OCH_3$ | N | |
| Q-19 | H | $CH_3$ | H | H | $CH_3$ | $CH_3$ | CH | |
| Q-19 | H | H | $CH_3$ | H | $CH_3$ | $CH_3$ | N | |
| Q-19 | H | H | H | $CH_3$ | $CH_3$ | $OCH_3$ | CH | |
| Q-19 | H | $CH_3$ | $CH_3$ | H | $CH_3$ | $OCH_3$ | N | |
| Q-19 | H | H | $CH_3$ | $CH_3$ | $OCH_3$ | $OCH_3$ | CH | |
| Q-19 | H | $CH_3$ | H | $CH_3$ | $OCH_3$ | $OCH_3$ | N | |
| Q-19 | H | H | H | H | $CH_3$ | $CH_3$ | CH | |
| Q-19 | H | $CH_3$ | $CH_3$ | $CH_3$ | $CH_3$ | $OCH_3$ | CH | |
| Q-19 | $CH_3$ | H | H | H | $CH_3$ | $OCH_3$ | N | |
| Q-19 | H | H | H | H | $OCH_3$ | 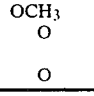 | CH | |

TABLE 7e

| General Structure 3 | | | | | | | |
|---|---|---|---|---|---|---|---|
| Q | R | R'3,'' | X | Y | Z | W' | m.p. °C. |
| Q-21 | H | H | $CH_3$ | $OCH_3$ | CH | O | |
| Q-21 | H | H | $CH_3$ | $OCH_3$ | N | O | |
| Q-21 | H | H | $OCH_3$ | $OCH_3$ | CH | O | |
| Q-21 | $CH_3$ | H | $OCH_3$ | $OCH_3$ | CH | O | |
| Q-21 | H | H | $OCH_3$ | $NHCH_3$ | CH | O | |
| Q-21 | H | H | $OCH_3$ | $OCH_3$ | N | O | |
| Q-21 | H | $CH_3$ | $CH_3$ | $OCH_3$ | CH | O | |
| Q-21 | $CH_3$ | $CH_3$ | $CH_3$ | $OCH_3$ | CH | O | |
| Q-21 | H | H | $CH_3$ | $CH_3$ | CH | O | |
| Q-21 | H | H | $CH_3$ | $CH_3$ | N | O | |
| Q-21 | H | H | $CH_3$ | $OCH_3$ | CH | S | |
| Q-21 | H | H | $CH_3$ | $OCH_3$ | N | S | |
| Q-21 | H | H | $OCH_3$ | $OCH_3$ | CH | S | |
| Q-21 | H | H | $OCH_3$ | $OCH_3$ | N | S | |
| Q-21 | H | $CH_3$ | $CH_3$ | $OCH_3$ | CH | S | |
| Q-21 | $CH_3$ | H | $CH_3$ | $OCH_3$ | CH | S | |
| Q-21 | H | H | $OCH_3$ | $N(CH_3)_2$ | N | S | |
| Q-22 | H | H | $CH_3$ | $OCH_3$ | CH | O | |
| Q-22 | H | H | $CH_3$ | $OCH_3$ | N | O | |
| Q-22 | H | H | $OCH_3$ | $OCH_3$ | CH | O | |
| Q-22 | H | H | $OCH_3$ | $OCH_3$ | N | O | |
| Q-22 | H | $CH_3$ | $CH_3$ | $OCH_3$ | CH | O | |
| Q-22 | H | $CH_3$ | $CH_3$ | $OCH_3$ | N | O | |
| Q-22 | $CH_3$ | $CH_3$ | $CH_3$ | $CH_3$ | CH | O | |
| Q-22 | H | H | $CH_3$ | $CH(OCH_3)_2$ | CH | O | |
| Q-22 | H | H | $CH_3$ | $C_2H_5$ | N | O | |
| Q-22 | H | H | $CH_3$ | $CH_3$ | CH | S | |
| Q-22 | H | H | $CH_3$ | $CH_3$ | N | S | |
| Q-22 | H | H | $CH_3$ | $OCH_3$ | CH | S | |
| Q-22 | H | H | $CH_3$ | $OCH_3$ | N | S | |
| Q-22 | H | H | $OCH_3$ | $OCH_3$ | CH | S | |
| Q-22 | H | H | $OCH_3$ | $OCH_3$ | N | S | |
| Q-22 | H | $CH_3$ | $CH_3$ | $OCH_3$ | CH | S | |

TABLE 7e-continued

General Structure 3

| Q | R | R'3," | X | Y | Z | W' | m.p. °C. |
|---|---|---|---|---|---|---|---|
| Q-22 | $CH_3$ | $CH_3$ | $CH_3$ | $OCH_3$ | CH | S | |
| Q-22 | $CH_3$ | H | $CH_3$ | $OCH_3$ | N | S | |
| Q-22 | H | H | $CH_3$ | 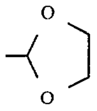 | CH | S | |
| Q-22 | H | H | $OCH_3$ | $C_2H_5$ | N | S | |
| Q-23 | H | H | $CH_3$ | $OCH_3$ | CH | — | |
| Q-23 | H | H | $CH_3$ | $OCH_3$ | N | — | |
| Q-23 | H | H | $OCH_3$ | $OCH_3$ | CH | — | |
| Q-23 | H | H | $OCH_3$ | $OCH_3$ | N | — | |
| Q-23 | H | $CH_3$ | $CH_3$ | $CH_3$ | CH | — | |
| Q-23 | H | $CH_3$ | $CH_3$ | $OCH_3$ | N | — | |
| Q-23 | $CH_3$ | H | $CH_3$ | $OCH_3$ | N | — | |
| Q-23 | $CH_3$ | $CH_3$ | $CH_3$ | $OCH_3$ | CH | — | |
| Q-23 | H | H | $CH_3$ | $OC_2H_5$ | N | — | |
| Q-23 | H | H | $CH_3$ | $CH_2OCH_3$ | CH | — | |
| Q-24 | H | H | $CH_3$ | $OCH_3$ | CH | — | |
| Q-24 | H | H | $CH_3$ | $OCH_3$ | N | — | |
| Q-24 | H | H | $OCH_3$ | $OCH_3$ | CH | — | |
| Q-24 | H | H | $OCH_3$ | $OCH_3$ | N | — | |
| Q-24 | H | $CH_3$ | $CH_3$ | $OCH_3$ | CH | — | |
| Q-24 | H | $CH_3$ | $CH_3$ | $CH_3$ | CH | — | |
| Q-24 | $CH_3$ | H | $CH_3$ | $CH_3$ | N | — | |
| Q-24 | H | H | $CH_3$ | $CF_3$ | CH | — | |
| Q-24 | H | H | $OCH_3$ | $OCF_2H$ | N | — | |
| Q-25 | H | H | $CH_3$ | $OCH_3$ | CH | —** | |
| Q-25 | H | H | $CH_3$ | $OCH_3$ | N | —** | |
| Q-25 | H | H | $OCH_3$ | $OCH_3$ | CH | —** | |
| Q-25 | H | H | $OCH_3$ | $OCH_3$ | N | —** | |
| Q-25 | $CH_3$ | H | $OCH_3$ | $OCH_3$ | N | —** | |
| Q-25 | H | H | $CH_3$ | $CH_3$ | CH | —** | |
| Q-25 | H | H | $CH_3$ | $CH_3$ | N | —** | |
| Q-25 | H | $CH_3$ | $CH_3$ | $OCH_3$ | CH | —** | |
| Q-25 | H | $CH_3$ | $CH_3$ | $OCH_3$ | N | —** | |
| Q-25 | $CH_3$ | $CH_3$ | $OCH_3$ | $OCH_3$ | N | —** | |
| Q-25 | H | H | $CH_3$ | $OCH_2CF_3$ | CH | —** | |
| Q-25 | H | H | $CH_3$ | $NHCH_3$ | N | —** | |
| Q-26 | H | H | $CH_3$ | $OCH_3$ | CH | —** | |
| Q-26 | H | H | $CH_3$ | $OCH_3$ | N | —** | |
| Q-26 | H | H | $OCH_3$ | $OCH_3$ | CH | —** | |
| Q-26 | H | $CH_3$ | $CH_3$ | $CH_3$ | N | —** | |
| Q-26 | H | $CH_3$ | $CH_3$ | $CH_3$ | CH | —** | |
| Q-26 | H | $CH_3$ | $CH_3$ | $OCH_3$ | N | —** | |
| Q-26 | H | $CH_3$ | $CH_3$ | $OCH_3$ | CH | —** | |
| Q-26 | H | $CH_3$ | $CH_3$ | $OCH_3$ | N | —** | |
| Q-26 | H | H | $CH_3$ | $CH_3$ | CH | —** | |
| Q-26 | H | H | $CH_3$ | $CH_3$ | N | —** | |
| Q-26 | H | $CH_3$ | $OCH_3$ | $OCH_3$ | CH | —** | |
| Q-26 | H | $CH_3$ | $OCH_3$ | $OCH_3$ | N | —** | |
| Q-26 | $CH_3$ | H | $CH_3$ | $OCH_3$ | CH | —** | |
| Q-26 | H | H | $CH_3$ | $N(CH_3)_2$ | CH | —** | |
| Q-26 | H | H | $CH_3$ | $N(CH_3)_2$ | N | —** | |
| Q-27 | H | H | $CH_3$ | $OCH_3$ | CH | —** | |
| Q-27 | H | H | $CH_3$ | $OCH_3$ | N | —** | |
| Q-27 | H | H | $OCH_3$ | $OCH_3$ | CH | —** | |
| Q-27 | H | H | $OCH_3$ | $OCH_3$ | N | —** | |
| Q-27 | H | H | $CH_3$ | $CH_3$ | CH | —** | |
| Q-27 | H | H | $CH_3$ | $CH_3$ | N | —** | |
| Q-27 | H | $CH_3$ | $CH_3$ | $CH_3$ | CH | —** | |
| Q-27 | H | H | Cl | $OC_2H_5$ | CH | —** | |
| Q-27 | H | $CH_3$ | $CH_3$ | $CH_3$ | N | —** | |
| Q-27 | H | $CH_3$ | $CH_3$ | $OCH_3$ | CH | —** | |
| Q-27 | H | $CH_3$ | $CH_3$ | $OCH_3$ | N | —** | |
| Q-27 | H | $CH_3$ | $OCH_3$ | $OCH_3$ | CH | —** | |
| Q-27 | H | $CH_3$ | $OCH_3$ | $OCH_3$ | N | —** | |
| Q-27 | $CH_3$ | $CH_3$ | $CH_3$ | $OCH_3$ | N | —** | |
| Q-27 | $CH_3$ | H | $CH_3$ | $OCH_3$ | N | —** | |
| Q-27 | H | H | $CH_3$ | $CH(OCH_3)_2$ | CH | —** | |
| Q-27 | H | H | $CH_3$ | $O(CH_2)_3CH_2Cl$ | CH | —** | |
| Q-25 | H | SH | $CH_3$ | $CH_3$ | CH | —** | |
| Q-25 | H | SH | $CH_3$ | $OCH_3$ | CH | —** | |
| Q-25 | H | SH | $OCH_3$ | $OCH_3$ | CH | —** | |
| Q-25 | H | SH | $OCH_3$ | Cl | CH | —** | |
| Q-25 | H | SH | $CH_3$ | $OCH_3$ | N | —** | |

TABLE 7e-continued

General Structure 3

| Q | R | R'3," | X | Y | Z | W' | m.p. °C. |
|---|---|---|---|---|---|---|---|
| Q-25 | H | SH | $OCH_3$ | $OCH_3$ | N | —** | |
| Q-25 | H | $SCH_3$ | $CH_3$ | $CH_3$ | CH | —** | |
| Q-25 | H | $SCH_3$ | $CH_3$ | $OCH_3$ | CH | —** | |
| Q-25 | H | $SCH_3$ | $OCH_3$ | $OCH_3$ | CH | —** | |
| Q-25 | H | $SCH_3$ | $OCH_3$ | Cl | CH | —** | |
| Q-25 | H | $SCH_3$ | CH | $OCH_3$ | N | —** | |
| Q-25 | H | $SCH_3$ | $OCH_3$ | $OCH_3$ | N | —** | |
| Q-25 | H | $SCH_2CH=CH_2$ | $CH_3$ | $CH_3$ | CH | —** | |
| Q-25 | H | $SCH_2CH=CH_2$ | $CH_3$ | $OCH_3$ | CH | —** | |
| Q-25 | H | $SCH_2CH=CH_2$ | $OCH_3$ | $OCH_3$ | CH | —** | |
| Q-25 | H | $SCH_2CH=CH_2$ | $OCH_3$ | Cl | CH | —** | |
| Q-25 | H | $SCH_2CH=CH_2$ | $CH_3$ | $OCH_3$ | N | —** | |
| Q-25 | H | $SCH_2CH=CH_2$ | $OCH_3$ | $OCH_3$ | N | —** | |
| Q-25 | $CH_3$ | $SCH_3$ | $OCH_3$ | $OCH_3$ | CH | —** | |
| Q-25 | $CH_3$ | SH | $OCH_3$ | $OCH_3$ | CH | —** | |
| Q-25 | $CH_3$ | $SCH_2CH=CH_2$ | $OCH_3$ | $OCH_3$ | CH | —** | |

$R_{11}$ is —, unless indicated by ** where $R_{11}$ is $CH_3$ in all Tables.

TABLE 7f

General Structure 3

| Q | R | $R_3$ | $R_4$ | $R_5$ | X | Y | Z | m.p. °C. |
|---|---|---|---|---|---|---|---|---|
| Q-29 | H | H | H | — | $CH_3$ | $OCH_3$ | CH | |
| Q-29 | H | H | H | — | $CH_3$ | $OCH_3$ | N | |
| Q-29 | H | H | H | — | $OCH_3$ | $OCH_3$ | CH | |
| Q-29 | H | H | H | — | $OCH_3$ | $OCH_3$ | N | |
| Q-29 | H | H | H | — | $CH_3$ | $CH_3$ | CH | |
| Q-29 | H | H | H | — | $CH_3$ | $CH_3$ | N | |
| Q-29 | H | $CH_3$ | H | — | $CH_3$ | $OCH_3$ | CH | |
| Q-29 | H | $CH_3$ | H | — | $CH_3$ | $CH_3$ | CH | |
| Q-29 | H | $CH_3$ | $CH_3$ | — | $CH_3$ | $OCH_3$ | N | |
| Q-29 | $CH_3$ | $CH_3$ | $CH_3$ | — | $CH_3$ | $CH_3$ | N | |
| Q-29 | $CH_3$ | H | H | — | $OCH_3$ | $OCH_3$ | CH | |
| Q-29 | H | H | H | — | $CH_3$ | $OC_2H_5$ | N | |
| Q-29 | H | H | H | — | Cl | $OCH_3$ | CH | |
| Q-36 | H | H | H | H | $CH_3$ | $OCH_3$ | CH | |
| Q-36 | $CH_3$ | H | H | H | $CH_3$ | $OCH_3$ | CH | |
| Q-36 | H | H | H | H | $CH_3$ | $OCH_3$ | N | |
| Q-36 | H | H | H | H | $OCH_3$ | $OCH_3$ | CH | |
| Q-36 | H | H | H | H | $OCH_3$ | $OCH_3$ | N | |
| Q-36 | H | H | H | H | $OCH_3$ | $C_2H_5$ | CH | |
| Q-36 | H | H | H | H | $CH_3$ | $CH_3$ | CH | |
| Q-36 | H | H | H | H | $CH_3$ | $CH_3$ | N | |
| Q-36 | H | $CH_3$ | H | H | $CH_3$ | $CH_3$ | CH | |
| Q-36 | H | H | $CH_3$ | H | $CH_3$ | $CH_3$ | N | |
| Q-36 | H | $CH_3$ | H | $CH_3$ | $CH_3$ | $OCH_3$ | CH | |
| Q-36 | H | $CH_3$ | $CH_3$ | H | $CH_3$ | $OCH_3$ | N | |
| Q-36 | H | $CH_3$ | $CH_3$ | $CH_3$ | $OCH_3$ | $OCH_3$ | CH | |
| Q-36 | $CH_3$ | H | H | H | $OCH_3$ | $OCH_3$ | N | |
| Q-36 | H | H | H | H | $CH_3$ | $NHCH_3$ | CH | |
| Q-36 | H | H | H | H | $CH_3$ | $N(CH_3)_2$ | CH | |
| Q-37 | H | H | H | — | $CH_3$ | $OCH_3$ | CH | |
| Q-37 | H | H | H | — | $CH_3$ | $OCH_3$ | N | |
| Q-37 | H | H | H | — | $OCH_3$ | $OCH_3$ | CH | |
| Q-37 | H | H | H | — | $OCH_3$ | $OCH_3$ | N | |
| Q-37 | H | H | H | — | $CH_3$ | $CH_3$ | CH | |
| Q-37 | H | 2-$CH_3$ | H | — | $CH_3$ | $CH_3$ | CH | |
| Q-37 | H | 4-$CH_3$ | H | — | $CH_3$ | $CH_3$ | N | |
| Q-37 | H | 5-$CH_3$ | H | — | $CH_3$ | OCH | CH | |
| Q-37 | H | H | H | — | $CH_3$ | $CH_3$ | N | |
| Q-37 | H | 2-$CH_3$ | 4-$CH_3$ | — | $CH_3$ | $OCH_3$ | N | |
| Q-37 | H | 2-$CH_3$ | 5-$CH_3$ | — | $OCH_3$ | $OCH_3$ | CH | |
| Q-37 | H | 4-$CH_3$ | 5-$CH_3$ | — | $OCH_3$ | $OCH_3$ | N | |
| Q-37 | $CH_3$ | H | H | — | $CH_3$ | $OCH_3$ | CH | |
| Q-37 | H | H | H | — | $CH_3$ | $CH(OCH_3)_2$ | CH | |
| Q-37 | H | H | H | — | Cl | $OCH_3$ | CH | |
| Q-38 | H | H | H | — | $CH_3$ | $OCH_3$ | CH | |
| Q-38 | H | H | H | — | $CH_3$ | $OCH_3$ | N | |
| Q-38 | H | H | H | — | $OCH_3$ | $OCH_3$ | CH | |
| Q-38 | H | H | H | — | $OCH_3$ | $OCH_3$ | N | |
| Q-38 | H | 2-$CH_3$ | H | — | $CH_3$ | $CH_3$ | CH | |
| Q-38 | H | 4-$CH_3$ | H | — | $CH_3$ | $CH_3$ | N | |
| Q-38 | H | 2-$CH_3$ | 4-$CH_3$ | — | $CH_3$ | $OCH_3$ | CH | |
| Q-38 | H | 4-$CH_3$ | 4-$CH_3$ | — | $CH_3$ | $OCH_3$ | N | |
| Q-38 | H | H | H | — | $CH_3$ | $CH_3$ | N | |
| Q-38 | $CH_3$ | 4-$CH_3$ | 6-$CH_3$ | — | $OCH_3$ | $OCH_3$ | CH | |

TABLE 7f-continued

General Structure 3

| Q | R | $R_3$ | $R_4$ | $R_5$ | X | Y | Z | m.p. °C. |
|---|---|---|---|---|---|---|---|---|
| Q-38 | H | H | H | — | $CH_3$ | 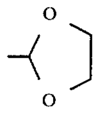 | CH | |
| Q-38 | H | H | H | — | $CH_3$ | $CH_3$ | CH | |
| Q-38 | H | H | H | — | $OCH_3$ | $C_2H_5$ | N | |
| Q-38 | H | H | H | — | $CH_3$ | $OCH_3$ | CH | |
| Q-39 | H | H | H | — | $CH_3$ | $OCH_3$ | N | |
| Q-39 | H | H | H | — | $CH_3$ | $CH_3$ | N | |
| Q-39 | H | H | H | — | $OCH_3$ | $OCH_3$ | CH | |
| Q-39 | H | H | H | — | $OCH_3$ | $OCH_3$ | N | |
| Q-39 | $CH_3$ | H | H | — | $OCH_3$ | $OCH_3$ | N | |
| Q-39 | H | 3-$CH_3$ | H | — | $CH_3$ | $CH_3$ | CH | |
| Q-39 | H | H | H | — | $CH_3$ | $CH_3$ | CH | |
| Q-39 | H | 5-$CH_3$ | H | — | $CH_3$ | $CH_3$ | N | |
| Q-39 | H | H | H | — | Cl | $OC_2H_5$ | CH | |
| Q-39 | H | 6-$CH_3$ | H | — | $CH_3$ | $OCH_3$ | CH | |
| Q-39 | H | 3-$CH_3$ | 5-$CH_3$ | — | $CH_3$ | $OCH_3$ | N | |
| Q-39 | H | 3-$CH_3$ | 6-$CH_3$ | — | $OCH_3$ | $OCH_3$ | CH | |
| Q-39 | H | 5-$CH_3$ | 6-$CH_3$ | — | $OCH_3$ | $OCH_3$ | N | |
| Q-39 | H | H | H | — | $OCH_3$ | $OC_2H_5$ | N | |
| Q-39 | H | H | H | — | $OCH_3$ | $CH_2OCH_3$ | N | |
| Q-40 | H | H | H | — | $CH_3$ | $CH_3$ | CH | |
| Q-40 | H | H | H | — | $CH_3$ | $OCH_3$ | CH | |
| Q-40 | H | H | H | — | $CH_3$ | $OCH_3$ | N | |
| Q-40 | H | H | H | — | $OCH_3$ | $OCH_3$ | CH | |
| Q-40 | H | H | H | — | $OCH_3$ | $OCH_3$ | N | |
| Q-40 | H | H | H | — | $CH_3$ | $CH_3$ | N | |
| Q-40 | H | 4-$CH_3$ | H | — | $CH_3$ | $CH_3$ | CH | |
| Q-40 | H | 5-$CH_3$ | H | — | $CH_3$ | $CH_3$ | N | |
| Q-40 | H | 6-$CH_3$ | H | — | $CH_3$ | $OCH_3$ | CH | |
| Q-40 | H | 4-$CH_3$ | 5-$CH_3$ | — | $CH_3$ | $OCH_3$ | N | |
| Q-40 | H | 4-$CH_3$ | 6-$CH_3$ | — | $OCH_3$ | $OCH_3$ | CH | |
| Q-40 | H | 5-$CH_3$ | 6-$CH_3$ | — | $OCH_3$ | $OCH_3$ | N | |
| Q-40 | $CH_3$ | H | H | — | $CH_3$ | $CH_3$ | CH | |
| Q-40 | H | H | H | — | $OCH_3$ | $CF_3$ | N | |
| Q-40 | H | H | H | — | $OCH_3$ | $OCF_2H$ | N | |
| Q-43 | H | H | H | — | $CH_3$ | $CH_3$ | CH | |
| Q-43 | H | H | H | — | $CH_3$ | $OCH_3$ | CH | |
| Q-43 | H | H | H | — | $CH_3$ | $OCH_3$ | N | |
| Q-43 | H | H | H | — | $OCH_3$ | $OCH_3$ | CH | |
| Q-43 | H | H | H | — | $OCH_3$ | $OCH_3$ | N | |
| Q-43 | $CH_3$ | H | H | — | $OCH_3$ | $OCH_3$ | CH | |
| Q-43 | H | $CH_3$ | $CH_3$ | — | $CH_3$ | $OCH_3$ | CH | |
| Q-43 | H | $CH_3$ | H | — | $CH_3$ | $CH_3$ | CH | |
| Q-43 | H | H | H | — | $CH_3$ | $CH_3$ | N | |
| Q-43 | H | H | H | — | $OCH_3$ | $OCH_2CF_3$ | N | |
| Q-43 | H | H | H | — | $OCH_3$ | $NHCH_3$ | N | |
| Q-44 | H | H | H | — | $CH_3$ | $OCH_3$ | CH | |
| Q-44 | H | H | H | — | $CH_3$ | $OCH_3$ | N | |
| Q-44 | H | H | H | — | $OCH_3$ | $OCH_3$ | CH | |
| Q-44 | H | H | H | — | $OCH_3$ | $OCH_3$ | N | |
| Q-44 | H | $CH_3$ | H | — | $CH_3$ | $CH_3$ | CH | |
| Q-44 | H | H | $CH_3$ | — | $CH_3$ | $CH_3$ | N | |
| Q-44 | H | $CH_3$ | $CH_3$ | — | $CH_3$ | $OCH_3$ | N | |
| Q-44 | $CH_3$ | H | H | — | $CH_3$ | $OCH_3$ | N | |
| Q-44 | H | H | H | — | $OCH_3$ | $N(CH_3)_2$ | N | |
| Q-44 | H | H | H | — | Br | $OCH_3$ | CH | |
| Q-44 | H | H | H | — | $CH_3$ | $CH_3$ | CH | |
| Q-44 | H | H | H | — | $CH_3$ | $CH_3$ | N | |
| Q-45 | H | H | — | — | $CH_3$ | $OCH_3$ | CH | |
| Q-45 | H | H | — | — | $CH_3$ | $OCH_3$ | N | |
| Q-45 | H | H | — | — | $OCH_3$ | $OCH_3$ | CH | |
| Q-45 | H | H | — | — | $OCH_3$ | $OCH_3$ | N | |
| Q-45 | H | $CH_3$ | — | — | $CH_3$ | $CH_3$ | CH | |
| Q-45 | $CH_3$ | H | — | — | $CH_3$ | $CH_3$ | N | |
| Q-45 | H | H | — | — | $OCH_3$ | $CH(OCH_3)_2$ | N | |
| Q-45 | H | H | — | — | $CH_3$ | $CH_3$ | CH | |
| Q-45 | H | H | — | — | $CH_3$ | $CH_3$ | N | |
| Q-45 | H | H | — | — | Cl | $OCH_3$ | CH | |

wherein W' is O.

TABLE 8a

General Structure 3 wherein Q is Q-5.

| R | $R_3$ | $R_4$ | $R_5$ | $R_6$ | $R_7$ | $R_8$ | X | Y | Z | m.p. °C. |
|---|---|---|---|---|---|---|---|---|---|---|
| H | H | H | H | H | H | H | $CH_3$ | $CH_3$ | N | |
| H | H | H | H | H | H | H | $CH_3$ | $OCH_3$ | CH | |
| H | H | H | H | H | H | H | $CH_3$ | $OCH_3$ | N | |
| H | H | H | H | H | H | H | $OCH_3$ | $OCH_3$ | CH | |
| H | H | H | H | H | H | H | $OCH_3$ | $OCH_3$ | N | |
| $CH_3$ | H | H | H | H | H | H | $OCH_3$ | $OCH_3$ | CH | |
| H | $CH_3$ | H | H | H | H | H | $CH_3$ | $CH_3$ | CH | |
| H | H | H | $CH_3$ | H | H | H | $CH_3$ | $CH_3$ | N | |
| H | H | H | H | H | $CH_3$ | H | $CH_3$ | $OCH_3$ | CH | |
| H | $CH_3$ | $CH_3$ | H | H | $CH_3$ | H | $CH_3$ | $OCH_3$ | N | |
| H | $CH_3$ | H | $CH_3$ | H | H | H | $OCH_3$ | $OCH_3$ | CH | |
| H | $CH_3$ | H | H | H | $CH_3$ | H | $OCH_3$ | $OCH_3$ | N | |
| H | H | H | $CH_3$ | H | $CH_3$ | H | $CH_3$ | $CH_3$ | CH | |
| H | $CH_3$ | H | $CH_3$ | H | $CH_3$ | H | $CH_3$ | $CH_3$ | N | |
| H | $CH_3$ | $CH_3$ | H | H | H | H | $CH_3$ | $OCH_3$ | CH | |
| H | H | H | H | $CH_3$ | H | H | $CH_3$ | $OCH_3$ | N | |
| H' | H | H | H | H | $CH_3$ | $CH_3$ | $OCH_3$ | $OCH_3$ | CH | |
| H | $CH_3$ | $CH_3$ | $CH_3$ | H | H | H | $OCH_3$ | $OCH_3$ | N | |
| H | $CH_3$ | $CH_3$ | H | H | $CH_3$ | H | $CH_3$ | $CH_3$ | CH | |
| H | H | H | $CH_3$ | $CH_3$ | $CH_3$ | H | $CH_3$ | $CH_3$ | N | |
| H | $CH_3$ | H | $CH_3$ | $CH_3$ | $CH_3$ | H | $CH_3$ | $OCH_3$ | CH | |
| H | $CH_3$ | $CH_3$ | $CH_3$ | H | $CH_3$ | H | $CH_3$ | $OCH_3$ | N | |
| H | $CH_3$ | H | $CH_3$ | H | $CH_3$ | $CH_3$ | $OCH_3$ | $OCH_3$ | CH | |
| H | $CH_3$ | H | $CH_3$ | $CH_3$ | $CH_3$ | $CH_3$ | $CH_3$ | $CH_3$ | CH | |
| H | $CH_3$ | H | $CH_3$ | $CH_3$ | $CH_3$ | $CH_3$ | $CH_3$ | $CH_3$ | CH | |
| H | $CH_3$ | $CH_3$ | $CH_3$ | $CH_3$ | $CH_3$ | H | $CH_3$ | $CH_3$ | N | |
| H | $CH_3$ | $CH_3$ | $CH_3$ | $CH_3$ | $CH_3$ | $CH_3$ | $CH_3$ | $OCH_3$ | CH | |
| $CH_3$ | H | H | H | H | H | H | $CH_3$ | $OCH_3$ | N | |
| H | H | H | H | H | H | H | $OCH_3$ | $CH(OCH_3)_2$ | N | |
| H | H | H | H | H | H | H | $OCH_3$ | 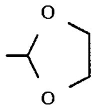 | N | |
| H | H | H | H | H | H | H | Cl | $OCH_3$ | CH | |
| H | H | H | H | H | H | H | $CH_3$ | $CH_3$ | CH | |

Wherein W'' is O.

TABLE 8b

General Structure 3 wherein Q is Q-6.

| Q | R | $R_3$ | $R_4$ | $R_5$ | $R_6$ | $R_7$ | $R_8$ | X | Y | Z | W'' | m.p. °C. |
|---|---|---|---|---|---|---|---|---|---|---|---|---|
| Q-6 | H | H | H | H | H | H | H | $CH_3$ | $CH_3$ | CH | O | |
| Q-6 | H | H | H | H | H | H' | H | $CH_3$ | $CH_3$ | N | O | |
| Q-6 | H | $CH_3$ | H | H | H | H | H | $CH_3$ | $OCH_3$ | CH | O | |
| Q-6 | H | H | H | $CH_3$ | H | H | H | $CH_3$ | $OCH_3$ | N | O | |
| Q-6 | H | H | H | H | H | $CH_3$ | H | $OCH_3$ | $OCH_3$ | CH | O | |
| Q-6 | H | $CH_3$ | H | $CH_3$ | H | H | H | $OCH_3$ | $OCH_3$ | N | O | |
| Q-6 | H | $CH_3$ | H | H | H | $CH_3$ | H | $CH_3$ | $CH_3$ | CH | O | |
| Q-6 | H | H | H | $CH_3$ | H | $CH_3$ | H | $CH_3$ | $CH_3$ | N | O | |
| Q-6 | H | $CH_3$ | $CH_3$ | H | H | H | H | $CH_3$ | $OCH_3$ | CH | O | |
| Q-6 | H | H | H | $CH_3$ | $CH_3$ | H | H | $CH_3$ | $OCH_3$ | N | O | |
| Q-6 | H | H | H | H | H | $CH_3$ | $CH_3$ | $OCH_3$ | $OCH_3$ | CH | O | |
| Q-6 | H | $CH_3$ | H | H | H | $CH_3$ | $CH_3$ | $OCH_3$ | $OCH_3$ | N | O | |
| Q-6 | H | $CH_3$ | $CH_3$ | H | H | $CH_3$ | H | $CH_3$ | $CH_3$ | CH | O | |
| Q-6 | H | $CH_3$ | H | $CH_3$ | $CH_3$ | H | H | $CH_3$ | $CH_3$ | N | O | |
| Q-6 | H | H | H | $CH_3$ | $CH_3$ | $CH_3$ | H | $CH_3$ | $OCH_3$ | CH | O | |
| Q-6 | H | $CH_3$ | $CH_3$ | $CH_3$ | H | H | H | $CH_3$ | $OCH_3$ | N | O | |
| Q-6 | H | H | H | $CH_3$ | $CH_3$ | $CH_3$ | H | $OCH_3$ | $OCH_3$ | CH | O | |
| Q-6 | H | $CH_3$ | H | $CH_3$ | $CH_3$ | $CH_3$ | H | $OCH_3$ | $OCH_3$ | N | O | |
| Q-6 | H | $CH_3$ | $CH_3$ | $CH_3$ | H | $CH_3$ | H | $CH_3$ | $CH_3$ | CH | O | |
| Q-6 | H | $CH_3$ | H | $CH_3$ | H | $CH_3$ | $CH_3$ | $CH_3$ | $CH_3$ | N | O | |
| Q-6 | H | $CH_3$ | $CH_3$ | $CH_3$ | $CH_3$ | H | H | $CH_3$ | $OCH_3$ | CH | O | |
| Q-6 | H | $CH_3$ | $CH_3$ | H | H | $CH_3$ | $CH_3$ | $CH_3$ | $OCH_3$ | N | O | |
| Q-6 | H | H | H | $CH_3$ | $CH_3$ | $CH_3$ | $CH_3$ | $OCH_3$ | $OCH_3$ | CH | O | |
| Q-6 | H | $CH_3$ | H | $CH_3$ | $CH_3$ | $CH_3$ | $CH_3$ | $OCH_3$ | $OCH_3$ | N | O | |
| Q-6 | H | $CH_3$ | $CH_3$ | $CH_3$ | H | $CH_3$ | $CH_3$ | $CH_3$ | $CH_3$ | CH | O | |
| Q-6 | H | $CH_3$ | $CH_3$ | $CH_3$ | $CH_3$ | $CH_3$ | H | $CH_3$ | $CH_3$ | N | O | |
| Q-6 | H | $CH_3$ | $CH_3$ | $CH_3$ | $CH_3$ | $CH_3$ | $CH_3$ | $CH_3$ | $OCH_3$ | CH | O | |
| Q-6 | $CH_3$ | H | H | H | H | H | H | $CH_3$ | $OCH_3$ | N | O | |
| Q-6 | H | H | H | H | H | H | H | Br | $OCH_3$ | CH | O | |
| Q-6 | H | H | H | H | H | H | H | Cl | $OC_2H_5$ | CH | O | |
| Q-6 | H | H | H | H | H | H | H | $OCH_3$ | $C_2H_5$ | CH | O | |
| Q-6 | H | H | H | H | H | H | H | $OCH_3$ | $OC_2H_5$ | CH | O | |

TABLE 8b-continued

General Structure 3 wherein Q is Q-6.

| Q | R | $R_3$ | $R_4$ | $R_5$ | $R_6$ | $R_7$ | $R_8$ | X | Y | Z | W'' | m.p. °C. |
|---|---|---|---|---|---|---|---|---|---|---|---|---|
| Q-6 | H | H | H | H | H | H | H | $CH_3$ | $OCH_3$ | CH | O | |
| Q-6 | H | H | H | H | H | H | H | $CH_3$ | $OCH_3$ | N | O | |
| Q-6 | H | H | H | H | H | H | H | $OCH_3$ | $CH_3$ | CH | O | |
| Q-6 | H | H | H | H | H | H | H | $OCH_3$ | $OCH_3$ | N | O | |
| Q-6 | $CH_3$ | H | H | H | H | H | H | $OCH_3$ | $OCH_3$ | CH | O | |
| Q-6 | H | H | H | H | H | H | H | $CH_3$ | $OCH_3$ | CH | S | |
| Q-6 | H | H | H | H | H | H | H | $CH_3$ | $OCH_3$ | N | S | |
| Q-6 | H | H | H | H | H | H | H | $OCH_3$ | $OCH_3$ | CH | S | |
| Q-6 | H | H | H | H | H | H | H | $OCH_3$ | $OCH_3$ | N | S | |
| Q-6 | H | H | H | H | H | H | H | $OCH_3$ | $C_2H_5$ | CH | S | |
| Q-6 | H | H | H | H | H | H | H | $CH_3$ | $CH_3$ | CH | S | |
| Q-6 | H | H | H | H | H | H | H | $CH_3$ | $CH_3$ | N | S | |
| Q-6 | H | $CH_3$ | H | H | H | H | H | $CH_3$ | $OCH_3$ | CH | S | |
| Q-6 | H | H | H | $CH_3$ | H | H | H | $CH_3$ | $OCH_3$ | N | S | |
| Q-6 | H | H | H | H | H | $CH_3$ | H | $OCH_3$ | $OCH_3$ | CH | S | |
| Q-6 | H | $CH_3$ | H | $CH_3$ | H | H | H | $OCH_3$ | $OCH_3$ | N | S | |
| Q-6 | H | $CH_3$ | H | H | H | $CH_3$ | H | $CH_3$ | $CH_3$ | CH | S | |
| Q-6 | H | H | H | $CH_3$ | H | $CH_3$ | H | $CH_3$ | $CH_3$ | N | S | |
| Q-6 | H | $CH_3$ | $CH_3$ | H | H | H | H | $CH_3$ | $OCH_3$ | CH | S | |
| Q-6 | H | H | H | $CH_3$ | $CH_3$ | H | H | $CH_3$ | $OCH_3$ | N | S | |
| Q-6 | H | H | H | H | H | H | H | $OCH_3$ | $CH_2OCH_3$ | CH | S | |
| Q-6 | H | H | H | H | H | H | H | $OCH_3$ | $CF_3$ | CH | S | |
| Q-6 | H | H | H | H | H | H | H | $OCH_3$ | $OCF_2H$ | CH | S | |
| Q-6 | H | H | H | H | H | $CH_3$ | $CH_3$ | $OCH_3$ | $OCH_3$ | CH | S | |
| Q-6 | H | $CH_3$ | H | H | H | $CH_3$ | $CH_3$ | $OCH_3$ | $OCH_3$ | N | S | |
| Q-6 | H | $CH_3$ | $CH_3$ | H | H | $CH_3$ | H | $CH_3$ | $CH_3$ | CH | S | |
| Q-6 | H | $CH_3$ | H | $CH_3$ | $CH_3$ | H | H | $CH_3$ | $CH_3$ | N. | S | |
| Q-6 | H | H | H | $CH_3$ | $CH_3$ | $CH_3$ | H | $CH_3$ | $OCH_3$ | CH | S | |
| Q-6 | H | $CH_3$ | $CH_3$ | $CH_3$ | H | H | H | $CH_3$ | $OCH_3$ | N | S | |
| Q-6 | H | H | H | $CH_3$ | $CH_3$ | $CH_3$ | H | $OCH_3$ | $OCH_3$ | CH | S | |
| Q-6 | H | $CH_3$ | H | $CH_3$ | $CH_3$ | $CH_3$ | H | $OCH_3$ | $OCH_3$ | N | S | |
| Q-6 | H | $CH_3$ | $CH_3$ | $CH_3$ | H | $CH_3$ | H | $CH_3$ | $CH_3$ | CH | S | |
| Q-6 | H | $CH_3$ | H | $CH_3$ | H | $CH_3$ | $CH_3$ | $CH_3$ | $CH_3$ | N | S | |
| Q-6 | H | $CH_3$ | $CH_3$ | $CH_3$ | $CH_3$ | H | H | $CH_3$ | $OCH_3$ | CH | S | |
| Q-6 | H | $CH_3$ | $CH_3$ | H | H | $CH_3$ | $CH_3$ | $CH_3$ | $OCH_3$ | N | S | |
| Q-6 | H | H | H | $CH_3$ | $CH_3$ | $CH_3$ | $CH_3$ | $OCH_3$ | $OCH_3$ | CH | S | |
| Q-6 | H | $CH_3$ | H | $CH_3$ | $CH_3$ | $CH_3$ | $CH_3$ | $OCH_3$ | $OCH_3$ | N | S | |
| Q-6 | H | $CH_3$ | $CH_3$ | $CH_3$ | H | $CH_3$ | $CH_3$ | $CH_3$ | $CH_3$ | CH | S | |
| Q-6 | H | $CH_3$ | $CH_3$ | $CH_3$ | $CH_3$ | $CH_3$ | H | $CH_3$ | $CH_3$ | N | S | |
| Q-6 | H | $CH_3$ | $CH_3$ | $CH_3$ | $CH_3$ | $CH_3$ | $CH_3$ | $CH_3$ | $OCH_3$ | CH | S | |
| Q-6 | $CH_3$ | H | H | H | H | H | H | $CH_3$ | $OCH_3$ | N | S | |

TABLE 8c

General Structure 3

| Q | R | $R_3$ | $R_4$ | $R_5$ | $R_6$ | X | Y | Z | W' | m.p. °C. |
|---|---|---|---|---|---|---|---|---|---|---|
| Q-7 | H | H | H | H | H | $CH_3$ | $OCH_3$ | CH | — | |
| Q-7 | H | H | H | H | H | $CH_3$ | $OCH_3$ | N | — | |
| Q-7 | H | H | H | H | H | $OCH_3$ | $OCH_3$ | CH | — | |
| Q-7 | H | H | H | H | H | $OCH_3$ | $OCH_3$ | N | — | |
| Q-7 | H | H | H | H | H | $CH_3$ | $CH_3$ | CH | — | |
| Q-7 | H | H | H | H | H | $CH_3$ | $CH_3$ | N | — | |
| Q-7 | H | $CH_3$ | H | H | H | $CH_3$ | $OCH_3$ | CH | — | |
| Q-7 | H | H | $CH_3$ | H | H | $CH_3$ | $OCH_3$ | N | — | |
| Q-7 | H | $CH_3$ | H | H | $CH_3$ | $OCH_3$ | $OCH_3$ | CH | — | |
| Q-7 | H | H | $CH_3$ | $CH_3$ | H | $OCH_3$ | $OCH_3$ | N | — | |
| Q-7 | H | $CH_3$ | $CH_3$ | H | H | $CH_3$ | $CH_3$ | CH | — | |
| Q-7 | H | $CH_3$ | $CH_3$ | $CH_3$ | H | $CH_3$ | $CH_3$ | N | — | |
| Q-7 | H | $CH_3$ | H | $CH_3$ | $CH_3$ | $CH_3$ | $OCH_3$ | CH | — | |
| Q-7 | H | $CH_3$ | $CH_3$ | $CH_3$ | $CH_3$ | $CH_3$ | $OCH_3$ | N | — | |
| Q-7 | $CH_3$ | H | H | H | H | $OCH_3$ | $OCH_3$ | CH | — | |
| Q-7 | $CH_3$ | $CH_3$ | $CH_3$ | $CH_3$ | $CH_3$ | $OCH_3$ | $OCH_3$ | CH | — | |
| Q-7 | H | H | H | H | H | $OCH_3$ | $OCH_2CF_3$ | CH | — | |
| Q-7 | H | H | H | H | H | $OCH_3$ | $NHCH_3$ | CH | — | |
| Q-7 | H | H | H | H | H | Cl | $OCH_3$ | CH | — | |
| Q-7 | H | H | H | H | H | $OCH_3$ | $OCH_3$ | CH | —* | |
| Q-7 | H | H | H | H | H | $OCH_3$ | $CH_3$ | N | —* | |
| Q-7 | H | H | H | H | H | $OCH_3$ | CH | CH | —* | |
| Q-16 | H | $CH_3$ | $CH_3$ | H | H | $CH_3$ | $OCH_3$ | CH | O | |
| Q-16 | H | $CH_3$ | $CH_3$ | H | H | $CH_3$ | $OCH_3$ | N | O | |
| Q-16 | H | $CH_3$ | $CH_3$ | H | H | $OCH_3$ | $OCH_3$ | CH | O | |
| Q-16 | H | $CH_3$ | $CH_3$ | H | H | $OCH_3$ | $OCH_3$ | N | O | |
| Q-16 | $CH_3$ | $CH_3$ | $CH_3$ | H | H | $CH_3$ | $OCH_3$ | N | O | |
| Q-16 | $CH_3$ | $CH_3$ | $CH_3$ | H | H | Cl | $OCH_3$ | CH | O | |
| Q-16 | H | $CH_3$ | $CH_3$ | H | H | $CH_3$ | $CH_3$ | CH | O | |
| Q-16 | H | $CH_3$ | $CH_3$ | H | H | $CH_3$ | $CH_3$ | N | O | |

TABLE 8c-continued

General Structure 3

| Q | R | $R_3$ | $R_4$ | $R_5$ | $R_6$ | X | Y | Z | W' | m.p. °C. |
|---|---|---|---|---|---|---|---|---|---|---|
| Q-16 | H | H | H | H | H | $CH_3$ | $OCH_3$ | CH | O | |
| Q-16 | H | H | H | H | H | $CH_3$ | $OCH_3$ | N | O | |
| Q-16 | H | H | H | H | H | $OCH_3$ | $OCH_3$ | CH | O | |
| Q-16 | H | H | H | H | H | $OCH_3$ | $OCH_3$ | N | O | |
| Q-16 | H | $CH_3$ | $CH_3$ | H | H | $OCH_3$ | $N(CH_3)_2$ | CH | O | |
| Q-16 | H | $CH_3$ | $CH_3$ | H | H | $OCH_3$ | $CH(OCH_3)_2$ | CH | O | |
| Q-16 | H | $CH_3$ | $CH_3$ | H | H | Cl | $OCH_3$ | CH | O | |
| Q-16 | H | $CH_3$ | $CH_3$ | H | H | $CH_3$ | $CH_2OCH_3$ | N | O | |
| Q-16 | H | $CH_3$ | H | H | H | $CH_3$ | $CH_3$ | CH | O | |
| Q-16 | H | H | H | $CH_3$ | H | $CH_3$ | $CH_3$ | N | O | |
| Q-16 | H | $CH_3$ | H | $CH_3$ | H | $CH_3$ | $OCH_3$ | N | O | |
| Q-16 | H | H | H | $CH_3$ | $CH_3$ | $CH_3$ | $OCH_3$ | CH | O | |
| Q-16 | H | $CH_3$ | H | $CH_3$ | $CH_3$ | $OCH_3$ | $OCH_3$ | CH | O | |
| Q-16 | H | $CH_3$ | $CH_3$ | $CH_3$ | H | $OCH_3$ | $OCH_3$ | N | O | |
| Q-16 | H | $CH_3$ | $CH_3$ | $CH_3$ | H | $CH_3$ | $CH_3$ | CH | O | |
| Q-16 | H | $CH_3$ | $CH_3$ | $CH_3$ | $CH_3$ | $CH_3$ | $CH_3$ | N | O | |
| Q-16 | H | $CH_3$ | $CH_3$ | H | H | $CH_3$ | $CH_3$ | CH | S | |
| Q-16 | H | $CH_3$ | $CH_3$ | H | H | $CH_3$ | $CH_3$ | N | S | |
| Q-16 | H | $CH_3$ | $CH_3$ | H | H | $CH_3$ | $OCH_3$ | CH | S | |
| Q-16 | H | $CH_3$ | $CH_3$ | H | H | $CH_3$ | $OCH_3$ | N | S | |
| Q-16 | H | $CH_3$ | $CH_3$ | H | H | $OCH_3$ | $OCH_3$ | CH | S | |
| Q-16 | H | $CH_3$ | $CH_3$ | H | H | $OCH_3$ | $OCH_3$ | N | S | |
| Q-16 | H | $CH_3$ | $CH_3$ | H | H | Cl | $OCH_3$ | CH | S | |
| Q-16 | H | $CH_3$ | $CH_3$ | H | H | $CH_3$ | $NHCH_3$ | N | S | |
| Q-16 | H | $CH_3$ | $CH_3$ | H | H | $CH_3$ | $N(CH_3)_2$ | N | S | |
| Q-16 | H | H | H | H | H | $CH_3$ | $OCH_3$ | CH | S | |
| Q-16 | H | H | H | H | H | $CH_3$ | $OCH_3$ | N | S | |
| Q-16 | H | H | H | H | H | $OCH_3$ | $OCH_3$ | CH | S | |
| Q-16 | H | H | H | H | H | $OCH_3$ | $OCH_3$ | N | S | |
| Q-16 | $CH_3$ | H | H | H | H | $CH_3$ | $CH_3$ | CH | S | |
| Q-16 | H | $CH_3$ | H | H | H | $CH_3$ | $CH_3$ | N | S | |
| Q-16 | H | H | H | $CH_3$ | H | $CH_3$ | $OCH_3$ | N | S | |
| Q-16 | H | $CH_3$ | H | $CH_3$ | H | $CH_3$ | $OCH_3$ | CH | S | |
| Q-16 | H | H | H | $CH_3$ | $CH_3$ | $OCH_3$ | $OCH_3$ | CH | S | |
| Q-16 | H | $CH_3$ | $CH_3$ | $CH_3$ | H | $OCH_3$ | $OCH_3$ | N | S | |
| Q-16 | H | $CH_3$ | $CH_3$ | $CH_3$ | H | $CH_3$ | $CH_3$ | CH | S | |
| Q-16 | H | $CH_3$ | H | $CH_3$ | $CH_3$ | $CH_3$ | $CH_3$ | N | S | |
| Q-16 | H | $CH_3$ | $CH_3$ | $CH_3$ | $CH_3$ | $CH_3$ | $OCH_3$ | CH | S | |
| Q-17 | H | H | H | H | H | Cl | $OCH_3$ | CH | — | |
| Q-17 | H | H | H | H | H | $CH_3$ | $CH_3$ | CH | — | |
| Q-17 | H | H | H | H | H | Cl | $OC_2H_5$ | CH | — | |
| Q-17 | H | H | H | H | H | $CH_3$ | $CH_3$ | N | — | |
| Q-17 | H | H | H | H | H | $OCH_3$ | $OCH_3$ | CH | — | |
| Q-17 | H | H | H | H | H | $OCH_3$ | $OCH_3$ | N | — | |
| Q-17 | H | H | H | H | H | $OCH_3$ | $OC_2H_5$ | CH | — | |
| Q-17 | H | H | H | H | H | $OCH_3$ | $OC_2H_5$ | N | — | |
| Q-17 | H | $CH_3$ | H | H | H | $CH_3$ | $CH_3$ | CH | — | |
| Q-17 | H | H | H | H | H | $CH_3$ | $CH(OCH_3)_2$ | N | — | |
| Q-17 | H | H | H | H | H | $CH_3$ | 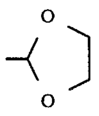 | N | — | |
| Q-17 | H | H | H | $CH_3$ | H | $CH_3$ | $CH_3$ | N | — | |
| Q-17 | H | $CH_3$ | $CH_3$ | H | H | $CH_3$ | $OCH_3$ | CH | — | |
| Q-17 | H | $CH_3$ | $CH_3$ | H | H | $CH_3$ | $OCH_3$ | N | — | |
| Q-17 | H | H | H | $CH_3$ | $CH_3$ | $OCH_3$ | $OCH_3$ | CH | — | |
| Q-17 | H | $CH_3$ | H | $CH_3$ | $CH_3$ | $OCH_3$ | $OCH_3$ | N | — | |
| Q-17 | H | $CH_3$ | $CH_3$ | $CH_3$ | H | $CH_3$ | $CH_3$ | CH | — | |
| Q-17 | H | $CH_3$ | $CH_3$ | $CH_3$ | H | $CH_3$ | $CH_3$ | N | — | |
| Q-17 | H | $CH_3$ | $CH_3$ | $CH_3$ | $CH_3$ | $CH_3$ | $OCH_3$ | CH | — | |
| Q-17 | $CH_3$ | H | H | H | H | $CH_3$ | $OCH_3$ | N | — | |

TABLE 8d

General Structure 3 wherein Q is Q-30

| R | $R_3$ | $R_4$ | $R_5$ | $R_6$ | $R_7$ | $R_8$ | $R_9$ | X | Y | Z | m.p. °C. |
|---|---|---|---|---|---|---|---|---|---|---|---|
| H | H | H | H | H | H | H | H | $CH_3$ | $OCH_3$ | CH | |
| H | H | H | H | H | H | H | H | $CH_3$ | $OCH_3$ | N | |
| H | H | H | H | H | H | H | H | $OCH_3$ | $OCH_3$ | CH | |
| H | H | H | H | H | H | H | H | $OCH_3$ | $OCH_3$ | N | |
| H | H | H | H | H | H | H | H | $CH_3$ | $CH_3$ | N | |
| H | H | H | H | H | H | H | H | $CH_3$ | $CH_3$ | CH | |
| $CH_3$ | H | H | H | H | H | H | H | $CH_3$ | $OCH_3$ | CH | |

TABLE 8d-continued

General Structure 3 wherein Q is Q-30

| R | $R_3$ | $R_4$ | $R_5$ | $R_6$ | $R_7$ | $R_8$ | $R_9$ | X | Y | Z | m.p. °C. |
|---|---|---|---|---|---|---|---|---|---|---|---|
| H | $CH_3$ | H | H | H | H | H | H | $CH_3$ | $OCH_3$ | N | |
| H | H | H | H | H | H | H | H | Cl | $OCH_3$ | CH | |
| H | H | $CH_3$ | H | H | H | H | H | $OCH_3$ | $OCH_3$ | CH | |
| H | H | H | H | $CH_3$ | H | H | H | $OCH_3$ | $OCH_3$ | N | |
| H | H | H | H | H | H | $CH_3$ | H | $CH_3$ | $CH_3$ | CH | |
| H | $CH_3$ | $CH_3$ | H | H | H | H | H | $CH_3$ | $CH_3$ | N | |
| H | $CH_3$ | H | H | $CH_3$ | H | H | H | $CH_3$ | $OCH_3$ | CH | |
| H | $CH_3$ | H | H | H | H | $CH_3$ | H | $CH_3$ | $OCH_3$ | N | |
| H | H | $CH_3$ | $CH_3$ | H | H | H | H | $OCH_3$ | $OCH_3$ | CH | |
| H | H | $CH_3$ | H | $CH_3$ | H | H | H | $OCH_3$ | $OCH_3$ | N | |
| H | H | $CH_3$ | H | H | H | $CH_3$ | H | $CH_3$ | $CH_3$ | CH | |
| H | H | H | H | $CH_3$ | $CH_3$ | H | H | $CH_3$ | $CH_3$ | N | |
| H | H | H | H | $CH_3$ | H | $CH_3$ | H | $CH_3$ | $OCH_3$ | CH | |
| H | H | H | H | H | H | $CH_3$ | $CH_3$ | $CH_3$ | $OCH_3$ | N | |
| H | $CH_3$ | $CH_3$ | $CH_3$ | H | H | H | H | $OCH_3$ | $OCH_3$ | CH | |
| H | $CH_3$ | $CH_3$ | H | $CH_3$ | H | H | H | $OCH_3$ | $OCH_3$ | N | |
| H | $CH_3$ | $CH_3$ | H | H | H | $CH_3$ | H | $CH_3$ | $CH_3$ | CH | |
| H | $CH_3$ | H | H | H | $CH_3$ | H | H | $CH_3$ | $CH_3$ | N | |
| H | $CH_3$ | H | H | $CH_3$ | H | $CH_3$ | H | $CH_3$ | $OCH_3$ | CH | |
| H | $CH_3$ | H | H | H | H | $CH_3$ | $CH_3$ | $CH_3$ | $OCH_3$ | N | |
| H | H | $CH_3$ | $CH_3$ | $CH_3$ | H | H | H | $OCH_3$ | $OCH_3$ | CH | |
| H | H | $CH_3$ | $CH_3$ | H | H | $CH_3$ | H | $OCH_3$ | $OCH_3$ | N | |
| H | H | $CH_3$ | H | $CH_3$ | $CH_3$ | H | H | $CH_3$ | $CH_3$ | CH | |
| H | H | $CH_3$ | H | $CH_3$ | H | $CH_3$ | H | $CH_3$ | $CH_3$ | N | |
| H | H | $CH_3$ | H | H | H | $CH_3$ | $CH_3$ | $CH_3$ | $OCH_3$ | CH | |
| H | H | H | H | $CH_3$ | $CH_3$ | $CH_3$ | H | $CH_3$ | $OCH_3$ | N | |
| H | H | H | H | $CH_3$ | H | $CH_3$ | $CH_3$ | $OCH_3$ | $OCH_3$ | CH | |
| H | $CH_3$ | $CH_3$ | $CH_3$ | $CH_3$ | H | H | H | $OCH_3$ | $OCH_3$ | N | |
| H | $CH_3$ | $CH_3$ | H | $CH_3$ | H | $CH_3$ | H | $CH_3$ | $CH_3$ | CH | |
| H | $CH_3$ | H | H | $CH_3$ | $CH_3$ | $CH_3$ | H | $CH_3$ | $OCH_3$ | N | |
| H | $CH_3$ | $CH_3$ | $CH_3$ | H | H | $CH_3$ | H | $CH_3$ | $OCH_3$ | CH | |
| H | $CH_3$ | H | H | $CH_3$ | H | $CH_3$ | $CH_3$ | $CH_3$ | $OCH_3$ | N | |
| H | $CH_3$ | $CH_3$ | H | $CH_3$ | $CH_3$ | H | H | $OCH_3$ | $OCH_3$ | CH | |
| H | $CH_3$ | $CH_3$ | H | H | H | $CH_3$ | $CH_3$ | $OCH_3$ | $OCH_3$ | N | |
| H | H | $CH_3$ | $CH_3$ | $CH_3$ | $CH_3$ | H | H | $CH_3$ | $CH_3$ | CH | |
| H | H | $CH_3$ | $CH_3$ | $CH_3$ | H | $CH_3$ | H | $CH_3$ | $CH_3$ | N | |
| H | H | $CH_3$ | H | $CH_3$ | $CH_3$ | $CH_3$ | H | $CH_3$ | $OCH_3$ | CH | |
| H | H | $CH_3$ | H | $CH_3$ | H | $CH_3$ | $CH_3$ | $CH_3$ | $OCH_3$ | N | |
| H | H | H | H | $CH_3$ | $CH_3$ | $CH_3$ | $CH_3$ | $OCH_3$ | $OCH_3$ | CH | |
| H | $CH_3$ | $CH_3$ | $CH_3$ | $CH_3$ | $CH_3$ | H | H | $OCH_3$ | $OCH_3$ | N | |
| H | $CH_3$ | $CH_3$ | H | $CH_3$ | $CH_3$ | $CH_3$ | H | $CH_3$ | $CH_3$ | CH | |
| H | $CH_3$ | $CH_3$ | H | $CH_3$ | H | $CH_3$ | $CH_3$ | $CH_3$ | $CH_3$ | N | |
| H | $CH_3$ | H | H | $CH_3$ | $CH_3$ | $CH_3$ | $CH_3$ | $CH_3$ | $OCH_3$ | CH | |
| H | $CH_3$ | $CH_3$ | $CH_3$ | H | H | $CH_3$ | $CH_3$ | $CH_3$ | $OCH_3$ | N | |
| H | H | $CH_3$ | $CH_3$ | $CH_3$ | H | $CH_3$ | $CH_3$ | $OCH_3$ | $OCH_3$ | CH | |
| H | H | $CH_3$ | H | $CH_3$ | $CH_3$ | $CH_3$ | $CH_3$ | $OCH_3$ | $OCH_3$ | N | |
| H | H | $CH_3$ | $CH_3$ | $CH_3$ | $CH_3$ | $CH_3$ | H | $CH_3$ | $CH_3$ | CH | |
| H | $CH_3$ | $CH_3$ | H | $CH_3$ | $CH_3$ | $CH_3$ | $CH_3$ | $CH_3$ | $CH_3$ | N | |
| H | $CH_3$ | $CH_3$ | $CH_3$ | $CH_3$ | H | $CH_3$ | $CH_3$ | $CH_3$ | $OCH_3$ | CH | |
| H | $CH_3$ | $CH_3$ | $CH_3$ | $CH_3$ | $CH_3$ | $CH_3$ | H | $CH_3$ | $OCH_3$ | N | |
| H | H | $CH_3$ | $CH_3$ | $CH_3$ | $CH_3$ | $CH_3$ | $CH_3$ | $OCH_3$ | $OCH_3$ | CH | |
| H | $CH_3$ | $CH_3$ | $CH_3$ | $CH_3$ | $CH_3$ | $CH_3$ | $CH_3$ | $OCH_3$ | $OCH_3$ | N | |
| $CH_3$ | $CH_3$ | $CH_3$ | $CH_3$ | $CH_3$ | $CH_3$ | $CH_3$ | $CH_3$ | $CH_3$ | $CH_3$ | CH | |
| H | H | H | H | H | H | H | H | $CH_3$ | $OC_2H_5$ | CH | |
| H | H | H | H | H | H | H | H | $CH_3$ | $CH_2OCH_3$ | CH | |

TABLE 8e

General Structure 3 wherein Q is Q-31.

| R | $R_3$ | $R_4$ | $R_5$ | $R_6$ | $R_7$ | $R_8$ | $R_9$ | $R_{10}$ | X | Y | Z | m.p. °C. |
|---|---|---|---|---|---|---|---|---|---|---|---|---|
| H | H | H | H | H | H | H | H | H | $CH_3$ | $OCH_3$ | CH | |
| H | H | H | H | H | H | H | H | H | $CH_3$ | $OCH_3$ | N | |
| H | H | H | H | H | H | H | H | H | $OCH_3$ | $OCH_3$ | CH | |
| H | H | H | H | H | H | H | H | H | $OCH_3$ | $OCH_3$ | N | |
| H | H | H | H | H | H | H | H | H | $CH_3$ | $CH_3$ | CH | |
| H | H | H | H | H | H | H | H | H | $CH_3$ | $CH_3$ | N | |
| H | H | H | H | H | H | H | H | H | Cl | $OCH_3$ | CH | |
| H | H | H | H | H | H | H | H | H | $CH_3$ | $C_2H_5$ | CH | |
| H | H | H | H | H | H | H | H | H | $CH_3$ | $CF_3$ | CH | |
| H | H | H | H | H | H | H | H | H | $CH_3$ | $OCF_2H$ | CH | |
| H | H | H | H | H | H | H | H | H | $CH_3$ | $OCH_2CF_3$ | CH | |
| H | $CH_3$ | H | H | H | H | H | H | H | $CH_3$ | $CH_3$ | CH | |
| H | H | H | $CH_3$ | H | H | H | H | H | $CH_3$ | $CH_3$ | N | |
| H | H | H | H | H | $CH_3$ | H | H | H | $CH_3$ | $OCH_3$ | CH | |
| H | H | H | H | H | H | H | $CH_3$ | H | $CH_3$ | $OCH_3$ | N | |
| H | $CH_3$ | $CH_3$ | H | H | H | H | H | H | $OCH_3$ | $OCH_3$ | CH | |

TABLE 8e-continued

General Structure 3 wherein Q is Q-31.

| R | $R_3$ | $R_4$ | $R_5$ | $R_6$ | $R_7$ | $R_8$ | $R_9$ | $R_{10}$ | X | Y | Z | m.p. °C. |
|---|---|---|---|---|---|---|---|---|---|---|---|---|
| H | H | H | $CH_3$ | $CH_3$ | H | H | H | H | $OCH_3$ | $OCH_3$ | N | |
| H | H | H | H | H | $CH_3$ | H | H | $CH_3$ | $CH_3$ | CH | | |
| | | | | | $CH_3$ | | | | | | | |
| H | H | H | H | H | H | H | $CH_3$ | $CH_3$ | $CH_3$ | $CH_3$ | N | |
| H | H | H | $CH_3$ | H | H | H | $CH_3$ | H | $CH_3$ | $OCH_3$ | CH | |
| H | $CH_3$ | H | H | H | $CH_3$ | H | H | H | $CH_3$ | $OCH_3$ | N | |
| H | $CH_3$ | H | $CH_3$ | H | H | H | H | H | $OCH_3$ | $OCH_3$ | CH | |
| H | H | H | H | H | $CH_3$ | H | $CH_3$ | H | $OCH_3$ | $OCH_3$ | N | |
| H | $CH_3$ | $CH_3$ | $CH_3$ | H | H | H | H | H | $CH_3$ | $CH_3$ | CH | |
| H | $CH_3$ | H | H | H | $CH_3$ | $CH_3$ | H | H | $CH_3$ | $CH_3$ | N | |
| H | H | H | $CH_3$ | $CH_3$ | H | H | $CH_3$ | H | $CH_3$ | $OCH_3$ | CH | |
| H | H | H | $CH_3$ | $CH_3$ | $CH_3$ | H | H | H | $CH_3$ | $OCH_3$ | N | |
| H | $CH_3$ | H | H | H | $CH_3$ | H | $CH_3$ | H | $OCH_3$ | $OCH_3$ | CH | |
| H | $CH_3$ | $CH_3$ | H | H | H | H | $CH_3$ | $CH_3$ | $OCH_3$ | $OCH_3$ | N | |
| H | $CH_3$ | H | H | H | $CH_3$ | $CH_3$ | $CH_3$ | H | $CH_3$ | $CH_3$ | CH | |
| H | $CH_3$ | H | $CH_3$ | H | $CH_3$ | H | $CH_3$ | H | $CH_3$ | $CH_3$ | N | |
| H | H | H | $CH_3$ | $CH_3$ | $CH_3$ | $CH_3$ | H | H | $CH_3$ | $OCH_3$ | CH | |
| H | $CH_3$ | $CH_3$ | $CH_3$ | H | H | H | $CH_3$ | $CH_3$ | $CH_3$ | $OCH_3$ | N | |
| H | $CH_3$ | H | $CH_3$ | $CH_3$ | $CH_3$ | H | $CH_3$ | H | $OCH_3$ | $OCH_3$ | CH | |
| H | $CH_3$ | H | $CH_3$ | H | $CH_3$ | $CH_3$ | $CH_3$ | H | $OCH_3$ | $OCH_3$ | N | |
| H | $CH_3$ | $CH_3$ | $CH_3$ | H | $CH_3$ | H | $CH_3$ | H | $CH_3$ | $CH_3$ | CH | |
| H | $CH_3$ | H | $CH_3$ | $CH_3$ | $CH_3$ | $CH_3$ | $CH_3$ | H | $CH_3$ | $CH_3$ | N | |
| H | $CH_3$ | H | $CH_3$ | $CH_3$ | $CH_3$ | H | $CH_3$ | $CH_3$ | $CH_3$ | $OCH_3$ | CH | |
| H | $CH_3$ | H | $CH_3$ | $CH_3$ | $CH_3$ | $CH_3$ | $CH_3$ | $CH_3$ | $CH_3$ | $OCH_3$ | N | |
| H | $CH_3$ | $CH_3$ | $CH_3$ | $CH_3$ | $CH_3$ | $CH_3$ | $CH_3$ | H | $OCH_3$ | $OCH_3$ | CH | |
| $CH_3$ | H | H | H | H | H | H | H | H | $OCH_3$ | $OCH_3$ | N | |
| H | H | H | H | H | H | H | H | H | $CH_3$ | $OCH_3$ | CH | * |
| H | H | H | H | H | H | H | H | H | $CH_3$ | $OCH_3$ | N | * |
| H | H | H | H | H | H | H | H | H | $OCH_3$ | $OCH_3$ | CH | * |
| H | H | H | H | H | H | H | H | H | $OCH_3$ | $OCH_3$ | N | * |
| H | H | H | H | H | H | H | H | H | $CH_3$ | $CH_3$ | CH | * |
| H | H | H | H | H | H | H | H | H | $CH_3$ | $CH_3$ | N | * |
| H | H | H | H | H | H | H | H | H | Cl | $OCH_3$ | CH | * |

*Wherein W" is O, unless indicated by ** where W" is S in all Tables.

TABLE 8f

General Structure 3 wherein Q is Q-32.

| R | $R_3$ | $R_4$ | $R_5$ | $R_6$ | $R_7$ | $R_8$ | $R_9$ | $R_{10}$ | X | Y | Z | W" |
|---|---|---|---|---|---|---|---|---|---|---|---|---|
| H | H | H | H | H | H | H | H | H | $CH_3$ | $CH_3$ | CH | O |
| H | H | H | H | H | H | H | H | H | $CH_3$ | $CH_3$ | N | O |
| H | H | H | H | H | H | H | H | H | Cl | $OCH_3$ | CH | O |
| H | H | H | H | H | H | H | H | H | $CH_3$ | $NHCH_3$ | CH | O |
| H | H | H | H | H | H | H | H | H | $CH_3$ | $N(CH_3)_2$ | CH | O |
| H | H | H | H | H | H | H | H | H | $CH_3$ | $CH(OCH_3)_2$ | CH | O |
| H | H | H | H | H | H | H | H | H | Br | $OCH_3$ | CH | O |
| H | $CH_3$ | H | H | H | H | H | H | H | $CH_3$ | $CH_3$ | CH | O |
| H | H | H | $CH_3$ | H | H | H | H | H | $CH_3$ | $CH_3$ | N | O |
| H | H | H | H | H | $CH_3$ | H | H | H | $CH_3$ | $OCH_3$ | CH | O |
| H | H | H | H | H | H | H | $CH_3$ | H | $CH_3$ | $OCH_3$ | N | O |
| H | $CH_3$ | $CH_3$ | H | H | H | H | H | H | $OCH_3$ | $OCH_3$ | CH | O |
| H | H | H | $CH_3$ | $CH_3$ | H | H | H | H | $OCH_3$ | $OCH_3$ | N | O |
| H | H | H | H | H | $CH_3$ | $CH_3$ | H | H | $CH_3$ | $CH_3$ | CH | O |
| H | H | H | H | H | H | H | $CH_3$ | $CH_3$ | $CH_3$ | $CH_3$ | N | O |
| H | H | H | $CH_3$ | H | H | H | $CH_3$ | H | $CH_3$ | $OCH_3$ | CH | O |
| H | $CH_3$ | H | H | H | $CH_3$ | H | H | H | $CH_3$ | $OCH_3$ | N | O |
| H | $CH_3$ | H | $CH_3$ | H | H | H | H | H | $OCH_3$ | $OCH_3$ | CH | O |
| H | H | H | H | H | $CH_3$ | H | $CH_3$ | H | $OCH_3$ | $OCH_3$ | N | O |
| H | $CH_3$ | $CH_3$ | $CH_3$ | H | H | H | H | H | $CH_3$ | $CH_3$ | CH | O |
| H | $CH_3$ | H | H | H | $CH_3$ | $CH_3$ | H | H | $CH_3$ | $CH_3$ | N | O |
| H | H | H | $CH_3$ | $CH_3$ | H | H | $CH_3$ | H | $CH_3$ | $OCH_3$ | CH | O |
| H | H | H | $CH_3$ | $CH_3$ | $CH_3$ | H | H | H | $CH_3$ | $OCH_3$ | N | O |
| H | $CH_3$ | H | H | H | $CH_3$ | H | $CH_3$ | H | $OCH_3$ | $OCH_3$ | CH | O |
| H | $CH_3$ | $CH_3$ | H | H | H | H | $CH_3$ | $CH_3$ | $OCH_3$ | $OCH_3$ | N | O |
| H | $CH_3$ | H | H | H | $CH_3$ | $CH_3$ | $CH_3$ | H | $CH_3$ | $CH_3$ | CH | O |
| H | $CH_3$ | H | $CH_3$ | H | $CH_3$ | H | $CH_3$ | H | $CH_3$ | $CH_3$ | N | O |
| H | H | H | $CH_3$ | $CH_3$ | $CH_3$ | $CH_3$ | H | H | $CH_3$ | $OCH_3$ | CH | O |
| H | $CH_3$ | $CH_3$ | $CH_3$ | H | H | H | $CH_3$ | $CH_3$ | $CH_3$ | $OCH_3$ | N | O |
| H | $CH_3$ | H | $CH_3$ | $CH_3$ | $CH_3$ | H | $CH_3$ | H | $OCH_3$ | $OCH_3$ | CH | O |
| H | $CH_3$ | H | $CH_3$ | H | $CH_3$ | $CH_3$ | $CH_3$ | H | $OCH_3$ | $OCH_3$ | N | O |
| H | $CH_3$ | $CH_3$ | $CH_3$ | H | $CH_3$ | H | $CH_3$ | H | $CH_3$ | $CH_3$ | CH | O |
| H | $CH_3$ | H | $CH_3$ | $CH_3$ | $CH_3$ | $CH_3$ | $CH_3$ | H | $CH_3$ | $CH_3$ | N | O |
| H | $CH_3$ | H | $CH_3$ | $CH_3$ | $CH_3$ | H | $CH_3$ | $CH_3$ | $CH_3$ | $OCH_3$ | CH | O |
| H | $CH_3$ | H | $CH_3$ | $CH_3$ | $CH_3$ | $CH_3$ | $CH_3$ | $CH_3$ | $CH_3$ | $OCH_3$ | N | O |
| H | $CH_3$ | $CH_3$ | $CH_3$ | $CH_3$ | $CH_3$ | $CH_3$ | $CH_3$ | H | $OCH_3$ | $OCH_3$ | CH | O |
| $CH_3$ | H | H | H | H | H | H | H | H | $OCH_3$ | $OCH_3$ | N | O |
| H | $CH_3$ | H | H | H | H | H | $CH_3$ | H | $CH_3$ | $OCH_3$ | CH | O |

TABLE 8f-continued

| General Structure 3 wherein Q is Q-32. | | | | | | | | | | | | |
|---|---|---|---|---|---|---|---|---|---|---|---|---|
| R | $R_3$ | $R_4$ | $R_5$ | $R_6$ | $R_7$ | $R_8$ | $R_9$ | $R_{10}$ | X | Y | Z | W'' |
| H | H | H | H | H | H | H | H | H | $CH_3$ | $OCH_3$ | CH | O |
| H | H | H | H | H | H | H | H | H | $CH_3$ | $OCH_3$ | N | O |
| H | H | H | H | H | H | H | H | H | $OCH_3$ | $OCH_3$ | CH | O |
| H | H | H | H | H | H | H | H | H | $OCH_3$ | $OCH_3$ | N | O |
| H | H | H | H | H | H | H | H | H | $CH_3$ | $OCH_3$ | CH | S |
| H | H | H | H | H | H | H | H | H | $CH_3$ | $OCH_3$ | N | S |
| H | H | H | H | H | H | H | H | H | $OCH_3$ | $OCH_3$ | CH | S |
| H | H | H | H | H | H | H | H | H | $OCH_3$ | $OCH_3$ | N | S |
| H | H | H | H | H | H | H | H | H | $CH_3$ | $CH_3$ | CH | S |
| H | H | H | H | H | H | H | H | H | $CH_3$ | $CH_3$ | N | S |
| H | H | H | H | H | H | H | H | H | Cl | $OCH_3$ | CH | S |
| H | H | H | H | H | H | H | H | H | $CH_3$ | 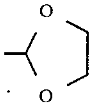 | CH | S |
| H | H | H | H | H | H | H | H | H | Cl | $OC_2H_5$ | CH | S |
| H | H | H | H | H | H | H | H | H | $CH_3$ | $C_2H_5$ | N | S |
| H | H | H | H | H | H | H | H | H | $CH_3$ | $OC_2H_5$ | N | S |
| H | $CH_3$ | H | H | H | H | H | H | H | $CH_3$ | $CH_3$ | CH | S |
| H | H | H | $CH_3$ | H | H | H | H | H | $CH_3$ | $CH_3$ | N | S |
| H | H | H | H | H | $CH_3$ | H | H | H | $CH_3$ | $OCH_3$ | CH | S |
| H | H | H | H | H | H | H | $CH_3$ | H | $CH_3$ | $OCH_3$ | N | S |
| H | $CH_3$ | $CH_3$ | H | H | H | H | H | H | $OCH_3$ | $OCH_3$ | CH | S |
| H | H | H | $CH_3$ | $CH_3$ | H | H | H | H | $OCH_3$ | $OCH_3$ | N | S |
| H | H | H | H | H | $CH_3$ | $CH_3$ | H | H | $CH_3$ | $CH_3$ | CH | S |
| H | H | H | H | H | H | H | $CH_3$ | $CH_3$ | $CH_3$ | $CH_3$ | N | S |
| H | H | H | $CH_3$ | H | H | H | $CH_3$ | H | $CH_3$ | $OCH_3$ | CH | S |
| H | $CH_3$ | H | H | H | $CH_3$ | H | H | H | $CH_3$ | $OCH_3$ | N | S |
| H | $CH_3$ | H | $CH_3$ | H | H | H | H | H | $OCH_3$ | $OCH_3$ | CH | S |
| H | H | H | H | H | $CH_3$ | H | $CH_3$ | H | $OCH_3$ | $OCH_3$ | N | S |
| H | $CH_3$ | $CH_3$ | $CH_3$ | H | H | H | H | H | $CH_3$ | $CH_3$ | CH | S |
| H | $CH_3$ | H | H | H | $CH_3$ | $CH_3$ | H | H | $CH_3$ | $CH_3$ | N | S |
| H | H | H | $CH_3$ | $CH_3$ | H | H | $CH_3$ | H | $CH_3$ | $OCH_3$ | CH | S |
| H | H | H | $CH_3$ | $CH_3$ | $CH_3$ | H | H | H | $CH_3$ | $OCH_3$ | N | S |
| H | $CH_3$ | H | H | H | $CH_3$ | H | $CH_3$ | H | $OCH_3$ | $OCH_3$ | CH | S |
| H | $CH_3$ | $CH_3$ | H | H | H | H | $CH_3$ | $CH_3$ | $OCH_3$ | $OCH_3$ | N | S |
| H | $CH_3$ | H | H | H | $CH_3$ | $CH_3$ | $CH_3$ | H | $CH_3$ | $CH_3$ | CH | S |
| H | $CH_3$ | H | $CH_3$ | H | $CH_3$ | H | $CH_3$ | H | $CH_3$ | $CH_3$ | N | S |
| H | H | H | $CH_3$ | $CH_3$ | $CH_3$ | $CH_3$ | H | H | $CH_3$ | $OCH_3$ | N | S |
| H | $CH_3$ | $CH_3$ | $CH_3$ | H | H | H | $CH_3$ | $CH_3$ | $CH_3$ | $OCH_3$ | N | S |
| H | $CH_3$ | H | $CH_3$ | $CH_3$ | $CH_3$ | H | $CH_3$ | H | $OCH_3$ | $OCH_3$ | CH | S |
| H | $CH_3$ | H | $CH_3$ | H | $CH_3$ | $CH_3$ | $CH_3$ | H | $OCH_3$ | $OCH_3$ | N | S |
| H | $CH_3$ | $CH_3$ | $CH_3$ | H | $CH_3$ | H | $CH_3$ | H | $CH_3$ | $CH_3$ | CH | S |
| H | $CH_3$ | H | $CH_3$ | $CH_3$ | $CH_3$ | $CH_3$ | $CH_3$ | H | $CH_3$ | $CH_3$ | N | S |
| H | $CH_3$ | H | $CH_3$ | $CH_3$ | $CH_3$ | H | $CH_3$ | $CH_3$ | $CH_3$ | $OCH_3$ | CH | S |
| H | $CH_3$ | H | $CH_3$ | $CH_3$ | $CH_3$ | $CH_3$ | $CH_3$ | $CH_3$ | $CH_3$ | $OCH_3$ | N | S |
| H | $CH_3$ | $CH_3$ | $CH_3$ | $CH_3$ | $CH_3$ | $CH_3$ | $CH_3$ | H | $OCH_3$ | $OCH_3$ | CH | S |
| $CH_3$ | H | H | H | H | H | H | H | H | $OCH_3$ | $OCH_3$ | N | S |
| H | $CH_3$ | H | H | H | H | H | $CH_3$ | H | $CH_3$ | $OCH_3$ | CH | S |

TABLE 8g

| General Structure 3 | | | | | | | | | | | |
|---|---|---|---|---|---|---|---|---|---|---|---|
| Q | R | $R_3$ | $R_4$ | $R_5$ | $R_6$ | $R_7$ | X | Y | Z | W | m.p. °C. |
| Q-41 | H | H | H | H | H | H | Cl | $OCH_3$ | CH | | |
| Q-41 | H | H | H | H | H | H | Br | $OCH_3$ | CH | | |
| Q-41 | H | H | H | H | H | H | Cl | $OC_2H_5$ | CH | | |
| Q-41 | H | H | H | H | H | H | $CH_3$ | $CH_3$ | N | | |
| Q-41 | H | H | H | H | H | H | $OCH_3$ | $OCH_3$ | CH | | |
| Q-41 | H | H | H | H | H | H | $OCH_3$ | $OCH_3$ | N | | |
| Q-41 | H | H | H | H | H | H | $OCH_3$ | $OC_2H_5$ | CH | | |
| Q-41 | H | H | H | H | H | H | $OCH_3$ | $OC_2H_5$ | N | | |
| Q-41 | H | H | H | H | H | H | $CH_3$ | $CH_3$ | CH | | |
| Q-41 | H | H | H | H | H | H | $CH_3$ | $OCH_3$ | N | | |
| Q-41 | H | H | H | H | H | H | $CH_3$ | $OCH_3$ | CH | | |
| Q-41 | H | H | H | H | H | H | $CH_3$ | $CH_2OCH_3$ | CH | | |
| Q-41 | H | H | H | H | H | H | $CH_3$ | $CF_3$ | N | | |
| Q-41 | H | H | H | H | H | H | $CH_3$ | $OCF_2H$ | N | | |
| Q-41 | H | $CH_3$ | H | H | H | H | $CH_3$ | $CH_3$ | CH | | |
| Q-41 | H | H | H | $CH_3$ | H | H | $CH_3$ | $CH_3$ | N | | |
| Q-41 | H | H | H | H | $CH_3$ | H | $CH_3$ | $OCH_3$ | CH | | |
| Q-41 | H | $CH_3$ | $CH_3$ | H | H | H | $CH_3$ | $OCH_3$ | N | | |
| Q-41 | H | $CH_3$ | $CH_3$ | H | H | H | $OCH_3$ | $OCH_3$ | CH | | |
| Q-41 | H | $CH_3$ | $CH_3$ | H | H | H | $OCH_3$ | $OCH_3$ | N | | |

TABLE 8g-continued

General Structure 3

| Q | R | $R_3$ | $R_4$ | $R_5$ | $R_6$ | $R_7$ | X | Y | Z | W | m.p. °C. |
|---|---|---|---|---|---|---|---|---|---|---|---|
| Q-41 | H | $CH_3$ | H | $CH_3$ | H | H | $CH_3$ | $CH_3$ | CH | | |
| Q-41 | H | $CH_3$ | H | H | $CH_3$ | H | $CH_3$ | $CH_3$ | N | | |
| Q-41 | H | H | H | $CH_3$ | $CH_3$ | H | $CH_3$ | $OCH_3$ | CH | | |
| Q-41 | H | H | H | H | $CH_3$ | $CH_3$ | $CH_3$ | $OCH_3$ | N | | |
| Q-41 | H | $CH_3$ | $CH_3$ | $CH_3$ | H | H | $OCH_3$ | $OCH_3$ | CH | | |
| Q-41 | H | $CH_3$ | $CH_3$ | H | $CH_3$ | H | $OCH_3$ | $OCH_3$ | N | | |
| Q-41 | H | $CH_3$ | H | $CH_3$ | $CH_3$ | H | $CH_3$ | $CH_3$ | CH | | |
| Q-41 | H | $CH_3$ | H | H | $CH_3$ | $CH_3$ | $CH_3$ | $CH_3$ | N | | |
| Q-41 | H | $CH_3$ | $CH_3$ | $CH_3$ | $CH_3$ | H | $CH_3$ | $OCH_3$ | CH | | |
| Q-41 | H | $CH_3$ | $CH_3$ | H | $CH_3$ | $CH_3$ | $CH_3$ | $OCH_3$ | N | | |
| Q-42 | H | H | H | H | H | H | $CH_3$ | $OCH_3$ | N | O | |
| Q-42 | H | H | H | H | H | H | $OCH_3$ | $OCH_3$ | CH | O | |
| Q-42 | H | H | H | H | H | H | $OCH_3$ | $OCH_3$ | N | O | |
| Q-42 | H | H | H | H | H | H | $CH_3$ | $OCH_3$ | CH | S | |
| Q-42 | H | H | H | H | H | H | $CH_3$ | $OCH_3$ | N | S | |
| Q-42 | H | H | H | H | H | H | $OCH_3$ | $OCH_3$ | CH | S | |
| Q-42 | H | H | H | H | H | H | $OCH_3$ | $OCH_3$ | N | S | |
| Q-42 | H | H | H | H | H | H | $CH_3$ | $CH_3$ | CH | S | |
| Q-42 | H | H | H | H | H | H | $CH_3$ | $CH_3$ | N | S | |
| Q-42 | H | H | H | H | H | H | $CH_3$ | 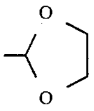 | N | S | |
| Q-42 | H | H | H | H | H | H | Br | $OC_2H_5$ | CH | S | |
| Q-42 | H | H | H | H | H | H | $OCH_3$ | $CH_2OCH_3$ | N | S | |
| Q-42 | $CH_3$ | H | H | H | H | H | $CH_3$ | $OCH_3$ | CH | S | |
| Q-42 | $CH_3$ | H | H | H | H | H | $CH_3$ | $OCH_3$ | N | S | |
| Q-42 | H | $CH_3$ | H | H | H | H | $CH_3$ | $CH_3$ | CH | S | |
| Q-42 | H | H | H | $CH_3$ | H | H | $CH_3$ | $CH_3$ | N | S | |
| Q-42 | H | H | H | H | $CH_3$ | H | $CH_3$ | $OCH_3$ | CH | S | |
| Q-42 | H | $CH_3$ | $CH_3$ | H | H | H | $CH_3$ | $OCH_3$ | N | S | |
| Q-42 | H | $CH_3$ | $CH_3$ | H | H | H | $OCH_3$ | $OCH_3$ | CH | S | |
| Q-42 | H | $CH_3$ | H | $CH_3$ | H | H | $OCH_3$ | $OCH_3$ | N | S | |
| Q-42 | H | $CH_3$ | H | H | $CH_3$ | H | $CH_3$ | $CH_3$ | CH | S | |
| Q-42 | H | H | H | $CH_3$ | $CH_3$ | H | $CH_3$ | $CH_3$ | N | S | |
| Q-42 | H | H | H | H | $CH_3$ | $CH_3$ | $CH_3$ | $OCH_3$ | CH | S | |
| Q-42 | H | $CH_3$ | $CH_3$ | $CH_3$ | H | H | $CH_3$ | $OCH_3$ | N | S | |
| Q-42 | H | $CH_3$ | $CH_3$ | H | $CH_3$ | H | $OCH_3$ | $OCH_3$ | CH | S | |
| Q-42 | H | $CH_3$ | H | $CH_3$ | $CH_3$ | H | $OCH_3$ | $OCH_3$ | N | S | |
| Q-42 | H | H | H | $CH_3$ | $CH_3$ | $CH_3$ | $CH_3$ | $CH_3$ | CH | S | |
| Q-42 | H | $CH_3$ | H | H | $CH_3$ | $CH_3$ | $CH_3$ | $CH_3$ | N | S | |
| Q-42 | H | $CH_3$ | $CH_3$ | $CH_3$ | $CH_3$ | H | $CH_3$ | $OCH_3$ | CH | S | |
| Q-42 | H | $CH_3$ | $CH_3$ | H | $CH_3$ | $CH_3$ | $CH_3$ | $OCH_3$ | N | S | |
| Q-42 | H | $CH_3$ | H | $CH_3$ | $CH_3$ | $CH_3$ | $OCH_3$ | $OCH_3$ | CH | S | |
| Q-42 | H | $CH_3$ | $CH_3$ | $CH_3$ | $CH_3$ | $CH_3$ | $OCH_3$ | $OCH_3$ | N | S | |
| Q-41 | H | $CH_3$ | H | $CH_3$ | $CH_3$ | $CH_3$ | $OCH_3$ | $OCH_3$ | CH | | |
| Q-41 | H | $CH_3$ | $CH_3$ | $CH_3$ | $CH_3$ | $CH_3$ | $OCH_3$ | $OCH_3$ | N | | |
| Q-41 | $CH_3$ | H | H | H | H | H | $CH_3$ | $CH_3$ | CH | | |
| Q-41 | $CH_3$ | H | H | H | H | H | $CH_3$ | $OCH_3$ | CH | | |

TABLE 9a

General Structure 3 wherein Q is Q-20.

| R | R'3 | X | Y | Z | W' | m.p. °C. |
|---|---|---|---|---|---|---|
| H | H | $CH_3$ | $OCH_3$ | CH | O | |
| H | H | $CH_3$ | $OCH_3$ | N | O | |
| H | H | $OCH_3$ | $OCH_3$ | CH | O | |
| H | H | $OCH_3$ | Cl | CH | O | |
| H | H | $OCH_3$ | $OCH_3$ | N | O | |
| H | H | $CH_3$ | $CH_3$ | CH | O | |
| H | $CH_3$ | $CH_3$ | $OCH_3$ | CH | O | |
| $CH_3$ | H | $CH_3$ | $OCH_3$ | N | O | |
| $CH_3$ | $CH_3$ | $OCH_3$ | $OCH_3$ | CH | O | |
| H | H | $CH_3$ | $OC_2H_5$ | N | O | |
| H | H | $CH_3$ | $CH_3$ | CH | S | |
| H | H | $CH_3$ | $CH_3$ | N | S | |
| H | H | $CH_3$ | $OCH_3$ | CH | S | |
| H | H | $CH_3$ | $OCH_3$ | N | S | |
| H | H | $OCH_3$ | $OCH_3$ | CH | S | |
| H | H | $OCH_3$ | $OCH_3$ | N | S | |
| $CH_3$ | H | $CH_3$ | $OCH_3$ | CH | S | |
| H | $CH_3$ | $CH_3$ | $OCH_3$ | N | S | |
| H | $CH_3$ | $CH_3$ | $CH_2OCH_3$ | N | S | |
| H | $C_2H_5$ | $CH_3$ | $CH_3$ | CH | O | |

TABLE 9a-continued

| General Structure 3 wherein Q is Q-20. | | | | | | |
|---|---|---|---|---|---|---|
| R | R'$_3$ | X | Y | Z | W' | m.p. °C. |
| H | $C_2H_5$ | $CH_3$ | $CH_3$ | N | O | |
| H | $C_2H_5$ | $CH_3$ | $OCH_3$ | CH | O | |
| H | $C_2H_5$ | $CH_3$ | $OCH_3$ | N | O | |
| H | $C_2H_5$ | $OCH_3$ | $OCH_3$ | CH | O | |
| H | $C_2H_5$ | $OCH_3$ | $OCH_3$ | N | O | |
| H | $C_2H_5$ | $OCH_3$ | Cl | CH | O | |
| H | $C_2H_5$ | $CH_3$ | $CH_3$ | CH | S | |
| H | $C_2H_5$ | $CH_3$ | $CH_3$ | N | S | |
| H | $C_2H_5$ | $CH_3$ | $OCH_3$ | CH | S | |
| H | $C_2H_5$ | $CH_3$ | $OCH_3$ | N | S | |
| H | $C_2H_5$ | $OCH_3$ | $OCH_3$ | CH | S | |
| H | $C_2H_5$ | $OCH_3$ | $OCH_3$ | N | S | |
| H | $C_2H_5$ | $OCH_3$ | Cl | CH | S | |
| H | $C_2H_5$ | $OCH_3$ | $N(CH_3)_2$ | N | S | |
| $CH_3$ | n-$C_3H_7$ | $OCH_3$ | $OCH_3$ | CH | O | |
| $CH_3$ | n-$C_3H_7$ | $CH_3$ | $CH_3$ | CH | O | |
| $CH_3$ | n-$C_3H_7$ | $CH_3$ | $OCH_3$ | CH | O | |
| $CH_3$ | n-$C_3H_7$ | $OCH_3$ | $OCH_3$ | CH | O | |
| $CH_3$ | n-$C_3H_7$ | $OCH_3$ | $OCH_3$ | N | O | |
| $CH_3$ | n-$C_3H_7$ | $OCH_3$ | Cl | CH | O | |
| $CH_3$ | n-$C_3H_7$ | $CH_3$ | $OCH_2CF_3$ | CH | O | |
| H | n-$C_3H_7$ | $CH_3$ | $CH_3$ | CH | S | |
| H | n-$C_3H_7$ | $CH_3$ | $OCH_3$ | CH | S | |
| H | n-$C_3H_7$ | $CH_3$ | $OCH_3$ | N | S | |
| H | n-$C_3H_7$ | $OCH_3$ | $OCH_3$ | CH | S | |
| H | n-$C_3H_7$ | $OCH_3$ | $OCH_3$ | N | S | |
| H | n-$C_3H_7$ | $OCH_3$ | Cl | CH | S | |
| H | n-$C_3H_7$ | $CH_3$ | $CH(OCH_3)_2$ | CH | S | |
| H | i-$C_3H_7$ | $CH_3$ | $CH_3$ | CH | O | |
| H | i-$C_3H_7$ | $CH_3$ | $OCH_3$ | CH | O | |
| H | i-$C_3H_7$ | $CH_3$ | $OCH_3$ | N | O | |
| H | i-$C_3H_7$ | $OCH_3$ | $OCH_3$ | CH | O | |
| H | i-$C_3H_7$ | $OCH_3$ | $OCH_3$ | N | O | |
| H | i-$C_3H_7$ | $OCH_3$ | Cl | CH | O | |
| H | i-$C_3H_7$ | $CH_3$ | $CH_3$ | N | O | |
| H | i-$C_3H_7$ | $OCH_3$ | 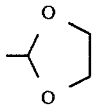 | CH | O | |
| $CH_3$ | i-$C_3H_7$ | $OCH_3$ | $OCH_3$ | CH | S | |
| H | i-$C_3H_7$ | $CH_3$ | $CH_3$ | CH | S | |
| H | i-$C_3H_7$ | $CH_3$ | $OCH_3$ | CH | S | |
| H | i-$C_3H_7$ | $CH_3$ | $OCH_3$ | N | S | |
| H | i-$C_3H_7$ | $OCH_3$ | $OCH_3$ | CH | S | |
| H | i-$C_3H_7$ | $OCH_3$ | $OCH_3$ | N | S | |
| H | i-$C_3H_7$ | $OCH_3$ | Cl | CH | S | |
| H | i-$C_3H_7$ | $CH_3$ | $OC_2H_5$ | N | S | |
| H | $SCH_3$ | $CH_3$ | $CH_3$ | CH | O | |
| H | $SCH_3$ | $CH_3$ | $OCH_3$ | CH | O | |
| H | $SCH_3$ | $CH_3$ | $OCH_3$ | N | O | |
| H | $SCH_3$ | $OCH_3$ | $OCH_3$ | CH | O | |
| H | $SCH_3$ | $OCH_3$ | $OCH_3$ | N | O | |
| H | $SCH_3$ | $OCH_3$ | Cl | CH | O | |
| H | $SCH_3$ | $OCH_3$ | $NHCH_3$ | CH | O | |
| $CH_3$ | $SCH_3$ | $OCH_3$ | $OCH_3$ | CH | S | |
| H | $SCH_3$ | $CH_3$ | $CH_3$ | CH | S | |
| H | $SCH_3$ | $CH_3$ | $CH_3$ | N | S | |
| H | $SCH_3$ | $CH_3$ | $OCH_3$ | CH | S | |
| H | $SCH_3$ | $CH_3$ | $OCH_3$ | N | S | |
| H | $SCH_3$ | $OCH_3$ | $OCH_3$ | CH | S | |
| H | $SCH_3$ | $OCH_3$ | $OCH_3$ | N | S | |
| H | $SCH_3$ | $OCH_3$ | Cl | CH | S | |
| $CH_3$ | $SC_2H_5$ | $OCH_3$ | $OCH_3$ | CH | O | |
| H | $SC_2H_5$ | $CH_3$ | $CH_3$ | CH | O | |
| H | $SC_2H_5$ | $CH_3$ | $CH_3$ | N | O | |
| H | $SC_2H_5$ | $CH_3$ | $OCH_3$ | CH | O | |
| H | $SC_2H_5$ | $CH_3$ | $OCH_3$ | N | O | |
| H | $SC_2H_5$ | $OCH_3$ | $OCH_3$ | CH | O | |
| H | $SC_2H_5$ | $OCH_3$ | $OCH_3$ | N | O | |
| H | $SC_2H_5$ | $OCH_3$ | Cl | CH | O | |
| H | $SC_2H_5$ | $CH_3$ | $CH_3$ | CH | S | |
| H | $SC_2H_5$ | $CH_3$ | $OCH_3$ | CH | S | |
| H | $SC_2H_5$ | $CH_3$ | $OCH_3$ | N | S | |
| H | $SC_2H_5$ | $OCH_3$ | $OCH_3$ | CH | S | |
| H | $SC_2H_5$ | $CH_3$ | $OCH_3$ | N | S | |
| H | $SC_2H_5$ | $OCH_3$ | Cl | CH | S | |
| H | $SC_2H_5$ | $CH_3$ | $OC_2H_5$ | N | S | |
| H | S—n-$C_3H_7$ | $CH_3$ | $CH_3$ | CH | O | |

TABLE 9a-continued

General Structure 3 wherein Q is Q-20.

| R | $R'_3$ | X | Y | Z | W' | m.p. °C. |
|---|---|---|---|---|---|---|
| H | S—n-$C_3H_7$ | $CH_3$ | $CH_2OCH_3$ | CH | O | |
| H | S—n-$C_3H_7$ | $CH_3$ | $OCH_3$ | CH | O | |
| H | S—n-$C_3H_7$ | $CH_3$ | $OCH_3$ | N | O | |
| H | S—n-$C_3H_7$ | $OCH_3$ | $OCH_3$ | CH | O | |
| H | S—n-$C_3H_7$ | $OCH_3$ | $OCH_3$ | N | O | |
| H | S—n-$C_3H_7$ | $OCH_3$ | Cl | CH | O | |
| $CH_3$ | S—n-$C_3H_7$ | $OCH_3$ | $OCH_3$ | CH | S | |
| H | S—n-$C_3H_7$ | $CH_3$ | $CH_3$ | CH | S | |
| H | S—n-$C_3H_7$ | $CH_3$ | $CH_3$ | N | S | |
| H | S—n-$C_3H_7$ | $CH_3$ | $OCH_3$ | CH | S | |
| H | S—n-$C_3H_7$ | $OCH_3$ | $OCH_3$ | CH | S | |
| H | S—n-$C_3H_7$ | $OCH_3$ | $OCH_3$ | N | S | |
| H | S—n-$C_3H_7$ | $CH_3$ | Cl | CH | S | |
| H | S—n-$C_3H_7$ | $CH_3$ | $OCH_3$ | CH | O | |
| H | S—n-$C_3H_7$ | $OCH_3$ | $OCH_3$ | CH | S | |
| H | S—n-$C_3H_7$ | $CH_3$ | $OCH_3$ | N | S | |
| $CH_3$ | S—n-$C_4H_9$ | $OCH_3$ | $OCH_3$ | CH | O | |
| H | S—n-$C_4H_9$ | $CH_3$ | $CH_3$ | CH | O | |
| H | S—n-$C_4H_9$ | $CH_3$ | $CH_3$ | N | O | |
| H | S—n-$C_4H_9$ | $CH_3$ | $OCH_3$ | CH | O | |
| H | S—n-$C_4H_9$ | $CH_3$ | $OCH_3$ | N | O | |
| H | S—n-$C_4H_9$ | $OCH_3$ | $OCH_3$ | CH | O | |
| H | S—n-$C_4H_9$ | $OCH_3$ | $OCH_3$ | N | O | |
| H | S—n-$C_4H_9$ | $OCH_3$ | Cl | CH | O | |
| H | S—n-$C_4H_9$ | $CH_3$ | $CH_3$ | CH | S | |
| H | S—n-$C_4H_9$ | $CH_3$ | $OCH_3$ | N | S | |
| H | S—n-$C_4H_9$ | $CH_3$ | $OCH_3$ | CH | S | |
| H | S—n-$C_4H_9$ | $OCH_3$ | $OCH_3$ | N | S | |
| H | S—n-$C_4H_9$ | $OCH_3$ | $OCH_3$ | CH | S | |
| H | S—n-$C_4H_9$ | $OCH_3$ | $OCH_3$ | N | S | |
| H | S—n-$C_4H_9$ | $OCH_3$ | $OCF_2H$ | N | S | |
| H | S—n-$C_4H_9$ | $OCH_3$ | $OCH_3$ | CH | O | |
| H | S—n-$C_4H_9$ | $CH_3$ | $OCH_3$ | N | O | |
| H | S—n-$C_4H_9$ | $OCH_3$ | $OCH_3$ | CH | S | |
| H | S—n-$C_4H_9$ | $CH_3$ | $OCH_3$ | CH | S | |
| H | S—n-$C_4H_9$ | $CH_3$ | $OCH_3$ | N | O | |
| H | S—n-$C_4H_9$ | $CH_3$ | $OCH_3$ | CH | O | |
| H | S—n-$C_4H_9$ | $OCH_3$ | $OCH_3$ | CH | S | |
| H | S—n-$C_4H_9$ | $OCH_3$ | $OCH_3$ | N | S | |
| H | S—n-$C_4H_9$ | $CH_3$ | $OCH_3$ | CH | O | |
| H | S—n-$C_4H_9$ | $OCH_3$ | $OCH_3$ | N | O | |
| H | S—n-$C_4H_9$ | $OCH_3$ | $OCH_3$ | CH | S | |
| H | S—n-$C_4H_9$ | $CH_3$ | $OCH_3$ | N | S | |
| H | $SCH_2CH=CH_2$ | $CH_3$ | $CH_3$ | CH | O | |
| H | $SCH_2CH=CH_2$ | $CH_3$ | $OCH_3$ | N | O | |
| H | $SCH_2CH=CH_2$ | $CH_3$ | $OCH_3$ | CH | O | |
| H | $SCH_2CH=CH_2$ | $OCH_3$ | $OCH_3$ | N | O | |
| H | $SCH_2CH=CH_2$ | $OCH_3$ | $OCH_3$ | CH | O | |
| H | $SCH_2CH=CH_2$ | $OCH_3$ | $OCH_3$ | N | O | |
| H | $SCH_2CH=CH_2$ | $OCH_3$ | Cl | CH | O | |
| H | $SCH_2CH=CH_2$ | $CH_3$ | $OCH_2CF_3$ | CH | O | |
| $CH_3$ | $SCH_2CH=CH_2$ | $OCH_3$ | $OCH_3$ | CH | S | |
| H | $SCH_2CH=CH_2$ | $CH_3$ | $CH_3$ | CH | S | |
| H | $SCH_2CH=CH_2$ | $CH_3$ | $CH_3$ | N | S | |
| H | $SCH_2CH=CH_2$ | $CH_3$ | $OCH_3$ | CH | S | |
| H | $SCH_2CH=CH_2$ | $CH_3$ | $OCH_3$ | N | S | |
| H | $SCH_2CH=CH_2$ | $OCH_3$ | $OCH_3$ | CH | S | |
| H | $SCH_2CH=CH_2$ | $OCH_3$ | $OCH_3$ | N | S | |
| H | $SCH_2CH=CH_2$ | $OCH_3$ | Cl | CH | S | |
| H | E—$SCH=CHCH_3$ | $CH_3$ | $OCH_3$ | CH | O | |
| H | E—$SCH=CHCH_3$ | $CH_3$ | $OCH_3$ | N | O | |
| H | E—$SCH=CHCH_3$ | $OCH_3$ | $OCH_3$ | CH | O | |
| H | E—$SCH=CHCH_3$ | $OCH_3$ | $OCH_3$ | N | O | |
| H | E—$SCH=CHCH_3$ | $CH_3$ | $OCH_3$ | N | S | |
| H | E—$SCH=CHCH_3$ | $CH_3$ | $OCH_3$ | CH | S | |
| H | E—$SCH=CHCH_3$ | $OCH_3$ | $OCH_3$ | CH | S | |
| H | E—$SCH=CHCH_3$ | $OCH_3$ | Cl | CH | S | |
| H | Z—$SCH=CHCH_3$ | $CH_3$ | $OCH_3$ | N | O | |
| H | Z—$SCH=CHCH_3$ | $OCH_3$ | $OCH_3$ | CH | O | |
| H | Z—$SCH=CHCH_3$ | $OCH_3$ | $OCH_3$ | N | O | |
| H | Z—$SCH=CHCH_3$ | $OCH_3$ | Cl | CH | O | |
| H | Z—$SCH=CHCH_3$ | $CH_3$ | $CH_3$ | CH | S | |
| H | Z—$SCH=CHCH_3$ | $OCH_3$ | $OCH_3$ | CH | S | |
| H | Z—$SCH=CHCH_3$ | $CH_3$ | $OCH_3$ | N | S | |
| H | Z—$SCH=CHCH_3$ | $OCH_3$ | $OCH_3$ | N | S | |
| H | $S(CH_2)_2CH=CH_2$ | $OCH_3$ | $OCH_3$ | CH | O | |
| H | $S(CH_2)_2CH=CH_2$ | $OCH_3$ | $OCH_3$ | N | O | |
| H | $S(CH_2)_2CH=CH_2$ | $CH_3$ | $OCH_3$ | CH | O | |
| H | $S(CH_2)_2CH=CH_2$ | $OCH_3$ | Cl | CH | O | |
| H | $S(CH_2)_2CH=CH_2$ | $OCH_3$ | $OCH_3$ | CH | S | |

TABLE 9a-continued

General Structure 3 wherein Q is Q-20.

| R | R'3 | X | Y | Z | W' | m.p. °C. |
|---|---|---|---|---|---|---|
| H | $S(CH_2)_2CH{=}CH_2$ | $CH_3$ | $OCH_3$ | N | S | |
| H | $S(CH_2)_2CH{=}CH_2$ | $OCH_3$ | $OCH_3$ | N | S | |
| H | $S(CH_2)_2CH{=}CH_2$ | $CH_3$ | $CH_3$ | CH | S | |
| H | $\underline{E}-SCH_2CH{=}CHCH_3$ | $OCH_3$ | $OCH_3$ | CH | O | |
| H | $\underline{E}-SCH_2CH{=}CHCH_3$ | $OCH_3$ | $OCH_3$ | N | O | |
| H | $\underline{E}-SCH_2CH{=}CHCH_3$ | $CH_3$ | $OCH_3$ | CH | O | |
| H | $\underline{E}-SCH_2CH{=}CHCH_3$ | $OCH_3$ | Cl | CH | O | |
| H | $\underline{E}-SCH_2CH{=}CHCH_3$ | $OCH_3$ | $OCH_3$ | CH | S | |
| H | $\underline{E}-SCH_2CH{=}CHCH_3$ | $CH_3$ | $OCH_3$ | N | S | |
| H | $\underline{E}-SCH_2CH{=}CHCH_3$ | $CH_3$ | $OCH_3$ | CH | S | |
| H | $\underline{E}-SCH_2CH{=}CHCH_3$ | $CH_3$ | $CH_3$ | CH | S | |
| H | $\underline{Z}-SCH_2CH{=}CHCH_3$ | $CH_3$ | $OCH_3$ | CH | O | |
| H | $\underline{Z}-SCH_2CH{=}CHCH_3$ | $CH_3$ | $OCH_3$ | N | O | |
| H | $\underline{Z}-SCH_2CH{=}CHCH_3$ | $OCH_3$ | $OCH_3$ | CH | O | |
| H | $\underline{Z}-SCH_2CH{=}CHCH_3$ | $OCH_3$ | Cl | CH | O | |
| H | $\underline{Z}-SCH_2CH{=}CHCH_3$ | $CH_3$ | $OCH_3$ | CH | S | |
| H | $\underline{Z}-SCH_2CH{=}CHCH_3$ | $CH_3$ | $OCH_3$ | N | S | |
| H | $\underline{Z}-SCH_2CH{=}CHCH_3$ | $OCH_3$ | $OCH_3$ | CH | S | |
| H | $\underline{Z}-SCH_2CH{=}CHCH_3$ | $OCH_3$ | $OCH_3$ | N | S | |
| H | $\underline{E}-SCH{=}CHC_2H_5$ | $OCH_3$ | $OCH_3$ | CH | O | |
| H | $\underline{E}-SCH{=}CHC_2H_5$ | $OCH_3$ | $OCH_3$ | N | O | |
| H | $\underline{E}-SCH{=}CHC_2H_5$ | $CH_3$ | $OCH_3$ | CH | O | |
| H | $\underline{E}-SCH{=}CHC_2H_5$ | $OCH_3$ | Cl | CH | O | |
| H | $\underline{E}-SCH{=}CHC_2H_5$ | $OCH_3$ | $OCH_3$ | CH | S | |
| H | $\underline{E}-SCH{=}CHC_2H_5$ | $CH_3$ | $CH_3$ | CH | S | |
| H | $\underline{E}-SCH{=}CHC_2H_5$ | $CH_3$ | $OCH_3$ | N | S | |
| H | $\underline{E}-SCH{=}CHC_2H_5$ | $CH_3$ | $OCH_3$ | CH | S | |
| H | $\underline{Z}-SCH{=}CHC_2H_5$ | $OCH_3$ | $OCH_3$ | CH | O | |
| H | $\underline{Z}-SCH{=}CHC_2H_5$ | $OCH_3$ | $OCH_3$ | N | O | |
| H | $\underline{Z}-SCH{=}CHC_2H_5$ | $CH_3$ | $CH_3$ | CH | O | |
| H | $\underline{Z}-SCH{=}CHC_2H_5$ | $CH_3$ | $OCH_3$ | N | O | |
| H | $\underline{Z}-SCH{=}CHC_2H_5$ | $OCH_3$ | $OCH_3$ | CH | S | |
| H | $\underline{Z}-SCH{=}CHC_2H_5$ | $CH_3$ | $OCH_3$ | CH | S | |
| H | $\underline{Z}-SCH{=}CHC_2H_5$ | $CH_3$ | $OCH_3$ | N | S | |
| H | $\underline{Z}-SCH{=}CHC_2H_5$ | $OCH_3$ | Cl | CH | S | |
| H | $SCH_2C{\equiv}CH$ | $CH_3$ | $OCH_3$ | CH | O | |
| H | $SCH_2C{\equiv}CH$ | $CH_3$ | $OCH_3$ | N | O | |
| H | $SCH_2C{\equiv}CH$ | $OCH_3$ | $OCH_3$ | CH | O | |
| H | $SCH_2C{\equiv}CH$ | $OCH_3$ | $OCH_3$ | N | O | |
| H | $SCH_2C{\equiv}CH$ | $CH_3$ | $OCH_3$ | CH | S | |
| H | $SCH_2C{\equiv}CH$ | $OCH_3$ | $OCH_3$ | N | S | |
| H | $SCH_2C{\equiv}CH$ | $OCH_3$ | $OCH_3$ | CH | S | |
| H | $SCH_2C{\equiv}CH$ | $OCH_3$ | Cl | CH | S | |
| $CH_3$ | $SCH_2C{\equiv}CH$ | $OCH_3$ | $OCH_3$ | CH | S | |
| H | $SC{\equiv}CCH_3$ | $CH_3$ | $CH_3$ | CH | O | |
| H | $SC{\equiv}CCH_3$ | $CH_3$ | $OCH_3$ | N | O | |
| H | $SC{\equiv}CCH_3$ | $CH_3$ | $OCH_3$ | CH | O | |
| H | $SC{\equiv}CCH_3$ | $OCH_3$ | $OCH_3$ | N | O | |
| H | $SC{\equiv}CCH_3$ | $OCH_3$ | $OCH_3$ | CH | S | |
| H | $SC{\equiv}CCH_3$ | $CH_3$ | $OCH_3$ | N | S | |
| H | $SC{\equiv}CCH_3$ | $CH_3$ | $OCH_3$ | CH | S | |
| H | $SC{\equiv}CCH_3$ | $OCH_3$ | $OCH_3$ | N | S | |
| H | $S(CH_2)_2C{\equiv}CH$ | $CH_3$ | $OCH_3$ | CH | O | |
| H | $S(CH_2)_2C{\equiv}CH$ | $CH_3$ | $OCH_3$ | N | O | |
| H | $S(CH_2)_2C{\equiv}CH$ | $OCH_3$ | $OCH_3$ | CH | O | |
| H | $S(CH_2)_2C{\equiv}CH$ | $OCH_3$ | $OCH_3$ | N | O | |
| H | $S(CH_2)_2C{\equiv}CH$ | $CH_3$ | $OCH_3$ | CH | S | |
| H | $S(CH_2)_2C{\equiv}CH$ | $CH_3$ | $OCH_3$ | N | S | |
| H | $S(CH_2)_2C{\equiv}CH$ | $OCH_3$ | $OCH_3$ | CH | S | |
| H | $S(CH_2)_2C{\equiv}CH$ | $OCH_3$ | $OCH_3$ | N | S | |
| H | $SCH_2C{\equiv}CCH_3$ | $CH_3$ | $CH_3$ | CH | O | |
| H | $SCH_2C{\equiv}CCH_3$ | $CH_3$ | $OCH_3$ | N | O | |
| H | $SCH_2C{\equiv}CCH_3$ | $CH_3$ | $OCH_3$ | CH | O | |
| H | $SCH_2C{\equiv}CCH_3$ | $OCH_3$ | $OCH_3$ | CH | O | |
| H | $SCH_2C{\equiv}CCH_3$ | $OCH_3$ | $OCH_3$ | CH | S | |
| H | $SCH_2C{\equiv}CCH_3$ | $OCH_3$ | $OCH_3$ | N | S | |
| H | $SCH_2C{\equiv}CCH_3$ | $CH_3$ | $OCH_3$ | CH | S | |
| H | $SCH_2C{\equiv}CCH_3$ | $OCH_3$ | Cl | CH | S | |
| H | $SC{\equiv}CC_2H_5$ | $CH_3$ | $OCH_3$ | N | O | |
| H | $SC{\equiv}CC_2H_5$ | $OCH_3$ | $OCH_3$ | CH | O | |
| H | $SC{\equiv}CC_2H_5$ | $OCH_3$ | $OCH_3$ | CH | S | |
| H | $SC{\equiv}CC_2H_5$ | $CH_3$ | $CH_3$ | CH | S | |
| $CH_3$ | $SC{\equiv}CC_2H_5$ | $CH_3$ | $OCH_3$ | CH | O | |
| H | $CH_2CN$ | $CH_3$ | $CH_3$ | CH | O | |
| H | $CH_2CN$ | $CH_3$ | $OCH_3$ | N | O | |
| H | $CH_2CN$ | $CH_3$ | $OCH_3$ | CH | O | |
| H | $CH_2CN$ | $OCH_3$ | $OCH_3$ | N | O | |
| H | $CH_2CN$ | $OCH_3$ | $OCH_3$ | CH | O | |
| H | $CH_2CN$ | $OCH_3$ | Cl | CH | O | |
| H | $CH_2CN$ | $CH_3$ | $NHCH_3$ | N | O | |

TABLE 9a-continued

General Structure 3 wherein Q is Q-20.

| R | $R'_3$ | X | Y | Z | W' | m.p. °C. |
|---|---|---|---|---|---|---|
| $CH_3$ | $CH_2CN$ | $OCH_3$ | $OCH_3$ | CH | S | |
| H | $CH_2CN$ | $CH_3$ | $CH_3$ | CH | S | |
| H | $CH_2CN$ | $CH_3$ | $CH_3$ | N | S | |
| H | $CH_2CN$ | $CH_3$ | $OCH_3$ | CH | S | |
| H | $CH_2CN$ | $CH_3$ | $OCH_3$ | N | S | |
| H | $CH_2CN$ | $OCH_3$ | $OCH_3$ | CH | S | |
| H | $CH_2CN$ | $OCH_3$ | $OCH_3$ | N | S | |
| H | $CH_2CN$ | $OCH_3$ | Cl | CH | S | |
| $CH_3$ | $CH_2CO_2CH_3$ | $CH_3$ | $OCH_3$ | CH | O | |
| H | $CH_2CO_2CH_3$ | $CH_3$ | $CH_3$ | CH | O | |
| H | $CH_2CO_2CH_3$ | $CH_3$ | $OCH_3$ | CH | O | |
| H | $CH_2CO_2CH_3$ | $CH_3$ | $OCH_3$ | N | O | |
| H | $CH_2CO_2CH_3$ | $OCH_3$ | $OCH_3$ | CH | O | |
| H | $CH_2CO_2CH_3$ | $OCH_3$ | $OCH_3$ | N | O | |
| H | $CH_2CO_2CH_3$ | $OCH_3$ | Cl | CH | O | |
| H | $CH_2CO_2CH_3$ | $CH_3$ | $CH_3$ | CH | S | |
| H | $CH_2CO_2CH_3$ | $CH_3$ | $OCH_3$ | N | S | |
| H | $CH_2CO_2CH_3$ | $CH_3$ | $OCH_3$ | CH | S | |
| H | $CH_2CO_2CH_3$ | $OCH_3$ | $OCH_3$ | N | S | |
| H | $CH_2CO_2CH_3$ | $OCH_3$ | $OCH_3$ | CH | S | |
| H | $CH_2CO_2CH_3$ | $OCH_3$ | Cl | CH | S | |
| H | $CH_2CO_2CH_3$ | $CH_3$ | $N(CH_3)_2$ | N | S | |
| H | $CH_2CO_2C_2H_5$ | $CH_3$ | $CH_3$ | CH | O | |
| H | $CH_2CO_2C_2H_5$ | $CH_3$ | $OCH_3$ | N | O | |
| H | $CH_2CO_2C_2H_5$ | $CH_3$ | $OCH_3$ | CH | O | |
| H | $CH_2CO_2C_2H_5$ | $OCH_3$ | $OCH_3$ | N | O | |
| H | $CH_2CO_2C_2H_5$ | $OCH_3$ | $OCH_3$ | CH | O | |
| H | $CH_2CO_2C_2H_5$ | $OCH_3$ | Cl | CH | O | |
| H | $CH_2CO_2C_2H_5$ | $OC_2H_5$ | Cl | CH | O | |
| $CH_3$ | $CH_2CO_2C_2H_5$ | $OCH_3$ | $OCH_3$ | CH | S | |
| H | $CH_2CO_2C_2H_5$ | $CH_3$ | $CH_3$ | CH | S | |
| H | $CH_2CO_2C_2H_5$ | $CH_3$ | $CH_3$ | N | S | |
| H | $CH_2CO_2C_2H_5$ | $CH_3$ | $OCH_3$ | CH | S | |
| H | $CH_2CO_2C_2H_5$ | $CH_3$ | $OCH_3$ | N | S | |
| H | $CH_2CO_2C_2H_5$ | $OCH_3$ | $OCH_3$ | CH | S | |
| H | $CH_2CO_2C_2H_5$ | $OCH_3$ | $OCH_3$ | N | S | |
| H | $CH_2CO_2C_2H_5$ | $OCH_3$ | Cl | CH | S | |
| $CH_3$ | $CH_2OCH_3$ | $OCH_3$ | $OCH_3$ | CH | O | |
| H | $CH_2OCH_3$ | $CH_3$ | $CH_3$ | CH | O | |
| H | $CH_2OCH_3$ | $CH_3$ | $CH_3$ | N | O | |
| H | $CH_2OCH_3$ | $CH_3$ | $OCH_3$ | CH | O | |
| H | $CH_2OCH_3$ | $CH_3$ | $OCH_3$ | N | O | |
| H | $CH_2OCH_3$ | $OCH_3$ | $OCH_3$ | CH | O | |
| H | $CH_2OCH_3$ | $OCH_3$ | $OCH_3$ | N | O | |
| H | $CH_2OCH_3$ | $OCH_3$ | Cl | CH | O | |
| H | $CH_2OCH_3$ | $CH_3$ | $CH_3$ | CH | S | |
| H | $CH_2OCH_3$ | $CH_3$ | $OCH_3$ | N | S | |
| H | $CH_2OCH_3$ | $CH_3$ | $OCH_3$ | CH | S | |
| H | $CH_2OCH_3$ | $OCH_3$ | $OCH_3$ | N | S | |
| H | $CH_2OCH_3$ | $OCH_3$ | $OCH_3$ | CH | S | |
| H | $CH_2OCH_3$ | $OCH_3$ | Cl | CH | S | |
| H | $CH_2OCH_3$ | $CH_3$ | $CH(OCH_3)_2$ | CH | S | |
| H | $CH_2OC_2H_5$ | $CH_3$ | $CH_3$ | CH | O | |
| H | $CH_2OC_2H_5$ | $CH_3$ | $OCH_3$ | N | O | |
| H | $CH_2OC_2H_5$ | $CH_3$ | $OCH_3$ | CH | O | |
| H | $CH_2OC_2H_5$ | $OCH_3$ | $OCH_3$ | N | O | |
| H | $CH_2OC_2H_5$ | $OCH_3$ | $OCH_3$ | CH | O | |
| H | $CH_2OC_2H_5$ | $OCH_3$ | Cl | CH | O | |
| H | $CH_2OC_2H_5$ | $OCH_3$ | Br | CH | O | |
| $CH_3$ | $CH_2OC_2H_5$ | $CH_3$ | $OCH_3$ | CH | S | |
| H | $CH_2OC_2H_5$ | $CH_3$ | $CH_3$ | CH | S | |
| H | $CH_2OC_2H_5$ | $CH_3$ | $CH_3$ | N | S | |
| H | $CH_2OC_2H_5$ | $CH_3$ | $OCH_3$ | CH | S | |
| H | $CH_2OC_2H_5$ | $CH_3$ | $OCH_3$ | N | S | |
| H | $CH_2OC_2H_5$ | $OCH_3$ | $OCH_3$ | CH | S | |
| H | $CH_2OC_2H_5$ | $OCH_3$ | $OCH_3$ | N | S | |
| H | $CH_2OC_2H_5$ | $OCH_3$ | Cl | CH | S | |
| $CH_3$ | $(CH_2)_2COCH_3$ | $OCH_3$ | $OCH_3$ | CH | O | |
| H | $(CH_2)_2COCH_3$ | $CH_3$ | $CH_3$ | CH | O | |
| H | $(CH_2)_2COCH_3$ | $CH_3$ | $CH_3$ | N | O | |
| H | $(CH_2)_2COCH_3$ | $CH_3$ | $OCH_3$ | CH | O | |
| H | $(CH_2)_2COCH_3$ | $CH_3$ | $OCH_3$ | N | O | |
| H | $(CH_2)_2COCH_3$ | $OCH_3$ | $OCH_3$ | CH | O | |
| H | $(CH_2)_2COCH_3$ | $OCH_3$ | $OCH_3$ | N | O | |
| H | $(CH_2)_2COCH_3$ | $OCH_3$ | Cl | CH | O | |
| H | $(CH_2)_2COCH_3$ | $CH_3$ | $CH_3$ | CH | S | |
| H | $(CH_2)_2COCH_3$ | $CH_3$ | $OCH_3$ | N | S | |
| H | $(CH_2)_2COCH_3$ | $CH_3$ | $OCH_3$ | CH | S | |
| H | $(CH_2)_2COCH_3$ | $OCH_3$ | $OCH_3$ | N | S | |
| H | $(CH_2)_2COCH_3$ | $OCH_3$ | $OCH_3$ | CH | S | |

TABLE 9a-continued

| General Structure 3 wherein Q is Q-20. | | | | | | |
|---|---|---|---|---|---|---|
| R | $R'_3$ | X | Y | Z | W' | m.p. °C. |
| H | $(CH_2)_2COCH_3$ | $OCH_3$ | Cl | CH | S | |
| H | $(CH_2)_2COCH_3$ | $CH_3$ | 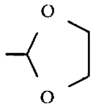 | CH | S | |
| H | $(CH_2)_2CN$ | $CH_3$ | $OCH_3$ | CH | O | |
| H | $(CH_2)_2CN$ | $CH_3$ | $OCH_3$ | N | O | |
| H | $(CH_2)_2CN$ | $OCH_3$ | $OCH_3$ | CH | O | |
| H | $(CH_2)_2CN$ | $OCH_3$ | $OCH_3$ | N | O | |
| H | $(CH_2)_2CN$ | $CH_3$ | $CH_3$ | CH | S | |
| H | $(CH_2)_2CN$ | $CH_3$ | $OCH_3$ | N | S | |
| H | $(CH_2)_2CN$ | $OCH_3$ | $OCH_3$ | CH | S | |
| H | $(CH_2)_2CN$ | $OCH_3$ | Cl | CH | S | |
| H | $CH(CH_3)CN$ | $OCH_3$ | $OCH_3$ | CH | O | |
| H | $CH(CH_3)CN$ | $OCH_3$ | $OCH_3$ | N | O | |
| H | $CH(CH_3)CN$ | $CH_3$ | $OCH_3$ | CH | S | |
| H | $CH(CH_3)CN$ | $CH_3$ | $OCH_3$ | N | S | |
| H | $(CH_2)_3CN$ | $CH_3$ | $OCH_3$ | CH | O | |
| H | $(CH_2)_3CN$ | $CH_3$ | $OCH_3$ | N | O | |
| H | $(CH_2)_3CN$ | $OCH_3$ | $OCH_3$ | CH | O | |
| H | $(CH_2)_3CN$ | $OCH_3$ | $OCH_3$ | N | O | |
| H | $(CH_2)_3CN$ | $CH_3$ | $CH_3$ | CH | S | |
| H | $(CH_2)_3CN$ | $CH_3$ | $OCH_3$ | N | S | |
| H | $(CH_2)_3CN$ | $OCH_3$ | $OCH_3$ | $CH_3$ | S | |
| H | $(CH_2)_3CN$ | $OCH_3$ | $OCH_3$ | N | S | |
| H | $CH_2CH(CH_3)CN$ | $CH_3$ | $OCH_3$ | CH | O | |
| H | $CH_2CH(CH_3)CN$ | $CH_3$ | $OCH_3$ | N | O | |
| H | $CH_2CH(CH_3)CN$ | $OCH_3$ | $OCH_3$ | CH | S | |
| H | $CH_2CH(CH_3)CN$ | $OCH_3$ | Cl | CH | S | |
| H | $CH_2CH(CH_3)CN$ | $CH_3$ | $CH_3$ | CH | O | |
| H | $CH_2CH(CH_3)CN$ | $CH_3$ | $OCH_3$ | N | O | |
| H | $CH_2CH(CH_3)CN$ | $OCH_3$ | $OCH_3$ | CH | S | |
| H | $CH_2CH(CH_3)CN$ | $OCH_3$ | $CH_3$ | CH | S | |
| $CH_3$ | $CH_2CH(CH_3)CN$ | $OCH_3$ | $OCH_3$ | CH | S | |
| H | $CH(CN)C_2H_5$ | $CH_3$ | $OCH_3$ | N | O | |
| H | $CH(CN)C_2H_5$ | $OCH_3$ | $OCH_3$ | CH | O | |
| H | $CH(CN)C_2H_5$ | $OCH_3$ | $OCH_3$ | N | S | |
| H | $CH(CN)C_2H_5$ | $OCH_3$ | Cl | CH | S | |
| H | $C(CH_3)_2CN$ | $CH_3$ | $CH_3$ | CH | O | |
| H | $C(CH_3)_2CN$ | $OCH_3$ | $OCH_3$ | CH | O | |
| H | $C(CH_3)_2CN$ | $OCH_3$ | $OCH_3$ | N | S | |
| H | $C(CH_3)_2CN$ | $OCH_3$ | $OCH_3$ | CH | S | |
| H | $CH(CH_3)CO_2CH_3$ | $OCH_3$ | $OCH_3$ | CH | O | |
| H | $CH(CH_3)CO_2CH_3$ | $OCH_3$ | $OCH_3$ | N | O | |
| H | $CH(CH_3)CO_2CH_3$ | $CH_3$ | $OCH_3$ | CH | S | |
| H | $CH(CH_3)CO_2CH_3$ | $CH_3$ | $OCH_3$ | N | S | |
| H | $(CH_2)_3CO_2CH_3$ | $CH_3$ | $OCH_3$ | CH | O | |
| H | $(CH_2)_3CO_2CH_3$ | $CH_3$ | $OCH_3$ | N | O | |
| H | $(CH_2)_3CO_2CH_3$ | $OCH_3$ | $OCH_3$ | CH | O | |
| H | $(CH_2)_3CO_2CH_3$ | $OCH_3$ | $OCH_3$ | N | O | |
| H | $(CH_2)_3CO_2CH_3$ | $CH_3$ | $OCH_3$ | CH | S | |
| H | $(CH_2)_3CO_2CH_3$ | $CH_3$ | $OCH_3$ | N | S | |
| H | $(CH_2)_3CO_2CH_3$ | $OCH_3$ | $OCH_3$ | CH | S | |
| H | $(CH_2)_3CO_2CH_3$ | $OCH_3$ | $OCH_3$ | N | S | |
| H | $CH_2CH(CH_3)CO_2CH_3$ | $CH_3$ | $OCH_3$ | CH | O | |
| H | $CH_2CH(CH_3)CO_2CH_3$ | $CH_3$ | $OCH_3$ | N | O | |
| H | $CH_2CH(CH_3)CO_2CH_3$ | $OCH_3$ | $OCH_3$ | CH | S | |
| H | $CH_2CH(CH_3)CO_2CH_3$ | $OCH_3$ | $OCH_3$ | N | S | |
| H | $CH_2CH(CH_3)CO_2CH_3$ | $CH_3$ | $OCH_3$ | CH | O | |
| H | $CH_2CH(CH_3)CO_2CH_3$ | $CH_3$ | $OCH_3$ | N | O | |
| H | $CH_2CH(CH_3)CO_2CH_3$ | $OCH_3$ | $OCH_3$ | CH | S | |
| H | $CH_2CH(CH_3)CO_2CH_3$ | $OCH_3$ | $OCH_3$ | N | S | |
| H | $CH(CO_2CH_3)C_2H_5$ | $CH_3$ | $OCH_3$ | N | O | |
| H | $CH(CO_2CH_3)C_2H_5$ | $OCH_3$ | $OCH_3$ | CH | O | |
| H | $CH(CO_2CH_3)C_2H_5$ | $OCH_3$ | $OCH_3$ | N | S | |
| H | $CH(CO_2CH_3)C_2H_5$ | $OCH_3$ | $OCH_3$ | CH | S | |
| H | $C(CH_3)_2CO_3CH_3$ | $CH_3$ | $OCH_3$ | N | O | |
| H | $C(CH_3)_2CO_3CH_3$ | $OCH_3$ | $OCH_3$ | CH | O | |
| H | $C(CH_3)_2CO_3CH_3$ | $CH_3$ | $OCH_3$ | N | S | |
| H | $C(CH_3)_2CO_3CH_3$ | $OCH_3$ | $OCH_3$ | CH | S | |
| H | $(CH_2)_2CO_2C_2H_5$ | $CH_3$ | $CH_3$ | CH | O | |
| H | $(CH_2)_2CO_2C_2H_5$ | $CH_3$ | $OCH_3$ | N | O | |
| H | $(CH_2)_2CO_2C_2H_5$ | $OCH_3$ | $OCH_3$ | CH | O | |
| H | $(CH_2)_2CO_2C_2H_5$ | $OCH_3$ | $OCH_3$ | N | O | |
| H | $(CH_2)_2CO_2C_2H_5$ | $OCH_3$ | $OCH_3$ | CH | S | |
| H | $(CH_2)_2CO_2C_2H_5$ | $CH_3$ | $OCH_3$ | N | S | |

TABLE 9a-continued

| General Structure 3 wherein Q is Q-20. | | | | | | |
|---|---|---|---|---|---|---|
| R | $R'_3$ | X | Y | Z | W' | m.p. °C. |
| H | $(CH_2)_2CO_2C_2H_5$ | $OCH_3$ | $OCH_3$ | CH | S | |
| H | $(CH_2)_2CO_2C_2H_5$ | $OCH_3$ | $OCH_3$ | N | S | |
| H | $CH(CH_3)CO_2C_2H_5$ | $OCH_3$ | $OCH_3$ | CH | O | |
| H | $CH(CH_3)CO_2C_2H_5$ | $OCH_3$ | $OCH_3$ | N | O | |
| H | $CH(CH_3)CO_2C_2H_5$ | $CH_3$ | $OCH_3$ | CH | S | |
| H | $CH(CH_3)CO_2C_2H_5$ | $CH_3$ | $OCH_3$ | N | S | |
| H | $(CH_2)_3CO_2C_2H_5$ | $CH_3$ | $OCH_3$ | CH | O | |
| H | $(CH_2)_3CO_2C_2H_5$ | $CH_3$ | $OCH_3$ | N | O | |
| H | $(CH_2)_3CO_2C_2H_5$ | $OCH_3$ | $OCH_3$ | CH | O | |
| H | $(CH_2)_3CO_2C_2H_5$ | $OCH_3$ | $OCH_3$ | N | O | |
| H | $(CH_2)_3CO_2C_2H_5$ | $CH_3$ | $OCH_3$ | CH | S | |
| H | $(CH_2)_3CO_2C_2H_5$ | $CH_3$ | $OCH_3$ | N | S | |
| H | $(CH_2)_3CO_2C_2H_5$ | $OCH_3$ | $OCH_3$ | CH | S | |
| H | $(CH_2)_3CO_2C_2H_5$ | $OCH_3$ | $OCH_3$ | N | S | |
| H | $CH_2CH(CH_3)CO_2C_2H_5$ | $CH_3$ | $OCH_3$ | CH | O | |
| H | $CH_2CH(CH_3)CO_2C_2H_5$ | $CH_3$ | $OCH_3$ | N | O | |
| H | $CH_2CH(CH_3)CO_2C_2H_5$ | $OCH_3$ | $OCH_3$ | CH | S | |
| H | $CH_2CH(CH_3)CO_2C_2H_5$ | $OCH_3$ | $OCH_3$ | N | S | |
| H | $CH_2CH(CH_3)CO_2C_2H_5$ | $CH_3$ | $OCH_3$ | CH | O | |
| H | $CH_2CH(CH_3)CO_2C_2H_5$ | $CH_3$ | $OCH_3$ | N | O | |
| H | $CH_2CH(CH_3)CO_2C_2H_5$ | $CH_3$ | $OCH_3$ | CH | S | |
| H | $CH_2CH(CH_3)CO_2C_2H_5$ | $OCH_3$ | $OCH_3$ | N | S | |
| H | $CH(CO_2C_2H_5)C_2H_5$ | $CH_3$ | $OCH_3$ | N | O | |
| H | $CH(CO_2C_2H_5)C_2H_5$ | $OCH_3$ | $OCH_3$ | CH | O | |
| H | $CH(CO_2C_2H_5)C_2H_5$ | $OCH_3$ | $OCH_3$ | N | S | |
| H | $CH(CO_2C_2H_5)C_2H_5$ | $OCH_3$ | $OCH_3$ | CH | S | |
| H | $C(CH_3)_2CO_2C_2H_5$ | $CH_3$ | $OCH_3$ | N | O | |
| H | $C(CH_3)_2CO_2C_2H_5$ | $OCH_3$ | $OCH_3$ | CH | O | |
| H | $C(CH_3)_2CO_2C_2H_5$ | $CH_3$ | $OCH_3$ | N | O | |
| H | $C(CH_3)_2CO_2C_2H_5$ | $OCH_3$ | $OCH_3$ | CH | S | |
| H | $(CH_2)_2OCH_3$ | $CH_3$ | $CH_3$ | CH | O | |
| H | $(CH_2)_2OCH_3$ | $CH_3$ | $OCH_3$ | N | O | |
| H | $(CH_2)_2OCH_3$ | $OCH_3$ | $OCH_3$ | CH | O | |
| H | $(CH_2)_2OCH_3$ | $OCH_3$ | $OCH_3$ | N | O | |
| H | $(CH_2)_2OCH_3$ | $OCH_3$ | $OCH_3$ | CH | S | |
| H | $(CH_2)_2OCH_3$ | $CH_3$ | $OCH_3$ | N | S | |
| H | $(CH_2)_2OCH_3$ | $OCH_3$ | $OCH_3$ | CH | S | |
| H | $(CH_2)_2OCH_3$ | $OCH_3$ | $OCH_3$ | N | S | |
| H | $CH(CH_3)OCH_3$ | $OCH_3$ | $OCH_3$ | CH | O | |
| H | $CH(CH_3)OCH_3$ | $OCH_3$ | $OCH_3$ | N | O | |
| H | $CH(CH_3)OCH_3$ | $CH_3$ | $OCH_3$ | CH | S | |
| H | $CH(CH_3)OCH_3$ | $CH_3$ | $OCH_3$ | N | S | |
| H | $(CH_2)_3OCH_3$ | $CH_3$ | $OCH_3$ | CH | O | |
| H | $(CH_2)_3OCH_3$ | $CH_3$ | $OCH_3$ | N | O | |
| H | $(CH_2)_3OCH_3$ | $OCH_3$ | $OCH_3$ | CH | O | |
| H | $(CH_2)_3OCH_3$ | $OCH_3$ | $OCH_3$ | N | O | |
| H | $(CH_2)_3OCH_3$ | $CH_3$ | $OCH_3$ | CH | S | |
| H | $(CH_2)_3OCH_3$ | $CH_3$ | $OCH_3$ | N | S | |
| H | $(CH_2)_3OCH_3$ | $OCH_3$ | $OCH_3$ | CH | S | |
| H | $(CH_2)_3OCH_3$ | $OCH_3$ | $OCH_3$ | N | S | |
| H | $CH_2CH(CH_3)OCH_3$ | $CH_3$ | $OCH_3$ | CH | 0 | |
| H | $CH_2CH(CH_3)OCH_3$ | $CH_3$ | $OCH_3$ | N | O | |
| H | $CH_2CH(CH_3)OCH_3$ | $OCH_3$ | $OCH_3$ | CH | S | |
| H | $CH_2CH(CH_3)OCH_3$ | $OCH_3$ | $OCH_3$ | N | S | |
| H | $CH_2CH(CH_3)OCH_3$ | $CH_3$ | $OCH_3$ | CH | O | |
| H | $CH_2CH(CH_3)OCH_3$ | $CH_3$ | $OCH_3$ | N | O | |
| H | $CH_2CH(CH_3)OCH_3$ | $CH_3$ | $OCH_3$ | CH | S | |
| H | $CH_2CH(CH_3)OCH_3$ | $OCH_3$ | $OCH_3$ | N | S | |
| H | $CH(OCH_3)C_2H_5$ | $CH_3$ | $OCH_3$ | N | O | |
| H | $CH(OCH_3)C_2H_5$ | $OCH_3$ | $OCH_3$ | CH | O | |
| H | $CH(OCH_3)C_2H_5$ | $OCH_3$ | $OCH_3$ | N | S | |
| H | $CH(OCH_3)C_2H_5$ | $OCH_3$ | $OCH_3$ | CH | S | |
| H | $C(CH_3)_2OCH_3$ | $CH_3$ | $OCH_3$ | N | O | |
| H | $C(CH_3)_2OCH_3$ | $OCH_3$ | $OCH_3$ | CH | O | |
| H | $C(CH_3)_2OCH_3$ | $CH_3$ | $OCH_3$ | N | O | |
| H | $C(CH_3)_2OCH_3$ | $OCH_3$ | $OCH_3$ | CH | S | |
| H | $(CH_2)_2OC_2H_5$ | $CH_3$ | $CH_3$ | CH | O | |
| H | $(CH_2)_2OC_2H_5$ | $CH_3$ | $OCH_3$ | N | O | |
| H | $(CH_2)_2OC_2H_5$ | $OCH_3$ | $OCH_3$ | CH | O | |
| H | $(CH_2)_2OC_2H_5$ | $OCH_3$ | $OCH_3$ | N | O | |
| H | $(CH_2)_2OC_2H_5$ | $OCH_3$ | $OCH_3$ | CH | S | |
| H | $(CH_2)_2OC_2H_5$ | $CH_3$ | $OCH_3$ | N | S | |
| H | $(CH_2)_2OC_2H_5$ | $OCH_3$ | $OCH_3$ | CH | S | |
| H | $(CH_2)_2OC_2H_5$ | $OCH_3$ | $OCH_3$ | N | S | |
| H | $CH(CH_3)OC_2H_5$ | $OCH_3$ | $OCH_3$ | CH | O | |
| H | $CH(CH_3)OC_2H_5$ | $OCH_3$ | $OCH_3$ | N | O | |
| H | $CH(CH_3)OC_2H_5$ | $CH_3$ | $OCH_3$ | CH | S | |
| H | $CH(CH_3)OC_2H_5$ | $CH_3$ | $OCH_3$ | N | S | |
| H | $(CH_2)_3OC_2H_5$ | $CH_3$ | $OCH_3$ | CH | O | |
| H | $(CH_2)_3OC_2H_5$ | $CH_3$ | $OCH_3$ | N | O | |

TABLE 9a-continued

| General Structure 3 wherein Q is Q-20. | | | | | | |
|---|---|---|---|---|---|---|
| R | R'3 | X | Y | Z | W' | m.p. °C. |
| H | $(CH_2)_3OC_2H_5$ | $OCH_3$ | $OCH_3$ | CH | O | |
| H | $(CH_2)_3OC_2H_5$ | $OCH_3$ | $OCH_3$ | N | O | |
| H | $(CH_2)_3OC_2H_5$ | $CH_3$ | $OCH_3$ | CH | S | |
| H | $(CH_2)_3OC_2H_5$ | $CH_3$ | $OCH_3$ | N | S | |
| H | $(CH_2)_3OC_2H_5$ | $OCH_3$ | $OCH_3$ | CH | S | |
| H | $(CH_2)_3OC_2H_5$ | $OCH_3$ | $OCH_3$ | N | S | |
| H | $CH_2CH(CH_3)OC_2H_5$ | $CH_3$ | $OCH_3$ | CH | O | |
| H | $CH_2CH(CH_3)OC_2H_5$ | $CH_3$ | $OCH_3$ | N | O | |
| H | $CH_2CH(CH_3)OC_2H_5$ | $OCH_3$ | $OCH_3$ | CH | S | |
| H | $CH_2CH(CH_3)OC_2H_5$ | $OCH_3$ | $OCH_3$ | N | S | |
| H | $CH(CH_3)CH_2OC_2H_5$ | $CH_3$ | $OCH_3$ | CH | O | |
| H | $CH(CH_3)CH_2OC_2H_5$ | $CH_3$ | $OCH_3$ | N | O | |
| H | $CH(CH_3)CH_2OC_2H_5$ | $CH_3$ | $OCH_3$ | CH | S | |
| H | $CH(CH_3)CH_2OC_2H_5$ | $OCH_3$ | $OCH_3$ | N | S | |
| H | $CH(OC_2H_5)C_2H_5$ | $CH_3$ | $OCH_3$ | N | O | |
| H | $CH(OC_2H_5)C_2H_5$ | $OCH_3$ | $OCH_3$ | CH | O | |
| H | $CH(OC_2H_5)C_2H_5$ | $OCH_3$ | $OCH_3$ | N | S | |
| H | $CH(OC_2H_5)C_2H_5$ | $OCH_3$ | $OCH_3$ | CH | S | |
| H | $CH(CH_3)_2OC_2H_5$ | $CH_3$ | $OCH_3$ | N | O | |
| H | $CH(CH_3)_2OC_2H_5$ | $OCH_3$ | $OCH_3$ | CH | O | |
| H | $CH(CH_3)_2OC_2H_5$ | $CH_3$ | $OCH_3$ | N | O | |
| H | $C(CH_3)_2OC_2H_5$ | $OCH_3$ | $OCH_3$ | CH | S | |
| H | $(CH_2)CH_2COCH_3$ | $CH_3$ | $CH_3$ | CH | O | |
| H | $(CH_2)CH_2COCH_3$ | $CH_3$ | $OCH_3$ | N | O | |
| H | $(CH_2)CH_2COCH_3$ | $OCH_3$ | $OCH_3$ | CH | O | |
| H | $(CH_2)CH_2COCH_3$ | $OCH_3$ | $OCH_3$ | N | O | |
| H | $(CH_2)CH_2COCH_3$ | $OCH_3$ | $OCH_3$ | CH | S | |
| H | $(CH_2)CH_2COCH_3$ | $CH_3$ | $OCH_3$ | N | S | |
| H | $(CH_2)CH_2COCH_3$ | $OCH_3$ | $OCH_3$ | CH | S | |
| H | $(CH_2)CH_2COCH_3$ | $OCH_3$ | $OCH_3$ | N | S | |
| H | $CH(CH_3)CH_2COCH_3$ | $OCH_3$ | $OCH_3$ | CH | O | |
| H | $CH(CH_3)CH_2COCH_3$ | $OCH_3$ | $OCH_3$ | N | O | |
| H | $CH(CH_3)CH_2COCH_3$ | $CH_3$ | $OCH_3$ | CH | S | |
| H | $CH(CH_3)CH_2COCH_3$ | $CH_3$ | $OCH_3$ | N | S | |
| H | $(CH_2)_3CH_2COCH_3$ | $CH_3$ | $OCH_3$ | CH | O | |
| H | $(CH_2)_3CH_2COCH_3$ | $CH_3$ | $OCH_3$ | N | O | |
| H | $(CH_2)_3CH_2COCH_3$ | $OCH_3$ | $OCH_3$ | CH | O | |
| H | $(CH_2)_3CH_2COCH_3$ | $OCH_3$ | $OCH_3$ | N | O | |
| H | $(CH_2)_3CH_2COCH_3$ | $CH_3$ | $OCH_3$ | CH | S | |
| H | $(CH_2)_3CH_2COCH_3$ | $CH_3$ | $OCH_3$ | N | S | |
| H | $(CH_2)_3CH_2COCH_3$ | $OCH_3$ | $OCH_3$ | CH | S | |
| H | $(CH_2)_3CH_2COCH_3$ | $OCH_3$ | $OCH_3$ | N | S | |
| H | $CH_2CH(CH_3)CH_2COCH_3$ | $CH_3$ | $OCH_3$ | CH | O | |
| H | $CH_2CH(CH_3)CH_2COCH_3$ | $CH_3$ | $OCH_3$ | N | O | |
| H | $CH_2CH(CH_3)CH_2COCH_3$ | $OCH_3$ | $OCH_3$ | CH | S | |
| H | $CH_2CH(CH_3)CH_2COCH_3$ | $OCH_3$ | $OCH_3$ | N | S | |
| H | $CH(CH_3)CH_2CH_2COCH_3$ | $CH_3$ | $OCH_3$ | CH | O | |
| H | $CH(CH_3)CH_2CH_2COCH_3$ | $CH_3$ | $OCH_3$ | N | O | |
| H | $CH(CH_3)CH_2CH_2COCH_3$ | $CH_3$ | $OCH_3$ | CH | S | |
| H | $CH(CH_3)CH_2CH_2COCH_3$ | $OCH_3$ | $OCH_3$ | N | S | |
| H | $CH(C_2H_5)CH_2COCH_3$ | $CH_3$ | $OCH_3$ | N | O | |
| H | $CH(C_2H_5)CH_2OCH_3$ | $OCH_3$ | $OCH_3$ | CH | O | |
| H | $CH(C_2H_5)CH_2OCH_3$ | $OCH_3$ | $OCH_3$ | N | S | |
| H | $CH(C_2H_5)CH_2OCH_3$ | $OCH_3$ | $OCH_3$ | CH | S | |
| H | $CH(CH_3)_2CH_2COCH_3$ | $CH_3$ | $OCH_3$ | N | O | |
| H | $CH(CH_3)_2CH_2COCH_3$ | $OCH_3$ | $OCH_3$ | CH | O | |
| H | $CH(CH_3)_2CH_2COCH_3$ | $CH_3$ | $OCH_3$ | N | O | |
| H | $C(CH_3)_2CH_2COCH_3$ | $OCH_3$ | $OCH_3$ | CH | S | |
| H | H | $OCH_3$ | $OCH_3$ | CH | O* | |
| H | H | $OCH_3$ | $OCH_3$ | CH | S* | |
| H | $CH_3$ | $OCH_3$ | $OCH_3$ | CH | O* | |
| H | $CH_3$ | $OCH_3$ | $OCH_3$ | CH | S* | |
| H | $SCH_3$ | $OCH_3$ | $OCH_3$ | CH | O* | |
| H | $SCH_3$ | $OCH_3$ | $OCH_3$ | CH | S* | |
| H | $SCH_2CH{=}CH_2$ | $OCH_3$ | $OCH_3$ | CH | O* | |
| H | $SCH_3CH{=}CH_2$ | $OCH_3$ | $OCH_3$ | CH | S* | |
| H | SH | $OCH_3$ | $OCH_3$ | CH | O* | |
| H | SH | $OCH_3$ | $OCH_3$ | CH | S* | |

W is O, unless indicated by * where W is S in all Tables.

TABLE 9b

| General Structure 3 wherein Q is Q-28. | | | | | | |
|---|---|---|---|---|---|---|
| R | $R_3$ | $R_4$ | X | Y | Z | m.p. °C. |
| H | H | H | $CH_3$ | $OCH_3$ | CH | 172-174 |
| H | H | H | $CH_3$ | $OCH_3$ | N | 206-208 |
| H | H | H | $OCH_3$ | $OCH_3$ | CH | 207-209 |

TABLE 9b-continued

| General Structure 3 wherein Q is Q-28. | | | | | | |
|---|---|---|---|---|---|---|
| R | $R_3$ | $R_4$ | X | Y | Z | m.p. °C. |
| H | H | H | $OCH_3$ | $OCH_3$ | N | 169-174 |
| H | H | H | $CH_3$ | $CH_3$ | CH | 231-232 |
| H | H | H | $CH_3$ | $CH_3$ | N | |

TABLE 9b-continued

| General Structure 3 wherein Q is Q-28. | | | | | | |
|---|---|---|---|---|---|---|
| R | $R_3$ | $R_4$ | X | Y | Z | m.p. °C. |
| H | $CH_3$ | H | $CH_3$ | $OCH_3$ | CH | |
| H | H | H | Cl | $OCH_3$ | CH | 208-210 |
| H | H | $CH_3$ | $CH_3$ | $OCH_3$ | N | |
| H | $CH_3$ | $CH_3$ | $OCH_3$ | $OCH_3$ | CH | |
| $CH_3$ | $CH_3$ | $CH_3$ | $OCH_3$ | $OCH_3$ | N | |
| H | H | H | $CH_3$ | 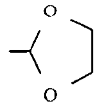 | CH | |
| H | H | H | $CH_3$ | $C_2H_5$ | CH | |
| H | $CH_3$ | H | $CH_3$ | $CH_3$ | CH | |
| H | $CH_3$ | H | $CH_3$ | $OCH_3$ | N | |
| H | $CH_3$ | H | $OCH_3$ | $OCH_3$ | CH | |
| H | $CH_3$ | H | $OCH_3$ | $OCH_3$ | N | |
| H | $CH_3$ | H | $OCH_3$ | Cl | CH | |
| H | $CH_3$ | H | $CH_3$ | $CH_3$ | N | |
| H | Cl | H | $CH_3$ | $CH_3$ | CH | |
| H | Cl | H | $CH_3$ | $CH_3$ | N | |
| H | Cl | H | $CH_3$ | $OCH_3$ | CH | |
| H | Cl | H | $CH_3$ | $OCH_3$ | N | |
| H | Cl | H | $OCH_3$ | $OCH_3$ | CH | |
| H | Cl | H | $OCH_3$ | $OCH_3$ | N | |
| H | Cl | H | $OCH_3$ | Cl | CH | |
| H | Cl | $CH_3$ | $CH_3$ | $OCH_3$ | CH | |
| H | Cl | $CH_3$ | $CH_3$ | $OCH_3$ | N | |
| H | Cl | $CH_3$ | $OCH_3$ | $OCH_3$ | CH | |
| H | Cl | $CH_3$ | $OCH_3$ | $OCH_3$ | N | |
| H | Br | H | $OCH_3$ | $OCH_3$ | CH | |
| H | Br | H | $CH_3$ | $CH_3$ | CH | |
| H | Br | H | $CH_3$ | $OCH_3$ | N | |
| H | Br | H | $CH_3$ | $OCH_3$ | CH | |
| H | Br | H | $OCH_3$ | $OCH_3$ | N | |
| H | Br | H | $OCH_3$ | $OCH_3$ | CH | |
| H | Br | H | $OCH_3$ | Cl | CH | |
| H | H | H | $OCH_3$ | $OCH_3$ | CH* | |
| H | $CH_3$ | H | $OCH_3$ | $OCH_3$ | CH* | |
| H | H | $CH_3$ | $OCH_3$ | $OCH_3$ | CH* | |
| H | $CH_3$ | $CH_3$ | $OCH_3$ | $OCH_3$ | CH* | |
| H | Cl | H | $OCH_3$ | $OCH_3$ | CH* | |
| H | Cl | $CH_3$ | $OCH_3$ | $OCH_3$ | CH* | |
| H | Br | H | $OCH_3$ | $OCH_3$ | CH* | |
| H | Br | $CH_3$ | $OCH_3$ | $OCH_3$ | CH* | |

*Wherein W is O, unless indicated by * where W is S in all Tables.

TABLE 9c

| General Structure 3 | | | | | | | | |
|---|---|---|---|---|---|---|---|---|
| Q | R | $R_3$ | $R_4$ | X | Y | Z | n' | m.p. °C. |
| Q-33 | H | H | H | $CH_3$ | $OCH_3$ | CH | 0 | |
| Q-33 | H | H | H | $CH_3$ | $OCH_3$ | N | 0 | |
| Q-33 | H | H | H | $OCH_3$ | $OCH_3$ | CH | 0 | |
| Q-33 | H | H | H | $OCH_3$ | $OCH_3$ | N | 0 | |
| Q-33 | H | H | H | $CH_3$ | $CH_3$ | CH | 0 | |
| Q-33 | H | 3-$CH_3$ | H | $CH_3$ | $OCH_3$ | CH | 0 | |
| Q-33 | H | 4-$CH_3$ | H | $CH_3$ | $OCH_3$ | CH | 0 | |
| Q-33 | H | 5-$CH_3$ | H | $CH_3$ | $OCH_3$ | CH | 0 | |
| Q-33 | H | H | H | $CH_3$ | $CH_3$ | N | 0 | |
| Q-33 | H | 6-$CH_3$ | H | $CH_3$ | $OCH_3$ | CH | 0 | |
| Q-33 | H | 3-$CH_3$ | 5-$CH_3$ | $CH_3$ | $OCH_3$ | N | 0 | |
| Q-33 | H | 4-$CH_3$ | 6-$CH_3$ | $CH_3$ | $OCH_3$ | N | 0 | |
| Q-33 | $CH_3$ | H | H | $OCH_3$ | $OCH_3$ | CH | 0 | |
| Q-33 | H | H | H | $CH_3$ | $CH_2OCH_3$ | CH | 0 | |
| Q-33 | H | H | H | Cl | $OC_2H_5$ | CH | 0 | |
| Q-33 | H | H | H | $CH_3$ | $CF_3$ | CH | 0 | |
| Q-33 | H | H | H | Cl | $OCH_3$ | CH | 1 | |
| Q-33 | H | H | H | $CH_3$ | $OCH_3$ | CH | 1 | |
| Q-33 | H | H | H | $CH_3$ | $OCH_3$ | N | 1 | |

TABLE 9c-continued

| General Structure 3 | | | | | | | | |
|---|---|---|---|---|---|---|---|---|
| Q | R | $R_3$ | $R_4$ | X | Y | Z | n' | m.p. °C. |
| Q-33 | H | H | H | $OCH_3$ | $OCH_3$ | CH | 1 | |
| Q-33 | H | H | H | $OCH_3$ | $OCH_3$ | N | 1 | |
| Q-33 | H | H | H | $CH_3$ | $CH_3$ | CH | 1 | |
| Q-33 | H | 3-$CH_3$ | H | $CH_3$ | $OCH_3$ | CH | 1 | |
| Q-33 | H | 4-$CH_3$ | H | $CH_3$ | $OCH_3$ | CH | 1 | |
| Q-33 | H | 5-$CH_3$ | H | $CH_3$ | $OCH_3$ | CH | 1 | |
| Q-33 | H | H | H | $CH_3$ | $CH_3$ | N | 1 | |
| Q-33 | H | 6-$CH_3$ | H | $CH_3$ | $OCH_3$ | CH | 1 | |
| Q-33 | H | 3-$CH_3$ | 5-$CH_3$ | $CH_3$ | $OCH_3$ | N | 1 | |
| Q-33 | H | 4-$CH_3$ | 6-$CH_3$ | $CH_3$ | $OCH_3$ | N | 1 | |
| Q-33 | $CH_3$ | H | H | $OCH_3$ | $OCH_3$ | CH | 1 | |
| Q-33 | H | H | H | $CH_3$ | $CH_2OCH_3$ | CH | 1 | |
| Q-33 | H | H | H | Cl | $OC_2H_5$ | CH | 1 | |
| Q-33 | H | H | H | $CH_3$ | $CF_3$ | CH | 1 | |
| Q-34 | H | H | H | $CH_3$ | $OCH_3$ | CH | 0 | |
| Q-34 | H | H | H | $CH_3$ | $OCH_3$ | N | 0 | |
| Q-34 | H | H | H | $OCH_3$ | $OCH_3$ | CH | 0 | |
| Q-34 | H | H | H | $OCH_3$ | $OCH_3$ | N | 0 | |
| Q-34 | H | 2-$CH_3$ | H | $CH_3$ | $CH_3$ | CH | 0 | |
| Q-34 | H | 4-$CH_3$ | H | $CH_3$ | $CH_3$ | N | 0 | |
| Q-34 | H | 5-$CH_3$ | H | $CH_3$ | $OCH_3$ | CH | 0 | |
| Q-34 | H | 6-$CH_3$ | H | $CH_3$ | $OCH_3$ | N | 0 | |
| Q-34 | H | 2-$CH_3$ | 6-$CH_3$ | $OCH_3$ | $OCH_3$ | CH | 0 | |
| Q-34 | H | 4-$CH_3$ | 6-$CH_3$ | $OCH_3$ | $OCH_3$ | N | 0 | |
| Q-34 | H | H | H | $CH_3$ | $CH_3$ | N | 0 | |
| Q-34 | $CH_3$ | H | H | $CH_3$ | $CH_3$ | CH | 0 | |
| Q-34 | H | H | H | $CH_3$ | $CH_3$ | CH | 0 | |
| Q-34 | H | H | H | $CH_3$ | $OCF_2H$ | CH | 0 | |
| Q-34 | H | H | H | $CH_3$ | $OCH_3$ | CH | 1 | |
| Q-34 | H | H | H | $CH_3$ | $OCH_3$ | N | 1 | |
| Q-34 | H | H | H | $OCH_3$ | $OCH_3$ | CH | 1 | |
| Q-34 | H | H | H | $OCH_3$ | $OCH_3$ | N | 1 | |
| Q-34 | H | 2-$CH_3$ | H | $CH_3$ | $CH_3$ | CH | 1 | |
| Q-34 | H | 4-$CH_3$ | H | $CH_3$ | $CH_3$ | N | 1 | |
| Q-34 | H | 5-$CH_3$ | H | $CH_3$ | $OCH_3$ | CH | 1 | |
| Q-34 | H | 6-$CH_3$ | H | $CH_3$ | $OCH_3$ | N | 1 | |
| Q-34 | H | 2-$CH_3$ | 6-$CH_3$ | $OCH_3$ | $OCH_3$ | CH | 1 | |
| Q-34 | H | 4-$CH_3$ | 6-$CH_3$ | $OCH_3$ | $OCH_3$ | N | 1 | |
| O-34 | H | H | H | $CH_3$ | $CH_3$ | N | 1 | |
| Q-34 | $CH_3$ | H | H | $CH_3$ | $CH_3$ | CH | 1 | |
| Q-34 | H | H | H | $CH_3$ | $CH_3$ | CH | 1 | |
| Q-34 | H | H | H | $CH_3$ | $OCF_2H$ | CH | 1 | |
| Q-35 | H | H | H | $CH_3$ | $OCH_3$ | CH | 0 | |
| Q-35 | H | H | H | $CH_3$ | $OCH_3$ | N | 0 | |
| Q-35 | H | H | H | $OCH_3$ | $OCH_3$ | CH | 0 | |
| Q-35 | H | H | H | $OCH_3$ | $OCH_3$ | N | 0 | |
| Q-35 | H | 2-$CH_3$ | H | $CH_3$ | $CH_3$ | CH | 0 | |
| Q-35 | H | H | H | Cl | $OCH_3$ | CH | 0 | |
| Q-35 | H | 3-$CH_3$ | H | $CH_3$ | $CH_3$ | N | 0 | |
| Q-35 | H | 2-$CH_3$ | 6-$CH_3$ | $CH_3$ | $OCH_3$ | CH | 0 | |
| Q-35 | H | 2-$CH_3$ | 3-$CH_3$ | $CH_3$ | $OCH_3$ | N | 0 | |
| Q-35 | H | 3-$CH_3$ | 5-$CH_3$ | $CH_3$ | $OCH_3$ | N | 0 | |
| Q-35 | H | H | H | $CH_3$ | $CH_3$ | N | 0 | |
| Q-35 | $CH_3$ | H | H | $OCH_3$ | $OCH_3$ | CH | 0 | |
| Q-35 | H | H | H | $CH_3$ | $OCH_2CF_3$ | CH | 0 | |
| Q-35 | H | H | H | $CH_3$ | $CH_3$ | CH | 0 | |
| Q-35 | H | H | H | $CH_3$ | $OCH_3$ | CH | 1 | |
| Q-35 | H | H | H | $CH_3$ | $OCH_3$ | N | 1 | |
| Q-35 | H | H | H | $OCH_3$ | $OCH_3$ | CH | 1 | |
| Q-35 | H | H | H | $OCH_3$ | $OCH_3$ | N | 1 | |
| Q-35 | H | 2-$CH_3$ | H | $CH_3$ | $CH_3$ | CH | 1 | |
| Q-35 | H | H | H | Cl | $OCH_3$ | CH | 1 | |
| Q-35 | H | 3-$CH_3$ | H | $CH_3$ | $CH_3$ | N | 1 | |
| Q-35 | H | 2-$CH_3$ | 6-$CH_3$ | $CH_3$ | $OCH_3$ | CH | 1 | |
| Q-35 | H | 2-$CH_3$ | 3-$CH_3$ | $CH_3$ | $OCH_3$ | N | 1 | |
| Q-35 | H | 3-$CH_3$ | 5-$CH_3$ | $CH_3$ | $OCH_3$ | N | 1 | |
| Q-35 | H | H | H | $CH_3$ | $CH_3$ | N | 1 | |
| Q-35 | $CH_3$ | H | H | $OCH_3$ | $OCH_3$ | CH | 1 | |
| Q-35 | H | H | H | $CH_3$ | $OCH_2CF_3$ | CH | 1 | |
| Q-35 | H | H | H | $CH_3$ | $CH_3$ | CH | 1 | |

TABLE 10

| General Structure 4 | | | | |
|---|---|---|---|---|
| Q | R | W' | W'' | A |
| Q-1 ($R_1$, $R_2$ = H) | H | — | — | A-2 ($X_1$ = $OCH_3$, $Y_1$ = O) |
| Q-1 ($R_1$, $R_2$ = H) | H | — | — | A-2 ($X_1$ = $CH_3$, $Y_1$ = O) |

TABLE 10-continued

| Q | R | W' | W'' | A |
|---|---|---|---|---|
| | General Structure 4 | | | |
| Q-1 ($R_1$, $R_2$ = H) | H | — | — | A-3 ($X_1$ = $OCH_3$) |
| Q-1 ($R_1$, $R_2$ = H) | H | — | — | A-4 ($X_1$, $Y_2$ = $CH_3$) |
| Q-1 ($R_1$, $R_2$ = H) | H | — | — | A-5 ($X_2$ = $OCH_3$, $Y_3$ = $CH_3$) |
| Q-1 ($R_1$, $R_2$ = H) | H | — | — | A-6 ($X_3$ = $CH_3$) |
| Q-2 ($R_3$, $R_4$, $R_5$ = H) | H | S | — | A-2 ($X_1$ = $CH_3$, $Y_1$ = O) |
| Q-2 ($R_3$, $R_4$, $R_5$ = H) | H | S | — | A-3 ($X_1$ = $OCH_3$) |
| Q-2 ($R_3$, $R_4$, $R_5$ = H) | H | O | — | A-4 ($X_1$, $Y_2$ = $CH_3$) |
| Q-3 ($R_3$, $R_4$, $R_5$ = H) | H | S | — | A-2 ($X_1$ = $OCH_3$, $Y_1$ = $CH_2$) |
| Q-3 ($R_3$, $R_4$, $R_5$ = H) | H | S | — | A-3 ($X_1$ = $CH_3$) |
| Q-3 ($R_3$, $R_4$, $R_5$ = H) | H | O | — | A-4 ($X_1$ = $CH_3$, $Y_2$ = H) |
| Q-4 ($R_3$, $R_4$, $R_5$ = H) | H | — | — | A-2 ($X_1$ = $OCH_3$, $Y_1$ = O) |
| Q-4 ($R_3$, $R_4$, $R_5$ = H) | H | — | — | A-5 ($X_2$ = $OCH_3$, $Y_3$ = $CH_3$) |
| Q-4 ($R_3$, $R_4$, $R_5$ = H) | H | — | — | A-6 ($X_3$ = $OCH_3$) |
| Q-7 ($R_3$, $R_4$, $R_5$, $R_6$ = H) | H | — | — | A-2 ($X_1$ = $OCF_2H$, $Y_1$ = O) |
| Q-7 ($R_3$, $R_4$, $R_5$, $R_6$ = H) | H | — | — | A-3 ($X_1$ = $OCH_2CH_3$) |
| Q-7 ($R_3$, $R_4$, $R_5$, $R_6$ = H) | H | — | — | A-4 ($X_1$ = $OCH_3$, $Y_2$ = $CH_3$) |
| Q-7 ($R_3$, $R_4$, $R_5$, $R_6$ = H) | H | — | — | A-5 ($X_2$ = $SCH_3$, $Y_3$ = $CH_3$) |
| Q-7 ($R_3$, $R_4$, $R_5$, $R_6$ = H) | H | — | — | A-6 ($X_3$ = $OCH_3$) |
| Q-10 ($R_3$, $R_4$ = H) | H | — | O | A-2 ($X_1$ = $OCH_3$, $Y_1$ = O) |
| Q-10 ($R_3$, $R_4$ = H) | H | — | O | A-3 ($X_1$ = $OCH_3$) |
| Q-10 ($R_3$, $R_4$ = H) | H | — | S | A-4 ($X_1$ = $CH_3$, $Y_2$ = $CH_3$) |
| Q-11 ($R_3$, $R_4$ = H) | H | — | O | A-2 ($X_1$ = $OCH_3$, $Y_1$ = $CH_2$) |
| Q-11 ($R_3$, $R_4$ = H) | H | — | O | A-3 ($X_1$ = $CH_3$) |
| Q-11 ($R_3$, $R_4$ = H) | H | — | S | A-4 ($X_1$ = $OCH_3$, $Y_2$ = H) |
| Q-16 ($R_3$, $R_4$, $R_5$, $R_6$ = H) | H | O | — | A-2 ($X_1$ = $CH_3$, $Y_1$ = O) |
| Q-16 ($R_3$, $R_4$, $R_5$, $R_6$ = H) | H | O | — | A-3 ($X_1$ = $CH_3$) |
| Q-16 ($R_3$, $R_4$, $R_5$, $R_6$ = H) | H | O | — | A-5 ($X_2$ = $OCH_3$, $Y_3$ = $CH_3$) |
| Q-16 ($R_3$, $R_4$, $R_5$, $R_6$ = H) | H | S | — | A-4 ($X_1$ = $CH_3$, $Y_2$ = $CH_3$) |
| Q-16 ($R_3$, $R_4$, $R_5$, $R_6$ = H) | H | S | — | A-5 ($X_2$ = $OCH_3$, $Y_3$ = $CH_2CH_3$) |
| Q-16 ($R_3$, $R_4$, $R_5$, $R_6$ = H) | H | S | — | A-6 ($X_3$ = $OCH_3$) |
| Q-20 ($R_3'$ = H) | H | S | — | A-2 ($X_1$ = $OCH_3$, $Y_1$ = O) |
| Q-20 ($R_3'$ = H) | H | O | — | A-2 ($X_1$ = $OCH_3$) |
| Q-20 ($R_3'$ = $CH_3$) | H | S | — | A-4 ($X_1$ = $OCH_3$, $Y_2$ = H) |
| Q-20 ($R_3'$ = $CH_3$) | H | O | — | A-2 ($X_1$ = $OCH_3$, $Y_1$ = O) |
| Q-20 ($R_3'$ = $SCH_3$) | H | S | — | A-3 ($X_1$ = $OCH_3$) |
| Q-20 ($R_3'$ = $SCH_3$) | H | O | — | A-4 ($X_1$ = $OCH_3$, $Y_2$ = $CH_3$) |
| Q-23 ($R_3$ = H) | H | — | — | A-3 ($X_1$ = $CH_3$) |
| Q-23 ($R_3$ = H) | H | — | — | A-4 ($X_1$ = $OCH_3$, $Y_2$ = $CH_3$) |
| Q-23 ($R_3$ = $CH_3$) | H | — | — | A-6 ($X_3$ = $OCH_3$) |
| Q-28 ($R_3''$ = H, $R_4$ = H) | H | — | — | A-2 ($X_1$ = $CH_3$, $Y_1$ = O) |
| Q-28 ($R_3''$ = Cl, $R_4$ = H) | H | — | — | A-3 ($X_1$ = $OCH_3$) |
| Q-28 ($R_3''$ = $CH_3$, $R_4$ = H) | H | — | — | A-4 ($X_1$ = $OCH_3$, $Y_2$ = $CH_3$) |
| Q-28 ($R_3''$ = H, $R_4$ = H) | H | — | — | A-5 ($X_2$ = $CH_3$, $Y_2$ = $CH_3$) |
| Q-28 ($R_3''$ = H, $R_4$ = H) | H | — | — | A-6 ($X_3$ = $CH_3$) |
| Q-33 ($R_3$, $R_4$ = H, n = O) | H | — | — | A-2 ($X_1$ = $OCH_3$, $Y_1$ = $CH_2$) |
| Q-33 ($R_3$, $R_4$ = H, n = O) | H | — | — | A-3 ($X_1$ = $CH_3$) |
| Q-33 ($R_3$, $R_4$ = H, n = O) | H | — | — | A-4 ($X_1$ = $OCH_3$, $Y_2$ = $CH_3$) |
| Q-36 ($R_3$, $R_4$, $R_5$ = H) | H | — | — | A-2 ($X_1$ = $OCH_3$, $Y_1$ = O) |
| Q-36 ($R_3$, $R_4$, $R_5$ = H) | H | — | — | A-3 ($X_1$ = $OCH_3$) |
| Q-36 ($R_3$, $R_4$, $R_5$ = H) | H | — | — | A-4 ($X_1$ = $OCH_3$, $Y_2$ = $CH_3$) |
| Q-39 ($R_3$, $R_4$ = H) | H | — | — | A-2 ($X_1$ = $CH_3$, $Y_1$ = $CH_2$) |
| Q-39 ($R_3$, $R_4$ = H) | H | — | — | A-3 ($X_1$ = $CH_3$) |
| Q-39 ($R_3$, $R_4$ = H) | H | — | — | A-4 ($X_1$ = $OCH_3$, $Y_2$ = H) |
| Q-1 ($R_1$, $R_2$ = H) | H | — | — | A-2 ($X_1$ = $OCH_3$, $Y_1$ = O)* |
| Q-7 ($R_3$, $R_4$, $R_5$, $R_6$ = H) | H | — | — | A-3 ($X_1$ = $OCH_2CH_3$)* |
| Q-15 ($R_3'$, $R_4$ = H) | H | — | O | A-2 ($X_1$ = $OCH_3$, $Y_1$ = O)* |
| Q-15 ($R_3'$, $R_4$ = H) | H | — | S | A-2 ($X_1$ = $OCH_3$, $Y_1$ = O)* |
| Q-20 ($R_3'$ = SH) | H | O | — | A-2 ($X_1$ = $OCH_3$, $Y_1$ = O)* |
| Q-20 ($R_3'$ = SH) | H | S | — | A-2 ($X_1$ = $OCH_3$, $Y_1$ = O)* |
| Q-28 ($R_3'$ = Cl, $R_4$ = H) | H | — | — | A-2 ($X_1$ = $OCH_3$, $Y_1$ = O)* |

W is O, unless indicated by * where W is S in all Tables.

TABLE 11

| Q | R | W' | W'' | A |
|---|---|---|---|---|
| | General Structure 5 | | | |
| Q-1 ($R_1$, $R_2$ = H) | H | — | — | A-2 ($X_1$ = $OCH_3$, $Y_1$ = O) |
| Q-1 ($R_1$, $R_2$ = H) | H | — | — | A-2 ($X_1$ = $CH_3$, $Y_1$ = O) |
| Q-1 ($R_1$, $R_2$ = H) | H | — | — | A-3 ($X_1$ = $OCH_3$) |
| Q-1 ($R_1$, $R_2$ = H) | H | — | — | A-4 ($X_1$, $Y_2$ = $CH_3$) |
| Q-1 ($R_1$, $R_2$ = H) | H | — | — | A-5 ($X_2$ = $OCH_3$, $Y_3$ = $CH_3$) |
| Q-1 ($R_1$, $R_2$ = H) | H | — | — | A-6 ($X_3$ = $CH_3$) |
| Q-2 ($R_3$, $R_4$, $R_5$ = H) | H | S | — | A-2 ($X_1$ = $CH_3$ , $Y_1$ = O) |
| Q-2 ($R_3$, $R_4$, $R_5$ = H) | H | S | — | A-3 ($X_1$ = $OCH_3$) |
| Q-2 ($R_3$, $R_4$, $R_5$ = H) | H | O | — | A-4 ($X_1$, $Y_2$ = $CH_3$) |
| Q-3 ($R_3$, $R_4$, $R_5$ = H) | H | S | — | A-2 ($X_1$ = $OCH_3$, $Y_1$ = $CH_2$) |
| Q-3 ($R_3$, $R_4$, $R_5$ = H) | H | S | — | A-3 ($X_1$ = $CH_3$) |
| Q-3 ($R_3$, $R_4$, $R_5$ = H) | H | O | — | A-4 ($X_1$ = $CH_3$, $Y_2$ = H) |

TABLE 11-continued

| Q | General Structure 5 R | W' | W'' | A |
|---|---|---|---|---|
| Q-4 ($R_3$, $R_4$, $R_5$ = H) | H | — | — | A-2 ($X_1$ = $OCH_3$, $Y_1$ = O) |
| Q-4 ($R_3$, $R_4$, $R_5$ = H) | H | — | — | A-5 ($X_2$ = $OCH_3$, $Y_3$ = $CH_3$) |
| Q-4 ($R_3$, $R_4$, $R_5$ = H) | H | — | — | A-6 ($X_3$ = $OCH_3$) |
| Q-7 ($R_3$, $R_4$, $R_5$, $R_6$ = H) | H | — | — | A-2 ($X_1$ = $OCF_2H$, $Y_1$ = O) |
| Q-7 ($R_3$, $R_4$, $R_5$, $R_6$ = H) | H | — | — | A-3 ($X_1$ = $OCH_2CH_3$) |
| Q-7 ($R_3$, $R_4$, $R_5$, $R_6$ = H) | H | — | — | A-4 ($X_1$ = $OCH_3$, $Y_2$ = $CH_3$) |
| Q-7 ($R_3$, $R_4$, $R_5$, $R_6$ = H) | H | — | — | A-5 ($X_2$ = $SCH_3$, $Y_3$ = $CH_3$) |
| Q-7 ($R_3$, $R_4$, $R_5$, $R_6$ = H) | H | — | — | A-6 ($X_3$ = $OCH_3$) |
| Q-10 ($R_3$, $R_4$ = H) | H | — | O | A-2 ($X_1$ = $OCH_3$, $Y_1$ = O) |
| Q-10 ($R_3$, $R_4$ = H) | H | — | O | A-3 ($X_1$ = $OCH_3$) |
| Q-10 ($R_3$, $R_4$ = H) | H | — | S | A-4 ($X_1$ = $CH_3$, $Y_2$ = $CH_3$) |
| Q-11 ($R_3$, $R_4$ = H) | H | — | O | A-2 ($X_1$ = $OCH_3$, $Y_1$ = $CH_2$) |
| Q-11 ($R_3$, $R_4$ = H) | H | — | O | A-3 ($X_1$ = $CH_3$) |
| Q-11 ($R_3$, $R_4$ = H) | H | — | S | A-4 ($X_1$ = $OCH_3$, $Y_2$ = H) |
| Q-16 ($R_3$, $R_4$, $R_5$, $R_6$ = H) | H | O | — | A-2 ($X_1$ = $CH_3$, $Y_1$ = O) |
| Q-16 ($R_3$, $R_4$, $R_5$, $R_6$ = H) | H | O | — | A-3 ($X_1$ = $CH_3$) |
| Q-16 ($R_3$, $R_4$, $R_5$, $R_6$ = H) | H | O | — | A-5 ($X_2$ = $OCH_3$, $Y_3$ = $CH_3$) |
| Q-16 ($R_3$, $R_4$, $R_5$, $R_6$ = H) | H | S | — | A-4 ($X_1$ = $CH_3$, $Y_2$ = $CH_3$) |
| Q-16 ($R_3$, $R_4$, $R_5$, $R_6$ = H) | H | S | — | A-5 ($X_2$ = $OCH_3$, $Y_3$ = $CH_2CH_3$) |
| Q-16 ($R_3$, $R_4$, $R_5$, $R_6$ = H) | H | S | — | A-6 ($X_3$ = $OCH_3$) |
| Q-20 ($R_3'$ = H) | H | S | — | A-2 ($X_1$ = $OCH_3$, $Y_1$ = O) |
| Q-20 ($R_3'$ = H) | H | O | — | A-2 ($X_1$ = $OCH_3$) |
| Q-20 ($R_3'$ = $CH_3$) | H | S | — | A-4 ($X_1$ = $OCH_3$, $Y_2$ = H) |
| Q-20 ($R_3'$ = $CH_3$) | H | O | — | A-2 ($X_1$ = $OCH_3$, $Y_1$ = O) |
| Q-20 ($R_3'$ = $SCH_3$) | H | S | — | A-3 ($X_1$ = $OCH_3$) |
| Q-20 ($R_3'$ = $SCH_3$) | H | O | — | A-4 ($X_1$ = $OCH_3$, $Y_2$ = $CH_3$) |
| Q-23 ($R_3$ = H) | H | — | — | A-3 ($X_1$ = $CH_3$) |
| Q-23 ($R_3$ = H) | H | — | — | A-4 ($X_1$ = $OCH_3$, $Y_2$ = $CH_3$) |
| Q-23 ($R_3$ = $CH_3$) | H | — | — | A-6 ($X_3$ = $OCH_3$) |
| Q-28 ($R_3''$ = H, $R_4$ = H) | H | — | — | A-2 ($X_1$ = $CH_3$, $Y_1$ = O) |
| Q-28 ($R_3''$ = Cl, $R_4$ = H) | H | — | — | A-3 ($X_1$ = $OCH_3$) |
| Q-28 ($R_3''$ = $CH_3$, $R_4$ = H) | H | — | — | A-4 ($X_1$ = $OCH_3$, $Y_2$ = $CH_3$) |
| Q-28 ($R_3''$ = H, $R_4$ = H) | H | — | — | A-5 ($X_2$ = $CH_3$, $Y_2$ = $CH_3$) |
| Q-28 ($R_3''$ = H, $R_4$ = H) | H | — | — | A-6 ($X_3$ = $CH_3$) |
| Q-33 ($R_3$, $R_4$ = H, n = O) | H | — | — | A-2 ($X_1$ = $OCH_3$, $Y_1$ = $CH_2$) |
| Q-33 ($R_3$, $R_4$ = H, n = O) | H | — | — | A-3 ($X_1$ = $CH_3$) |
| Q-33 ($R_3$, $R_4$ = H, n = O) | H | — | — | A-4 ($X_1$ = $OCH_3$, $Y_2$ = $CH_3$) |
| Q-36 ($R_3$, $R_4$, $R_5$ = H) | H | — | — | A-2 ($X_1$ = $OCH_3$, $Y_1$ = O) |
| Q-36 ($R_3$, $R_4$, $R_5$ = H) | H | — | — | A-3 ($X_1$ = $OCH_3$) |
| Q-36 ($R_3$, $R_4$, $R_5$ = H) | H | — | — | A-4 ($X_1$ = $OCH_3$, $Y_2$ = $CH_3$) |
| Q-39 ($R_3$, $R_4$ = H) | H | — | — | A-2 ($X_1$ = $CH_3$, $Y_1$ = $CH_2$) |
| Q-39 ($R_3$, $R_4$ = H) | H | — | — | A-3 ($X_1$ = $CH_3$) |
| Q-39 ($R_3$, $R_4$ = H) | H | — | — | A-4 ($X_1$ = $OCH_3$, $Y_2$ = H) |

TABLE 12

| Q | General Structure 6 R | W' | W'' | A |
|---|---|---|---|---|
| Q-1 ($R_1$, $R_2$ = H) | H | — | — | A-2 ($X_1$ = $OCH_3$, $Y_1$ = O) |
| Q-1 ($R_1$, $R_2$ = H) | H | — | — | A-2 ($X_1$ = $CH_3$, $Y_1$ = O) |
| Q-1 ($R_1$, $R_2$ = H) | H | — | — | A-3 ($X_1$ = $OCH_3$) |
| Q-1 ($R_1$, $R_2$ = H) | H | — | — | A-4 ($X_1$, $Y_2$ = $CH_3$) |
| Q-1 ($R_1$, $R_2$ = H) | H | — | — | A-5 ($X_2$ = $OCH_3$, $Y_3$ = $CH_3$) |
| Q-1 ($R_1$, $R_2$ = H) | H | — | — | A-6 ($X_3$ = $CH_3$) |
| Q-2 ($R_3$, $R_4$, $R_5$ = H) | H | S | — | A-2 ($X_1$ = $CH_3$, $Y_1$ = O) |
| Q-2 ($R_3$, $R_4$, $R_5$ = H) | H | S | — | A-3 ($X_1$ = $OCH_3$) |
| Q-2 ($R_3$, $R_4$, $R_5$ = H) | H | O | — | A-4 ($X_1$, $Y_2$ = $CH_3$) |
| Q-3 ($R_3$, $R_4$, $R_5$ = H) | H | S | — | A-2 ($X_1$ = $OCH_3$, $Y_1$ = $CH_2$) |
| Q-3 ($R_3$, $R_4$, $R_5$ = H) | H | S | — | A-3 ($X_1$ = $CH_3$) |
| Q-3 ($R_3$, $R_4$, $R_5$ = H) | H | O | — | A-4 ($X_1$ = $CH_3$, $Y_2$ = H) |
| Q-4 ($R_3$, $R_4$, $R_5$ = H) | H | — | — | A-2 ($X_1$ = $OCH_3$, $Y_1$ = O) |
| Q-4 ($R_3$, $R_4$, $R_5$ = H) | H | — | — | A-5 ($X_2$ = $OCH_3$, $Y_3$ = $CH_3$) |
| Q-4 ($R_3$, $R_4$, $R_5$ = H) | H | — | — | A-6 ($X_3$ = $OCH_3$) |
| Q-7 ($R_3$, $R_4$, $R_5$, $R_6$ = H) | H | — | — | A-2 ($X_1$ = $OCF_2H$, $Y_1$ = O) |
| Q-7 ($R_3$, $R_4$, $R_5$, $R_6$ = H) | H | — | — | A-3 ($X_1$ = $OCH_2CH_3$) |
| Q-7 ($R_3$, $R_4$, $R_5$, $R_6$ = H) | H | — | — | A-4 ($X_1$ = $OCH_3$, $Y_2$ = $CH_3$) |
| Q-7 ($R_3$, $R_4$, $R_5$, $R_6$ = H) | H | — | — | A-5 ($X_2$ = $SCH_3$, $Y_3$ = $CH_3$) |
| Q-7 ($R_3$, $R_4$, $R_5$, $R_6$ = H) | H | — | — | A-6 ($X_3$ = $OCH_3$) |
| Q-10 ($R_3$, $R_4$ = H) | H | — | O | A-2 ($X_1$ = $OCH_3$, $Y_1$ = O) |
| Q-10 ($R_3$, $R_4$ = H) | H | — | O | A-3 ($X_1$ = $OCH_3$) |
| Q-10 ($R_3$, $R_4$ = H) | H | — | S | A-4 ($X_1$ = $CH_3$, $Y_2$ = $CH_3$) |
| Q-11 ($R_3$, $R_4$ = H) | H | — | O | A-2 ($X_1$ = $OCH_3$, $Y_1$ = $CH_2$) |
| Q-11 ($R_3$, $R_4$ = H) | H | — | O | A-3 ($X_1$ = $CH_3$) |
| Q-11 ($R_3$, $R_4$ = H) | H | — | S | A-4 ($X_1$ = $OCH_3$, $Y_2$ = H) |
| Q-16 ($R_3$, $R_4$, $R_5$, $R_6$ = H) | H | O | — | A-2 ($X_1$ = $CH_3$, $Y_1$ = O) |
| Q-16 ($R_3$, $R_4$, $R_5$, $R_6$ = H) | H | O | — | A-3 ($X_1$ = $CH_3$) |
| Q-16 ($R_3$, $R_4$, $R_5$, $R_6$ = H) | H | O | — | A-5 ($X_2$ = $OCH_3$, $Y_3$ = $CH_3$) |
| Q-16 ($R_3$, $R_4$, $R_5$, $R_6$ = H) | H | S | — | A-4 ($X_1$ = $CH_3$, $Y_2$ = $CH_3$) |

TABLE 12-continued

| Q | General Structure 6 R | W' | W'' | A |
|---|---|---|---|---|
| Q-16 ($R_3$, $R_4$, $R_5$, $R_6$ = H) | H | S | — | A-5 ($X_2$ = $OCH_3$, $Y_3$ = $CH_2CH_3$) |
| Q-16 ($R_3$, $R_4$, $R_5$, $R_6$ = H) | H | S | — | A-6 ($X_3$ = $OCH_3$) |
| Q-20 ($R_3'$ = H) | H | S | — | A-2 ($X_1$ = $OCH_3$, $Y_1$ = O) |
| Q-20 ($R_3'$ = H) | H | O | — | A-2 ($X_1$ = $OCH_3$) |
| Q-20 ($R_3'$ = $CH_3$) | H | S | — | A-4 ($X_1$ = $OCH_3$, $Y_2$ = H) |
| Q-20 ($R_3'$ = $CH_3$) | H | O | — | A-2 ($X_1$ = $OCH_3$, $Y_1$ = O) |
| Q-20 ($R_3'$ = $SCH_3$) | H | S | — | A-3 ($X_1$ = $OCH_3$) |
| Q-20 ($R_3'$ = $SCH_3$) | H | O | — | A-4 ($X_1$ = $OCH_3$, $Y_2$ = $CH_3$) |
| Q-23 ($R_3$ = H) | H | — | — | A-3 ($X_1$ = $CH_3$) |
| Q-23 ($R_3$ = H) | H | — | — | A-4 ($X_1$ = $OCH_3$, $Y_2$ = $CH_3$) |
| Q-23 ($R_3$ = $CH_3$) | H | — | — | A-6 ($X_3$ = $OCH_3$) |
| Q-28 ($R_3''$ = H, $R_4$ = H) | H | — | — | A-2 ($X_1$ = $CH_3$, $Y_1$ = O) |
| Q-28 ($R_3''$ = Cl, $R_4$ = H) | H | — | — | A-3 ($X_1$ = $OCH_3$) |
| Q-28 ($R_3''$ = $CH_3$, $R_4$ = H) | H | — | — | A-4 ($X_1$ = $OCH_3$, $Y_2$ = $CH_3$) |
| Q-28 ($R_3''$ = H, $R_4$ = H) | H | — | — | A-5 ($X_2$ = $CH_3$, $Y_2$ = $CH_3$) |
| Q-28 ($R_3''$ = H, $R_4$ = H) | H | — | — | A-6 ($X_3$ = $CH_3$) |
| Q-33 ($R_3$, $R_4$ = H, n = O) | H | — | — | A-2 ($X_1$ = $OCH_3$, $Y_1$ = $CH_2$) |
| Q-33 ($R_3$, $R_4$ = H, n = O) | H | — | — | A-3 ($X_1$ = $CH_3$) |
| Q-33 ($R_3$, $R_4$ = H, n = O) | H | — | — | A-4 ($X_1$ = $OCH_3$, $Y_2$ = $CH_3$) |
| Q-36 ($R_3$, $R_4$, $R_5$ = H) | H | — | — | A-2 ($X_1$ = $OCH_3$, $Y_1$ = O) |
| Q-36 ($R_3$, $R_4$, $R_5$ = H) | H | — | — | A-3 ($X_1$ = $OCH_3$) |
| Q-36 ($R_3$, $R_4$, $R_5$ = H) | H | — | — | A-4 ($X_1$ = $OCH_3$, $Y_2$ = $CH_3$) |
| Q-39 ($R_3$, $R_4$ = H) | H | — | — | A-2 ($X_1$ = $CH_3$, $Y_1$ = $CH_2$) |
| Q-39 ($R_3$, $R_4$ = H) | H | — | — | A-3 ($X_1$ = $CH_3$) |
| Q-39 ($R_3$, $R_4$ = H) | H | — | — | A-4 ($X_1$ = $OCH_3$, $Y_2$ = H) |

TABLE 13

General Structure 7

| Q | n | | R | $R_1$ | $R_2$ | $R_3$ | $R_{3'}$ | $R_4$ | $R_5$ | $R_6$ | W' or W'' | X | Y | Z |
|---|---|---|---|---|---|---|---|---|---|---|---|---|---|---|
| Q-1 | 1 | H | H | H | — | — | — | — | — | O | — | $CH_3$ | $CH_3$ | CH |
| Q-1 | 1 | H | H | H | — | — | — | — | — | O | — | $CH_3$ | $OCH_3$ | CH |
| Q-1 | 1 | H | H | H | — | — | — | — | — | O | — | $OCH_3$ | $OCH_3$ | CH |
| Q-1 | 1 | H | H | H | — | — | — | — | — | O | — | $OCH_3$ | CH | N |
| Q-1 | 1 | H | H | H | — | — | — | — | — | O | — | $OCH_3$ | $OCH_3$ | N |
| Q-1 | 1 | H | H | H | — | — | — | — | — | O | — | $OCH_3$ | Cl | CH |
| Q-1 | 1 | H | H | H | — | — | — | — | — | S | — | $OCH_3$ | $OCH_3$ | CH |
| Q-1 | 2 | H | H | H | — | — | — | — | — | O | — | $CH_3$ | $CH_3$ | CH |
| Q-1 | 2 | H | H | H | — | — | — | — | — | O | — | $CH_3$ | $OCH_3$ | CH |
| Q-1 | 2 | H | H | H | — | — | — | — | — | O | — | $OCH_3$ | $OCH_3$ | CH |
| Q-1 | 2 | H | H | H | — | — | — | — | — | O | — | $CH_3$ | $OCH_3$ | N |
| Q-1 | 2 | H | H | H | — | — | — | — | — | O | — | $OCH_3$ | $OCH_3$ | N |
| Q-1 | 2 | H | H | H | — | — | — | — | — | O | — | $OCH_3$ | Cl | CH |
| Q-1 | 2 | H | H | H | — | — | — | — | — | S | — | $OCH_3$ | $OCH_3$ | CH |
| Q-7 | 1 | H | — | — | H | — | H | H | H | O | — | $CH_3$ | $CH_3$ | CH |
| Q-7 | 1 | H | — | — | H | — | H | H | H | O | — | $CH_3$ | $OCH_3$ | CH |
| Q-7 | 1 | H | — | — | H | — | H | H | H | O | — | $OCH_3$ | $OCH_3$ | CH |
| Q-7 | 1 | H | — | — | H | — | H | H | H | O | — | $CH_3$ | $OCH_3$ | N |
| Q-7 | 1 | H | — | — | H | — | H | H | H | O | — | $OCH_3$ | $OCH_3$ | N |
| Q-7 | 1 | H | — | — | H | — | H | H | H | O | — | $OCH_3$ | Cl | CH |
| Q-7 | 1 | H | — | — | H | — | H | H | H | S | — | $OCH_3$ | $OCH_3$ | CH |
| Q-7 | 2 | H | — | — | H | — | H | H | H | O | — | $CH_3$ | $CH_3$ | CH |
| Q-7 | 2 | H | — | — | H | — | H | H | H | O | — | $OCH_3$ | $OCH_3$ | CH |
| Q-7 | 2 | H | — | — | H | — | H | H | H | O | — | $OCH_3$ | $OCH_3$ | CH |
| Q-7 | 2 | H | — | — | H | — | H | H | H | O | — | $OCH_3$ | CH | N |
| Q-7 | 2 | H | — | — | H | — | H | H | H | O | — | $OCH_3$ | $OCH_3$ | N |
| Q-7 | 2 | H | — | — | H | — | H | H | H | O | — | $OCH_3$ | Cl | CH |
| Q-7 | 2 | H | — | — | H | — | H | H | H | S | — | $OCH_3$ | $OCH_3$ | CH |
| Q-11 | 1 | H | — | — | H | — | H | — | — | O | O | $CH_3$ | $CH_3$ | CH |
| Q-11 | 1 | H | — | — | H | — | H | — | — | O | O | $CH_3$ | $OCH_3$ | CH |
| Q-11 | 1 | H | — | — | H | — | H | — | — | O | O | $OCH_3$ | $OCH_3$ | CH |
| Q-11 | 1 | H | — | — | H | — | H | — | — | O | O | $CH_3$ | $OCH_3$ | N |
| Q-11 | 1 | H | — | — | H | — | H | — | — | O | O | $OCH_3$ | $OCH_3$ | N |
| Q-11 | 1 | H | — | — | H | — | H | — | — | O | O | $OCH_3$ | Cl | CH |
| Q-11 | 1 | H | — | — | H | — | H | — | — | S | O | $OCH_3$ | $OCH_3$ | CH |
| Q-11 | 2 | H | — | — | H | — | H | — | — | O | O | $CH_3$ | $CH_3$ | CH |
| Q-11 | 2 | H | — | — | H | — | H | — | — | O | O | $CH_3$ | $OCH_3$ | CH |
| Q-11 | 2 | H | — | — | H | — | H | — | — | O | O | $OCH_3$ | $OCH_3$ | CH |
| Q-11 | 2 | H | — | — | H | — | H | — | — | O | O | $OCH_3$ | $CH_3$ | N |
| Q-11 | 2 | H | — | — | H | — | H | — | — | O | O | $OCH_3$ | $OCH_3$ | N |
| Q-11 | 2 | H | — | — | H | — | H | — | — | O | O | $OCH_3$ | Cl | CH |
| Q-11 | 2 | H | — | — | H | — | H | — | — | S | O | $OCH_3$ | $OCH_3$ | CH |
| Q-15 | 1 | H | — | — | — | $CH_3$ | H | — | — | O | O | $CH_3$ | $CH_3$ | CH |
| Q-15 | 1 | H | — | — | — | $CH_3$ | H | — | — | O | O | $OCH_3$ | $OCH_3$ | CH |
| Q-15 | 1 | H | — | — | — | $CH_3$ | H | — | — | O | O | $OCH_3$ | $OCH_3$ | CH |
| Q-15 | 1 | H | — | — | — | $CH_3$ | H | — | — | O | O | $CH_3$ | $OCH_3$ | N |

TABLE 13-continued

General Structure 7

| Q | n | | R | R1 | R2 | R3 | R3' | R4 | R5 | R6 W' or W'' | X | Y | Z |
|---|---|---|---|---|---|---|---|---|---|---|---|---|---|
| Q-15 | 1 | H | — | — | — | $CH_3$ | H | — | — | O | O | $OCH_3$ | $OCH_3$ | N |
| Q-15 | 1 | H | — | — | — | $CH_3$ | H | — | — | O | O | $OCH_3$ | Cl | CH |
| Q-15 | 1 | H | — | — | — | $CH_3$ | H | — | — | S | O | $OCH_3$ | $OCH_3$ | CH |
| Q-15 | 2 | H | — | — | — | $CH_3$ | H | — | — | O | O | $CH_3$ | $CH_3$ | CH |
| Q-15 | 2 | H | — | — | — | $CH_3$ | H | — | — | O | O | $OCH_3$ | $CH_3$ | CH |
| Q-15 | 2 | H | — | — | — | $CH_3$ | H | — | — | O | O | $OCH_3$ | $OCH_3$ | CH |
| Q-15 | 2 | H | — | — | — | $CH_3$ | H | — | — | O | O | $OCH_3$ | $CH_3$ | N |
| Q-15 | 2 | H | — | — | — | $CH_3$ | H | — | — | O | O | $OCH_3$ | $OCH_3$ | N |
| Q-15 | 2 | H | — | — | — | $CH_3$ | H | — | — | O | O | $OCH_3$ | Cl | CH |
| Q-15 | 2 | H | — | — | — | $CH_3$ | H | — | — | S | O | $OCH_3$ | $OCH_3$ | CH |
| Q-15 | 1 | H | — | — | — | $CH_3$ | H | — | — | O | S | $CH_3$ | $CH_3$ | CH |
| Q-15 | 1 | H | — | — | — | $CH_3$ | H | — | — | O | S | $CH_3$ | $OCH_3$ | CH |
| Q-15 | 1 | H | — | — | — | $CH_3$ | H | — | — | O | S | $OCH_3$ | $OCH_3$ | CH |
| Q-15 | 1 | H | — | — | — | $CH_3$ | H | — | — | O | S | $CH_3$ | $OCH_3$ | N |
| Q-15 | 1 | H | — | — | — | $CH_3$ | H | — | — | O | S | $OCH_3$ | $OCH_3$ | N |
| Q-15 | 1 | H | — | — | — | $CH_3$ | H | — | — | O | S | $OCH_3$ | Cl | CH |
| Q-15 | 1 | H | — | — | — | $CH_3$ | H | — | — | S | S | $OCH_3$ | $OCH_3$ | CH |
| Q-15 | 2 | H | — | — | — | $CH_3$ | H | — | — | O | S | $CH_3$ | $CH_3$ | CH |
| Q-15 | 2 | H | — | — | — | $CH_3$ | H | — | — | O | S | $CH_3$ | $OCH_3$ | CH |
| Q-15 | 2 | H | — | — | — | $CH_3$ | H | — | — | O | S | $OCH_3$ | $OCH_3$ | CH |
| Q-15 | 2 | H | — | — | — | $CH_3$ | H | — | — | O | S | $CH_3$ | $OCH_3$ | N |
| Q-15 | 2 | H | — | — | — | $CH_3$ | H | — | — | O | S | $OCH_3$ | $OCH_3$ | N |
| Q-15 | 2 | H | — | — | — | $CH_3$ | H | — | — | O | S | $OCH_3$ | Cl | CH |
| Q-15 | 2 | H | — | — | — | $CH_3$ | H | — | — | S | S | $OCH_3$ | $OCH_3$ | CH |
| Q-20 | 1 | H | — | — | — | $SCH_3$ | H | — | — | O | O | $CH_3$ | $CH_3$ | CH |
| Q-20 | 1 | H | — | — | — | $SCH_3$ | H | — | — | O | O | $CH_3$ | $OCH_3$ | CH |
| Q-20 | 1 | H | — | — | — | $SCH_3$ | H | — | — | O | O | $OCH_3$ | $OCH_3$ | CH |
| Q-20 | 1 | H | — | — | — | $SCH_3$ | H | — | — | O | O | $CH_3$ | $OCH_3$ | N |
| Q-20 | 1 | H | — | — | — | $SCH_3$ | H | — | — | O | O | $OCH_3$ | $OCH_3$ | N |
| Q-20 | 1 | H | — | — | — | $SCH_3$ | H | — | — | O | O | $OCH_3$ | Cl | CH |
| Q-20 | 1 | H | — | — | — | $SCH_3$ | H | — | — | S | O | $OCH_3$ | $OCH_3$ | CH |
| Q-20 | 2 | H | — | — | — | $SCH_3$ | H | — | — | O | O | $CH_3$ | $CH_3$ | CH |
| Q-20 | 2 | H | — | — | — | $SCH_3$ | H | — | — | O | O | $CH_3$ | $OCH_3$ | CH |
| Q-20 | 2 | H | — | — | — | $SCH_3$ | H | — | — | O | O | $OCH_3$ | $OCH_3$ | CH |
| Q-20 | 2 | H | — | — | — | $SCH_3$ | H | — | — | O | O | $CH_3$ | $OCH_3$ | N |
| Q-20 | 2 | H | — | — | — | $SCH_3$ | H | — | — | O | O | $OCH_3$ | $OCH_3$ | N |
| Q-20 | 2 | H | — | — | — | $SCH_3$ | H | — | — | O | O | $OCH_3$ | Cl | CH |
| Q-20 | 2 | H | — | — | — | $SCH_3$ | H | — | — | S | O | $OCH_3$ | $OCH_3$ | CH |
| Q-28 | 1 | H | — | — | — | Cl | H | — | — | O | — | $CH_3$ | $CH_3$ | CH |
| Q-28 | 1 | H | — | — | — | Cl | H | — | — | O | — | $CH_3$ | $OCH_3$ | CH |
| Q-28 | 1 | H | — | — | — | Cl | H | — | — | O | — | $OCH_3$ | $OCH_3$ | CH |
| Q-28 | 1 | H | — | — | — | Cl | H | — | — | O | — | $OCH_3$ | CH | N |
| Q-28 | 1 | H | — | — | — | Cl | H | — | — | O | — | $OCH_3$ | $OCH_3$ | N |
| Q-28 | 1 | H | — | — | — | Cl | H | — | — | O | — | $OCH_3$ | Cl | CH |
| Q-28 | 1 | H | — | — | — | Cl | H | — | — | S | — | $OCH_3$ | $OCH_3$ | CH |
| Q-28 | 2 | H | — | — | — | Cl | H | — | — | O | — | $CH_3$ | $CH_3$ | CH |
| Q-28 | 2 | H | — | — | — | Cl | H | — | — | O | — | $CH_3$ | $OCH_3$ | CH |
| Q-28 | 2 | H | — | — | — | Cl | H | — | — | O | — | $OCH_3$ | $OCH_3$ | CH |
| Q-28 | 2 | H | — | — | — | Cl | H | — | — | O | — | $OCH_3$ | CH | N |
| Q-28 | 2 | H | — | — | — | Cl | H | — | — | O | — | $OCH_3$ | $OCH_3$ | N |
| Q-28 | 2 | H | — | — | — | Cl | H | — | — | O | — | $OCH_3$ | Cl | CH |
| Q-28 | 2 | H | — | — | — | Cl | H | — | — | S | — | $OCH_3$ | $OCH_3$ | CH |
| Q-1 | 1 | $CH_3$ | H | H | — | — | — | — | — | O | — | $OCH_3$ | $OCH_3$ | CH |
| Q-1 | 2 | $CH_3$ | H | H | — | — | — | — | — | O | — | $OCH_3$ | $OCH_3$ | CH |
| Q-7 | 1 | $CH_3$ | — | — | H | — | H | H | H | O | — | $OCH_3$ | $OCH_3$ | CH |
| Q-7 | 2 | $CH_3$ | — | — | H | — | H | H | H | O | — | $OCH_3$ | $OCH_3$ | CH |
| Q-11 | 1 | $CH_3$ | — | — | H | — | H | — | — | O | O | $OCH_3$ | $OCH_3$ | CH |
| Q-11 | 2 | $CH_3$ | — | — | H | — | H | — | — | O | O | $OCH_3$ | $OCH_3$ | CH |
| Q-15 | 1 | $CH_3$ | — | — | — | $CH_3$ | H | — | — | O | O | $OCH_3$ | $OCH_3$ | CH |
| Q-15 | 2 | $CH_3$ | — | — | — | $CH_3$ | H | — | — | O | O | $OCH_3$ | $OCH_3$ | CH |
| Q-15 | 1 | $CH_3$ | — | — | — | $CH_3$ | H | — | — | O | S | $OCH_3$ | $OCH_3$ | CH |
| Q-15 | 2 | $CH_3$ | — | — | — | $CH_3$ | H | — | — | O | S | $OCH_3$ | $OCH_3$ | CH |
| Q-20 | 1 | $CH_3$ | — | — | — | $SCH_3$ | H | — | — | O | O | $OCH_3$ | $OCH_3$ | CH |
| Q-20 | 2 | $CH_3$ | — | — | — | $SCH_3$ | H | — | — | O | O | $OCH_3$ | $OCH_3$ | CH |
| Q-28 | 1 | $CH_3$ | — | — | — | Cl | H | — | — | O | — | $OCH_3$ | $OCH_3$ | CH |
| Q-28 | 2 | $CH_3$ | — | — | — | Cl | H | — | — | O | — | $OCH_3$ | $OCH_3$ | CH |

TABLE 14

General Structure 8

| Q | n | R | R1 | R2 | R3 | R3' | R4 | R5 | R6 | W | W' or W'' | X | Y | Z |
|---|---|---|---|---|---|---|---|---|---|---|---|---|---|---|
| Q-1 | 1 | H | H | H | — | — | — | — | — | O | — | $CH_3$ | $CH_3$ | CH |
| Q-1 | 1 | H | H | H | — | — | — | — | — | O | — | $CH_3$ | $OCH_3$ | CH |
| Q-1 | 1 | H | H | H | — | — | — | — | — | O | — | $OCH_3$ | $OCH_3$ | CH |

TABLE 14-continued

General Structure 8

| Q | n | R | $R_1$ | $R_2$ | $R_3$ | $R_{3'}$ | $R_4$ | $R_5$ | $R_6$ | W | W' or W'' | X | Y | Z |
|---|---|---|---|---|---|---|---|---|---|---|---|---|---|---|
| Q-1 | 1 | H | H | H | — | — | — | — | — | O | — | $OCH_3$ | CH | N |
| Q-1 | 1 | H | H | H | — | — | — | — | — | O | — | $OCH_3$ | $OCH_3$ | N |
| Q-1 | 1 | H | H | H | — | — | — | — | — | O | — | $OCH_3$ | Cl | CH |
| Q-1 | 1 | H | H | H | — | — | — | — | — | S | — | $OCH_3$ | $OCH_3$ | CH |
| Q-1 | 2 | H | H | H | — | — | — | — | — | O | — | $CH_3$ | $CH_3$ | CH |
| Q-1 | 2 | H | H | H | — | — | — | — | — | O | — | $CH_3$ | $OCH_3$ | CH |
| Q-1 | 2 | H | H | H | — | — | — | — | — | O | — | $OCH_3$ | $OCH_3$ | CH |
| Q-1 | 2 | H | H | H | — | — | — | — | — | O | — | $CH_3$ | $OCH_3$ | N |
| Q-1 | 2 | H | H | H | — | — | — | — | — | O | — | $OCH_3$ | $OCH_3$ | N |
| Q-1 | 2 | H | H | H | — | — | — | — | — | O | — | $OCH_3$ | Cl | CH |
| Q-1 | 2 | H | H | H | — | — | — | — | — | S | — | $OCH_3$ | $OCH_3$ | CH |
| Q-7 | 1 | H | — | — | H | — | H | H | H | O | — | $CH_3$ | $CH_3$ | CH |
| Q-7 | 1 | H | — | — | H | — | H | H | H | O | — | $CH_3$ | $OCH_3$ | CH |
| Q-7 | 1 | H | — | — | H | — | H | H | H | O | — | $OCH_3$ | $OCH_3$ | CH |
| Q-7 | 1 | H | — | — | H | — | H | H | H | O | — | $CH_3$ | $OCH_3$ | N |
| Q-7 | 1 | H | — | — | H | — | H | H | H | O | — | $OCH_3$ | $OCH_3$ | N |
| Q-7 | 1 | H | — | — | H | — | H | H | H | O | — | $OCH_3$ | Cl | CH |
| Q-7 | 1 | H | — | — | H | — | H | H | H | S | — | $OCH_3$ | $OCH_3$ | CH |
| Q-7 | 2 | H | — | — | H | — | H | H | H | O | — | $CH_3$ | $CH_3$ | CH |
| Q-7 | 2 | H | — | — | H | — | H | H | H | O | — | $OCH_3$ | $OCH_3$ | CH |
| Q-7 | 2 | H | — | — | H | — | H | H | H | O | — | $OCH_3$ | $OCH_3$ | CH |
| Q-7 | 2 | H | — | — | H | — | H | H | H | O | — | $OCH_3$ | CH | N |
| Q-7 | 2 | H | — | — | H | — | H | H | H | O | — | $OCH_3$ | $OCH_3$ | N |
| Q-7 | 2 | H | — | — | H | — | H | H | H | O | — | $OCH_3$ | Cl | CH |
| Q-7 | 2 | H | — | — | H | — | H | H | H | S | — | $OCH_3$ | $OCH_3$ | CH |
| Q-11 | 1 | H | — | — | H | — | H | — | — | O | O | $CH_3$ | $CH_3$ | CH |
| Q-11 | 1 | H | — | — | H | — | H | — | — | O | O | $CH_3$ | $OCH_3$ | CH |
| Q-11 | 1 | H | — | — | H | — | H | — | — | O | O | $OCH_3$ | $OCH_3$ | CH |
| Q-11 | 1 | H | — | — | H | — | H | — | — | O | O | $CH_3$ | $OCH_3$ | N |
| Q-11 | 1 | H | — | — | H | — | H | — | — | O | O | $OCH_3$ | $OCH_3$ | N |
| Q-11 | 1 | H | — | — | H | — | H | — | — | O | O | $OCH_3$ | Cl | CH |
| Q-11 | 1 | H | — | — | H | — | H | — | — | S | O | $OCH_3$ | $OCH_3$ | CH |
| Q-11 | 2 | H | — | — | H | — | H | — | — | O | O | $CH_3$ | $CH_3$ | CH |
| Q-11 | 2 | H | — | — | H | — | H | — | — | O | O | $CH_3$ | $OCH_3$ | CH |
| Q-11 | 2 | H | — | — | H | — | H | — | — | O | O | $OCH_3$ | $OCH_3$ | CH |
| Q-11 | 2 | H | — | — | H | — | H | — | — | O | O | $OCH_3$ | $CH_3$ | N |
| Q-11 | 2 | H | — | — | H | — | H | — | — | O | O | $OCH_3$ | $OCH_3$ | N |
| Q-11 | 2 | H | — | — | H | — | H | — | — | O | O | $OCH_3$ | Cl | CH |
| Q-11 | 2 | H | — | — | H | — | H | — | — | S | O | $OCH_3$ | $OCH_3$ | CH |
| Q-15 | 1 | H | — | — | — | $CH_3$ | H | — | — | O | O | $CH_3$ | $CH_3$ | CH |
| Q-15 | 1 | H | — | — | — | $CH_3$ | H | — | — | O | O | $CH_3$ | $OCH_3$ | CH |
| Q-15 | 1 | H | — | — | — | $CH_3$ | H | — | — | O | O | $OCH_3$ | $OCH_3$ | CH |
| Q-15 | 1 | H | — | — | — | $CH_3$ | H | — | — | O | O | $CH_3$ | $OCH_3$ | N |
| Q-15 | 1 | H | — | — | — | $CH_3$ | H | — | — | O | O | $OCH_3$ | $OCH_3$ | N |
| Q-15 | 1 | H | — | — | — | $CH_3$ | H | — | — | O | O | $OCH_3$ | Cl | CH |
| Q-15 | 1 | H | — | — | — | $CH_3$ | H | — | — | S | O | $OCH_3$ | $OCH_3$ | CH |
| Q-15 | 2 | H | — | — | — | $CH_3$ | H | — | — | O | O | $CH_3$ | $CH_3$ | CH |
| Q-15 | 2 | H | — | — | — | $CH_3$ | H | — | — | O | O | $OCH_3$ | $CH_3$ | CH |
| Q-15 | 2 | H | — | — | — | $CH_3$ | H | — | — | O | O | $OCH_3$ | $OCH_3$ | CH |
| Q-15 | 2 | H | — | — | — | $CH_3$ | H | — | — | O | O | $OCH_3$ | $CH_3$ | N |
| Q-15 | 2 | H | — | — | — | $CH_3$ | H | — | — | O | O | $OCH_3$ | $OCH_3$ | N |
| Q-15 | 2 | H | — | — | — | $CH_3$ | H | — | — | O | O | $OCH_3$ | Cl | CH |
| Q-15 | 2 | H | — | — | — | $CH_3$ | H | — | — | S | O | $OCH_3$ | $OCH_3$ | CH |
| Q-15 | 1 | H | — | — | — | $CH_3$ | H | — | — | O | S | $CH_3$ | $CH_3$ | CH |
| Q-15 | 1 | H | — | — | — | $CH_3$ | H | — | — | O | S | $CH_3$ | $OCH_3$ | CH |
| Q-15 | 1 | H | — | — | — | $CH_3$ | H | — | — | O | S | $OCH_3$ | $OCH_3$ | CH |
| Q-15 | 1 | H | — | — | — | $CH_3$ | H | — | — | O | S | $CH_3$ | $OCH_3$ | N |
| Q-15 | 1 | H | — | — | — | $CH_3$ | H | — | — | O | S | $OCH_3$ | $OCH_3$ | N |
| Q-15 | 1 | H | — | — | — | $CH_3$ | H | — | — | O | S | $OCH_3$ | Cl | CH |
| Q-15 | 1 | H | — | — | — | $CH_3$ | H | — | — | S | S | $OCH_3$ | $OCH_3$ | CH |
| Q-15 | 2 | H | — | — | — | $CH_3$ | H | — | — | O | S | $CH_3$ | $CH_3$ | CH |
| Q-15 | 2 | H | — | — | — | $CH_3$ | H | — | — | O | S | $CH_3$ | $OCH_3$ | CH |
| Q-15 | 2 | H | — | — | — | $CH_3$ | H | — | — | O | S | $OCH_3$ | $OCH_3$ | CH |
| Q-15 | 2 | H | — | — | — | $CH_3$ | H | — | — | O | S | $CH_3$ | $OCH_3$ | N |
| Q-15 | 2 | H | — | — | — | $CH_3$ | H | — | — | O | S | $OCH_3$ | $OCH_3$ | N |
| Q-15 | 2 | H | — | — | — | $CH_3$ | H | — | — | O | S | $CH_3$ | Cl | CH |
| Q-15 | 2 | H | — | — | — | $CH_3$ | H | — | — | S | S | $OCH_3$ | $OCH_3$ | CH |
| Q-20 | 1 | H | — | — | — | $SCH_3$ | H | — | — | O | O | $CH_3$ | $CH_3$ | CH |
| Q-20 | 1 | H | — | — | — | $SCH_3$ | H | — | — | O | O | $CH_3$ | $OCH_3$ | CH |
| Q-20 | 1 | H | — | — | — | $SCH_3$ | H | — | — | O | O | $OCH_3$ | $OCH_3$ | CH |
| Q-20 | 1 | H | — | — | — | $SCH_3$ | H | — | — | O | O | $CH_3$ | $OCH_3$ | N |
| Q-20 | 1 | H | — | — | — | $SCH_3$ | H | — | — | O | O | $OCH_3$ | $OCH_3$ | N |
| Q-20 | 1 | H | — | — | — | $SCH_3$ | H | — | — | O | O | $OCH_3$ | Cl | CH |
| Q-20 | 1 | H | — | — | — | $SCH_3$ | H | — | — | S | O | $OCH_3$ | $OCH_3$ | CH |
| Q-20 | 2 | H | — | — | — | $SCH_3$ | H | — | — | O | O | $CH_3$ | $CH_3$ | CH |
| Q-20 | 2 | H | — | — | — | $SCH_3$ | H | — | — | O | O | $CH_3$ | $OCH_3$ | CH |
| Q-20 | 2 | H | — | — | — | $SCH_3$ | H | — | — | O | O | $OCH_3$ | $OCH_3$ | CH |
| Q-20 | 2 | H | — | — | — | $SCH_3$ | H | — | — | O | O | $CH_3$ | $OCH_3$ | N |

TABLE 14-continued

General Structure 8

| Q | n | R | $R_1$ | $R_2$ | $R_3$ | $R_{3'}$ | $R_4$ | $R_5$ | $R_6$ | W | W' or W'' | X | Y | Z |
|---|---|---|---|---|---|---|---|---|---|---|---|---|---|---|
| Q-20 | 2 | H | — | — | — | $SCH_3$ | H | — | — | O | O | $OCH_3$ | $OCH_3$ | N |
| Q-20 | 2 | H | — | — | — | $SCH_3$ | H | — | — | O | O | $OCH_3$ | Cl | CH |
| Q-20 | 2 | H | — | — | — | $SCH_3$ | H | — | — | S | O | $OCH_3$ | $OCH_3$ | CH |
| Q-28 | 1 | H | — | — | — | Cl | H | — | — | O | — | $CH_3$ | $CH_3$ | CH |
| Q-28 | 1 | H | — | — | — | Cl | H | — | — | O | — | $CH_3$ | $OCH_3$ | CH |
| Q-28 | 1 | H | — | — | — | Cl | H | — | — | O | — | $OCH_3$ | $OCH_3$ | CH |
| Q-28 | 1 | H | — | — | — | Cl | H | — | — | O | — | $OCH_3$ | CH | N |
| Q-28 | 1 | H | — | — | — | Cl | H | — | — | O | — | $OCH_3$ | $OCH_3$ | N |
| Q-28 | 1 | H | — | — | — | Cl | H | — | — | O | — | $OCH_3$ | Cl | CH |
| Q-28 | 1 | H | — | — | — | Cl | H | — | — | S | — | $OCH_3$ | $OCH_3$ | CH |
| Q-28 | 2 | H | — | — | — | Cl | H | — | — | O | — | $CH_3$ | $CH_3$ | CH |
| Q-28 | 2 | H | — | — | — | Cl | H | — | — | O | — | $CH_3$ | $OCH_3$ | CH |
| Q-28 | 2 | H | — | — | — | Cl | H | — | — | O | — | $OCH_3$ | $OCH_3$ | CH |
| Q-28 | 2 | H | — | — | — | Cl | H | — | — | O | — | $OCH_3$ | CH | N |
| Q-28 | 2 | H | — | — | — | Cl | H | — | — | O | — | $OCH_3$ | $OCH_3$ | N |
| Q-28 | 2 | H | — | — | — | Cl | H | — | — | O | — | $OCH_3$ | Cl | CH |
| Q-28 | 2 | H | — | — | — | Cl | H | — | — | S | — | $OCH_3$ | $OCH_3$ | CH |
| Q-1 | 1 | $CH_3$ | H | H | — | — | — | — | — | O | — | $OCH_3$ | $OCH_3$ | CH |
| Q-1 | 2 | $CH_3$ | H | H | — | — | — | — | — | O | — | $OCH_3$ | $OCH_3$ | CH |
| Q-7 | 1 | $CH_3$ | — | — | H | — | H | H | H | O | — | $OCH_3$ | $OCH_3$ | CH |
| Q-7 | 2 | $CH_3$ | — | — | H | — | H | H | H | O | — | $OCH_3$ | $OCH_3$ | CH |
| Q-11 | 1 | $CH_3$ | — | — | H | — | H | — | — | O | O | $OCH_3$ | $OCH_3$ | CH |
| Q-11 | 2 | $CH_3$ | — | — | H | — | H | — | — | O | O | $OCH_3$ | $OCH_3$ | CH |
| Q-15 | 1 | $CH_3$ | — | — | — | $CH_3$ | H | — | — | O | O | $OCH_3$ | $OCH_3$ | CH |
| Q-15 | 2 | $CH_3$ | — | — | — | $CH_3$ | H | — | — | O | O | $OCH_3$ | $OCH_3$ | CH |
| Q-15 | 1 | $CH_3$ | — | — | — | $CH_3$ | H | — | — | O | S | $OCH_3$ | $OCH_3$ | CH |
| Q-15 | 2 | $CH_3$ | — | — | — | $CH_3$ | H | — | — | O | S | $OCH_3$ | $OCH_3$ | CH |
| Q-20 | 1 | $CH_3$ | — | — | — | $SCH_3$ | H | — | — | O | O | $OCH_3$ | $OCH_3$ | CH |
| Q-20 | 2 | $CH_3$ | — | — | — | $SCH_3$ | H | — | — | O | O | $OCH_3$ | $OCH_3$ | CH |
| Q-28 | 1 | $CH_3$ | — | — | — | Cl | H | — | — | O | — | $OCH_3$ | $OCH_3$ | CH |
| Q-28 | 2 | $CH_3$ | — | — | — | Cl | H | — | — | O | — | $OCH_3$ | $OCH_3$ | CH |

TABLE 15

General Structure 9

| Q | n | R | $R_1$ | $R_2$ | $R_3$ | $R_{3'}$ | $R_4$ | $R_5$ | $R_6$ | W | W' or W'' | X | Y | Z |
|---|---|---|---|---|---|---|---|---|---|---|---|---|---|---|
| Q-1 | 1 | H | H | H | — | — | — | — | — | O | — | $CH_3$ | $CH_3$ | CH |
| Q-1 | 1 | H | H | H | — | — | — | — | — | O | — | $CH_3$ | $OCH_3$ | CH |
| Q-1 | 1 | H | H | H | — | — | — | — | — | O | — | $OCH_3$ | $OCH_3$ | CH |
| Q-1 | 1 | H | H | H | — | — | — | — | — | O | — | $OCH_3$ | CH | N |
| Q-1 | 1 | H | H | H | — | — | — | — | — | O | — | $OCH_3$ | $OCH_3$ | N |
| Q-1 | 1 | H | H | H | — | — | — | — | — | O | — | $OCH_3$ | Cl | CH |
| Q-1 | 1 | H | H | H | — | — | — | — | — | S | — | $OCH_3$ | $OCH_3$ | CH |
| Q-1 | 2 | H | H | H | — | — | — | — | — | O | — | $CH_3$ | $CH_3$ | CH |
| Q-1 | 2 | H | H | H | — | — | — | — | — | O | — | $CH_3$ | $OCH_3$ | CH |
| Q-1 | 2 | H | H | H | — | — | — | — | — | O | — | $OCH_3$ | $OCH_3$ | CH |
| Q-1 | 2 | H | H | H | — | — | — | — | — | O | — | $CH_3$ | $OCH_3$ | N |
| Q-1 | 2 | H | H | H | — | — | — | — | — | O | — | $OCH_3$ | $OCH_3$ | N |
| Q-1 | 2 | H | H | H | — | — | — | — | — | O | — | $OCH_3$ | Cl | CH |
| Q-1 | 2 | H | H | H | — | — | — | — | — | S | — | $OCH_3$ | $OCH_3$ | CH |
| Q-7 | 1 | H | — | — | H | — | H | H | H | O | — | $CH_3$ | $CH_3$ | CH |
| Q-7 | 1 | H | — | — | H | — | H | H | H | O | — | $CH_3$ | $OCH_3$ | CH |
| Q-7 | 1 | H | — | — | H | — | H | H | H | O | — | $OCH_3$ | $OCH_3$ | CH |
| Q-7 | 1 | H | — | — | H | — | H | H | H | O | — | $CH_3$ | $OCH_3$ | N |
| Q-7 | 1 | H | — | — | H | — | H | H | H | O | — | $OCH_3$ | $OCH_3$ | N |
| Q-7 | 1 | H | — | — | H | — | H | H | H | O | — | $OCH_3$ | Cl | CH |
| Q-7 | 1 | H | — | — | H | — | H | H | H | S | — | $OCH_3$ | $OCH_3$ | CH |
| Q-7 | 2 | H | — | — | H | — | H | H | H | O | — | $CH_3$ | $CH_3$ | CH |
| Q-7 | 2 | H | — | — | H | — | H | H | H | O | — | $OCH_3$ | $OCH_3$ | CH |
| Q-7 | 2 | H | — | — | H | — | H | H | H | O | — | $OCH_3$ | $OCH_3$ | CH |
| Q-7 | 2 | H | — | — | H | — | H | H | H | O | — | $OCH_3$ | CH | N |
| Q-7 | 2 | H | — | — | H | — | H | H | H | O | — | $OCH_3$ | $OCH_3$ | N |
| Q-7 | 2 | H | — | — | H | — | H | H | H | O | — | $OCH_3$ | Cl | CH |
| Q-7 | 2 | H | — | — | H | — | H | H | H | S | — | $OCH_3$ | $OCH_3$ | CH |
| Q-11 | 1 | H | — | — | H | — | H | — | — | O | O | $CH_3$ | $CH_3$ | CH |
| Q-11 | 1 | H | — | — | H | — | H | — | — | O | O | $CH_3$ | $OCH_3$ | CH |
| Q-11 | 1 | H | — | — | H | — | H | — | — | O | O | $OCH_3$ | $OCH_3$ | CH |
| Q-11 | 1 | H | — | — | H | — | H | — | — | O | O | $CH_3$ | $OCH_3$ | N |
| Q-11 | 1 | H | — | — | H | — | H | — | — | O | O | $OCH_3$ | $OCH_3$ | N |
| Q-11 | 1 | H | — | — | H | — | H | — | — | O | O | $OCH_3$ | Cl | CH |
| Q-11 | 1 | H | — | — | H | — | H | — | — | S | O | $OCH_3$ | $OCH_3$ | CH |
| Q-11 | 2 | H | — | — | H | — | H | — | — | O | O | $CH_3$ | $CH_3$ | CH |
| Q-11 | 2 | H | — | — | H | — | H | — | — | O | O | $CH_3$ | $OCH_3$ | CH |

TABLE 15-continued

General Structure 9

| Q | n | R | $R_1$ | $R_2$ | $R_3$ | $R_{3'}$ | $R_4$ | $R_5$ | $R_6$ | W | W' or W'' | X | Y | Z |
|---|---|---|---|---|---|---|---|---|---|---|---|---|---|---|
| Q-11 | 2 | H | — | — | H | — | H | — | — | O | O | $OCH_3$ | $OCH_3$ | CH |
| Q-11 | 2 | H | — | — | H | — | H | — | — | O | O | $OCH_3$ | CH | N |
| Q-11 | 2 | H | — | — | H | — | H | — | — | O | O | $OCH_3$ | $OCH_3$ | N |
| Q-11 | 2 | H | — | — | H | — | H | — | — | O | O | $OCH_3$ | Cl | CH |
| Q-11 | 2 | H | — | — | H | — | H | — | — | S | O | $OCH_3$ | $OCH_3$ | CH |
| Q-15 | 1 | H | — | — | — | $CH_3$ | H | — | — | O | O | $CH_3$ | $CH_3$ | CH |
| Q-15 | 1 | H | — | — | — | $CH_3$ | H | — | — | O | O | $CH_3$ | $OCH_3$ | CH |
| Q-15 | 1 | H | — | — | — | $CH_3$ | H | — | — | O | O | $OCH_3$ | $OCH_3$ | CH |
| Q-15 | 1 | H | — | — | — | $CH_3$ | H | — | — | O | O | $CH_3$ | $OCH_3$ | N |
| Q-15 | 1 | H | — | — | — | $CH_3$ | H | — | — | O | O | $OCH_3$ | $OCH_3$ | N |
| Q-15 | 1 | H | — | — | — | $CH_3$ | H | — | — | O | O | $OCH_3$ | Cl | CH |
| Q-15 | 1 | H | — | — | — | $CH_3$ | H | — | — | O | S | $OCH_3$ | $OCH_3$ | CH |
| Q-15 | 2 | H | — | — | — | $CH_3$ | H | — | — | O | O | $CH_3$ | $CH_3$ | CH |
| Q-15 | 2 | H | — | — | — | $CH_3$ | H | — | — | O | O | $OCH_3$ | $CH_3$ | CH |
| Q-15 | 2 | H | — | — | — | $CH_3$ | H | — | — | O | O | $OCH_3$ | $OCH_3$ | CH |
| Q-15 | 2 | H | — | — | — | $CH_3$ | H | — | — | O | O | $OCH_3$ | $CH_3$ | N |
| Q-15 | 2 | H | — | — | — | $CH_3$ | H | — | — | O | O | $OCH_3$ | $OCH_3$ | N |
| Q-15 | 2 | H | — | — | — | $CH_3$ | H | — | — | O | O | $OCH_3$ | Cl | CH |
| Q-15 | 2 | H | — | — | — | $CH_3$ | H | — | — | S | O | $OCH_3$ | $OCH_3$ | CH |
| Q-15 | 1 | H | — | — | — | $CH_3$ | H | — | — | O | S | $CH_3$ | $CH_3$ | CH |
| Q-15 | 1 | H | — | — | — | $CH_3$ | H | — | — | O | S | $CH_3$ | $OCH_3$ | CH |
| Q-15 | 1 | H | — | — | — | $CH_3$ | H | — | — | O | S | $OCH_3$ | $OCH_3$ | CH |
| Q-15 | 1 | H | — | — | — | $CH_3$ | H | — | — | O | S | $CH_3$ | $OCH_3$ | N |
| Q-15 | 1 | H | — | — | — | $CH_3$ | H | — | — | O | S | $OCH_3$ | $OCH_3$ | N |
| Q-15 | 1 | H | — | — | — | $CH_3$ | H | — | — | O | S | $OCH_3$ | Cl | CH |
| Q-15 | 1 | H | — | — | — | $CH_3$ | H | — | — | S | S | $OCH_3$ | $OCH_3$ | CH |
| Q-15 | 2 | H | — | — | — | $CH_3$ | H | — | — | O | S | $CH_3$ | $CH_3$ | CH |
| Q-15 | 2 | H | — | — | — | $CH_3$ | H | — | — | O | S | $CH_3$ | $OCH_3$ | CH |
| Q-15 | 2 | H | — | — | — | $CH_3$ | H | — | — | O | S | $OCH_3$ | $OCH_3$ | CH |
| Q-15 | 2 | H | — | — | — | $CH_3$ | H | — | — | O | S | $CH_3$ | $OCH_3$ | N |
| Q-15 | 2 | H | — | — | — | $CH_3$ | H | — | — | O | S | $OCH_3$ | $OCH_3$ | N |
| Q-15 | 2 | H | — | — | — | $CH_3$ | H | — | — | O | S | $OCH_3$ | Cl | CH |
| Q-15 | 2 | H | — | — | — | $CH_3$ | H | — | — | S | S | $OCH_3$ | $OCH_3$ | CH |
| Q-20 | 1 | H | — | — | — | $SCH_3$ | H | — | — | O | O | $CH_3$ | $CH_3$ | CH |
| Q-20 | 1 | H | — | — | — | $SCH_3$ | H | — | — | O | O | $CH_3$ | $OCH_3$ | CH |
| Q-20 | 1 | H | — | — | — | $SCH_3$ | H | — | — | O | O | $OCH_3$ | $OCH_3$ | CH |
| Q-20 | 1 | H | — | — | — | $SCH_3$ | H | — | — | O | O | $CH_3$ | $OCH_3$ | N |
| Q-20 | 1 | H | — | — | — | $SCH_3$ | H | — | — | O | O | $OCH_3$ | $OCH_3$ | N |
| Q-20 | 1 | H | — | — | — | $SCH_3$ | H | — | — | O | O | $OCH_3$ | Cl | CH |
| Q-20 | 1 | H | — | — | — | $SCH_3$ | H | — | — | S | O | $OCH_3$ | $OCH_3$ | CH |
| Q-20 | 2 | H | — | — | — | $SCH_3$ | H | — | — | O | O | $CH_3$ | $CH_3$ | CH |
| Q-20 | 2 | H | — | — | — | $SCH_3$ | H | — | — | O | O | $CH_3$ | $OCH_3$ | CH |
| Q-20 | 2 | H | — | — | — | $SCH_3$ | H | — | — | O | O | $OCH_3$ | $OCH_3$ | CH |
| Q-20 | 2 | H | — | — | — | $SCH_3$ | H | — | — | O | O | $CH_3$ | $OCH_3$ | N |
| Q-20 | 2 | H | — | — | — | $SCH_3$ | H | — | — | O | O | $OCH_3$ | $OCH_3$ | N |
| Q-20 | 2 | H | — | — | — | $SCH_3$ | H | — | — | O | O | $OCH_3$ | Cl | CH |
| Q-20 | 2 | H | — | — | — | $SCH_3$ | H | — | — | S | O | $OCH_3$ | $OCH_3$ | CH |
| Q-28 | 1 | H | — | — | — | Cl | H | — | — | O | — | $CH_3$ | $CH_3$ | CH |
| Q-28 | 1 | H | — | — | — | Cl | H | — | — | O | — | $CH_3$ | $OCH_3$ | CH |
| Q-28 | 1 | H | — | — | — | Cl | H | — | — | O | — | $OCH_3$ | $OCH_3$ | CH |
| Q-28 | 1 | H | — | — | — | Cl | H | — | — | O | — | $OCH_3$ | CH | N |
| Q-28 | 1 | H | — | — | — | Cl | H | — | — | O | — | $OCH_3$ | $OCH_3$ | N |
| Q-28 | 1 | H | — | — | — | Cl | H | — | — | O | — | $OCH_3$ | Cl | CH |
| Q-28 | 1 | H | — | — | — | Cl | H | — | — | S | — | $OCH_3$ | $OCH_3$ | CH |
| Q-28 | 2 | H | — | — | — | Cl | H | — | — | O | — | $CH_3$ | $CH_3$ | CH |
| Q-28 | 2 | H | — | — | — | Cl | H | — | — | O | — | $CH_3$ | $OCH_3$ | CH |
| Q-28 | 2 | H | — | — | — | Cl | H | — | — | O | — | $OCH_3$ | $OCH_3$ | CH |
| Q-28 | 2 | H | — | — | — | Cl | H | — | — | O | — | $OCH_3$ | CH | N |
| Q-28 | 2 | H | — | — | — | Cl | H | — | — | O | — | $OCH_3$ | $OCH_3$ | N |
| Q-28 | 2 | H | — | — | — | Cl | H | — | — | O | — | $OCH_3$ | Cl | CH |
| Q-28 | 2 | H | — | — | — | Cl | H | — | — | S | — | $OCH_3$ | $OCH_3$ | CH |
| Q-1 | 1 | $CH_3$ | H | H | — | — | — | — | — | O | — | $OCH_3$ | $OCH_3$ | CH |
| Q-1 | 2 | $CH_3$ | H | H | — | — | — | — | — | O | — | $OCH_3$ | $OCH_3$ | CH |
| Q-7 | 1 | $CH_3$ | — | — | H | — | H | H | H | O | — | $OCH_3$ | $OCH_3$ | CH |
| Q-7 | 2 | $CH_3$ | — | — | H | — | H | H | H | O | — | $OCH_3$ | $OCH_3$ | CH |
| Q-11 | 1 | $CH_3$ | — | — | H | — | H | — | — | O | O | $OCH_3$ | $OCH_3$ | CH |
| Q-11 | 2 | $CH_3$ | — | — | H | — | H | — | — | O | O | $OCH_3$ | $OCH_3$ | CH |
| Q-15 | 1 | $CH_3$ | — | — | — | $CH_3$ | H | — | — | O | O | $OCH_3$ | $OCH_3$ | CH |
| Q-15 | 2 | $CH_3$ | — | — | — | $CH_3$ | H | — | — | O | O | $OCH_3$ | $OCH_3$ | CH |
| Q-15 | 1 | $CH_3$ | — | — | — | $CH_3$ | H | — | — | O | S | $OCH_3$ | $OCH_3$ | CH |
| Q-15 | 2 | $CH_3$ | — | — | — | $CH_3$ | H | — | — | O | S | $OCH_3$ | $OCH_3$ | CH |
| Q-20 | 1 | $CH_3$ | — | — | — | $SCH_3$ | H | — | — | O | O | $OCH_3$ | $OCH_3$ | CH |
| Q-20 | 2 | $CH_3$ | — | — | — | $SCH_3$ | H | — | — | O | O | $OCH_3$ | $OCH_3$ | CH |
| Q-28 | 1 | $CH_3$ | — | — | — | Cl | H | — | — | O | — | $OCH_3$ | $OCH_3$ | CH |
| Q-28 | 2 | $CH_3$ | — | — | — | Cl | H | — | — | O | — | $OCH_3$ | $OCH_3$ | CH |

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 16

| | Active | Weight Percent* | |
|---|---|---|---|
| | Ingredient | Diluent(s) | Surfactant(s) |
| Wettable Powders | 20-90 | 0-74 | 1-10 |
| Oil Suspensions, Emulsion, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient Plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc. New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

In the following examples, all parts are by weight unless otherwise indicated.

EXAMPLE 7

| Wettable Powder | |
|---|---|
| N—[(4,6-dimethylpyrimidin-2-yl)aminocarbonyl]-3-(isoxazol-3-yl)-2-thiophenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
|---|---|
| 3-(isoxazol-3-yl)-N—[(4-methoxy-6-methylpyrimidin-2-yl)-aminocarbonyl]-2-thiophenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example 8 | 5% |
| attapulgite granules (U.S.S. 20-40 mesh; 0.84-0.42 mm) | 95% |

A slurry of wettable powder containing 25% solids is sprayed on the surface of attapulgite granules in a double-cone blender. The granules are dried and packaged.

EXAMPLE 10

| Extruded Pellet | |
|---|---|
| N—[(4,6-dimethoxypyrimidin-2-yl)aminocarbonyl]-3-(isoxazol-3-yl)-2-thiophenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Low Strength Granule | |
|---|---|
| N—[(4,6-dimethylpyrimidin-2-yl)aminocarbonyl]- | 0.1% |

-continued

| Low Strength Granule | |
|---|---|
| 3-(isoxazol-3-yl)-2-thiophenesulfonamide attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 12

| Granule | |
|---|---|
| 3-(isoxazol-3-yl)-N—[(4-methoxy-6-methyl-pyrimidin-2-yl)-aminocarbonyl]-2-thiophenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 13

| Low Strength Granule | |
|---|---|
| N—[(4,6-dimethoxypyrimidin-2-yl)aminocarbonyl]-3-(isoxazol-3-yl)-2-thiophenesulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| N—[(4,6-dimethylpyrimidin-2-yl)aminocarbonyl]-3-(isoxazol-3-yl)-2-thiophenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| 3-(isoxazol-3-yl)-N—[(4-methoxy-6-methyl-pyrimidin-2-yl)-aminocarbonyl]-2-thiophenesulfonamide, sodium salt | 5% |
| water | 95% |

The salt is added directly to the water with stirring to produce the solution, which may then be packaged for use.

EXAMPLE 16

| High Strength Concentrate | |
|---|---|
| N—[(4,6-dimethoxypyrimidin-2-yl)aminocarbonyl]-3-(isoxazol-3-yl)-2-thiophenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

17

| Wettable Powder | |
|---|---|
| N—[(4,6-dimethylpyrimidin-2-yl)aminocarbonyl]-3-(isoxazol-3-yl)-2-thiophenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 18

| Wettable Powder | |
|---|---|
| 3-(isoxazol-3-yl)-N—[(4-methoxy-6-methyl-pyrimidin-2-yl)-aminocarbonyl]-2-thiophenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

| Oil Suspension | |
|---|---|
| N—[(4,6-dimethoxypyrimidin-2-yl)aminocarbonyl]-3-(isoxazol-3-yl)-2-thiophenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 20

| Dust | |
|---|---|
| N—[(4,6-dimethylpyrimidin-2-yl)aminocarbonyl]-3-(isoxazol-3-yl)-2-thiophenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 21

| Oil Suspension | |
|---|---|
| 3-(isoxazol-3-yl)-N—[(4-methoxy-6-methylpyrimidin-2-yl)-aminocarbonyl]-2-thiophenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 22

| Wettable Powder | |
|---|---|
| N—[(4,6-dimethoxypyrimidin-2-yl)aminocarbonyl]-3-(isoxazol-3-yl)-2-thiophenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 23

| Wettable Powder | |
|---|---|
| N—[(4-chloro-6-methoxypyrimidin-2-yl)aminocarbonyl]-3-(1H-pyrrol-1-yl)-2-thiophenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 24

| Wettable Powder | |
|---|---|
| N—[(4,6-dimethoxy-1,3,5-triazin-2-yl)aminocarbonyl]-3-(1H-pyrrol-1-yl)-2-thiophenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 25

| Extruded Pellet | |
|---|---|
| N—[(4,6-dimethyl-1,3,5-triazin-2-yl)aminocarbonyl]-3-(1H-pyrrol-1-yl)-2-thiophenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 26

| Low Strength Granule | |
|---|---|
| N—[(4,6-dimethylpyrimidin-2-yl)aminocarbonyl]-3-(isoxazol-3-yl)-2-thiophenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 27

| Granule | |
|---|---|
| N—[(4,6-dimethoxypyrimidin-2-yl)aminocarbonyl]-3-(1H-pyrrol-1-yl)-2-thiophenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 28

| Low Strength Granule | |
|---|---|
| N—[(4-methoxy-6-methyl-1,3,5-triazin-2-yl)aminocarbonyl]-3-(1H-pyrrol-1-yl)-2-thiophenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 29

| Aqueous Suspension | |
|---|---|
| N—[(4-methoxy-6-methylpyrimidin-2-yl)aminocarbonyl]-3-(1H-pyrrol-1-yl)-2-thiophenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 30

| Solution | |
|---|---|
| 3-(5-chloro-1H-1,2,4-triazol-1-yl)-N—[(4,6-dimethoxypyrimidin-2-yl)aminocarbonyl]-2-thiophenesulfonamide, sodium salt | 5% |
| water | 95% |

The salt is added directly to the water with stirring to produce the solution, which may then be packaged for use.

Utility

Test results indicate that the compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, especially wheat, barley and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicide, examples of which are those of the triazine, triazole, uracil, urea, amide, diphenylether, carbamate and bipyridylium types. The compounds may also be used in combination with mefluidide.

The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, cotton, sugar beet, rice, wheat and nutsedge tubers (*Cyperus rotundus*) were planted in a growth medium and treated pre-emergence with the chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings are based on a numerical scale extending from 0=no injury, to 10=complete kill. The accompanying descriptive symbols have the following meanings:

C=chlorosis or necrosis;
G=growth retardation;
H=formative effects;
U=unusual pigmentation.

The compounds are highly active herbicides. Wheat exhibits tolerance.

Compounds

Compound 1

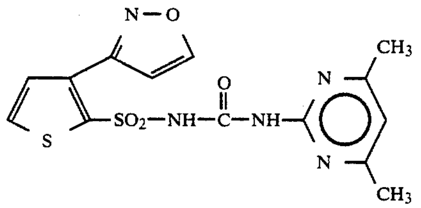

Compound 2

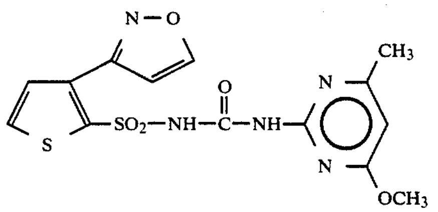

-continued
Compounds
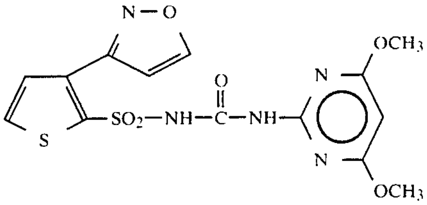
Compound 3
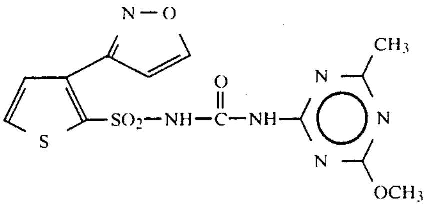
Compound 4
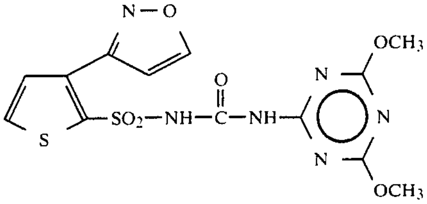
Compound 5
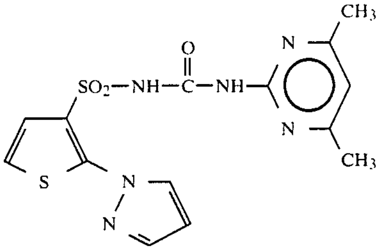
Compound 6
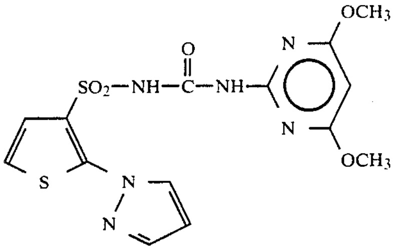
Compound 7
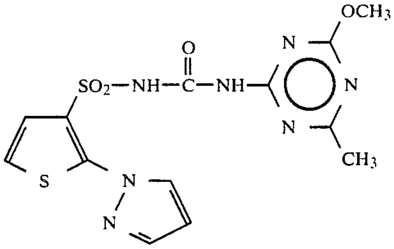
Compound 8
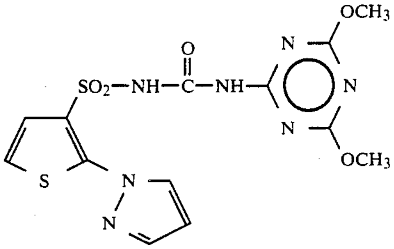
Compound 9
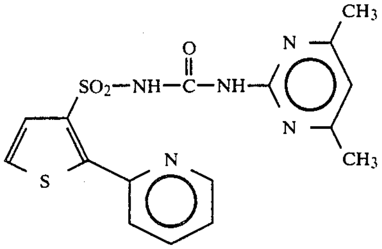
Compound 10
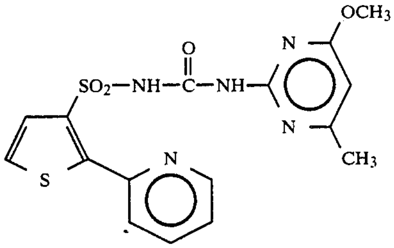
Compound 11
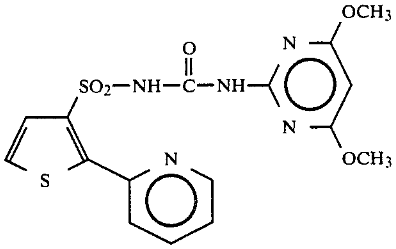
Compound 12
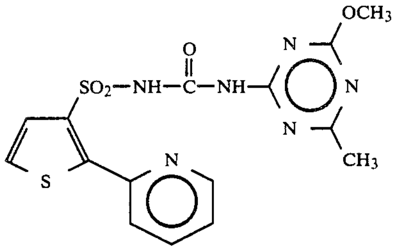
Compound 13
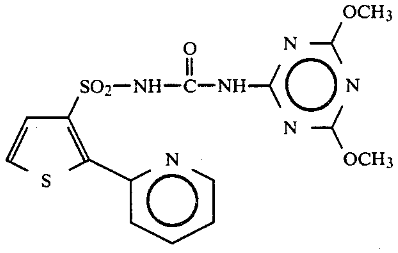
Compound 14

-continued
Compounds
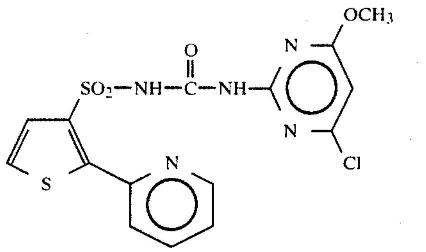
Compound 15
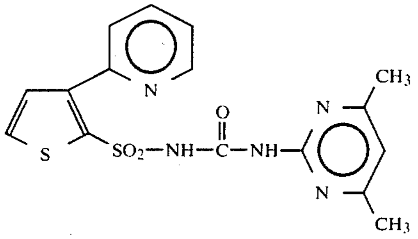
Compound 16
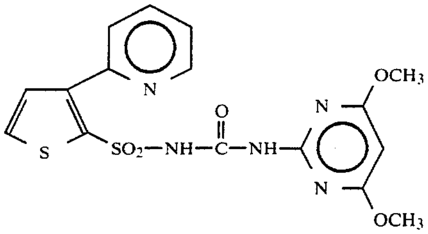
Compound 17
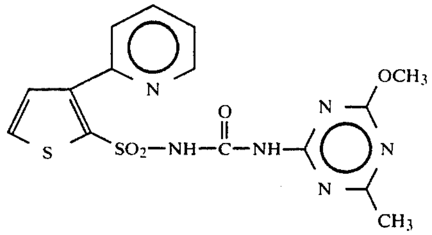
Compound 18
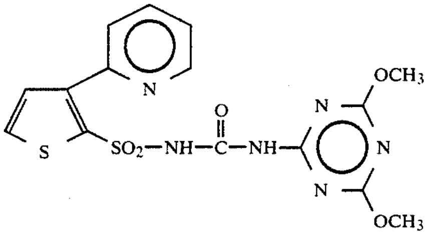
Compound 19
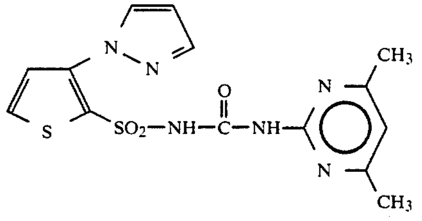
Compound 20
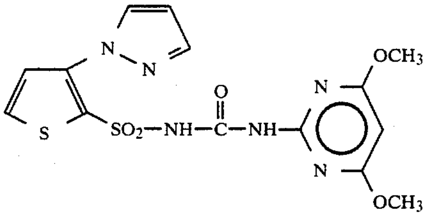
Compound 21
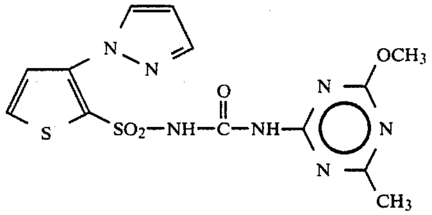
Compound 22
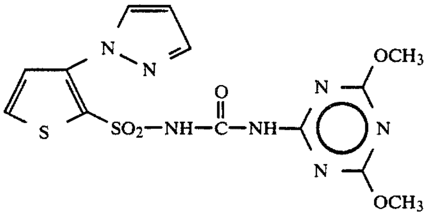
Compound 23
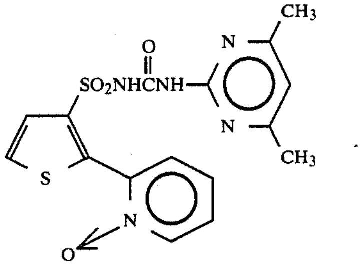
Compound 24
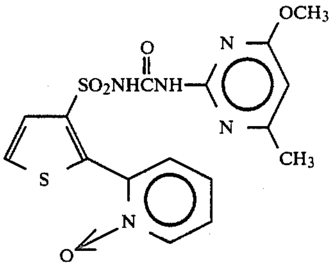
Compound 25
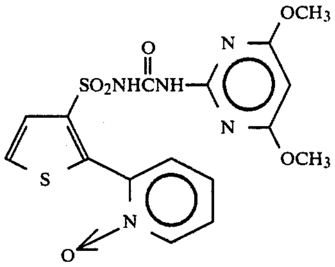
Compound 26

-continued
Compounds
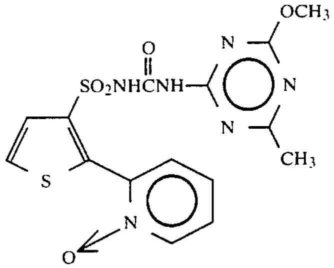
Compound 27
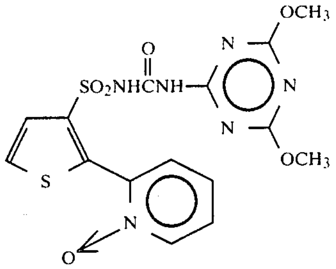
Compound 28
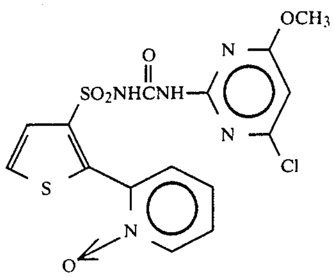
Compound 29
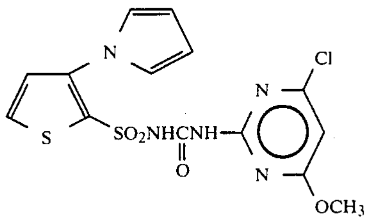
Compound 30
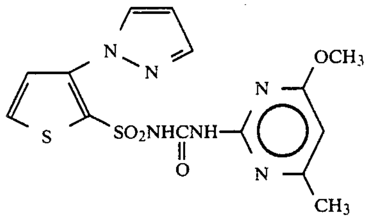
Compound 31
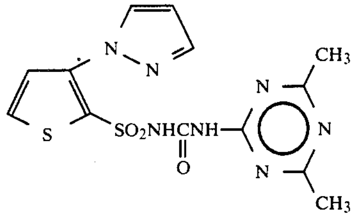
Compound 32
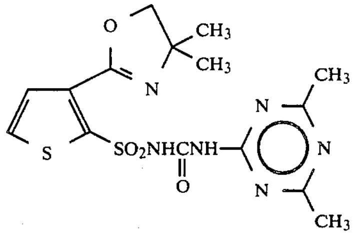
Compound 33
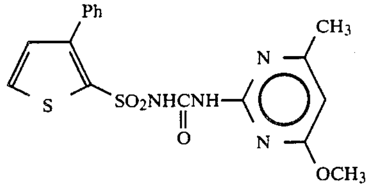
Compound 34
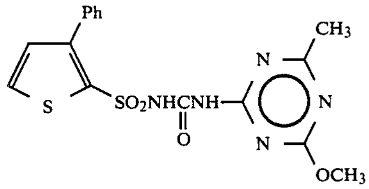
Compound 35
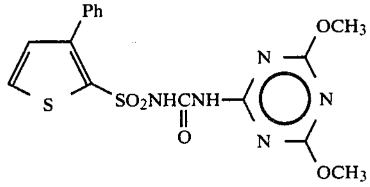
Compound 36
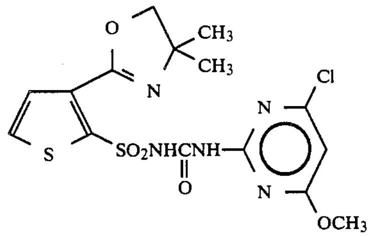
Compound 37
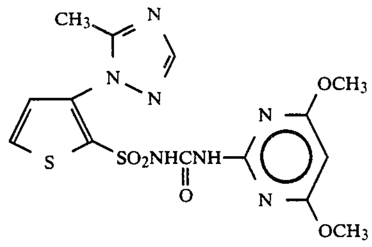
Compound 38

-continued
Compounds
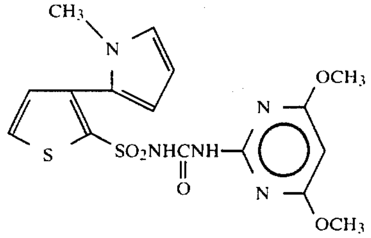
Compound 39
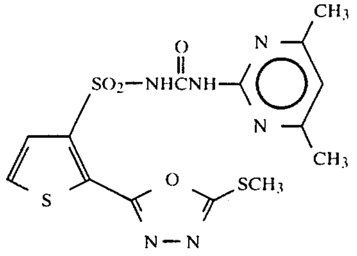
Compound 40
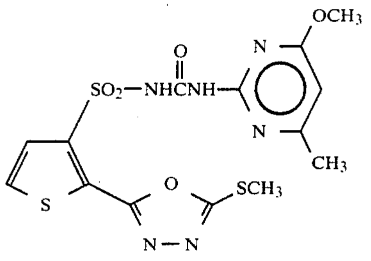
Compound 41
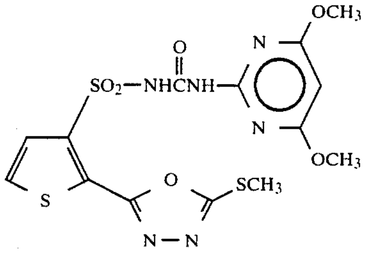
Compound 42
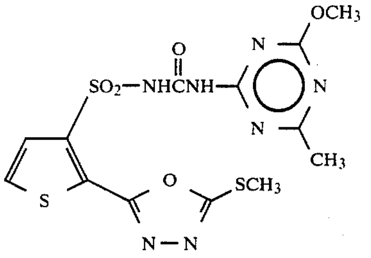
Compound 43
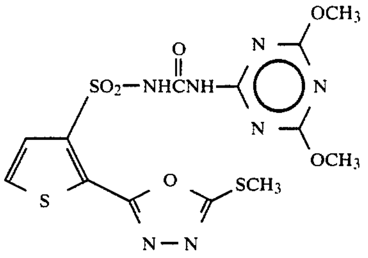
Compound 44
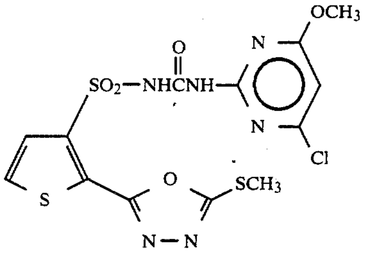
Compound 45
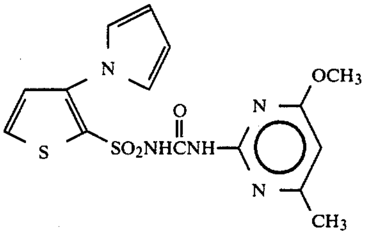
Compound 46
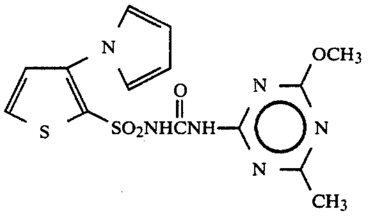
Compound 47
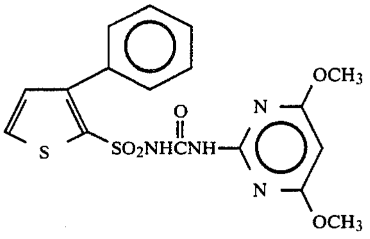
Compound 48
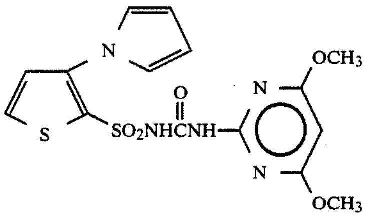
Compound 49
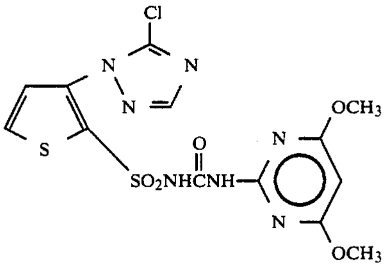
Compound 50

-continued
Compounds
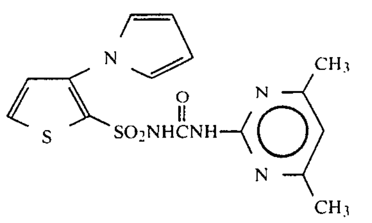
Compound 51
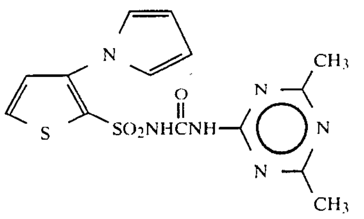
Compound 52
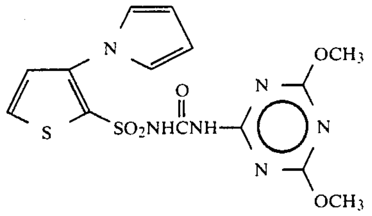
Compound 53
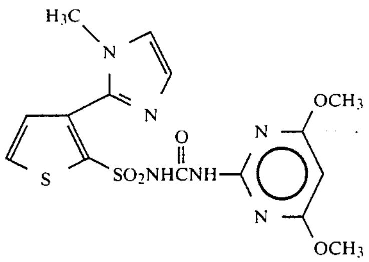
Compound 54
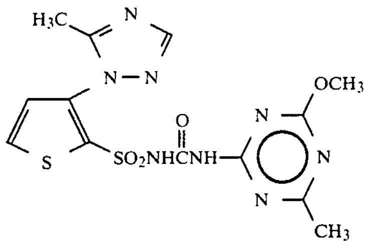
Compound 55
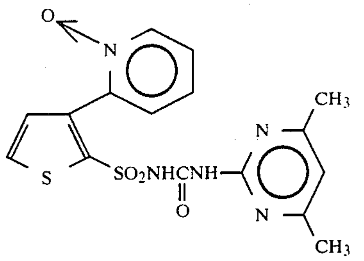
Compound 56
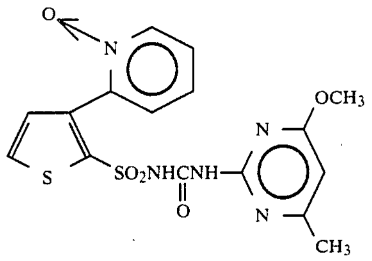
Compound 57
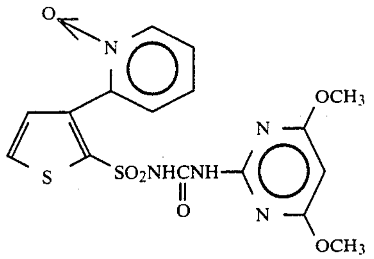
Compound 58
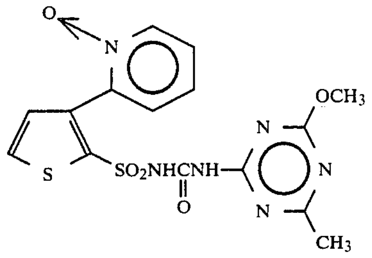
Compound 59
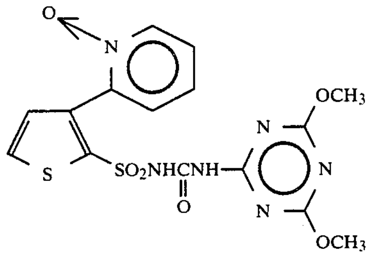
Compound 60
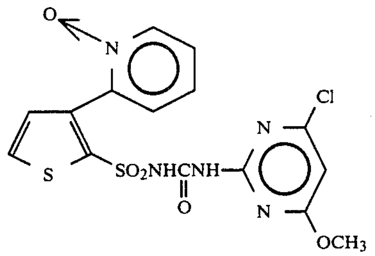
Compound 61
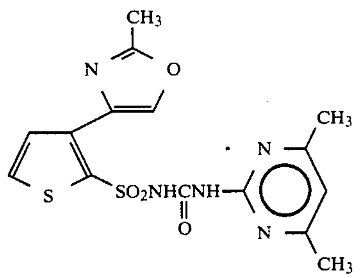
Compound 62

-continued
Compounds
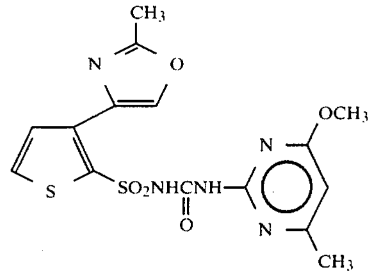
Compound 63
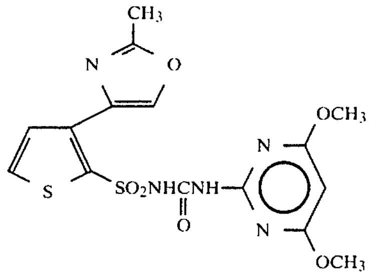
Compound 64
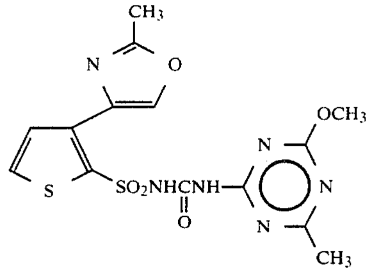
Compound 65
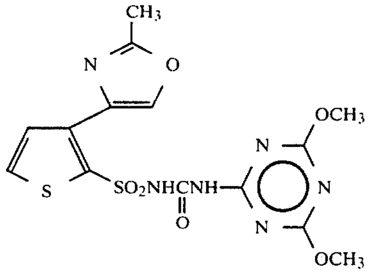
Compound 66
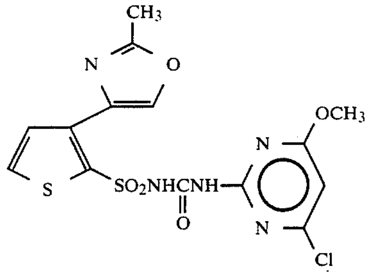
Compound 67
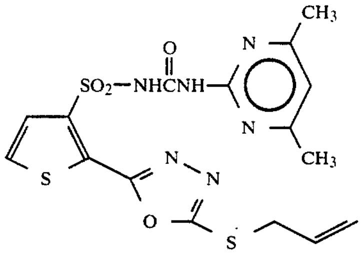
Compound 68
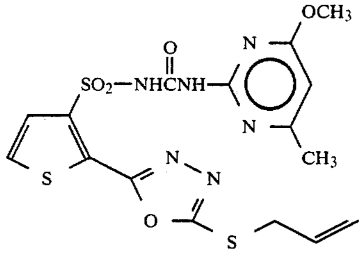
Compound 69
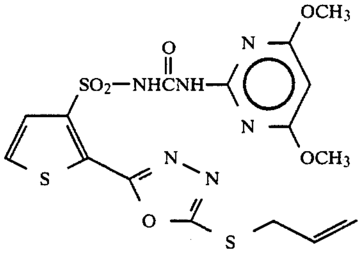
Compound 70
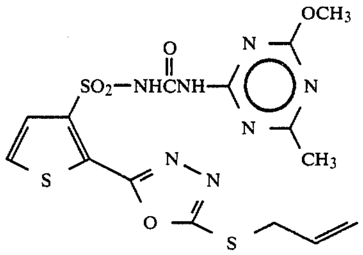
Compound 71
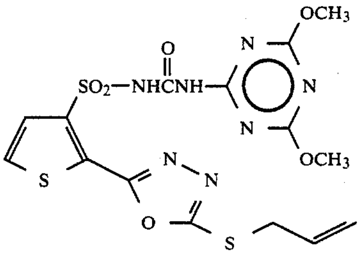
Compound 72
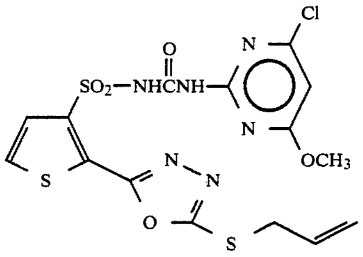
Compound 73
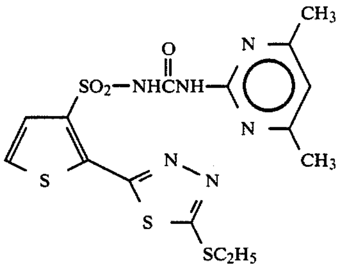
Compound 74

-continued
Compounds
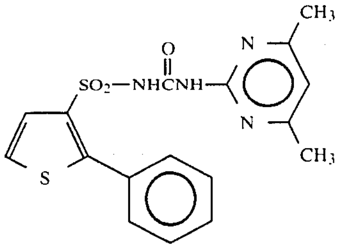
Compound 75
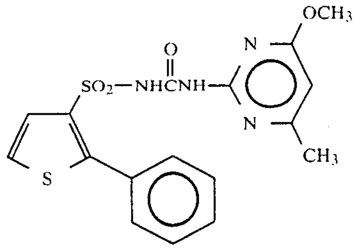
Compound 76
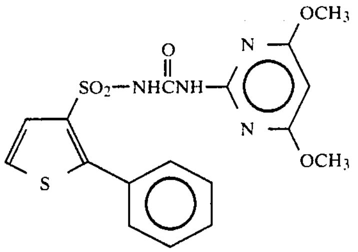
Compound 77
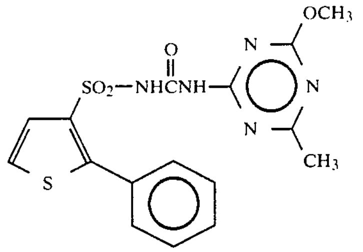
Compound 78
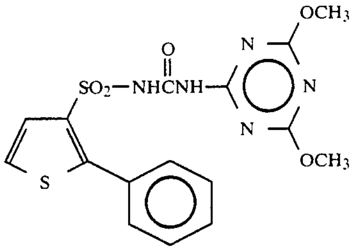
Compound 79
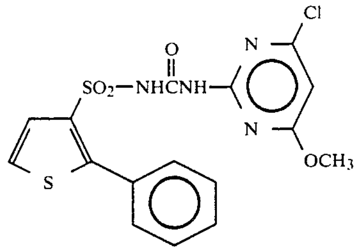
Compound 80
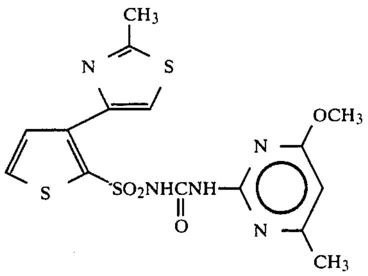
Compound 81
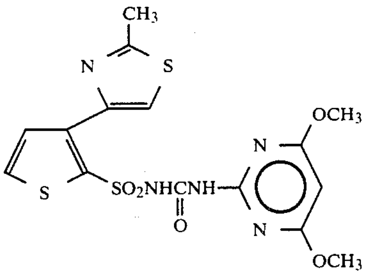
Compound 82
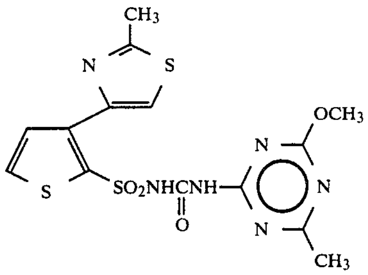
Compound 83
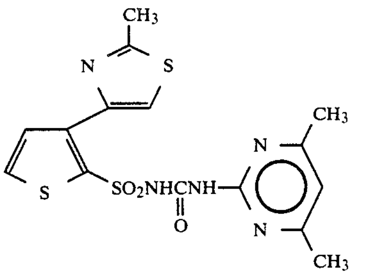
Compound 84
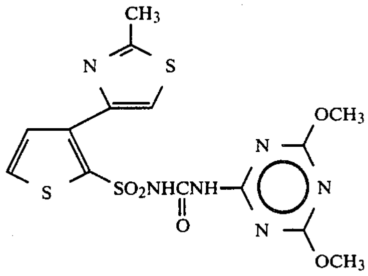
Compound 85
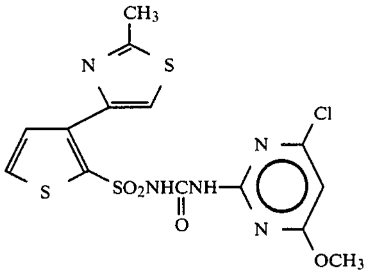
Compound 86

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 4 2 | Cmpd. 5 2 | Cmpd. 6 0.05 | Cmpd. 7 0.05 | Cmpd. 8 0.05 | Cmpd. 9 0.05 | Cmpd. 10 0.05 | Cmpd. 11 0.05 | Cmpd. 12 0.05 | Cmpd. 13 0.05 | Cmpd. 14 0.05 |
|---|---|---|---|---|---|---|---|---|---|---|---|---|---|---|---|---|
| | | | | | | | | POST-EMERGENCE | | | | | | | | |
| Morningglory | 2C,5G | 4C,9G | 10C | 0 | 0 | 2C,5G | 1C | 0 | 1C,3G | 3C,8H | 5C,8H | 2C,5G | 10C | 10C | 9C | 9C |
| Cocklebur | 4C,9G | 9C | 10C | 0 | 0 | 1C | 1C | 2C,3H | 6G | 4C,9G | 2G | 2C,6H | 2C,7G | 4C,9G | 9C | 3C,8G |
| Sicklepod | 2C,8H | 9C | 9C | 0 | 0 | 2C,6G | 1C | 1C | 5C,9G | 3C,3H | 4C,5G | 3C,3H | 2C,7G | 4C,8G | 4C,7G | 4C,8G |
| Nutsedge | 9C | 9C | 10C | 0 | 0 | 0 | 0 | 0 | 9G | 0 | 0 | 7G | 8G | 10C | 3G | 3G |
| Crabgrass | 0 | 2C,6G | 2C,6G | 0 | 0 | 0 | 0 | 0 | 0 | 0 | 0 | 0 | 1H | 0 | 0 | 0 |
| Barnyardgrass | 10C | 9C | 9C | 0 | 0 | 0 | 0 | 0 | 4G | 0 | 0 | 3G | 8H | 3C,8H | 0 | 0 |
| Wild Oats | 2G | 2C,6G | 0 | 0 | 0 | 0 | 0 | 0 | 0 | 0 | 0 | 2C,3G | 0 | 0 | 0 | 0 |
| Wheat | 0 | 1C | 0 | 0 | 0 | 0 | 0 | 0 | 0 | 0 | 0 | 3G | 0 | 0 | 0 | 0 |
| Corn | 5U,9G | 9C | 5C,9G | 0 | 0 | 0 | 0 | 0 | 3G | 0 | 0 | 1C,4H | 3C,9H | 2C,6H | 2G | 3G |
| Soybean | 5C,9G | 9C | 9C | 3G | 1H | 2C,7G | 0 | 1C,4H | 5C,9G | 3C,8H | 3C,7H | 3C,9G | 4C,9G | 4C,9G | 4C,9G | 4C,9G |
| Rice | 2C,8G | 3C,9G | 5G | 0 | 0 | 0 | 0 | 2C,4G | 3G | 4G | 2G | 6G | 2C,5G | 1C,4G | 0 | 0 |
| Sorghum | 9C | 3C,9H | 4C,9G | 0 | 0 | 0 | 0 | 2C,4G | 2C,5G | 3G | 0 | 3C,7G | 5C,9H | 3C,7H | 0 | 0 |
| Sugar beet | 5C,9G | 9C | 9C | 0 | 0 | 5C,9G | 3C,5G | 3C,8H | 9C | 9C | 9C | 2C,7G | 3C,8G | 9C | 9C | 10C |
| Cotton | 4C,9G | 6C,9G | 9C | 0 | 0 | 2C,9G | 1C | 2C,8H | 9C | 4C,9H | 4C,8H | 3C,9H | 9C | 9C | 5C,9G | 4C,9H |
| Bush bean | | | | | | — | — | — | — | — | — | — | — | — | — | — |
| Cheatgrass | | | | | | | | | | | | | | | | |
| Velvetleaf | | | | | | | | | | | | | | | | |
| | | | | | | | | PRE-EMERGENCE | | | | | | | | |
| Morningglory | 2G | 9C | 9G | 0 | 0 | 5G | 0 | 2G | 7G | 8G | 9G | 5G | 9G | 9G | 6G | 9G |
| Cocklebur | 9G | 9H | 9H | 0 | 0 | 5G | 0 | — | 7G | 5G | 5H | — | 8H | 8H | 4G | 8H |
| Sicklepod | 8G | 9C | 9C | 0 | 0 | 2C | 0 | 2C | 7G | 3C,8G | 5C,9G | 2C | 7G | 8G | 2C,3H | 8G |
| Nutsedge | 10E | 10E | 10E | 0 | 0 | 0 | 0 | 0 | 10E | 0 | 5G | 0 | 0 | 2G | 0 | 0 |
| Crabgrass | 0 | 4G | 4G | 0 | 0 | 0 | 0 | 0 | 2G | 0 | 0 | 0 | 0 | 0 | 0 | 0 |
| Barnyardgrass | 5G | 3C,9H | 3C,9H | 0 | 0 | 0 | 0 | 0 | 2C,4G | 0 | 0 | 0 | 2C,8H | 2C,5G | 0 | 0 |
| Wild Oats | 2C,7G | 3C,8G | 2C,7G | 0 | 0 | 0 | 0 | 0 | 2C | 0 | 0 | 0 | 2C,4G | 0 | 0 | 0 |
| Wheat | 5G | 6G | 0 | 0 | 0 | 0 | 0 | 0 | 0 | 0 | 2G | 0 | 0 | 0 | 0 | 0 |
| Corn | 2C,9H | 3C,9H | 2C,9H | 0 | 0 | 5G | 0 | 0 | 4G | 3G | 5G | 2G | 4C,9H | 2C,7G | 4G | 4G |
| Soybean | 3C,6H | 9H | 2C,8H | 0 | 0 | 2C,3G | 0 | 3G | 2C,7H | 3C,5H | 4C,7G | 2C,3H | 8H | 2C,5H | 3C,6G | 2C,6G |
| Rice | 8H | 9G | 8G | 0 | 0 | 1C | 0 | 5G | 2C,5G | 3G | 5G | 0 | 7G | 1C | 0 | 0 |
| Sorghum | 2C,9G | 6C,9H | 2C,9H | 0 | 0 | 2G | 0 | 5G | 3C,7H | 2G | 0 | 2C,4H | 3C,9H | 5G | 0 | 0 |
| Sugar beet | 5C,9G | 10C | 9C | 0 | 0 | 4C,9G | 0 | 3C,6G | 9C | 9C | 5C,9G | 4G | 5C,9G | 8G | 3C,7G | 4C,7G |
| Cotton | 9G | 10C | 9G | 0 | 0 | 2C,5G | 0 | 6G | 9G | 6G | 3C,7H | 6G | 8G | 8G | 2C,7G | 8G |
| Velvetleaf | | | | | | | | | | | | | | | | |
| Cheatgrass | | | | | | | | | | | | | | | | |

| Rate kg/ha | Cmpd. 15 0.05 | Cmpd. 16 0.05 | Cmpd. 17 0.05 | Cmpd. 18 0.05 | Cmpd. 19 0.05 | Cmpd. 20 0.05 | Cmpd. 21 0.05 | Cmpd. 22 0.05 | Cmpd. 23 0.05 | Cmpd. 24 0.05 | Cmpd. 25 0.05 | Cmpd. 26 0.05 | Cmpd. 27 0.05 | Cmpd.28 0.05 | Cmpd. 29 0.05 | Cmpd. 30 0.05 |
|---|---|---|---|---|---|---|---|---|---|---|---|---|---|---|---|---|
| | | | | | | | | POST-EMERGENCE | | | | | | | | |
| Morningglory | 2C,6G | 10C | 10C | 5C,9G | 5C,9G | 10C | 9C | 4C,9G | 10C | 2C,8H | 10C | 4C,9G | 4C,7H | 4C,9G | 1C,2H | 2C,7G |
| Cocklebur | 2C,5G | 5C,9G | 9C | 10C | 9C | 9C | 9C | 9C | 10C | 5G | 5C,9G | 5C,9G | 4C,9H | 4C,8H | 2C,5H | 2C,7H |
| Sicklepod | 1C | 4C,8G | 5C,9G | 5C,9G | 6C,9G | 2C,4G | 9C | 2C | 5C,8H | | | | | | | |
| Nutsedge | 2C,9G | 3C,9G | 9C | 0 | 2C,3G | 2C,8G | 9C | 0 | 0 | 0 | 5G | 3C,9G | 0 | 0 | 0 | 2G |
| Crabgrass | 0 | 0 | 3G | 0 | 0 | 0 | 0 | 0 | 0 | 0 | 5G | 3G | 0 | 0 | 0 | 0 |
| Barnyardgrass | 0 | 4C,9H | 4C,8G | 2H | 0 | 3C,8H | 3H | 3G | 0 | 0 | 3C,8H | 3C,9H | 0 | 0 | 2C,5H | 7H |
| Wild Oats | 0 | 3C,9G | 0 | 0 | 0 | 3C,3G | 0 | 0 | 0 | 0 | 0 | 0 | 0 | 0 | 0 | 0 |
| Wheat | 0 | 0 | 0 | 0 | 0 | 2G | 0 | 0 | 0 | 0 | 0 | 2G | 0 | 0 | 0 | 0 |
| Corn | 0 | 3C,9H | 1C,3H | 0 | 0 | 2C,7H | 2G | 2C,3H | 0 | 0 | 4C,9G | 3C,9H | 0 | 0 | 0 | 0 |
| Soybean | 1C | 5C,9G | 5C,9G | 5C,9G | 5C,9G | 4C,9H | 4C,9G | 4C,9G | 4C,9G | 2C,7G | 4C,9G | 4C,9G | 3C,8H | 3C,8G | 0 | 2H |
| Rice | 0 | 4C,9G | 3G | 0 | 0 | 2C,8G | 0 | 0 | 0 | 2G | 3C,8G | 3C,8G | 0 | 0 | 0 | 5C,9G |

TABLE A-continued

| | | | | | | | | | | | | | | | | |
|---|---|---|---|---|---|---|---|---|---|---|---|---|---|---|---|---|
| Sorghum | 1C | 3C,9H | 2C,7G | 0 | 0 | 3C,9H | 3C,5H | 0 | 0 | 2C | 4C,9H | 3C,8H | 0 | 0 | 1C,2H | 2C,6H |
| Sugar beet | 0 | 3C,8G | 9C | 9C | 9C | 9C | 9C | 9C | 9C | 0 | 9C | 9C | 4C,8H | 4C,9H | 0 | 5C,9H |
| Cotton | 4C,8G | 5C,9H | 9C | 5C,9H | 9C | 9C | 9C | 4C,9H | 4C,9H | 2G | 5C,9H | 5C,9G | 3C,6G | 3C,7G | 0 | 5C,9G |
| Bush bean | — | — | — | — | — | — | — | — | — | | | | | | | |
| Cheatgrass | | | | | | | | | | 0 | 3C,8G | 5G | 0 | 0 | 0 | 0 |
| Velvetleaf | | | | | | | | | | 2C,5H | 9C | 5C,9G | 3C,7H | 0 | 3G | 2G |
| | | | | | | | PRE-EMERGENCE | | | | | | | | | |
| Morningglory | 7G | 8G | 9G | 4C,9G | 9G | 8G | 9G | 8H | 8G | 0 | 9G | 8G | 3C,3H | 0 | 0 | 7G |
| Cocklebur | 0 | 7H | 8H | 7H | 3C,7H | 5H | 8H | 2C | 5H | 0 | 3C,5H | 9H | 0 | 0 | 0 | 4H |
| Sicklepod | 0 | 5G | 7G | 4C,7G | 4C,8G | 5G | 8G | 2C,4G | 5G | | | | | | | |
| Nutsedge | 0 | 0 | 6G | 0 | 0 | 0 | 10E | 0 | 0 | 0 | 0 | 0 | 0 | 0 | 0 | 7G |
| Crabgrass | 0 | 0 | 0 | 0 | 0 | 0 | 0 | 0 | 0 | 0 | 1C | 0 | 0 | 0 | 0 | 0 |
| Barnyardgrass | 0 | 5G | 3C,9H | 0 | 0 | 0 | 2H | 0 | 0 | 0 | 1C | 3H | 0 | 0 | 0 | 0 |
| Wild Oats | 0 | 4G | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 |
| Corn | 0 | 2G | 3G | 0 | 0 | 2C,8H | 7G | 2C,5G | 2C,4G | 0 | 5C,8G | 4C,3G | 0 | 0 | 0 | 2C,7G |
| Soybean | 0 | 2H | 3C,6H | 2C,5G | 3C,6H | 4C,5G | 2C,6H | 4C,5H | 4C,6G | 0 | 4C,7H | 3C,4G | 0 | 2C | 0 | 1H |
| Rice | 0 | 5G | 4G | 0 | 0 | 2C,5G | 5G | 3G | 0 | 0 | 5G | 2C | 2H | 4G | 0 | 2C,4G |
| Sorghum | 0 | 2C,5G | 3C,7H | 0 | 0 | 3C,9H | 5H | 0 | 0 | 0 | 4C,7G | 3C,7G | 2G | 0 | 0 | 3C,6H |
| Sugar beet | 0 | 8G | 5C,9G | 5C,9G | 5C,9G | 5C,9G | 4C,9G | 4C,9G | 4C,9G | 0 | 4C,9G | 4C,8G | 0 | 0 | 0 | 8G |
| Cotton | 6G | 4G | 9G | 5G | 2C,6G | 8G | 9G | 2C,7G | 6G | 0 | 3C,7H | 7G | 0 | 0 | 0 | 9G |
| Velvetleaf | | | | | | | | | | 0 | 3C,6H | 5H | 0 | 0 | 0 | 8G |
| Cheatgrass | | | | | | | | | | 0 | 4G | 0 | 0 | 0 | 0 | 2G |
| Rate kg/ha | Cmpd. 31 0.05 | Cmpd. 32 0.05 | Cmpd. 33 0.05 | Cmpd. 34 0.05 | Cmpd. 35 0.05 | Cmpd. 36 0.05 | Cmpd. 37 0.05 | Cmpd. 38 0.05 | Cmpd. 39 0.05 | Cmpd. 40 0.05 | Cmpd. 41 0.05 | Cmpd. 42 0.05 | Cmpd. 43 0.05 | Cmpd. 44 0.05 | Cmpd. 45 0.05 | Cmpd. 46 0.05 |
| | | | | | | | POST-EMERGENCE | | | | | | | | | |
| Morningglory | 9C | 4C,8G | 0 | 10C | 9C | 9C | 5G | 9C | 4H | 5C,9G | 10C | 9C | 4C,9G | 4C,9G | 2C,4G | 7G |
| Cocklebur | 9C | 4C,9H | 0 | 9C | 10C | 10C | 2C,8G | 10 | 0 | 4C,9G | 9C | 9C | 5C,9G | 5C,9G | 2C,5G | 5C,9H |
| Sicklepod | | | | | | | | | | | | | | | | |
| Nutsedge | 6C,9G | 4G | 0 | 5G | 0 | 2G | 0 | 5C,9G | 0 | 3C,5G | 4C,8G | 5C,9G | 0 | 0 | 0 | 4C,9G,8X |
| Crabgrass | 3G | 0 | 0 | 3G | 0 | 0 | 0 | 4C,5G | 0 | 0 | 2G | 2G | 0 | 0 | 0 | 0 |
| Barnyardgrass | 3C,7G | 2H | 0 | 3C,7H | 0 | 0 | 0 | 9C | 0 | 4G | 4C,9H | 4C,9H | 0 | 0 | 0 | 3C,9H |
| Wild Oats | 0 | 0 | 0 | 0 | 0 | 0 | 0 | 2C,2G | 0 | 0 | 0 | 0 | 0 | 0 | 0 | 2G |
| Wheat | 0 | 0 | 0 | 0 | 0 | 0 | 0 | 8G | 0 | 0 | 0 | 0 | 0 | 0 | 0 | 2G |
| Corn | 3C,8H | 0 | 0 | 2H,5G | 0 | 0 | 0 | 5C,9H | 0 | 1H | 3C,7H | 3H | 0 | 0 | 0 | 3C,9H |
| Soybean | 4C,9G | 3C,7H | 2G | 4C,9G | 5C,9G | 5C,9G | 2G | 5C,9G | 0 | 4H | 4C,8H | 2C,7G | 2G | 0 | 0 | 4C,9G |
| Rice | 5G | 0 | 0 | 4G | 0 | 0 | 0 | 9C | 0 | 8G | 8G | 6G | 0 | 0 | 0 | 9C |
| Sorghum | 3C,9H | 0 | 0 | 2C,5G | 0 | 0 | 0 | 4C,9G | 0 | 2C,8G | 4C,8H | 3C,8H | 0 | 0 | 0 | 3C,9H |
| Sugar beet | 10C | 4C,8H | 2H | 2C,6G | 9C | 9C | 4G | 9C | 2H | 3C,8H | 9C | 9C | 9C | 9C | 2C,3H | 10C |
| Cotton | 9C | 4C,8G | 2G | 9C | 10C | 10C | 5G | 9C | 0 | 4C,9H | 10C | 10C | 3C,9G | 4C,9G | 6G | 10C |
| Bush bean | | | | | | | | | | | | | | | | |
| Cheatgrass | 6G | 0 | 0 | 5G | 0 | 0 | 0 | 9C | 0 | 2C,6G | 3C,5G | 8G | 0 | 0 | 0 | 4C,9G |
| Velvetleaf | 10C | 3C,9G | 0 | 10C | 10C | 3C,7G | 7G | 9C | 0 | 9C | 10C | 10C | 5C,8G | 2C,5G | 3C,8G | 5C,9H |
| | | | | | | | PRE-EMERGENCE | | | | | | | | | |
| Morningglory | 9G | 8G | 0 | 9H | 9G | 9G | 0 | 9C | 0 | 3C | 6G | 7G | 2C,6G | 7H | 5G | 8H |
| Cocklebur | 9H | 3G | 0 | — | — | — | 0 | 9H | 0 | 4H | 4G | 5G | 2G | 0 | 0 | 8H |
| Sicklepod | | | | | | | | | | | | | | | | |
| Nutsedge | 8G | 0 | 0 | 10E | 0 | 3G | 0 | 5C,9H | 0 | 0 | 0 | 0 | 0 | 0 | 0 | 0 |
| Crabgrass | 0 | 0 | 0 | 0 | 0 | 0 | 0 | 5G | 0 | 0 | 0 | 2G | 0 | 0 | 0 | 0 |
| Barnyardgrass | 2C,5H | 0 | 0 | 7G | 0 | 0 | 0 | 4C,9H | 0 | 0 | 1C,3H | 4C,7G | 0 | 0 | 0 | 2C,6H |
| Wild Oats | 2G | 0 | 0 | 3C | 0 | 0 | 0 | 3G | 0 | 0 | 0 | 0 | 0 | 0 | 0 | 6G |
| Wheat | 0 | 0 | 0 | 2G | 0 | 0 | 0 | 8H | 0 | 0 | 0 | 0 | 0 | 0 | 0 | 5G |

TABLE A-continued

| | | | | | | | | | | | | | | | | |
|---|---|---|---|---|---|---|---|---|---|---|---|---|---|---|---|---|
| Corn | 3C,9H | 0 | 0 | 2C,8G | 3G | 0 | 0 | 9H | 0 | 0 | 3G | 6G | 0 | 0 | 0 | 2C,9H |
| Soybean | 4C,8H | 6H | 0 | 4C,8H | 9H | 8H | 0 | 4C,8H | 0 | 0 | 4G | 2C,5G | 2G | 0 | 0 | 2C,9H |
| Rice | 4C,8G | 0 | 0 | 5G | 0 | 0 | 0 | 10E | 0 | 0 | 5G | 8G | 0 | 2C | 0 | 3C,5G |
| Sorghum | 4C,9H | 1C | 0 | 2C,5G | 0 | 0 | 0 | 5C,9H | 0 | 0 | 2C,5G | 4C,9G | 0 | 1C | 2C,4G | 3C,8H |
| Sugar beet | 9C | 9C | 4G | 9C | 9C | 9C | 4G | 5C,9G | 0 | 4G | 8G | 5C,9G | 4C,8G | 7G | 8G | 9C |
| Cotton | 9G | 8G | 0 | 9G | 9G | 9G | 0 | 2C,9G | 0 | 4G | 8G | 8G | 7G | 3G | 5G | 8G |
| Velvetleaf | 10E | 4G | 0 | 9C | 9C | 8G | 0 | 9H,9G | 0 | 3G | 8H | — | 3G | 2H | 3G | 9G |
| Cheatgrass | 9G | 0 | 0 | 8G | 0 | 0 | 0 | 5C,9H | 0 | 0 | 5G | 8G | 0 | 0 | 0 | 2C,8G |
| Rate kg/ha | Cmpd. 47 0.05 | Cmpd. 48 0.05 | Cmpd. 49 0.05 | Cmpd. 50 0.05 | Cmpd. 51 0.05 | Cmpd. 52 0.05 | Cmpd. 53 0.05 | Cmpd. 54 0.05 | Cmpd. 55 0.05 | Cmpd. 56 0.05 | Cmpd. 57 0.05 | Cmpd. 58 0.05 | Cmpd. 59 0.05 | Cmpd. 60 0.05 | Cmpd. 61 0.05 | Cmpd. 62 0.05 |
| | | | | | | | POST-EMERGENCE | | | | | | | | | |
| Morningglory | 5C,9G | 4C,8G | 4C,9H | 10C | 3C,7H | 0 | 5C,9G | 5C,9G | 0 | 5C,9G | 10C | 9C | 4C,9G | 9C | 4C,9G | 2C,8G |
| Cocklebur | 10C | 4C,9H | 10C | 10C | 4C,9H | 2C,7G | 8H | 4C,9G | 0 | 5C,9G | 9C | 10C | 9C | 10C | 5C,9G | 10C |
| Sicklepod | | | | | | | | | | | | | | | | |
| Nutsedge | 0 | 4C,9G | 2C,9G | 5C,9G | 2C,5G | 0 | 2G | 0 | 0 | 9G | 2C,9G | 8G | 0 | 0 | 3C,8G | 5G |
| Crabgrass | 2C,6H | 0 | 0 | 8G | 0 | 0 | 0 | 4G | 0 | 0 | 3C,7G | 5G | 2G | 0 | 0 | 4G |
| Barnyardgrass | 3C,9H | 2H | 4C,8H | 9C | 3C,9H | 2C,4H | 2C,7H | 4C,8H | 4H | 4C,9H | 9C | 5C,9H | 4H | 2H | 5H | 3C,5H |
| Wild Oats | 0 | 0 | 0 | 3C,5G | 0 | 0 | 0 | 0 | 0 | 3G | 2C,5G | 3C,5G | 0 | 0 | 0 | 0 |
| Wheat | 0 | 0 | 0 | 2C,4G | 0 | 0 | 0 | 0 | 0 | 2G | 2C,8G | 9G | 0 | 0 | 0 | 0 |
| Corn | 5C,8G | 0 | 2C,7H | 5C,9H | 9G | 3C,6H | 2C,8G | 0 | 0 | 3C,9H | 5C,9G | 3C,9H | 5H | 0 | 3H | 2C,9G |
| Soybean | 5C,9G | 4C,9G | 3C,8G | 5C,9G | 2C,9G | 3C,5G | 4C,9G | 3C,9G | 0 | 4C,9G | 9C | 9C | 4C,8G | 4C,9G | 2C,3G | 4C,9G |
| Rice | 5C,9G | 0 | 5C,9G | 6C,9G | 2C,9G | 2C,8G | 3C,8G | 2C,3G | 0 | 2C,8G | 5C,9G | 5C,9G | 0 | 0 | 3G | 3C,9G |
| Sorghum | 2C,8H | 2G | 3C,7H | 5C,9H | 3C,9H | 2C,5G | 3C,7H | 2C,6G | 3G | 3C,9H | 5C,9G | 4C,9H | 0 | 0 | 2C,7G | 3C,8H |
| Sugar beet | 4C,9H | 3C,6G | 5C,9G | 9C | 3C,8H | 5C,9H | 9C | 5C,9G | 1H | 3C,7G | 4C,9H | 5C,9H | 3C,7G | 9C | 4G | 9C |
| Cotton | 9C | 10C | 10C | 9C | 3C,7H | 0 | 5C,9G | 5C,9G | 0 | 3C,5G | 4C,9H | 5C,9G | 3C,4G | 3C,7G | 2G | 5C,9G |
| Bush bean | | | | | | | | | | | | | | | | |
| Cheatgrass | 4G | 0 | 1C | 9C | 2C,6G | 0 | 0 | 5G | 0 | 2C,8G | 2C,9G | 3C,9G | 0 | 0 | 2G | 6G |
| Velvetleaf | 5C,9G | 4C | 4C,9G | 10C | 5C,9G | 2C,4G | 4C,9G | 4C,8G | 0 | 4C,8H | 5C,9G | 9C | 4C,8H | 2C,4G | 3C,6G | 5C,9G |
| | | | | | | | PRE-EMERGENCE | | | | | | | | | |
| Morningglory | 7G | 9G | 9G | 9G | 5G | 4H | 6G | 7H | 0 | 2C | 3C,7H | 3C,7H | 2H | 3H | 2C,5G | 2C,6G |
| Cocklebur | 8G | 7H | 7G | 9H | 5H | 3H | 2C,5G | 0 | 0 | 1C | 3C,3H | 3C,6H | 0 | 0 | 2C | 3C,7H |
| Sicklepod | | | | | | | | | | | | | | | | |
| Nutsedge | 0 | 10E | 9G | 8G | 0 | 0 | 5G | 0 | 0 | 0 | 0 | 4G | 0 | 0 | 0 | 4G |
| Crabgrass | 0 | 0 | 0 | 7G | 0 | 4G | 0 | 0 | 0 | 0 | 0 | 0 | 0 | 0 | 0 | 3G |
| Barnyardgrass | 5G | 2C | 3C,8H | 2C,9H | 6G | 1H | 0 | 0 | 0 | 0 | 0 | 4G | 0 | 0 | 0 | 0 |
| Wild Oats | 0 | 0 | 0 | 6G | 0 | 0 | 0 | 0 | 0 | 0 | 0 | 0 | 0 | 0 | 0 | 0 |
| Wheat | 0 | 0 | 0 | 6G | 0 | 0 | 0 | 0 | 0 | 0 | 0 | 0 | 0 | 0 | 0 | 0 |
| Corn | 5G | 3G | 3C,5G | 2C,9H | 2C,8H | 2G | 2C,5G | 0 | 0 | 2C | 3C,5G | 3C,4G | 3G | 0 | 0 | 2C,7G |
| Soybean | 5G | 2H,4G | 4G | 9H | 1C,3G | 0 | 2C | 0 | 0 | 0 | 3C,3H | 3C,5G | 0 | 0 | 0 | 2C,2H |
| Rice | 5G | 3G | 0 | 10E | 3C,5G | 0 | 3G | 0 | 0 | 0 | 0 | 3C | 0 | 2G | 0 | 3G |
| Sorghum | 2G | 2C,5G | 2C,8H | 6C,9G | 3C,8H | 0 | 1C | 0 | 0 | 0 | 3C | 3C,4G | 0 | 0 | 2C | 3G |
| Sugar beet | 5C,9G | 8G | 8G | 5C,9G | 2C,9G | 5G | 4C,9G | 7G | 0 | 0 | 3C,6G | 4C,7G | 0 | 0 | 0 | 7G |
| Cotton | 6G | 8G | 8G | 9G | 8G | 3G | 8G | 2G | 0 | 0 | 2C | 6G | 0 | 3G | 2C | 8G |
| Velvetleaf | 7G | 8G | 8G | 5C,9G | 6G | 5G | 4G | 0 | 0 | 0 | 4C,5G | 3C,5G | 0 | 0 | 0 | 6G |
| Cheatgrass | 0 | 5G | 3G | 8G | 3C,7G | 0 | 0 | 0 | 0 | 0 | 0 | 0 | 0 | 0 | 0 | 4G |
| Rate kg/ha | Cmpd. 63 0.05 | Cmpd. 64 0.05 | Cmpd. 65 0.05 | Cmpd. 66 0.05 | Cmpd. 67 0.05 | Cmpd. 68 0.05 | Cmpd. 69 0.05 | Cmpd. 70 0.05 | Cmpd. 71 0.05 | Cmpd. 72 0.05 | Cmpd. 73 0.05 | Cmpd. 74 0.05 | Cmpd. 75 0.05 | Cmpd. 76 0.05 | Cmpd. 77 0.05 | Cmpd. 78 0.05 |
| | | | | | | | POST-EMERGENCE | | | | | | | | | |
| Morningglory | 10C | 10C | 9C | 5C,9G | 2C,9G | 5G | 9C | 2C,7G | 5G | 2C,5G | 2C,6G | 2C,6G | 10C | 5C,9H | 2C,5G | 10C |
| Cocklebur | 10C | 10C | 9C | 4C,9G | 5C,9G | 5G | 6G | 5G | 4G | 2G | 0 | 5G | 2C,6G | 3C,8G | 3C,9H | 10C |
| Sicklepod | | | | | | | | | | | | | | | | |

TABLE A-continued

| | | | | | | | | | | | | | | | | |
|---|---|---|---|---|---|---|---|---|---|---|---|---|---|---|---|---|
| Nutsedge | 2C,9G | 9C | 0 | 0 | 3C,9G | 2C,8G | 2C,9G | 9G | 0 | 0 | 0 | 8G | 5G | 2C,6G | 8G | 4G |
| Crabgrass | 5G | 5G | 0 | 2G | 2G | 0 | 2C,6G | 3C,8G | 0 | 0 | 1C | 2G | 2G | 3G | 2G | 2G |
| Barnyardgrass | 3C,9H | 9H | 3H | 2H | 8H | 2C,5G | 3C,9H | 9H | 0 | 0 | 2C,8H | 4C,9H | 3G | 3C,7H | 0 | 0 |
| Wild Oats | 0 | 0 | 0 | 0 | 0 | 0 | 2G | 0 | 0 | 0 | 0 | 3C,8G | 0 | 0 | 0 | 0 |
| Wheat | 0 | 0 | 0 | 0 | 0 | 0 | 2G | 0 | 0 | 0 | 0 | 3G | 0 | 0 | 0 | 0 |
| Corn | 2U,9G | 3C,9H | 6H | 6H | 5H | 1C,2G | 2C,9H | 1C,4G | 0 | 0 | 0 | 9H | 0 | 3C,8H | 0 | 0 |
| Soybean | 9C | 9C | 5C,9G | 4C,9G | 2C,7G | 3H,8G | 4C,9G | 2C,8H | 3H | 1H | 3H | 4C,9G | 4C,9G | 5C,9G | 5C,9G | |
| Rice | 4C,9G | 2C,8G | 3G | 0 | 3G | 2C,6G | 2C,8G | 3C,9G | 0 | 0 | 5G | 5C,9G | 5G | 8G | 0 | 1C |
| Sorghum | 4C,9H | 3C,9H | 5G | 3G | 2C,8G | 2C,8H | 3C,9G | 3C,9G | 0 | 1C | 2C,9H | 5C,9G | 2G | 3C,8H | 0 | 0 |
| Sugar beet | 9C | 9C | 9C | 9C | 9C | 9C | 9C | 9C | 5C,9G | 2C,7G | 3C,7G | 5C,9H | 1H | 2C,5G | 5G | 9C |
| Cotton | 10C | 10C | 2C,8G | 2C,3G | 5C,9G | 3C,9H | 2C,9G | 9C | 2C,9G | 2C,5G | 3C,7H | 4C,9H | 9C | 9C | 9C | 5C,9G |
| Bush bean | | | | | | | | | | | | | | | | |
| Cheatgrass | 2C,8G | 8G | 0 | 0 | 0 | 2C,9G | 3C,9G | 3C,9G | 0 | 0 | 0 | 2C,9G | 4G | 8G | 0 | 0 |
| Velvetleaf | 10C | 10C | 9C | 4C,9G | 3C,9G | 2C.8G | 9C | 9C | 2C,6G | 2G | 5G | 5C,9G | 4C,9G | 10C | 9C | 10C |
| | | | | | | | PRE-EMERGENCE | | | | | | | | | |
| Morningglory | 8G | 8G | 2C,5G | 2C,5H | 0 | 2G | 2C,7G | 9G | 5G | 2G | 6H | 4G | 10C | 9G | 2C,8G | 9G |
| Cocklebur | 6G | 8H | 2C,5H | 2H | 0 | 0 | 6G | 7G | 0 | 0 | 0 | 0 | 2C,8G | — | 7H | 9H |
| Sicklepod | | | | | | | | | | | | | | | | |
| Nutsedge | 10E | 5G | 0 | 0 | 0 | 0 | 6G | 2C,9G | 0 | 0 | 0 | 0 | 0 | 7G | 4G | 0 |
| Crabgrass | 5G | 0 | 0 | 0 | 0 | 3G | 4G | 5G | 0 | 0 | 0 | 0 | 1C | 2G | 2G | 0 |
| Barnyardgrass | 3C,8H | 5G | 2C | 0 | 2C | 0 | 3C,7H | 2C,9H | 0 | 0 | 0 | 1C | 3C.5G | 3C.7H | 4H | 1H |
| Wild Oats | 0 | 0 | 0 | 0 | 0 | 0 | 2C,7G | 4G | 0 | 0 | 0 | 0 | 0 | 3G | 0 | 0 |
| Wheat | 0 | 0 | 0 | 0 | 0 | 0 | 5G | 2G | 0 | 0 | 0 | 4G | 2G | 4G | 2G | 0 |
| Corn | 3C,9G | 2C,5G | 2C,6G | 2G | 2G | 2C,5G | 2C,8H | 2C,8G | 0 | 0 | 0 | 2C,4G | 4G | 3C.7G | 4G | 0 |
| Soybean | 3C,8H | 4H | 2C,4G | 6G | 3G | 1C | 2C,6G | 6G | 0 | 0 | 0 | 5G | 3C,3H | 3C,6H | 0 | 4G |
| Rice | 7G | 2G | 0 | 0 | 2G | 2C,5G | 3C,8H | 3C,9H | 0 | 0 | 5G | 9H | 2G | 5G | 5G | 0 |
| Sorghum | 3C,9H | 2C,9G | 2C,8G | 2G | 3C,6G | 3C,8G | 3C,9G | 2C,9H | 3G | 0 | 2C,8G | 3C,8H | 2G | 5G | 2G | 0 |
| Sugar beet | 5C,9G | 3C,9G | 5C,9G | 4C,9G | 7G | 2C,8G | 9G | 3C,8G | 5G | 0 | 3C,6G | 4C.8G | 3C.7H | 9G | 8G | 9C |
| Cotton | 9G | 9G | 8G | 7G | 6G | 6G | 8G | 9G | 0 | 0 | 3C,6G | 8G | 8G | 8G | 6G | 9G |
| Velvetleaf | 4C,9G | 8G | 3C,3H | 2C,4G | 0 | 5G | 4C,9G | 5C,9G | 0 | 0 | 3G | 2G | 5C.9G | 5C.9G | 8G | 10C |
| Cheatgrass | 8H | 0 | 0 | 0 | 0 | 5G | 2C,8G | 9H | 0 | 0 | 0 | 6G | 3C.6G | 8G | 5G | 0 |

| Rate kg/ha | Cmpd. 79 0.05 | Cmpd. 80 0.05 | Cmpd. 81 0.05 | Cmpd. 82 0.05 | Cmpd. 83 0.05 | Cmpd. 84 0.05 | Cmpd. 85 0.05 | Cmpd. 86 0.05 |
|---|---|---|---|---|---|---|---|---|
| | | | POST-EMERGENCE | | | | | |
| Morningglory | 9C | 2C.8H | 4C.9G | 10C | 7G | 2C.5G | 10C | 2C.3G |
| Cocklebur | 9C | 2H | 4C.9H | 10C | 3C.9G | 3C.9H | 5C.9G | 6G |
| Sicklepod | | | | | | | | |
| Nutsedge | 4G | 0 | 2C.5G | 7G | 0 | 4G | 0 | 5G |
| Crabgrass | 0 | 0 | 0 | 4G | 0 | 0 | 5G | 3G |
| Barnyardgrass | 0 | 0 | 9H | 4C.9H | 2H | 5H | 2H | 3C.8H |
| Wild Oats | 0 | 0 | 0 | 0 | 0 | 0 | 0 | 0 |
| Wheat | 0 | 0 | 0 | 0 | 0 | 0 | 0 | 0 |
| Corn | 0 | 0 | 3C.9H | 0 | 0 | 3C.8H | 0 | 0 |
| Soybean | 5C,9G | 1C.4G | 5C.9G | 4C.9G | 4C.9G | 4C.8G | 4C.9G | 0 |
| Rice | 0 | 0 | 2G | 2G | 0 | 4G | 0 | 0 |
| Sorghum | 0 | 0 | 3C.4H | 2C.5H | 2H | 3C.7G | 2G | 3C.6H |
| Sugar beet | 9C | 0 | 4C.9H | 9C | 4C.9G | 3C.6G | 5C.9G | 0 |
| Cotton | 9C | 9C | 4C.9G | 9C | 2C.5G | 2C.5G | 2G | 0 |
| Bush bean | | | | | | | | |
| Cheatgrass | 0 | 0 | 2C.5G | 3G | 0 | 5G | 0 | 0 |
| Velvetleaf | 2C,7G | 10C | 10C | 10C | 4C.9G | 4C.9G | 4C.8H | 4G |
| | | | PRE-EMERGENCE | | | | | |

TABLE A-continued

| | | | | | | | | |
|---|---|---|---|---|---|---|---|---|
| Morningglory | 9G | 9G | 3G | 7H | 0 | 7G | 5H | 5G |
| Cocklebur | 8H | 5G | 3C,6H | — | 0 | 0 | 0 | 0 |
| Sicklepod | | | | | | | | |
| Nutsedge | 3G | 5G | 5G | 0 | 0 | 0 | 0 | 0 |
| Crabgrass | 0 | 0 | 0 | 0 | 0 | 4G | 0 | 0 |
| Barnyardgrass | 0 | 0 | 3C,7G | 3H | 0 | 2G | 2G | 0 |
| Wild Oats | 0 | 0 | 0 | 0 | 0 | 0 | 0 | 0 |
| Wheat | 0 | 0 | 0 | 0 | 0 | 0 | 0 | 0 |
| Corn | 0 | 0 | 3C,9H | 2C,5G | 0 | 2C,5G | 0 | 2G |
| Soybean | 2C,6H | 0 | 3C,2H | 2C | 0 | 2C,5G | 0 | 0 |
| Rice | 0 | 0 | 4G | 0 | 0 | 0 | 0 | 0 |
| Sorghum | 0 | 0 | 3C,8H | 3C,8H | 0 | 3C,7H | 2G | 2C,8G |
| Sugar beet | 10C | 10C | 4C,9G | 8G | 5G | 7G | 5G | 7G |
| Cotton | 9G | 5G | 8G | 6G | 0 | 6G | 5G | 7G |
| Velvetleaf | 7G | 6G | 9C | 4C,8G | 2G | 2C,5G | 0 | 0 |
| Cheatgrass | 0 | 2G | 7G | 0 | 0 | 0 | 0 | 0 |

Test B

Postemergence

Two round pans (25 cm diameter by 12.5 cm deep) were filled with Woodstown sandy loam soil. One pan was planted with blackgrass (Alopacurus myosuroides), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti), and giant foxtail (Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Pre-emergence

Two round pans (25 cm diameter by 12.5 cm deep) were filled with Woodstown sandy loam soil. One pan was planted with blackgrass (Alopacurus myosuroides), sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response utilizing the rating system as described for Test A. The data are summarized in Table B.

The high herbicidal activity and the tolerance of wheat as observed in Test A were confirmed.

TABLE B

| | Compound 1 | | | | Compound 2 | | | | Compound 3 | | | |
|---|---|---|---|---|---|---|---|---|---|---|---|---|
| | POST-EMERGENCE | | | | | | | | | | | |
| Rate g/ha | 62 | 16 | 4 | 1 | 62 | 16 | 4 | 1 | 62 | 16 | 4 | 1 |
| Corn | 10G | 8G | 2G | 0 | 10G | 9G | 7G | 2G | 8G | 4G | 0 | 0 |
| Wheat | 2G | 0 | 0 | 0 | 2G | 0 | 0 | 0 | 0 | 0 | 0 | 0 |
| Rice | 10G | 7G | 3G | 0 | 9G | 5G | 2G | 0 | 2G | 0 | 0 | 0 |
| Soybean | 10G | 10G | 8G | 2G | 10G | 10G | 10G | 8G | 10G | 10G | 10G | 4G |
| Cotton | 10G | 10G | 4G | 0 | 10G | 10G | 10G | 5G | 10G | 10G | 9G | 2G |
| Sugar beet | 10G | 10G | 7G | 3G | 10G | 10G | 10G | 6G | 10G | 10G | 10G | 8G |
| Crabgrass | 6G | 5G | 2G | 0 | 5G | 4G | 3G | 0 | 6G | 2G | 0 | 0 |
| Johnsongrass | 10G | 6G | 3G | 0 | 10G | 8G | 5G | 0 | 8G | 4G | 2G | 0 |
| Blackgrass | 7G | 4G | 0 | 0 | 5G | 0 | 0 | 0 | 0 | 0 | 0 | 0 |
| Barnyardgrass | 10G | 9G | 3G | 0 | 9G | 8G | 3G | 0 | 9G | 4G | 2G | 0 |
| Nutsedge | 10G | 10G | 4G | 0 | 10G | 10G | 10G | 9G | 10G | 10G | 10G | 9G |
| Giant Foxtail | 10G | 5G | 2G | 0 | 7G | 3G | 0 | 0 | 5G | 2G | 0 | 0 |
| Wild Oats | 2G | 0 | 0 | 0 | 2G | 0 | 0 | 0 | 0 | 0 | 0 | 0 |
| Cocklebur | 10G | 9G | 4G | 0 | 10G | 10G | 7G | 2G | 10G | 6G | 2G | 0 |
| Morningglory | 9G | 2G | 0 | 0 | 10G | 10G | 6G | 2G | 9G | 7G | 3G | 0 |
| Teaweed | 10G | 10G | 3G | 0 | 6G | 3G | 0 | 0 | 6G | 4G | 0 | 0 |
| Sicklepod | 10G | 5G | 2G | 0 | 10G | 10G | 6G | 0 | 10G | 8G | 4G | 0 |
| Jimsonweed | 7G | 4G | 0 | 0 | 9G | 4G | 2G | 0 | 7G | 4G | 0 | 0 |
| Velvetleaf | 10G | 10G | 4G | 2G | 10G | 10G | 9G | 2G | 10G | 10G | 9G | 3G |
| | PRE-EMERGENCE | | | | | | | | | | | |
| Rate g/ha | 250 | 62 | 16 | 4 | 250 | 62 | 16 | 4 | 250 | 62 | 16 | 4 |
| Corn | 10G | 7G | 3G | 0 | 10G | 8G | 5G | 0 | 10G | 4G | 0 | 0 |
| Wheat | 3G | 0 | 0 | 0 | 3G | 0 | 0 | 0 | 0 | 0 | 0 | 0 |
| Rice | 10E | 10G | 8G | 7G | 10G | 9G | 7G | 4G | 10G | 8G | 6G | 3G |
| Soybean | 10G | 8G | 7G | 3G | 10G | 9G | 5G | 2C | 10G | 8G | 4G | 2C |
| Cotton | 10G | 9G | 5G | 2G | 10G | 10G | 9G | 6G | 9G | 10G | 8G | 2G |
| Sugar beet | 10G | 10G | 7G | 4G | 10G | 10G | 8G | 4G | 10G | 10G | 8G | 5G |
| Crabgrass | 6G | 2G | 0 | 0 | 7G | 3G | 0 | 0 | 6G | 3G | 2G | 0 |
| Johnsongrass | 10G | 9G | 8G | 3G | 10G | 10G | 8G | 3G | 9G | 10G | 4G | 0 |
| Blackgrass | 10G | 8G | 4G | 2G | 10G | 8G | 4G | 0 | 5G | 2G | 0 | 0 |
| Barnyardgrass | 9G | 7G | 2G | 0 | 10G | 6G | 5G | 2G | 9G | 6G | 4G | 0 |
| Nutsedge | 10G | 9G | 6G | 2G | 10E | 9G | 4G | 0 | 10G | 9G | 8G | 3G |
| Giant Foxtail | — | 6G | 2G | 0 | 10G | 6G | — | 2G | 9G | 6G | — | 0 |
| Wild Oats | 5G | 2G | 0 | 0 | 2G | 0 | 0 | 0 | 0 | 0 | 0 | 0 |
| Cocklebur | 10G | 8G | 3G | 0 | 9G | 8G | 5G | 2G | 8G | 5G | 4G | 2G |
| Morningglory | 5G | 3G | 0 | 0 | 8G | 4G | 0 | 0 | 9G | 3G | 0 | 0 |
| Teaweed | 10G | 5G | 2G | 0 | 10G | 7G | 3G | 0 | 10G | 9G | 5G | 2G |
| Sicklepod | 9G | 4G | 2G | 0 | 8G | 5G | 0 | 0 | 9G | 3G | 0 | 0 |
| Jimsonweed | 10G | 5G | 2G | 0 | 10G | 8G | 3G | 0 | 10G | 9G | 6G | 2G |
| Velvetleaf | 10G | 8G | 3G | 0 | 10G | 9G | 6G | 3G | 10G | 10G | 5G | 0 |

Test C

Two plastic pans with polyethylene liners were filled with prepared Sassafras sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and rapeseed (*Brassia napus*). The other pan was planted with seeds of Russian thistle (*Salsola kali*), cleavers (*Galium aparine*), speedwell (*Veronica persica*), kochia (*Kochia scoparia*), shepherspurse (*Capsella bursa-pastoris*), (*Matricaria inodora*), black nightshade (*Solanum nigrum*), wild buckwheat (*Polygonum convolvulus*) and sugar beets (*Beta vulgaris*). The above two pans were treated pre-emergence. At the same time two pans in which the above plant species were already growing were treated post-emergence. Plant heights at the time of treatment ranged from 1–20 cm depending on plant species.

Compound #3 were diluted with a non-phytotoxic solvent and sprayed over the top of the pans. An untreated control and a solvent alone control were included for comparison. All treatments were maintained in the greenhouse for 19–22 days at which time the treatments were compared to the controls and the effects visually rated. The recorded data are presented in Table C. Compound #3 has high herbicidal activity at rates of application which are non-injurious to wheat and barley.

TABLE C

| | Compound 3 | | | |
|---|---|---|---|---|
| Rate kg/ha | 0.125 | 0.06 | 0.03 | 0.015 |
| POST-EMERGENCE ON SASSAFRAS SANDY LOAM SOIL | | | | |
| Wheat | 0 | 0 | 0 | 0 |
| Barley | 0 | 0 | 0 | 0 |
| Wild Oats | 0 | 0 | 0 | 0 |
| Cheatgrass | 6G | 3G | 2G | 0 |
| Blackgrass | 0 | 0 | 0 | 0 |
| Annual Bluegrass | 2G | 2G | 0 | 0 |
| Green Foxtail | 8G | 8G | 6G | 6G |
| Italian Ryegrass | 3G | 2G | 0 | 0 |
| Rapeseed | 10C | 10C | 9G | 8G |
| Matricaria inodora | 9G | 9G | 9G | 9G |
| Galium | 10C | 10C | 10C | 10C |
| Russian Thistle | 10C | 10C | 10C | 7G |
| Shepherdspurse | 8G | 8G | 8G | 6G |
| Kochia | 7G | 4G | 0 | 0 |
| Black Nightshade | 4G | 3G | 2G | 0 |
| Speedwell | 7G | 6G | 0 | 0 |
| Wild Buckwheat | 10G | 10C | 10C | 7G |
| Sugarbeet | 10C | 10C | 10C | 9G |
| PRE-EMERGENCE ON SASSAFRAS SANDY LOAM SOIL | | | | |
| Wheat | 0 | 0 | 0 | 0 |
| Barley | 1G | 0 | 0 | 0 |
| Wild Oats | 3G | 3G | 0 | 0 |
| Cheatgrass | 9G | 8G | 7G | 5G |
| Blackgrass | 6G | 5G | 5G | 4G |
| Annual Bluegrass | 5G | 4G | 4G | 3G |
| Green Foxtail | 9G | 8G | 7G | 7G |
| Italian Ryegrass | 6G | 6G | 6G | 4G |
| Rapeseed | 10C | 10C | 10C | 9G |
| Matricaria inodora | 9G | 8G,5C | 8G,5C | 8G,5C |
| Galium | 10C | 9G | 8G | 7G |
| Russian Thistle | 10C | 10C | 10C | 10C |
| Shepherdspurse | 9G,8C | 9G,8C | 9G,3C | 9G,3C |
| Kochia | 10C | 10C | 10C | 10C |
| Black Nightshade | 8G | 7G | 7G | 7G |
| Speedwell | 9G | 8G,5C | 7G | 6G,3C |
| Wild Buckwheat | 8G | 8G | 7G | 6G |
| Sugarbeet | 10C | 10C | 10C | 9G,7C |

What is claimed is:

1. A compound of Formula Ia, Ib, or Ic

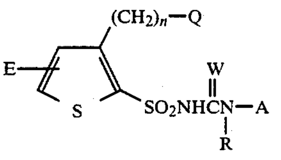

Ia

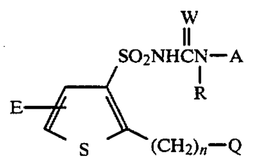

Ib

-continued

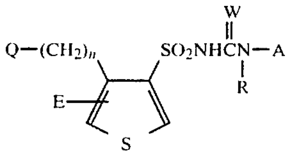

Ic wherein

R is H or $CH_3$;

n is 0, 1 or 2;

Q is a saturated 5- or 6-membered ring containing 1 heteroatom selected from sulfur, nitrogen or oxygen or an unsaturated 5- or 6-membered ring containing 1–3 heteroatoms selected from 0–1 sulfur, 0–1 oxygen or 0–3 nitrogen and Q may optionally be substituted by one or more groups selected from SH, $C_1$–$C_4$ alkyl, $C_3$–$C_4$ alkenyl, $C_1$–$C_3$ haloalkyl, halogen, $C_1$–$C_3$ alkoxy, $C_1$–$C_4$ alkylthio, $C_3$–$C_4$ alkenylthio, $C_3$–$C_4$ alkenyloxy, $C_1$–$C_2$ haloalkoxy, $C_1$–$C_2$ haloalkylthio, $C_3$–$C_4$ alkynylthio, $C_1$–$C_4$ cyanoalkylthio, $C_1$–$C_2$ alkylcarbonylmethylthio or $C_1$–$C_2$ alkoxycarbonylmethylthio;

E is H, $C_1$–$C_2$ alkyl, $C_1$–$C_2$ alkoxy, halogen, $NO_2$, $C_1$–$C_2$ haloalkyl, $C_1$–$C_2$ alkylthio, $C_1$–$C_2$ alkylsulfonyl, $C_1$–$C_2$ alkoxycarbonyl, $C_1$–$C_2$ dialkylaminosulfamoyl;

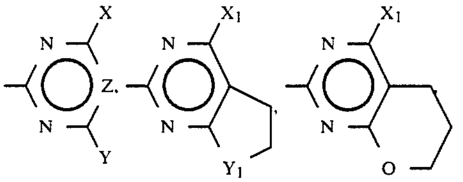

A-1 A-2 A-3

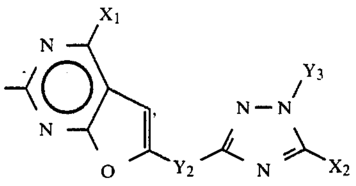

A-4 A-5

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_3$–$C_5$ cycloalkyl, $C_2$–$C_4$ alkynyl, $C(O)R_c$,

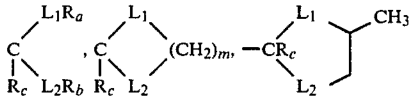

or $N(OCH_3)CH_3$;

m is 2 or 3;

$L_1$ and $L_2$ are independently O or S;

$R_a$ and $R_b$ are independently $C_1$–$C_2$ alkyl;

$R_c$ is H or $CH_3$;

Z is CH;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$; and $Y_3$ is $CH_3$, $CH_2CH_3$ or $CH_2CF_3$;

and their agriculturally suitable salts; provided that (1) when X is F, Cl, Br or I, then Y is $OCF_2H$, $OCH_3$, $OC_2H_5$, $NH_2$, $N(OCH_3)CH_3$, $NHCH_3$, $N(CH_3)_2$;

(2) the total number of carbon atoms of Q must be less than or equal to 8;

(3) when Q is a saturated 5- or 6-membered ring containing one nitrogen atom, it is bonded to the thiophene ring through carbon; and when W is S, then R is H, A is A-1 and Y is $CH_3$, $OCH_3$, $OC_2H_5$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

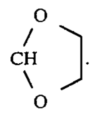

2. A compound of claim 1 wherein

Q is

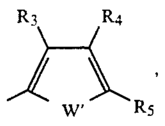

Q-2

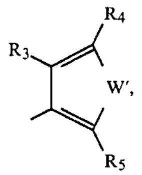

Q-3

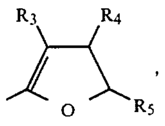

Q-4

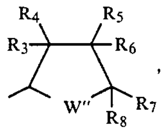

Q-5

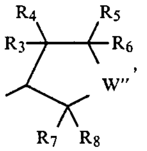

Q-6

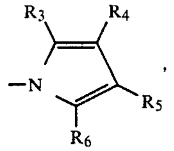

Q-7

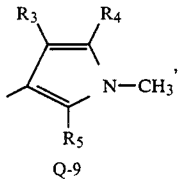

Q-9

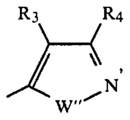

Q-10

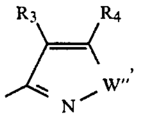

Q-11

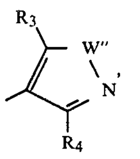

Q-12

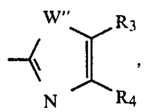

Q-13

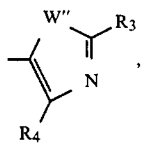

Q-14

-continued

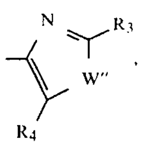

Q-15

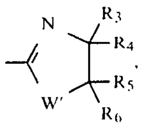

Q-16

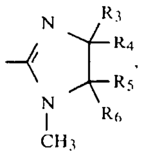

Q-17

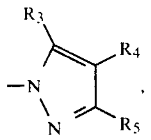

Q-18

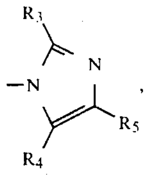

Q-19

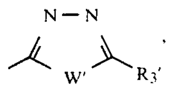

Q-20

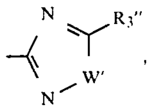

Q-21

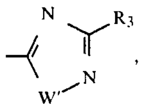

Q-22

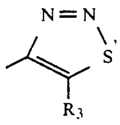

Q-23

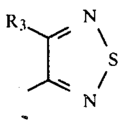

Q-24

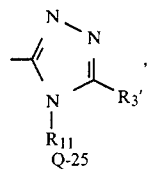

Q-25

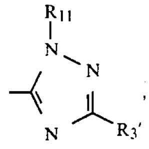

Q-26

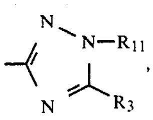

Q-27

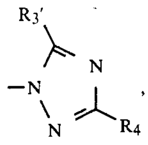

Q-28

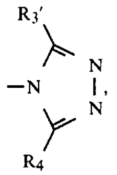

Q-29

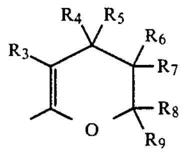

Q-30

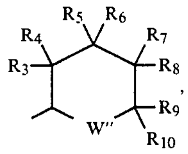

Q-31

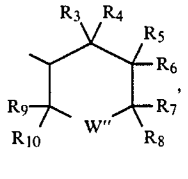

Q-32

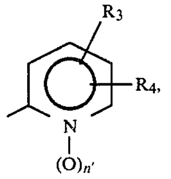

Q-33

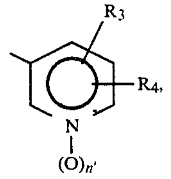

Q-34

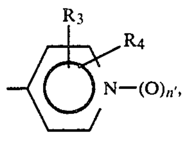

Q-35

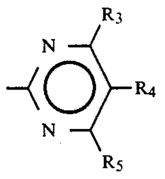

Q-36

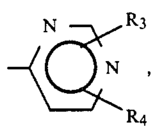

Q-37

-continued

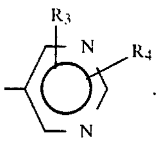 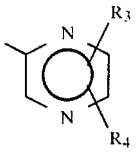 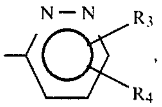

Q-38 Q-39 Q-40

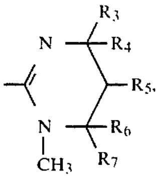 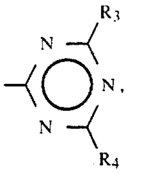

Q-41 Q-43

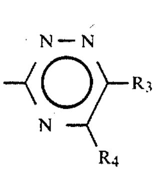 or 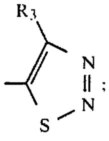

Q-44 Q-45

$R_3$, $R_4$, $R_5$, $R_6$, $R_7$, $R_8$, $R_9$ and $R_{10}$ are independently H or $CH_3$;

n' is 0 or 1;

$R_3'$ is H, SH, $C_1$–$C_3$ alkyl, $C_1$–$C_4$ alkylthio, $C_3$–$C_4$ alkenylthio, $C_3$–$C_4$ alkynylthio, $C_1$–$C_3$ cyanoalkylthio, $SCH_2CO_2CH_3$, $SCH_2CO_2C_2H_5$, $SCH_2C(O)CH_3$, halogen, $C_1$–$C_3$ alkoxy or $OCH_2CH{=}CH_2$;

$R_3''$ is H, $CH_3$, Cl or Br;

W' is O or S;

W'' is O, S or $NR_{11}$;

$R_{11}$ is H, $C_1$–$C_3$ alkyl or $CH_2CH{=}CH_2$.

3. A compound of claim 2 wherein E is H; A is A-1; X is $CH_3$, $OCH_3$, $OC_2H_5$, Cl or Br; Y is H, $CH_3$, $OCH_3$, $C_2H_5$, $OC_2H_5$, $CH_2OCH_3$, $CF_3$, $OCF_2H$, cyclopropyl, $OCH_2CF_3$, $NHCH_3$, $N(CH_3)_2$, $CH(OCH_3)_2$ or

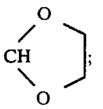;

n' is O; and $R_3'$ and $R_3''$ are independently H, $CH_3$ or Cl; R is H; and W is O.

4. A compound of claim 3 wherein n is O.

5. A compound of claim 4 wherein Y is $C_1$–$C_2$ alkyl, $OCH_3$, or $OCF_2H$.

6. A compound of claim 5 where $R_1$ is H and $R_2$ is H or Cl.

7. A compound of claim 6 of Formula Ia.

8. A compound of claim 6 of Formula Ib.

9. A compound of claim 6 of Formula Ic.

10. A compound of claim 7 where Q is Q-1, Q-2, Q-3, Q-5, Q-7, Q-10, Q-11, Q-15, Q-16, Q-20, Q-23, Q-28, Q-36 or Q-39.

11. A compound of claim 8 where Q is Q-1, Q-2, Q-3, Q-5, Q-7, Q-10, Q-11, Q-15, Q-16, Q-20, Q-23, Q-28, Q-36 or Q-39.

12. A compound of claim 9 where Q is Q-1, Q-2, Q-3, Q-5, Q-7, Q-10, Q-11, Q-15, Q-16, Q-20, Q-23, Q-28, Q-36 or Q-39.

13. The compound of claim 1 which is N-[(4,6-dimethylpyrimidin-2-yl)aminocarbonyl]-3-(isoxazol-3-yl)-2-thiophenesulfonamide.

14. The compound of claim 1 which is 3-(isoxazol-3-yl)-N-[(4-methoxy-6-methylpyrimidin-2-yl)aminocarbonyl]-2-thiophenesulfonamide.

15. The compound of claim 1 which is N-[(4,6-dimethoxypyrimidin-2-yl)aminocarbonyl]-3-(isoxazol-3-yl)-2-thiophenesulfonamide.

16. The compound of claim 1 which is 3-(5-chloro-1H-1,2,4-triazol-1-yl)-N-[(4,6-dimethoxypyrimidin-2-yl)aminocarbonyl]-2-thiophenesulfonamide.

17. The compound of claim 1 which is N-[(4-methoxy-6-methylpyrimidin-2-yl)aminocarbonyl-3-(1H-pyrrol-1-yl)-2-thiophenesulfonamide.

18. The compound of claim 1 which is N-[(4,6-dimethoxypyrimidin-2-yl)aminocarbonyl]-3-(1H-pyrrol-1-yl)-2-thiophenesulfonamide.

19. The compound of claim 1 which is N-[(4,6-dimethylpyrimidin-2-yl)aminocarbonyl]-3-(1H-pyrrol-1-yl)-2-thiophenesulfonamide.

20. The compound of claim 1 which is N-[(4-chloro-6-methoxypyrimidin-2-yl)aminocarbonyl]-3-(2-methyl-4-thiazolyl))-2-thiophenesulfonamide.

21. The compound of claim 1 which is N-[(4-methoxy-6-methylpyrimidin-2-yl)aminocarbonyl]3-(2-methyl-4-thiazolyl)-2-thiophenesulfonamide.

22. The compound of claim 1 which is N-[(4,6-dimethoxypyrimidin-2-yl)aminocarbonyl]-3-(2-methyl-4-thiazolyl)-2-thiophenesulfonamide.

23. A composition suitable for controlling the growth of undesired vegetation which comprises an effective amount of a compound of claim 1 and at least one of the following: surfactant, solid or liquid diluent.

24. A composition suitable for controlling the growth of undesired vegetation which comprises an effective amount of a compound of claim 10 and at least one of the following: surfactant, solid or liquid diluent.

25. A composition suitable for controlling the growth of undesired vegetation which comprises an effective amount of a compound of claim 11 and at least one of the following: surfactant, solid or liquid diluent.

26. A composition suitable for controlling the growth of undesired vegetation which comprises an effective amount of a compound of claim 12 and at least one of the following: surfactant, solid or liquid diluent.

27. A method for controlling the growth of undesired vegetation which comprises applying to the locus to be protected an effective amount of a compound of claim 1.

28. A method for controlling the growth of undesired vegetation which comprises applying to the locus to be protected an effective amount of a compound of claim 10.

29. A method for controlling the growth of undesired vegetation which comprises applying to the locus to be protected an effective amount of a compound of claim 11.

30. A method for controlling the growth of undesired vegetation which comprises applying to the locus to be protected an effective amount of a compound of claim 12.

* * * * *